(12) United States Patent
Krishnan et al.

(10) Patent No.: US 10,786,438 B2
(45) Date of Patent: Sep. 29, 2020

(54) RECOMBINANT NUCLEIC ACIDS ENCODING COSMETIC PROTEIN(S) FOR AESTHETIC APPLICATIONS

(71) Applicant: Krystal Biotech, Inc., Pittsburgh, PA (US)

(72) Inventors: Suma Krishnan, San Francisco, CA (US); Trevor Parry, San Diego, CA (US); Pooja Agarwal, Mars, PA (US)

(73) Assignee: Krystal Biotech, Inc., Pittsburgh, PA (US)

( * ) Notice: Subject to any disclaimer, the term of this patent is extended or adjusted under 35 U.S.C. 154(b) by 0 days.

(21) Appl. No.: 16/395,896

(22) Filed: Apr. 26, 2019

(65) Prior Publication Data

US 2019/0328644 A1    Oct. 31, 2019

Related U.S. Application Data

(60) Provisional application No. 62/663,476, filed on Apr. 27, 2018.

(51) Int. Cl.
| | |
|---|---|
| *A61K 35/763* | (2015.01) |
| *A61K 9/00* | (2006.01) |
| *A61K 39/12* | (2006.01) |
| *A61K 39/00* | (2006.01) |
| *C12N 15/86* | (2006.01) |
| *C12N 7/00* | (2006.01) |
| *A61K 8/65* | (2006.01) |
| *A61K 8/64* | (2006.01) |
| *A61Q 19/08* | (2006.01) |

(52) U.S. Cl.
CPC .............. *A61K 8/65* (2013.01); *A61K 8/64* (2013.01); *A61Q 19/08* (2013.01); *A61K 2800/86* (2013.01); *A61K 2800/91* (2013.01); *C12N 2710/16621* (2013.01); *C12N 2710/16631* (2013.01)

(58) Field of Classification Search
None
See application file for complete search history.

(56) References Cited

U.S. PATENT DOCUMENTS

| | | |
|---|---|---|
| 5,658,724 A | 8/1997 | Deluca et al. |
| 5,998,174 A | 12/1999 | Glorioso et al. |
| 6,106,826 A | 8/2000 | Brandt et al. |
| 6,719,982 B1 | 4/2004 | Coffin |
| 6,846,670 B2 | 1/2005 | Schwartz |
| 6,887,490 B1 | 5/2005 | Jahoda et al. |
| 9,314,505 B2 | 4/2016 | Wise et al. |
| 9,877,990 B2 | 1/2018 | Krishnan et al. |
| 10,155,016 B2 | 12/2018 | Krishnan et al. |
| 10,441,614 B2 | 10/2019 | Krishnan et al. |
| 10,525,090 B2 * | 1/2020 | Krishnan ............ A61K 9/0014 |
| 2003/0082142 A1 | 5/2003 | Coffin et al. |
| 2004/0005663 A1 * | 1/2004 | Bell ...................... C07K 14/78 435/69.1 |
| 2004/0018592 A1 * | 1/2004 | Bell ...................... C07K 14/78 435/69.1 |
| 2008/0299182 A1 | 12/2008 | Zhang |
| 2013/0331547 A1 | 12/2013 | Hall et al. |
| 2014/0256798 A1 | 9/2014 | Osborn et al. |
| 2014/0288155 A1 | 9/2014 | Hovnanian et al. |
| 2014/0341877 A1 | 11/2014 | Kolattukudy |
| 2015/0352191 A1 | 12/2015 | South et al. |
| 2016/0153000 A1 | 6/2016 | Glorioso |
| 2017/0290866 A1 | 10/2017 | Krishnan et al. |
| 2019/0160122 A1 | 5/2019 | Krishnan et al. |
| 2020/0071703 A1 | 3/2020 | Giuliano et al. |

FOREIGN PATENT DOCUMENTS

| | | |
|---|---|---|
| CN | 102 212 559 | 4/2014 |
| WO | WO 1999/064094 | 12/1999 |
| WO | WO 2000/040734 | 7/2000 |
| WO | WO 2012/001170 | 1/2012 |
| WO | WO 2013/121202 | 8/2013 |
| WO | WO 2015/009952 | 1/2015 |
| WO | WO 2015/117021 | 8/2015 |
| WO | WO 2015/181211 | 12/2015 |
| WO | WO 2016/128374 | 8/2016 |
| WO | WO 2016/128783 | 8/2016 |
| WO | WO 2016/141315 | 9/2016 |
| WO | WO 2017/165813 | 9/2017 |

OTHER PUBLICATIONS

Collagen—Wikipedia p. 1-10, downloaded Aug. 20, 2019.*
Agrawal et al., Skin Barrier Defects in Atopic Dermatitis; Curr Allergy Asthma Rep (2014) 14:433 pp. 1-11.*
Collagen, type VII, alpha 1 From Wikipedia, the free encyclopedia; pp. 1-7; downloaded Jun. 24, 2020.*
International Search Report and Written Opinion for PCT/US2019/29422, dated Jul. 10, 2019, 13 pages.
Aldawsari et al., "Progress in Topical siRNA Delivery Approaches for Skin Disorders," Curr Pharm Des. 2015;21 (31):4594-605.
Andtbacka et. al., "Talimogene Laherparepvec Improves Durable Response Rate in Patients With Advanced Melanoma," J Clin Oncol. Sep. 1, 2015;33(25):2780-8.
Asgari et al., "In vitro fibrillogenesis of tropocollagen type III in collagen type I affects its relative fibrillar topology and mechanics," Scientific Reports (2017) 7 Article ID:1392.
Bastian et al., "Herpes simplex virus type 1 immediate-early protein ICP22 is required for VICE domain formation during productive viral infection." J Viral. Mar. 2010;84(5):2384-94. doi: 10.1128/JVI.01686-09. Epub Dec. 23, 2009.

(Continued)

*Primary Examiner* — Maria G Leavitt
(74) *Attorney, Agent, or Firm* — Morrison & Foerster LLP

(57) ABSTRACT

The present disclosure provides recombinant nucleic acids comprising one or more polynucleotides encoding one or more cosmetic proteins (e.g., one or more human collagen proteins); viruses comprising the recombinant nucleic acids; compositions (e.g., cosmetic formulations) comprising the recombinant nucleic acids and/or viruses; methods of their use; and articles of manufacture or kits thereof.

28 Claims, 35 Drawing Sheets
(26 of 35 Drawing Sheet(s) Filed in Color)
Specification includes a Sequence Listing.

(56) References Cited

OTHER PUBLICATIONS

Baumann et al., "Comparison of smooth-gel hyaluronic acid dermal fillers with cross-linked bovine collagen: a multicenter, double-masked, randomized, within-subject study," Dermatol Surg (2007) 33 Suppl 2:s128-135.
Brown et al., "Subject global evaluation and subject satisfaction using injectable poly-L-lactic acid versus human collagen for the correction of nasolabial fold wrinkles," Plast Reconstr Surg (2011) 127(4):1684-1692.
Burton EA, Fink DJ, Glorioso JC. Gene delivery using herpes simplex virus vectors. DNA Cell Biol. Dec. 2002;21(12):915-36.
Chamorro et al., "Gene Editing for the Efficient Correction of a Recurrent COL7A1 Mutation in Recessive Dystrophic Epidermolysis Bullosa Keratinocytes", Molecular Therapy—Nucleic Acids, vol. 5, 2016, e307.
Cheng et al., "The content and ratio of type I and III collagen in skin differ with age and injury," African Journal of Biotechnology (2011) 10(13):2524-2529.
Christiano AM. Collagen, type VII, alpha 1 (epidermolysis bullosa, dystrophic, dominant and recessive) [*Homo sapiens*]. NCBI Reference Sequence: NP_000085.1. Dep. Mar. 19, 1999.
Cole et al., "Extracellular matrix regulation of fibroblast function: redefining our perspective on skin aging," Journal of Cell Communication and Signaliing (2018) 12:35-43.
Communication pursuant to Article 94(3) EPC for EP 16826873.8, dated Apr. 17, 2019, 7 pages.
De Silva et al., "Herpes Virus Amplicon Vectors", Viruses, vol. 1, 2009, pp. 594-629.
Deluca et al., "Isolation and Characterization of Deletion Mutants of Herpes Simplex Virus Type 1 in the Gene Encoding Immediate-Early Regulatory Protein ICP4", Journal of Virology, vol. 56, No. 2, Nov. 1985, pp. 558-570.
Eming SA, Krieg T, Davidson JM. Gene therapy and wound healing. Clin Dermatol. Jan.-Feb. 2007;25(1):79-92.
European Medicines Agency, "Assement Report on Imlygic," Published Oct. 22, 2015.
FDA Briefing Document, "Cellular, Tissue, and Gene Therpies Advisory Committee and Oncologic Drugs Advisory Committee Meeting," dated Apr. 29, 2015.
Final Office Action received for U.S. Appl. No. 15/393,151, dated Aug. 31, 2017, 13 pages.
Fink et al., "Gene therapy for pain: Results of a Phase I clinical trial," Ann Neurol (2011) 70(2):207-212.
Fink, "Gene transfer to the peripheral nervous system: Treatments for polyneuropathy and for pain," (2011) p. 53-58.
Fisher et al., "Pathophysiology of Premature Skin Aging Induced by Ultraviolet Light," N Engl J Med (1997) 337:1419-1429.
Ganceviciene et al., "Skin anti-aging strategies," Dermato-endocrinology (2012) 4:308-319.
Georgiadis et al., "Lentiviral Engineered Fibroblasts Expressing Codon- Optimized COL7A1 Restore Anchoring Fibrils in RDEB", Journal of Investigative Dermatology, vol. 136, 2016, pp. 284-292.
Glorioso JC. Herpes simplex viral vectors: late bloomers with big potential. Hum Gene Ther. Feb. 2014;25(2):83-91.
Gorouchi et al., "Role of topical peptides in preventing or treating aged skin," International Journal of Cosmetic Science (2009) 31:327-345.
Goto et al., "Fibroblasts Show More Potential as Target Cells than Keratinocytes in COL7A1 Gene Therapy of Dystrophic Epidermolysis Bullosa", Journal of Investigative Dermatology, vol. 126, 2006, pp. 766-772.
Grant, Kyle, "Production and Purification of Highly Replication Defective Hsv- 1 Based Gene Therapy Vectors", Doctoral Dissertation, University of Pittsburgh, 2008, 137 pages.
Gurevich et al., "Successful in vivo COL7A1 gene delivery and correction of recessive dystrophic epidermolysis bullosa (RDEB) skin using an off the shelf HSV-1 vector (KB103)", J Invest Derm. vol. 138, Iss. 5 Supp. May 2018, p. S129. Available online Apr. 19, 2018.
Harrington et al., "Efficacy and safety of talimogene laherparepvec versus granulocyte-macrophage colony-stimulating factor in patients with stage IIB/C and IVMIa melanoma: subanalysis of the Phase III OPTiM trial," Onco Targets and Therapy (2016) 9:7081-7093.
Harrow et al., "HSV1716 injection into the brain adjacent to tumour following surgical resection of high-grade glioma: safety data and long-term survival," Gene Therapy (2004) 11:1648-1658.
Heikkinen et al., "Diremerization of human lysyl hydroxylase 3 (LH3) is mediated by the amino acids 541 547," Matrix Biology (2010) 30(1):27-33.
Hennig et al., HEK293-based production platform for y-retroviral (self-inactivating) vectors: application for safe and efficient transfer of COL7A1 cDNA. Hum Gene Ther Clin Dev. Dec. 2014;25(4):218-28.
Humbert et al., "In the shadow of the wrinkle: experimental models," Journal of Cosmetic Dermatology (2011) 11:79-83.
International Preliminary Report on Patentability received for PCT Patent Application No. PCT/US2016/068974, dated Oct. 18, 2018, 11 pages.
International Search Report and Written Opinion received for PCT Patent Application No. PCT/US2016/068974, dated May 18, 2017, 18 pages.
Invitation to Pay Additional Fee received for PCT Patent Application No. PCT/US2016/068974, dated Mar. 27, 2017, 2 pages.
Kim et al., "Microneedles for Drug and Vaccine Delivery", Advanced Drug Delivery Reviews, vol. 64, 2012, pp. 1547-1568.
Lachmann R. Herpes simplex virus-based vectors. Int J Exp Pathol. Oct. 2004; 85(4):177-90.
Lemperle et al., "A classification of facial wrinkles," Plastic and Reconstructive Surgery (2001) 1735-1750.
Lewin et al. "Gene therapy for autosomal dominant disorders of keratin", J Investig Dermatol Symp Proc. Oct. 2005;10(1):47-61.
Liu et al., "The Use of Type I and Type III Injectable Human Collagen for Dermal Fill: 10 Years of Clinical Experience in China," Semin Plast Surg (2005) 19(3):241-250.
Liu et al., "Type III collagen is crucial for collagen I fibrillogenesis and for normal cardiovascular development," Proc Natl Acad Sci USA (1997) 94:1852-1856.
Lu et al., "Topical Application of Viral Vectors for Epidermal Gene Transfer", The Journal of Investigative Dermatology, vol. 108, No. 5, May 1997, pp. 803-808.
Marconi et al., "HSV as a Vector in Vaccine Development and Gene Therapy. In: Madame Curie Bioscience Database [Internet]. Austin (TX): Landes Bioscience; 2000-2013.
Markert et al., "Conditionally replicating herpes simplex virus mutant, G207 for the treatment of malignant glioma: results of a phase I trial," Gene Ther (2000) 7:867-874.
Mayr et al., "Gene Therapy for the COL7A1 Gene", Chapter 23, Intech, 2013, pp. 561-589.
Nakao et al., "Intratumoral injection of herpes simplex virus HF10 in recurrent breast cancer," Ann Oncol (2004) 15(6):988-989.
Ng et al., "Fibroblast-Derived Dermal Matrix Drives Development of Aggressive Cutaneous Squamous Cell Carcinoma in Patients with Recessive Dystrophic Epidermolysis Bullosa", Cancer Research, vol. 72, No. 14, Jul. 15, 2012, pp. 3522-3534.
Non-Final Office Action received for U.S. Appl. No. 15/393,151, dated Apr. 14, 2017, 13 pages.
Non-Final Office Action received for U.S. Appl. No. 15/851,488, dated May 14, 2018, 10 pages.
Non-Final Office Action received for U.S. Appl. No. 16/177,153, dated May 9, 2019, 13 pages.
Notice of Allowance received for U.S. Appl. No. 15/393,151, dated Dec. 6, 2017, 11 pages.
Notice of Allowance received for U.S. Appl. No. 15/851,488, dated Oct. 29, 2018, 11 pages.
Notice of Allowance received for U.S. Appl. No. 16/177,153, dated Aug. 30, 2019, 10 pages.
Nuutila et al., "Recombinant human collagen III gel for transplantation of autologous skin cells in porcine full-thickness wounds," J Tissue Eng Regen Med (2015) 9:1386-1393.

(56) References Cited

OTHER PUBLICATIONS

Ortiz-Urda et al., "Injection of Genetically Engineered Fibroblasts Corrects Regenerated Human Epidermolysis Bullosa Skin Tissue", The Journal of Clinical Investigation, vol. 111, No. 2, Jan. 2003, pp. 251-255.
Papanastassiou et al., "The potential for efficacy of the modified (ICP 34.5–) herpes simplex virus HSV1716 following intratumoural injection into human malignant glioma: a proof of principle study," Gene Ther (2002) 9:398-406.
Qin et al., "Rapamycin Protects Skin Fibroblasts from Ultraviolet B-Induced Photoaging by Suppressing the Production of Reactive Oxygen Species," Cell Physiol Biochem (2018) 46:1849-1860.
Quan et al., "Role of Age-Associated Alterations of the Dermal Extracellular Matrix Microenvironment in Human Skin Aging," Gerontology (2015) 61(5):427-434.
Rampling et al., "Toxicity evaluation of replication-competent herpes simplex virus (ICP 34.5 null mutant 1716) in patients with recurrent malignant glioma," Gene Ther (2000) 7:859-866.
Rayess et al., "A Cross-sectional Analysis of Adverse Events and Litigation for Injectable Fillers," JAMA Facial Plast Surg (2018) 20(3):207-214.
Ricard-Blum, "The Collagen Family," Cold Spring Harb Perspect Biol (2011) 3:a004978.
Rittie et al., "Natural and Sun-Induced Aging of Human Skin," Cold Spring Harb Perspect Med (2015) 5:a015370.
Salmon-Ehr et al., "Implication of Interleukin-4 in Wound Healing", Laboratory Investigation, vol. 80, No. 8, Aug. 2000, pp. 1337-1343.
Samaniego et al., "Persistence and Expression of the Herpes Simplex Virus Genome in the Absence of Immediate-Early Proteins", Journal of Virology, vol. 72, No. 4, Apr. 1998, pp. 3307-3320.
Sankar et al., "A novel role for keratin 17 in coordinating oncogenic transformation and cellular adhersion in eqing sarcoma," Molecular and Cellular Biology (2013) 33(22):4448-4460.
Siegle et al., "Intradermal Implantation of Bovine Collagen: Humoral Immune Responses Associated with Clinical Reactions," Arch Dermatol (1984) 120:183-187.
Siprashvili et al., "Long-term type VII collagen restoration to human epidermolysis bullosa skin tissue," Hum Gene Ther. Oct. 2010;21(10):1299-310.
Smith et al., "A Randomized, Bilateral, Prospective Comparison of Calcium Hydroxylapatite Microspheres versus Human-Based Collagen for the Correction of Nasolabial Folds," Dermatol Surg (2007) 33:S112-S121.
Stow et al., Isolation and characterization of a herpes simplex virus type 1 mutant containing a deletion within the gene encoding the immediate early polypeptide Vmw110. J Gen Viral. Dec. 1986;67 ( Pt 12):2571-85.
Summary of safety and effectiveness data of CosmoDerm™ 1 Human-Based collagen. Approval date to applicant Mar. 11, 2003.
Thangapazham et al., "Alteration of Skin Properties with Autologous Dermal Fibroblasts," Int J Mol Sci (2014) 15:8407-8427.
Uitto et al., "Progress toward Treatment and Cure of Epidermolysis Bullosa: Summary of the DEBRA International Research Symposium EB2015", Journal of Investigative Dermatology, vol. 136, 2016, pp. 352-358.
U.S. Unpublished U.S. Appl. No. 16/381,557, filed Apr. 11, 2019, titled "Compositions and Methods for the Treatment of Autosomal Recessive Congenital Ichthyosis" (Copy not submitted herewith pursuant to the waiver of 37 C.F.R. § 1.98(a)(2)(iii)).
U.S. Unpublished U.S. Appl. No. 16/581,150, filed Sep. 24, 2019, titled "Compositions and Methods for the Treatment of Netherton Syndrome" (Copy not submitted herewith pursuant to the waiver of 37 C.F.R. § 1.98(a)(2)(iii)).
U.S. Unpublished U.S. Appl. No. 16/598,982, filed Oct. 10, 2019, titled "Compositions and Methods for the Treatment of Wounds, Disorders, and Diseases of the Skin" (Copy not submitted herewith pursuant to the waiver of 37 C.F.R. § 1.98(a)(2)(iii)).
Volk et al., "Diminished Type III Collagen Promotes Myofibroblast Differentiation and Increases Scar Deposition in Cutaneous Wound Healing," Cells Tissues Organs (2011) 194:25-37.
Wang et al., "Comparative Effectiveness of Antinociceptive Gene Therapies in Animal Models of Diabetic Neuropathic Pain", Gene Therapy, vol. 20, 2013, pp. 742-750.
Wang et al., "Wound healing," J Chin Med Assoc (2018) 81:94-101.
Watanabe et al., "Properties of a Herpes Simplex Virus Multiple Immediate- early Gene-Deleted Recombinant as a Vaccine Vector", Virology, vol. 357, 2007, pp. 186-198.
Watson et al., "Autologous Fibroblasts for Treatment of Facial Rhytids and Dermal Depressions," Arch Facial Plast Surg (1999) 1:165-170.
Watt et al., "Lysyl Hydroxylase 3 Localizes to Epidermal Basement Membrane and is Reduced in Patients with Recessive Dystrophic Epidermolysis Bullosa", Plos One, 10(9):e0137639.
Weiss et al., "The Role of Interleukin 10 in the Pathogenesis and Potential Treatment of Skin Diseases", Journal of the American Academy of Dermatology, vol. 50, No. 5, May 2004, pp. 657-675.
White et al., "Evaluation and optimization of the administration of a selectively replicating herpes simplex viral vector to the brain by convection-enhanced delivery", Cancer Gene Ther. May 2011;18(5):358-69. doi: 10.1038/ cgt.2011.2. Epub Mar. 4, 2011.
Wolfe et al., "Engineering Herpes Simplex Viral Vectors for Therapeutic Gene Transfer", Chapter 6, Gene and Cell Therapy, 2004, pp. 103-129.
Woodley et al., "Normal and Gene-Corrected Dystrophic Epidermolysis Bullosa Fibroblasts Alone Can Produce Type VII Collagen at the Basement Membrane Zone", The Journal of Investigative Dermatology, vol. 121, No. 5, Nov. 2003, pp. 1021-1028.
Woodley, et al., "Intradermal Injection of Lentiviral Vectors Corrects Regenerated Human Dystrophic Epidermolysis Bullosa Skin Tissue in Vivo", Molecular Therapy, vol. 10, No. 2, Aug. 2004, pp. 318-326.
Yano et al., "Regulatory approval for autologous human cells and tissue products in the United States, the European Union, and Japan," Regenerative Therapy (2015) 1:45-56.
Yoon et al., "Anti-wrinkle effect of bone morphogenetic protein receptor 1 a-extracellular domain (BMPR1a-ECD)," BMB Rep (2013) 46(9):465-470.
Yutskovskaya et al., "A Randomized, Split-Face, Histomorphological Study Comparing a Volumetric Calcium Hydroxylapatite and a Hyaluornic Acid-Based Dermal Filler," J Drugs Dermatol (2014) 13(9):47-52.
Zeng et al., "Preclinical Safety Studies on Autologous Cultured Human Skin Fibroblast Transplantation," Cell Transplant (2014) 23:39-49.
Zhao et al., "Preliminary Survival Studies on Autologous Cultured Skin Fibroblasts Transplantation by Injection," Cell Transplant (2008) 17:775-783.
Shen et al., "Herpes simplex virus 1 (HSV-1) for cancer treatment," Cancer Gene Therapy (2006) 13: 975-992.
Armstrong, "Krystal gets more skin in the epidermolysis bullosa game," Vantage, Mar. 5, 2019, 6 pages.
Armstrong and Gardner, "Krystal gets a flying start in epidermolysis bullosa gene therapy," Vantage, Oct. 17, 2018, 6 pages.
ClinicalTrials.gov, NCT03536143: "Topical Bercolagene Telserpavec (KB103) Gene Therapy to Restore Functional Collagen VII for the Treatment of Dystrophic Epidermolysis Bullosa (GEM-1)," May 24, 2018, 5 pages.
ClinicalTrials.gov, NCT04047732: "Topical KB105 Gene Therapy for the Treatment of TGM1-deficient Autosomal Recessive Congenital Ichthyosis (ARCI)," Aug. 7, 2019, 5 pages.
ClinicalTrials.gov, NCT04214002: "The Natural History of Wounds in Patients With Dystrophic Epidermolysis Bullosa (DEB)," Dec. 30, 2019, 5 pages.
Kopecki and Cowin, "Commentary: New advances in the development of therapies for treating inherited skin fragility disorders," Wound Practice and Research (2015) 23(4):184-190.
Non-Final Office Action for U.S. Appl. No. 16/598,982, dated Feb. 20, 2020, 10 pages.
Salam, "Krystal's KB103 splits experts' thoughts on potential for HSV-1 risk in dystrophic epidermolysis bullosa patients, but final Phase I/II efficacy assured," Biopharm. Insight. Nov. 7, 2018, 3 pages.

(56) References Cited

OTHER PUBLICATIONS

Goins et al. "Engineering HSV-1 Vectors for Gene Therapy," Methods Mol Biol (2014) 1144: 63-79.
Theopold et al., "A novel replication-defective HSV-1 vector for regulatable gene delivery to wounds," Journal of the American College of Surgeons (2004) 199(3):57-58.

* cited by examiner

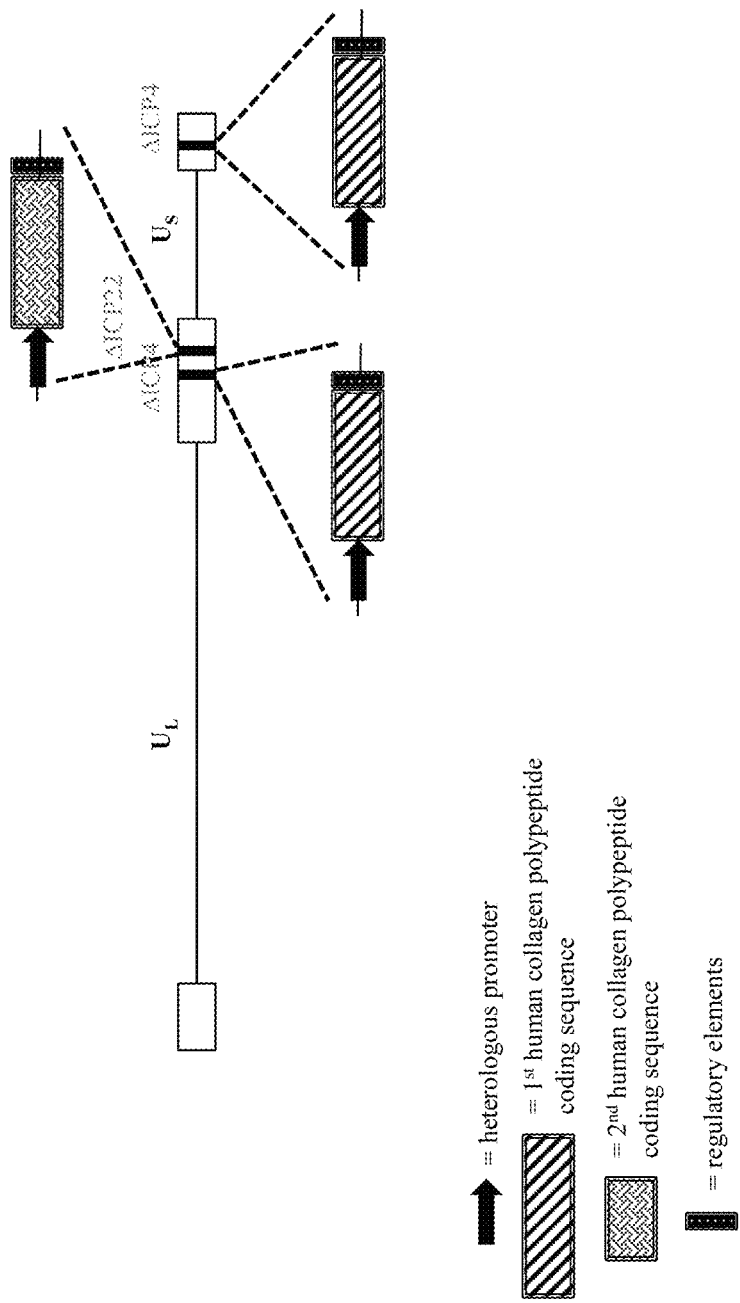

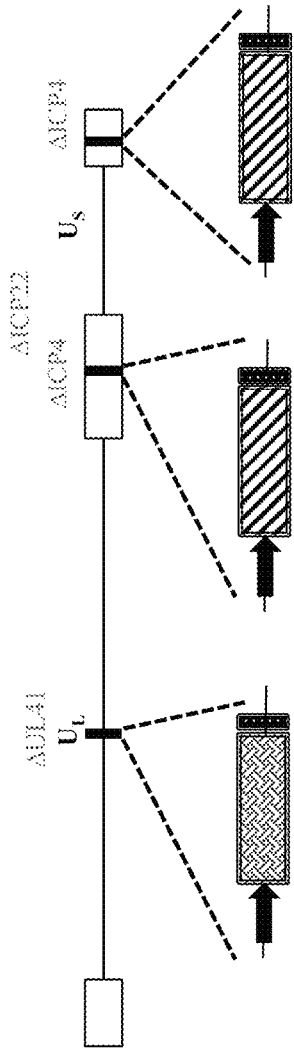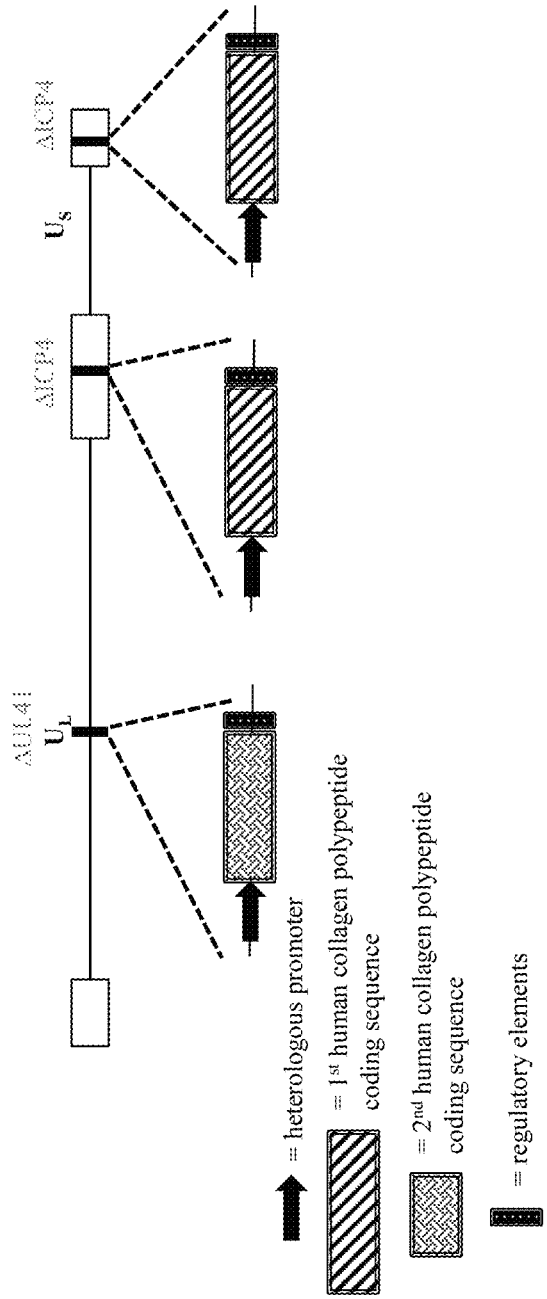

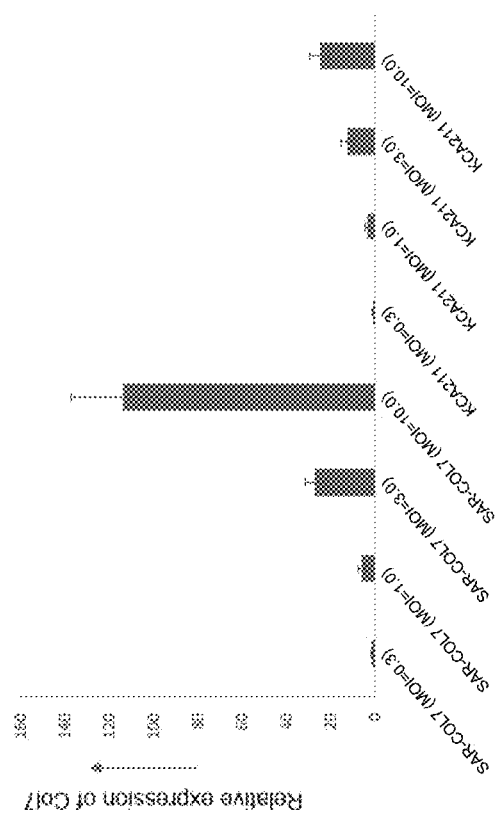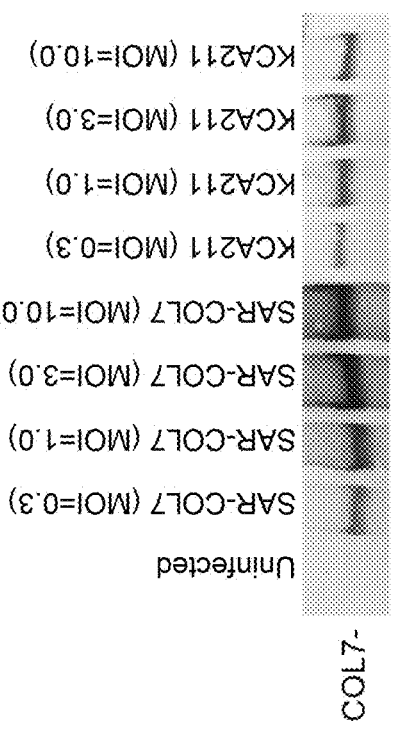

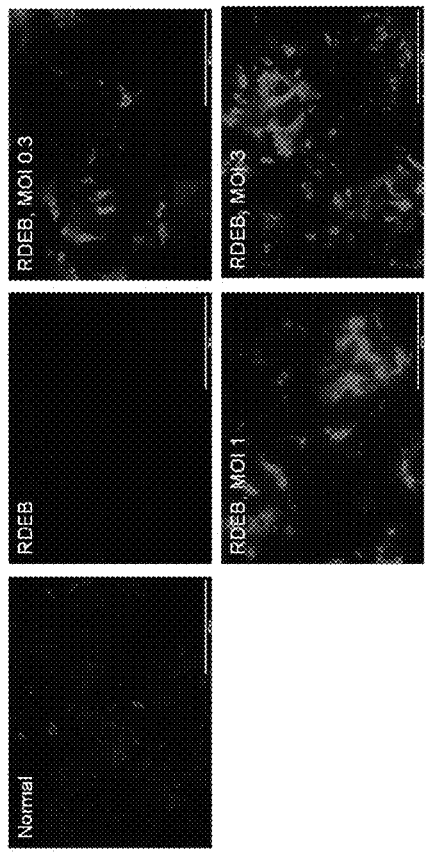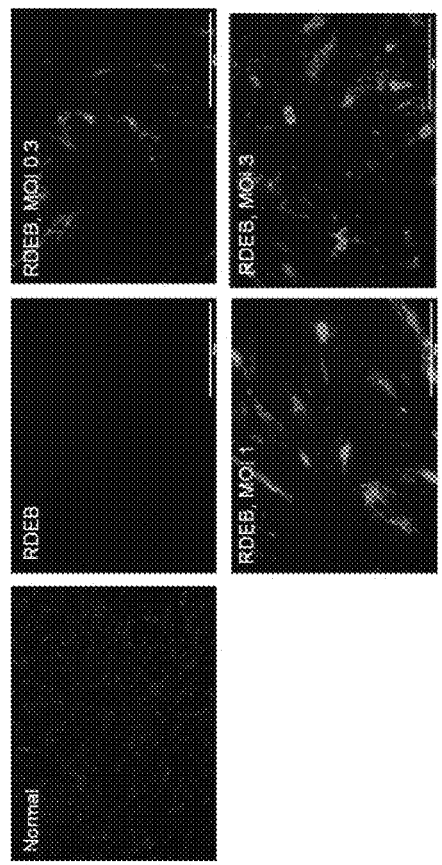

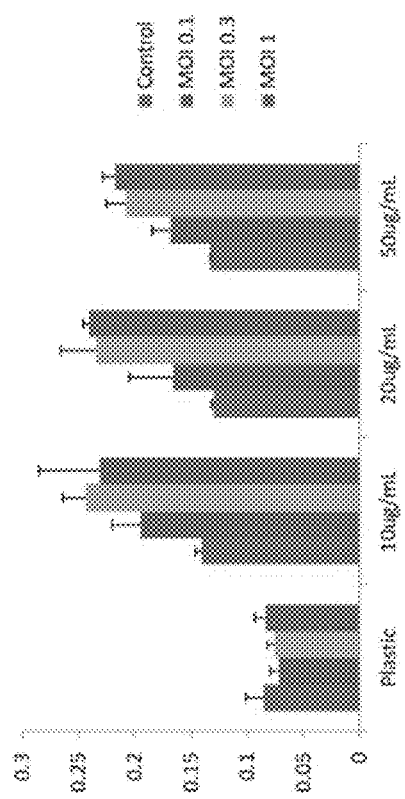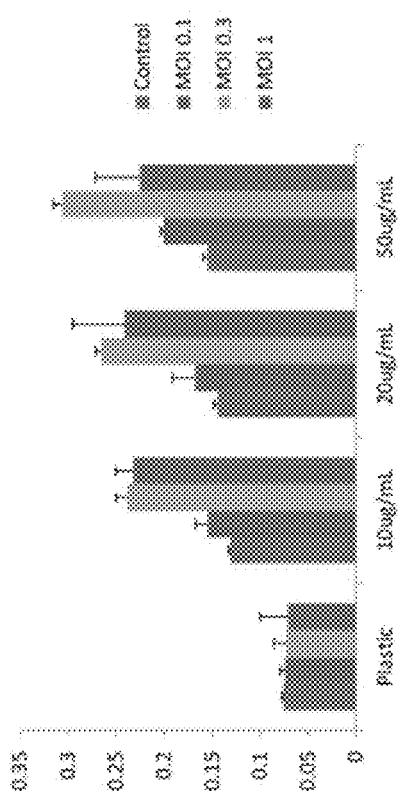

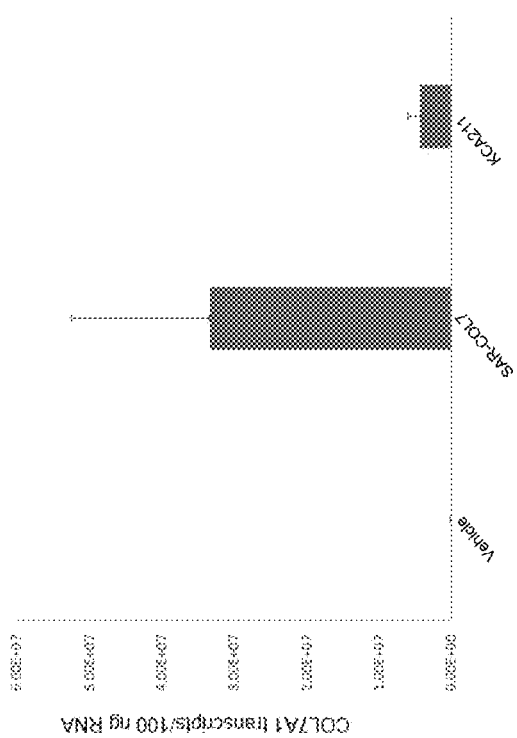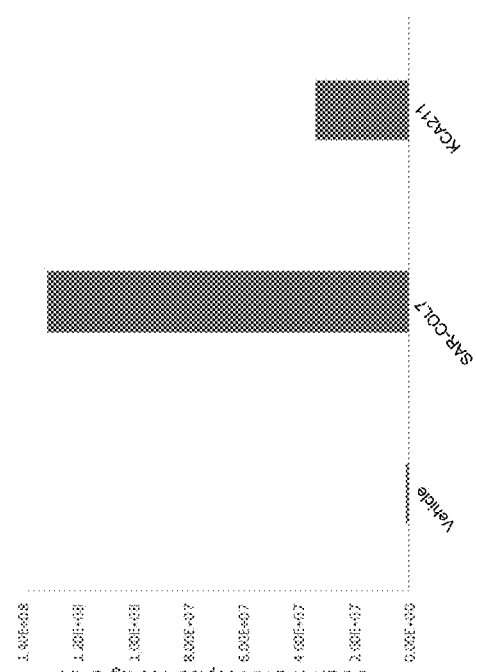

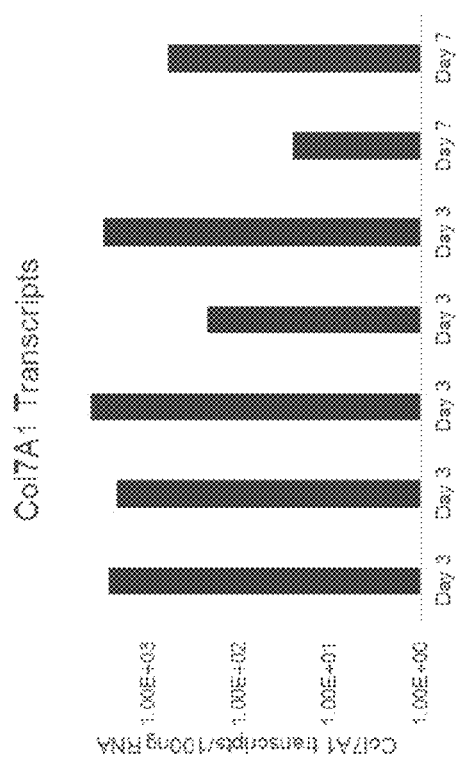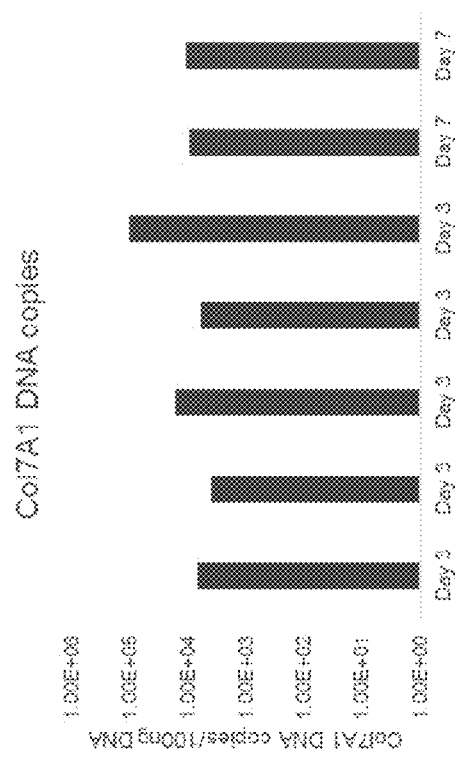

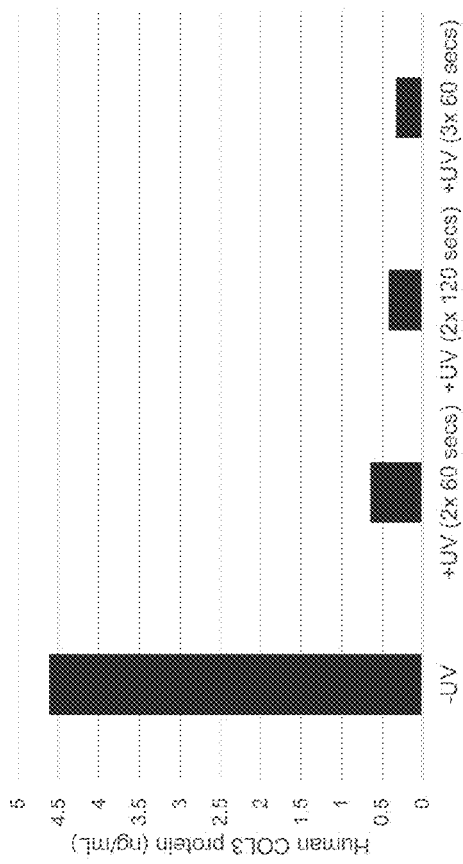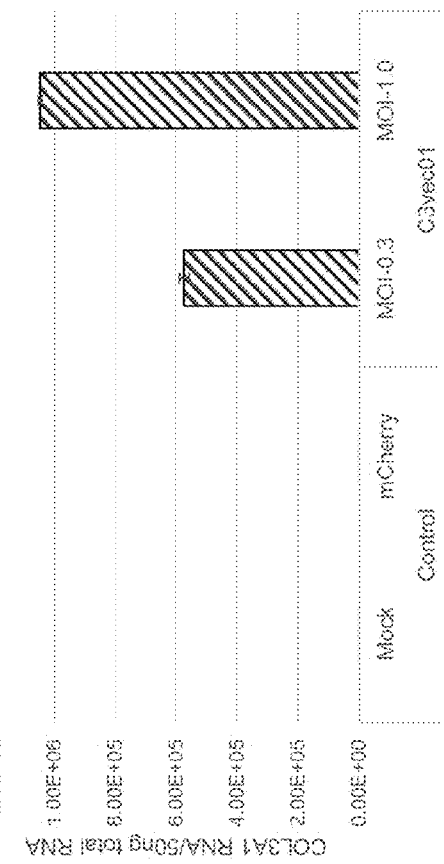

Human *COL3A1* DNA

Human *COL3A1* Transcripts

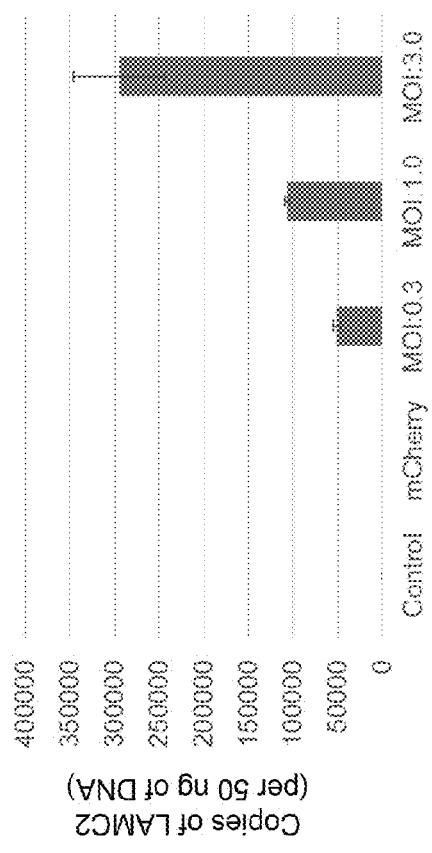
FIG. 28A LAMC2 DNA
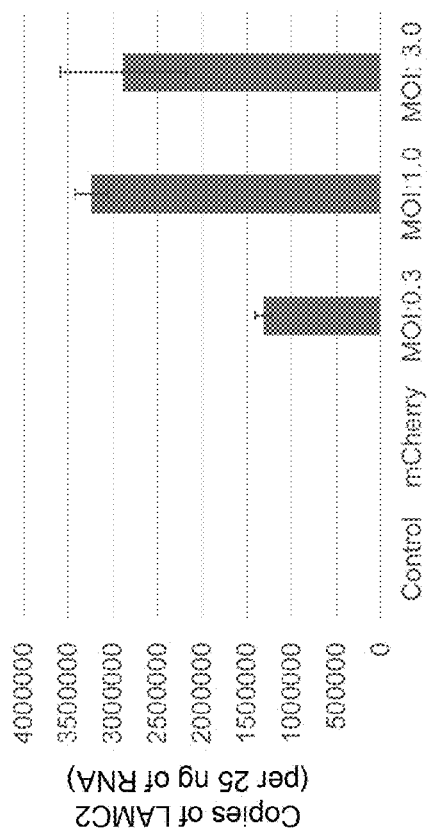
FIG. 28B LAMC2 transcript

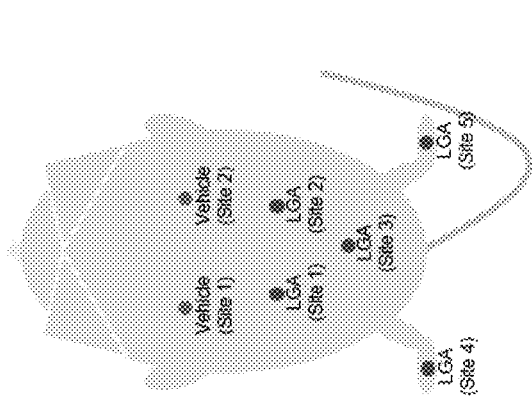
FIG. 29A
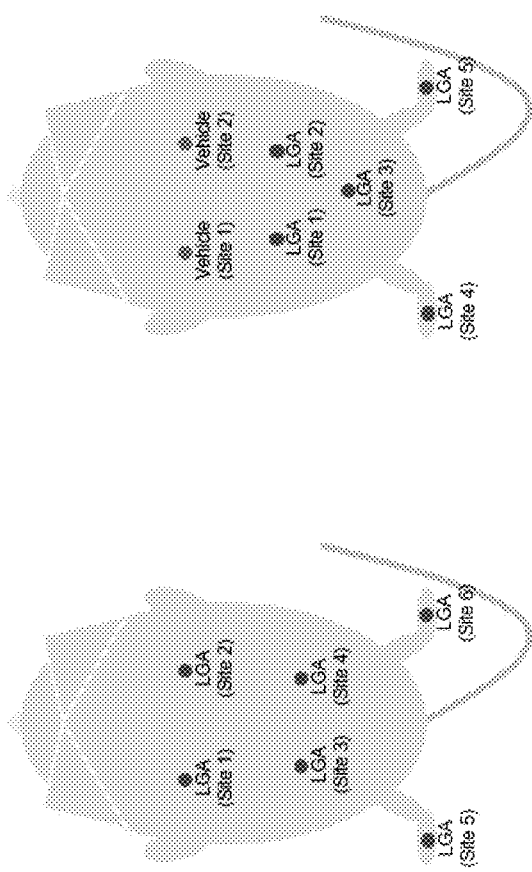
FIG. 29B
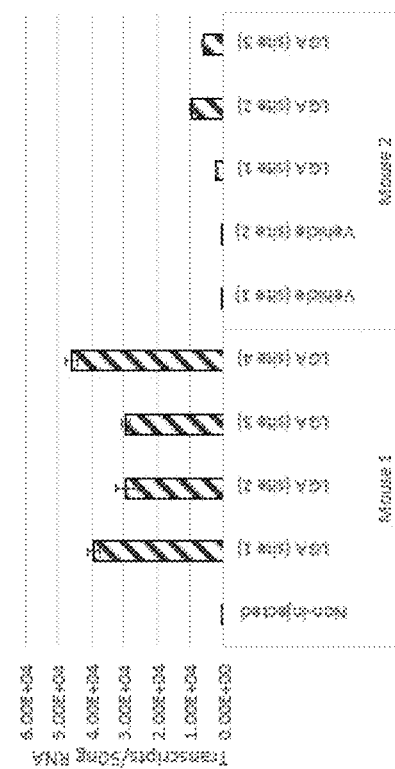
FIG. 29C
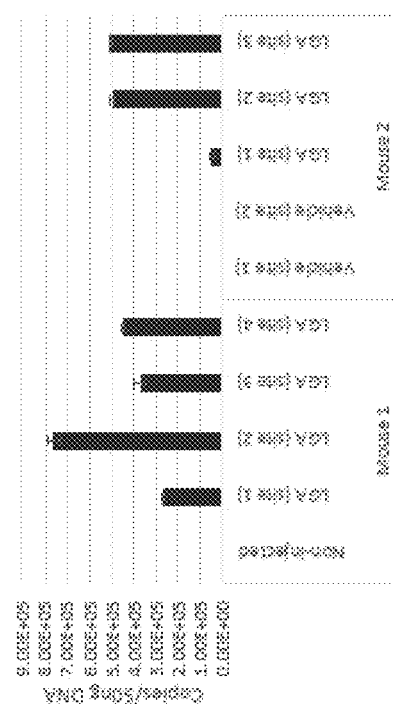

RECOMBINANT NUCLEIC ACIDS ENCODING COSMETIC PROTEIN(S) FOR AESTHETIC APPLICATIONS

CROSS REFERENCE TO RELATED APPLICATIONS

This application claims the priority benefit of U.S. Provisional Application Ser. No. 62/663,476, filed Apr. 27, 2018, which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761342000600SEQLIST.txt, date recorded: Apr. 26, 2019, size: 437 KB).

FIELD OF THE INVENTION

The present disclosure relates, in part, to recombinant nucleic acids comprising one or more polynucleotides encoding one or more cosmetic proteins (e.g., one or more human collagen proteins); to viruses comprising the recombinant nucleic acids; to compositions (e.g., cosmetic formulations) comprising the recombinant nucleic acids and/or viruses; to methods of their use; and to articles of manufacture or kits thereof.

BACKGROUND

Skin, like all organs in the human body, undergoes sequential and often cumulative alterations with the passage of time. Aging of the skin occurs as the result of numerous factors, including inherent changes within the skin, the effects of gravity and facial muscles acting on the skin, soft tissue loss or shift, and loss of tissue elasticity. Interestingly, the "aged" phenotype of skin may be accelerated by environmental factors, most notably, chronic exposure to ultraviolet irradiation (e.g., from the sun). Clinically, the aged phenotype of skin may be described as wrinkled, sagging, and/or generally less elastic and resilient than its youthful counterpart, although variations within this phenotype exist between natural, chronological aging and photoaging.

The dermal extracellular matrix (ECM) comprises the bulk of skin and confers both strength and resiliency. Collagen, a major component of the connective tissue providing support to the skin, decreases as a person ages. In aged skin, collagen fibrils display high levels of degradation and fragmentation, and are replenished by dermal fibroblasts at diminishing rates. These degraded and fragmented collagen bundles become looser and lose strength (disrupting the structural organization of the dermal ECM), and inextricably leads to an "aged" manifestation of the skin.

Numerous skincare products have been developed for improving the appearance of human skin. Wrinkles and skin folds are commonly treated with dermal and subdermal injections of aesthetic facial fillers; however, such a superficial approach does not address the structural changes underlying skin aging, in particular, the damage or loss of collagen. Thus, there exists a clear need for alternative strategies to supplement, strengthen, or replace dermal ECM components (e.g., human collagen), in individuals desiring to combat or reverse the physiological effects of skin aging.

All references cited herein, including patent applications, patent publications, non-patent literature, and NCBI/UniProtKB/Swiss-Prot Accession numbers are herein incorporated by reference in their entirety, as if each individual reference were specifically and individually indicated to be incorporated by reference.

BRIEF SUMMARY

In order to meet these and other needs, provided herein are recombinant nucleic acids (e.g., recombinant herpes viral genomes) encoding one or more cosmetic proteins for use in viruses (e.g., herpes viruses), compositions, formulations, medicaments, and/or methods for aesthetic/cosmetic applications (e.g., treating wrinkles). The present inventors have shown that the recombinant, attenuated viruses described herein were capable of 1) effectively transducing human epidermal/dermal cells, and 2) successfully expressing the encoded exogenous human collagen (mRNA and protein), where the protein could then localize to the appropriate region in skin-equivalent organotypic cultures (see e.g., Example 2). Moreover, the present inventors have shown that the viruses described herein may be successfully administered either topically or intradermally without significant host cell cytotoxicity, allowing for the human collagen expressed from these viruses to localize to the appropriate region of the dermal ECM after in vivo administration without observable damage to the skin (see e.g., Examples 3 and 7). In addition, the present inventors have shown that multiple different HSV backbones can be used to construct viruses expressing human collagens (see e.g., Example 2), that multiple strategies can be employed to successfully express more than one human collagen protein from a single recombinant genome (see e.g., Example 5), and that candidate viruses can successfully express human collagen proteins in multiple relevant in vitro and in vivo models of chronological or UV-induced skin aging (see e.g., Examples 6 and 7). Furthermore, the present inventors have shown that the viruses described herein can be successfully engineered to express other cosmetic proteins (e.g., human laminins) both in vitro and in vivo, where these proteins localize to the appropriate region of the dermal ECM (see e.g., Example 8). Without wishing to be bound by theory, the data described herein provides strong evidence that the recombinant nucleic acids and/or viruses of the present disclosure may constitute a novel means for delivering cosmetic proteins (e.g., human collagen proteins, such as human Collagen 1 and human Collagen 3), and in particular, to supplement or replace natural human dermal ECM proteins in aesthetic applications (e.g., to reduce the appearance of age or photo-induced wrinkles).

Accordingly, certain aspects of the present disclosure relate to a recombinant herpes virus genome comprising a first polynucleotide encoding a first polypeptide comprising a first cosmetic protein. In some embodiments, the recombinant herpes virus genome comprises two or more copies of the first polynucleotide. In some embodiments, the recombinant herpes virus genome is replication competent. In some embodiments, the recombinant herpes virus genome is replication defective. In some embodiments that may be combined with any of the preceding embodiments, the recombinant herpes virus genome is selected from a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any derivatives thereof. In some embodiments that may be combined with any of the preceding embodiments, the recombinant herpes virus genome is a recombinant herpes simplex virus genome. In some embodiments, the recombinant herpes simplex virus genome is a recombinant type 1 herpes simplex virus (HSV-1) genome, a recombinant type 2 herpes simplex virus (HSV-2) genome, or any derivatives thereof.

In some embodiments, the recombinant herpes simplex virus genome is a recombinant type 1 herpes simplex virus (HSV-1) genome. In some embodiments that may be combined with any of the preceding embodiments, the recombinant herpes simplex virus genome comprises an inactivating mutation. In some embodiments that may be combined with any of the preceding embodiments, the inactivating mutation is in a herpes simplex virus gene. In some embodiments, the inactivating mutation is a deletion of the coding sequence of the herpes simplex virus gene. In some embodiments, the herpes simplex virus gene is selected from Infected Cell Protein (ICP) 0, ICP4, ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivating mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivating mutation in the UL41 gene. In some embodiments that may be combined with any of the preceding embodiments, the recombinant herpes simplex virus genome comprises an inactivating mutation in one or both copies of the ICP0 gene. In some embodiments that may be combined with any of the preceding embodiments, the recombinant herpes simplex virus genome comprises an inactivating mutation in the ICP27 gene. In some embodiments that may be combined with any of the preceding embodiments, the recombinant herpes simplex virus genome comprises an inactivating mutation in the UL55 gene. In some embodiments that may be combined with any of the preceding embodiments, the recombinant herpes simplex virus genome comprises an inactivating mutation in the Joint region. In some embodiments, the recombinant herpes simplex virus genome comprises a deletion of the Joint region. In some embodiments that may be combined with any of the preceding embodiments, the recombinant herpes simplex virus genome comprises the first polynucleotide within one or both of the ICP4 viral gene loci.

In some embodiments that may be combined with any of the preceding embodiments, the first cosmetic protein is selected from a first collagen protein, a first fibronectin protein, a first elastin protein, a first lumican protein, a first vitronectin protein, a first vitronectin receptor protein, a first laminin protein, a first neuromodulator protein, and a first fibrillin protein. In some embodiments that may be combined with any of the preceding embodiments, the first cosmetic protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21 and 53-64. In some embodiments, the first cosmetic protein is a structural extracellular matrix protein (e.g., a collagen protein, an elastin protein, a fibronectin protein, a laminin protein, a fibrillin protein, etc.). In some embodiments, the first cosmetic protein is a collagen protein, an elastin protein, a fibronectin protein, or a laminin protein (e.g., a human collagen protein, a human elastin protein, a human fibronectin protein, or a human laminin protein). In some embodiments that may be combined with any of the preceding embodiments, the first collagen protein is a human collagen protein. In some embodiments that may be combined with any of the preceding embodiments, the first collagen protein is selected from a Collagen alpha-1(I) chain polypeptide (COL1-1), Collagen alpha-2(I) chain polypeptide (COL1-2), a Collagen alpha-1(II) chain polypeptide (COL2), a Collagen alpha-1(III) chain polypeptide (COL3), a Collagen alpha-1(IV) chain polypeptide (COL4-1), a Collagen alpha-2(IV) chain polypeptide (COL4-2), a Collagen alpha-3(IV) chain polypeptide (COL4-3), a Collagen alpha-4(IV) chain polypeptide (COL4-4), a Collagen alpha-5(IV) chain polypeptide (COL4-5), a Collagen alpha-6(IV) chain polypeptide (COL4-6), a Collagen alpha-1(V) chain polypeptide (COL5-1), a Collagen alpha-2(V) chain polypeptide (COL5-2), a Collagen alpha-3(V) chain polypeptide (COL5-3), a Collagen alpha-1(VI) chain polypeptide (COL6-1), a Collagen alpha-2(VI) chain polypeptide (COL6-2), a Collagen alpha-3(VI) chain polypeptide (COL6-3), a Collagen alpha-4(VI) chain polypeptide (COL6-4), a Collagen alpha-5(VI) chain polypeptide (COL6-5), a Collagen alpha-6(VI) chain polypeptide (COL6-6), a Collagen alpha-1(VIII) chain polypeptide (COL8), a Collagen alpha-1(IX) chain polypeptide (COL9-1), a Collagen alpha-2(IX) chain polypeptide (COL9-2), a Collagen alpha-3(IX) chain polypeptide (COL9-3), a Collagen alpha-1(X) chain polypeptide (COL10), a Collagen alpha-1(XI) chain polypeptide (COL11-1), a Collagen alpha-2(XI) chain polypeptide (COL11-2), a Collagen alpha-1(XII) chain polypeptide (COL12), a Collagen alpha-1(XIII) chain polypeptide (COL13), a Collagen alpha-1(XIV) chain polypeptide (COL14), a Collagen alpha-1(XV) chain polypeptide (COL15), a Collagen alpha-1(XVI) chain polypeptide (COL16), a Collagen alpha-1(XVII) chain polypeptide (COL17), a Collagen alpha-1(XVIII) chain polypeptide (COL18), a Collagen alpha-1(XIX) chain polypeptide (COL19), a Collagen alpha-1(XX) chain polypeptide (COL20), a Collagen alpha-1(XXI) chain polypeptide (COL21), a Collagen alpha-1(XXII) chain polypeptide (COL22), a Collagen alpha-1(XXIII) chain polypeptide (COL23), a Collagen alpha-1(XXIV) chain polypeptide (COL24), a Collagen alpha-1(XXV) chain polypeptide (COL25), a Collagen alpha-1(XXVI) chain polypeptide (COL26), a Collagen alpha-1(XXVII) chain polypeptide (COL27), and a Collagen alpha-1(XXVIII) chain polypeptide (COL28). In some embodiments that may be combined with any of the preceding embodiments, the first collagen protein is selected from COL1-1, COL1-2, COL3, COL4-1, COL4-2, COL6-1, and COL17. In some embodiments that may be combined with any of the preceding embodiments, the first collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments that may be combined with any of the preceding embodiments, the first collagen protein is COL3. In some embodiments that may be combined with any of the preceding embodiments, the first collagen protein is human COL3. In some embodiments that may be combined with any of the preceding embodiments, the first collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 17. In some embodiments that may be combined with any of the preceding embodiments, the first cosmetic protein is not a Collagen alpha-1(VII) chain polypeptide (COL7).

In some embodiments, the first polypeptide consists essentially of the first cosmetic protein. In some embodiments, the first polypeptide consists of the first cosmetic protein. In some embodiments, the first polypeptide comprises: (a) the first cosmetic protein; (b) a further cosmetic protein; and (c) a linker polypeptide linking (a) to (b). In some embodiments, the further cosmetic protein is selected from a collagen protein, a fibronectin protein, a elastin protein, a lumican protein, a vitronectin protein, a vitronectin receptor protein, a laminin protein, a neuromodulator protein, and a fibrillin protein. In some embodiments, the further cosmetic protein is a structural extracellular matrix protein (e.g., a collagen protein, an elastin protein, a fibronectin protein, a laminin protein, a fibrillin protein, etc.). In some embodiments, the further cosmetic protein is a collagen protein, an elastin protein, a fibronectin protein, or a laminin protein (e.g., a human collagen protein, a human elastin protein, a human fibronectin protein, or a human laminin protein). In some embodiments, the further collagen protein (e.g., a further human collagen protein) is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the further collagen protein (e.g., a further human collagen protein) is selected from COL1-1, COL1-2, COL3, COL4-1, COL4-2, COL5-1, COL7, and COL17. In some embodiments, the first cosmetic protein and the further cosmetic protein are different. In some embodiments, the first cosmetic protein is COL1-1 (e.g., human COL1-1) and the further cosmetic protein is COL1-2 (e.g., human COL1-2). In some embodiments, the linker polypeptide is a cleavable linker polypeptide. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected SEQ ID NOS: 28-31.

In some embodiments that may be combined with any of the preceding embodiments, the first polynucleotide encodes a polycistronic mRNA comprising: (a) a first open reading frame (ORF) encoding the first polypeptide; (b) a second ORF encoding an additional cosmetic protein; and (c) an internal ribosomal entry site (IRES) separating (a) and (b). In some embodiments, the additional cosmetic protein is selected from a collagen protein, a fibronectin protein, a elastin protein, a lumican protein, a vitronectin protein, a vitronectin receptor protein, a laminin protein, a neuromodulator protein, and a fibrillin protein. In some embodiments, the additional cosmetic protein is a structural extracellular matrix protein (e.g., a collagen protein, an elastin protein, a fibronectin protein, a laminin protein, a fibrillin protein, etc.). In some embodiments, the additional cosmetic protein is a collagen protein, an elastin protein, a fibronectin protein, or a laminin protein (e.g., a human collagen protein, a human elastin protein, a human fibronectin protein, or a human laminin protein). In some embodiments, the additional collagen protein (e.g., an additional human collagen protein) is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the additional collagen protein (e.g., an additional human collagen protein) is selected from COL1-1, COL1-2, COL3, COL4-1, COL4-2, COL5-1, COL7, and COL17. In some embodiments, the first cosmetic protein and the additional cosmetic protein are different. In some embodiments, the first cosmetic protein is COL1-1 (e.g., human COL1-1) and the additional cosmetic protein is COL1-2 (e.g., human COL1-2). In some embodiments, the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23.

In some embodiments that may be combined with any of the preceding embodiments, the recombinant herpes virus genome further comprises a second polynucleotide encoding a second cosmetic protein. In some embodiments, the second cosmetic protein is selected from a collagen protein, a fibronectin protein, a elastin protein, a lumican protein, a vitronectin protein, a vitronectin receptor protein, a laminin protein, a neuromodulator protein, and a fibrillin protein. In some embodiments, the second cosmetic protein is a structural extracellular matrix protein (e.g., a collagen protein, an elastin protein, a fibronectin protein, a laminin protein, a fibrillin protein, etc.). In some embodiments, the second cosmetic protein is a collagen protein, an elastin protein, a fibronectin protein, or a laminin protein (e.g., a human collagen protein, a human elastin protein, a human fibronectin protein, or a human laminin protein). In some embodiments, the second collagen protein (e.g., a second human collagen protein) is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the second collagen protein (e.g., a second human collagen protein) is selected from COL1-1, COL1-2, COL3, COL4-1, COL4-2, COL5-1, COL7, and COL17. In some embodiments, the first and second cosmetic proteins are different. In some embodiments, the first cosmetic protein is COL1-1 (e.g., human COL1-1) and the second cosmetic protein is COL1-2 (e.g., human COL1-2). In some embodiments, the first cosmetic protein is COL1-1 (e.g., human COL1-1) and the second cosmetic protein is COL3 (e.g., human COL3).

In some embodiments that may be combined with any of the preceding embodiments, the recombinant herpes virus genome has reduced cytotoxicity when introduced into a target cell, as compared to a corresponding wild-type herpes virus genome. In some embodiments, the target cell is a cell of the epidermis and/or dermis. In some embodiments, the target cell is a human cell. In some embodiments, the target cell is a fibroblast.

Other aspects of the present disclosure relate to a herpes virus comprising any of the recombinant herpes virus genomes described herein. In some embodiments, the herpes virus is replication competent. In some embodiments, the herpes virus is replication defective. In some embodiments, the herpes virus is attenuated. In some embodiments that may be combined with any of the preceding embodiments, the herpes virus has reduced cytotoxicity as compared to a corresponding wild-type herpes virus. In some embodiments that may be combined with any of the preceding embodiments, the herpes virus is selected from a herpes simplex virus, a varicella zoster virus, a human cytomegalovirus, a herpesvirus 6A, a herpesvirus 6B, a herpesvirus 7, and a Kaposi's sarcoma-associated herpesvirus. In some embodiments that may be combined with any of the preceding embodiments, the herpes virus is a herpes simplex virus. In some embodiments, the herpes simplex virus is a type 1 herpes simplex virus (HSV-1), a type 2 herpes simplex virus (HSV-2), or any derivatives thereof. In some embodiments, the herpes simplex virus is a type 1 herpes simplex virus (HSV-1).

Other aspects of the present disclosure relate to a composition comprising: (a) any of the recombinant herpes virus genomes described herein and/or any of the herpes viruses described herein; and (b) an excipient. In some embodiments, the composition is sterile. In some embodiments that may be combined with any of the preceding embodiments, the composition is suitable for topical, transdermal, subcutaneous, intradermal, oral, intranasal, intratracheal, sublingual, buccal, rectal, vaginal, inhaled, intravenous, intraarterial, intramuscular, intracardiac, intraosseous, intraperitoneal, transmucosal, intravitreal, subretinal, intraarticular, peri-articular, local, or epicutaneous administration. In some embodiments that may be combined with any of the preceding embodiments, the composition is suitable for intradermal administration. In some embodiments that may be combined with any of the preceding embodiments, the composition is suitable for superficial injection. In some embodiments that may be combined with any of the preceding embodiments, the composition is a cosmetic composition. In some embodiments that may be combined with any of the preceding embodiments, the composition is a skin care product.

Other aspects of the present disclosure relate to the use of any of the recombinant herpes virus genomes described herein and/or any of the herpes viruses described herein as a medicament (e.g., for an aesthetic indication).

Other aspects of the present disclosure relate to the use of any of the recombinant herpes virus genomes described herein and/or any of the herpes viruses described herein as a therapy (e.g., as an aesthetic or cosmetic therapy).

Other aspects of the present disclosure relate to the use of any of the recombinant herpes virus genomes described herein and/or any of the herpes viruses described herein in the manufacture of a medicament useful for treating one or more signs or symptoms of dermatological aging.

Other aspects of the present disclosure relate to a method of enhancing, increasing, augmenting, and/or supplementing the levels of one or more dermal extracellular matrix proteins in a subject, the method comprising administering to the subject an effective amount of any of the herpes viruses described herein and/or any of the compositions described herein.

Other aspects of the present disclosure relate to a method of enhancing, increasing, augmenting, and/or supplementing the levels of one or more collagen proteins in a subject, the method comprising administering to the subject an effective amount of any of the herpes viruses described herein and/or any of the compositions described herein. In some embodiments, the one or more collagen proteins are collagen 3. In some embodiments, the levels of endogenous collagen 3 are reduced as a result of chronological or photo-aging.

Other aspects of the present disclosure relate to a method of enhancing, increasing, augmenting, and/or supplementing the soft tissue of a subject, the method comprising administering to the subject an effective amount of any of the herpes viruses described herein and/or any of the compositions described herein. In some embodiments, the composition is injected into the soft tissue of the subject.

Other aspects of the present disclosure relate to a method of improving skin condition, quality, and/or appearance in a subject in need thereof, the method comprising administering to the subject an effective amount of any of the herpes viruses described herein and/or any of the compositions described herein. In some embodiments, the composition is administered to one or more sites of sun damage or other UV exposure, rough texture, skin sagging, wrinkles, or any combinations thereof.

Other aspects of the present disclosure relate to a method of reducing the appearance of one or more superficial depressions in the skin of a subject in need thereof, the method comprising administering to the subject an effective amount of any of the herpes viruses described herein and/or any of the compositions described herein. In some embodiments, the one or more superficial depressions in the skin are selected from the group consisting of nasolabial folds, crows' feet, frown lines, worry lines, scars, glabellar lines, brow ptosis, tear troughs, nasojugal lines, bunny lines, cheek/mid-face ptosis, marionette lines, poppy dimpling, smile lines, laugh lines, chin creases, neck lines, platysma bands, and any combinations thereof.

Other aspects of the present disclosure relate to a method of increasing and/or improving at least one of texture, smoothness, elasticity, or tension of the skin of a subject in need thereof, the method comprising administering to the subject an effective amount of any of the herpes viruses described herein and/or any of the compositions described herein.

In some embodiments that may be combined with any of the preceding embodiments, the skin of the subject is aging skin. In some embodiments that may be combined with any of the preceding embodiments, the skin of the subject has been damaged due to exposure to ultraviolet light. In some embodiments that may be combined with any of the preceding embodiments, the skin of the subject is wrinkled.

Other aspects of the present disclosure relate to a method of diminishing one or more dermatological signs of aging in a subject in need thereof, the method comprising administering to the subject an effective amount of any of the herpes viruses described herein and/or any of the compositions described herein. In some embodiments, the diminishing of one or more dermatological signs of aging is indicated by the: (a) treatment, reduction, and/or prevention of fine lines and/or wrinkles; (b) reduction of skin pore size; (c) improvement in skin thickness, plumpness, and/or tautness; (d) improvement in skin smoothness, suppleness, and/or softness; (e) improvement in skin tone, radiance, and/or clarity; (f) improvement in procollagen and/or collagen production; (g) improvement in skin texture and or promotion of retexturization; (h) improvement in appearance of skin contours; (i) restoration of skin luster and/or brightness; (j) improvement of skin appearance decreased by aging and/or menopause; (k) improvement in skin moisturization; (l) increase in skin elasticity and/or resiliency; (m) treatment, reduction, and/or prevention or skin sagging; (n) improvement in skin firmness; (o) reduction of pigment spots, mottled skin, and/or scars (such as acne scars); (p) improvement of optical properties of skin by light diffraction or reflection; or (q) any combinations thereof.

In some embodiments that may be combined with any of the preceding embodiments, the subject is a human. In some embodiments that may be combined with any of the preceding embodiments, the herpes virus or composition is administered topically, transdermally, subcutaneously, epicutaneously, intradermally, orally, sublingually, buccally, rectally, vaginally, intravenously, intraarterially, intramuscularly, intraosseously, intracardially, intraperitoneally, transmucosally, intravitreally, subretinally, intraarticularly, periarticularly, locally, or via inhalation to the subject. In some embodiments that may be combined with any of the preceding embodiments, the herpes virus or composition is administered intradermally to the subject. In some embodiments that may be combined with any of the preceding embodiments, the herpes virus or composition is administered by superficial injection.

Other aspects of the present disclosure relate to a composition comprising: a herpes simplex virus (HSV) comprising a recombinant nucleic acid, wherein the recombinant nucleic acid comprises a first polynucleotide encoding a first polypeptide comprising a first human collagen protein, and an excipient. In some embodiments, the recombinant nucleic acid comprises two or more copies of the first polynucleotide. In some embodiments that may be combined with any of the preceding embodiments, the HSV is replication-defective. In some embodiments that may be combined with any of the preceding embodiments, the HSV is replication-competent. In some embodiments that may be combined with any of the preceding embodiments, the HSV is a herpes simplex type 1 virus, a herpes simplex type 2 virus, or any derivatives thereof.

In some embodiments, the recombinant nucleic acid is a herpes simplex virus amplicon. In some embodiments, the herpes simplex virus amplicon is an HSV-1 amplicon or an HSV-1 hybrid amplicon. In some embodiments, the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

In some embodiments, the recombinant nucleic acid is a recombinant herpes simplex virus genome. In some embodiments, the recombinant herpes simplex virus genome is a recombinant HSV-1 genome, a recombinant HSV-2 genome, or any derivatives thereof. In some embodiments that may be combined with any of the preceding embodiments, the recombinant herpes simplex virus genome comprises an inactivating mutation in a herpes simplex virus gene. In some embodiments, the herpes simplex virus gene is selected from the group consisting of Infected Cell Protein (ICP) 0, ICP4, ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivation mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivation mutation in the UL41 gene. In some embodiments that may be combined with any of the preceding embodiments, the recombinant herpes simplex virus genome comprises an inactivation mutation in the ICP0 gene. In some embodiments that may be combined with any of the preceding embodiments, the recombinant herpes simplex virus genome comprises an inactivation mutation in the ICP27 gene. In some embodiments that may be combined with any of the preceding embodiments, the inactivating mutation is a deletion of the coding sequence of the gene(s).

In some embodiments that may be combined with any of the preceding embodiments, the recombinant herpes simplex virus genome comprises the first polynucleotide within a viral gene locus. In some embodiments that may be combined with any of the preceding embodiments, the recombinant herpes simplex virus genome comprises the first polynucleotide within one or both copies of the ICP4 viral gene loci. In some embodiments that may be combined with any of the preceding embodiments, the recombinant herpes simplex virus genome comprises the first polynucleotide within the ICP22 viral gene locus. In some embodiments that may be combined with any of the preceding embodiments, the recombinant herpes simplex virus genome comprises the first polynucleotide within the UL41 viral gene locus. In some embodiments that may be combined with any of the preceding embodiments, the HSV has reduced cytotoxicity as compared to a wild-type herpes simplex virus.

In some embodiments that may be combined with any of the preceding embodiments, the first human collagen protein is selected from Collagen alpha-1(I) chain polypeptide (COL1-1), Collagen alpha-2(I) chain polypeptide (COL1-2), a Collagen alpha-1(II) chain polypeptide (COL2), a Collagen alpha-1(III) chain polypeptide (COL3), a Collagen alpha-1(IV) chain polypeptide (COL4-1), a Collagen alpha-2(IV) chain polypeptide (COL4-2), a Collagen alpha-3(IV) chain polypeptide (COL4-3), a Collagen alpha-4(IV) chain polypeptide (COL4-4), a Collagen alpha-5(IV) chain polypeptide (COL4-5), a Collagen alpha-6(IV) chain polypeptide (COL4-6), a Collagen alpha-1(V) chain polypeptide (COL5-1), a Collagen alpha-2(V) chain polypeptide (COL5-2), a Collagen alpha-3(V) chain polypeptide (COL5-3), a Collagen alpha-1(VI) chain polypeptide (COL6-1), a Collagen alpha-2(VI) chain polypeptide (COL6-2), a Collagen alpha-3(VI) chain polypeptide (COL6-3), a Collagen alpha-4(VI) chain polypeptide (COL6-4), a Collagen alpha-5(VI) chain polypeptide (COL6-5), a Collagen alpha-6(VI) chain polypeptide (COL6-6), a Collagen alpha-1(VII) chain polypeptide (COL7), a Collagen alpha-1(VIII) chain polypeptide (COL8), a Collagen alpha-1(IX) chain polypeptide (COL9-1), a Collagen alpha-2(IX) chain polypeptide (COL9-2), a Collagen alpha-3(IX) chain polypeptide (COL9-3), a Collagen alpha-1(X) chain polypeptide (COL10), a Collagen alpha-1(XI) chain polypeptide (COL11-1), a Collagen alpha-2(XI) chain polypeptide (COL11-2), a Collagen alpha-1(XII) chain polypeptide (COL12), a Collagen alpha-1(XIII) chain polypeptide (COL13), a Collagen alpha-1(XIV) chain polypeptide (COL14), a Collagen alpha-1(XV) chain polypeptide (COL15), a Collagen alpha-1(XVI) chain polypeptide (COL16), a Collagen alpha-1(XVII) chain polypeptide (COL17), a Collagen alpha-1(XVIII) chain polypeptide (COL18), a Collagen alpha-1(XIX) chain polypeptide (COL19), a Collagen alpha-1(XX) chain polypeptide (COL20), a Collagen alpha-1(XXI) chain polypeptide (COL21), a Collagen alpha-1(XXII) chain polypeptide (COL22), a Collagen alpha-1(XXIII) chain polypeptide (COL23), a Collagen alpha-1(XXIV) chain polypeptide (COL24), a Collagen alpha-1(XXV) chain polypeptide (COL25), a Collagen alpha-1(XXVI) chain polypeptide (COL26), a Collagen alpha-1(XXVII) chain polypeptide (COL27), and a Collagen alpha-1(XXVIII) chain polypeptide (COL28). In some embodiments that may be combined with any of the preceding embodiments, the first human collagen protein is selected from COL1-1, COL1-2, COL3, COL4-1, COL5-1, COL7, and COL17. In some embodiments that may be combined with any of the preceding embodiments, the nucleic acid sequence encoding the first human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments that may be combined with any of the preceding embodiments, the first human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments that may be combined with any of the preceding embodiments, the first human collagen protein is not COL7.

In some embodiments that may be combined with any of the preceding embodiments, the first polypeptide comprises: (a) the first human collagen protein; (b) a further human collagen protein; and (c) a linker polypeptide linking (a) to (b). In some embodiments, the linker polypeptide is a cleavable linker polypeptide. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 28-31. In some embodiments, the further human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the further human collagen protein is selected from COL1-1, COL1-2, COL3, COL4-1, COL5-1, COL7, and COL17. In some embodiments, the nucleic acid sequence encoding the further human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the further human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first human collagen protein and the further human collagen protein are different.

In some embodiments that may be combined with any of the preceding embodiments, the first polynucleotide encodes a polycistronic mRNA comprising: (a) a first open reading frame (ORF) encoding the first polypeptide; (b) a second ORF encoding an additional human collagen protein; and (c) an internal ribosomal entry site (IRES) separating (a) and (b). In some embodiments, the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23. In some embodiments, the additional human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the additional human collagen protein is selected from COL1-1, COL1-2, COL3, COL4-1, COL5-1, COL7, and COL17. In some embodiments, the nucleic acid sequence encoding the additional human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the additional human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first human collagen protein and the additional human collagen protein are different.

In some embodiments that may be combined with any of the preceding embodiments, the recombinant nucleic acid further comprises a second polynucleotide encoding a second human collagen protein. In some embodiments, the recombinant nucleic acid comprises two or more copies of the second polynucleotide. In some embodiments, the second human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL5-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the second human collagen protein is selected from COL1-1, COL1-2, COL3, COL4-1, COL5-1, COL7, and COL17. In some embodiments, the nucleic acid sequence encoding the second human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the second human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first and second human collagen proteins are different.

In some embodiments that may be combined with any of the preceding embodiments, the recombinant nucleic acid is a recombinant herpes simplex virus genome, and wherein the recombinant herpes simplex virus genome comprises the second polynucleotide within a viral gene locus. In some embodiments, the recombinant herpes simplex virus genome comprises the second polynucleotide within one or both copies of the ICP4 viral gene loci. In some embodiments, the recombinant herpes simplex virus genome comprises the second polynucleotide within the ICP22 viral gene locus. In some embodiments, the recombinant herpes simplex virus genome comprises the second polynucleotide within the UL41 viral gene locus. In some embodiments, the recombinant herpes simplex virus genome comprises the first polynucleotide within one or both copies of the ICP4 viral gene loci and the second polynucleotide within the ICP22 viral gene locus. In some embodiments, the recombinant herpes simplex virus genome comprises the first polynucleotide within one or both copies of the ICP4 viral gene loci and the second polynucleotide within the UL41 viral gene locus.

In some embodiments that may be combined with any of the preceding embodiments, the excipient is adapted for cutaneous (systemic or topical), transdermal, subcutaneous, and/or intradermal administration. In some embodiments that may be combined with any of the preceding embodiments, the excipient comprises a hydroxypropyl methylcellulose gel. In some embodiments that may be combined with any of the preceding embodiments, the excipient is adapted for intradermal administration. In some embodiments that may be combined with any of the preceding embodiments, the excipient comprises a phosphate buffer. In some embodiments that may be combined with any of the preceding embodiments, the excipient comprises glycerol. In some embodiments that may be combined with any of the preceding embodiments, the excipient comprises a lipid carrier. In some embodiments that may be combined with any of the preceding embodiments, the excipient comprises a nanoparticle carrier.

In some embodiments that may be combined with any of the preceding embodiments, the composition is a cosmetic composition. In some embodiments, the cosmetic composition is a skin care product.

Other aspects of the present disclosure relate to a kit comprising any of the compositions described herein and instructions for administering the composition.

Other aspects of the present disclosure relate to a method of enhancing, increasing, augmenting, and/or supplementing the levels of one or more human collagen proteins in a subject, the method comprising administering to the subject an effective amount of any of the compositions described herein.

Other aspects of the present disclosure relate to a method of enhancing, increasing, augmenting, and/or supplementing soft tissue of a subject, the method comprising administering to the subject an effective amount of any of the compositions described herein. In some embodiments, the composition is injected into a soft tissue of the subject.

Other aspects of the present disclosure relate to a method of improving skin quality, condition and/or appearance in a subject in need thereof, the method comprising administering to the subject an effective amount of any of the compositions described herein. In some embodiments, the condition is selected from sun damage, aging, UV exposure, rough texture, skin sagging, wrinkles, and any combinations thereof.

Other aspects of the present disclosure relate to a method of reducing the appearance of one or more superficial depressions in the skin of a subject in need thereof, the method comprising administering to the subject an effective amount of any of the compositions described herein. In some embodiments, administration of the composition reduces the appearance of the one or more superficial depressions in the skin of the subject for at least about three months, at least about six months, at least about nine months, or at least about 12 months. In some embodiments, the appearance of the one or more superficial depressions in the skin of the subject is reduced after administration of the composition, as compared to the appearance of the one or more superficial depression in the skin of the subject prior to administration of the composition.

Other aspects of the present disclosure relate to a method of increasing and/or improving at least one of texture, smoothness, elasticity, or tension of the skin of a subject in need thereof, the method comprising administering to the subject an effective amount of any of the compositions described herein. In some embodiments, the skin of the subject maintains at least one of an increased and/or improved texture, smoothness, elasticity, or tension for at least about three months, at least about six months, at least about nine months, or at least about 12 months after administration of the composition. In some embodiments, at least one of texture, smoothness, elasticity, or tension of the skin of the subject is increased and/or improved after administration of the composition, as compared to the texture, smoothness, elasticity, or tension of the skin of the subject prior to administration of the composition.

In some embodiments that may be combined with any of the preceding embodiments, the skin of the subject is aging skin. In some embodiments that may be combined with any of the preceding embodiments, the skin of the subject has been damaged due to exposure to ultraviolet light. In some embodiments that may be combined with any of the preceding embodiments, the skin of the subject is wrinkled.

Other aspects of the present disclosure relate to a method of diminishing one or more dermatological signs of aging in a subject in need thereof, the method comprising administering to the subject an effective amount of any of the compositions described herein. In some embodiments, the diminishing of one or more dermatological signs of aging is selected from: (a) treatment, reduction, and/or prevention of fine lines and/or wrinkles; (b) reduction of skin pore size; (c) improvement in skin thickness, plumpness, and/or tautness; (d) improvement in skin smoothness, suppleness, and/or softness; (e) improvement in skin tone, radiance, and/or clarity; (f) improvement in procollagen and/or collagen production; (g) improvement in skin texture and or promotion of retexturization; (h) improvement in appearance of skin contours; (i) restoration of skin luster and/or brightness; (j) improvement of skin appearance decreased by aging and/or menopause; (k) improvement in skin moisturization; (l) increase in skin elasticity and/or resiliency; (m) treatment, reduction, and/or prevention or skin sagging; (n) improvement in skin firmness; (o) reduction of pigment spots, mottled skin, and/or acne scars; (p) improvement of optical properties of skin by light diffraction or reflection; and (q) any combinations thereof. In some embodiments, the one or more dermatological signs of aging in the subject is diminished after administration of the composition, as compared to the one or more dermatological signs of aging in the subject prior to administration of the composition.

In some embodiments that may be combined with any of the preceding embodiments, the subject is a human. In some embodiments that may be combined with any of the preceding embodiments, the composition is administered cutaneously (systemically or topically), transdermally, subcutaneously, or intradermally to the subject. In some embodiments, the composition is administered by superficial injection. In some embodiments, the composition is administered intradermally to the subject. In some embodiments, the composition is administered once to the subject. In some embodiments, the composition is administered at least twice to the subject. In some embodiments, at least about 15, at least about 30, at least about 60, at least about 90, or at least about 120 days passes between administrations. In some embodiments that may be combined with any of the preceding embodiments, the composition is administered to one or more affected and/or unaffected areas of the subject. In some embodiments that may be combined with any of the preceding embodiments, the skin of the is abraded prior to administration.

Other aspects of the present disclosure relate to a recombinant nucleic acid comprising a first polynucleotide encoding a first polypeptide comprising a first human collagen protein, wherein the recombinant nucleic acid is a recombinant herpes simplex virus genome. In some embodiments, the recombinant nucleic acid comprises two or more copies of the first polynucleotide. In some embodiments, the recombinant herpes simplex virus genome is a recombinant HSV-1 genome, a recombinant HSV-2 genome, or any derivatives thereof.

In some embodiments that may be combined with any of the preceding embodiments, the recombinant herpes simplex virus genome comprises an inactivating mutation in a herpes simplex virus gene. In some embodiments, the herpes simplex virus gene is selected from the group consisting of Infected Cell Protein (ICP) 0, ICP4, ICP22, ICP27, ICP47, thymidine kinase (tk), Long Unique Region (UL) 41, and UL55. In some embodiments that may be combined with any of the preceding embodiments, the recombinant herpes simplex virus genome comprises an inactivation mutation in one or both copies of the ICP4 gene. In some embodiments that may be combined with any of the preceding embodiments, the recombinant herpes simplex virus genome comprises an inactivating mutation in the ICP22 gene. In some embodiments that may be combined with any of the preceding embodiments, the recombinant herpes simplex virus genome comprises an inactivation mutation in the UL41 gene. In some embodiments that may be combined with any of the preceding embodiments, the recombinant herpes simplex virus genome comprises an inactivation mutation in the ICP0 gene. In some embodiments that may be combined with any of the preceding embodiments, the recombinant herpes simplex virus genome comprises an inactivation mutation in the ICP27 gene. In some embodiments that may be combined with any of the preceding embodiments, the inactivating mutation is a deletion of the coding sequence of the gene(s).

In some embodiments that may be combined with any of the preceding embodiments, the recombinant herpes simplex virus genome comprises the first polynucleotide within a viral gene locus. In some embodiments that may be combined with any of the preceding embodiments, the recombinant herpes simplex virus genome comprises the first polynucleotide within one or both copies of the ICP4 viral gene loci. In some embodiments that may be combined with any of the preceding embodiments, the recombinant herpes simplex virus genome comprises the first polynucleotide within the ICP22 viral gene locus. In some embodiments that may be combined with any of the preceding embodiments, the recombinant herpes simplex virus genome comprises the first polynucleotide within the UL41 viral gene locus. In some embodiments that may be combined with any of the preceding embodiments, the HSV has reduced cytotoxicity as compared to a wild-type herpes simplex virus.

In some embodiments that may be combined with any of the preceding embodiments, the first human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL2. In some embodiments that may be combined with any of the preceding embodiments, the first human collagen protein is selected from COL1-1, COL1-2, COL3, COL4-1, COL5-1, COL7, and COL17. In some embodiments that may be combined with any of the preceding embodiments, the nucleic acid sequence encoding the first human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments that may be combined with any of the preceding embodiments, the first human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments that may be combined with any of the preceding embodiments, the first human collagen protein is not COL7.

In some embodiments that may be combined with any of the preceding embodiments, the first polypeptide comprises: (a) the first human collagen protein; (b) a further human collagen protein; and (c) a linker polypeptide linking (a) to (b). In some embodiments, the linker polypeptide is a cleavable linker polypeptide. In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 28-31. In some embodiments, the further human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the further human collagen protein is selected from COL1-1, COL1-2, COL3, COL4-1, COL5-1, COL7, and COL17. In some embodiments, the nucleic acid sequence encoding the further human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the further human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first human collagen protein and the further human collagen protein are different.

In some embodiments that may be combined with any of the preceding embodiments, the first polynucleotide encodes a polycistronic mRNA comprising: (a) a first open reading frame (ORF) encoding the first polypeptide; (b) a second ORF encoding an additional human collagen protein; and (c) an internal ribosomal entry site (IRES) separating (a) and (b). In some embodiments, the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23. In some embodiments, the additional human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the additional human collagen protein is selected from COL1-1, COL1-2, COL3, COL4-1, COL5-1, COL7, and COL17. In some embodiments, the nucleic acid sequence encoding the additional human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the additional human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first human collagen protein and the additional human collagen protein are different.

In some embodiments that may be combined with any of the preceding embodiments, the recombinant nucleic acid further comprises a second polynucleotide encoding a second human collagen protein. In some embodiments, the recombinant nucleic acid comprises two or more copies of the second polynucleotide. In some embodiments, the second human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL5-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28. In some embodiments, the second human collagen protein is selected from COL1-1, COL1-2, COL3, COL4-1, COL5-1, COL7, and COL17. In some embodiments, the nucleic acid sequence encoding the second human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, the second human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, the first and second human collagen proteins are different.

In some embodiments that may be combined with any of the preceding embodiments, the recombinant herpes simplex virus genome comprises the second polynucleotide within a viral gene locus. In some embodiments, the recombinant herpes simplex virus genome comprises the second polynucleotide within one or both copies of the ICP4 viral gene loci. In some embodiments, the recombinant herpes simplex virus genome comprises the second polynucleotide within the ICP22 viral gene locus. In some embodiments, the recombinant herpes simplex virus genome comprises the second polynucleotide within the UL41 viral gene locus. In some embodiments, the recombinant herpes simplex virus genome comprises the first polynucleotide within one or both copies of the ICP4 viral gene loci and the second polynucleotide within the ICP22 viral gene locus. In some embodiments, the recombinant herpes simplex virus genome comprises the first polynucleotide within one or both copies of the ICP4 viral gene loci and the second polynucleotide within the UL41 viral gene locus.

Other aspects of the present disclosure relate to a host cell comprising any of the recombinant nucleic acids described herein. In some embodiments, the host cell is a eukaryotic cell. In some embodiments, the host cell is a mammalian cell. In some embodiments, the host cell is a human cell or a non-human primate cell. In some embodiments, the host cell is a Vero cell. In some embodiments, the host cell is a complementing host cell.

Other aspects of the present disclosure relate to a method of collecting a herpes simplex virus, the method comprising: (a) contacting a complementing host cell with any of the recombinant nucleic acids described herein; and (b) collecting the herpes simplex virus generated by the complementing host cell.

Other aspects of the present disclosure relate to a method of collecting a herpes simplex virus, the method comprising; (a) culturing a host cell comprising any of the recombinant nucleic acids described herein; and (b) collecting the herpes simplex virus generated by the host cell.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A shows a wild-type herpes simplex virus genome.

1F shows a modified herpes simplex virus genome comprising deletions of the coding sequences of ICP4 (both copies) and ICP22, with a polynucleotide containing 1) the coding sequence of a first human collagen polypeptide operably linked to a first heterologous promoter, and 2) the coding sequence of a second human collagen polypeptide operably linked to a second heterologous promoter, integrated at each of the ICP4 loci. The first and second human collagen polypeptides are encoded on opposite strands of DNA. FIG. 1N shows a modified herpes simplex virus genome comprising deletions of the coding sequences of ICP4 (both copies) and UL41, with a first polynucleotide containing the coding sequence of a first human collagen polypeptide operably linked to a heterologous promoter integrated at each of the ICP4 loci, and a second polynucleotide containing the coding sequence of a second human collagen polypeptide operably linked to a heterologous promoter integrated at the UL41 locus.

FIG. 2A shows a schematic of the virus "KCA211". FIG. 2B shows a schematic of the virus "SAR-COL7".

FIGS. 3A-B show human COL7 expression in HaCaT cells infected with KCA211 or SAR-COL7 at the indicated MOIs. FIG. 3A shows human COL7 expression in HaCaT cells infected with KCA211 or SAR-COL7 at the indicated MOIs, as assessed by qPCR. Data is shown as fold change relative to SAR-COL7, after normalization to GAPDH. FIG. 3B shows human COL7 expression in uninfected HaCaT cells, or HaCaT cells infected with KCA211 or SAR-COL7 at the indicated MOIs, as assessed by western blot analysis.

FIGS. 4A-B show immunofluorescence images of human COL7 expression in mock infected primary human cells isolated from a healthy patient (Normal), and mock or SAR-COL7 infected primary human cells isolated from a patient suffering from recessive dystrophic epidermolysis bullosa (RDEB). FIG. 4A shows human COL7 expression in mock infected wild-type and RDEB primary human keratinocytes, or in RDEB primary human keratinocytes infected with SAR-COL7 at the indicated multiplicity of infections (MOIs). FIG. 4B shows human COL7 expression in mock infected wild-type and RDEB primary human fibroblasts, or in RDEB primary human fibroblasts infected with SAR-COL7 at the indicated MOIs.

FIG. 5A shows human COL7 expression in mock infected wild-type (N-HDK) and RDEB (EB-HDK) primary human keratinocytes, or in RDEB primary human keratinocytes infected with SAR-COL7 at the indicated MOIs. COL7 expression is shown as the relative fold change over mock infected wild-type primary human keratinocytes. FIG. 5B shows human COL7 expression in mock infected wild-type (N-HDF) and RDEB (EB-HDF) primary human fibroblasts, or in RDEB primary human fibroblasts infected with SAR-COL7 at the indicated MOIs. COL7 expression is shown as the relative fold change over mock infected wild-type primary human fibroblasts.

FIGS. 6A-B show cellular adhesion of uninfected (control) or SAR-COL7 infected RDEB primary human keratinocytes to untreated (plastic) or treated wells of a microwell plate. FIG. 6A shows cellular adhesion to untreated wells (plastic), or wells treated with increasing concentrations of rat tail Collagen 1. FIG. 6B shows cellular adhesion to untreated wells (plastic), or wells treated with increasing concentrations of human plasma fibronectin.

FIG. 8A shows human COL7A1 transcripts levels/100 ng total RNA in mouse skin at day 3 after infection. FIG. 8B shows copy number of human COL7A1 DNA/100 ng total DNA in mouse skin at day 3 after infection. FIG. 8C shows human COL7A1 transcripts levels/100 ng total RNA in mouse skin at day 6 after infection. FIG. 8D shows copy number of human COL7A1 DNA/100 ng total DNA in mouse skin at day 6 after infection.

FIGS. 9A-B show representative immunofluorescence images of human COL7 expression in mouse skin after delivery of SAR-COL7. FIG. 9A shows a representative immunofluorescent image of human COL7 expression in mouse skin after intradermal delivery of SAR-COL7. FIG. 9B shows a representative immunofluorescent image of human COL7 expression in mouse skin after topical delivery of SAR-COL7.

FIGS. 10A-B show human COL7A1 transcript and genome levels observed in BALB/c mouse skin after intradermal delivery of vehicle, SAR-COL7, or KCA211, as assessed by qPCR. FIG. 10A shows human COL7A1 transcripts levels/100 ng total RNA in BALB/c mouse skin. FIG. 10B shows copy number of human COL7A1 DNA/100 ng total DNA in BALB/c mouse skin.

FIG. 11A shows human COL7A1 transcripts levels/100 ng total RNA in hypomorph mouse skin. FIG. 11B shows copy number of human COL7A1 DNA/100 ng total DNA in hypomorph mouse skin.

FIG. 12A shows control (GFP) and SAR-COL7 immunofluorescence imaging from hypomorph mouse 1 (harvested at day 3) at 10 and 20× magnification. FIG. 12B shows SAR-COL7 immunofluorescence imaging from hypomorph mouse 2 and hypomorph mouse 3 (harvested at day 7). The figure represents a tiled image of 16 fields acquired with a 10× lens, capturing the entire skin section.

FIG. 14A shows electron micrograph images of infected hypomorph mouse skin stained with an antibody specific to the NC2 domain of human COL7 (LH24). FIG. 14B shows electron micrograph images of infected hypomorph mouse skin stained with an antibody specific to the NC1 domain of human COL7 (NP185).

FIGS. 15A-B show human COL7A1 transcript and genome levels observed at each injection site in hypomorph mouse skin after low-dose intradermal delivery of SAR-COL7, as assessed by qPCR. Each bar represents a single sample at the indicated time point. FIG. 15A shows human COL7A1 transcripts levels/100 ng total RNA in hypomorph mouse skin. FIG. 15B shows copy number of human COL7A1 DNA/100 ng total DNA in hypomorph mouse skin.

FIG. 17A shows the levels of human COL1A1 transcripts present in Vero cells 5 days after infection with the indicated HSV clones, as determined by qRT-PCR analysis. Data is presented for two replicates ±SEM. FIG. 17B shows the levels of human COL1A2 transcripts present in Vero cells 5 days after infection with the indicated HSV clones, as determined by qRT-PCR analysis. Data is presented for two replicates ±SEM. FIG. 17C shows western blot analysis of human COL1A1 and COL1A2 protein expression in Vero cells 5 days after infection with the indicated COL1A1/COL1A2 positive clones, as determined by qRT-PCR. Uninfected (mock) Vero cells were used as a negative control; GAPDH was used as a loading control.

FIG. 19A shows the levels of human COL3A1 transcripts present in immortalized human keratinocytes (HKs) after infection with C3vec01 at the indicated MOIs. Uninfected (mock) and HSV-mCherry-infected (mCherry) cells were used as negative controls. Data is presented for two replicates ±SEM. FIG. 19B shows representative immunofluorescence images of human COL3 protein expression in immortalized human keratinocytes 48 hours after infection with C3vec01 at the indicated MOIs. Uninfected (mock) cells were used as negative controls.

FIG. 20A shows the levels of human COL3A1 transcripts present in immortalized human dermal fibroblasts (HDFs) after infection with C3vec01 at the indicated MOIs. Uninfected (mock) and HSV-mCherry-infected (mCherry) cells were used as negative controls. Data is presented for two replicates ±SEM. FIG. 20B shows representative immunofluorescence images of human COL3 protein expression in immortalized human dermal fibroblasts 48 hours after infection with C3vec01 at the indicated MOIs. Uninfected (mock) cells were used as negative controls.

FIG. 21A shows the levels of human COL3A1 transcripts present in primary HDFs harvested from either a 65-year-old female patient or a 73-year-old male patient (vendor 1) after infection with C3vec01 at the indicated MOIs. Uninfected (mock) cells were used as a negative control. Data is presented for two replicates ±SEM. FIG. 21B shows western blot analysis of human COL3A1 protein expression in primary HDFs harvested from a 73-year-old male patient (vendor 1) after infection with C3vec01 at the indicated MOIs. Uninfected (mock) cells were used as a negative control; recombinant human COL3A1 (rCOL3A1) was used as a positive control; GAPDH was used as a loading control. FIG. 21C shows the levels of human COL3A1 transcripts present in primary HDFs harvested from either a 75-year-old female patient or a 73-year-old male patient (vendor 2) after infection with C3vec01 at the indicated MOIs. Uninfected (mock) cells were used as a negative control. Data is presented for two replicates ±SEM. FIG. 21D shows western blot analysis of human COL3A1 protein expression in primary HDFs harvested from a 75-year-old female patient (vendor 2) after infection with C3vec01 at the indicated MOIs. Uninfected (mock) cells were used as a negative control; recombinant human COL3A1 (rCOL3A1) was used as a positive control; GAPDH was used as a loading control.

FIGS. 22A-B show human COL3 nucleic acid and protein analyses in immortalized human dermal fibroblasts (HDFs) upon UV exposure. FIG. 22A shows the concentration of COL3 secreted into the supernatant of cultured HDFs 24 hours after exposure to various dosages and times of UV light, as assessed by ELISA. Supernatant collected from non-UV exposed (-UV) HDFs cultured in parallel was used as a control. FIG. 22B shows the levels of human COL3A1 transcripts present in UV-exposed immortalized human dermal fibroblasts (HDFs) after infection with C3vec01 at the indicated MOIs. Uninfected (mock) and HSV-mCherry-infected (mCherry) cells were used as negative controls. Data is presented for two replicates ±SEM.

FIG. 23A shows the levels of human COL3A1 DNA present in skin biopsies taken from young and old mice 48 hours after being intradermally administered either C3vec01 or vehicle control, as assessed by qPCR analysis. FIG. 23B shows the levels of human COL3A1 transcripts present in skin biopsies taken from young and old mice 48 hours after being intradermally administered either C3vec01 or vehicle control, as assessed by qRT-PCR analysis. For each condition in the qPCR and qRT-PCR analysis, data is presented as the average of four tissue samples (two replicates/tissue sample) ±SEM. FIG. 23C shows representative immunofluorescence images of human COL3 expression in skin biopsies taken from young and old mice 48 hours after being intradermally administered C3vec01. A young mouse intradermally administered vehicle alone was used as a negative control. DAPI staining was used to visualize nuclei.

FIG. 24A shows expression of wild-type human LAMB3 in infected Vero cells, as assessed by qPCR analysis. FIG. 24B shows expression of wild-type human LamB3 protein in infected Vero cells, as assessed by western blot.

FIG. 27A shows expression of wild-type human LAMC2 in infected Vero cells, as assessed by qPCR analysis. FIG. 27B shows expression of codon-optimized human LAMC2 in infected Vero cells, as assessed by qPCR analysis. FIG. 27C shows expression of wild-type and codon-optimized human LamC2 protein in infected Vero cells, as assessed by western blot. The boxed viral isolate "LGA" expressing codon-optimized LamC2 was selected for additional experimentation.

FIGS. 28A-C show human LAMC2 expressed from viral isolate "LGA" in immortalized primary human keratinocytes infected at the indicated multiplicities of infection (MOIs). FIG. 28A shows the viral genome copy number in primary immortalized human keratinocytes after infection with viral isolate "LGA" at the indicated MOIs. FIG. 28B shows the transcript level of codon-optimized LAMC2 expressed in primary immortalized human keratinocytes after infection with viral isolate "LGA" at the indicated MOIs. FIG. 28C shows expression of human LamC2 protein in primary immortalized human keratinocytes after infection with viral isolate "LGA" at the indicated MOIs, as assessed by western blot.

FIGS. 29A-D show LAMC2 nucleic acid and protein analysis of skin biopsies taken from control (vehicle)- or HSV isolate "LGA"-treated mice 72 hours after intradermal application. FIG. 29A shows a schematic of the intradermal injection sites on the treated animals. FIG. 29B shows the levels of human LAMC2 DNA present in skin biopsies taken from mice 72 hours after being intradermally administered either HSV isolate LGA or vehicle control, as assessed by qPCR analysis. FIG. 29C shows the levels of human LAMC2 transcripts present in skin biopsies taken from mice 72 hours after being intradermally administered either HSV isolate LGA or vehicle control, as assessed by qRT-PCR analysis. For each condition in the qPCR and qRT-PCR analysis, data is presented as the average of two replicates ±SEM. FIG. 29D shows representative immunofluorescence images of human LAMC2 expression in skin biopsies taken from mice 72 hours after being intradermally administered HSV isolate LGA. A site that was intradermally administered vehicle alone was used as a negative control. DAPI staining was used to visualize nuclei; pKal staining was used to visualize mouse laminin-332.

DETAILED DESCRIPTION

In some embodiments, the present disclosure relates to recombinant nucleic acids (e.g., recombinant herpes viral genomes) encoding one or more cosmetic proteins, and to uses of these recombinant nucleic acids in viruses (e.g., in a herpes virus), compositions, formulations, medicaments, and/or methods for delivering one or more cosmetic proteins to the skin, such as onto, into, and/or through the skin (e.g., to the dermal ECM). In some embodiments, the present disclosure relates to recombinant nucleic acids (e.g., recombinant herpes viral genomes) encoding one or more cosmetic proteins, and to uses of these recombinant nucleic acids in viruses (e.g., in a herpes virus), compositions, formulations, medicaments, and/or methods in order to increase, augment, and/or supplement one or more dermal ECM proteins (e.g., one or more collagen proteins). In some embodiments, the present disclosure relates to recombinant nucleic acids (e.g., recombinant herpes viral genomes) encoding one or more cosmetic proteins, and to uses of these recombinant nucleic acids in viruses (e.g., in a herpes virus), compositions, formulations, medicaments, and/or methods in the aesthetic context (e.g., to reduce one or more dermatological signs of aging). In some embodiments, the present disclosure relates to compositions comprising a recombinant herpes viral vector and methods comprising the delivery of the recombinant herpes viral vector onto, into, and/or through the skin of a mammal, wherein the recombinant herpes viral vector comprises a promoter operable in a mammalian cell and a heterologous nucleic acid which is expressed to achieve a cosmetic effect in mammalian skin. The heterologous nucleic acid may be delivered to a mammalian target skin cell of a mammal, comprising contacting the epidermis, dermis, or subcutaneous tissue of the mammal with the composition comprising the recombinant herpes viral vector, under conditions whereby the recombinant herpes viral vector is transported onto, into, and/or through the epidermis, dermis or subcutaneous tissue and introduced into the target skin cell, where it is expressed Without wishing to be bound by theory, it is believed that administering one or more of the recombinant nucleic acids, viruses, and/or formulations described herein to an individual will allow for increased production of functional dermal ECM proteins (e.g., human collagen) in the individual. Furthermore, without wishing to be bound by theory, it is believed that increasing, augmenting, and/or supplementing the levels of cosmetic proteins in an individual by administering one or more of the recombinant nucleic acids, viruses, and/or formulations described herein will lead to at least one of: 1) the enhancement, augmentation, and/or supplementation of soft tissue; 2) the improvement of skin quality, condition, and/or appearance; 3) the reduction of one or more superficial depressions in the skin (e.g., wrinkles); 4) the improvement of texture, smoothness, elasticity, and/or tension of the skin; and/or 5) the reduction of one or more dermatological signs of aging. Ultimately, without wishing to be bound by theory, it is believed that the recombinant nucleic acids, viruses, compositions, and methods described herein provide a novel strategy for delivering functional cosmetic proteins in aesthetic settings.

Figure 1A:
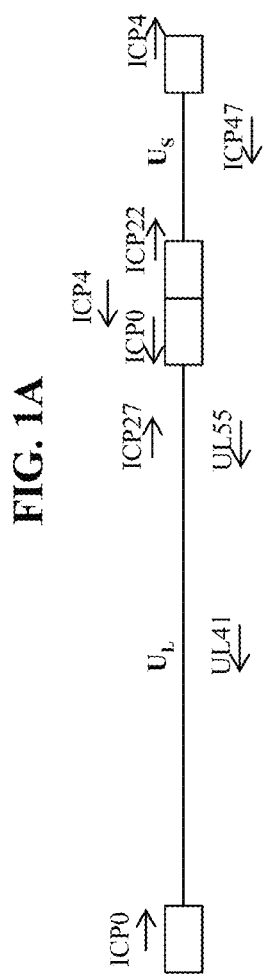
FIGS. 1A-N show schematics of wild-type and modified herpes simplex virus genomes.

The following description sets forth exemplary methods, parameters, and the like. It should be recognized, however, that such a description is not intended as a limitation on the scope of the present disclosure but is instead provided as a description of exemplary embodiments.

I. GENERAL TECHNIQUES

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Gene Transfer Vectors for Mammalian Cells* (J. M. Miller and M. P. Calos, eds., 1987); PCR: *The Polymerase Chain Reaction*, (Mullis et al., eds., 1994); *Short Protocols in Molecular Biology* (Wiley and Sons, 1999).

II. DEFINITIONS

Before describing the present disclosure in detail, it is to be understood that the present disclosure is not limited to particular compositions or biological systems, which can, of course, vary. It is also to be understood that the terminology used herein is for the purpose of describing particular embodiments only and is not intended to be limiting.

As used herein, the singular forms "a", "an" and "the" include plural referents unless the content clearly dictates otherwise. Thus, for example, reference to "a molecule" optionally includes a combination of two or more such molecules, and the like.

As used herein, the term "and/or" may include any and all combinations of one or more of the associated listed items. For example, the term "a and/or b" may refer to "a alone", "b alone", "a or b", or "a and b"; the term "a, b, and/or c" may refer to "a alone", "b alone", "c alone", "a or b", "a or c", "b or c", "a, b, or c", "a and b", "a and c", "b and c", or "a, b, and c"; etc.

As used herein, the term "about" refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising", "consisting", and "consisting essentially of" aspects and embodiments.

As used herein, the terms "polynucleotide", "nucleic acid sequence", "nucleic acid", and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications.

As used herein, a nucleic acid is "operatively linked" or "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, "operatively linked" or "operably linked" means that the DNA sequences being linked are contiguous.

As used herein, the term "vector" refers to discrete elements that are used to introduce heterologous nucleic acids into cells for either expression or replication thereof. An expression vector includes vectors capable of expressing nucleic acids that are operatively linked with regulatory sequences, such as promoter regions, that are capable of effecting expression of such nucleic acids. Thus, an expression vector may refer to a DNA or RNA construct, such as a plasmid, a phage, recombinant virus or other vector that, upon introduction into an appropriate host cell, results in expression of the nucleic acids. Appropriate expression vectors are well known to those of skill in the art and include those that are replicable in eukaryotic cells, and those that remain episomal or those which integrate into the host cell genome.

As used herein, an "open reading frame" or "ORF" refers to a continuous stretch of nucleic acids, either DNA or RNA, that encode a protein or polypeptide. Typically, the nucleic acids comprise a translation start signal or initiation codon, such as ATG or AUG, and a termination codon.

As used herein, an "untranslated region" or "UTR" refers to untranslated nucleic acids at the 5' and/or 3' ends of an open reading frame. The inclusion of one or more UTRs in a polynucleotide may affect post-transcriptional regulation, mRNA stability, and/or translation of the polynucleotide.

As used herein, the term "transgene" refers to a polynucleotide that is capable of being transcribed into RNA and translated and/or expressed under appropriate conditions, after being introduced into a cell. In some aspects, it confers a desired property to a cell into which it was introduced, or otherwise leads to a desired cosmetic, therapeutic, or diagnostic outcome.

As used herein, the terms "polypeptide," "protein," and "peptide" are used interchangeably and may refer to a polymer of two or more amino acids.

As used herein, a "subject", "host", or an "individual" refers to any animal classified as a mammal, including humans, domestic and farm animals, and zoo, sports, or pet animals, such as dogs, horses, cats, cows, as well as animals used in research, such as mice, rats, hamsters, rabbits, and non-human primates, etc. In some embodiments, the mammal is human.

As used herein, the terms "pharmaceutical formulation" or "pharmaceutical composition" refer to a preparation which is in such a form as to permit the biological activity of the active ingredient(s) to be effective, and which contains no additional components which are unacceptably toxic to a subject to which the composition or formulation would be administered. "Pharmaceutically acceptable" excipients (e.g., vehicles, additives) are those which can reasonably be administered to a subject to provide an effective dose of the active ingredient(s) employed.

As used herein, "cutaneous administration" or "cutaneously administering" refers to the delivery of a composition to a subject by contacting, directly or otherwise, a formulation comprising the composition to all ("systemic") or a portion ("topical") of the skin of a subject. The term encompasses several routes of administration including, but not limited to, topical and transdermal. Topical administration may be used as a means to deliver a composition to the epidermis or dermis of a subject, or to specific strata thereof.

As used herein, "treatment" refers to clinical intervention designed to alter the natural course of the individual or cell being treated during the course of clinical pathology. Desirable effects of treatment include decreasing the rate of disease/disorder/defect progression, ameliorating or palliating the disease/disorder/defect state, and remission or improved prognosis. For example, an individual is successfully "treated" if one or more symptoms associated with dermatological aging are reduced, mitigated, or eliminated, including the reduction or elimination of wrinkles.

As used herein, the term "delaying progression of" a disease/disorder/defect refers to deferring, hindering, slowing, retarding, stabilizing, and/or postponing development of the disease/disorder/defect (e.g., skin wrinkles). This delay can be of varying lengths or time, depending on the history of the disease/disorder/defect and/or the individual being treated. As is evident to one of ordinary skill in the art, a sufficient or significant delay can, in effect, encompass prevention, in that the individual does not develop the disease/disorder/defect.

III. RECOMBINANT NUCLEIC ACIDS

Certain aspects of the present disclosure relate to recombinant nucleic acids (e.g., isolated recombinant nucleic acids) comprising one or more polynucleotides (e.g., one or more, two or more, three or more, four or more, five or more, ten or more, etc.) encoding a cosmetic protein. Any suitable cosmetic protein described herein or known in the art may be encoded by the polynucleotides of the present disclosure, including, for example, collagen proteins, fibronectins, elastins, lumicans, vitronectins/vitronectin receptors, laminins, neuromodulators, fibrillins, additional dermal ECM proteins, etc. In some embodiments, the cosmetic protein is a structural extracellular matrix protein (e.g., a collagen, elastin, fibronectin, laminin, fibrillin, etc.). In some embodiments, the cosmetic protein is a collagen, elastin, fibronectin, or laminin protein (e.g., a human collagen, elastin, fibronectin, or laminin protein).

In some embodiments, the present disclosure relates to recombinant nucleic acids (e.g., isolated recombinant nucleic acids) comprising one or more polynucleotides (e.g., one or more, two or more, three or more, four or more, five or more, ten or more, etc.) encoding a collagen protein. In some embodiments, the collagen protein is a human collagen protein. In some embodiments, the present disclosure relates to recombinant nucleic acids comprising one or more polynucleotides encoding a homotrimeric collagen (e.g., a homotrimeric human collagen, such as human Collagen 3 (e.g., comprising three COL3A1 (COL3) polypeptides) or human Collagen 7 (e.g., comprising three COL7A1 (COL7) polypeptides). In some embodiments, the present disclosure relates to recombinant nucleic acids comprising one or more polynucleotides encoding a heterotrimeric collagen (e.g., a heterotrimeric human collagen, such as human Collagen 1 (e.g., comprising two COL1A1 (COL1-1) polypeptides and one COL1A2 (COL1-2) polypeptide) or human Collagen 4 (e.g., comprising two COL4A1 (COL4-1) polypeptides and one COL4A2 (COL4-2) polypeptide). In some embodiments, the present disclosure relates to recombinant nucleic acids comprising one or more polynucleotides encoding a homotrimeric collagen and a heterotrimeric collagen (e.g., a recombinant nucleic acid comprising one or more polynucleotides encoding a human Collagen 1 and a human Collagen 3). In some embodiments, the present disclosure relates to recombinant nucleic acids comprising one or more polynucleotides encoding human Collagen 1. In some embodiments, the present disclosure relates to recombinant nucleic acids comprising one or more polynucleotides encoding human Collagen 3.

In some embodiments, the present disclosure relates to recombinant nucleic acids comprising a first polynucleotide encoding a first polypeptide comprising a first cosmetic protein (e.g., a first human collagen protein). In some embodiments, the first polypeptide consists essentially of or consists of the first cosmetic protein (e.g., consists essentially of or consists of a first human collagen protein). In some embodiments, the present disclosure relates to recombinant nucleic acids comprising a first polynucleotide encoding a first polypeptide comprising: a first cosmetic protein (e.g., a first human collagen protein), a linker polypeptide, and a further cosmetic protein (e.g., a further human collagen protein). In some embodiments, the first and further cosmetic proteins (e.g., the first and further human collagen proteins) are the same. In some embodiments, the first and further cosmetic proteins (e.g., the first and further human collagen proteins) are different. In some embodiments, the linker polypeptide is a cleavable linker polypeptide.

In some embodiments, the present disclosure relates to recombinant nucleic acids comprising a first polynucleotide encoding a first polypeptide comprising a first cosmetic protein (e.g., a first human collagen protein), wherein the first polynucleotide encodes a polycistronic mRNA comprising: a first open reading frame (ORF) encoding the first polypeptide, an internal ribosomal entry site (IRES), and a second ORF encoding an additional cosmetic protein (e.g., an additional human collagen protein). In some embodiments, the first and additional cosmetic proteins (e.g., the first and additional human collagen proteins) are the same. In some embodiments, the first and additional cosmetic proteins (e.g., the first and additional human collagen proteins) are different.

In some embodiments, the present disclosure relates to recombinant nucleic acids comprising a first polynucleotide encoding a first polypeptide comprising a first cosmetic protein (e.g., a first human collagen protein), and a second polynucleotide encoding a second cosmetic protein (e.g., a second human collagen protein). In some embodiments, the first and second cosmetic proteins (e.g., the first and second human collagen proteins) are the same. In some embodiments, the first and second cosmetic proteins (e.g., the first and second human collagen proteins) are different.

In some embodiments, the recombinant nucleic acid is a vector. In some embodiments, the recombinant nucleic acid is a viral vector. In some embodiments, the recombinant nucleic acid is a herpes viral vector. In some embodiments, the recombinant nucleic acid is a herpes simplex virus amplicon. In some embodiments, the recombinant nucleic acid is a recombinant herpes virus genome. In some embodiments, the recombinant nucleic acid is a recombinant herpes simplex virus genome. In some embodiments, the recombinant herpes simplex virus genome is a recombinant type 1 herpes simplex virus (HSV-1) genome.

Polynucleotides Encoding Cosmetic Proteins
Polynucleotides Encoding Collagen Proteins In some embodiments, the present disclosure relates to a recombinant nucleic acid comprising one or more polynucleotides comprising the coding sequence of a collagen gene. The coding sequence of any collagen gene (including any isoform thereof) from any suitable species known in the art may be encoded by a polynucleotide of the present disclosure, including, for example, human collagen genes (see e.g., NCBI Gene IDs: 1277, 1278, 1281, 1282, 1284, 1291, 1294, 1308, etc.), mouse collagen genes (see, e.g., NCBI Gene IDs: 12842, 12843, 12825, 12826, 12827, 12833, 12836, 12821, etc.), chimpanzee collagen genes (see e.g., NCBI Gene IDs: 104001053, 455117, 459815, 452689, 452661, 450204, 101056895, 101058306, etc.), rat collagen genes (see e.g., NCBI Gene IDs: 29393, 84352, 84032, 290905, 306628, 294337, 301012, 294027, etc.), rabbit collagen genes (see e.g., NCBI Gene IDs: 100347598, 100008997, 100009177, 100358256, 100358522, 100343947, 100356561, 100339335, etc.) etc. Methods of identifying collagen gene homologs/orthologs from additional species are known to one of ordinary skill in the art, including, for example, using a nucleic acid sequence alignment program such as the BLAST® blastn suite. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the collagen genes (and/or coding sequences thereof) described herein or known in the art.

In some embodiments, a polynucleotide of the present disclosure comprises a codon-optimized variant of the coding sequence of any of the collagen genes described herein or known in the art. In some embodiments, use of a codon-optimized variant of the coding sequence of a collagen gene increases stability and/or yield of heterologous expression (RNA and/or protein) of the encoded collagen protein in a target cell (such as a cell of the epidermis and/or dermis), as compared to the stability and/or yield of heterologous expression of a corresponding, non-codon-optimized, wild-type sequence. Any suitable method known in the art for performing codon optimization of a sequence for expression in one or more target cells (e.g., one or more human cells) may be used, including, for example, by the methods described by Fath et al. (PLoS One. 2011 Mar. 3; 6(3): e17596).

In some embodiments, the present disclosure relates to one or more polynucleotides (i.e., one or more first polynucleotides and/or one or more second polynucleotides) comprising the coding sequence of a human collagen gene. Any suitable human collagen gene (including any isoform thereof) known in the art may be encoded by a nucleic acid of the present disclosure, including, for example, a COL1A1 gene (see e.g., NCBI Gene ID: 1277; SEQ ID NO: 1), a COL1A2 gene (see e.g., NCBI Gene ID: 1278; SEQ ID NO: 3), a COL2A1 gene (see e.g., NCBI Gene ID: 1280), a COL3A1 gene (see e.g., NCBI Gene ID: 1281; SEQ ID NO: 5), a COL4A1 gene (see e.g., NCBI Gene ID: 1282; SEQ ID NO: 7), a COL4A2 gene (see e.g., NCBI Gene ID: 1284), a COL4A3 gene (see e.g., NCBI Gene ID: 1285), a COL4A4 gene (see e.g., NCBI Gene ID: 1286), a COL4A5 gene (see e.g., NCBI Gene ID: 1287), a COL4A6 gene (see e.g., NCBI Gene ID: 1288), a COL5A1 gene (see e.g., NCBI Gene ID: 1289), a COL5A2 gene (see e.g., NCBI Gene ID: 1290), a COL5A3 gene (see e.g., NCBI Gene ID: 50509), a COL6A1 gene (see e.g., NCBI Gene ID: 1291; SEQ ID NO: 9), a COL6A2 gene (see e.g., NCBI Gene ID: 1292), a COL6A3 gene (see e.g., NCBI Gene ID: 1293), a COL6A4 gene (see e.g., NCBI Gene ID: 344875), a COL6A5 gene (see e.g., NCBI Gene ID: 256076), a COL6A6 gene (see e.g., NCBI Gene ID: 131873), a COL7A1 gene (see e.g., NCBI Gene ID: 1294; SEQ ID NO: 10), a COL8A1 gene (see e.g., NCBI Gene ID: 1295), a COL9A1 gene (see e.g., NCBI Gene ID: 1297), a COL9A2 gene (see e.g., NCBI Gene ID: 1298), a COL9A3 gene (see e.g., NCBI Gene ID: 1299), a COL10A1 gene (see e.g., NCBI Gene ID: 1300), a COL11A1 gene (see e.g., NCBI Gene ID: 1301), a COL11A2 gene (see e.g., NCBI Gene ID: 1302), a COL12A1 gene (see e.g., NCBI Gene ID: 1303), a COL13A1 gene (see e.g., NCBI Gene ID: 1305), a COL14A1 gene (see e.g., NCBI Gene ID: 7373), a COL15A1 gene (see e.g., NCBI Gene ID: 1306), a COL16A1 gene (see e.g., NCBI Gene ID: 1307), a COL17A1 gene (see e.g., NCBI Gene ID: 1308; SEQ ID NO: 12), a COL18A1 gene (see e.g., NCBI Gene ID: 80781), a COL19A1 gene (see e.g., NCBI Gene ID: 1310), a COL20A1 gene (see e.g., NCBI Gene ID: 57642), a COL21A1 gene (see e.g., NCBI Gene ID: 81578), a COL22A1 gene (see e.g., NCBI Gene ID: 169044), a COL23A1 gene (see e.g., NCBI Gene ID: 91522), a COL24A1 gene (see e.g., NCBI Gene ID: 255631), a COL25A1 gene (see e.g., NCBI Gene ID: 84570), a COL26A1 gene (see e.g., NCBI Gene ID: 136227), a COL27A1 gene (see e.g., NCBI Gene ID: 85301), a COL28A1 gene (see e.g., NCBI Gene ID: 340267), etc. In some embodiments, a polynucleotide (i.e., one or more first polynucleotides and/or one or more second polynucleotides) of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the human collagen genes (and/or coding sequences thereof) described herein or known in the art.

In some embodiments, a polynucleotide (i.e., one or more first polynucleotides and/or one or more second polynucleotides) of the present disclosure comprises a codon-optimized variant of any of the human collagen genes described herein. In some embodiments, use of a codon-optimized variant of a human collagen gene increases stability and/or yield of heterologous expression (RNA and/or protein) of the human collagen in a target cell (such as a human keratinocyte or fibroblast), as compared to the stability and/or yield of heterologous expression of a corresponding non-codon-optimized, wild-type sequence.

In some embodiments, a polynucleotide of the present disclosure comprises the coding sequence of the human COL1A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 1 or SEQ ID NO: 2. In some embodiments, a polynucleotide of the present disclosure comprises the sequence of SEQ ID NO: 1 or SEQ ID NO: 2.

In some embodiments, a polynucleotide of the present disclosure comprises a 5' truncation, a 3' truncation, or a fragment of the sequence of SEQ ID NO: 1 or SEQ ID NO: 2. In some embodiments, the 5' truncation, 3' truncation, or fragment of the sequence of SEQ ID NO: 1 or SEQ ID NO: 2 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, but fewer than 4395, consecutive nucleotides of SEQ ID NO: 1 or SEQ ID NO: 2. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4392 of SEQ ID NO: 1 or SEQ ID NO: 2. In some embodiments, a polynucleotide of the present disclosure comprises the sequence of nucleic acids 1-4392 of SEQ ID NO: 1 or SEQ ID NO: 2.

In some embodiments, a polynucleotide of the present disclosure comprises the coding sequence of the human COL1A2 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 3 or SEQ ID NO: 4. In some embodiments, a polynucleotide of the present disclosure comprises the sequence of SEQ ID NO: 3 or SEQ ID NO: 4.

In some embodiments, a polynucleotide of the present disclosure comprises a 5' truncation, a 3' truncation, or a fragment of the sequence of SEQ ID NO: 3 or SEQ ID NO: 4. In some embodiments, the 5' truncation, 3' truncation, or fragment of the sequence of SEQ ID NO: 3 or SEQ ID NO: 4 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, but fewer than 4101, consecutive nucleotides of SEQ ID NO: 3 or SEQ ID NO: 4. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4098 of SEQ ID NO: 3 or SEQ ID NO: 4. In some embodiments, a polynucleotide of the present disclosure comprises the sequence of nucleic acids 1-4098 of SEQ ID NO: 3 or SEQ ID NO: 4.

In some embodiments, a polynucleotide of the present disclosure comprises the coding sequence of the human COL3A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 5 or SEQ ID NO: 6. In some embodiments, a polynucleotide of the present disclosure comprises the sequence of SEQ ID NO: 5 or SEQ ID NO: 6.

In some embodiments, a polynucleotide of the present disclosure comprises a 5' truncation, a 3' truncation, or a fragment of the sequence of SEQ ID NO: 5 or SEQ ID NO: 6. In some embodiments, the 5' truncation, 3' truncation, or fragment of the sequence of SEQ ID NO: 5 or SEQ ID NO: 6 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, but fewer than 4401, consecutive nucleotides of SEQ ID NO: 5 or SEQ ID NO: 6. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4398 of SEQ ID NO: 5 or SEQ ID NO: 6. In some embodiments, a polynucleotide of the present disclosure comprises the sequence of nucleic acids 1-4398 of SEQ ID NO: 5 or SEQ ID NO: 6.

In some embodiments, a polynucleotide of the present disclosure comprises the coding sequence of the human COL4A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 7 or SEQ ID NO: 8. In some embodiments, a polynucleotide of the present disclosure comprises the sequence of SEQ ID NO: 7 or SEQ ID NO: 8.

In some embodiments, a polynucleotide of the present disclosure comprises a 5' truncation, a 3' truncation, or a fragment of the sequence of SEQ ID NO: 7 or SEQ ID NO: 8. In some embodiments, the 5' truncation, 3' truncation, or fragment of the sequence of SEQ ID NO: 7 or SEQ ID NO: 8 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, at least 4500, at least 5000, but fewer than 5010, consecutive nucleotides of SEQ ID NO: 7 or SEQ ID NO: 8. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-5007 of SEQ ID NO: 7 or SEQ ID NO: 8. In some embodiments, a polynucleotide of the present disclosure comprises the sequence of nucleic acids 1-5007 of SEQ ID NO: 7 or SEQ ID NO: 8.

In some embodiments, a polynucleotide of the present disclosure comprises the coding sequence of the human COL6A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 9 or SEQ ID NO: 10. In some embodiments, a polynucleotide of the present disclosure comprises the sequence of SEQ ID NO: 9 or SEQ ID NO: 10.

In some embodiments, a polynucleotide of the present disclosure comprises a 5' truncation, a 3' truncation, or a fragment of the sequence of SEQ ID NO: 9 or SEQ ID NO: 10. In some embodiments, the 5' truncation, 3' truncation, or fragment of the sequence of SEQ ID NO: 9 or SEQ ID NO: 10 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, but fewer than 3087, consecutive nucleotides of SEQ ID NO: 9 or SEQ ID NO: 10. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3084 of SEQ ID NO: 9 or SEQ ID NO: 10. In some embodiments, a polynucleotide of the present disclosure comprises the sequence of nucleic acids 1-3084 of SEQ ID NO: 9 or SEQ ID NO: 10.

In some embodiments, a polynucleotide of the present disclosure comprises the coding sequence of the human COL7A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 11 or SEQ ID NO: 12. In some embodiments, a polynucleotide of the present disclosure comprises the sequence of SEQ ID NO: 11 or SEQ ID NO: 12.

In some embodiments, a polynucleotide of the present disclosure comprises a 5' truncation, a 3' truncation, or a fragment of the sequence of SEQ ID NO: 11 or SEQ ID NO: 12. In some embodiments, the 5' truncation, 3' truncation, or fragment of the sequence of SEQ ID NO: 11 or SEQ ID NO: 12 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, at least 4500, at least 5000, at least 5500, at least 6000, at least 6500, at least 7000, at least 7500, at least 8000, at least 8500, but fewer than 8835, consecutive nucleotides of SEQ ID NO: 11 or SEQ ID NO: 12. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-8832 of SEQ ID NO: 11 or SEQ ID NO: 12. In some embodiments, a polynucleotide of the present disclosure comprises the sequence of nucleic acids 1-8832 of SEQ ID NO: 11 or SEQ ID NO: 12.

In some embodiments, a polynucleotide of the present disclosure comprises the coding sequence of the human COL17A1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 13 or SEQ ID NO: 14. In some embodiments, a polynucleotide of the present disclosure comprises the sequence of SEQ ID NO: 13 or SEQ ID NO: 14.

In some embodiments, a polynucleotide of the present disclosure comprises a 5' truncation, a 3' truncation, or a fragment of the sequence of SEQ ID NO: 13 or SEQ ID NO: 14. In some embodiments, the 5' truncation, 3' truncation, or fragment of the sequence of SEQ ID NO: 13 or SEQ ID NO: 14 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, but fewer than 4494, consecutive nucleotides of SEQ ID NO: 13 or SEQ ID NO: 14. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-4491 of SEQ ID NO: 13 or SEQ ID NO: 14. In some embodiments, a polynucleotide of the present disclosure comprises the sequence of nucleic acids 1-4491 of SEQ ID NO: 13 or SEQ ID NO: 14.

In some embodiments, a polynucleotide of the present disclosure encoding one or more human collagen proteins (e.g., a first human collagen protein, a further human collagen protein, an additional human collagen protein, and/or a second human collagen protein) has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14. In some embodiments, a polynucleotide of the present disclosure encoding one or more human collagen proteins (e.g., a first human collagen protein, a further human collagen protein, an additional human collagen protein, and/or a second human collagen protein) comprises a sequence selected from SEQ ID NOS: 1-14.

Polynucleotides Encoding Fibronectin Proteins

In some embodiments, the present disclosure relates to a recombinant nucleic acid comprising one or more polynucleotides comprising the coding sequence of a fibronectin gene. The coding sequence of any fibronectin gene (including any isoform thereof) from any suitable species known in the art may be encoded by a polynucleotide of the present disclosure, including, for example, a human fibronectin gene (see e.g., NCBI Gene ID: 2335), a mouse fibronectin gene (see, e.g., NCBI Gene ID: 14268), a chimpanzee fibronectin gene (see e.g., NCBI Gene ID: 459926), a rat fibronectin gene (see e.g., NCBI Gene ID: 25661), a rabbit fibronectin gene (see e.g., NCBI Gene ID: 100328589), etc. Methods of identifying fibronectin gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the fibronectin genes (and/or coding sequences thereof) described herein or known in the art. In some embodiments, a polynucleotide of the present disclosure comprises a codon-optimized variant of any of the fibronectin genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human fibronectin gene. In some embodiments, a polynucleotide of the present disclosure comprises the coding sequence of the human FN1 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 35 or SEQ ID NO: 36. In some embodiments, a polynucleotide of the present disclosure comprises the sequence of SEQ ID NO: 35 or SEQ ID NO: 36.

In some embodiments, a polynucleotide of the present disclosure comprises a 5' truncation, a 3' truncation, or a fragment of the sequence of SEQ ID NO: 35 or SEQ ID NO: 36. In some embodiments, the 5' truncation, 3' truncation, or fragment of the sequence of SEQ ID NO: 35 or SEQ ID NO: 36 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, at least about 4500, at least about 5000, at least about 5500, at least about 6000, at least about 6500, at least about 7000, but fewer than 7434, consecutive nucleotides of SEQ ID NO: 35 or SEQ ID NO: 36. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-7431 of SEQ ID NO: 35 or SEQ ID NO: 36. In some embodiments, a polynucleotide of the present disclosure comprises the sequence of nucleic acids 1-7431 of SEQ ID NO: 35 or SEQ ID NO: 36.

Polynucleotides Encoding Elastin Proteins

In some embodiments, the present disclosure relates to a recombinant nucleic acid comprising one or more polynucleotides comprising the coding sequence of an elastin gene. The coding sequence of any elastin gene (including any isoform thereof) from any suitable species known in the art may be encoded by a polynucleotide of the present disclosure, including, for example, a human elastin gene (see e.g., NCBI Gene ID: 2006), a mouse elastin gene (see, e.g., NCBI Gene ID: 13717), a chimpanzee elastin gene (see e.g., NCBI Gene ID: 463943), a rat elastin gene (see e.g., NCBI Gene ID: 25043), a rabbit elastin gene (see e.g., NCBI Gene ID: 100344271), etc. Methods of identifying elastin gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the elastin genes (and/or coding sequences thereof) described herein or known in the art. In some embodiments, a polynucleotide of the present disclosure comprises a codon-optimized variant of any of the elastin genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human elastin gene. In some embodiments, a polynucleotide of the present disclosure comprises the coding sequence of the human ELN gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 37 or SEQ ID NO: 38. In some embodiments, a polynucleotide of the present disclosure comprises the sequence of SEQ ID NO: 37 or SEQ ID NO: 38.

In some embodiments, a polynucleotide of the present disclosure comprises a 5' truncation, a 3' truncation, or a fragment of the sequence of SEQ ID NO: 37 or SEQ ID NO: 38. In some embodiments, the 5' truncation, 3' truncation, or fragment of the sequence of SEQ ID NO: 37 or SEQ ID NO: 38 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2250, but fewer than 2361, consecutive nucleotides of SEQ ID NO: 37 or SEQ ID NO: 38. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-2358 of SEQ ID NO: 37 or SEQ ID NO: 38. In some embodiments, a polynucleotide of the present disclosure comprises the sequence of nucleic acids 1-2358 of SEQ ID NO: 37 or SEQ ID NO: 38.

Polynucleotides Encoding Lumican Proteins

In some embodiments, the present disclosure relates to a recombinant nucleic acid comprising one or more polynucleotides comprising the coding sequence of a lumican gene. The coding sequence of any lumican gene (including any isoform thereof) from any suitable species known in the art may be encoded by a polynucleotide of the present disclosure, including, for example, a human lumican gene (see e.g., NCBI Gene ID: 4060), a mouse lumican gene (see, e.g., NCBI Gene ID: 17022), a chimpanzee lumican gene (see e.g., NCBI Gene ID: 452119), a rat lumican gene (see e.g., NCBI Gene ID: 81682), a rabbit lumican gene (see e.g., NCBI Gene ID: 100008665), etc. Methods of identifying lumican gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the lumican genes (and/or coding sequences thereof) described herein or known in the art. In some embodiments, a polynucleotide of the present disclosure comprises a codon-optimized variant of any of the lumican genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human lumican gene. In some embodiments, a polynucleotide of the present disclosure comprises the coding sequence of the human LUM gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 39 or SEQ ID NO: 40. In some embodiments, a polynucleotide of the present disclosure comprises the sequence of SEQ ID NO: 39 or SEQ ID NO: 40.

In some embodiments, a polynucleotide of the present disclosure comprises a 5' truncation, a 3' truncation, or a fragment of the sequence of SEQ ID NO: 39 or SEQ ID NO: 40. In some embodiments, the 5' truncation, 3' truncation, or fragment of the sequence of SEQ ID NO: 39 or SEQ ID NO: 40 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, but fewer than 1017, consecutive nucleotides of SEQ ID NO: 39 or SEQ ID NO: 40. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-1014 of SEQ ID NO: 39 or SEQ ID NO: 40. In some embodiments, a polynucleotide of the present disclosure comprises the sequence of nucleic acids 1-1014 of SEQ ID NO: 39 or SEQ ID NO: 40.

Polynucleotides Encoding Vitronectin and Vitronectin Receptor Proteins

In some embodiments, the present disclosure relates to a recombinant nucleic acid comprising one or more polynucleotides comprising the coding sequence of a vitronectin or vitronectin receptor gene. The coding sequence of any vitronectin or vitronectin receptor gene (including any isoform thereof) from any suitable species known in the art may be encoded by a polynucleotide of the present disclosure, including, for example, a human vitronectin or vitronectin receptor gene (see e.g., NCBI Gene IDs: 7448 and 3685), a mouse vitronectin or vitronectin receptor gene (see, e.g., NCBI Gene IDs: 22370 and 16410), a chimpanzee vitronectin or vitronectin receptor gene (see e.g., NCBI Gene IDs: 738261 and 459807), a rat vitronectin or vitronectin receptor gene (see e.g., NCBI Gene IDs: 29169 and 257645), a rabbit vitronectin or vitronectin receptor gene (see e.g., NCBI Gene IDs: 100009128 and 100008956), etc. Methods of identifying vitronectin or vitronectin receptor gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the vitronectin or vitronectin receptor genes (and/or coding sequences thereof) described herein or known in the art. In some embodiments, a polynucleotide of the present disclosure comprises a codon-optimized variant of any of the vitronectin or vitronectin receptor genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human vitronectin or vitronectin receptor gene. In some embodiments, a polynucleotide of the present disclosure comprises the coding sequence of the human VTN gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 41 or SEQ ID NO: 42. In some embodiments, a polynucleotide of the present disclosure comprises the sequence of SEQ ID NO: 41 or SEQ ID NO: 42.

In some embodiments, a polynucleotide of the present disclosure comprises a 5' truncation, a 3' truncation, or a fragment of the sequence of SEQ ID NO: 41 or SEQ ID NO: 42. In some embodiments, the 5' truncation, 3' truncation, or fragment of the sequence of SEQ ID NO: 41 or SEQ ID NO: 42 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least about 1250, but fewer than 1437, consecutive nucleotides of SEQ ID NO: 41 or SEQ ID NO: 42. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-1034 of SEQ ID NO: 41 or SEQ ID NO: 42. In some embodiments, a polynucleotide of the present disclosure comprises the sequence of nucleic acids 1-1034 of SEQ ID NO: 41 or SEQ ID NO: 42.

Polynucleotides Encoding Laminin Proteins

In some embodiments, the present disclosure relates to a recombinant nucleic acid comprising one or more polynucleotides comprising the coding sequence of a laminin gene. The coding sequence of any laminin gene (including any isoform thereof) from any suitable species known in the art may be encoded by a polynucleotide of the present disclosure, including, for example, human laminin genes (see e.g., NCBI Gene IDs: 284217, 3908, 3909, 3910, 3911, 3912, 3913, 3914, 3915, 3918, and 10319), mouse laminin genes (see e.g., NCBI Gene IDs: 16774, 16780, and 16782), chimpanzee laminin genes (see e.g., NCBI Gene IDs: 455339, 469668, and 457571), rat laminin genes (see e.g., NCBI Gene IDs: 307582, 305078, and 192362), rabbit laminin genes (see e.g., NCBI Gene IDs: 100346886 and 100342905), etc. Methods of identifying laminin gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the laminin genes (and/or coding sequences thereof) described herein or known in the art. In some embodiments, a polynucleotide of the present disclosure comprises a codon-optimized variant of any of the laminin genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human laminin gene, such as a human LAMA1 gene (see e.g., NCBI Gene ID: 284217), a human LAMA2 gene (see e.g., NCBI Gene ID: 3908), a human LAMA3 gene (see e.g., NCBI Gene ID: 3909), a human LAMA4 gene (see e.g., NCBI Gene ID: 3910), a human LAMA5 gene (see e.g., NCBI Gene ID: 3911), a human LAMB1 gene (see e.g., NCBI Gene ID: 3912), a human LAMB2 gene (see e.g., NCBI Gene ID: 3913), a human LAMB3 gene (see e.g., NCBI Gene ID: 3914), a human LAMC1 gene (see e.g., NCBI Gene ID: 3915), a human LAMC2 gene (see e.g., NCBI Gene ID: 3918), or a human LAMC3 gene (see e.g., NCBI Gene ID: 10319).

In some embodiments, a polynucleotide of the present disclosure comprises the coding sequence of the human LAMA3 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 43 or SEQ ID NO: 44. In some embodiments, a polynucleotide of the present disclosure comprises the sequence of SEQ ID NO: 43 or SEQ ID NO: 44.

In some embodiments, a polynucleotide of the present disclosure comprises a 5' truncation, a 3' truncation, or a fragment of the sequence of SEQ ID NO: 43 or SEQ ID NO: 44. In some embodiments, the 5' truncation, 3' truncation, or fragment of the sequence of SEQ ID NO: 43 or SEQ ID NO: 44 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, at least 4000, at least about 4500, at least about 5000, but fewer than 5175, consecutive nucleotides of SEQ ID NO: 43 or SEQ ID NO: 44. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-5172 of SEQ ID NO: 43 or SEQ ID NO: 44. In some embodiments, a polynucleotide of the present disclosure comprises the sequence of nucleic acids 1-5172 of SEQ ID NO: 43 or SEQ ID NO: 44.

In some embodiments, a polynucleotide of the present disclosure comprises the coding sequence of the human LAMB3 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 45 or SEQ ID NO: 46. In some embodiments, a polynucleotide of the present disclosure comprises the sequence of SEQ ID NO: 45 or SEQ ID NO: 46.

In some embodiments, a polynucleotide of the present disclosure comprises a 5' truncation, a 3' truncation, or a fragment of the sequence of SEQ ID NO: 45 or SEQ ID NO: 46. In some embodiments, the 5' truncation, 3' truncation, or fragment of the sequence of SEQ ID NO: 45 or SEQ ID NO: 46 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, but fewer than 3519, consecutive nucleotides of SEQ ID NO: 45 or SEQ ID NO: 46. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3516 of SEQ ID NO: 45 or SEQ ID NO: 46. In some embodiments, a polynucleotide of the present disclosure comprises the sequence of nucleic acids 1-3516 of SEQ ID NO: 45 or SEQ ID NO: 46.

In some embodiments, a polynucleotide of the present disclosure comprises the coding sequence of the human LAMC2 gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 47 or SEQ ID NO: 48. In some embodiments, a polynucleotide of the present disclosure comprises the sequence of SEQ ID NO: 47 or SEQ ID NO: 48.

In some embodiments, a polynucleotide of the present disclosure comprises a 5' truncation, a 3' truncation, or a fragment of the sequence of SEQ ID NO: 47 or SEQ ID NO: 48. In some embodiments, the 5' truncation, 3' truncation, or fragment of the sequence of SEQ ID NO: 47 or SEQ ID NO: 48 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least 1250, at least 1500, at least 1750, at least 2000, at least 2500, at least 3000, at least 3500, but fewer than 3582, consecutive nucleotides of SEQ ID NO: 47 or SEQ ID NO: 48. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3579 of SEQ ID NO: 47 or SEQ ID NO: 48. In some embodiments, a polynucleotide of the present disclosure comprises the sequence of nucleic acids 1-3579 of SEQ ID NO: 47 or SEQ ID NO: 48.

Polynucleotides Encoding Neuromodulator Proteins

In some embodiments, the present disclosure relates to a recombinant nucleic acid comprising one or more polynucleotides comprising the coding sequence of a neuromodulator gene. The coding sequence of any neuromodulator gene (including any isoform thereof) from any suitable species known in the art may be encoded by a polynucleotide of the present disclosure, including, for example, a *Clostridium botulinum* neuromodulator gene (see e.g., NCBI Gene IDs: 5185061 and 39483740), etc. Methods of identifying neuromodulator gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the neuromodulator genes (and/or coding sequences thereof) described herein or known in the art. In some embodiments, a polynucleotide of the present disclosure comprises a codon-optimized variant of any of the neuromodulator genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a *Clostridium botulinum* neuromodulator gene.

In some embodiments, a polynucleotide of the present disclosure comprises the coding sequence of the *Clostridium botulinum* botA gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 49 or SEQ ID NO: 50. In some embodiments, a polynucleotide of the present disclosure comprises the sequence of SEQ ID NO: 49 or SEQ ID NO: 50.

In some embodiments, a polynucleotide of the present disclosure comprises a 5' truncation, a 3' truncation, or a fragment of the sequence of SEQ ID NO: 49 or SEQ ID NO: 50. In some embodiments, the 5' truncation, 3' truncation, or fragment of the sequence of SEQ ID NO: 49 or SEQ ID NO: 50 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least about 1250, at least 1500, at least 1750, at least 2000, at least 2500, at least 3000, at least 3500, but fewer than 3891, consecutive nucleotides of SEQ ID NO: 49 or SEQ ID NO: 50. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3888 of SEQ ID NO: 49 or SEQ ID NO: 50. In some embodiments, a polynucleotide of the present disclosure comprises the sequence of nucleic acids 1-3888 of SEQ ID NO: 49 or SEQ ID NO: 50.

In some embodiments, a polynucleotide of the present disclosure comprises the coding sequence of the *Clostridium botulinum* botB gene (or a codon-optimized variant thereof). In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 51 or SEQ ID NO: 52. In some embodiments, a polynucleotide of the present disclosure comprises the sequence of SEQ ID NO: 51 or SEQ ID NO: 52.

In some embodiments, a polynucleotide of the present disclosure comprises a 5' truncation, a 3' truncation, or a fragment of the sequence of SEQ ID NO: 51 or SEQ ID NO: 52. In some embodiments, the 5' truncation, 3' truncation, or fragment of the sequence of SEQ ID NO: 51 or SEQ ID NO: 52 is a polynucleotide that has at least 25, at least 50, at least 75, at least 100, at least 125, at least 150, at least 175, at least 200, at least 250, at least 300, or at least 350, at least 400, at least 450, at least 500, at least 750, at least 1000, at least about 1250, at least 1500, at least 1750, at least 2000, at least 2500, at least 3000, at least 3500, but fewer than 3876, consecutive nucleotides of SEQ ID NO: 51 or SEQ ID NO: 52. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of nucleic acids 1-3873 of SEQ ID NO: 51 or SEQ ID NO: 52. In some embodiments, a polynucleotide of the present disclosure comprises the sequence of nucleic acids 1-3873 of SEQ ID NO: 51 or SEQ ID NO: 52.

Polynucleotides Encoding Fibrillin Proteins

In some embodiments, the present disclosure relates to a recombinant nucleic acid comprising one or more polynucleotides comprising the coding sequence of a fibrillin gene. The coding sequence of any fibrillin gene (including any isoform thereof) from any suitable species known in the art may be encoded by a polynucleotide of the present disclosure, including, for example, human fibrillin genes (see e.g., NCBI Gene IDs: 2200, 2201, and 84467), mouse fibrillin genes (see e.g., NCBI Gene IDs: 14118 and 14119), chimpanzee fibrillin genes (see e.g., NCBI Gene IDs: 453411, 471621, and 455669), rat fibrillin genes (see e.g., NCBI Gene IDs: 83727 and 689008), rabbit fibrillin genes (see e.g., NCBI Gene IDs: 100350931, 100357126, and 100359336), etc. Methods of identifying fibrillin gene homologs/orthologs from additional species are known to one of ordinary skill in the art. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the fibrillin genes (and/or coding sequences thereof) described herein or known in the art. In some embodiments, a polynucleotide of the present disclosure comprises a codon-optimized variant of any of the fibrillin genes (and/or coding sequences thereof) described herein or known in the art.

In some embodiments, the present disclosure relates to one or more polynucleotides (i.e., one or more first polynucleotides and/or one or more second polynucleotides) comprising the coding sequence of a human fibrillin gene, such as a human FBN1 gene (see e.g., NCBI Gene ID: 2200), a human FBN2 gene (see e.g., NCBI Gene ID: 2201), or a human FBN3 gene (see e.g., NCBI Gene ID: 84467).

Exemplary Polynucleotides

In some embodiments, a polynucleotide of the present disclosure encoding one or more cosmetic proteins (e.g., a first cosmetic protein, a further cosmetic protein, an additional cosmetic protein, and/or a second cosmetic protein) has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14 or 35-52. In some embodiments, a polynucleotide of the present disclosure encoding one or more cosmetic proteins (e.g., a first cosmetic protein, a further cosmetic protein, an additional cosmetic protein, and/or a second cosmetic protein) comprises a sequence selected from SEQ ID NOS: 1-14 or 35-52.

In some embodiments, a polynucleotide of the present disclosure encoding one or more cosmetic proteins (e.g., a first cosmetic protein, a further cosmetic protein, an additional cosmetic protein, and/or a second cosmetic protein) has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NOS: 1-14, 35-38, or 43-48. In some embodiments, a polynucleotide of the present disclosure encoding one or more cosmetic proteins (e.g., a first cosmetic protein, a further cosmetic protein, an additional cosmetic protein, and/or a second cosmetic protein) comprises a sequence selected from SEQ ID NOS: 1-14, 35-38, or 43-48.

A polynucleotide of the present disclosure encoding a cosmetic protein (e.g., a human collagen protein) may further encode additional coding and non-coding sequences. Examples of additional coding and non-coding sequences may include, but are not limited to, sequences encoding additional polypeptide tags (e.g., encoded in-frame with the cosmetic protein in order to produce a fusion protein), introns (e.g., native, modified, or heterologous introns), 5' and/or 3' UTRs (e.g., native, modified, or heterologous 5' and/or 3' UTRs), and the like. Examples of suitable polypeptide tags may include, but are not limited to, any combination of purification tags, such as his-tags, flag-tags, maltose binding protein and glutathione-S-transferase tags, detection tags, such as tags that may be detected photometrically (e.g., green fluorescent protein, red fluorescent protein, etc.) and tags that have a detectable enzymatic activity (e.g., alkaline phosphatase, etc.), tags containing secretory sequences, signal sequences, leader sequences, and/or stabilizing sequences, protease cleavage sites (e.g., furin cleavage sites, TEV cleavage sites, Thrombin cleavage sites, etc.), and the like. In some embodiments, the 5' and/or 3'UTRs increase the stability, localization, and/or translational efficiency of the polynucleotides. In some embodiments, the 5' and/or 3'UTRs improve the level and/or duration of protein expression. In some embodiments, the 5' and/or 3'UTRs include elements (e.g., one or more miRNA binding sites, etc.) that may block or reduce off-target expression (e.g., inhibiting expression in specific cell types (e.g., neuronal cells), at specific times in the cell cycle, at specific developmental stages, etc.). In some embodiments, the 5' and/or 3'UTRs include elements (e.g., one or more miRNA binding sites, etc.) that may enhance cosmetic protein expression in specific cell types (such as human keratinocytes and/or fibroblasts).

In some embodiments, a polynucleotide of the present disclosure encoding a cosmetic protein (e.g., a human collagen protein) is operably linked to one or more (e.g., one or more, two or more, three or more, four or more, five or more, ten or more, etc.) regulatory sequences. The term "regulatory sequence" may include enhancers, insulators, promoters, and other expression control elements (e.g., polyadenylation signals). Any suitable enhancer(s) known in the art may be used, including, for example, enhancer sequences from mammalian genes (such as globin, elastase, albumin, α-fetoprotein, insulin and the like), enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like), and any combinations thereof. Any suitable insulator(s) known in the art may be used, including, for example, HSV chromatin boundary (CTRL/CTCF-binding/insulator) elements CTRL1 and/or CTRL2, chicken hypersensitive site 4 insulator (cHS4), human HNRPA2B1-CBX3 ubiquitous chromatin opening element (UCOE), the scaffold/matrix attachment region (S/MAR) from the human interferon beta gene (IFNB1), and any combinations thereof. Any suitable promoter (e.g., suitable for transcription in mammalian host cells) known in the art may be used, including, for example, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), promoters from heterologous mammalian genes (such as the actin promoter (e.g., the (3-actin promoter), a ubiquitin promoter (e.g., a ubiquitin C (UbC) promoter), a phosphoglycerate kinase (PGK) promoter, an immunoglobulin promoter, from heat-shock promoters, and the like), promoters from homologous mammalian genes (e.g., native human collagen, fibronectin, elastin, lumican, vitronectin, laminin, and/or fibrillin promoters), synthetic promoters (such as the CAGG promoter), and any combinations thereof, provided such promoters are compatible with the host cells. Regulatory sequences may include those which direct constitutive expression of a nucleic acid, as well as tissue-specific regulatory and/or inducible or repressible sequences.

In some embodiments, a polynucleotide of the present disclosure encoding cosmetic protein (e.g., a human collagen protein) is operably linked to one or more heterologous promoters. In some embodiments, the one or more heterologous promoters are one or more of constitutive promoters, tissue-specific promoters, temporal promoters, spatial promoters, inducible promoters and repressible promoters. In some embodiments, the one or more heterologous promoters are one or more of the human cytomegalovirus (HCMV) immediate early promoter, the human elongation factor-1 (EF1) promoter, the human (3-actin promoter, the human UbC promoter, the human PGF promoter, the synthetic CAGG promoter, and any combinations thereof. In some embodiments, a polynucleotide of the present disclosure encoding a cosmetic protein (e.g., a human collagen protein) is operably linked to an HCMV promoter.

In some embodiments, a polynucleotide of the present disclosure does not comprise the coding sequence of (e.g., a transgene encoding) a Collagen alpha-1 (VII) chain polypeptide (COL7). In some embodiments, a polynucleotide of the present disclosure does not comprise the coding sequence of (e.g., a transgene encoding) a Lysyl hydroxylase 3 polypeptide (LH3). In some embodiments, a polynucleotide of the present disclosure does not comprise the coding sequence of (e.g., a transgene encoding) a Keratin type I cytoskeletal 17 polypeptide (KRT17). In some embodiments, a polynucleotide of the present disclosure does not comprise the coding sequence of (e.g., a transgene encoding) a transglutaminase (TGM) polypeptide (e.g., a human transglutaminase polypeptide such as a human TGM1 polypeptide). In some embodiments, a polynucleotide of the present disclosure does not comprise the coding sequence of (e.g., a transgene encoding) a laminin subunit beta-3 polypeptide (LAMB3). In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, and/or any chimeric polypeptides thereof. In some embodiments, a polynucleotide of the present disclosure does not comprise the coding sequence of (e.g., a transgene encoding) a Collagen alpha-1 (VII) chain polypeptide, a Lysyl hydroxylase 3 polypeptide, a Keratin type I cytoskeletal 17 polypeptide, a transglutaminase (TGM) polypeptide (e.g., a human transglutaminase polypeptide such as a human TGM1 polypeptide), a laminin subunit beta-3 (LAMB3) polypeptide (e.g., a human LamB3 polypeptide) and/or any chimeric polypeptides thereof.

Cosmetic Proteins
Collagen Proteins

In some embodiments, the present disclosure relates to one or more polynucleotides encoding a full-length collagen protein or any isoforms or portions thereof. Any collagen protein from any suitable species known in the art may be encoded by a polynucleotide of the present disclosure, including, for example, human collagen proteins (see e.g., UniProt accession numbers P02452, P08123, P02461, P02462, P08572, P12109, Q02388, Q9UMD9. etc.), mouse collagen proteins (see, e.g., UniProt accession numbers P11087, Q01149, P08121, P02463, P08122, Q04857, Q63870, Q07563, etc.), chimpanzee collagen proteins (see e.g., UniProt accession numbers A0A2I3SM98, A0A2J8L483, H2QJ46, K7C8P4, K7C8W0, A0A2J8M8U9, H2QMJ5, H2Q2J4, etc.), rat collagen proteins (see e.g., UniProt accession numbers P02454, P02466, P13941, P02466, F1M6Q3, D3ZUL3, D3ZE04, D3ZE04, etc.), rabbit collagen proteins (see e.g., UniProt accession numbers G1T4A5, Q28668, G1T8J0, G1U9R7, G1T548, G1T380, G1T548, etc.) etc. Methods of identifying collagen protein homologs/orthologs from additional species are known to one of ordinary skill in the art, including, for example, using an amino acid sequence alignment program such as the BLAST® blastp suite or OrthoDB. In some embodiments, a collagen polypeptide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the collagen polypeptides described herein or known in the art.

In some embodiments, the present disclosure relates to one or more polynucleotides encoding a human collagen protein. Any suitable human collagen protein known in the art may be encoded by a polynucleotide of the present disclosure, including, for example, a Collagen alpha-1(I) chain polypeptide (COL1-1) (see e.g., UniProt accession number P02452; SEQ ID NO: 15), a Collagen alpha-2(I) chain polypeptide (COL1-2) (see e.g., UniProt accession number P08123; SEQ ID NO: 16), a Collagen alpha-1(II) chain polypeptide (COL2) (see e.g., UniProt accession number P02458), a Collagen alpha-1(III) chain polypeptide (COL3) (see e.g., UniProt accession number P2461; SEQ ID NO: 17), a Collagen alpha-1(IV) chain polypeptide (COL4-1) (see e.g., UniProt accession number P02462; SEQ ID NO: 18), a Collagen alpha-2(IV) chain polypeptide (COL4-2) (see e.g., UniProt accession number P08572), a Collagen alpha-3(IV) chain polypeptide (COL4-3) (see e.g., UniProt accession number Q01955), a Collagen alpha-4(IV) chain polypeptide (COL4-4) (see e.g., UniProt accession number P53420), a Collagen alpha-5(IV) chain polypeptide (COL4-5) (see e.g., UniProt accession number 29400), a Collagen alpha-6(IV) chain polypeptide (COL4-6) (see e.g., UniProt accession number Q14031), a Collagen alpha-1(V) chain polypeptide (COL5-1) (see e.g., UniProt accession number P20908), a Collagen alpha-2(V) chain polypeptide (COL5-2) (see e.g., UniProt accession number P05997), a Collagen alpha-3(V) chain polypeptide (COL5-3) (see e.g., UniProt accession number P25940), a Collagen alpha-1(VI) chain polypeptide (COL6-1) (see e.g., UniProt accession number P12109; SEQ ID NO: 19), a Collagen alpha-2(VI) chain polypeptide (COL6-2) (see e.g., UniProt accession number P12110), a Collagen alpha-3(VI) chain polypeptide (COL6-3) (see e.g., UniProt accession number P12111), a Collagen alpha-4(VI) chain polypeptide (COL6-4), a Collagen alpha-5(VI) chain polypeptide (COL6-5) (see e.g., UniProt accession number A8TX70), a Collagen alpha-6(VI) chain polypeptide (COL6-6) (see e.g., UniProt accession number A6NMZ7), a Collagen alpha-1(VII) chain polypeptide (COL7) (see e.g., UniProt accession number Q02388; SEQ ID NO: 20), a Collagen alpha-1(VIII) chain polypeptide (COL8) (see e.g., UniProt accession number P27658), a Collagen alpha-1(IX) chain polypeptide (COL9-1) (see e.g., UniProt accession number P20849), a Collagen alpha-2(IX) chain polypeptide (COL9-2) (see e.g., UniProt accession number Q14055), a Collagen alpha-3(IX) chain polypeptide (COL9-3) (see e.g., UniProt accession number Q14050), a Collagen alpha-1(X) chain polypeptide (COL10) (see e.g., UniProt accession number Q03692), a Collagen alpha-1(XI) chain polypeptide (COL11-1) (see e.g., UniProt accession number P12107), a Collagen alpha-2(XI) chain polypeptide (COL11-2) (see e.g., UniProt accession number P13942), a Collagen alpha-1(XII) chain polypeptide (COL12) (see e.g., UniProt accession number Q99715), a Collagen alpha-1 (XIII) chain polypeptide (COL13) (see e.g., UniProt accession number Q5TAT6), a Collagen alpha-1(XIV) chain polypeptide (COL14) (see e.g., UniProt accession number Q05707), a Collagen alpha-1(XV) chain polypeptide (COL15) (see e.g., UniProt accession number P39059), a Collagen alpha-1(XVI) chain polypeptide (COL16) (see e.g., UniProt accession number Q07092), a Collagen alpha-1(XVII) chain polypeptide (COL17) (see e.g., UniProt accession number Q9UMD9; SEQ ID NO: 21), a Collagen alpha-1(XVIII) chain polypeptide (COL18) (see e.g., UniProt accession number P39060), a Collagen alpha-1(XIX) chain polypeptide (COL19) (see e.g., UniProt accession number Q14993), a Collagen alpha-1(XX) chain polypeptide (COL20) (see e.g., UniProt accession number Q9P218), a Collagen alpha-1(XXI) chain polypeptide (COL21) (see e.g., UniProt accession number Q96P44), a Collagen alpha-1(XXII) chain polypeptide (COL22) (see e.g., UniProt accession number Q8NFW1), a Collagen alpha-1(XXIII) chain polypeptide (COL23) (see e.g., UniProt accession number Q86Y22), a Collagen alpha-1(XXIV) chain polypeptide (COL24) (see e.g., UniProt accession number Q17RW2), a Collagen alpha-1(XXV) chain polypeptide (COL25) (see e.g., UniProt accession number Q9BXS0), a Collagen alpha-1(XXVI) chain polypeptide (COL26) (see e.g., UniProt accession number Q96A83), a Collagen alpha-1(XXVII) chain polypeptide (COL27) (see e.g., UniProt accession number Q8IZC6), a Collagen alpha-1(XXVIII) chain polypeptide (COL28) (see e.g., UniProt accession number Q2UY09), etc. In some embodiments, a polynucleotide of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence encoding any of the human collagen polypeptides described herein or known in the art. Methods of identifying additional human collagen or collagen-like polypeptide homologs/orthologs are known to one of ordinary skill in the art, including, for example, using an amino acid sequence alignment program such as the BLAST® blastp suite or OrthoDB.

In some embodiments, a polynucleotide of the present disclosure encodes a human COL1-1 protein. In some embodiments, a polynucleotide encoding a COL1-1 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 15. In some embodiments, a polynucleotide encoding a human COL1-1 protein is a polynucleotide that encodes a polypeptide comprising the amino acid sequence of SEQ ID NO: 15.

In some embodiments, a polynucleotide encoding a COL1-1 protein is a polynucleotide that encodes an N-terminal truncation, a C-terminal truncation, or a fragment of the amino acid sequence of SEQ ID NO: 15. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, but fewer than 1464, consecutive amino acids of SEQ ID NO: 15.

In some embodiments, a polynucleotide of the present disclosure encodes a human COL1-2 protein. In some embodiments, a polynucleotide encoding a COL1-2 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 16. In some embodiments, a polynucleotide encoding a human COL1-2 protein is a polynucleotide that encodes a polypeptide comprising the amino acid sequence of SEQ ID NO: 16.

In some embodiments, a polynucleotide encoding a COL1-2 protein is a polynucleotide that encodes an N-terminal truncation, a C-terminal truncation, or a fragment of the amino acid sequence of SEQ ID NO: 16. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, but fewer than 1366, consecutive amino acids of SEQ ID NO: 16.

In some embodiments, a polynucleotide of the present disclosure encodes a human COL3 protein. In some embodiments, a polynucleotide encoding a COL3 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 17. In some embodiments, a polynucleotide encoding a human COL3 protein is a polynucleotide that encodes a polypeptide comprising the amino acid sequence of SEQ ID NO: 17.

In some embodiments, a polynucleotide encoding a COL3 protein is a polynucleotide that encodes an N-terminal truncation, a C-terminal truncation, or a fragment of the amino acid sequence of SEQ ID NO: 17. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, but fewer than 1466, consecutive amino acids of SEQ ID NO: 17.

In some embodiments, a polynucleotide of the present disclosure encodes a human COL4-1 protein. In some embodiments, a polynucleotide encoding a COL4-1 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 18. In some embodiments, a polynucleotide encoding a human COL4-1 protein is a polynucleotide that encodes a polypeptide comprising the amino acid sequence of SEQ ID NO: 18.

In some embodiments, a polynucleotide encoding a COL4-1 protein is a polynucleotide that encodes an N-terminal truncation, a C-terminal truncation, or a fragment of the amino acid sequence of SEQ ID NO: 18. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, at least 1500, at least 1600, but fewer than 1669, consecutive amino acids of SEQ ID NO: 18.

In some embodiments, a polynucleotide of the present disclosure encodes a human COL6A-1 protein. In some embodiments, a polynucleotide encoding a COL6-1 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 19. In some embodiments, a polynucleotide encoding a human COL6-1 protein is a polynucleotide that encodes a polypeptide comprising the amino acid sequence of SEQ ID NO: 19.

In some embodiments, a polynucleotide encoding a COL6-1 protein is a polynucleotide that encodes an N-terminal truncation, a C-terminal truncation, or a fragment of the amino acid sequence of SEQ ID NO: 19. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, but fewer than 1028, consecutive amino acids of SEQ ID NO: 19.

In some embodiments, a polynucleotide of the present disclosure encodes a human COL7 protein. In some embodiments, a polynucleotide encoding a COL7 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 20. In some embodiments, a polynucleotide encoding a human COL7 protein is a polynucleotide that encodes a polypeptide comprising the amino acid sequence of SEQ ID NO: 20.

In some embodiments, a polynucleotide encoding a COL7 protein is a polynucleotide that encodes an N-terminal truncation, a C-terminal truncation, or a fragment of the amino acid sequence of SEQ ID NO: 20. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, at least 2000, at least 2100, at least 2200, at least 2300, at least 2400, at least 2500, at least 2600, at least 2700, at least 2800, at least 2900, but fewer than 2944, consecutive amino acids of SEQ ID NO: 20.

In some embodiments, a polynucleotide of the present disclosure encodes a human COL17 protein. In some embodiments, a polynucleotide encoding a COL17 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 21. In some embodiments, a polynucleotide encoding a human COL17 protein is a polynucleotide that encodes a polypeptide comprising the amino acid sequence of SEQ ID NO: 21.

In some embodiments, a polynucleotide encoding a COL17 protein is a polynucleotide that encodes an N-terminal truncation, a C-terminal truncation, or a fragment of the amino acid sequence of SEQ ID NO: 21. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, but fewer than 1497, consecutive amino acids of SEQ ID NO: 21.

In some embodiments, one or more human collagen proteins of the present disclosure (e.g., a first human collagen protein, a further human collagen protein, an additional human collagen protein, and/or a second human collagen protein) comprise an amino acid sequence comprising at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21. In some embodiments, one or more human collagen proteins of the present disclosure (e.g., a first human collagen protein, a further human collagen protein, an additional human collagen protein, and/or a second human collagen protein) comprise a sequence selected from SEQ ID NOS: 15-21.

In some embodiments, one or more human collagen proteins of the present disclosure (e.g., a first human collagen protein, a further human collagen protein, an additional human collagen protein, and/or a second human collagen protein) comprise an amino acid sequence comprising at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-17. In some embodiments, one or more human collagen proteins of the present disclosure (e.g., a first human collagen protein, a further human collagen protein, an additional human collagen protein, and/or a second human collagen protein) comprise a sequence selected from SEQ ID NOS: 15-17.

Fibronectin Proteins

In some embodiments, the present disclosure relates to one or more polynucleotides encoding a full-length fibronectin protein or any isoforms or portions thereof. Any fibronectin protein from any suitable species known in the art may be encoded by a polynucleotide of the present disclosure, including, for example, a human fibronectin protein (see e.g., UniProt accession number P02751), a mouse fibronectin protein (see, e.g., UniProt accession number P11276), a chimpanzee fibronectin protein (see e.g., UniProt accession number P11276), a rat fibronectin protein (see e.g., UniProt accession number P04937), a rabbit fibronectin protein (see e.g., UniProt accession number P04937), etc. Methods of identifying fibronectin protein homologs/orthologs from additional species are known to one of ordinary skill in the art. In some embodiments, a fibronectin protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the fibronectin proteins described herein or known in the art.

In some embodiments, a polynucleotide of the present disclosure encodes a human fibronectin protein. In some embodiments, a polynucleotide encoding a human fibronectin protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 53. In some embodiments, a polynucleotide encoding a human fibronectin protein is a polynucleotide that encodes a polypeptide comprising the amino acid sequence of SEQ ID NO: 53.

In some embodiments, a polynucleotide encoding a human fibronectin protein is a polynucleotide that encodes an N-terminal truncation, a C-terminal truncation, or a fragment of the amino acid sequence of SEQ ID NO: 53. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, at least 2000, at least 2100, at least 2200, at least 2300, at least 2400, but fewer than 2477, consecutive amino acids of SEQ ID NO: 53.

Elastin and Associated Proteins

Elastic fibers in the extracellular matrix give elastic properties to the tissue. The elastic fibers generally contain two morphologically distinct components—the mature elastin fibers, and the micro-fibrils which mainly contain fibrillin and are associated with further proteins such as the micro-fibrils associated glycoproteins (MAGPs), fibulines, and the elastin-micro-fibrills-interface localized proteins (EMILIN). Elastin and its soluble precursor tropoelastin belong to the major structural proteins of the body.

In some embodiments, the present disclosure relates to one or more polynucleotides encoding an elastin or elastin-associated protein, including a tropoelastin, a fibrillin, a micro-fibrils associated glycoprotein, a fibuline, or an elastin-micro-fibrills-interface localized protein. In some embodiments, the present disclosure relates to one or more polynucleotides encoding a full-length elastin protein or any isoforms or portions thereof. Any elastin protein from any suitable species known in the art may be encoded by a polynucleotide of the present disclosure, including, for example, a human elastin protein (see e.g., UniProt accession number P15502), a mouse elastin protein (see, e.g., UniProt accession number P15502), a chimpanzee elastin protein (see e.g., UniProt accession number H2QUQ6), a rat elastin protein (see e.g., UniProt accession number Q99372), etc. Methods of identifying elastin protein homologs/orthologs from additional species are known to one of ordinary skill in the art. In some embodiments, an elastin protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the elastin proteins described herein or known in the art.

In some embodiments, a polynucleotide of the present disclosure encodes a human elastin protein. In some embodiments, a polynucleotide encoding a human elastin protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 54. In some embodiments, a polynucleotide encoding a human elastin protein is a polynucleotide that encodes a polypeptide comprising the amino acid sequence of SEQ ID NO: 54.

In some embodiments, a polynucleotide encoding a human elastin protein is a polynucleotide that encodes an N-terminal truncation, a C-terminal truncation, or a fragment of the amino acid sequence of SEQ ID NO: 54. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, but fewer than 786, consecutive amino acids of SEQ ID NO: 54.

Lumican Proteins

In some embodiments, the present disclosure relates to one or more polynucleotides encoding a full-length lumican protein or any isoforms or portions thereof. Any lumican protein from any suitable species known in the art may be encoded by a polynucleotide of the present disclosure, including, for example, a human lumican protein (see e.g., UniProt accession number P51884), a mouse lumican protein (see, e.g., UniProt accession number P51885), a chimpanzee lumican protein (see e.g., UniProt accession number H2Q6L3), a rat lumican protein (see e.g., UniProt accession number H2Q6L3), a rabbit lumican protein (see e.g., UniProt accession number O46379), etc. Methods of identifying lumican protein homologs/orthologs from additional species are known to one of ordinary skill in the art. In some embodiments, a lumican protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the lumican proteins described herein or known in the art.

In some embodiments, a polynucleotide of the present disclosure encodes a human lumican protein. In some embodiments, a polynucleotide encoding a human lumican protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 55. In some embodiments, a polynucleotide encoding a human lumican protein is a polynucleotide that encodes a polypeptide comprising the amino acid sequence of SEQ ID NO: 55.

In some embodiments, a polynucleotide encoding a human lumican protein is a polynucleotide that encodes an N-terminal truncation, a C-terminal truncation, or a fragment of the amino acid sequence of SEQ ID NO: 55. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, but fewer than 338, consecutive amino acids of SEQ ID NO: 55.

Vitronectin and Vitronectin Receptor Proteins

In some embodiments, the present disclosure relates to one or more polynucleotides encoding a full-length vitronectin or vitronectin receptor protein or any isoforms or portions thereof. Any vitronectin or vitronectin receptor protein from any suitable species known in the art may be encoded by a polynucleotide of the present disclosure, including, for example, a human vitronectin or vitronectin receptor protein (see e.g., UniProt accession numbers P04004 and P06756), a mouse vitronectin or vitronectin receptor protein (see, e.g., UniProt accession numbers P29788 and P43406), a chimpanzee vitronectin or vitronectin receptor protein (see e.g., UniProt accession numbers H2QCH3 and H2R6C3), a rat vitronectin or vitronectin receptor protein (see e.g., UniProt accession number Q7TQ11), a rabbit vitronectin or vitronectin receptor protein (see e.g., UniProt accession number P22458), etc. Methods of identifying vitronectin or vitronectin receptor protein homologs/orthologs from additional species are known to one of ordinary skill in the art. In some embodiments, a vitronectin or vitronectin receptor protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the vitronectin or vitronectin receptor proteins described herein or known in the art.

In some embodiments, a polynucleotide of the present disclosure encodes a human vitronectin protein. In some embodiments, a polynucleotide encoding a human vitronectin protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 56. In some embodiments, a polynucleotide encoding a human vitronectin protein is a polynucleotide that encodes a polypeptide comprising the amino acid sequence of SEQ ID NO: 56.

In some embodiments, a polynucleotide encoding a human vitronectin protein is a polynucleotide that encodes an N-terminal truncation, a C-terminal truncation, or a fragment of the amino acid sequence of SEQ ID NO: 56. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, but fewer than 478, consecutive amino acids of SEQ ID NO: 56.

Laminin Proteins

In some embodiments, the present disclosure relates to one or more polynucleotides encoding a full-length laminin protein or any isoforms or portions thereof. Any laminin protein from any suitable species known in the art may be encoded by a polynucleotide of the present disclosure, including, for example, a human laminin protein (see e.g., UniProt accession numbers P25391, P24043, Q16787, Q16363, O15230, P07942, P55268, Q13751, P11047, Q13753, and Q9Y6N6), a mouse laminin protein (see e.g., UniProt accession numbers Q61789, Q61087, and Q61092), a chimpanzee laminin protein (see e.g., UniProt accession numbers H2QEC7, H2R041, and H2Q0R2), a rat laminin protein (see e.g., UniProt accession numbers D3ZN05, F1LPI5, and F1LRH4), a rabbit laminin protein (see e.g., UniProt accession numbers G1SY40 and A0A0B5JSH0), etc. Methods of identifying laminin protein homologs/orthologs from additional species are known to one of ordinary skill in the art. In some embodiments, a laminin protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the laminin proteins described herein or known in the art.

In some embodiments, a polynucleotide of the present disclosure encodes a human laminin protein, such as a human Laminin subunit alpha-1 (LamA1) polypeptide (see e.g., UniProt accession number P25391), a human Laminin subunit alpha-2 (LamA2) polypeptide (see e.g., UniProt accession number P24043), a human Laminin subunit alpha-3 (LamA3) polypeptide (see e.g., UniProt accession number Q16787), a human Laminin subunit alpha-4 (LamA4) polypeptide (see e.g., UniProt accession number Q16363), a human Laminin subunit alpha-5 (LamA5) polypeptide (see e.g., UniProt accession number O15230), a human Laminin subunit beta-1 (LamB1) polypeptide (see e.g., UniProt accession number P07942), a human Laminin subunit beta-2 (LamB2) polypeptide (see e.g., UniProt accession number P55268), a human Laminin subunit beta-3 (LamB3) polypeptide (see e.g., UniProt accession number Q13751), a human Laminin subunit gamma-1 (LamC1) polypeptide (see e.g., UniProt accession number P11047), a human Laminin subunit gamma-2 (LamC2) polypeptide (see e.g., UniProt accession number Q13753), a human Laminin subunit gamma-3 (LamC3) polypeptide (see e.g., UniProt accession number Q9Y6N6), etc.

In some embodiments, a polynucleotide of the present disclosure encodes a human LamA3 polypeptide. In some embodiments, a polynucleotide encoding a human LamA3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 57. In some embodiments, a polynucleotide encoding a human LamA3 polypeptide is a polynucleotide that encodes a polypeptide comprising the amino acid sequence of SEQ ID NO: 57.

In some embodiments, a polynucleotide encoding a human LamA3 polypeptide is a polynucleotide that encodes an N-terminal truncation, a C-terminal truncation, or a fragment of the amino acid sequence of SEQ ID NO: 57. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, at least 3000, at least 3250, but fewer than 3333, consecutive amino acids of SEQ ID NO: 57.

In some embodiments, a polynucleotide of the present disclosure encodes a human LamB3 polypeptide. In some embodiments, a polynucleotide encoding a human LamB3 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 58. In some embodiments, a polynucleotide encoding a human LamB3 polypeptide is a polynucleotide that encodes a polypeptide comprising the amino acid sequence of SEQ ID NO: 58.

In some embodiments, a polynucleotide encoding a LamB3 polypeptide is a polynucleotide that encodes an N-terminal truncation, a C-terminal truncation, or a fragment of the amino acid sequence of SEQ ID NO: 58. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, but fewer than 1172, consecutive amino acids of SEQ ID NO: 58.

In some embodiments, a polynucleotide of the present disclosure encodes a human LamC2 polypeptide. In some embodiments, a polynucleotide encoding a human LamC2 polypeptide is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 59. In some embodiments, a polynucleotide encoding a human LamC2 polypeptide is a polynucleotide that encodes a polypeptide comprising the amino acid sequence of SEQ ID NO: 59.

In some embodiments, a polynucleotide encoding a LamC2 polypeptide is a polynucleotide that encodes an N-terminal truncation, a C-terminal truncation, or a fragment of the amino acid sequence of SEQ ID NO: 59. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, but fewer than 1193, consecutive amino acids of SEQ ID NO: 59.

Neuromodulator Proteins

In some embodiments, the present disclosure relates to one or more polynucleotides encoding a full-length neuromodulator protein or any isoforms or portions thereof. Any neuromodulator protein from any suitable species known in the art may be encoded by a polynucleotide of the present disclosure, including, for example, a *Clostridium botulinum* protein (see e.g., UniProt accession numbers P0DPI0, Q45894, P0DPI1, P10844, and B1INP5), etc. Methods of identifying neuromodulator protein homologs/orthologs from additional species are known to one of ordinary skill in the art. In some embodiments, a neuromodulator protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the neuromodulator proteins described herein or known in the art.

In some embodiments, a polynucleotide of the present disclosure encodes a *Clostridium botulinum* neuromodulator protein.

In some embodiments, a polynucleotide of the present disclosure encodes a *Clostridium botulinum* neurotoxin type A protein In some embodiments, a polynucleotide encoding a *Clostridium botulinum* neurotoxin type A protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 60. In some embodiments, a polynucleotide encoding a *Clostridium botulinum* neurotoxin type A protein is a polynucleotide that encodes a polypeptide comprising the amino acid sequence of SEQ ID NO: 60. In some embodiments, a *Clostridium botulinum* neurotoxin type A protein of the present disclosure comprises an alanine to valine mutation at a position corresponding to position 27 of SEQ ID NO: 60.

In some embodiments, a polynucleotide encoding a *Clostridium botulinum* neurotoxin type A protein is a polynucleotide that encodes an N-terminal truncation, a C-terminal truncation, or a fragment of the amino acid sequence of SEQ ID NO: 60. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, but fewer than 1296, consecutive amino acids of SEQ ID NO: 60.

In some embodiments, a polynucleotide of the present disclosure encodes a *Clostridium botulinum* neurotoxin type B protein In some embodiments, a polynucleotide encoding a *Clostridium botulinum* neurotoxin type B protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 61. In some embodiments, a polynucleotide encoding a *Clostridium botulinum* neurotoxin type B protein is a polynucleotide that encodes a polypeptide comprising the amino acid sequence of SEQ ID NO: 61.

In some embodiments, a polynucleotide encoding a *Clostridium botulinum* neurotoxin type B protein is a polynucleotide that encodes an N-terminal truncation, a C-terminal truncation, or a fragment of the amino acid sequence of SEQ ID NO: 61. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 600, at least 700, at least 800, at least 900, at least 1000, at least 1100, at least 1200, but fewer than 1291, consecutive amino acids of SEQ ID NO: 61.

Fibrillin Proteins

In some embodiments, the present disclosure relates to one or more polynucleotides encoding a full-length fibrillin protein or any isoforms or portions thereof. Any fibrillin protein from any suitable species known in the art may be encoded by a polynucleotide of the present disclosure, including, for example, a human fibrillin protein (see e.g., UniProt accession numbers P35555, P35556, and Q75N90), a mouse fibrillin protein (see, e.g., UniProt accession numbers Q61554 and Q61555), a chimpanzee fibrillin protein (see e.g., UniProt accession numbers A0A2I3RTE4 and K7CZX0), a rat fibrillin protein (see e.g., UniProt accession number G3V9M6 and F1M5Q4), a rabbit fibrillin protein (see e.g., UniProt accession number G1SKM2, G1SUS5, and G1T1H4), etc. Methods of identifying fibrillin protein homologs/orthologs from additional species are known to one of ordinary skill in the art. In some embodiments, a fibrillin protein of the present disclosure comprises a sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of any of the fibrillin proteins described herein or known in the art.

In some embodiments, a polynucleotide of the present disclosure encodes a human fibrillin protein.

In some embodiments, a polynucleotide of the present disclosure encodes a human fibrillin-1 protein. In some embodiments, a polynucleotide encoding a human fibrillin-1 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 62. In some embodiments, a polynucleotide encoding a human fibrillin-1 protein is a polynucleotide that encodes a polypeptide comprising the amino acid sequence of SEQ ID NO: 62.

In some embodiments, a polynucleotide encoding a human fibrillin-1 protein is a polynucleotide that encodes an N-terminal truncation, a C-terminal truncation, or a fragment of the amino acid sequence of SEQ ID NO: 62. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, but fewer than 2871, consecutive amino acids of SEQ ID NO: 62.

In some embodiments, a polynucleotide of the present disclosure encodes a human fibrillin-2 protein. In some embodiments, a polynucleotide encoding a human fibrillin-2 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 63. In some embodiments, a polynucleotide encoding a human fibrillin-2 protein is a polynucleotide that encodes a polypeptide comprising the amino acid sequence of SEQ ID NO: 63.

In some embodiments, a polynucleotide encoding a human fibrillin-2 protein is a polynucleotide that encodes an N-terminal truncation, a C-terminal truncation, or a fragment of the amino acid sequence of SEQ ID NO: 63. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, but fewer than 2912, consecutive amino acids of SEQ ID NO: 63.

In some embodiments, a polynucleotide of the present disclosure encodes a human fibrillin-3 protein. In some embodiments, a polynucleotide encoding a human fibrillin-3 protein is a polynucleotide that encodes a polypeptide comprising an amino acid sequence having at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of SEQ ID NO: 64. In some embodiments, a polynucleotide encoding a human fibrillin-3 protein is a polynucleotide that encodes a polypeptide comprising the amino acid sequence of SEQ ID NO: 64.

In some embodiments, a polynucleotide encoding a human fibrillin-3 protein is a polynucleotide that encodes an N-terminal truncation, a C-terminal truncation, or a fragment of the amino acid sequence of SEQ ID NO: 64. N-terminal truncations, C-terminal truncations, or fragments may comprise at least 10, at least 12, at least 14, at least 16, at least 18, at least 20, at least 30, at least 40, at least 50, at least 75, at least 100, at least 200, at least 300, at least 400, at least 500, at least 750, at least 1000, at least 1250, at least 1500, at least 1750, at least 2000, at least 2250, at least 2500, at least 2750, but fewer than 2809, consecutive amino acids of SEQ ID NO: 64.

Exemplary Cosmetic Polypeptides

In some embodiments, one or more cosmetic proteins of the present disclosure (e.g., a first cosmetic protein, a further cosmetic protein, an additional cosmetic protein, and/or a second cosmetic protein) comprise an amino acid sequence comprising at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21 or 53-64. In some embodiments, one or more cosmetic proteins of the present disclosure (e.g., a first cosmetic protein, a further cosmetic protein, an additional cosmetic protein, and/or a second cosmetic protein) comprises a sequence selected from SEQ ID NOS: 15-21 or 53-64.

In some embodiments, one or more cosmetic proteins of the present disclosure (e.g., a first cosmetic protein, a further cosmetic protein, an additional cosmetic protein, and/or a second cosmetic protein) comprise an amino acid sequence comprising at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 15-21, 53-54, or 57-59. In some embodiments, one or more cosmetic proteins of the present disclosure (e.g., a first cosmetic protein, a further cosmetic protein, an additional cosmetic protein, and/or a second cosmetic protein) comprise a sequence selected from SEQ ID NOS: 15-21, 53-54, or 57-59.

First Polynucleotides

In some embodiments, the present disclosure relates to a recombinant nucleic acid comprising a first polynucleotide encoding a first polypeptide comprising a first cosmetic protein. The first cosmetic protein may be any of the cosmetic proteins described herein or known in the art, including, for example a collagen protein, a fibronectin, an elastin, a lumican, a vitronectin/vitronectin receptor, a laminin, a neuromodulator, a fibrillin, etc. In some embodiments, the first cosmetic protein is a structural extracellular matrix protein (e.g., a collagen, elastin, fibronectin, laminin, fibrillin, etc.). In some embodiments, the first cosmetic protein is a collagen, elastin, fibronectin, or laminin protein (e.g., a human collagen, elastin, fibronectin, or laminin protein).

In some embodiments, a recombinant nucleic acid of the present disclosure comprises one copy of the first polynucleotide. In some embodiments, a recombinant nucleic acid of the present disclosure comprises two or more (e.g., two or more, three or more, four or more, five or more, ten or more, etc.) copies of the first polynucleotide. In some embodiments, a recombinant nucleic acid of the present disclosure comprises two copies of the first polynucleotide.

In some embodiments, the first cosmetic protein is a first human collagen protein. The first human collagen protein may be any of the human collagen proteins described herein or known in the art. In some embodiments, the first human collagen protein is selected from COL1-1, COL1-2, COL2, COL3, COL4-1, COL4-2, COL4-3, COL4-4, COL4-5, COL4-6, COL5-1, COL5-2, COL5-3, COL5-1, COL5-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, or COL28. In some embodiments, the first human collagen protein is selected from COL1-1, COL1-2, COL3, COL4-1, COL4-2, COL5-1, COL7, or COL17. In some embodiments, the first human collagen protein is COL1-1. In some embodiments, the first human collagen protein is COL1-2. In some embodiments, the first human collagen protein is COL3. In some embodiments, the first human collagen protein is COL4-1. In some embodiments, the first human collagen protein is COL4-2. In some embodiments, the first human collagen protein is COL6-1. In some embodiments, the first human collagen protein is COL7. In some embodiments, the first human collagen protein is not COL7. In some embodiments, the first human collagen protein is COL17.

In some embodiments, the first polypeptide consists essentially of the first cosmetic protein. In some embodiments, the first polypeptide consists of the first cosmetic protein. In some embodiments, the first polypeptide is the first cosmetic protein.

Chimeric Polypeptides

In some embodiments, the first polypeptide is a chimeric polypeptide comprising the first cosmetic protein. In some embodiments, the first polypeptide is a chimeric polypeptide comprising the first cosmetic protein and a further cosmetic protein. In some embodiments, the chimeric polypeptide comprises a linker polypeptide linking the first cosmetic protein and the further cosmetic protein. In some embodiments, the chimeric polypeptide comprises, from n-terminus to c-terminus, the first cosmetic protein—the linker polypeptide—the further cosmetic protein. The first and/or further cosmetic proteins may be any of the cosmetic proteins described herein or known in the art, including, for example a collagen protein, a fibronectin, an elastin, a lumican, a vitronectin/vitronectin receptor, a laminin, a neuromodulator, a fibrillin, etc. In some embodiments, the first and/or further cosmetic protein is a structural extracellular matrix protein (e.g., a collagen, elastin, fibronectin, laminin, fibrillin, etc.). In some embodiments, the first and/or further cosmetic protein is a collagen, elastin, fibronectin, or laminin protein (e.g., a human collagen, elastin, fibronectin, or laminin protein). In some embodiments, the first and further cosmetic proteins are the same. In some embodiments, the first and further cosmetic proteins are different.

In some embodiments, the linker polypeptide is a cleavable linker polypeptide. Any cleavable linker polypeptide known in the art may be used in the chimeric polypeptides of the present disclosure, including, for example, a T2A linker, a P2A linker, a E2A linker, and F2A linker, etc. In some embodiments, the linker polypeptide is a T2A linker polypeptide. An exemplary nucleic acid sequence encoding a T2A linker polypeptide is provided as SEQ ID NO: 24. An exemplary amino acid sequence of a T2A linker polypeptide is provided as SEQ ID NO: 28. In some embodiments, the linker polypeptide is a P2A linker polypeptide. An exemplary nucleic acid sequence encoding a P2A linker polypeptide is provided as SEQ ID NO: 25. An exemplary amino acid sequence of a P2A linker polypeptide is provided as SEQ ID NO: 29. In some embodiments, the linker polypeptide is an E2A linker polypeptide. An exemplary nucleic acid sequence encoding an E2A linker polypeptide is provided as SEQ ID NO: 26. An exemplary amino acid sequence of an E2A linker polypeptide is provided as SEQ ID NO: 30. In some embodiments, the linker polypeptide is an F2A linker polypeptide. An exemplary nucleic acid sequence encoding an F2A linker polypeptide is provided as SEQ ID NO: 27. An exemplary amino acid sequence of an F2A linker polypeptide is provided as SEQ ID NO: 31.

In some embodiments, the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from SEQ ID NOS: 28-31. In some embodiments, the linker polypeptide comprises a sequence selected from SEQ ID NOS: 28-31.

In some embodiments, the first cosmetic protein is a first collagen protein (e.g., a first human collagen protein), and the further cosmetic protein is a further collagen protein (e.g., a further human collagen protein). An exemplary nucleic acid sequence encoding a chimeric polypeptide comprising a first human collagen protein, a linker polypeptide, and a further human collagen protein is provided as SEQ ID NO: 32.

In some embodiments, the first cosmetic protein is a first human collagen protein, and the further cosmetic protein is a further human collagen protein. The further human collagen protein may be any of the human collagen proteins described herein or known in the art. In some embodiments, the further human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, or COL28. In some embodiments, the further human collagen protein is selected from COL1-1, COL1-2, COL3, COL4-1, COL4-2, COL5-1, COL7, or COL17. In some embodiments, the further human collagen protein is COL1-1. In some embodiments, the further human collagen protein is COL1-2. In some embodiments, the further human collagen protein is COL3. In some embodiments, the further human collagen protein is COL4-1. In some embodiments, the further human collagen protein is COL4-2. In some embodiments, the further human collagen protein is COL6-1. In some embodiments, the further human collagen protein is COL7. In some embodiments, the further human collagen protein is not COL7. In some embodiments, the further human collagen protein is COL17. In some embodiments, the first human collagen protein and the further human collagen protein are the same. In some embodiments, the first human collagen protein and the further human collagen protein are different.

In some embodiments, the first human collagen protein is COL1-1, and the further human collagen protein is selected from COL1-2, COL3, COL4-1, COL4-2, COL5-1, COL7, or COL17. In some embodiments, the first human collagen protein is COL1-1, and the further human collagen protein is COL1-2. In some embodiments, the first human collagen protein is COL1-1, and the further human collagen protein is COL3.

In some embodiments, the first human collagen protein is COL1-2, and the further human collagen protein is COL1-1, COL3, COL4-1, COL4-2, COL5-1, COL7, or COL17. In some embodiments, the first human collagen protein is COL1-2, and the further human collagen protein is COL1-1.

In some embodiments, the first human collagen protein is COL3, and the further human collagen protein is selected from COL1-1, COL1-2, COL4-1, COL4-2, COL5-1, COL7, or COL17.

In some embodiments, the first human collagen protein is COL4-1, and the further human collagen protein is COL1-1, COL1-2, COL3, COL4-2, COL5-1, COL7, or COL17. In some embodiments, the first human collagen protein is COL4-1, and the further human collagen protein is COL4-2.

In some embodiments, the first human collagen protein is COL6-1, and the further human collagen protein is selected from COL1-1, COL1-2, COL3, COL4-1, COL4-2, COL7, or COL17.

In some embodiments, the first human collagen protein is COL7, and the further human collagen protein is COL1-1, COL1-2, COL3, COL4-1, COL4-2, COL5-1, or COL17.

In some embodiments, the first human collagen protein is COL17, and the further human collagen protein is COL1-1, COL1-2, COL3, COL4-1, COL4-2, COL5-1, or COL7.

In some embodiments, the first cosmetic protein is a first laminin protein (e.g., a first human laminin protein), and the further cosmetic protein is a further laminin protein (e.g., a further human laminin protein). In some embodiments, the first cosmetic protein is a first human laminin protein, and the further cosmetic protein is a further human laminin protein. The further human laminin protein may be any of the human laminin proteins described herein or known in the art. In some embodiments, the first human laminin protein is a human LamA3 polypeptide and the further human laminin protein is a human LamB3 polypeptide. In some embodiments, the first human laminin protein is a human LamA3 polypeptide and the further human laminin protein is a human LamC2 polypeptide. In some embodiments, the first human laminin protein is a human LamB3 polypeptide and the further human laminin protein is a human LamC2 polypeptide.

In some embodiments, the first polynucleotide encodes a monocistronic mRNA. In some embodiments, the monocistronic mRNA comprises an open reading frame (ORF) encoding the first polypeptide.

In some embodiments, the first polynucleotide encodes a polycistronic mRNA. In some embodiments, the polycistronic mRNA comprises an open reading frame (ORF) encoding the first polypeptide.

Polycistronic mRNA

In some embodiments, the first polynucleotide encodes a polycistronic mRNA. In some embodiments, the polycistronic mRNA comprises an open reading frame (ORF) encoding the first polypeptide. In some embodiments, the first polynucleotide encodes a polycistronic mRNA comprising: 1) a first open reading frame (ORF) encoding the first polypeptide, and 2) a second open reading frame (ORF) encoding an additional cosmetic protein. In some embodiments, the polycistronic mRNA further comprises an internal ribosomal entry site (IRES) separating the first ORF and the second ORF. In some embodiments, the polycistronic mRNA comprises, from 5' to 3', the first ORF encoding the first polypeptide—the IRES—the second ORF encoding the additional cosmetic protein. The first polypeptide may be any of the first polypeptides described herein. The additional cosmetic protein may be any of the cosmetic proteins described herein or known in the art, including, for example a collagen protein, a fibronectin, an elastin, a lumican, a vitronectin/vitronectin receptor, a laminin, a neuromodulator, a fibrillin, etc. In some embodiments, the additional cosmetic protein is a structural extracellular matrix protein (e.g., a collagen, elastin, fibronectin, laminin, fibrillin, etc.). In some embodiments, the additional cosmetic protein is a collagen, elastin, fibronectin, or laminin protein (e.g., a human collagen, elastin, fibronectin, or laminin protein).

Any suitable IRES known in the art may be used in the polycistronic mRNAs of the present disclosure, including, for example, a virally-derived IRES (e.g. an IRES derived from a poliovirus, rhinovirus, encephalomyocarditis virus (EMCV), foot-and-mouth disease virus, hepatitis C virus, classic swine fever virus, rous sarcoma virus, human immunodeficiency virus, cricket paralysis virus, Kaposi's sarcoma-associated herpesvirus, etc.), a cellular mRNA-derived IRES (e.g. an IRES derived from growth factor mRNAs, such as fibroblast growth factor 2, platelet-derived growth factor B, and vascular endothelial growth factor; an IRES derived from transcription factor mRNAs, such as antennapedia, ultrabithorax, and NF-κB repressing factor; an IRES derived from oncogene mRNAs, such as c-myc, pim-1, and protein kinase$58^{PITSLRE}$, etc.), a synthetic IRES (e.g., a CP148 IRES), and others (see e.g., Mokrejs et al. (2007) A Bioinformatical Approach to the Analysis of Viral and Cellular Internal Ribosome Entry Sites. Columbus F editors. New Messenger RNA Research Communications. Hauppauge, N.Y.: Nova Science Publishers; pp. 133-166). In some embodiments, the IRES is a CP148 IRES. An exemplary nucleic acid sequence encoding a CP148 IRES is provided as SEQ ID NO: 22. In some embodiments, the IRES is an EMCV IRES. An exemplary nucleic acid sequence encoding an EMCV IRES is provided as SEQ ID NO: 23.

In some embodiments, the nucleic acid sequence encoding the IRES comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23. In some embodiments, the nucleic acid sequence encoding the IRES comprises the sequence of SEQ ID NO: 22 or SEQ ID NO: 23.

In some embodiments, the first polypeptide is a first collagen protein (e.g., a first human collagen protein), and the additional cosmetic protein is an additional collagen protein (e.g., an additional human collagen protein). An exemplary nucleic acid encoding a polycistronic mRNA comprising a first ORF, an IRES, and second ORF is provided as SEQ ID NO: 33 or SEQ ID NO: 34. The additional human collagen protein may be any of the human collagen proteins described herein. In some embodiments, the additional human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, or COL28. In some embodiments, the additional human collagen protein is selected from COL1-1, COL1-2, COL3, COL4-1, COL4-2, COL5-1, COL7, or COL17. In some embodiments, the additional human collagen protein is COL1-1. In some embodiments, the additional human collagen protein is COL1-2. In some embodiments, the additional human collagen protein is COL3. In some embodiments, the additional human collagen protein is COL4-1. In some embodiments, the additional human collagen protein is COL4-2. In some embodiments, the additional human collagen protein is COL7-1. In some embodiments, the additional human collagen protein is COL7. In some embodiments, the additional human collagen protein is not COL7. In some embodiments, the additional human collagen protein is COL17. In some embodiments, the first human collagen protein and the additional human collagen protein are the same. In some embodiments, the first human collagen protein and the additional human collagen protein are different.

In some embodiments, the first human collagen protein is COL1-1, and the additional human collagen protein is selected from COL1-2, COL3, COL4-1, COL4-2, COL5-1, COL7, or COL17. In some embodiments, the first human collagen protein is COL1-1, and the additional human collagen protein is COL1-2. In some embodiments, the first human collagen protein is COL1-1, and the additional human collagen protein is COL3.

In some embodiments, the first human collagen protein is COL1-2, and the additional human collagen protein is selected from COL1-1, COL3, COL4-1, COL4-2, COL5-1, COL7, or COL17. In some embodiments, the first human collagen protein is COL1-2, and the additional human collagen protein is COL1-1.

In some embodiments, the first human collagen protein is COL3, and the additional human collagen protein is selected from COL1-1, COL1-2, COL4-1, COL4-2, COL5-1, COL7, or COL17.

In some embodiments, the first human collagen protein is COL4-1, and the additional human collagen protein is selected from COL1-1, COL1-2, COL3, COL4-2, COL6-1, COL7, or COL17. In some embodiments, the first human collagen protein is COL4-1, and the additional human collagen protein is COL4-2.

In some embodiments, the first human collagen protein is COL6-1, and the additional human collagen protein is selected from COL1-1, COL1-2, COL3, COL4-1, COL4-2, COL7, or COL17.

In some embodiments, the first human collagen protein is COL7, and the additional human collagen protein is selected from COL1-1, COL1-2, COL3, COL4-1, COL4-2, COL6-1, or COL17.

In some embodiments, the first human collagen protein is COL17, and the additional human collagen protein is selected from COL1-1, COL1-2, COL3, COL4-1, COL4-2, COL6-1, or COL7.

In some embodiments, the first polypeptide is a first collagen protein (e.g., a first human collagen protein), and the additional cosmetic protein is an additional collagen protein (e.g., an additional human collagen protein).

In some embodiments, the first polypeptide is a first laminin protein (e.g., a first human laminin protein), and the additional cosmetic protein is an additional laminin protein (e.g., an additional human laminin protein). In some embodiments, the first polypeptide is a first human laminin protein, and the additional cosmetic protein is an additional human laminin protein. The additional human laminin protein may be any of the human laminin proteins described herein or known in the art. In some embodiments, the first human laminin protein is a human LamA3 polypeptide and the additional human laminin protein is a human LamB3 polypeptide. In some embodiments, the first human laminin protein is a human LamA3 polypeptide and the additional human laminin protein is a human LamC2 polypeptide. In some embodiments, the first human laminin protein is a human LamB3 polypeptide and the additional human laminin protein is a human LamC2 polypeptide.

Second Polynucleotides

In some embodiments, the present disclosure relates to a recombinant nucleic acid further comprising a second polynucleotide encoding a second cosmetic protein. The second cosmetic protein may be any of the cosmetic proteins described herein or known in the art, including, for example a collagen protein, a fibronectin, an elastin, a lumican, a vitronectin/vitronectin receptor, a laminin, a neuromodulator, a fibrillin, etc. In some embodiments, the second cosmetic protein is a structural extracellular matrix protein (e.g., a collagen, elastin, fibronectin, laminin, fibrillin, etc.). In some embodiments, the second cosmetic protein is a collagen, elastin, fibronectin, or laminin protein (e.g., a human collagen, elastin, fibronectin, or laminin protein). In some embodiments, the first and second cosmetic proteins are the same. In some embodiments, the first and second cosmetic proteins are different. In some embodiments, the recombinant nucleic acid comprises one copy of the second polynucleotide. In some embodiments, the recombinant nucleic acid comprises two or more (e.g., two or more, three or more, four or more, five or more, ten or more, etc.) copies of the second polynucleotide. In some embodiments, the recombinant nucleic acid comprises two copies of the second polynucleotide.

In some embodiments, the second cosmetic protein is a collagen protein. In some embodiments, the second cosmetic protein is a second human collagen protein. The second human collagen protein may be any of the human collagen proteins described herein. In some embodiments, the second human collagen protein is selected from COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, or COL28. In some embodiments, the second human collagen protein is selected from COL1-1, COL1-2, COL3, COL4-1, COL5-1, COL7, or COL17. In some embodiments, the second human collagen protein is COL1-1. In some embodiments, the second human collagen protein is COL1-2. In some embodiments, the second human collagen protein is COL3. In some embodiments, the second human collagen protein is COL4-1. In some embodiments, the second human collagen protein is COL4-2. In some embodiments, the second human collagen protein is COL6-1. In some embodiments, the second human collagen protein is COL7. In some embodiments, the second human collagen protein is not COL7. In some embodiments, the second human collagen protein is COL17.

In some embodiments, the first polynucleotide encodes a first collagen protein and the second polynucleotide encodes a second collagen protein. In some embodiments, the first polynucleotide encodes a first human collagen protein and the second polynucleotide encodes a second human collagen protein. In some embodiments, the first human collagen protein (encoded by the first polynucleotide) and the second human collagen protein (encoded by the second polynucleotide) are the same. In some embodiments, the first human collagen protein (encoded by the first polynucleotide) and the second human collagen protein (encoded by the second polynucleotide) are different.

In some embodiments, the first human collagen protein is COL1-1, and the second human collagen protein is selected from COL1-2, COL3, COL4-1, COL4-2, COL5-1, COL7, or COL17. In some embodiments, the first human collagen protein is COL1-1, and the second human collagen protein is COL1-2. In some embodiments, the first human collagen protein is COL1-1, and the second human collagen protein is COL3.

In some embodiments, the first human collagen protein is COL1-2, and the second human collagen protein is selected from COL1-1, COL3, COL4-1, COL4-2, COL5-1, COL7, or COL17. In some embodiments, the first human collagen protein is COL1-2, and the second human collagen protein is COL1-1.

In some embodiments, the first human collagen protein is COL3, and the second human collagen protein is selected from COL1-1, COL1-2, COL4-1, COL4-2, COL5-1, COL7, or COL17.

In some embodiments, the first human collagen protein is COL4-1, and the second human collagen protein is selected from COL1-2, COL1-2, COL3, COL4-2, COL6-1, COL7, or COL17. In some embodiments, the first human collagen protein is COL4-1, and the second human collagen protein is COL4-2.

In some embodiments, the first human collagen protein is COL6-1, and the second human collagen protein is selected from COL1-1, COL1-2, COL3, COL4-1, COL4-2, COL7, or COL17.

In some embodiments, the first human collagen protein is COL7, and the second human collagen protein is selected from COL1-1, COL1-2, COL3, COL4-1, COL4-2, COL6-1, or COL17.

In some embodiments, the first human collagen protein is COL17, and the second human collagen protein is selected from COL1-1, COL1-2, COL3, COL4-1, COL4-2, COL6-1, or COL7.

In some embodiments, the first polynucleotide encodes a first laminin protein (e.g., a first human laminin protein), and the second polynucleotide encodes a second laminin protein (e.g., a second human laminin protein). In some embodiments, the first polynucleotide encodes a first human laminin polypeptide and the second polynucleotide encodes a second human laminin protein. The second human laminin protein may be any of the human laminin proteins described herein or known in the art. In some embodiments, the first human laminin protein is a human LamA3 polypeptide and the second human laminin protein is a human LamB3 polypeptide. In some embodiments, the first human laminin protein is a human LamA3 polypeptide and the second human laminin protein is a human LamC2 polypeptide. In some embodiments, the first human laminin protein is a human LamB3 polypeptide and the second human laminin protein is a human LamC2 polypeptide Recombinant Nucleic Acids In some embodiments, the present disclosure relates to recombinant nucleic acids comprising any one or more of the polynucleotides described herein. In some embodiments, the recombinant nucleic acid comprises one copy of the first polynucleotide. In some embodiments, the recombinant nucleic acid comprises two copies of the first polynucleotide. In some embodiments, the recombinant nucleic acid comprises one copy of the first polynucleotide and one copy of the second polynucleotide. In some embodiments, the recombinant nucleic acid comprises one copy of the first polynucleotide and two copies of the second polynucleotide. In some embodiments, the recombinant nucleic acid comprises two copies of the first polynucleotide and one copy of the second polynucleotide. In some embodiments, the recombinant nucleic acid comprises two copies of the first polynucleotide and two copies of the second polynucleotide.

In some embodiments, the recombinant nucleic acid is a vector (e.g., an expression vector, a display vector, etc.). In some embodiments, the vector is a DNA vector or an RNA vector. Generally, vectors suitable to maintain, propagate, and/or express polynucleotides to produce one or more polypeptides in a subject may be used. Examples of suitable vectors may include, for example, plasmids, cosmids, episomes, transposons, and viral vectors (e.g., adenoviral vectors, adeno-associated viral vectors, vaccinia viral vectors, Sindbis-viral vectors, measles vectors, herpes viral vectors, lentiviral vectors, retroviral vectors, etc.). In some embodiments, the vector is a herpes viral vector. In some embodiments, the vector is capable of autonomous replication in a host cell. In some embodiments, the vector is incapable of autonomous replication in a host cell. In some embodiments, the vector can integrate into a host DNA. In some embodiments, the vector cannot integrate into a host DNA (e.g., is episomal). Methods of making vectors containing one or more polynucleotides of interest are well known to one of ordinary skill in the art, including, for example, by chemical synthesis, or by artificial manipulation of isolated segments of nucleic acids (e.g., by genetic engineering techniques).

In some embodiments, a recombinant nucleic acid of the present disclosure is a herpes simplex virus (HSV) amplicon. Herpes virus amplicons, including the structural features and methods of making the same, are generally known to one of ordinary skill in the art (see e.g., de Silva S. and Bowers W. "Herpes Virus Amplicon Vectors". *Viruses* 2009, 1, 594-629). In some embodiments, the herpes simplex virus amplicon is an HSV-1 amplicon. In some embodiments, the herpes simplex virus amplicon is an HSV-1 hybrid amplicon. Examples of HSV-1 hybrid amplicons may include, but are not limited to, HSV/AAV hybrid amplicons, HSV/EBV hybrid amplicons, HSV/EBV/RV hybrid amplicons, and/or HSV/Sleeping Beauty hybrid amplicons. In some embodiments, the amplicon is an HSV/AAV hybrid amplicon. In some embodiments, the amplicon is an HSV/Sleeping Beauty hybrid amplicon.

In some embodiments, a recombinant nucleic acid of the present disclosure is a recombinant herpes virus genome. The recombinant herpes virus genome may be a recombinant genome from any member of the Herpesviridae family of DNA viruses known in the art, including, for example, a recombinant herpes simplex virus genome, a recombinant varicella zoster virus genome, a recombinant human cytomegalovirus genome, a recombinant herpesvirus 6A genome, a recombinant herpesvirus 6B genome, a recombinant herpesvirus 7 genome, a recombinant Kaposi's sarcoma-associated herpesvirus genome, and any combinations or any derivatives thereof. In some embodiments, the recombinant herpes virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes virus genes. In some embodiments, the recombinant herpes virus genome is attenuated (e.g., as compared to a corresponding, wild-type herpes virus genome). In some embodiments, the recombinant herpes virus genome is replication-competent. In some embodiments, the recombinant herpes virus genome is replication-defective In some embodiments, the recombinant nucleic acid is a recombinant herpes simplex virus (HSV) genome. In some embodiments, the recombinant herpes simplex virus genome is a recombinant type 1 herpes simplex virus (HSV-1) genome, a recombinant type 2 herpes simplex virus (HSV-2) genome, or any derivatives thereof. In some embodiments, the recombinant herpes simplex virus genome is a recombinant HSV-1 genome. In some embodiments, the recombinant herpes simplex virus genome is replication-competent. In some embodiments, the recombinant herpes simplex virus genome is replication-defective. In some embodiments, the recombinant herpes simplex virus genome comprises one or more (e.g., one or more, two or more, three or more, four or more, five or more, six or more, seven or more, eight or more, nine or more, ten or more, etc.) inactivating mutations. In some embodiments, the one or more inactivating mutations are in one or more (e.g., one or more, two or more, three or more, four or more, five or more, six or more, seven or more, eight or more, nine or more, ten or more, etc.) herpes simplex virus genes. As used herein, an "inactivating mutation" may refer to any mutation that results in a gene or regulon product (RNA or protein) having reduced, undetectable, or eliminated quantity and/or function (e.g., as compared to a corresponding sequence lacking the inactivating mutation). Examples of inactivating mutations may include, but are not limited to, deletions, insertions, point mutations, and rearrangements in transcriptional control sequences (promoters, enhancers, insulators, etc.) and/or coding sequences of a given gene or regulon. Any suitable method of measuring the quantity of a gene or regulon product known in the art may be used, including, for example, qPCR, Northern blots, RNAseq, western blots, ELISAs, etc.

In some embodiments, the recombinant herpes simplex virus genome comprises an inactivating mutation in at least one, at least two, at least three, at least four, at least five, at least six, at least seven, or all eight of the Infected Cell Protein (or Infected Cell Polypeptide) (ICP) 0, ICP4, ICP22, ICP27, ICP47, thymidine kinase (tk), Long Unique Region (UL) 41 and/or UL55 herpes simplex virus genes. In some embodiments, the recombinant herpes simplex virus genome does not comprise an inactivating mutation in the ICP34.5 and/or ICP47 herpes simplex virus genes (e.g., to avoid production of an immune-stimulating virus). In some embodiments, the recombinant herpes simplex virus genome does not comprise an inactivating mutation in the ICP34.5 herpes simplex virus gene (one or both copies). In some embodiments, the recombinant herpes simplex virus genome does not comprise an inactivating mutation in the ICP47 herpes simplex virus gene. In some embodiments, the recombinant herpes simplex virus genome does not comprise an inactivating mutation in the ICP34.5 (one or both copies) and ICP47 herpes simplex virus genes. In some embodiments, the recombinant herpes simplex virus genome is not oncolytic.

In some embodiments, the recombinant herpes simplex virus genome comprises an inactivating mutation in the ICP0 gene (one or both copies). In some embodiments, the recombinant herpes simplex virus genome comprises an inactivating mutation in the ICP0 gene (one or both copies), and further comprises an initiating mutation in the ICP4 (one or both copies) ICP22, ICP27, ICP47, UL41, and/or UL55 genes. In some embodiments, the recombinant herpes simplex virus genome comprises an inactivating mutation in the ICP0 gene (one or both copies), and an inactivating mutation in the ICP4 gene (one or both copies). In some embodiments, the recombinant herpes simplex virus genome comprises an inactivating mutation in the ICP0 gene (one or both copies), and an inactivating mutation in the ICP22 gene. In some embodiments, the recombinant herpes simplex virus genome comprises an inactivating mutation in the ICP0 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), and an inactivating mutation in the ICP22 gene. In some embodiments, the recombinant herpes simplex virus genome comprises an inactivating mutation in the ICP0 gene (one or both copies), an inactivating mutation in the ICP4 gene (one or both copies), and an inactivating mutation in the UL41 gene. In some embodiments, the recombinant herpes simplex virus genome comprises an inactivating mutation in the ICP0 gene (one or both copies), an inactivating mutation in the ICP22 gene, and an inactivating mutation in the UL41 gene. In some embodiments, the recombinant herpes simplex virus genome comprises an inactivating mutation in the ICP0 gene (one or both copies), an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP0 (one or both copies), ICP4 (one or both copies), ICP22, and/or UL41 genes. In some embodiments, the recombinant herpes simplex virus genome further comprises an inactivating mutation in the ICP27, ICP47, and/or UL55 genes.

In some embodiments, the recombinant herpes simplex virus genome comprises an inactivating mutation in the ICP4 gene (one or both copies). In some embodiments, the recombinant herpes complex virus genome comprises an inactivating mutation in the ICP4 (one or both copies, and further comprises an inactivating mutation in the ICP0 (one or both copies), ICP22, ICP27, ICP47, UL41, and/or UL55 genes. In some embodiments, the recombinant herpes simplex virus genome comprises an inactivating mutation in the ICP4 gene (one or both copies), and an inactivating mutation in the ICP22 gene. In some embodiments, the recombinant herpes simplex virus genome comprises an inactivating mutation in the ICP4 gene (one or both copies), and an inactivating mutation in the UL41 gene. In some embodiments, the recombinant herpes simplex virus genome comprises an inactivating mutation in the ICP4 gene (one or both copies), an inactivating mutation in the ICP22 gene, and an inactivating mutation in the UL41 gene. In some embodiments, the inactivating mutation is a deletion of the coding sequence of the ICP4 (one or both copies), ICP22, and/or UL41 genes. In some embodiments, the recombinant herpes simplex virus genome further comprises an inactivating mutation in the ICP0, ICP27, ICP47, and/or UL55 genes.

In some embodiments, the recombinant herpes simplex virus genome comprises an inactivating mutation in the ICP22 gene. In some embodiments, the recombinant herpes simplex virus genome comprises an inactivating mutation in the ICP22 gene, and further comprises an inactivating mutation in the ICP0 (one or both copies), ICP4 (one or both copies), ICP27, ICP47, UL41, and/or UL55 genes. In some embodiments, the recombinant herpes simplex virus genome comprises an inactivating mutation in the ICP22 gene, and an inactivating mutation UL41 gene. In some embodiments, the inactivating mutation is a deletion of the coding sequence of the ICP22 and/or UL41 genes. In some embodiments, the recombinant herpes simplex virus genome further comprises an inactivating mutation in the ICP0 (one or both copies), ICP4 (one or both copies), ICP27, ICP47, and/or UL55 genes.

In some embodiments, the recombinant herpes simplex virus genome comprises an inactivating mutation in the ICP27 gene. In some embodiments, the recombinant herpes simplex virus genome comprises an inactivating mutation in the ICP27 gene, and further comprises an inactivating mutation in the ICP0 (one or both copies), ICP4 (one or both copies), ICP22, ICP47, UL41, and/or UL55 genes. In some embodiments, the inactivating mutation is a deletion of the coding sequence of the ICP27 gene.

In some embodiments, the recombinant herpes simplex virus genome comprises an inactivating mutation in the ICP47 gene. In some embodiments, the recombinant herpes simplex virus genome comprises an inactivating mutation in the ICP47 gene, and further comprises an inactivating mutation in the ICP0 (one or both copies), ICP4 (one or both copies), ICP22, ICP27, UL41, and/or UL55 genes. In some embodiments, the inactivating mutation is a deletion of the coding sequence of the ICP47 gene.

In some embodiments, the recombinant herpes simplex virus genome comprises an inactivating mutation in the UL41 gene. In some embodiments, the recombinant herpes simplex virus genome comprises an inactivating mutation in the UL41 gene, and further comprises an inactivating mutation in the ICP0 (one or both copies), ICP4 (one or both copies), ICP22, ICP27, ICP47, and/or UL55 genes. In some embodiments, the inactivating mutation is a deletion of the coding sequence of the UL41 gene.

In some embodiments, the recombinant herpes simplex virus genome comprises an inactivating mutation in the UL55 gene. In some embodiments, the recombinant herpes simplex virus genome comprises an inactivating mutation in the UL55 gene, and further comprises an inactivating mutation in the ICP0 (one or both copies), ICP4 (one or both copies), ICP22, ICP27, ICP47, and/or UL41 genes. In some embodiments, the inactivating mutation is a deletion of the coding sequence of the UL55 gene.

In some embodiments, the recombinant herpes simplex virus genome comprises an inactivating mutation in (e.g., a deletion of) the internal repeat (Joint) region comprising the internal repeat long (IRL) and internal repeat short (IRS) regions. In some embodiments, inactivation (e.g., deletion) of the Joint region eliminates one copy each of the ICP4 and ICP0 genes. In some embodiments, inactivation (e.g., deletion) of the Joint region further inactivates (e.g., deletes) the promoter for the ICP22 and ICP47 genes. If desired, expression of one or both of these genes can be restored by insertion of an immediate early promoter into the recombinant herpes simplex virus genome (see e.g., Hill et al. (1995). Nature 375(6530): 411-415; Goldsmith et al. (1998). J Exp Med 187(3): 341-348). Without wishing to be bound by theory, it is believed that inactivating (e.g., deleting) the Joint region may contribute to the stability of the recombinant herpes simplex virus genome and/or allow for the recombinant herpes simplex virus genome to accommodate more and/or larger transgenes.

In some embodiments, the recombinant herpes simplex virus genome comprises an inactivating mutation in the ICP4 (one or both copies), ICP22, and ICP27 genes. In some embodiments, the recombinant herpes simplex virus genome comprises an inactivating mutation in the ICP4 (one or both copies), ICP27, and UL55 genes. In some embodiments, the recombinant herpes simplex virus genome comprises an inactivating mutation in the ICP4 (one or both copies), ICP22, ICP27, ICP47, and UL55 genes. In some embodiments, the inactivating mutation in the ICP4 (one or both copies), ICP27, and/or UL55 genes is a deletion of the coding sequence of the ICP4 (one or both copies), ICP27, and/or UL55 genes. In some embodiments, the inactivating mutation in the ICP22 and ICP47 genes is a deletion in the promoter region of the ICP22 and ICP47 genes (e.g., the ICP22 and ICP47 coding sequences are intact but are not transcriptionally active). In some embodiments, the recombinant herpes simplex virus genome comprises a deletion in the coding sequence of the ICP4 (one or both copies), ICP27, and UL55 genes, and a deletion in the promoter region of the ICP22 and ICP47 genes. In some embodiments, the recombinant herpes simplex virus genome further comprises an inactivating mutation in the ICP0 and/or UL41 genes.

In some embodiments, the recombinant herpes simplex virus genome comprises an inactivating mutation in the ICP0 (one or both copies) gene. In some embodiments, the recombinant herpes simplex virus genome comprises an inactivating mutation in the ICP0 (one or both copies) and ICP4 (one or both copies) genes. In some embodiments, the recombinant herpes simplex virus genome comprises an inactivating mutation in the ICP0 (one or both copies), ICP4 (one or both copies), and ICP22 genes. In some embodiments, the recombinant herpes simplex virus genome comprises an inactivating mutation in the ICP0 (one or both copies), ICP4 (one or both copies), ICP22, and ICP27 genes. In some embodiments, the recombinant herpes simplex virus genome comprises an inactivating mutation in the ICP0 (one or both copies), ICP4 (one or both copies), ICP22, ICP27 and UL55 genes. In some embodiments, the inactivating mutation in the ICP0 (one or both copies), ICP4 (one or both copies), ICP22, ICP27 and/or UL55 genes comprises a deletion of the coding sequence of the ICP0, ICP4 (one or both copies), ICP22, ICP27 and/or UL55 genes. In some embodiments, the recombinant herpes simplex virus genome further comprises an inactivating mutation in the ICP47 and/or the UL41 genes.

In some embodiments, a recombinant herpes simplex virus genome comprises one or more polynucleotides of the present disclosure within one, two, three, four, five, six, seven or more viral gene loci. Examples of suitable viral loci may include, without limitation, the ICP0 (one or both copies), ICP4 (one or both copies), ICP22, ICP27, ICP47, tk, UL41 and UL55 herpes simplex viral gene loci. In some embodiments, a recombinant herpes simplex virus genome comprises one or more polynucleotides of the present disclosure within one or both of the viral ICP4 gene loci (e.g., a recombinant virus carrying a first polynucleotide encoding a first human collagen protein in one or both of the ICP4 loci; a recombinant virus carrying a second polynucleotide encoding a second human collagen protein in one or both of the ICP4 loci; etc.). In some embodiments, a recombinant herpes simplex virus genome comprises one or more polynucleotide of the present disclosure within the viral ICP22 gene locus (e.g., a recombinant virus carrying a first polynucleotide encoding a first human collagen protein in the ICP22 locus; a recombinant virus carrying a second polynucleotide encoding a second human collagen protein in the ICP22 locus; etc.). In some embodiments, a recombinant herpes simplex virus genome comprises one or more polynucleotide of the present disclosure within the viral UL41 gene locus (e.g., a recombinant virus carrying a first polynucleotide encoding a first human collagen protein in the UL41 locus; a recombinant virus carrying a second polynucleotide encoding a second human collagen protein in the UL41 locus; etc.). In some embodiments, a recombinant herpes simplex virus genome comprises one or more polynucleotides of the present disclosure within one or both of the viral ICP4 gene loci, and one or more polynucleotides of the present disclosure within the viral ICP22 locus (e.g., a recombinant virus carrying a first polynucleotide encoding a first human collagen protein in one or both of the ICP4 loci and a second polynucleotide encoding a second human collagen protein in the ICP22 locus; a recombinant virus carrying a second polynucleotide encoding a second human collagen protein in one or both of the ICP4 loci and a first polynucleotide encoding a first human collagen protein in the ICP22 locus; etc.). In some embodiments, a recombinant herpes simplex virus genome comprises one or more polynucleotides of the present disclosure within one or both of the viral ICP4 gene loci, and one or more polynucleotides of the present disclosure within the viral UL41 locus (e.g., a recombinant virus carrying a first polynucleotide encoding a first human collagen protein in one or both of the ICP4 loci and a second polynucleotide encoding a second human collagen protein in the UL41 locus; a recombinant virus carrying a second polynucleotide encoding a second human collagen protein in one or both of the ICP4 loci and a first polynucleotide encoding a first human collagen protein in the UL41 locus; etc.). In some embodiments, a recombinant herpes simplex virus genome comprises one or more polynucleotides of the present disclosure within one or both of the viral ICP4 gene loci, one or more polynucleotides of the present disclosure within the viral ICP22 locus, and one or more polynucleotides of the present disclosure within the viral UL41 locus (e.g., a recombinant virus carrying a first polynucleotide encoding a first human collagen protein in one or both of the ICP4 loci and a second polynucleotide encoding a second human collagen protein in the ICP22 and UL41 loci; a recombinant virus carrying a second polynucleotide encoding a second human collagen protein in one or both of the ICP4 loci and a first polynucleotide encoding a first human collagen protein in the ICP22 and UL41 loci; etc.).

In some embodiments, the recombinant herpes virus genome (e.g., a recombinant herpes simplex virus genome) has been engineered to decrease or eliminate expression of one or more toxic herpes simplex genes (such as one or both copies of the HSV ICP0 gene, one or both copied of the HSV ICP4 gene, the ICP22 gene, and/or the UL41 gene). In some embodiments, the recombinant herpes virus genome (e.g., a recombinant herpes simplex virus genome) has been engineered to reduce cytotoxicity of the recombinant genome (e.g., when introduced into a target cell) as compared to a corresponding wild-type herpes virus genome (e.g., a wild-type herpes simplex virus genome). In some embodiments, cytotoxicity (e.g., in human keratinocytes and/or fibroblast cells) of the recombinant virus genome (e.g., a recombinant herpes simplex virus genome) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). In some embodiments, cytotoxicity (e.g., in human keratinocytes and/or fibroblast cells) of the recombinant herpes virus genome (e.g., a recombinant herpes simplex virus genome) is reduced by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more as compared to a corresponding wild-type herpes virus genome (e.g., measuring the relative cytotoxicity of a recombinant ΔICP4 (one or both copies) herpes simplex virus genome vs. a wild-type herpes simplex virus genome in human keratinocytes or fibroblasts (primary cells or cell lines); measuring the relative cytotoxicity of a recombinant ΔICP4 (one or both copies)/ΔICP22 herpes simplex virus genome vs. a wild-type herpes simplex virus genome in human keratinocytes or fibroblasts (primary cells or cell lines); etc.). Methods of measuring cytotoxicity are known to one of ordinary skill in the art, including, for example, through the use of vital dyes (formazan dyes), protease biomarkers, an MTT assay (or an assay using related tetrazolium salts such as XTT, MTS, water-soluble tetrazolium salts, etc.), measuring ATP content, etc.

In some embodiments, the recombinant herpes virus genome (e.g., a recombinant herpes simplex virus genome) has been engineered to reduce its impact on host cell proliferation after exposure of the target cell to the recombinant genome, as compared to a corresponding wild-type herpes virus genome (e.g., a wild-type herpes simplex virus genome). In some embodiments, the target cell is a human cell. In some embodiments, the target cell is a cell of the epidermis and/or dermis. In some embodiments, the target cell is a keratinocyte and/or fibroblast. In some embodiments, host cell proliferation (e.g., human keratinocytes and/or fibroblast cells) after exposure to the recombinant genome is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). In some embodiments, host cell proliferation (e.g., human keratinocytes and/or fibroblast cells) after exposure to the recombinant genome is at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, or at least about 1000-fold faster as compared to host cell proliferation after exposure to a corresponding wild-type herpes virus genome (e.g., measuring the relative cellular proliferation after exposure to a recombinant ΔICP4 (one or both copies) herpes simplex virus genome vs. cellular proliferation after exposure to a wild-type herpes simplex virus genome in human keratinocytes or fibroblasts (primary cells or cell lines); measuring the relative cellular proliferation after exposure to a recombinant ΔICP4 (one or both copies)/ΔICP22 herpes simplex virus genome vs. cellular proliferation after exposure to a wild-type herpes simplex virus genome in human keratinocytes or fibroblasts (primary cells or cell lines); etc.). Methods of measuring cellular proliferation are known to one of ordinary skill in the art, including, for example, through the use of a Ki67 cell proliferation assay, a BrdU cell proliferation assay, etc.

A vector (e.g., herpes viral vector) may include one or more polynucleotides of the present disclosure in a form suitable for expression of the polynucleotide in a host cell. Vectors may include one or more regulatory sequences operatively linked to the polynucleotide to be expressed (e.g., as described above).

In some embodiments, a recombinant nucleic acid of the present disclosure (e.g., a recombinant herpes simplex virus genome) comprises one or more of the polynucleotides described herein inserted in any orientation in the recombinant nucleic acid. If the recombinant nucleic acid comprises two or more polynucleotides described herein (e.g., two or more, three or more, etc.), the polynucleotides may be inserted in the same orientation or opposite orientations to one another. Without wishing to be bound be theory, incorporating two polynucleotides (e.g., two transgenes) into a recombinant nucleic acid (e.g., a vector) in an antisense orientation may help to avoid read-through and ensure proper expression of each polynucleotide.

IV. VIRUSES

Certain aspects of the present disclosure relate to viruses comprising any of the polynucleotides and/or recombinant nucleic acids described herein. In some embodiments, the virus is capable of infecting one or more target cells of a subject (e.g., a human). In some embodiments, the virus is suitable for delivering the polynucleotides and/or recombinant nucleic acids into one or more target cells of a subject (e.g., a human subject). In some embodiments, the one or more target cell are one or more human cells. In some embodiments, the one or more target cells are one or more cells of the skin (e.g., one or more cells of the epidermis, dermis, and/or subcutis). In some embodiments, the one or more cells are selected from keratinocytes, melanocytes, Langerhans cells, Merkel cells, mast cells, fibroblasts, and/or adipocytes. In some embodiments, the one or more cells are keratinocytes. In some embodiments, the one or more cells reside in the stratum corneum, stratum granulosum, stratum spinulosum, stratum basale, and/or basement membrane. In some embodiments, the one or more target cells are one or more epidermal cells.

Any suitable virus known in the art may be used, including, for example, adenovirus, adeno-associated virus, retrovirus, lentivirus, sendai virus, herpes virus (e.g., a herpes simplex virus), vaccinia virus, and/or any hybrid virus thereof. In some embodiments, the virus is attenuated. In some embodiments, the virus is replication-defective. In some embodiments, the virus is replication-competent. In some embodiments, the virus has been modified to alter its tissue tropism relative to the tissue tropism of an unmodified, wild-type virus. In some embodiments, the virus has reduced cytotoxicity as compared to a corresponding wild-type virus. Methods for producing a virus comprising recombinant nucleic acids are well known to one of ordinary skill in the art.

In some embodiments, the virus is a member of the Herpesviridae family of DNA viruses, including, for example, a herpes simplex virus, a varicella zoster virus, a human cytomegalovirus, a herpesvirus 6A, a herpesvirus 6B, a herpesvirus 7, and a Kaposi's sarcoma-associated herpesvirus, etc. In some embodiments, the herpes virus is attenuated. In some embodiments, the herpes virus is replication-defective. In some embodiments, the herpes virus is replication-competent. In some embodiments, the herpes virus has reduced cytotoxicity as compared to a corresponding wild-type herpes virus. In some embodiments, the herpes virus is not oncolytic.

In some embodiments, the virus is a herpes simplex virus. Herpes simplex viruses comprising recombinant nucleic acids may be produced by a process disclosed, for example, in WO2015/009952 and/or WO2017/176336. In some embodiments, the herpes simplex virus is attenuated. In some embodiments, the herpes simplex virus is replication-competent. In some embodiments, the herpes simplex virus is replication-defective. In some embodiments, the herpes simplex virus is a herpes simplex type 1 virus (HSV-1), a herpes simplex type 2 virus (HSV-2), or any derivatives thereof. In some embodiments, the herpes simplex virus is a herpes simplex type 1 virus (HSV-1). In some embodiments, the HSV-1 is attenuated. In some embodiments, the HSV-1 has reduced cytotoxicity as compared to a corresponding wild-type HSV-1. In some embodiments, the HSV-1 is not oncolytic.

In some embodiments, the herpes simplex virus has been modified to alter its tissue tropism relative to the tissue tropism of an unmodified, wild-type herpes simplex virus. In some embodiments, the herpes simplex virus comprises a modified envelope. In some embodiments, the modified envelope comprises one or more (e.g., one or more, two or more, three or more, four or more, etc.) mutant herpes simplex virus glycoproteins. Examples of herpes simplex virus glycoproteins may include, but are not limited to, the glycoproteins gB, gC, gD, gH, and gL. In some embodiments, the modified envelope alters the herpes simplex virus tissue tropism relative to a wild-type herpes simplex virus.

In some embodiments, the transduction efficiency (in vitro and/or in vivo) of a virus of the present disclosure (e.g., a herpes virus) for one or more target cells (e.g., one or more human keratinocytes and/or fibroblasts) is at least about 25%. For example, the transduction efficiency of the virus for one or more target cells may be at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, or more. In some embodiments, the virus is a herpes simplex virus and the transduction efficiency of the virus for one or more target cells (e.g., one or more human keratinocytes and/or fibroblasts) is about 85% to about 100%. In some embodiments, the virus is a herpes simplex virus and the transduction efficiency of the virus for one or more target cells (e.g., one or more human keratinocytes and/or fibroblasts) is at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100%. Methods of measuring viral transduction efficiency in vitro or in vivo are well known to one of ordinary skill in the art, including, for example, qPCR analysis, deep sequencing, western blotting, fluorometric analysis (such as fluorescent in situ hybridization (FISH), fluorescent reporter gene expression, immunofluorescence, FACS), etc.

V. COMPOSITIONS AND FORMULATIONS

Certain aspects of the present disclosure relate to compositions and formulations (e.g., pharmaceutical compositions and formulations) comprising any of the recombinant nucleic acids (e.g., a recombinant herpes virus genome) and/or viruses (e.g., a herpes virus comprising a recombinant genome described herein (such as a herpes simplex virus comprising a recombinant herpes simplex virus genome), and an excipient or carrier (e.g., a pharmaceutically acceptable excipient or carrier). In some embodiments, the composition or formulation is a cosmetic composition or formulation (e.g., a skin care product).

In some embodiments, the composition or formulation comprises any one or more of the viruses (e.g., herpes viruses) described herein. In some embodiments, the composition or formulation comprises from about $10^4$ to about $10^{12}$ plaque forming units (PFU)/mL of the virus. For example, the composition or formulation may comprise from about $10^4$ to about $10^{12}$, about $10^5$ to about $10^{12}$, about $10^6$ to about $10^{12}$, about $10^7$ to about $10^{12}$, about $10^8$ to about $10^{12}$, about $10^9$ to about $10^{12}$, about $10^{10}$ to about $10^{12}$, about $10^{11}$ to about $10^{12}$, about $10^4$ to about $10^{11}$, about $10^5$ to about $10^{11}$, about $10^6$ to about $10^{11}$, about $10^7$ to about $10^{11}$, about $10^8$ to about $10^{11}$, about $10^9$ to about $10^{11}$, about $10^{10}$ to about $10^{11}$, about $10^4$ to about $10^{10}$, about $10^5$ to about $10^{10}$, about $10^6$ to about $10^{10}$, about $10^7$ to about $10^{10}$, about $10^8$ to about $10^{10}$, about $10^9$ to about $10^{10}$, about $10^4$ to about $10^9$, about $10^5$ to about $10^9$, about $10^6$ to about $10^9$, about $10^7$ to about $10^9$, about $10^8$ to about $10^9$, about $10^4$ to about $10^8$, about $10^5$ to about $10^8$, about $10^6$ to about 108, about $10^7$ to about $10^8$, about $10^4$ to about $10^7$, about $10^5$ to about $10^7$, about $10^6$ to about $10^7$, about $10^4$ to about $10^6$, about $10^5$ to about $10^6$, or about $10^4$ to about $10^5$ PFU/mL of the virus. In some embodiments, the composition or formulation comprises about $10^4$, about $10^5$, about $10^6$, about $10^7$, about $10^8$, about $10^9$, about $10^{10}$, about $10^{11}$, or about $10^{12}$ PFU/mL of the virus.

Compositions and formulations (e.g., pharmaceutical compositions and formulations) as described herein can be prepared by mixing the active ingredient(s) (such as a recombinant nucleic acid or a virus) having the desired degree of purity with one or more acceptable carriers or excipients. Acceptable carriers or excipients (e.g., pharmaceutically acceptable carriers or excipients) are generally nontoxic to recipients at the dosages and concentrations employed, and may include, but are not limited to: buffers (such as phosphate, citrate, acetate, and other organic acids); antioxidants (such as ascorbic acid and methionine); preservatives (such as octadecyldimethylbenzyl ammonium chloride, benzalkonium chloride, benzethonium chloride, phenol, butyl or benzyl alcohol, alkyl parabens, catechol, resorcinol, cyclohexanol, 3-pentanol, and m-cresol); amino acids (such as glycine, glutamine, asparagine, histidine, arginine, or lysine); low molecular weight (less than about 10 residues) polypeptides; proteins (such as serum albumin, gelatin, or immunoglobulins); polyols (such as glycerol, e.g., formulations including 10% glycerol); hydrophilic polymers (such as polyvinylpyrrolidone); monosaccharides, disaccharides, and other carbohydrates (including glucose, mannose, or dextrins); chelating agents (such as EDTA); sugars (such as sucrose, mannitol, trehalose, or sorbitol); salt-forming counter-ions (such as sodium); metal complexes (such as Zn-protein complexes); liposomes (e.g., cationic lipids); nanoparticle carriers; and/or non-ionic surfactants (such as polyethylene glycol (PEG)). A thorough discussion of carriers is available in REMINGTON'S PHARMACEUTICAL SCIENCES (Mack Pub. Co., N.J. 1991).

In some embodiments, the composition or formulation comprises one or more lipid (e.g., cationic lipid) carriers. In some embodiments, the composition or formulation comprises one or more nanoparticle carriers. Nanoparticles are submicron (less than about 1000 nm) sized drug delivery vehicles that can carry encapsulated drugs (such as synthetic small molecules, proteins, peptides, cells, viruses, and nucleic acid-based biotherapeutics for rapid or controlled release. A variety of molecules (e.g., proteins, peptides, recombinant nucleic acids, etc.) can be efficiently encapsulated in nanoparticles using processes well known in the art. In some embodiments, a molecule "encapsulated" in a nanoparticle may refer to a molecule (such as a virus) that is contained within the nanoparticle or attached to and/or associated with the surface of the nanoparticle, or any combination thereof. Nanoparticles for use in the compositions or formulations described herein may be any type of biocompatible nanoparticle known in the art, including, for example, nanoparticles comprising poly(lactic acid), poly (glycolic acid), PLGA, PLA, PGA, and any combinations thereof (see e.g., Vauthier et al. Adv Drug Del Rev. (2003) 55: 519-48; US2007/0148074; US2007/0092575; US2006/0246139; U.S. Pat. Nos. 5,753,234; 7,081,483; and WO2006/052285).

In some embodiments, the carrier or excipient (e.g., a pharmaceutically acceptable carrier or excipient) may be adapted for or suitable for any administration route known in the art, including, for example, intravenous, intramuscular, subcutaneous, cutaneous, intranasal, intratracheal, sublingual, buccal, topical, oral, transdermal, intradermal, intraperitoneal, intraorbital, intravitreal, subretinal, transmucosal, intraarticular, by superficial injection, by implantation, by inhalation, intrathecal, intraventricular, and/or intranasal administration. In some embodiments, the carrier or excipient (e.g., pharmaceutically acceptable carrier or excipient) is adapted for or suitable for topical, transdermal, subcutaneous, and/or intradermal administration. In some embodiments, the carrier or excipient is adapted for or suitable for topical, transdermal, and/or intradermal administration. In some embodiments, the carrier or excipient is adapted for or suitable for superficial injection.

Examples of carriers or excipients adapted for or suitable for use in a topical, transdermal, subcutaneous, superficial, and/or intradermal application/administration may include, but are not limited to, ointments, oils, pastes, creams, aerosols, suspensions, emulsions, fatty ointments, gels, powders, liquids, lotions, solutions, sprays, patches (e.g., transdermal patches or microneedle patches), adhesive strips, a microneedle or microneedle arrays, and inhalants. In some embodiments, the carrier or excipient (e.g., the pharmaceutically acceptable carrier or excipient) comprises one or more (e.g., one or more, two or more, three or more, four or more, five or more, etc.) of an ointment, oil, paste, cream, aerosol, suspension, emulsion, fatty ointment, gel, powder, liquid lotion, solution, spray, adhesive strip, and an inhalant. In some embodiments, the carrier comprises a patch (e.g. a patch that adheres to the skin), such as a transdermal patch or a microneedle patch. In some embodiments, the carrier comprises a microneedle or microneedle array. Methods for making and using microneedle arrays suitable for composition delivery are generally known in the art (Kim Y. et al. "Microneedles for drug and vaccine delivery". *Advanced Drug Delivery Reviews* 2012, 64 (14): 1547-68).

In some embodiments, the composition or formulation (e.g., the pharmaceutical composition or formulation) is adapted for or suitable for any administration route known in the art, including, for example, intravenous, intramuscular, subcutaneous, cutaneous, oral, intranasal, intratracheal, sublingual, buccal, topical, transdermal, intradermal, intraperitoneal, intraorbital, intravitreal, subretinal, transmucosal, intraarticular, by superficial injection, by implantation, by inhalation, intrathecal, intraventricular, and/or intranasal administration. In some embodiments, the composition or formulation is adapted for or suitable for cutaneous, topical, transdermal, subcutaneous, and/or intradermal administration. In some embodiments, the pharmaceutical composition or formulation is adapted for or suitable for topical, transdermal, and/or intradermal administration. In some embodiments, the composition or formulation is adapted for or suitable for intradermal administration. In some embodiments, the composition of formulation is adapted for or suitable for superficial injection.

In some embodiments, the composition or formulation (e.g., pharmaceutical composition or formulation) further comprises one or more additional components. Examples of additional components may include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; sweetenings; flavorings; perfuming agents; colorants; moisturizers; sunscreens; antibacterial agents; agents able to stabilize polynucleotides or prevent their degradation, and the like. In some embodiments, the composition or formulation comprises a hydroxypropyl methylcellulose gel. In some embodiments, the composition or formulation comprises a phosphate buffer. In some embodiments, the composition or formulation comprises glycerol (e.g., at about 1%, about 2%, about 3%, about 4%, about 5%, about 6%, about 7%, about 8%, about 9%, about 10%, about 15%, etc.).

Compositions and formulations (e.g., pharmaceutical compositions and formulations) to be used for in vivo administration are generally sterile. Sterility may be readily accomplished, e.g., by filtration through sterile filtration membranes.

In some embodiments, any of the recombinant nucleic acids, viruses, and/or compositions or formulations described herein may be used to deliver one or more polynucleotides encoding a collagen protein (e.g., a human collagen protein such as Collagen 3) into one or more cells of a subject (e.g., one or more collagen-deficient cells). In some embodiments, any of the recombinant nucleic acids, viruses, and/or compositions or formulations described herein may be used in a therapy. In some embodiments, any of the recombinant nucleic acids, viruses, and/or compositions or formulations described herein may be used in the treatment of a cosmetic or aesthetic condition that would benefit from the expression of a collagen polypeptide (e.g., a cosmetic or aesthetic condition associated with a collagen deficiency (such as aged and/or UV-damaged skin)). In some embodiments, any of the recombinant nucleic acids, viruses, and/or compositions or formulations described herein may be used in the treatment of dermatological aging (e.g., as described below).

In some embodiments, any of the recombinant nucleic acids, viruses, and/or compositions or formulations described herein may be used in the preparation or manufacture of a medicament. In some embodiments, any of the recombinant nucleic acids, viruses, and/or compositions or formulations described herein may be used in the preparation or manufacture of a medicament useful for delivering one or more polynucleotides encoding a collagen protein (e.g., a human collagen protein such as Collagen 3) into one or more cells of a subject (e.g., one or more collagen-deficient cells). In some embodiments, any of the recombinant nucleic acids, viruses, and/or compositions or formulations described herein may be used in the preparation or manufacture of a medicament useful for the treatment of a cosmetic or aesthetic condition that would benefit from the expression of a collagen polypeptide (e.g., a cosmetic or aesthetic condition associated with a collagen deficiency (such as aged and/or UV-damaged skin)). In some embodiments, any of the recombinant nucleic acids, viruses, and/or compositions or formulations described herein may be used in the preparation or manufacture of a medicament useful for the treatment of dermatological aging (e.g., as described below).

VI. METHODS

Certain aspects of the present disclosure relate to a method of enhancing, increasing, augmenting, and/or supplementing the levels of one or more dermal extracellular matrix proteins in a subject (e.g., in one or more cells of a subject) comprising administering to the subject any of the recombinant nucleic acids, viruses, medicaments, and/or compositions described herein. In some embodiments, the subject is a human.

Other aspects of the present disclosure relate to method of stabilizing or improving the structure and/or organization of the dermal extracellular matrix in a subject comprising administering to the subject any of the recombinant nucleic acids, viruses, medicaments, and/or compositions described herein. In some embodiments, the subject is a human.

Other aspects of the present disclosure relate to a method of enhancing, increasing, augmenting, and/or supplementing the levels of one or more human collagen proteins in a subject (e.g., in one or more cells of a subject) comprising administering to the subject any of the recombinant nucleic acids, viruses, medicaments, and/or compositions described herein. In some embodiments, the subject is a human.

In some embodiments, administration of the recombinant nucleic acid, virus, medicament, and/or composition to the subject increases collagen (e.g., COL1-1; COL1-2; COL3; COL1-1 and COL1-2; COL1-1 and COL3; etc.) levels (transcript or protein levels) in one or more cells of the subject by at least about 10%, as compared to the endogenous levels of the collagen(s) in one or more corresponding untreated cells (e.g., one or more cells prior to treatment, one or more uninfected cells during treatment, etc.) of the subject. For example, administration of the recombinant nucleic acid, virus, medicament, and/or composition may increase collagen levels (transcript or protein levels) in one or more cells of the subject by at least about 10%, at least about 15%, at least about 20%, at least about 25%, at least about 30%, at least about 40%, at least about 50%, at least about 60%, at least about 70%, at least about 80%, at least about 90%, at least about 95%, at least about 99%, or more, as compared to the endogenous levels of the collagen(s) in one or more corresponding untreated cells of the subject. In some embodiments, administration of the recombinant nucleic acid, virus, medicament, and/or composition to the subject increases collagen levels (transcript or protein levels) in one or more cells of the subject by at least about 2-fold, as compared to the endogenous levels of the collagen(s) in one or more corresponding untreated cells (e.g., one or more cells prior to treatment, one or more uninfected cells during treatment, etc.) of the subject. For example, administration of the recombinant nucleic acid, virus, medicament, and/or composition may increase collagen levels (transcript or protein levels) in one or more cells of the subject by at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 50-fold, at least about 75-fold, at least about 100-fold, at least about 250-fold, at least about 500-fold, at least about 750-fold, at least about 1000-fold, or more, as compared to the endogenous levels of the collagen(s) in one or more corresponding untreated cells of the subject. Methods of measuring transcript or protein levels from a sample are well known to one of ordinary skill in the art, including, for example, by qPCR, RNAseq, ELISA, western blot, mass spectrometry, etc.

Other aspects of the present disclosure relate to a method of enhancing, increasing, augmenting, and/or supplementing the soft tissue of a subject comprising administering to the subject any of the recombinant nucleic acids, viruses, medicaments, and/or compositions described herein. In some embodiments, the subject is a human. In some embodiments, the recombinant nucleic acids, viruses, medicaments, and/or compositions are injected into a soft tissue of the subject. In some embodiments, the skin of the subject is aging skin. In some embodiments, the skin of the subject has been damaged due to exposure to ultraviolet light (e.g., from the sun, from a tanning bed, etc.). In some embodiments, the skin of the subject is wrinkled.

In some embodiments, the recombinant nucleic acids, viruses, medicaments, and/or compositions may be used in a method to repair and/or augment the soft tissue of a subject. In some embodiments, "tissue repair" refers to the restoration of tissue architecture and/or function and encompasses tissue regeneration and replacement. In some embodiments, repair or augmentation of the soft tissue refers to procedures that are used to restore the youthful appearance of skin (e.g., as compared to "aged" skin whose appearance is due to defects resulting from chronological aging or other physical, chemical, or UV damage). In some embodiments, the recombinant nucleic acids, viruses, medicaments, and/or compositions are useful in cosmetic soft tissue applications, such as to fill wrinkles, lines, folds, scars, and to enhance dermal tissue (e.g., plump thin lips, fill in sunken eyes and/or shallow cheeks, etc.).

Other aspects of the present disclosure relate to a method of improving skin quality, condition, and/or appearance in a subject in need thereof comprising administering to the subject any of the recombinant nucleic acids, viruses, medicaments, and/or compositions described herein. In some embodiments, the subject is a human. In some embodiments, the skin condition is one or more of sun damage, aging, UV exposure, rough texture, skin sagging, and/or wrinkles. Improvement of skin quality, condition, and/or appearance (e.g., as compared to before treatment) may be assessed using any appropriate method or scale known in the art, including, for example, FACE Q, GAIS, etc. In some embodiments, the skin of the subject is aging skin. In some embodiments, the skin of the subject has been damaged due to exposure to ultraviolet light (e.g., from the sun, from a tanning bed, etc.). In some embodiments, the skin of the subject is wrinkled.

Other aspects of the present disclosure relate to a method of reducing the appearance of one or more superficial depressions in the skin of a subject in need thereof comprising administering to the subject any of the recombinant nucleic acids, viruses, medicaments, and/or compositions described herein. In some embodiments, the subject is a human. In some embodiments, administration of the recombinant nucleic acid, virus, medicaments, and/or composition reduces the appearance of one or more superficial depressions in the skin of the subject for at least about three months, at least about six months, at least about nine months, or at least about 12 months. In some embodiments, the appearance of one or more superficial depressions in the skin of the subject is reduced after administration of the composition, as compared to the appearance of the one or more superficial depression in the skin of the subject prior to administration of the composition. In some embodiments, the one or more superficial depressions in the skin are one or more of fine lines and wrinkles (e.g., forehead wrinkles, "crow's feet", wrinkles at the edges of the eye or mouth, etc.). In some embodiments, the treatment of one or more superficial skin depressions is measured by an improvement in skin texture or skin quality, such as smoothness, hydration, and elasticity, as compared to non-treated skin. In some embodiments, the treatment of one or more superficial skin depressions is measured by a reduction in the severity (e.g., depth) of the superficial depressions and/or a reduction in the number of fine lines or wrinkles in a given area of skin. In some embodiments, the skin of the subject is aging skin. In some embodiments, the skin of the subject has been damaged due to exposure to ultraviolet light (e.g., from the sun, from a tanning bed, etc.). In some embodiments, the skin of the subject is wrinkled.

Other aspects of the present disclosure relate to a method of increasing and/or improving at least one of texture, smoothness, elasticity, and/or tension of the skin of a subject comprising administering to the subject any of the recombinant nucleic acids, viruses, medicaments, and/or compositions described herein. In some embodiments, the subject is a human. In some embodiments, the skin of the subject maintains at least one of an increased and/or improved texture, smoothness, elasticity, or tension for at least about three months, at least about six months, at least about nine months, or at least about 12 months after administration of the composition. In some embodiments, at least one of texture, smoothness, elasticity, or tension of the skin of the subject is increased and/or improved after administration of the composition, as compared to the texture, smoothness, elasticity, or tension of the skin of the subject prior to administration of the composition. Methods of measuring texture, smoothness, elasticity, and/or tensions of the skin are known to one of skill in the art. In some embodiments, the skin of the subject is aging skin. In some embodiments, the skin of the subject has been damaged due to exposure to ultraviolet light (e.g., from the sun, from a tanning bed, etc.). In some embodiments, the skin of the subject is wrinkled.

Other aspects of the present disclosure relate to a method of diminishing one or more dermatological signs of aging in a subject in need thereof comprising administering to the subject an effective amount of any of the recombinant nucleic acids, viruses, medicaments, and/or compositions described herein. In some embodiments, the subject is a human. In some embodiments, diminishing one or more dermatological signs of aging include any one of more of the following: treatment, reduction, and/or prevention of fine lines and/or wrinkles; reduction of skin pore size; improvement in skin thickness, plumpness, and/or tautness; improvement in skin smoothness, suppleness, and/or softness; improvement in skin tone, radiance, and/or clarity; improvement in procollagen and/or collagen production; improvement in skin texture and or promotion of retexturization; improvement in appearance of skin contours; restoration of skin luster and/or brightness; improvement of skin appearance decreased by aging and/or menopause; improvement in skin moisturization; increase in skin elasticity and/or resiliency; treatment, reduction, and/or prevention or skin sagging; improvement in skin firmness; reduction of pigment spots, mottled skin, and/or scars (such as acne scars); and/or improvement of optical properties of skin by light diffraction or reflection. In some embodiments, the one or more dermatological signs of aging in the subject is diminished after administration of the composition, as compared to the one or more dermatological signs of aging in the subject prior to administration of the composition. Any suitable method for measuring one or more signs of dermatological aging known in the art may be used.

In some embodiments, one or more portions of the skin of the subject is abraded or made more permeable prior to treatment with an effective amount of any of the recombinant nucleic acids, viruses, medicaments, and/or compositions described herein. Any suitable method of abrading the skin or increasing skin permeability known in the art may be used, including, for example, use of a dermal roller, repeated use of adhesive strips to remove layers of skin cells (tape stripping), scraping with a scalpel or blade, use of sandpaper, use of chemical permeation enhancers or electrical energy, use of sonic or ultrasonic energy, use of light (e.g., laser) energy, use of micron-sized needles or blades with a length suitable to pierce but not completely pass through the epidermis, etc.

In some embodiments, the methods of the present disclosure are for cosmetic applications, such as to reduce or eliminate one or more superficial depressions in the skin, to reduce or eliminate one or more wrinkles, and/or to prevent the occurrence or reoccurrence of one or more wrinkles. In some embodiments, the one or more superficial depressions in the skin or wrinkles are selected from nasolabial folds, crows' feet, frown lines, worry lines, scars, glabellar lines, brow ptosis, tear troughs, nasojugal lines, bunny lines, cheek/mid-face ptosis, marionette lines, poppy dimpling, smile lines, laugh lines, chin creases, neck lines, platysma bands, and any combinations thereof.

In some embodiments, an "effective amount" is at least the minimum amount required to affect a measurable improvement in or prevention of one or more signs or symptoms of a particular condition (e.g., a cosmetic condition such as skin aging). An "effective amount" may vary according to factors such as the age, sex, and weight of the patient. An effective amount is also one in which any toxic or detrimental effects of the treatment are outweighed by the beneficial effects. An effective amount can be administered in one or more administrations. For purposes of the present disclosure, an effective amount of a recombinant nucleic acid, virus, medicament, and/or composition is an amount sufficient to accomplish a measurable improvement either directly or indirectly. As is understood in the clinical context, an effective amount of a recombinant nucleic acid, virus, medicament, and/or composition may or may not be achieved in conjunction with another drug, compound, or composition. Thus, an "effective amount" may be considered in the context of administering one or more agents, and a single agent may be considered to be given in an effective amount if, in conjunction with one or more other agents, a desirable result may be or is achieved.

In some embodiments, the recombinant nucleic acid, virus, medicament, and/or composition is administered once to the subject. In some embodiments, the recombinant nucleic acid, virus, medicament, and/or composition is administered at least twice (e.g., at least 2 times, at least 3 times, at least 4 times, at least 5 times, at least 10 times, etc.) to the subject. In some embodiments, at least about 15 days (e.g., at least about 15 days, at least about 20 days, at least about 30 days, at least about 40 days, at least about 50 days, at least about 60 days, at least about 70 days, at least about 80 days, at least about 90 days, at least about 100 days, at least about 120 days, etc.) pass between administrations (e.g., between the first and second administrations, between the second and third administrations, etc.).

The recombinant nucleic acids, viruses, medicaments, and/or compositions or formulations described herein may be administered by any suitable method or route known in the art, including, without limitation, by oral administration, sublingual administration, buccal administration, topical administration, rectal administration, via inhalation, transdermal administration, subcutaneous injection, intradermal injection, superficial injection, intravenous (IV) injection, intra-arterial injection, intramuscular injection, intracardiac injection, intraosseous injection, intraperitoneal injection, transmucosal administration, vaginal administration, intraurethral administration, intravitreal administration, intraorbital administration, subretinal administration, intra-articular administration, peri-articular administration, local administration, epicutaneous administration, or any combinations thereof. The present disclosure thus encompasses methods of delivering any of the recombinant nucleic acids, viruses, medicaments, and/or compositions or formulations described herein to an individual.

In some embodiments, the recombinant nucleic acids, viruses, medicaments, and/or compositions or formulations are administered cutaneously, topically, transdermally, subcutaneously, or intradermally to the subject. In some embodiments, the recombinant nucleic acids, viruses, medicaments, and/or compositions or formulations are administered intradermally and/or subcutaneously. In some embodiments, the recombinant nucleic acids, viruses, medicaments, and/or compositions or formulations are administered via superficial injection. In some embodiments, the recombinant nucleic acids, viruses, medicaments, and/or compositions or formulations are administered topically and/or transdermally. In some embodiments, the recombinant nucleic acids, viruses, medicaments, and/or compositions or formulations are administered one, two, three, four, five or more times per day. In some embodiments, the recombinant nucleic acids, viruses, medicaments, and/or compositions or formulations are administered to one or more affected (e.g., wrinkled) areas of an individual. In some embodiments, the composition is administered to one or more unaffected areas of the individual.

In some embodiments, the recombinant nucleic acids, viruses, medicaments, and/or compositions are administered at a superficial depth in the skin. In some embodiments, the recombinant nucleic acids, viruses, medicaments, and/or compositions are introduced into the skin at a depth of about 2000 microns or less. For example, the recombinant nucleic acids, viruses, medicaments, and/or compositions may be administered into the skin at a depth of about 2000 microns or less, at about 1750 microns or less, at about 1500 microns or less, at about 1250 microns or less, at about 1000 microns or less, at about 900 microns or less, at about 800 microns or less, at about 700 microns or less, at about 600 microns or less, or at about 500 microns or less. In some embodiments, the recombinant nucleic acids, viruses, medicaments, and/or compositions are introduced at an injection depth between about 0.5 mm and 5.0 mm. For example, the recombinant nucleic acids, viruses, medicaments, and/or compositions may be introduced at an injection depth of between about 0.5 mm and 5.0 mm, about 0.5 mm and 4.5 mm, about 0.5 mm and 4.0 mm, about 0.5 mm and 3.5 mm, about 0.5 mm and 3.0 mm, about 0.5 mm and 2.5 mm, about 0.5 mm and 2.0 mm, about 0.5 mm and 1.5 mm, about 0.5 mm and 1.0 mm, 1.0 mm and 5.0 mm, about 1.0 mm and 4.5 mm, about 1.0 mm and 4.0 mm, about 1.0 mm and 3.5 mm, about 1.0 mm and 3.0 mm, about 1.0 mm and 2.5 mm, about 1.0 mm and 2.0 mm, about 1.0 mm and 1.5 mm, 1.5 mm and 5.0 mm, about 1.5 mm and 4.5 mm, about 1.5 mm and 4.0 mm, about 1.5 mm and 3.5 mm, about 1.5 mm and 3.0 mm, about 1.5 mm and 2.5 mm, about 1.5 mm and 2.0 mm, etc.

In some embodiments, the recombinant nucleic acids, viruses, medicaments, and/or compositions are administered by injections spaced apart by a distance of between about 1 mm to about 30 mm. For example, the recombinant nucleic acids, viruses, medicaments, and/or compositions may be administered by injections spaced apart by a distance of between about 1 mm and 30 mm, 2 mm and 30 mm, 5 mm and 30 mm, 10 mm and 30 mm, 15 mm and 30 mm, 1 mm and 20 mm, 2 mm and 20 mm, 5 mm and 20 mm, 10 mm and 20 mm, 15 mm and 20 mm, 1 mm and 15 mm, 2 mm and 15 mm, 5 mm and 15 mm, 10 mm and 15 mm, 1 mm and 10 mm, 2 mm and 10 mm, 5 mm and 10 mm, 1 mm and 5 mm, 2 mm and 5 mm, etc. In some embodiments, the injections are spaced apart by a distance of at least about 1 mm, at least about 2 mm, at least about 5 mm, at least about 10 mm, at least about 15 mm, at least about 20 mm, at least about 30 mm or more.

Numerous areas of the body may be treated with the recombinant nucleic acids, viruses, medicaments, and/or compositions described herein, including, for example, the face, forehead, lips, scalp, neck, arms, hands, legs, knees, feet, chest, back, groin, buttocks, thighs, etc. In some embodiments, the recombinant nucleic acids, viruses, medicaments, and/or compositions are administered to the face. In some embodiments, the recombinant nucleic acids, viruses, medicaments, and/or compositions are administered to one or more nasolabial folds. In some embodiments, the recombinant nucleic acids, viruses, medicaments, and/or compositions are administered around one or both eyes. In some embodiments, the recombinant nucleic acids, viruses, medicaments, and/or compositions are administered to one or more crows' feet. In some embodiments, the recombinant nucleic acids, viruses, medicaments, and/or compositions are administered to one or more frown lines. In some embodiments, the recombinant nucleic acids, viruses, medicaments, and/or compositions are administered to one or more scars (e.g., acne scars). In some embodiments, the recombinant nucleic acids, viruses, medicaments, and/or compositions are administered to one or more glabellar lines. In some embodiments, the recombinant nucleic acids, viruses, medicaments, and/or compositions are administered to one or more brow ptosis. In some embodiments, the recombinant nucleic acids, viruses, medicaments, and/or compositions are administered to one or more deep tear troughs. In some embodiments, the recombinant nucleic acids, viruses, medicaments, and/or compositions are administered to one or more nasojugal lines. In some embodiments, the recombinant nucleic acids, viruses, medicaments, and/or compositions are administered to one or more bunny lines. In some embodiments, the recombinant nucleic acids, viruses, medicaments, and/or compositions are administered to one or more cheek/mid-face ptosis. In some embodiments, the recombinant nucleic acids, viruses, medicaments, and/or compositions are administered to one or more marionette lines. In some embodiments, the recombinant nucleic acids, viruses, medicaments, and/or compositions are administered to one or sites of poppy dimpling. In some embodiments, the recombinant nucleic acids, viruses, medicaments, and/or compositions are administered to one or more chin creases. In some embodiments, the recombinant nucleic acids, viruses, medicaments, and/or compositions are administered to one or more neck lines. In some embodiments, the recombinant nucleic acids, viruses, medicaments, and/or compositions are administered to one or more platysma bands.

In some embodiments, the recombinant nucleic acid expresses the cosmetic protein(s) (e.g., human collagens) when the recombinant nucleic acid is delivered into one or more target cells of a subject. In some embodiments, expression of the cosmetic protein(s) (e.g., human collagens) enhances, increases, augments, and/or supplements the levels of human collagen in one or more target cells. In some embodiments, expression of the cosmetic protein(s) (e.g., human collagens) enhances, increases, augments, and/or supplements the levels of human collagen secreted by one or more target cells. In some embodiments, expression of the cosmetic protein(s) (e.g., human collagens) enhances, increases, augments, and/or supplements the levels of human collagen in the extracellular matrix. In some embodiments, expression of the cosmetic protein(s) (e.g., human collagens) enhances, increases, augments, and/or supplements the stability of the extracellular matrix in the subject. In some embodiments, expression of the cosmetic protein(s) (e.g., human collagens) enhances, augments, and/supplements the soft tissue of the subject. In some embodiments, expression of the cosmetic protein(s) (e.g., human collagens) improves the skin quality, condition, and/or appearance of the individual. In some embodiments, expression of the cosmetic protein(s) (e.g., human collagens) reduces one or more superficial depressions (e.g., wrinkles) in the skin of the subject. In some embodiments, expression of the cosmetic protein(s) (e.g., human collagens) improves the texture, smoothness, elasticity, and/or tension of the skin of the subject. In some embodiments, expression of the cosmetic protein(s) (e.g., human collagens) reduces one or more dermatological signs of aging in the subject.

VII. HOST CELLS

Certain aspects of the present disclosure relate to one or more host cells comprising any of the recombinant nucleic acids described herein. Any suitable host cell (prokaryotic or eukaryotic) known in the art may be used, including, for example: prokaryotic cells including eubacteria, such as Gram-negative or Gram-positive organisms, for example Enterobacteriaceae such as *Escherichia* (e.g., *E. coli*), *Enterobacter, Erminia, Klebsiella, Proteus, Salmonella* (e.g., *S. typhimurium*), *Serratia* (e.g., *S. marcescans*), and *Shigella*, as well as Bacilli such as *B. subtilis* and *B. licheniformis*; fungal cells (e.g., *S. cerevisiae*); insect cells (e.g., S2 cells, etc.); and mammalian cells, including monkey kidney CV1 line transformed by SV40 (COS-7, ATCC CRL 1651), human embryonic kidney line (293 or 293 cells subcloned for growth in suspension culture), baby hamster kidney cells (BHK, ATCC CCL 10), mouse Sertoli cells (TM4), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells, MRC 5 cells, FS4 cells, human hepatoma line (Hep G2), Chinese hamster ovary (CHO) cells, including DHFR" CHO cells, and myeloma cell lines such as NS0 and Sp2/0. In some embodiments, the host cell is a human or non-human primate cell. In some embodiments, the host cell is a Vero cell. In some embodiments, the host cell is a complementing host cell. In some embodiments, the host cell (e.g., the Vero cell) expresses one or more herpes simplex virus genes (e.g., an ICP4 gene). In some embodiments, the host cells are cells from a cell line. Examples of suitable host cells or cell lines may include, but are not limited to, 293, HeLa, SH-Sy5y, Hep G2, CACO-2, A549, L929, 3T3, K562, CHO-K1, MDCK, HUVEC, Vero, N20, COS-7, PSN1, VCaP, CHO cells, and the like.

In some embodiments, the recombinant nucleic acid is a herpes simplex viral vector. In some embodiments, the recombinant nucleic acid is a herpes simplex virus amplicon. In some embodiments, the recombinant nucleic acid is an HSV-1 amplicon or HSV-1 hybrid amplicon. In some embodiments, a host cell comprising a helper virus is contacted with an HSV-1 amplicon or HSV-1 hybrid amplicon described herein, resulting in the production of a virus comprising one or more recombinant nucleic acids described herein. In some embodiments, the virus is collected from the supernatant of the contacted host cell. Methods of generating virus by contacting host cells comprising a helper virus with an HSV-1 amplicon or HSV-1/hybrid amplicon are known in the art.

In some embodiments, the host cell is a complementing host cell. In some embodiments, the complementing host cell expresses one or more genes that are inactivated in any of the viral vectors described herein. In some embodiments, the complementing host cell is contacted with a recombinant herpes virus genome (e.g., a recombinant herpes simplex virus genome) described herein. In some embodiments, contacting a complementing host cell with a recombinant herpes virus genome results in the production of a herpes virus comprising one or more recombinant nucleic acids described herein. In some embodiments, the virus is collected from the supernatant of the contacted host cell. Methods of generating virus by contacting complementing host cells with a recombinant herpes simplex virus are generally described in WO2015/009952 and/or WO2017/176336.

VIII. ARTICLES OF MANUFACTURE OR KITS

Certain aspects of the present disclosure relate to an article of manufacture or a kit comprising any of the recombinant nucleic acids, viruses, medicaments and/or compositions or formulations (e.g., pharmaceutical compositions or formulations) described herein. In some embodiments, the article of manufacture or kit comprises a package insert comprising instructions for administering the recombinant nucleic acid, virus, medicament, and/or composition or formulation (e.g., to treat a dermal extracellular matrix protein (e.g., collagen) deficiency and/or to correct one or more dermatological signs of aging).

Suitable containers for the recombinant nucleic acids, viruses, medicaments and/or compositions or formulations may include, for example, bottles, vials, bags, tubes, and syringes. The container may be formed from a variety of materials such as glass, plastic (such as polyvinyl chloride or polyolefin), or metal alloy (such as stainless steel or hastelloy). In some embodiments, the container comprises a label on, or associated with the container, wherein the label indicates directions for use. The article of manufacture or kit may further include other materials desirable from a commercial and user standpoint, including other buffers, diluents, filters, needles, syringes, package inserts, and the like.

IX. ENUMERATED EMBODIMENTS

Embodiment 1

A composition comprising: (a) a herpes simplex virus (HSV) comprising a recombinant nucleic acid, wherein the recombinant nucleic acid comprises a first polynucleotide encoding a first polypeptide comprising a first human collagen protein, and (b) an excipient.

Embodiment 2

The composition of embodiments 1, wherein the recombinant nucleic acid comprises two or more copies of the first polynucleotide.

Embodiment 3

The composition of embodiment 1 or 2, wherein the HSV is replication-defective.

Embodiment 4

The composition of embodiment 1 or 2, wherein the HSV is replication-competent.

Embodiment 5

The composition of any one of embodiments 1-4, wherein the HSV is a herpes simplex type 1 virus, a herpes simplex type 2 virus, or any derivatives thereof.

Embodiment 6

The composition of any one of embodiments 1-5, wherein the recombinant nucleic acid is a herpes simplex virus amplicon.

Embodiment 7

The composition of embodiment 6, wherein the herpes simplex virus amplicon is an HSV-1 amplicon or an HSV-1 hybrid amplicon.

Embodiment 8

The composition of embodiment 7, wherein the HSV-1 hybrid amplicon is an HSV/AAV hybrid amplicon, an HSV/EBV hybrid amplicon, and HSV/EBV/RV hybrid amplicon, or an HSV/Sleeping Beauty hybrid amplicon.

Embodiment 9

The composition of any one of embodiments 1-5, wherein the recombinant nucleic acid is a recombinant herpes simplex virus genome.

Embodiment 10

The composition of embodiment 9, wherein the recombinant herpes simplex virus genome is a recombinant HSV-1 genome, a recombinant HSV-2 genome, or any derivatives thereof.

Embodiment 11

The composition of embodiment 9 or 10, wherein the recombinant herpes simplex virus genome comprises an inactivating mutation in a herpes simplex virus gene.

Embodiment 12

The composition of embodiment 11, wherein the herpes simplex virus gene is selected from the group consisting of Infected Cell Protein (ICP) 0, ICP4, ICP22, ICP27, ICP47, thymidine kinase (tk), Long Unique Region (UL) 41, and UL55.

Embodiment 13

The composition of embodiment 12, wherein the recombinant herpes simplex virus genome comprises an inactivation mutation in one or both copies of the ICP4 gene.

Embodiment 14

The composition of embodiment 12 or 13, wherein the recombinant herpes simplex virus genome comprises an inactivating mutation in the ICP22 gene.

Embodiment 15

The composition of any one of embodiments 12-14, wherein the recombinant herpes simplex virus genome comprises an inactivation mutation in the UL41 gene.

Embodiment 16

The composition of any one of embodiments 12-15, wherein the recombinant herpes simplex virus genome comprises an inactivation mutation in the ICP0 gene.

Embodiment 17

The composition of any one of embodiments 12-16, wherein the recombinant herpes simplex virus genome comprises an inactivation mutation in the ICP27 gene.

Embodiment 18

The composition of any one of embodiments 11-17, wherein the inactivating mutation is a deletion of the coding sequence of the gene(s).

Embodiment 19

The composition of any one of embodiments 9-18, wherein the recombinant herpes simplex virus genome comprises the first polynucleotide within a viral gene locus.

Embodiment 20

The composition of any one of embodiments 9-19, wherein the recombinant herpes simplex virus genome comprises the first polynucleotide within one or both copies of the ICP4 viral gene loci.

Embodiment 21

The composition of any one of embodiments 9-20, wherein the recombinant herpes simplex virus genome comprises the first polynucleotide within the ICP22 viral gene locus.

Embodiment 22

The composition of any one of embodiment 9-21, wherein the recombinant herpes simplex virus genome comprises the first polynucleotide within the UL41 viral gene locus.

Embodiment 23

The composition of any one of embodiments 1-22, wherein the HSV has reduced cytotoxicity as compared to a wild-type herpes simplex virus.

Embodiment 24

The composition of any one of embodiments 1-23, wherein the first human collagen protein is selected from the group consisting of Collagen alpha-1(I) chain polypeptide (COL1-1), Collagen alpha-2(I) chain polypeptide (COL1-2), a Collagen alpha-1(II) chain polypeptide (COL2), a Collagen alpha-1(III) chain polypeptide (COL3), a Collagen alpha-1(IV) chain polypeptide (COL4-1), a Collagen alpha-2(IV) chain polypeptide (COL4-2), a Collagen alpha-3(IV) chain polypeptide (COL4-3), a Collagen alpha-4(IV) chain polypeptide (COL4-4), a Collagen alpha-5(IV) chain polypeptide (COL4-5), a Collagen alpha-6(IV) chain polypeptide (COL4-6), a Collagen alpha-1(V) chain polypeptide (COL5-1), a Collagen alpha-2(V) chain polypeptide (COL5-2), a Collagen alpha-3(V) chain polypeptide (COL5-3), a Collagen alpha-1(VI) chain polypeptide (COL6-1), a Collagen alpha-2(VI) chain polypeptide (COL6-2), a Collagen alpha-3(VI) chain polypeptide (COL6-3), a Collagen alpha-4(VI) chain polypeptide (COL6-4), a Collagen alpha-5(VI) chain polypeptide (COL6-5), a Collagen alpha-6(VI) chain polypeptide (COL6-6), a Collagen alpha-1(VII) chain polypeptide (COL7), a Collagen alpha-1(VIII) chain polypeptide (COL8), a Collagen alpha-1(IX) chain polypeptide (COL9-1), a Collagen alpha-2(IX) chain polypeptide (COL9-2), a Collagen alpha-3(IX) chain polypeptide (COL9-3), a Collagen alpha-1(X) chain polypeptide (COL10), a Collagen alpha-1(XI) chain polypeptide (COL11-1), a Collagen alpha-2(XI) chain polypeptide (COL11-2), a Collagen alpha-1(XII) chain polypeptide (COL12), a Collagen alpha-1(XIII) chain polypeptide (COL13), a Collagen alpha-1(XIV) chain polypeptide (COL14), a Collagen alpha-1(XV) chain polypeptide (COL15), a Collagen alpha-1(XVI) chain polypeptide (COL16), a Collagen alpha-1(XVII) chain polypeptide (COL17), a Collagen alpha-1(XVIII) chain polypeptide (COL18), a Collagen alpha-1(XIX) chain polypeptide (COL19), a Collagen alpha-1(XX) chain polypeptide (COL20), a Collagen alpha-1(XXI) chain polypeptide (COL21), a Collagen alpha-1(XXII) chain polypeptide (COL22), a Collagen alpha-1(XXIII) chain polypeptide (COL23), a Collagen alpha-1(XXIV) chain polypeptide (COL24), a Collagen alpha-1(XXV) chain polypeptide (COL25), a Collagen alpha-1(XXVI) chain polypeptide (COL26), a Collagen alpha-1(XXVII) chain polypeptide (COL27), and a Collagen alpha-1(XXVIII) chain polypeptide (COL28).

Embodiment 25

The composition of any one of embodiments 1-24, wherein the first human collagen protein is selected from the group consisting of COL1-1, COL1-2, COL3, COL4-1, COL6-1, COL7, and COL17.

Embodiment 26

The composition of any one of embodiments 1-25, wherein the nucleic acid sequence encoding the first human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 27

The composition of any one of embodiments 1-26, wherein the first human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 28

The composition of any one of embodiments 1-27, wherein the first human collagen protein is not COL7.

Embodiment 29

The composition of any one of embodiments 1-28, wherein the first polypeptide comprises: (a) the first human collagen protein; (b) a further human collagen protein; and (c) a linker polypeptide linking (a) to (b).

Embodiment 30

The composition of embodiment 29, wherein the linker polypeptide is a cleavable linker polypeptide.

Embodiment 31

The composition of embodiment 29 or 30, wherein the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 28-31

Embodiment 32

The composition of any one of embodiments 29-31, wherein the further human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 33

The composition of any one of embodiments 29-32, wherein the further human collagen protein is selected from the group consisting of COL1-1, COL1-2, COL3, COL4-1, COL5-1, COL7, and COL17.

Embodiment 34

The composition of any one of embodiments 29-33, wherein the nucleic acid sequence encoding the further human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 35

The composition of any one of embodiments 29-34, wherein the further human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 36

The composition of any one of embodiments 29-35, wherein the first human collagen protein and the further human collagen protein are different.

Embodiment 37

The composition of any one of embodiments 1-36, wherein the first polynucleotide encodes a polycistronic mRNA comprising: (a) a first open reading frame (ORF) encoding the first polypeptide; (b) a second ORF encoding an additional human collagen protein; and (c) an internal ribosomal entry site (IRES) separating (a) and (b).

Embodiment 38

The composition of embodiment 37, wherein the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23.

Embodiment 39

The composition of embodiment 37 or 38, wherein the additional human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 40

The composition of any one of embodiments 37-39, wherein the additional human collagen protein is selected from the group consisting of COL1-1, COL1-2, COL3, COL4-1, COL5-1, COL7, and COL17.

Embodiment 41

The composition of any one of embodiments 37-40, wherein the nucleic acid sequence encoding the additional human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 42

The composition of any one of embodiments 37-41, wherein the additional human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 43

The composition of any one of embodiments 37-42, wherein the first human collagen protein and the additional human collagen protein are different.

Embodiment 44

The composition of any one of embodiments 1-43, wherein the recombinant nucleic acid further comprises a second polynucleotide encoding a second human collagen protein.

Embodiment 45

The composition of embodiment 44, wherein the recombinant nucleic acid comprises two or more copies of the second polynucleotide.

Embodiment 46

The composition of embodiment 44 or 45, wherein the second human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 47

The composition of any one of embodiments 44-46, wherein the second human collagen protein is selected from the group consisting of COL1-1, COL1-2, COL3, COL4-1, COL5-1, COL7, and COL17.

Embodiment 48

The composition of any one of embodiments 44-48, wherein the nucleic acid sequence encoding the second human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 49

The composition of any one of embodiments 44-48, wherein the second human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 50

The composition of any one of embodiments 44-49, wherein the first and second human collagen proteins are different.

Embodiment 51

The composition of any one of embodiments 44-50, wherein the recombinant nucleic acid is a recombinant herpes simplex virus genome, and wherein the recombinant herpes simplex virus genome comprises the second polynucleotide within a viral gene locus.

Embodiment 52

The composition of embodiment 51, wherein the recombinant herpes simplex virus genome comprises the second polynucleotide within one or both copies of the ICP4 viral gene loci.

Embodiment 53

The composition of embodiment 51 or 52, wherein the recombinant herpes simplex virus genome comprises the second polynucleotide within the ICP22 viral gene locus.

Embodiment 54

The composition of any one of embodiments 51-53, wherein the recombinant herpes simplex virus genome comprises the second polynucleotide within the UL41 viral gene locus.

Embodiment 55

The composition of any one of embodiments 51-54, wherein the recombinant herpes simplex virus genome comprises the first polynucleotide within one or both copies of the ICP4 viral gene loci and the second polynucleotide within the ICP22 viral gene locus.

Embodiment 56

The composition of any one of embodiments 51-54, wherein the recombinant herpes simplex virus genome comprises the first polynucleotide within one or both copies of the ICP4 viral gene loci and the second polynucleotide within the UL41 viral gene locus.

Embodiment 57

The composition of any one of embodiments 1-56, wherein the excipient is adapted for cutaneous (systemic or topical), transdermal, subcutaneous, and/or intradermal administration.

Embodiment 58

The composition of any one of embodiments 1-57, wherein the excipient comprises a hydroxypropyl methylcellulose gel.

Embodiment 59

The composition of any one of embodiments 1-58, wherein the excipient is adapted for intradermal administration.

Embodiment 60

The composition of any one of embodiments 1-59, wherein the excipient comprises a phosphate buffer.

Embodiment 61

The composition of any one of embodiments 1-60, wherein the excipient comprises glycerol.

Embodiment 62

The composition of any one of embodiments 1-61, wherein the excipient comprises a lipid carrier.

Embodiment 63

The composition of any one of embodiments 1-62, wherein the excipient comprises a nanoparticle carrier.

Embodiment 64

The composition of any one of embodiments 1-63, wherein the composition is a cosmetic composition.

Embodiment 65

The composition of embodiment 64, wherein the cosmetic composition is a skin care product.

Embodiment 66

A kit comprising: (a) the composition of any one of embodiment 1-65; and (b) instructions for administering the composition.

Embodiment 67

A method of enhancing, increasing, augmenting, and/or supplementing the levels of one or more human collagen proteins in a subject, the method comprising administering to the subject an effective amount of the composition of any one of embodiments 1-65.

Embodiment 68

A method of enhancing, increasing, augmenting, and/or supplementing soft tissue of a subject, the method comprising administering to the subject an effective amount of the composition of any one of embodiments 1-65.

Embodiment 69

The method of embodiment 68, wherein the composition is injected into a soft tissue of the subject.

Embodiment 70

A method of improving skin quality, condition and/or appearance in a subject in need thereof, the method comprising administering to the subject an effective amount of the composition of any one of embodiments 1-65.

Embodiment 71

The method of embodiment 70, wherein the condition is selected from the group consisting of sun damage, aging, UV exposure, rough texture, skin sagging, wrinkles, and any combinations thereof.

Embodiment 72

A method of reducing the appearance of one or more superficial depressions in the skin of a subject in need thereof, the method comprising administering to the subject an effective amount of the composition of any one of embodiments 1-65.

Embodiment 73

The method of embodiment 72, wherein administration of the composition reduces the appearance of the one or more superficial depressions in the skin of the subject for at least about three months, at least about six months, at least about nine months, or at least about 12 months.

Embodiment 74

The method of embodiment 72 or 73, wherein the appearance of the one or more superficial depressions in the skin of the subject is reduced after administration of the composition, as compared to the appearance of the one or more superficial depression in the skin of the subject prior to administration of the composition.

Embodiment 75

A method of increasing and/or improving at least one of texture, smoothness, elasticity, or tension of the skin of a subject in need thereof, the method comprising administering to the subject an effective amount of the composition of any one of embodiments 1-65.

Embodiment 76

The method of embodiment 75, wherein the skin of the subject maintains at least one of an increased and/or improved texture, smoothness, elasticity, or tension for at least about three months, at least about six months, at least about nine months, or at least about 12 months after administration of the composition.

Embodiment 77

The method of embodiment 75 or 76, wherein at least one of texture, smoothness, elasticity, or tension of the skin of the subject is increased and/or improved after administration of the composition, as compared to the texture, smoothness, elasticity, or tension of the skin of the subject prior to administration of the composition.

Embodiment 78

The method of any one of embodiments 70-77, wherein the skin of the subject is aging skin.

Embodiment 79

The method of any one of embodiments 70-78, wherein the skin of the subject has been damaged due to exposure to ultraviolet light.

Embodiment 80

The method of any one of embodiments 70-79, wherein the skin of the subject is wrinkled.

Embodiment 81

A method of diminishing one or more dermatological signs of aging in a subject in need thereof, the method comprising administering to the subject an effective amount of the composition of any one of embodiments 1-65.

Embodiment 82

The method of embodiment 81, wherein the diminishing of one or more dermatological signs of aging is selected from the group consisting of: (a) treatment, reduction, and/or prevention of fine lines and/or wrinkles; (b) reduction of skin pore size; (c) improvement in skin thickness, plumpness, and/or tautness; (d) improvement in skin smoothness, suppleness, and/or softness; (e) improvement in skin tone, radiance and/or clarity; (f) improvement in procollagen and/or collagen production; (g) improvement in skin texture and or promotion of retexturization; (h) improvement in appearance of skin contours; (i) restoration of skin luster and/or brightness; (j) improvement of skin appearance decreased by aging and/or menopause; (k) improvement in skin moisturization; (l) increase in skin elasticity and/or resiliency; (m) treatment, reduction, and/or prevention or skin sagging; (n) improvement in skin firmness; (o) reduction of pigment spots, mottled skin, and/or acne scars; (p) improvement of optical properties of skin by light diffraction or reflection; and (q) any combinations thereof.

Embodiment 83

The method of embodiment 81 or 82, wherein the one or more dermatological signs of aging in the subject is diminished after administration of the composition, as compared to the one or more dermatological signs of aging in the subject prior to administration of the composition.

Embodiment 84

The method of any one of embodiments 67-83, wherein the subject is a human.

Embodiment 85

The method of any one of embodiments 67-84, wherein the composition is administered cutaneously (systemically or topically), transdermally, subcutaneously, or intradermally to the subject.

Embodiment 86

The method of any one of embodiments 67-85, wherein the composition is administered by superficial injection.

Embodiment 87

The method of any one of embodiments 67-85, wherein the composition is administered intradermally to the subject.

Embodiment 88

The method of any one of embodiments 67-87, wherein the composition is administered once to the subject.

Embodiment 89

The method of any one of embodiments 67-87, wherein the composition is administered at least twice to the subject.

Embodiment 90

The method of embodiment 89, wherein at least about 15, at least about 30, at least about 60, at least about 90, or at least about 120 days passes between administrations.

Embodiment 91

The method of any one of embodiments 67-90, wherein the composition is administered to one or more affected and/or unaffected areas of the subject.

Embodiment 92

The method of any one of embodiments 67-91, wherein the skin of the subject is abraded prior to administration.

Embodiment 93

A recombinant nucleic acid comprising a first polynucleotide encoding a first polypeptide comprising a first human collagen protein, wherein the recombinant nucleic acid is a recombinant herpes simplex virus genome.

Embodiment 94

The recombinant nucleic acid of embodiment 93, wherein the recombinant nucleic acid comprises two or more copies of the first polynucleotide.

Embodiment 95

The recombinant nucleic acid of embodiment 93 or 94, wherein the recombinant herpes simplex virus genome is a recombinant HSV-1 genome, a recombinant HSV-2 genome, or any derivatives thereof.

Embodiment 96

The recombinant nucleic acid of any one of embodiments 93-95, wherein the recombinant herpes simplex virus genome comprises an inactivating mutation in a herpes simplex virus gene.

Embodiment 97

The recombinant nucleic acid of embodiment 96, wherein the herpes simplex virus gene is selected from the group consisting of ICP0, ICP4, ICP22, ICP27, ICP47, tk, UL41, and UL55.

Embodiment 98

The recombinant nucleic acid of embodiment 97, wherein the recombinant herpes simplex virus genome comprises an inactivation mutation in one or both copies of the ICP4 gene.

Embodiment 99

The recombinant nucleic acid of embodiment 97 or 98, wherein the recombinant herpes simplex virus genome comprises an inactivating mutation in the ICP22 gene.

Embodiment 100

The recombinant nucleic acid of any one of embodiments 97-99, wherein the recombinant herpes simplex virus genome comprises an inactivation mutation in the UL41 gene.

Embodiment 101

The recombinant nucleic acid of any one of embodiments 97-100, wherein the recombinant herpes simplex virus genome comprises an inactivation mutation in the ICP0 gene.

Embodiment 102

The recombinant nucleic acid of any one of embodiments 97-101, wherein the recombinant herpes simplex virus genome comprises an inactivation mutation in the ICP27 gene.

Embodiment 103

The recombinant nucleic acid of any one of embodiments 96-102, wherein the inactivating mutation is a deletion of the coding sequence of the gene(s).

Embodiment 104

The recombinant nucleic acid of any one of embodiments 93-103, wherein the recombinant herpes simplex virus genome comprises the first polynucleotide within a viral gene locus.

Embodiment 105

The recombinant nucleic acid of any one of embodiments 93-104, wherein the recombinant herpes simplex virus genome comprises the first polynucleotide within one or both copies of the ICP4 viral gene loci.

Embodiment 106

The recombinant nucleic acid of any one of embodiments 93-105, wherein the recombinant herpes simplex virus genome comprises the first polynucleotide within the ICP22 viral gene locus.

Embodiment 107

The recombinant nucleic acid of any one of 93-106, wherein the recombinant herpes simplex virus genome comprises the first polynucleotide within the UL41 viral gene locus.

Embodiment 108

The recombinant nucleic acid of any one of embodiments 93-107, wherein the first human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL5-1, COL5-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 109

The recombinant nucleic acid of any one of embodiments 93-108, wherein the first human collagen protein is selected from the group consisting of COL1-1, COL1-2, COL3, COL4-1, COL5-1, COL7, and COL17.

Embodiment 110

The recombinant nucleic acid of any one of embodiments 93-109, wherein the nucleic acid sequence encoding the first human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 111

The recombinant nucleic acid of any one of embodiments 93-110, wherein the first human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 112

The recombinant nucleic acid of any one of embodiments 93-111, wherein the first human collagen protein is not COL7.

Embodiment 113

The recombinant nucleic acid of any one of embodiments 93-112, wherein the first polypeptide comprises: (a) the first human collagen protein; (b) a further human collagen protein; and (c) a linker polypeptide linking (a) to (b).

Embodiment 114

The recombinant nucleic acid of embodiment 113, wherein the linker polypeptide is a cleavable linker polypeptide.

Embodiment 115

The recombinant nucleic acid of embodiment 113 or 114, wherein the linker polypeptide comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 28-31.

Embodiment 116

The recombinant nucleic acid of any one of embodiments 113-115, wherein the further human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL5-1, COL5-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 117

The recombinant nucleic acid of any one of embodiments 113-116, wherein the further human collagen protein is selected from the group consisting of COL1-1, COL1-2, COL3, COL4-1, COL5-1, COL7, and COL17.

Embodiment 118

The recombinant nucleic acid of any one of embodiments 113-117, wherein the nucleic acid sequence encoding the further human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 119

The recombinant nucleic acid of any one of embodiments 113-118, wherein the further human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 120

The recombinant nucleic acid of any one of embodiments 113-119, wherein the first human collagen protein and the further human collagen protein are different.

Embodiment 121

The recombinant nucleic acid of any one of embodiments 93-120, wherein the first polynucleotide encodes a polycistronic mRNA comprising: (a) a first open reading frame (ORF) encoding the first polypeptide; (b) a second ORF encoding an additional human collagen protein; and (c) an internal ribosomal entry site (IRES) separating (a) and (b).

Embodiment 122

The recombinant nucleic acid of embodiment 121, wherein the nucleic acid sequence encoding the IRES has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from SEQ ID NO: 22 or SEQ ID NO: 23.

Embodiment 123

The recombinant nucleic acid of embodiment 121 or 122, wherein the additional human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 124

The recombinant nucleic acid of any one of embodiments 121-123, wherein the additional human collagen protein is selected from the group consisting of COL1-1, COL1-2, COL3, COL4-1, COL5-1, COL7, and COL17.

Embodiment 125

The recombinant nucleic acid of any one of embodiments 121-124, wherein the nucleic acid sequence encoding the additional human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 126

The recombinant nucleic acid of any one of embodiments 121-125, wherein the additional human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 127

The recombinant nucleic acid of any one of embodiments 121-126, wherein the first human collagen protein and the additional human collagen protein are different.

Embodiment 128

The recombinant nucleic acid of any one of embodiments 93-127, wherein the recombinant nucleic acid further comprises a second polynucleotide encoding a second human collagen protein.

Embodiment 129

The recombinant nucleic acid of embodiment 128, wherein the recombinant nucleic acid comprises two or more copies of the second polynucleotide.

Embodiment 130

The recombinant nucleic acid of embodiment 128 or 129, wherein the second human collagen protein is selected from the group consisting of COL1-1, COL1-2, COL2, COL3, COL4-1, COL4-2, COL4-3, COL4-4, COL4-5, COL4-6, COL5-1, COL5-2, COL5-3, COL6-1, COL6-2, COL6-3, COL6-4, COL6-5, COL6-6, COL7, COL8, COL9-1, COL9-2, COL9-3, COL10, COL11-1, COL11-2, COL12, COL13, COL14, COL15, COL16, COL17, COL18, COL19, COL20, COL21, COL22, COL23, COL24, COL25, COL26, COL27, and COL28.

Embodiment 131

The recombinant nucleic acid of any one of embodiments 128-130, wherein the second human collagen protein is selected from the group consisting of COL1-1, COL1-2, COL3, COL4-1, COL5-1, COL7, and COL17.

Embodiment 132

The recombinant nucleic acid of any one of embodiments 128-131, wherein the nucleic acid sequence encoding the second human collagen protein has at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOS: 1-14.

Embodiment 133

The recombinant nucleic acid of any one of embodiments 128-132, wherein the second human collagen protein comprises a sequence having at least 80%, at least 85%, at least 90%, at least 91%, at least 92%, at least 93%, at least 94%, at least 95%, at least 96%, at least 97%, at least 98%, at least 99%, or 100% sequence identity to an amino acid sequence selected from the group consisting of SEQ ID NOS: 15-21.

Embodiment 134

The recombinant nucleic acid of any one of embodiments 128-133, wherein the first and second human collagen proteins are different.

Embodiment 135

The recombinant nucleic acid of any one of embodiments 128-134, wherein the recombinant herpes simplex virus genome comprises the second polynucleotide within a viral gene locus.

Embodiment 136

The recombinant nucleic acid of embodiment 135, wherein the recombinant herpes simplex virus genome comprises the second polynucleotide within one or both copies of the ICP4 viral gene loci.

Embodiment 137

The recombinant nucleic acid of embodiment 135 or 136, wherein the recombinant herpes simplex virus genome comprises the second polynucleotide within the ICP22 viral gene locus.

Embodiment 138

The recombinant nucleic acid of any one of embodiments 135-137, wherein the recombinant herpes simplex virus genome comprises the second polynucleotide within the UL41 viral gene locus.

Embodiment 139

The recombinant nucleic acid of any one of embodiments 135-138, wherein the recombinant herpes simplex virus genome comprises the first polynucleotide within one or both copies of the ICP4 viral gene loci and the second polynucleotide within the ICP22 viral gene locus.

Embodiment 140

The recombinant nucleic acid of any one of embodiments 135-138, wherein the recombinant herpes simplex virus genome comprises the first polynucleotide within one or both copies of the ICP4 viral gene loci and the second polynucleotide within the UL41 viral gene locus.

Embodiment 141

A host cell comprising the recombinant nucleic acid of any one embodiments 93-140.

Embodiment 142

The host cell of embodiment 141, wherein the host cell is a eukaryotic cell.

Embodiment 143

The hose cell of embodiment 141 or 142, wherein the host cell is a mammalian cell.

Embodiment 144

The host cell of any one of embodiments 141-143, wherein the host cell is a human cell or a non-human primate cell.

Embodiment 145

The host cell of any one of embodiments 141-144, wherein the host cell is a Vero cell.

Embodiment 146

The host cell of any one of embodiments 141-145, wherein the cost cell is a complementing host cell.

Embodiment 147

A method of collecting a herpes simplex virus, the method comprising: (a) contacting a complementing host cell with the recombinant nucleic acid of any one of embodiments 93-140; and (b) collecting the herpes simplex virus generated by the complementing host cell.

Embodiment 148

A method of collecting a herpes simplex virus, the method comprising: (a) culturing the host cell of any one of embodiments 141-146; and (b) collecting the herpes simplex virus generated by the host cell.

The specification is considered to be sufficient to enable one skilled in the art to practice the present disclosure. Various modifications of the present disclosure in addition to those shown and described herein will become apparent to those skilled in the art from the foregoing description and fall within the scope of the appended claims.

EXAMPLES

The present disclosure will be more fully understood by reference to the following examples. It should not, however, be construed as limiting the scope of the present disclosure. It is understood that the examples and embodiments described herein are for illustrative purposes only and that various modifications or changes in light thereof will be suggested to persons skilled in the art, and are to be included within the spirit and purview of this application and scope of the appended claims.

Example 1: Modified Herpes Simplex Virus Vectors Encoding Human Collagen Protein(s)

Figure 1B:
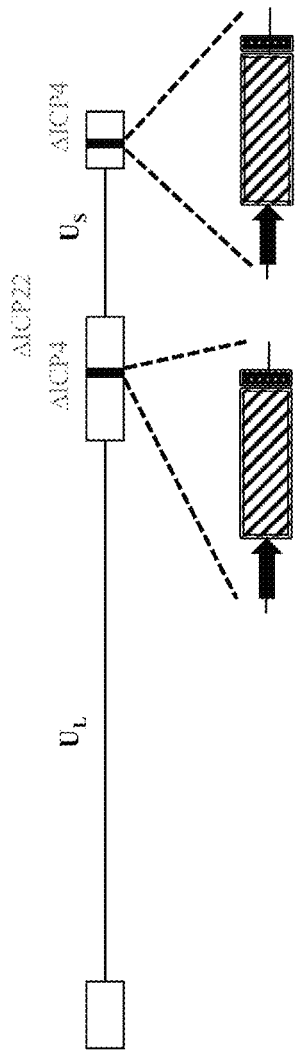
FIG. 1B shows a modified herpes simplex virus genome comprising deletions of the coding sequences of ICP4 (both copies) and ICP22, with a polynucleotide containing the coding sequence of a first human collagen polypeptide operably linked to a heterologous promoter integrated at each of the ICP4 loci.
Figure 1C:
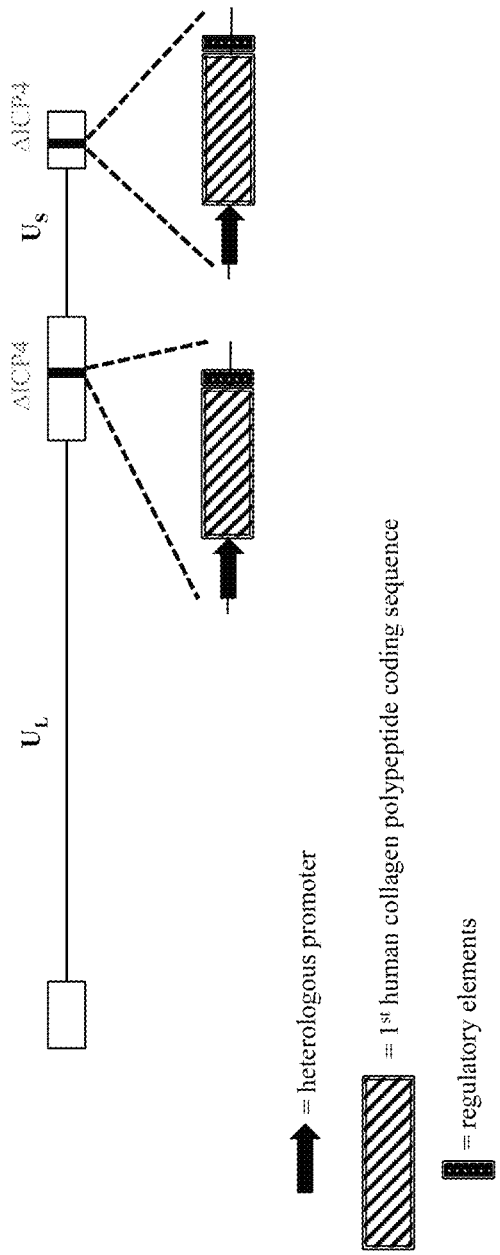
FIG. 1C shows a modified herpes simplex virus genome comprising deletions of the coding sequence of ICP4 (both copies), with a polynucleotide containing the coding sequence of a first human collagen polypeptide operably linked to a heterologous promoter integrated at each of the ICP4 loci.
Figure 1D:
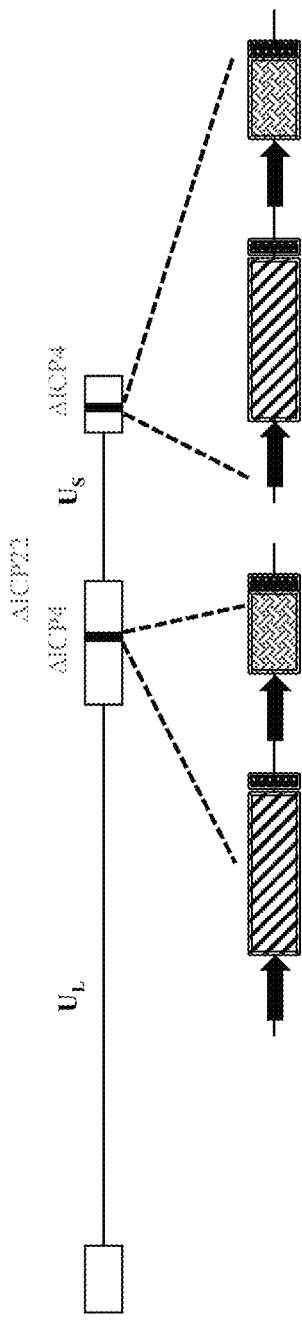
FIG. 1D shows a modified herpes simplex virus genome comprising deletions of the coding sequences of ICP4 (both copies) and ICP22, with a polynucleotide containing 1) the coding sequence of a first human collagen polypeptide operably linked to a first heterologous promoter, and 2) the coding sequence of a second human collagen polypeptide operably linked to a second heterologous promoter, integrated at each of the ICP4 loci. Both the first and second human collagen polypeptides are encoded on the same strand of DNA.
Figure 1E:
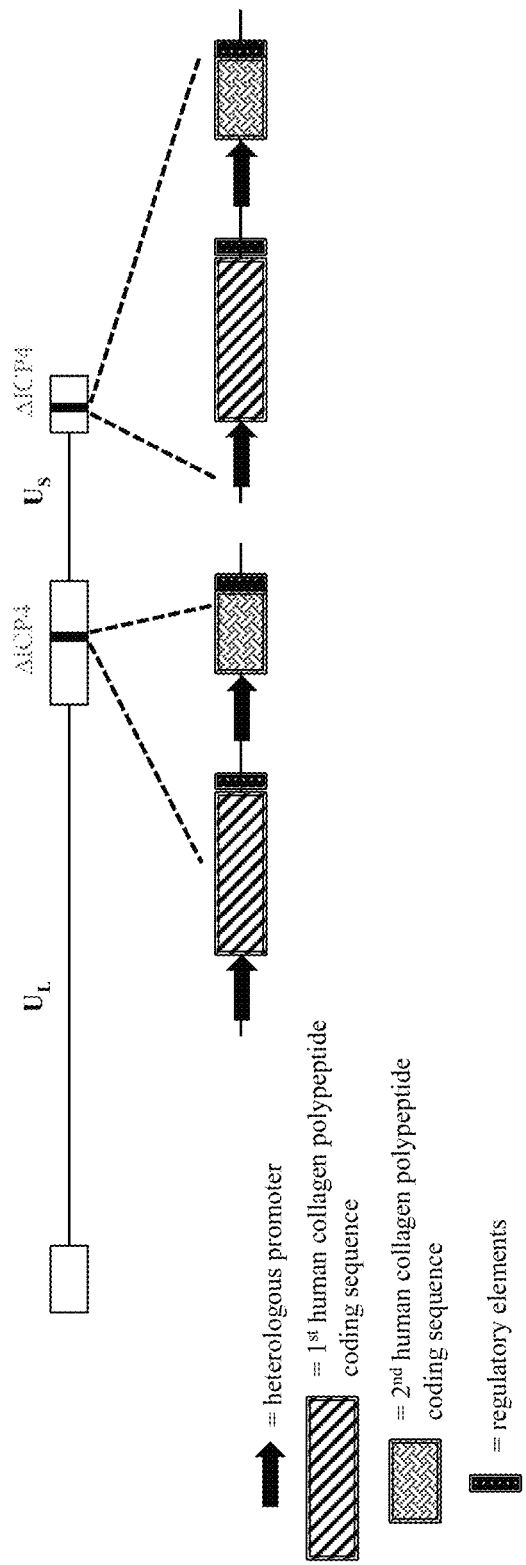
FIG. 1E shows a modified herpes simplex virus genome comprising deletions of the coding sequence of ICP4 (both copies), with a polynucleotide containing 1) the coding sequence of a first human collagen polypeptide operably linked to a first heterologous promoter, and 2) the coding sequence of a second human collagen polypeptide operably linked to a second heterologous promoter, integrated at each of the ICP4 loci. Both the first and second human collagen polypeptides are encoded on the same strand of DNA. FIG.
Figure 1F:
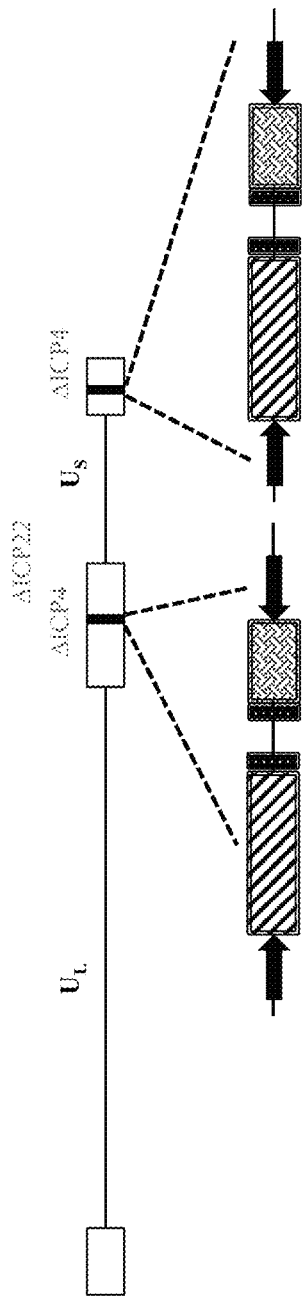
FIG. 1G shows a modified herpes simplex virus genome comprising deletions of the coding sequence of ICP4 (both copies), with a polynucleotide containing 1) the coding sequence of a first human collagen polypeptide operably linked to a first heterologous promoter, and 2) the coding sequence of a second human collagen polypeptide operably linked to a second heterologous promoter, integrated at each of the ICP4 loci. The first and second human collagen polypeptides are encoded on opposite strands of DNA.
FIG. 1H shows a modified herpes simplex virus genome comprising deletions of the coding sequences of ICP4 (both copies) and ICP22, with a polynucleotide encoding a polycistronic mRNA operably linked to a heterologous promoter integrated at each of the ICP4 loci. The polycistronic mRNA contains the coding sequence of a first human collagen polypeptide and a second human collagen polypeptide separated by an internal ribosomal entry site (IRES).
FIG. 1I shows a modified herpes simplex virus genome comprising deletions of the coding sequence of ICP4 (both copies), with a polynucleotide encoding a polycistronic mRNA operably linked to a heterologous promoter integrated at each of the ICP4 loci. The polycistronic mRNA contains the coding sequence of a first human collagen polypeptide and a second human collagen polypeptide separated by an internal ribosomal entry site (IRES).
FIG. 1J shows a modified herpes simplex virus genome comprising deletions of the coding sequences of ICP4 (both copies) and ICP22, with a polynucleotide containing the coding sequence of a chimeric polypeptide operably linked to a heterologous promoter integrated at each of the ICP4 loci. The chimeric polypeptide comprises the amino acid sequence of a first human collagen polypeptide and second human collagen polypeptide separated by a cleavable linker.
FIG. 1K shows a modified herpes simplex virus genome comprising deletions of the coding sequence of ICP4 (both copies), with a polynucleotide containing the coding sequence of a chimeric polypeptide operably linked to a heterologous promoter integrated at each of the ICP4 loci. The chimeric polypeptide comprises the amino acid sequence of a first human collagen polypeptide and second human collagen polypeptide separated by a cleavable linker.
FIG. 1L shows a modified herpes simplex virus genome comprising deletions of the coding sequences of ICP4 (both copies) and ICP22, with a first polynucleotide containing the coding sequence of a first human collagen polypeptide operably linked to a heterologous promoter integrated at each of the ICP4 loci, and a second polynucleotide containing the coding sequence of a second human collagen polypeptide operably linked to a heterologous promoter integrated at the ICP22 locus.
FIG. 1M shows a modified herpes simplex virus genome comprising deletions of the coding sequences of ICP4 (both copies), ICP22, and UL41, with a first polynucleotide containing the coding sequence of a first human collagen polypeptide operably linked to a heterologous promoter integrated at each of the ICP4 loci, and a second polynucleotide containing the coding sequence of a second human collagen polypeptide operably linked to a heterologous promoter integrated at the UL41 locus.
Figure 1G:
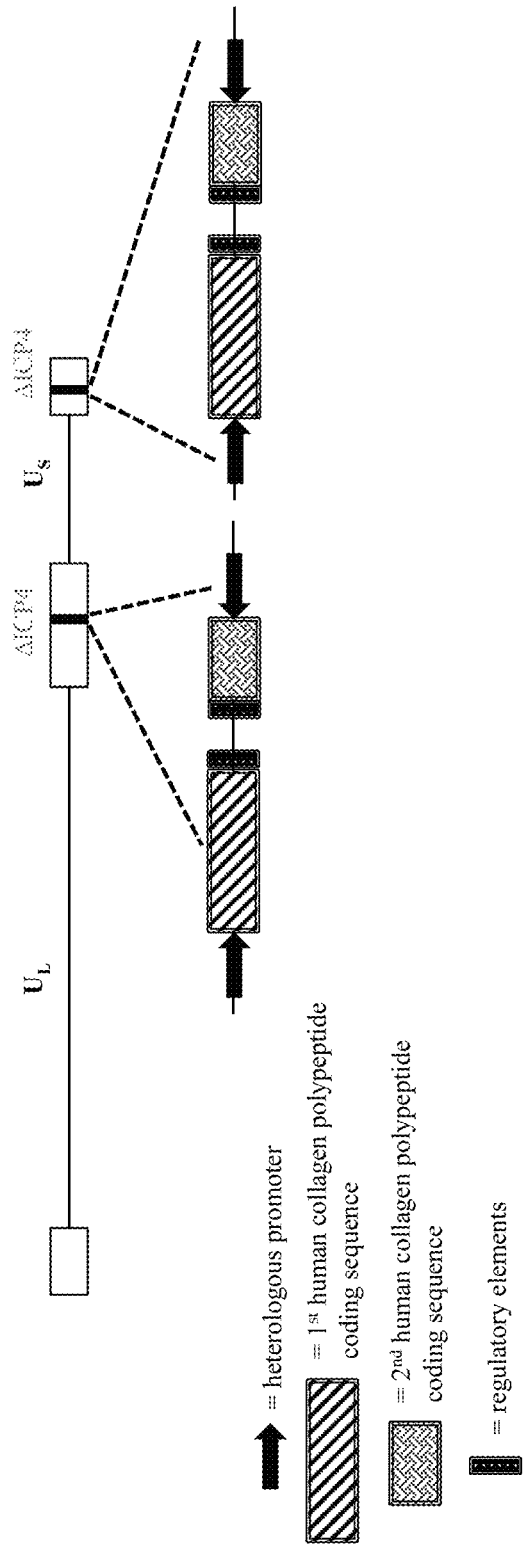
Figure 1H:
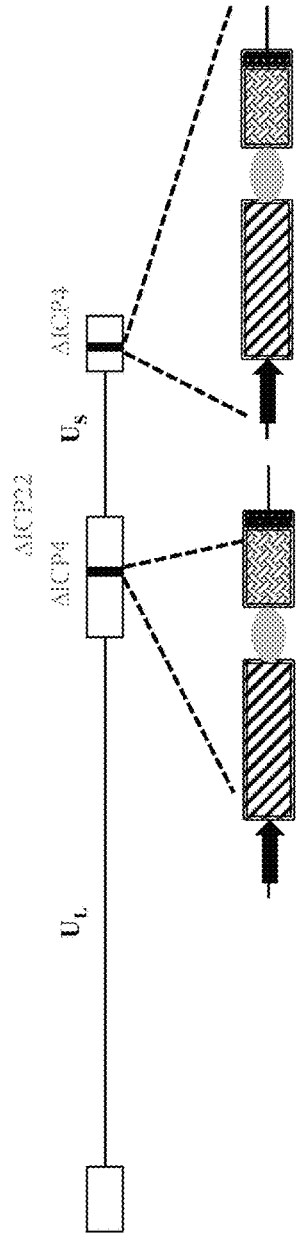
Figure 1I:
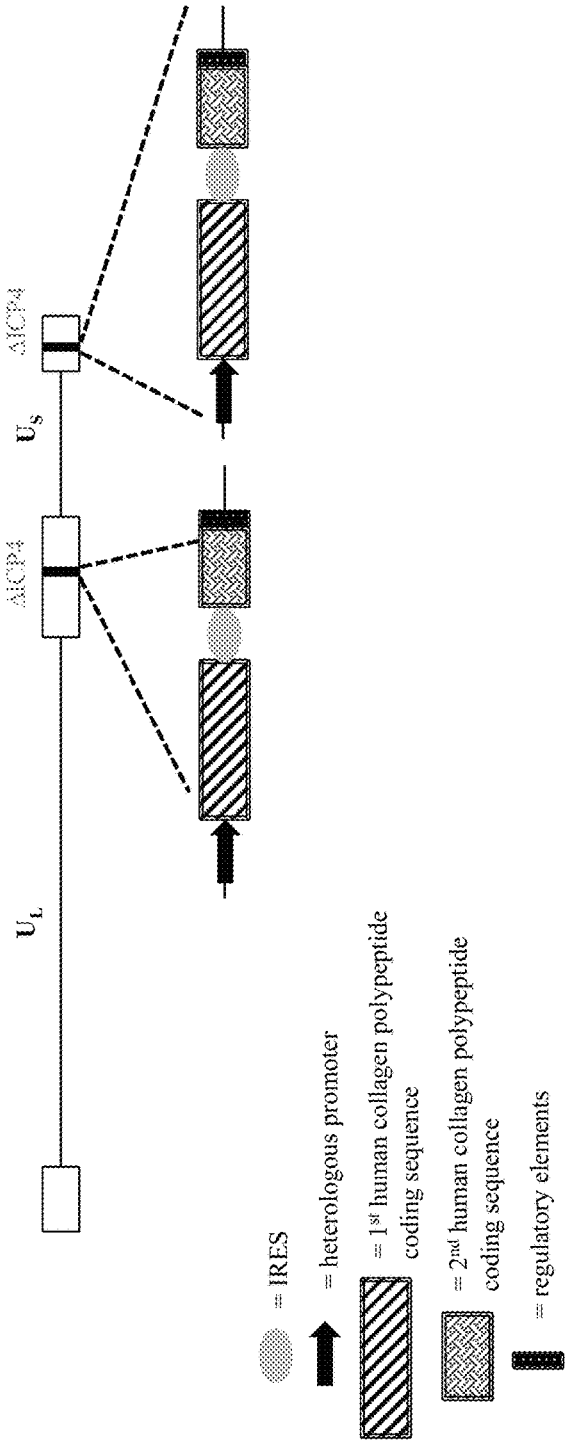
Figure 1J:
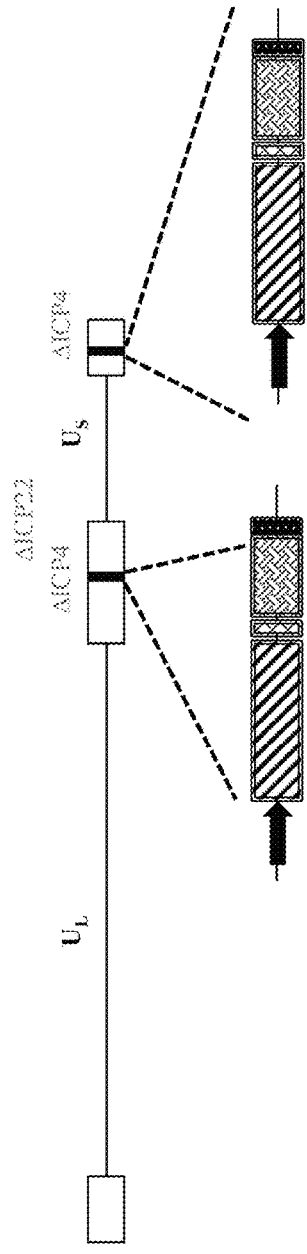
Figure 1K:
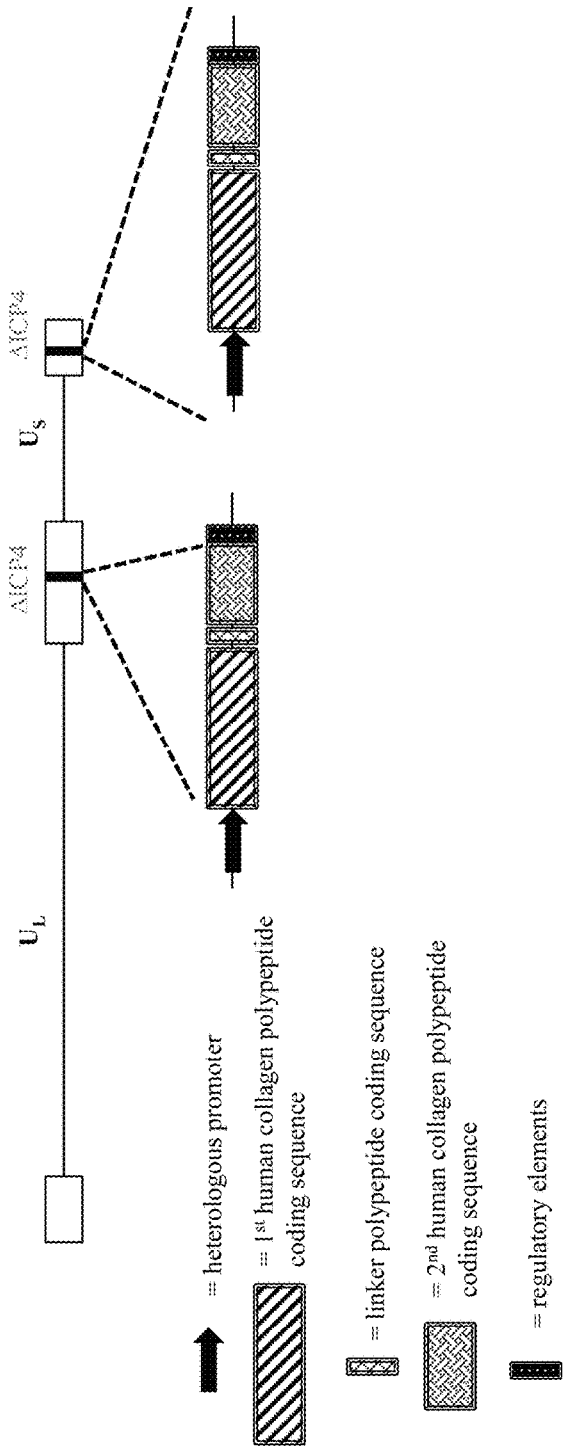

To make modified herpes simplex virus genome vectors capable of expressing human collagen protein(s) in a target mammalian cell (such as a human keratinocyte or fibroblast), a herpes simplex virus genome (FIG. 1A) is first modified to inactivate one or more herpes simplex virus genes. Such modifications may decrease the toxicity of the genome in mammalian cells. Next, variants of these modified/attenuated recombinant viral constructs are generated such that they carry one or more polynucleotides encoding human collagen protein(s). These variants include: 1) a recombinant ΔICP4/ΔICP22-modified HSV-1 genome comprising expression cassettes containing the coding sequence of a first human collagen protein under the control of a heterologous promoter integrated at each ICP4 locus (FIG. 1B); 2) a recombinant ΔICP4-modified HSV-1 genome comprising expression cassettes containing the coding sequence of a first human collagen protein under the control of a heterologous promoter integrated at each ICP4 locus (FIG. 1C); 3) a recombinant ΔICP4/ΔICP22-modified HSV-1 genome comprising expression cassettes containing the coding sequence of a first human collagen protein under the control of a first heterologous promoter and the coding sequence of a second human collagen protein under the control of a second heterologous promoter on the same strand of DNA integrated at each ICP4 locus (FIG. 1D); 4) a recombinant ΔICP4-modified HSV-1 genome comprising expression cassettes containing the coding sequence of a first human collagen protein under the control of a first heterologous promoter and the coding sequence of a second human collagen protein under the control of a second heterologous promoter on the same strand of DNA integrated at each ICP4 locus (FIG. 1E); 5) a recombinant ΔICP4/ΔICP22-modified HSV-1 genome comprising expression cassettes containing the coding sequence of a first human collagen protein under the control of a first heterologous promoter and the coding sequence of a second human collagen protein under the control of a second heterologous promoter on opposite strands of DNA integrated at each ICP4 locus (FIG. 1F); 6) a recombinant ΔICP4-modified HSV-1 genome comprising expression cassettes containing the coding sequence of a first human collagen protein under the control of a first heterologous promoter and the coding sequence of a second human collagen protein under the control of a second heterologous promoter on opposite strands of DNA integrated at each ICP4 locus (FIG. 1G); 7) a recombinant ΔICP4/ΔICP22-modified HSV-1 genome comprising expression cassettes encoding a polycistronic mRNA under the control of a heterologous promoter integrated at each of the ICP4 loci, where the polycistronic mRNA contains the coding sequence of a first human collagen protein and the coding sequence of a second human collagen protein separated by an internal ribosomal entry site (IRES) (FIG. 1H); 8) a recombinant ΔICP4-modified HSV-1 genome comprising expression cassettes encoding a polycistronic mRNA under the control of a heterologous promoter integrated at each of the ICP4 loci, where the polycistronic mRNA contains the coding sequence of a first human collagen protein and the coding sequence of a second human collagen protein separated by an internal ribosomal entry site (IRES) (FIG. 1I); 9) a recombinant ΔICP4/ΔICP22-modified HSV-1 genome comprising expression cassettes containing the coding sequence of a chimeric protein under the control of a heterologous promoter integrated at each of the ICP4 loci, where the chimeric protein contains the amino acid sequence of a first human collagen protein and the amino acid sequence of a second human collagen protein separated by the amino acid sequence of a linker polypeptide (FIG. 1J); 10) a recombinant ΔICP4-modified HSV-1 genome comprising expression cassettes containing the coding sequence of a chimeric protein under the control of a heterologous promoter integrated at each of the ICP4 loci, where the chimeric protein contains the amino acid sequence of a first human collagen protein and the amino acid sequence of a second human collagen protein separated by the amino acid sequence of a linker polypeptide (FIG. 1K); 11) a recombinant ΔICP4/ΔICP22-modified HSV-1 genome comprising expression cassettes containing the coding sequence of a first human collagen protein under the control of a heterologous promoter integrated at each of the ICP4 loci, and an expression cassette containing the coding sequence of a second human collagen protein under the control of a heterologous promoter integrated at the ICP22 locus (FIG. 1L); 12) a recombinant ΔICP4/ΔICP22/ΔUL41-modified HSV-1 genome comprising expression cassettes containing the coding sequence of a first human collagen protein under the control of a heterologous promoter integrated at each of the ICP4 loci, and an expression cassette containing the coding sequence of a second human collagen protein under the control of a heterologous promoter integrated at the UL41 locus (FIG. 1M); and 13) a recombinant ΔICP4/ΔUL41-modified HSV-1 genome comprising expression cassettes containing the coding sequence of a first human collagen protein under the control of a heterologous promoter integrated at each of the ICP4 loci, and an expression cassette containing the coding sequence of a second human collagen protein under the control of a heterologous promoter integrated at the UL41 locus (FIG. 1N).

These modified herpes simplex virus genome vectors are transfected into engineered Vero cells that are modified to express one or more herpes virus genes. These engineered Vero cells secrete replication-defective herpes simplex virus with the modified genomes packaged therein into the supernatant. The supernatant is then collected, concentrated, and sterile filtered through a 5 µm filter.

Example 2: Construction and In Vitro Analysis of HSV Candidates Encoding Human COL7

Collagen alpha-1(VII) chain protein (COL7) functions to strengthen and stabilize the skin. Briefly, COL7A1 transcripts are translated, the resulting COL7 peptides are post-translationally modified by hydroxylation and glycosylation, and glycosylated COL7 tri-peptides form a triple helix known as pro-collagen, which is secreted from the cell. The pro-collagen associates into higher-order structures upon secretion, forming anchoring fibrils, which are then available to help organize, stabilize, and aid in the adherence of the epithelial basement membrane. The epithelial basement membrane is responsible for anchoring the epithelium to the underlying loose connective tissue and is essential for dermal-epidermal stability (dermo-epidermal junction integrity). Dystrophic epidermolysis bullosa is an inherited genetic condition caused by mutations in the COL7A1 gene; mutations in this gene impair the ability of COL7 to properly connect the epidermis to the dermis in dystrophic epidermolysis bullosa patients, leading to fragile skin. Recessive dystrophic epidermolysis bullosa (RDEB), the most severe form of epidermolysis bullosa, is most often characterized by extensive blistering and scarring of the skin and mucosal membranes.

The following example describes the construction of a recombinant herpes simplex type-1 viruses modified to express human Collagen alpha-1(VII) chain polypeptide (COL7), and further provides experiments showing that the recombinant HSV was capable of expressing functional human collagen in vitro in primary human keratinocytes and fibroblasts from healthy and RDEB patients.

Materials and Methods

Virus Construction

Figure 2A:
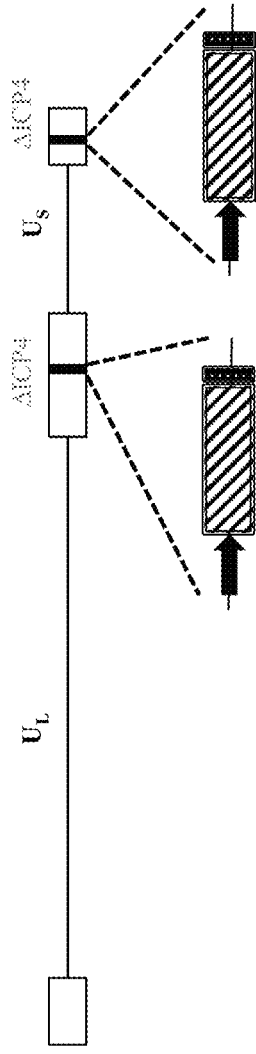
FIGS. 2A-B show schematics of replication-defective herpes simplex type-1 viruses carrying human collagen 7 (COL7) expression cassettes.

The "KCA211" viral vector (FIG. 2A) was generated as follows: a wild-type herpes simplex virus genome was first modified by deleting the coding sequence of both copies of the viral ICP4 gene (ΔICP4). The ΔICP4-modified viral genome was also engineered to contain an mCherry expression cassette in each of the ICP4 loci. The viral genome was then further modified to encode wild-type human COL7. Briefly, a plasmid containing the coding sequence for wild-type COL7 (under control of the hCMV promoter) flanked by the upstream (US) and downstream (DS) regions of ICP4 was transfected into Vero cells modified to express the herpes virus ICP4 gene. These transfected cells were then infected with the modified ΔICP4 mCherry-expressing virus described above. The US and DS ICP4 regions flanking COL7 allowed for a double crossover and replacement of each of the mCherry loci. Visual screening for the absence of mCherry fluorescence was then used to identify cells containing recombined virus.

Figure 2B:
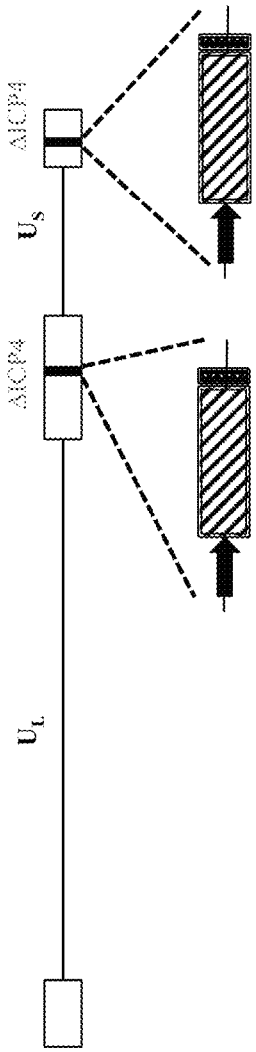

The "SAR-COL7" viral vector (FIG. 2B) was generated as follows: a wild-type herpes simplex virus genome was first modified by deleting the coding sequence of both copies of the viral ICP4 gene as well as the single copy ICP22 gene (ΔICP4/ΔICP22). The ΔICP4/ΔICP22-modified viral genome was also engineered to contain an mCherry expression cassette in each of the ICP4 loci. The viral genome was then further modified to encode wild-type human COL7. Briefly, a plasmid containing the coding sequence for wild-type COL7 (under control of the hCMV promoter) flanked by the upstream (US) and downstream (DS) regions of ICP4 was transfected into Vero cells modified to express the herpes virus ICP4 gene. These transfected cells were then infected with the modified ΔICP4/ΔICP22 mCherry-expressing virus described above. The US and DS ICP4 regions flanking COL7 allowed for a double crossover and replacement of each of the mCherry loci. Visual screening for the absence of mCherry fluorescence was then used to identify cells containing recombined virus.

Cell Culture

Cells were previously isolated from skin biopsies taken as part of routine surgical or diagnostic procedures. Informed written consent was obtained from each patient, or in the case of children, from the parent or legal guardian. This study was performed in accordance with the Helsinki declaration. All cells were cultured at 37° C. in 5% $CO_2$. Human fibroblasts were grown in Dulbecco's modified essential medium supplemented with 10% fetal bovine serum (PEAK® serum, cat. no. PS-FB1). RDEB and normal keratinocytes were cultured in DMEM/Ham's F12 medium (3:1) supplemented with 10% FBS, 10 ng/mL epidermal growth factor, 10-10 cholera toxin, 0.4 µg/mL hydrocortisone, 5 µg/mL transferrin, 5 µg/mL insulin, and 5 µg/mL liothyronine. All media contained ascorbic acid (150 µM). Keratinocytes were grown in the presence of a mitotically activated feeder layer of 3T3 cells and in the presence of 10 µM of the Rho-kinase inhibitor Y-27632.

Virus Infections

Viral aliquots were stored at −80° C., and were left to defrost under the tissue culture laminar flow hood before use. Target cell number was determined prior to infection after detaching cells from the tissue culture plastic and counting on a hemocytometer. Multiplicity of infection (MOI) was calculated from the virus titer and target cell number, and the appropriate volume of virus stock was diluted in 10% serum containing DMEM and incubated with the target cells for 2 hours at 37° C. Virus was then removed, and fresh media was supplied to target cells after washing twice with pre-warmed media.

Western Blots

Keratinocytes were plated in a 100 mm dish at $8 \times 10^5$ to achieve 70-80% confluency the following day. 48 hours after infection, cells were lysed with radioimmunoprecipitation assay buffer. Lysate was placed in a centrifuge for 5 minutes at 4° C., and the supernatant was mixed with a 6× Laemmli loading buffer. Before loading onto SDS-PAGE, the samples were boiled for 5 minutes at 95° C. For COL7 detection, 5-30 µg of protein was loaded on a 6% acrylamide gel. The primary antibody used for COL7 detection was a rabbit antibody (Sigma, cat. no. HPA042420). Resolved proteins were transferred onto a nitrocellulose membrane, blocked in PBS-0.1% Tween with 5% milk or 5% BSA according to requirements of the primary antibody, and incubated overnight with the primary antibody. After incubation with IgG-HRP conjugated secondary antibody (Santa Cruz Biotechnology), the membrane was incubated with western blotting substrate (ThermoFisher Scientific, cat. no. 32106) and exposed to film (ThermoFisher Scientific, cat. no. 34090).

qRT-PCR

RNA was isolated using RNeasy® Mini Kit (Qiagen) according to the manufacturer's protocol. RNA extractions were quantified using a NanoDrop™ spectrophotometer (Fisher Scientific), and 1.5 µg RNA was used for cDNA synthesis using a SuperScript III First-Strand Synthesis system (Invitrogen). For qPCR, SYBR Select Master mix (Life Technologies) was used, and cDNA samples were diluted 1:25 to serve as template. Experiments were performed in triplicate.

Adhesion Assay 96-well plates were left uncoated, or were coated with 10, 20, or 50 µg/mL rat tail collagen 1 (BD Biosciences) or human fibronectin (Millipore) in 100 4, reaction volume at 4° C. overnight, then washed with PBS, and blocked with PBS+0.1% BSA for 1 hour at 37° C. Mock (control) or SAR-COL7 infected RDEB keratinocytes ($2.4 \times 10^4$ cells in 100 4, of DMEM/HamF12+0.1% BSA) were added to the plates and incubated at 37° C. for 90 minutes. Wells were washed three times with PBS to remove any unbound cells, and adherent cells were fixed with PFE for 20 minutes. The fixed cells were then treated with 70% ethanol, stained with crystal violet, resolved in 100% ethanol, and quantified by measuring absorbance at 630 nM with a Flex Station 3 plate reader (Molecular Devices).

Organotypic Skin Equivalents

Bovine fibrinogen (90% clottable, MP Biomedicals) was dissolved in 1.1% NaCl at 37° C. for 4 hours and then filtered with a 0.45 µm nylon membrane filter. Fibroblasts were collected with the use of trypsin and centrifugation and were resuspended in media to a final concentration of $2 \times 10^6$ cells/mL. 150 4, of the cell suspension was mixed with 1 mL of thrombin (3 IU—Sigma Aldrich), and the cell/thrombin mix was added to fibrinogen at a ratio of 1:1. The mixture was quickly but gently distributed at 1 mL/well into a 12-well plate and incubated at 37° C. After 20 minutes, medium supplemented with ascorbic acid and aprotinin (Sigma) at a final concentration of 10 µg/mL was added. The matrices were left to mature for 5-7 days while medium was changed every other day. Keratinocytes were plated on top at $2 \times 10^6$ cells/well, and on the next day the culture was raised to the air-liquid interface on a metal grid, and treatment with amlexanox was started. Medium was changed every other day with fresh drug, ascorbic acid and aprotinin. Cultures were collected at one or two weeks of treatment and frozen with OCT in liquid nitrogen-cooled isopentane. 8 µm sections were cut using a cryostat (Avantik QS11) and immunostained with polyclonal anti-COL7 antibody at a dilution of 1:800. Nuclei were counterstained with DAPI (Invitrogen).

Results

First, COL7 expression from modified HSV was assessed by qPCR and western blot analyses in the HaCaT human keratinocyte cell line to determine whether the modified HSVs were capable of expressing their cargo. HaCaT cells were transduced with either SAR-COL7 or KCA211 at MOIs ranging from 0.3-10. 48 hours after infection, cells were collected and processed for either qPCR (FIG. 3A) or western blot (FIG. 3B) analyses. The results demonstrated that full length COL7 was expressed in a dose-dependent manner from human keratinocytes infected with either modified HSV.

Next, immunofluorescence experiments were conducted to visualize COL7 expression in primary RDEB keratinocytes or RDEB fibroblasts infected for 24-48 hours with SAR-COL7 at various MOIs (ranging from 0.1 to 10). A strong COL7 signal was observed at all doses of SAR-COL7 tested for both keratinocytes (FIG. 4A) and fibroblasts (FIG. 4B), as compared to uninfected normal and RDEB keratinocytes and fibroblasts. The infection efficiencies of SAR-COL7 at MOIs of 0.1-1 in fibroblasts ranged from 16-36%. The infection efficiencies of SAR-COL7 at MOIs of 3.0 and above in fibroblasts were >90%.

Figure 5A:
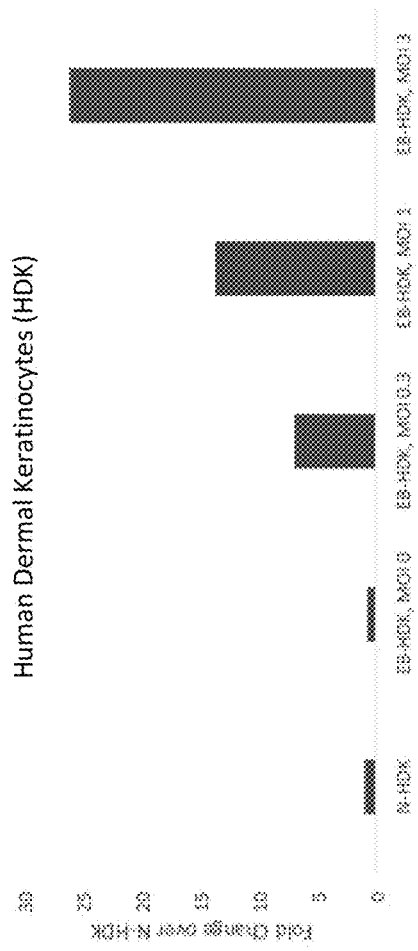
FIGS. 5A-B show quantitative PCR analysis of human COL7 expression in mock infected primary human cells isolated from a healthy patient, and mock or SAR-COL7 infected primary human cells isolated from a patient suffering from recessive dystrophic epidermolysis bullosa (EB).
Figure 5B:
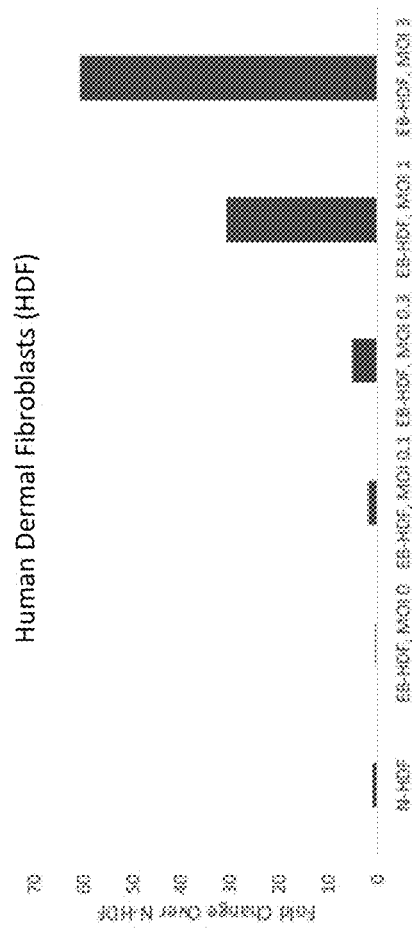

RDEB patient-derived human dermal keratinocytes (HDKs) and fibroblasts (HDFs) were infected with SAR-COL7 at varying MOIs in order to evaluate COL7A1 RNA expression. Normal HDKs and HDFs, as well as mock infected RDEB HDKs and HDFs, were used as negative controls. Dose-dependent increases in COL7A1 transcripts were observed in both HDKs (FIG. 5A) and HDFs (FIG. 5B) infected with SAR-COL7. The relative fold change in COL7A1 transcript expression after infection vs. uninfected healthy HDKs (Table 1A) or uninfected healthy HDFs (Table 1B) was also calculated. The use of COL7A1-encoding HSV was capable of increasing COL7A1 transcript expression by approximately 26-fold in RDEB HDKs and 60-fold in RDEB HDFs relative to wild-type COL7A1 transcript levels in healthy HDKs and HDFs at an MOI of 3.

TABLE 1A

COL7A1 expression in HDKs

| Cell type: | MOI: | Fold change over N-HDK: |
| --- | --- | --- |
| Normal HDKs (N-HDK) | 0 | 1.00 |
| RDEB HDKs (EB-HDK) | 0 | 0.79 |
| RDEB HDKs (EB-HDK) | 0.3 | 7.00 |
| RDEB HDKs (EB-HDK) | 1.0 | 13.73 |
| RDEB HDKs (EB-HDK) | 3.0 | 26.25 |

TABLE IB

COL7A1 expression in HDFs

| Cell type: | MOI: | Fold change over N-HDF: |
| --- | --- | --- |
| Normal HDFs (N-HDF) | 0 | 1.000 |
| RDEB HDFs (EB-HDF) | 0 | 0.340 |
| RDEB HDFs (EB-HDF) | 0.1 | 1.805 |
| RDEB HDFs (EB-HDF) | 0.3 | 5.134 |

TABLE IB-continued

COL7A1 expression in HDFs

| Cell type: | MOI: | Fold change over N-HDF: |
|---|---|---|
| RDEB HDFs (EB-HDF) | 1.0 | 30.788 |
| RDEB HDFs (EB-HDF) | 3.0 | 60.571 |

Next, the functionality of human COL7 expressed from SAR-COL7 was tested by a cell adhesion assay. The ability of uninfected RDEB keratinocytes, and RDEB keratinocytes infected with SAR-COL7 at varying MOIs, to adhere to wells treated with Collagen 1 or fibronectin was studied. Interestingly, RDEB keratinocytes infected with SAR-COL7 showed increased adhesion to Collagen 1 (FIG. 6A) and fibronectin (FIG. 6B) in dose-dependent manner using a plate-based adhesion assay.

Figure 7:
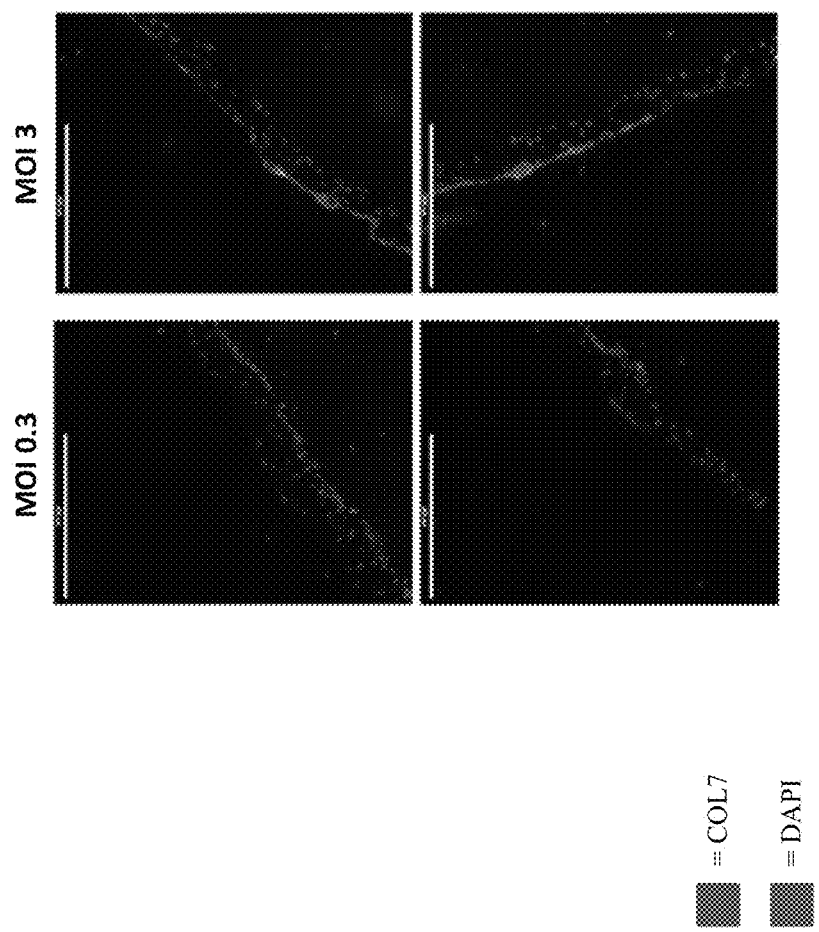
FIG. 7 show representative immunofluorescence images of human COL7 expression and deposition at the basement membrane zone (BMZ) at day 5 in organotypic cultures constructed with SAR-COL7 infected RDEB primary human keratinocytes and fibroblasts. Both keratinocytes and fibroblasts were infected in situ at the indicated MOI after culture construction.

Finally, a skin equivalent (SE) organotypic culture composed of RDEB fibroblasts and keratinocytes was used to evaluate the expression of COL7 from SAR-COL7 at the Basement Membrane Zone (BMZ). Organ cultures were constructed with RDEB or normal fibroblasts and keratinocytes. RDEB cells were either infected with SAR-COL7 prior to organ culture construction (data not shown), or SAR-COL7 was added drop-wise onto the cultures prior to raising at the air-liquid interface (FIG. 7). The resulting skin equivalents (SEs) were isolated, sectioned, and stained for immunofluorescence to detect COL7 protein expression. COL7 was detected in these organotypic cultures from cells infected with SAR-COL7, and the initiation of COL7 protein deposition at the BMZ was observed. This data suggested that not only could SAR-COL7 deliver COL7A1 and express COL7 protein efficiently, but the COL7 protein began to organize in organotypic cultures similar to the pattern of organization expected for COL7 protein in vivo.

Taken together, the data provided herein indicated that replication-defective HSV may be employed as a vehicle for effectively delivering and expressing high levels of functional human collagen in wild-type primary human cells, as well as primary human cells isolated from patients suffering from a collagen deficiency, without any obvious toxicity in either 2D or 3D culture systems.

Example 3: In Vivo Analysis of an HSV Candidate Encoding Human COL7 in Wild-Type Animals The following example describes experiments showing that recombinant viruses constructed and validated in vitro in human cells (see Example 2 above) were capable of expressing the encoded human collagen in vivo in wild-type animals. The purpose of the study was, in part, to evaluate the skin biodistribution of HSV-mediated collagen expression in healthy immunocompetent animals.

Materials and Methods
Test Article

The active ingredient in the formulations administered to mice was the modified herpes simplex virus SAR-COL7 or KCA211 (see Example 2 above) at a titer of $4.8 \times 10^8$ plaque forming units (PFU)/mL formulated in PBS+10% glycerol. The vehicle used for intradermal administration was Dulbecco's phosphate-buffered saline (DPBS)+10% glycerol. The vehicle used for topical administration was 3% hydroxypropyl methylcellulose (HPMC) gel formulated in sterile double distilled water.

Animals

Healthy male BALB/c mice between 6 and 10 weeks of age were used. All procedures used in the protocol were in compliance with applicable animal welfare acts and were approved by the local Institutional Animal Care and Use Committee (IACUC).

Intradermal Injections

Prior to and during test article administration, mice were anesthetized using a cocktail of Dexdomitor (30 µL or 0.05 mg/mL) and Telzol (50 µL of 10 mg/mL). The sedative was reversed with Antisedan (50 µL of 0.5 mg/mL). The back and flank areas were shaved using an electrical pet clipper, and the area was wiped with an alcohol wipe. Intradermal injections were performed using the Mantoux technique with a syringe and 27G needle (VWR, cat. no. BD305620), ensuring creation of a superficial "bleb" at each site. The virus was kept on dry ice, was thawed at room temperature, and was administered within 30 minutes of thawing. Two intradermal injections were administered to the back of each mouse, and the edges of the "bleb" were marked with a permanent marker.

Topical Application

Topical administration was conducted either on open wounds or abraded or scarified skin. The back and flank regions were shaved using electrical clippers. Scarification was performed by gently abrading the skin with a mechanical Dremel followed by superficial perforation with a 22G needle. For creation of a wound, a 5-6 mm diameter biopsy of the skin was removed using sharp scissors. In order to contain the topical formulation to the abraded or wounded site, a well was created from cut and autoclaved tops of 1.5 mL micro-centrifuge tubes. The lids were retained, and the cut side was covered with transparent adhesive dressing. The "wells" were adhered to the abraded/wounded region using surgical glue with the lid side down. 100 µL of SAR-COL7 was mixed with 20 µL of topical vehicle and was applied to the wound site by injection through the transparent adhesive in order to contain the topical gel on the wound and prevent leakage.

Tissue Collection

At the indicated time points following SAR-COL7 administration, the mice were euthanized, and the injection site was removed using an 8 mm biopsy punch. One half of the biopsy was quick-frozen using liquid nitrogen, while the other half was embedded in OCT and cryopreserved for immunofluorescence staining.

Real Time Quantitative PCR

Quick-frozen biopsy halves were stored at −80° C. until analysis. For processing and analysis, samples were resuspended in 3504, RLT buffer prepared with fresh DTT following the manufacturer's protocol (Qiagen). The sample were sonicated 3 times at 25% amplitude with intermittent incubation for 1 minute on ice, and DNA and RNA extractions were performed according to the manufacturer's protocol (Qiagen AllPrep DNA and RNA extraction kit). Both RNA and DNA samples were resuspended in distilled, deionized RNAse free water and quantified spectrophotometrically on a Take3 microplate reader (BioRad).

Absolute quantification of COL7AJ DNA copies and RNA transcripts was performed by Taqman Real Time PCR analysis using a custom primer/probe assay that spanned the 3' end of the human COL7A1 open reading frame and the 3' UTR, specifically detecting the COL7A1 transgene. 100 ng of DNA and RNA was used for the qPCR and qRT-PCR assays respectively, and a plasmid standard containing the region to be amplified was prepared in 100 ng mouse genomic or RNA matrix. GAPDH was used as the control for both analyses.

Immunofluorescent Staining

OCT frozen tissue was sectioned at 5-8 μm and left to air dry for up to 1 hour. The slides were dipped in 100% methanol for 10 minutes at −20° C. and left to air dry. The methanol-fixed sections were rehydrated through 3 washes in PBS (5 minutes each) at room temperature. The sections were incubated with a blocking solution composed of 10% serum (mixed species) for 1 hour at room temperature in a humid chamber. The excess blocking solution was removed and a drop of primary antibody (anti-human collagen 7, Sigma, cat. no. HPA042420; anti-integrin alpha 6 (clone goH3), BD Biosciences, cat. no. 555734) solution, prepared in 5% blocking solution, was applied on each section (30-50 μL/section). The sections were incubated with the primary antibody for 16 hours at 4° C., washed 3 time in PBS for 5 minutes each at room temperature, and secondary antibody (anti-rabbit AF 647, Invitrogen, cat. no. A21244; anti-rat AF-594, Invitrogen, cat. no. A11007) was applied at a 1:400 dilution in PBS for 1 hour at room temperature in a humid chamber. The 3 times PBS wash was repeated, then slides were immersed in Hoechst solution (1:1000) for 5 minutes at room temperature. The 3 times PBS wash was repeated, and the stained sections were mounted with mounting media (Fluorometer G, Southern Biotech, cat. no. 0100-01) and covered with a coverslip. The sections were imaged after dehydration (approximately 24 hours) using a Widefield Fluorescence Microscope.

Results

A total of 30 male BALB/c mice divided into 6 groups were used for this study. SAR-COL7 was administered either by intradermal injection or topical application on day 1, and a subset of mice were harvested on day 3, and the remaining mice on day 6. Animals in group 2 received a low dose of SAR-COL7 ($4.8 \times 10^6$ pfu/site) in the same volume by intradermal injection, and group 1 served as a control for the intradermal cohorts. In groups 4, 5, and 6, the topical vehicle (group 4) or SAR-COL7 in topical gel (groups 5 and 6) was applied either to a wounded (groups 4 and 6) or abraded (group 5) area in a total volume of 120 μL. Tissues were harvested and processed for qPCR and immunofluorescence analysis as described above.

Figure 8A:
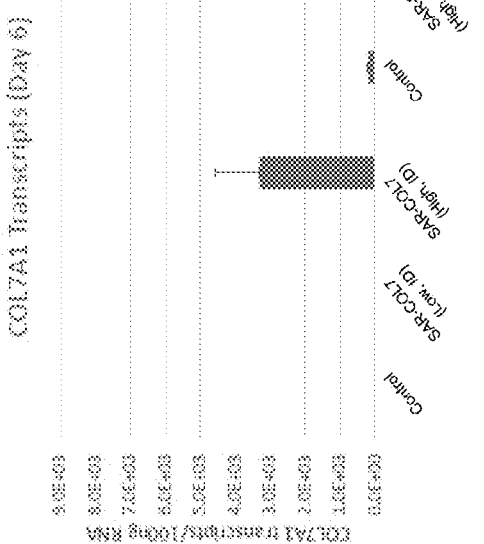
FIGS. 8A-D show human COL7A1 transcript and genome levels observed in uninfected mouse skin (control), or in mouse skin after topical or intradermal delivery of SAR-COL7, as assessed by qPCR. Error bars represent SEM.
Figure 8C:
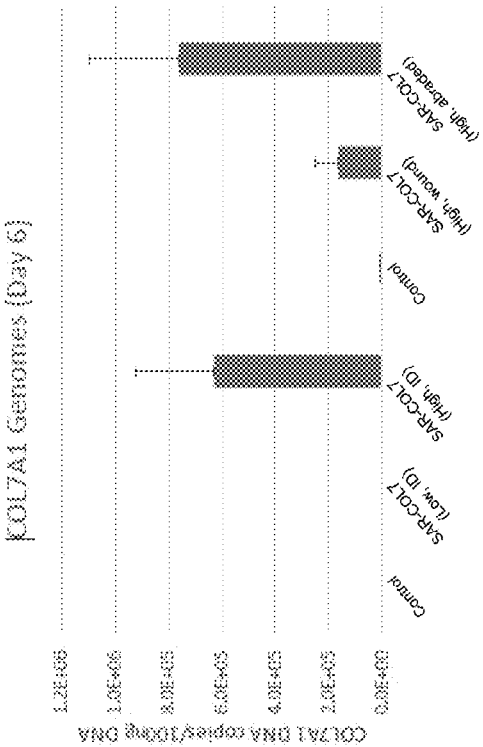
Figure 8B:
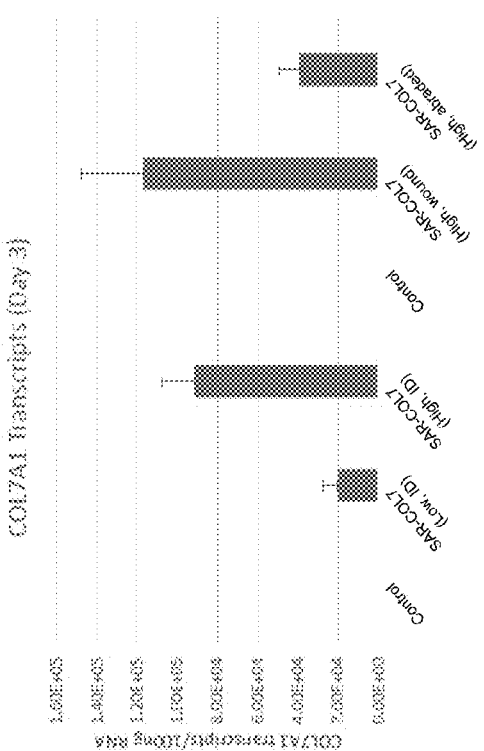
Figure 8D:
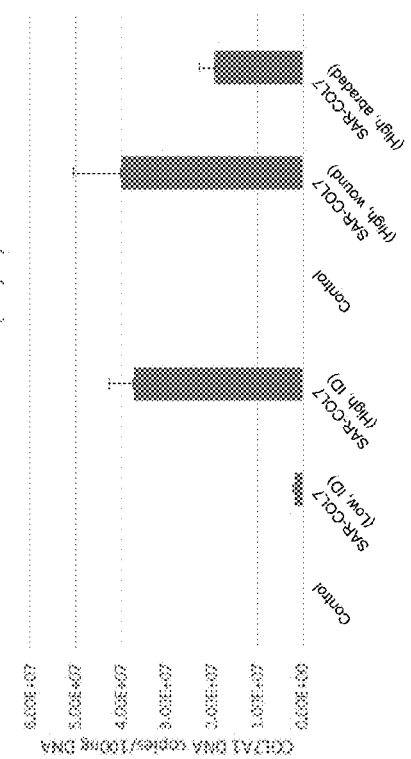

Post-sacrifice qPCR analysis was undertaken. COL7A1 transcripts and DNA levels were detected in all cohorts that received SAR-COL7 either by intradermal or topical application (FIGS. 8A-D), and a clear dose response was observed. Transcript and DNA levels were comparable between intradermal and topical cohorts (SAR-COL7 high ID, high wound, and high abraded), suggesting that topical application was as efficient at delivering COL7A1 as intradermal injection. Overall, the DNA and RNA levels were lower in the day 6 samples (FIGS. 8C-D) than the day 3 samples (FIGS. 8A-B), which was not unexpected since SAR-COL7 is a non-integrating vector that remains episomal (which would be expected to clear over time).

Next, immunofluorescence experiments were conducted to visualize COL7 expression after SAR-COL7 infection in vivo. As observed in the representative images provided in FIGS. 9A-B, COL7 was detected in most of the animal cohorts at both time points examined. Many samples showed correct localization of COL7 at the BMZ and around the hair follicles. In some instances, specifically with intradermal application, strong COL7 expression was observed in deeper layers of the skin, closer to the underlying fascia, possibly due to the injection being subcutaneous rather than intradermal. Similarly, in many of the abraded skin samples where the BMZ was likely removed during abrasion (as suggested by the lack of representative goH3 staining), the strong COL7 staining was limited to the skin surface. Overall, the presence of COL7 in the immunofluorescence samples strongly supported the robust efficacy of the modified HSV SAR-COL7.

In addition, the ability of KCA211 to express human COL7 was tested in vivo and compared to SAR-COL7 administration. KCA211 was found to also express the COL7 transgene in vivo in immunocompetent mice (FIGS. 10A-B).

Taken together, the data indicated that modified HSV was capable of delivering and expressing a human collagen protein in vivo in healthy, immunocompetent animals after topical or intradermal administration, and further, that collagen expression from topically administered virus into compromised skin or open wounds was comparable to intradermal administration into intact skin.

Example 4: In Vivo Analysis of Low and High Doses of an HSV Candidate Encoding Human COL7 in Hypomorphic Animals The following example describes experiments showing that recombinant viruses constructed and validated in vitro in human cells (see Example 2 above) and in vivo in wild-type mice (see Example 3 above) were capable of expressing functional human collagen in vivo in COL7 hypomorphic mice. The purpose of the study was, in part, to evaluate the skin biodistribution of HSV-mediated collagen expression in COL7-deficient, immunocompetent animals.

Materials and Methods

Unless indicated to the contrary, experiments were conducted as described in Example 3 above.

Hypomorphic Mice

The COL7 hypomorphic mouse model (Fritsch et al. J Clin Invest. 2008 May; 118(5):1669-79) was used in this study. This hypomorphic mouse model is an immunocompetent animal model for dystrophic epidermolysis bullosa (DEB) in which the mice express about 10% of normal levels of COL7. Their phenotype closely resembles characteristics of severe human DEB, including mucocutaneous blistering, nail dystrophy, and mitten deformities of the extremities.

The mice were generated by flp/frt-mediated removal of exon 2 of mouse COL7A1. Animals lacking both functional copies of COL7A1 (Col7a1flNew/flNeo), referred to as COL7 "hypomorphic mice", expressed about 10% of normal levels of COL7. From a total of 15 breeding pairs, 58 pups were obtained, with the litters ranging from 2-7 mice/litter. Out of these 58 pups, 6 were genotyped to be hypomorphs. Mice were genotyped with DNA extracted from an ear punch tissue sample. PCR analysis detected the presence of a loxP site upstream of exon 2 of COL7A1. Wild-type (WT) mice showed a band at 269 base pairs (bp), hypomorph mice showed a band at 435 bp, and heterozygous mice showed both bands. All procedures were in compliance with applicable animal welfare acts and were approved by the local Institutional Animal Care and Use Committee (IACUC).

Intradermal Injections

Prior to and during test article administration, mice were maintained under inhalation anesthesia using 2% isoflurane. Eye ointment (Puralube® Vet) was applied on the eyes to prevent dryness. Intradermal injections were performed using the Mantoux technique with a 31G needle. Up to four intradermal injections were administered to the back of each mouse at the specified doses.

Tissue Collection

Prior to tissue collection, animals were euthanized by $CO_2$ inhalation followed by cervical dislocation. The injection sites were biopsied using sharp scissors.

Hematoxylin and Eosin (H&E) Staining

Cryopreserved tissues were sectioned at a thickness of 5-8 μm and left to air dry for up to one hour. The slides were dipped in 100% methanol for ten minutes at −20° C. and left to air dry. Methanol fixed sections were rehydrated in PBS for 5 minutes at room temperature. The sections were incubated in hematoxylin (Weigert's modified hematoxylin) for 5-10 minutes at room temperature, followed by a wash in PBS for 15 minutes at room temperature. The sections were then rinsed in Eosin (Eosin Y solution, cat. no. HT110116) 3 times followed by one rinse in water.

The sections were gradually dehydrated with ethanol by dipping in 70% ethyl alcohol 10 times, 95% ethyl alcohol ten time, and 100% ethyl alcohol ten times. The sections were set to dry, mounted with mounting media (Fischer Scientific, cat. no. SPF15-100) and covered with a coverslip. The sections were imaged after dehydration (approximately 24 hours) using a bright field microscope.

Electron Microscopy

Skin was prepared for electron microscopy by immersion in 1.5% glutaraldehyde/1.5% paraformaldehyde in Dulbecco's serum free media (SFM) containing 0.05% tannic acid for a minimum of one hour, followed by an extensive rinse in SFM, and a post-fixation step in 1% $OsO_4$ for 60 minutes. The samples were washed in SFM then dehydrated in a graded series of ethanol to 100%, rinsed in propylene oxide, and infiltrated in Spurr's epoxy over a total time of two hours, accelerated via microwave energy. Samples were polymerized at 70° C. over 18 hours. Additional samples were prepared by extensively rinsing in SFM then immersing in mouse IgM LH24 antibody or mouse IgG NP185 antibody diluted 1:5 in SFM overnight at 4° C. The samples were then rinsed extensively in SFM, exposed to gold enhancement solution (Nanoprobes) for 15 minutes on ice, then rapidly warmed to 25° C. and incubated an additional 5 minutes. The samples were rinsed with ice cold SFM, fixed, and embedded.

Results

Three hypomorphic mice were used for the high-dose SAR-COL7 study. All mice received a dose of 4.6×10$^7$ PFU/50 μL/injection site by intradermal injection on day 1 (Table 2). Each animal was shaved and injected at 4 sites on the back, including 1 control injection and 3 SAR-COL7 injections. One animal (mouse 3) received a second injection at the same 4 sites on day 3. One mouse (mouse 1) was sacrificed on day 3, while mouse 2 and mouse 3 were sacrificed on day 7.

TABLE 2 study design for intradermal injection of high-dose SAR-COL7

| Sample: | Mouse: | Treatment (Day 1): | Treatment (Day 3): | Day of Sacrifice: |
|---|---|---|---|---|
| 1 | 1 | HSV-GFP | PBS | Day 3 |
| 2 | | SAR-COL7 | — | |
| 3 | | SAR-COL7 | — | |
| 4 | | SAR-COL7 | — | |
| 5 | 2 | PBS | PBS | Day 7 |
| 6 | | SAR-COL7 | — | |
| 7 | | SAR-COL7 | — | |
| 8 | | SAR-COL7 | — | |
| 9 | 3 | PBS | PBS | Day 7 |
| 10 | | SAR-COL7 | SAR-COL7 | |
| 11 | | SAR-COL7 | SAR-COL7 | |
| 12 | | SAR-COL7 | SAR-COL7 | |

Figure 11A:
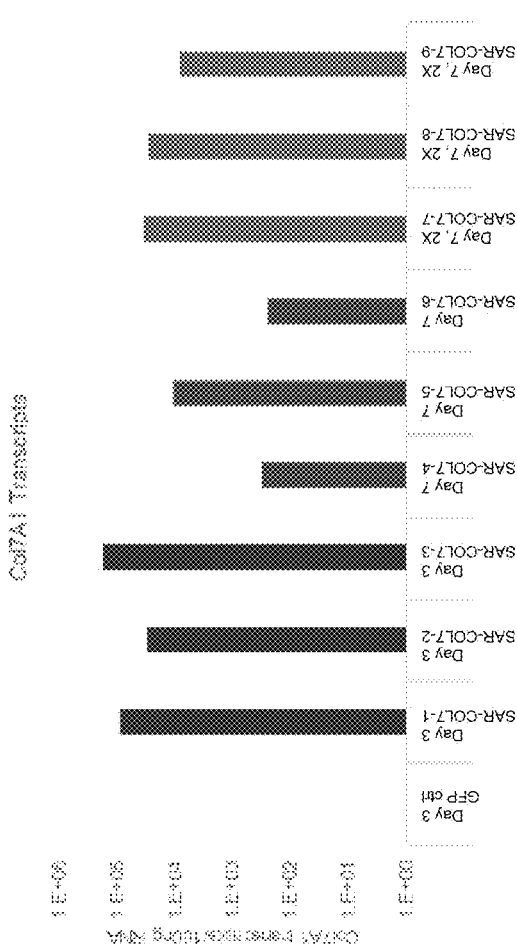
FIGS. 11A-B show human COL7A1 transcript and genome levels observed at each injection site in hypomorph mouse skin after high-dose intradermal delivery of HSV-GFP (GFP ctrl) or SAR-COL7, as assessed by qPCR. Each bar represents a single sample at the indicated time point.
Figure 11B:
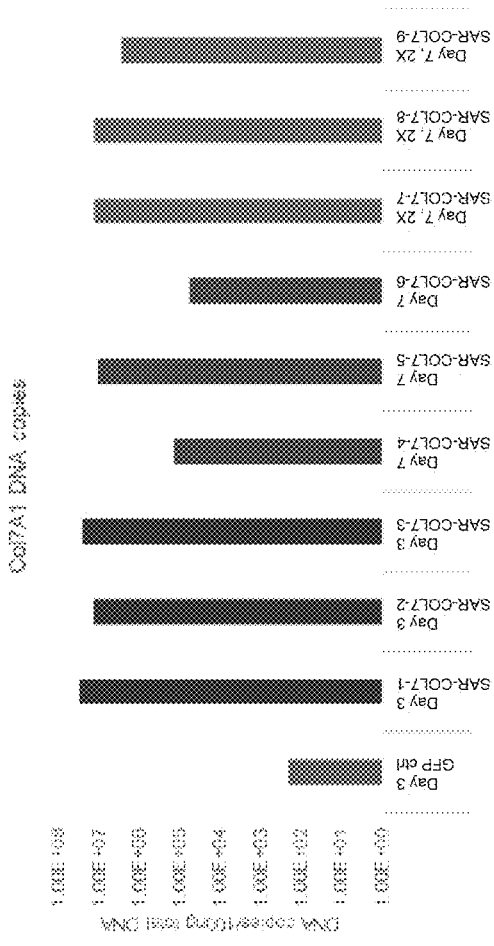

Post-sacrifice qPCR analysis was undertaken. COL7A1 transcripts (FIG. 11A) and DNA levels (FIG. 11B) were detected at each viral injection site in all three mice. Transcript levels in all of the control samples (PBS or HSV-GFP) were at or below the level of detection in the assay, so only 1 control (day 3, sample 1, HSV-GFP) was included for comparison in the graphs. Some decrease in DNA and transcript levels by day 7 after single administration of SAR-COL7 (mouse 2) was observed; however, DNA and transcript levels increased upon re-administration of SAR-COL7 (mouse 3).

Figure 12A:
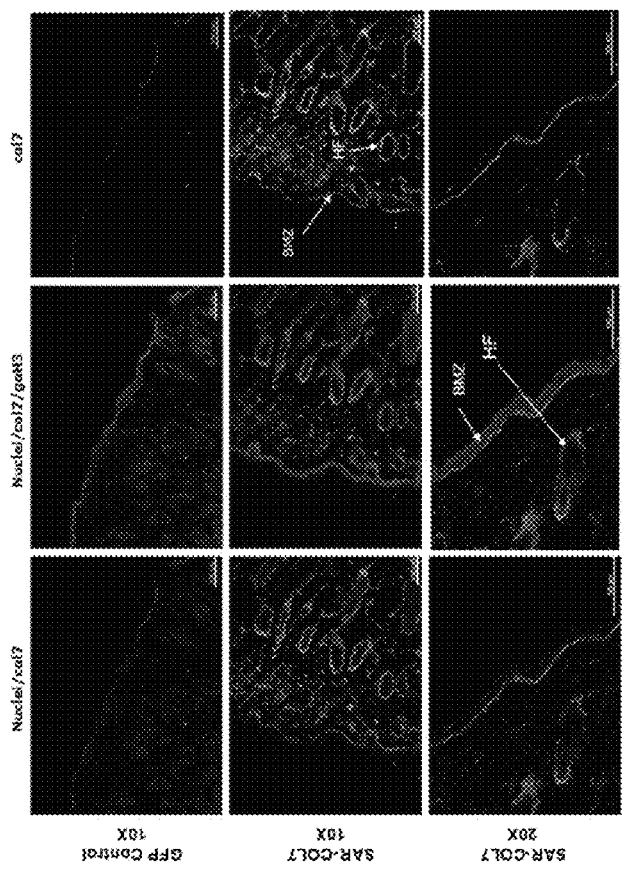
FIGS. 12A-B show representative immunofluorescence images of human COL7 expression in hypomorph mouse skin after high-dose intradermal delivery of HSV-GFP (GFP Control) or SAR-COL7.
Figure 12B:
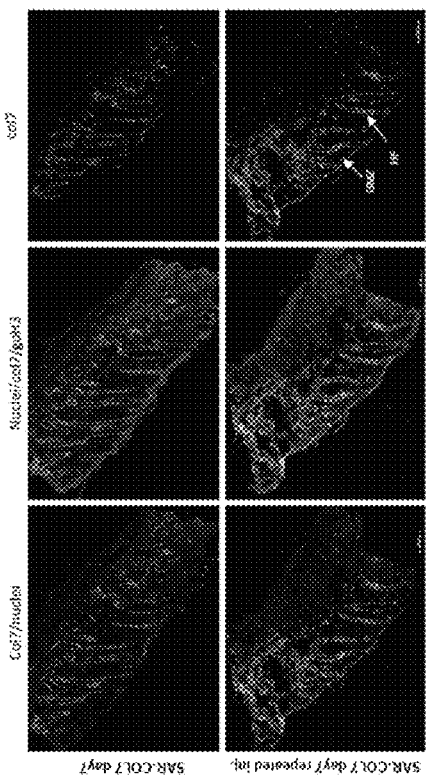
Figure 13:
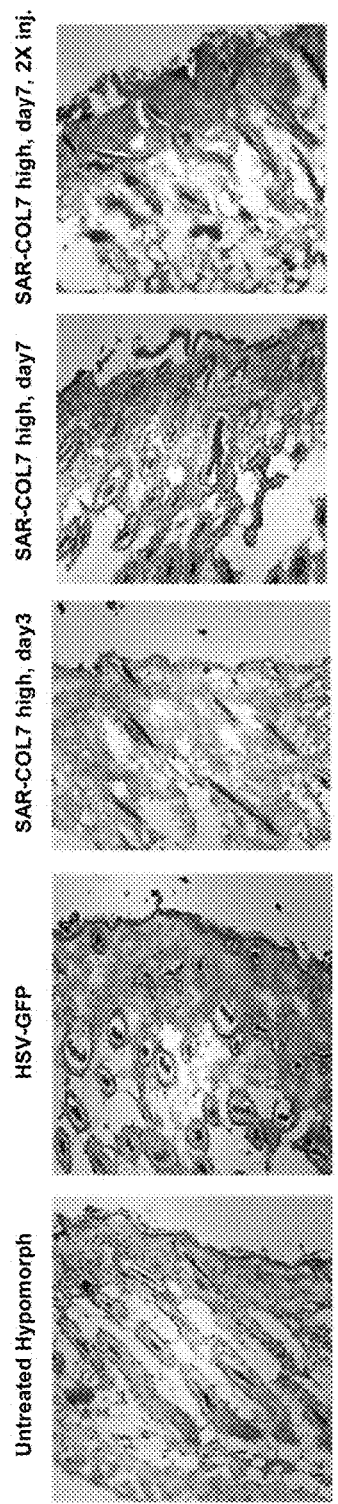
FIG. 13 shows H&E stained samples from hypomorph mouse 1, 2, and 3 (harvested at days 3 and 3). The samples were taken from untreated hypomorph mouse skin, and hypomorph mouse skin after intradermal delivery of HSV-GFP or SAR-COL7.

Next, immunofluorescence (IF) experiments were conducted to visualize COL7 expression in hypomorphic mice after SAR-COL7 infection in vivo (FIGS. 12A-B). The IF experiments demonstrated that robust and widespread COL7 protein expression was observed in the BMZ, as well as around the hair follicles (HF), at both the day 3 and day 7 timepoints. No negative impact on skin morphology (even after repeat administration) was observed, as the SAR-COL7 treated samples showed a normal skin morphology with no obvious signs of fibrosis or acute inflammation (FIG. 13). Overall, the presence of COL7 in the immunofluorescence samples strongly supported the robust efficacy of SAR-COL7 in delivering human collagen capable of being secreted and appropriately organized in the underlying skin substructures.

Figure 14B:
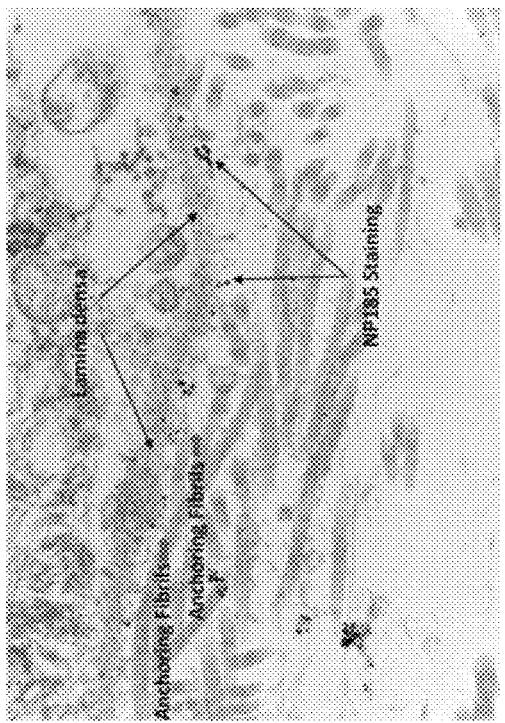
FIGS. 14A-B show representative electron micrograph images of human COL7 expression in hypomorph mouse skin after intradermal delivery of SAR-COL7. The lamina densa is the dark band indicated through the middle of the images; the black dots are the stained NC domains of human COL71 the blue arrows indicate the formation of anchoring fibrils.
Figure 14A:
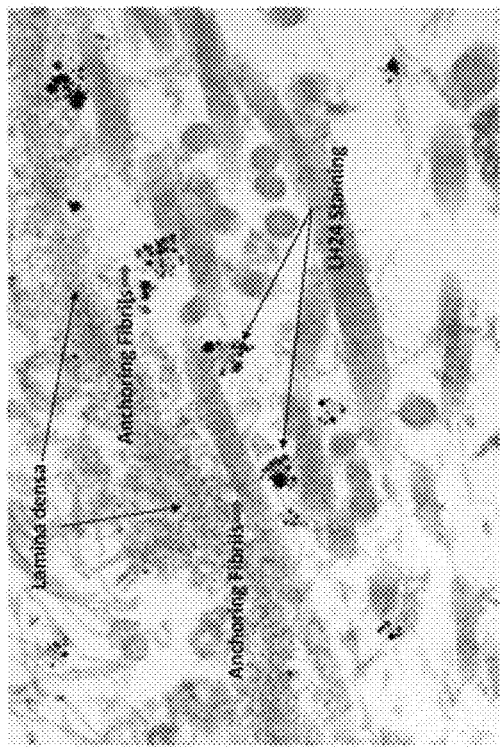

Day 3 biopsies were also evaluated for anchoring fibril formation by electron microscopy. In appropriately structured anchoring fibrils, the NC1 domain of COL7 (which is stained with the NP158 antibody) aligns towards the lamina densa, while the NC2 domain of COL7 (which is stained with the LH24 antibody) aligns away from the lamina densa. Biopsies from SAR-COL7-injected mice showed COL7 staining with both the LH24 (FIG. 14A) and NP185 (FIG. 14B) antibodies, and importantly, the electron microscopy (EM) images revealed the formation of anchoring fibrils. The lamina densa was observed as a dark band through the middle of the EM images. The NC2 domains of the exogenous human COL7 were positioned away from the lamina densa, while the NC1 domains of the exogenous human COL7 were positioned along the lamina densa, as would be expected in properly formed anchoring fibrils. This data indicated that SAR-COL7 could not only express an encoded human COL7 that was capable of being secreted and appropriately organized at the BMZ, but that the secreted COL7 was functional and properly positioned in the resulting anchoring fibrils, supporting the skin tissue of the hypomorphic mice.

Three additional hypomorphic mice were used for the low-dose SAR-COL7 study. All mice received a dose of 6.4×10$^6$ PFU/50 μL/injection site of SAR-COL7 in 3 (mouse 1) or 2 (mouse 2 and 3) sites by intradermal injection on day 1 (Table 3).

TABLE 3 study design for intradermal injection of low-dose SAR-COL7

| Mouse: | Treatment Day: | No. of Injection Sites: | Termination Day: |
|---|---|---|---|
| 1 | 1 | 3 | 3 |
| 2 | 1 | 2 | 3 |
| 3 | 1 | 2 | 7 |

Figure 16:
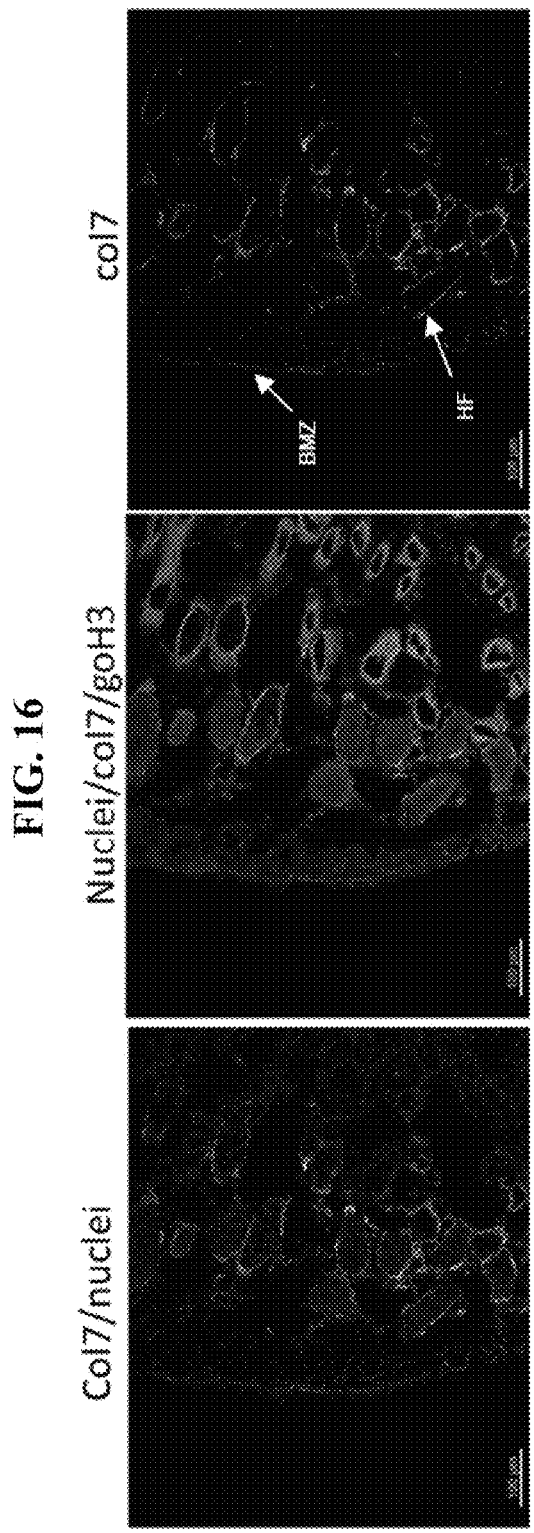
FIG. 16 shows representative immunofluorescence images of human COL7 expression in hypomorph mouse skin (from mouse 1) after low-dose intradermal delivery of SAR-COL7.
Figure 17C:
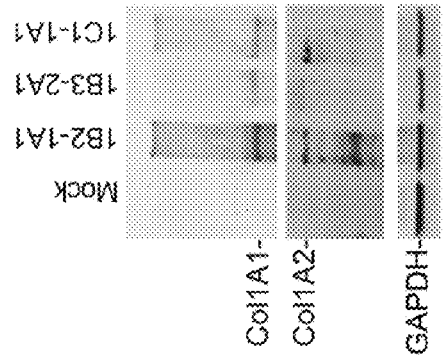
FIGS. 17A-C show human COL1A1 and COL1A2 nucleic acid and protein analyses in Vero cells infected with the indicated clones of HSV encoding COL1A1 alone (inserted into the ICP4 loci) or COL1A1 and COL1A2 (inserted into the ICP4 and ICP22 loci, respectively).
Figure 18:
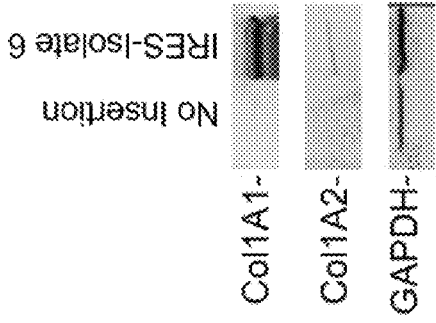
FIG. 18 shows western blot analysis of human COL1A1 and COL1A2 protein expression in Vero cells 5 days after infection with an HSV isolate encoding a COL1A1-IRES-COL1A2 sequence (IRES-Isolate 6) inserted into the ICP4 loci. Infection with an isolate that does not contain the IRES construct (no insertion) was used as a negative control; GAPDH was used as a loading control.
Figure 17A:
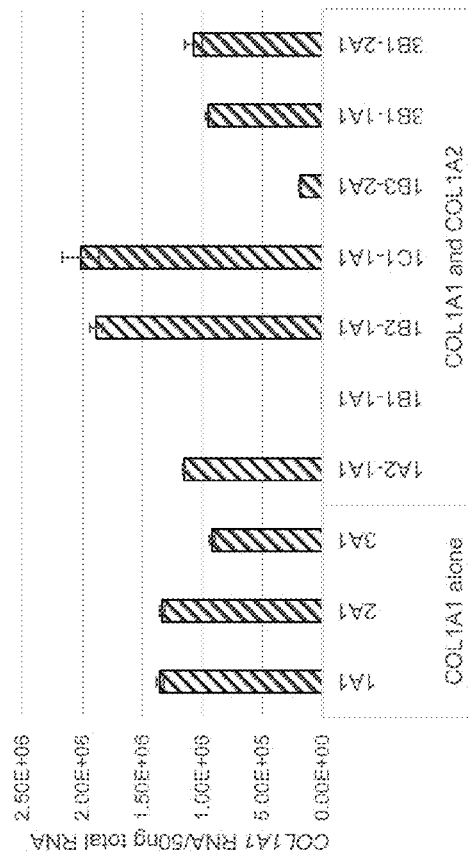
Figure 17B:
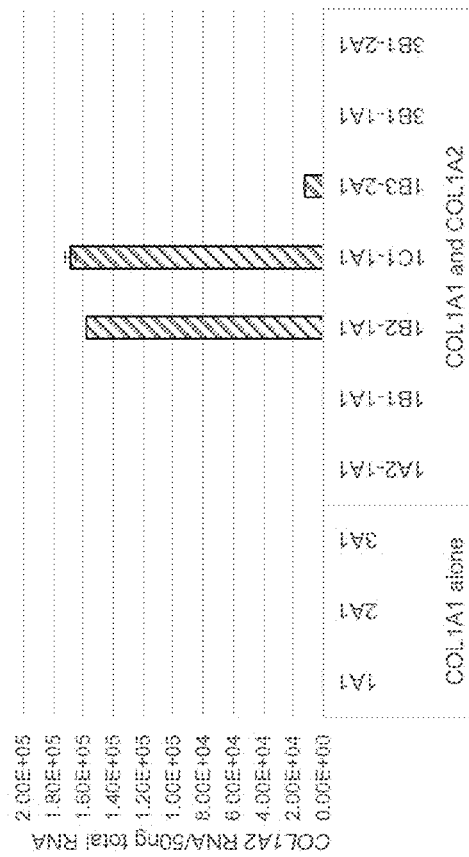

Post-sacrifice qPCR analysis was undertaken. COL7A1 transcripts (FIG. 15A) and DNA levels (FIG. 15B) were detected at each viral injection site in all three mice. A dose response was observed. While both DNA and transcript levels of COL7A1 were lower in these low-dose samples relative to those observed in high-dose study, COL7A1 expression was still detectable. Despite an approximate 2 log reduction in DNA or RNA levels, COL7 protein was still detectable in the skin of low-dose SAR-COL7 injected animals (FIG. 16). The COL7 protein was observed in both the BMZ and around the hair follicles. The data indicated that even at lower dosages, the modified HSV was still effective at delivering and expressing the encoded human collagen protein, which was then secreted and localized to the appropriate region of the skin.

Taken together, the data provided in the examples indicated that the modified HSVs described herein were able to: 1) transduce skin cells to produce functional human collagen in vitro and in organotypic culture (see Example 2); 2) transduce skin and deliver human collagen in vivo in healthy, immunocompetent animals after both topical and intradermal applications (see Example 3); and 3) transduce skin, deliver human collagen, and initiate the formation of anchoring fibrils in vivo in collagen-deficient animals (see Example 4). Without wishing to be bound by theory, it is believed that the recombinant vectors described herein provide a desirable strategy for delivering functional human collagen to the skin, allowing for novel approaches to support the dermis and/or epidermis in cosmetic settings.

Example 5: Construction and Validation of Multiple Engineered HSVs Encoding Human Collagen 1

The following example describes two different approaches for engineering a recombinant HSV-1 to successfully express human Collagen 1. Because human Collagen 1 is a heterotrimeric macromolecule comprising two copies of a COL1A1 polypeptide and one copy of a COL1A2 polypeptide, two distinct strategies were undertaken to generate a single HSV genome encoding both human COL1A1 and COL1A2; these two approaches are generally depicted in FIGS. 1H-1I and 1L, and described in detail below.

As a first approach, a recombinant HSV-1 was initially engineered to incorporate a human COL1A1 expression cassette, containing a heterologous promoter and polyA sequence, into each of the ICP4 loci as described in Example 2 above. Multiple plaques of viruses putatively containing the human COL1A1 cassette were picked and screened by infection in Vero cells to test for COL1A1 expression (data not shown). At least three isolates (clones 1A1, 2A1, and 3A1) were positive for human COL1A1 transgene expression. Next, the human COL1A1-positive clones 1A1 and 2A1 were then engineered to incorporate a human COL1A2 expression cassette, containing a different heterologous promoter than the COL1A1 cassette and its own polyA sequence, inserted into the ICP22 locus. Seven isolates (clones 1A2-1A1, 1B2-1A1, 1C1-1A1, 1B3-2A1, 3B1-1A1, and 3B1-2A1) were then screened to identify attenuated HSV-1 viruses capable of expressing both human COL1A1 and COL1A2, and thus, full-length human Collagen 1.

Vero cells were infected with one of the seven putative COL1A1-COL1A2-positive isolates or one of three of the COL1A1-alone isolates (as a negative control for COL1A2 expression) in order to identify recombinant HSV-1 clones capable of expressing both transgenes. Infections of the Vero cells were allowed to proceed for five days, cells were harvested by gentle scraping, and cell pellets were collected by centrifugation at 6000×g for five minutes. Half of each pellet was harvested for qRT-PCR analysis, while the other half was processed for western botting. Absolute quantification of COL1A1 or COL1A2 RNA copies was performed by Taqman Real-Time PCR analysis using custom primer/probe assays that span the 3' end of the human COL1A1 or COL1A2 open reading frame (ORF) and the 3' untranslated region (UTR), and are specific to the transgene. RNA extracted from cells infected with all three COL1A1-alone viruses, and cells infected with 6/7 of the COL1A1-COL1A2 viruses, were positive for human COL1A1 transgene expression (FIG. 17A). Interestingly, only 3/7 of the COL1A1-COL1A2 viruses (clones 1B2-1A1, 1C1-1A1, and 1B3-2A1) also expressed detectable levels of human COL1A2 (FIG. 17B). Western blotting of COL1A1 and COL1A2 protein expression in cell lysates infected with these three isolates was performed to ensure that the transgenes were expressed at both the nucleic acid and protein levels. Briefly, cell pellets were resuspended in RIPA buffer containing Halt protease inhibitor cocktail, incubated at 4° C. for ten minutes, and were then treated with benzonase for 10 minutes at room temperature. Samples were then diluted with 4×LDS sample buffer containing 5% 2-mercaptoethanol, and resolved on Tris-Glycine gels. Mock-infected Vero cell lysate was loaded on the gel as a negative control. Proteins were transferred to PVDF, blocked, and then stained overnight with primary antibody (anti-human COL1A1, ThermoFisher cat. no. PA5-29569; anti-human COL1A2, Abcam cat. no. ab96723; or anti-GAPDH, Abcam cat. no. ab9485). Stained membranes were then washed, incubated with secondary antibody, then developed. In agreement with the qRT-PCR analysis, all three clones were capable of expressing both human COL1A1 and COL1A2 proteins at detectable levels (FIG. 17C).

A second approach was pursued in parallel to generate COL1A1-COL1A2-positive recombinant, attenuated HSV vectors. Here, a polynucleotide construct was generated which encoded, from 5' to 3', a human COL1A1 ORF, a synthetic IRES, and a human COL1A2 ORF. This IRES-based construct (encoded in an expression cassette also containing a heterologous promoter and a polyA sequence) was then inserted into each of the ICP4 loci, as described in Example 2 above. Multiple plaques were picked and screened to identify vectors with correctly inserted IRES constructs. Briefly, Vero cells were infected with putative IRES viral isolates, infections were allowed to proceed for five days, and cells were harvested and processed for qPCR and qRT-PCR analysis. Absolute quantification of insert DNA and RNA copies was performed by Taqman Real-Time PCR analysis using custom primer/probe assays that recognize the synthetic IRES. 13 viral isolates were screened by qPCR and qRT-PCR analysis; only one of these isolates (isolate 6) tested positive for the IRES DNA and RNA transcripts comprising the IRES sequence (data not shown). To confirm that this isolate was capable of expressing both human COL1A1 and COL1A2 at the protein level, infected Vero cells were processed for western blotting as described above. A viral isolate (isolate 1) that showed no expression cassette incorporation by qPCR and transgene expression by qRT-PCR was used as a negative control. Paralleling the qPCR/qRT-PCR data, viral isolate 6 was capable of expressing both human COL1A1 and COL1A2 protein after infection (FIG. 18).

Taken together, the data presented in this sample indicate that: (1) multiple recombinant HSV-1 vectors were successfully constructed that were proficient in expressing both human COL1A1 and COL1A2 after infecting targeted cells; (2) vectors can be engineered to express heterotrimeric human collagen proteins; and (3) multiple different approaches can be taken to express multiple proteins from a single recombinant genome. Without wishing to be bound by theory, it is believed that successful expression of human Collagen 1 from a recombinant HSV-1 genome provides support for the use of engineered HSV to express any heterotrimeric collagen protein (e.g., human Collagen 4).

Example 6: Construction, Validation, and In Vitro Characterization of an Engineered HSV Encoding Human Collagen 3

The following example describes the engineering of a recombinant HSV-1 that successfully expressed human Collagen 3 (termed C3vec01). In addition, the following example describes in vitro experiments establishing multiple relevant 2D cell culture model systems suitable for characterizing the efficacy of C3vec01, including the use of immortalized human keratinocytes and fibroblasts in dose-ranging studies, the use of primary human dermal fibroblasts biopsied from multiple aged human patients as a model of C3vec01-mediated Collagen 3 rescue in older patients, and the use of in vitro UV-irradiated immortalized human fibroblasts as a model for sun exposure/skin aging.

Human skin is largely composed of collagen-rich connective tissue which is produced, organized, and maintained by dermal fibroblasts. Dermal collagen represents >90% (dry weight) of human skin and is composed primarily of COL1 and COL3 fibrils at a typical ratio of about 85:15. These fibrils provide strength to the skin and are critical for the maintenance of skin tissue architecture.

Skin aging characteristics are largely due to aberrant collagen homeostasis, resulting in a net collagen deficiency; biosynthesis of collagen is reduced, collagen fibril fragmentation is increased, and there is a progressive loss of dermal collagen, all of which contribute to the aged phenotype. Skin aging is influenced by a combination of both internal and external factors: intrinsic factors—the passage of time, genetics, cellular metabolism, hormones, etc.; and extrinsic—chronic light exposure, pollution, ionizing radiation, etc. These factors together lead to cumulative structural and physiological alterations to the skin, ultimately leading to the appearance of, and worsening in, skin wrinkles.

Skin rejuvenation, the process of reversing or repairing irregularities in the skin (such as wrinkles), is achieved, in part, by the synthesis of new collagen (neocollagenesis). In the skin, neocollagenesis is affected by the deposition of, and complex interactions between, collagens 1 and 3. COL3 appears early during collagen fibrillogenesis, and the subsequent replacement of this COL3 by COL1 is a critical step for collagen fibril maturation and extracellular matrix reorganization (Wang, et al., 2018, Journal of the Chinese Medical Association, 81(2), pp. 94-101). In addition, COL3 both regulates the dimensions of COL1 fibers (Liu, et al., 1997, Proc Natl Acad Sci USA, 94(5), pp. 1853-6) and enhances COL1 elasticity (Asgari, et al., 2017, Sci Rep, 7(1), p. 1392). As such, the appearance of early COL3 expression, and ensuing replacement with COL1, has been used as a marker of efficacy for injectable facial fillers in humans (Yutskovskaya, et al., 2014, J Drugs Dermatol, 13(9), pp. 1047-52).

All experiments were conducted as described above unless noted otherwise.

To begin, a recombinant HSV-1 was engineered to incorporate a human COL3A1 expression cassette, containing a heterologous promoter and polyA sequence, into each of the ICP4 loci. Multiple plaques of viruses putatively containing the human COL3A1 cassette were picked and screened by infection in Vero cells to test for COL3A1 expression (data not shown). One of the high expressing clones, termed C3vec01, was subsequently selected for additional in vitro (described below) and in vivo (Example 7) analyses.

Figure 19A:
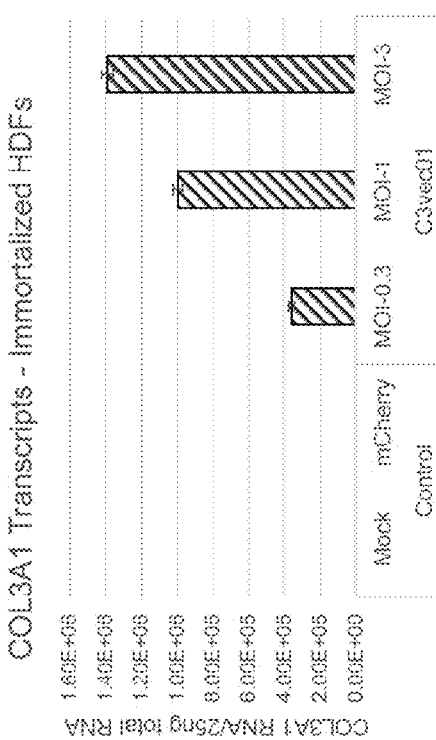
FIGS. 19A-B show human COL3 nucleic acid and protein analyses in immortalized human keratinocytes (HaCaTs) infected with C3vec01.
Figure 19B:
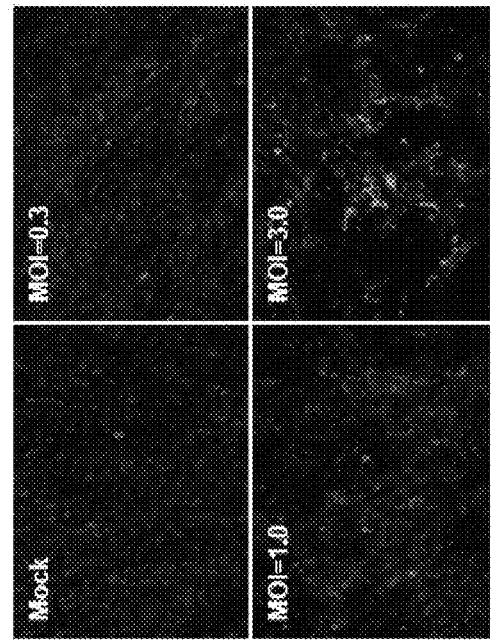
Figure 20A:
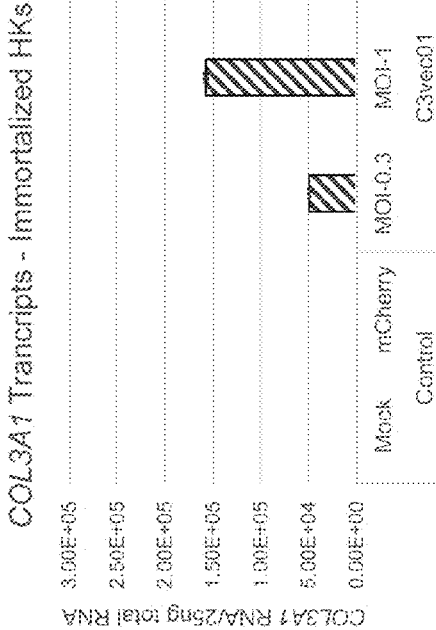
FIGS. 20A-B show human COL3 nucleic acid and protein analyses in immortalized human dermal fibroblasts (HDFs) infected with C3vec01.
Figure 20B:
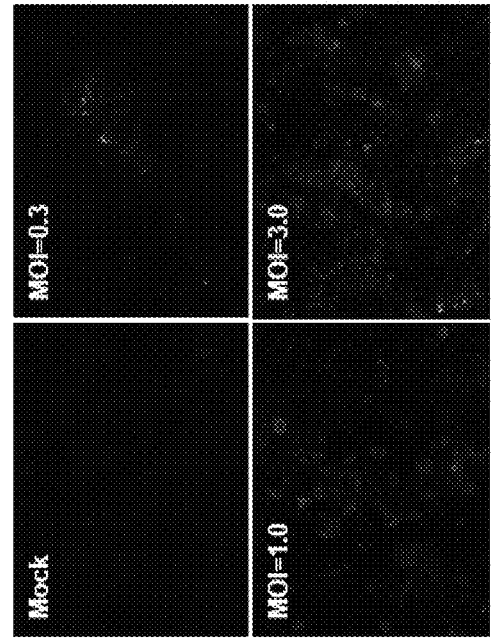

First, a dose-ranging study was conducted to determine the efficacy of C3vec01-mediated delivery of its encoded human cargo in both immortalized human keratinocytes (FIG. 19) and immortalized human dermal fibroblasts (FIG. 20). The immortalized cells were infected for 48 hours at various multiplicities of infection (MOI) ranging from 0.3 to 3, and human Collagen 3 expression was quantitatively and qualitatively measured via multiple assays. Dose-dependent increases were observed in both effector DNA by qPCR analysis (data not shown) and effector transcript levels by qRT-PCR analysis in the immortalized HKs and HDFs (FIGS. 19A and 20A, respectively). Mock infected cells, and cells infected with a virus containing the same HSV-1 backbone as C3vec01 but instead encoding an mCherry effector, were used as negative controls. Paralleling these results, a dose-dependent increase in COL3 protein expression after C3vec01 infection was observed by immunofluorescence in immortalized HKs (FIG. 19B) and HDFs (FIG. 20B). While the immortalized HDFs expressed endogenous human COL3 prior to infection (as expected), a significant increase in COL3 expression was observed after infection with C3vec01, even at a low dose (primary anti-COL3 antibody, Abcam cat. no. ab7778). Little-to-no detectable endogenous COL3 was observed in the uninfected immortalized keratinocytes. Importantly, no significant effect on cell morphology or viability was observed in immortalized keratinocytes or fibroblasts infected with C3vec01, even at high doses.

As the skin ages, resident dermal fibroblasts produce less Collagen 3, and the ratio of COL1:COL3 in the skin skews towards Collagen 1. In order to provide skin rejuvenation through the synthesis of new Collagen 3, it was important to understand whether C3vec01 would be capable of effectively infecting aged dermal fibroblasts and robustly express its encoded human Collagen 3. As such, the ability of C3vec01 to infect aged primary dermal fibroblasts and express exogenous Collagen 3 at multiple MOIs was tested in cells sourced from two different vendors. Table 4 below provides donor information for the four primary HDF samples used in this study.

TABLE 4

| primary human dermal fibroblast donors | | | | | | |
|---|---|---|---|---|---|---|
| Age | Sex | Race | Tissue | Cat. No. | Lot No. | Company |
| 73 | M | Caucasian | Skin/eyelid | C-12302 | 435Z009.2 | PromoCell |
| 65 | F | Caucasian | Skin/eyelid | C-12302 | 417Z010.2 | PromoCell |

TABLE 4-continued primary human dermal fibroblast donors

| Age | Sex | Race | Tissue | Cat. No. | Lot No. | Company |
|---|---|---|---|---|---|---|
| 73 | M | Caucasian | Left lower back | CC-2511 | 0000633428 | Lonza |
| 75 | F | Caucasian | Back | CC-2511 | 18TL057585 | Lonza |

Figure 21A:
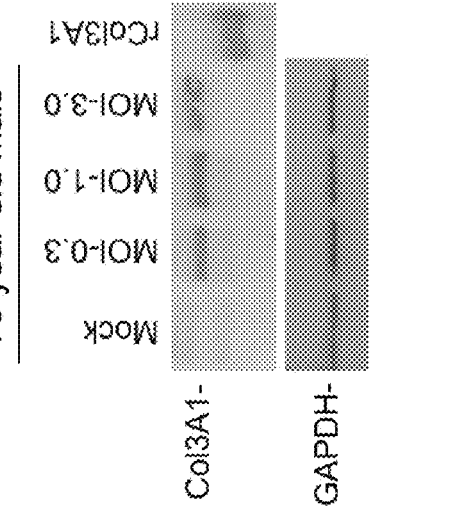
FIGS. 21A-D show human COL3 nucleic acid and protein analyses in aged primary human fibroblasts (HDFs), sourced from two different vendors, infected with C3vec01 at the indicated MOIs.
Figure 21B:
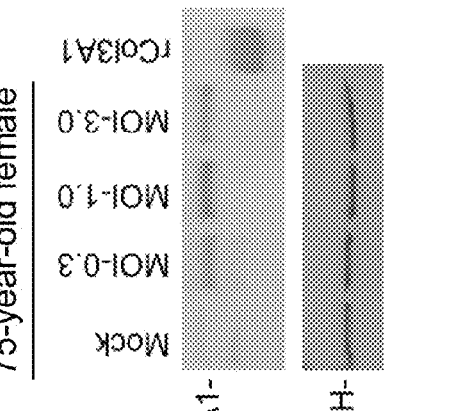
Figure 21C:
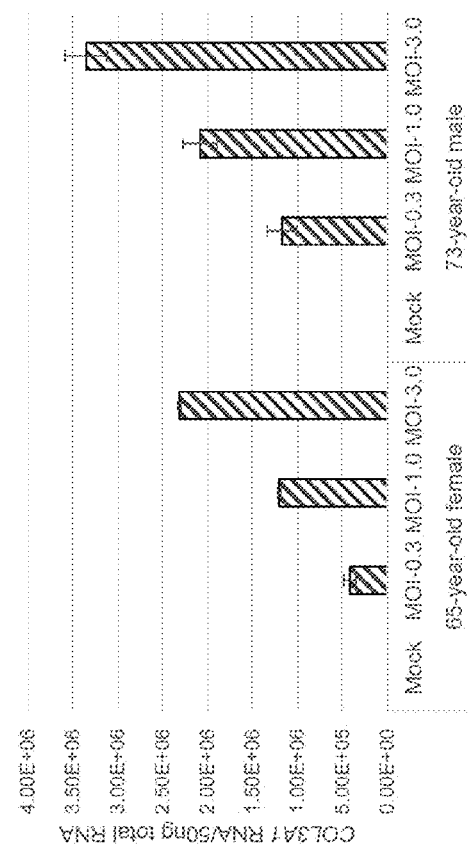
Figure 21D:
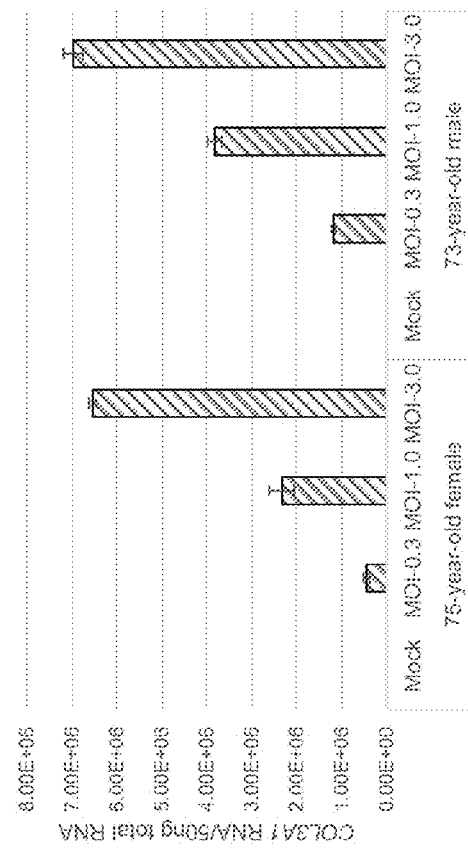

As compared to the immortalized HDFs, a similar dose-dependent increase with comparable or higher COL3 transcript levels was observed after C3vec01 infection of the primary HDFs from vendor 1 (FIG. 21A) and vendor 2 (FIG. 21C). A sample of representative primary cells from each vendor was also tested for COL3 expression by western blot analysis (primary anti-COL3 antibody, Abcam cat. no. ab7778). C3vec01 was capable of rescuing high levels of human Collagen 3 expression in primary HDFs biopsied from a 73-year-old male patient (FIR. 21B) and a 75-year-old female patient (FIG. 21D), even at the lowest MOI tested.

Finally, the ability of C3vec01 to induce robust Collagen 3 expression in UV-exposed immortalized human fibroblasts was tested. Sun exposure, and the corresponding UV damage, is known to be the single largest extrinsic contributor to the aged skin phenotype, and multiple groups have employed an in vitro skin fibroblast UV-exposure system to model certain aspects of photoaging (see e.g., Qin et al. 2018, Cell Physiol Biochem 46(5):1849-1860). To confirm that UV exposure caused human dermal fibroblasts to secrete less Collagen 3 (as would be expected given the phenotype of photo-aged skin), COL3 secretion into the supernatants of cultured immortalized human dermal fibroblasts was measured by ELISA before and after three different levels of UV exposure (FIG. 22A). Indeed, UV irradiation of cultured fibroblasts significantly reduced endogenous COL3 expression. COL1 expression were monitored in parallel in this experiment, and were not significantly affected by UV irradiation, indicating that UV exposure induced specific repression of COL3, as opposed to global suppression of protein synthesis. Next, the ability of C3vec01 to infect UV-irradiated immortalized HDFs and express exogenous COL3 was tested. Here, immortalized HDFs were exposed to UV-irradiation, and then allowed to recover for 24 hours prior to infection with C3vec01 at an MOI of 0.3 or 1. 48 hours after infection, exogenous human COL3 was assessed by qRT-PCR analysis. Strong COL3 expression was detected in C3vec01-infected, UV-irradiated HDFs at both tested MOIs (FIG. 22B), indicating that C3vec01 efficiently transduced photo-damaged cells and delivered its encoded cargo. Mock infected cells, and cells infected with a virus containing the same HSV-1 backbone as C3vec01 but instead encoding an mCherry effector, were used as negative controls to ensure specificity of transgene detection.

Taken together, the data presented in this example indicates that the recombinant HSV-1 vector C3vec01 efficiently transduces multiple human skin cell types, is capable of rescuing Collagen 3 expression in aged primary fibroblasts harvested from old patients, and is capable of salvaging Collagen 3 expression from UV-damaged HDFs. Without wishing to be bound by theory, it is believed that the data supports the use of a recombinant HSV encoding human Collagen 3 to correct the collagen defects of aged skin.

Example 7: In Vivo Characterization of Intradermally Administered C3vec01

The following example described in vivo experiments establishing methods of intradermally administering C3vec01 in young and old healthy immunocompetent animals.

All experiments were conducted as described above unless noted otherwise.

All procedures conducted in this example were in compliance with applicable animal welfare acts and were approved by the local Institutional Animal Care and Use Committee (IACUC).

The backs of mice were shaved before further manipulations. C3vec01 (or vehicle control) was then injected intradermally to four sites in the backs of the mice. After infection and the subsequent recovery period, the animals were euthanized, and the treatment sites were removed using an 8 mm punch biopsy. One half of each biopsy was quick-frozen in liquid nitrogen for qPCR/qRT-PCR analysis, while the other half was processed for immunofluorescence analysis.

Tissue samples were processed for nucleic acid and protein analysis as described above. For COL3 immunofluorescence staining, a rabbit anti-human Collagen 3 primary antibody (Abcam, cat. no. ab7778), and an Alexa Fluor® 488-conjugated secondary antibody were used. Tissue samples were mounted in mounting media containing DAPI to visualize nuclei.

An in vivo pharmacology study was conducted in young (6-8-week-old) and old (approximately 13-month-old) C57BL/6 mice to evaluate C3vec01-mediated expression of human COL3 in immunocompetent animals upon intradermal administration of the vector. A total of 10 animals were used for this study. The back of each mouse was first shaved and then intradermally injected with $2 \times 10^8$ PFU/site of C3vec01 (or vehicle control) at 4 sites/animal. Injected sited were biopsied at either 48-hours or 1-week post-dosing, and were evaluated for human COL3 expression by qPCR and immunofluorescence. Table 5 below provides a synopsis of the experimental design.

TABLE 5 study design and test article administration

| Group No. | N | Test Article | Mouse | Route of Administration | Volume of Test Article | Location, No. of Sites | Termination (day) |
|---|---|---|---|---|---|---|---|
| 1 | 1 | Vehicle | Young | Intradermal | 100 µL | Back, 4 | 2 |
| 2 | 2 | C3vec01 | Young | Intradermal | 100 µL | Back, 4 | 2 |
| 3 | 2 | C3vec01 | Young | Intradermal | 100 µL | Back, 4 | 7 |
| 4 | 1 | Vehicle | Old | Intradermal | 100 µL | Back, 4 | 2 |
| 5 | 2 | C3vec01 | Old | Intradermal | 100 µL | Back, 4 | 2 |
| 6 | 2 | C3vec01 | Old | Intradermal | 100 µL | Back, 4 | 7 |

Figure 23A:
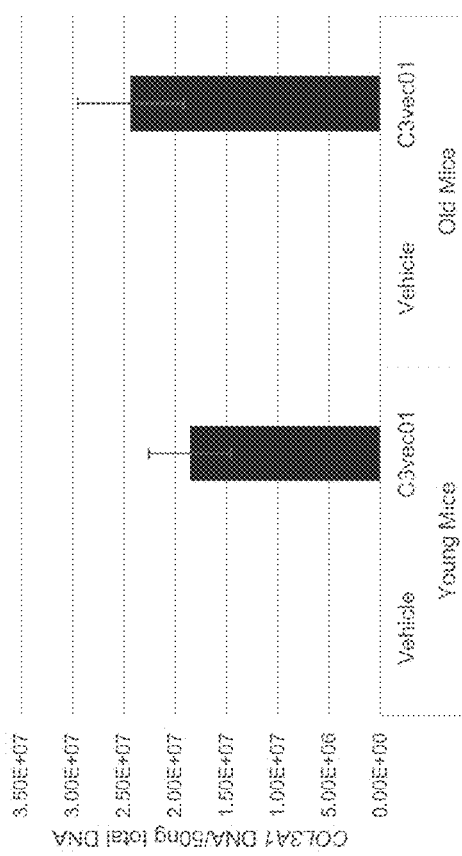
FIGS. 23A-C show COL3 nucleic acid and protein analyses of skin biopsies taken from control- or C3vec01-treated young (6-8-week-old) and old (~13-months-old) C57BL/6 mice 48 hours after intradermal application.
Figure 23B:
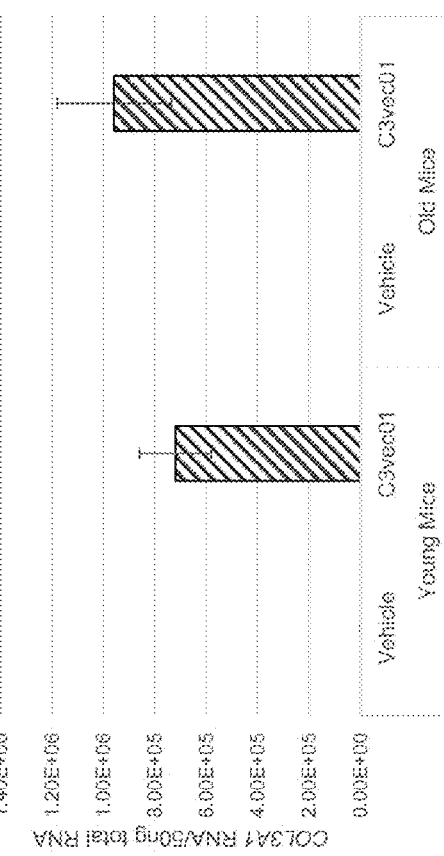
Figure 23C:
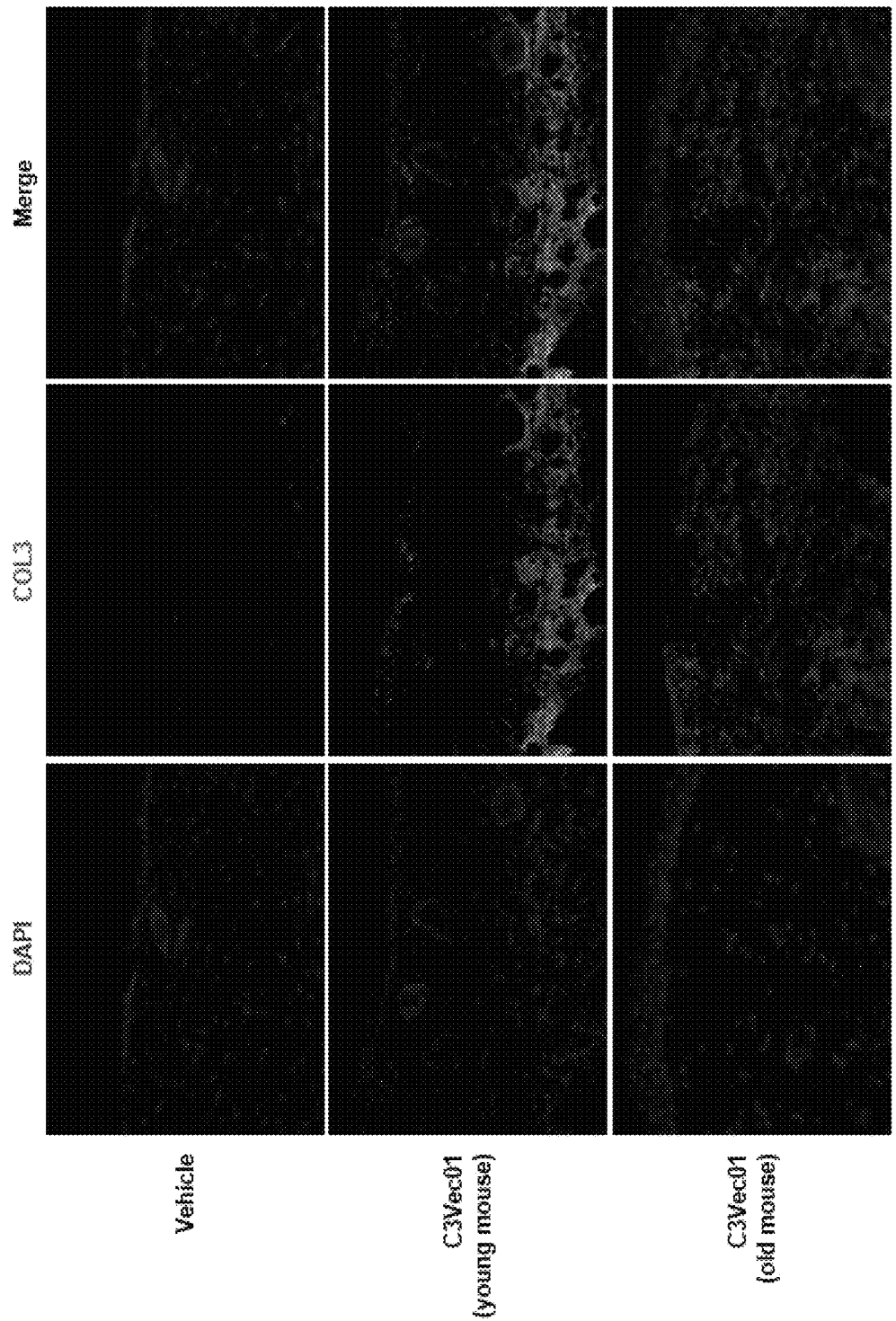

Intradermal delivery of C3vec01 led to high levels of transduced vector genomes detected in skin biopsies harvested 48-hours post-injection (FIG. 23A), as well as yielded high levels of human Collagen 3 transcripts in both young and old mice (FIG. 23B). Immunofluorescence-based detection also showed visibly increased levels of human COL3 throughout the dermis in C3vec01-treated skin relative to vehicle-treated skin (FIG. 23C), correlating with transcript levels.

Taken together, the data provided in this example indicates that can efficiently transduce skin and express human Collagen 3 in vivo after intradermal injection. Without wishing to be bound by theory, it is believed that the in vivo study presented here lends further support for the use of HSV-1 as a novel gene therapy to delivery human Collagen 3 in the aesthetic setting.

Figure 24A:
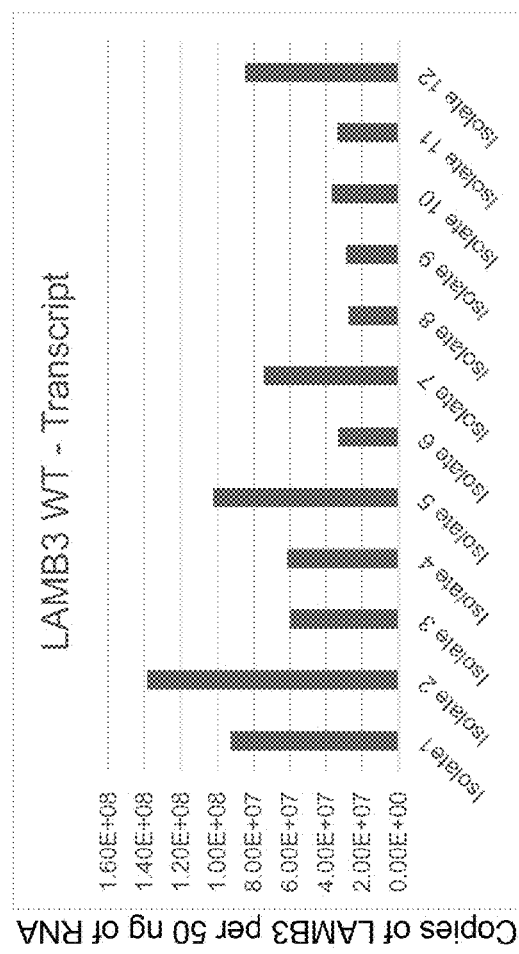
FIGS. 24A-B show expression of wild-type (WT) human LamB3 in Vero cells infected with the indicated viral isolates.
Figure 24B:
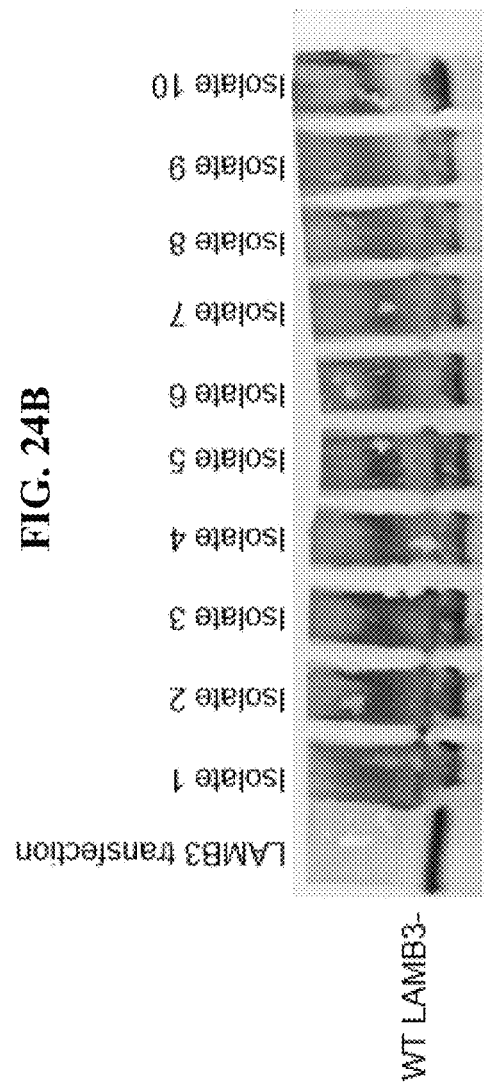

Example 8: Generation and Validation of Modified Herpes Simplex Virus Vectors Encoding Human Laminins To begin, recombinant herpes virus vectors were engineered to incorporate either wild-type or codon-optimized variants of two human laminin proteins, LAMB3 or LAMC2, as described in Example 3 above. A number of isolates were picked for each type of virus. To test whether certain isolates were capable of expressing the encoded wild-type human LAMB3 protein, ICP4-complementing Vero cells were plated in 6-well plates and were infected with 12 untitered viral isolates of wild-type LamB3-encoding viruses until completion of infection. After infection, RNA was harvested, cDNA was generated, and expression of wild-type LamB3 from each isolate was determined by qPCR (FIG. 24A). All 12 isolates were capable of expressing wild-type human LamB3 in the transduced Vero cells at varying levels. The ability of 10 of these isolates to express human LamB3 was also tested by western blot. ICP4-complementing Vero cells were plated in 6-well plates and were infected with 10 untitered viral isolates of wild-type LamB3 expressing viruses until completion of infection. A well of Vero cells was transfected with a LamB3 expression plasmid as a positive control. After infection, the cells were collected by gentle scraping, centrifuged to collect cell pellets, culture medium was aspirated, and the cell pellets were washed once with PBS. Following washing, each cell pellet was resuspended in 200 µL RIPA buffer containing protease inhibitors, and the resuspensions were incubated at 4° C. for 20 minutes with gentile agitation every 5 minutes. After incubation, the samples were centrifuged at 17,000×g for 5 minutes, the supernatant was removed, and 4×LDS reducing sample buffer containing 5% 2-mercaptomethanol was added to each clarified supernatant. The samples were then boiled for 10 minutes before loading on a 4-20% Tris-Glycine polyacrylamide gel. After electrophoresis, the protein was transferred to a PVDF membrane, and the membrane was blocked for 30 minutes in 5% milk/TBS. Primary rabbit anti-LamB3 antibody (Abcam, cat. No. ab128864) was then added to the PVDF membrane at 1:1000 dilution in 5% milk/TBS and incubated overnight at RT° C. (~16 hours). The blots were then washed 3× for 5 minutes each with TBS, and then stained with an AP-conjugated goat anti-rabbit IgG antibody (Sigma, cat. No. A3687) in 5% milk/TBS for 1 hour at RT° C. The membranes were then washed 3× for 5 minutes each with TBS, BCIP/NBT was added, and the blots were developed for ~10 minutes at RT° C. In agreement with the qPCR data, all 10 viral isolates were capable of expressing the encoded wild-type human LamB3 at varying levels (FIG. 24B).

Figure 25:
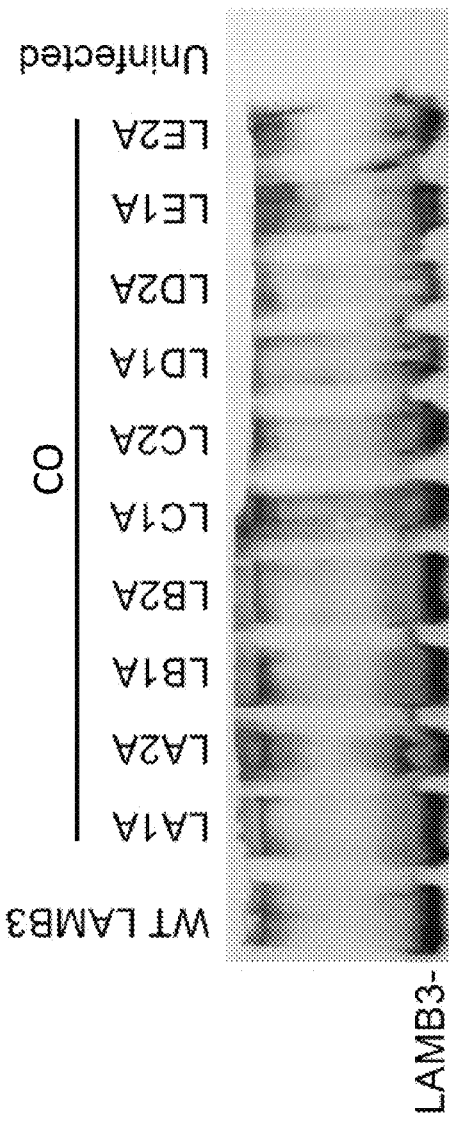
FIG. 25 shows expression of wild-type (WT) or codon-optimized (CO) human LamB3 protein in Vero cells infected with the indicated viral isolates, as assessed by western blot. Uninfected Vero cells were used as a negative control.

Viruses encoding codon-optimized variants of human LamB3 were also tested for their ability to express their cargo in Vero cells by western blot analysis. Briefly, 10 untitered viral isolates of codon-optimized (CO) LamB3-encoding viruses were used to infect Vero cells, cell pellets were collected, each pellet was resuspended in RIPA buffer containing protease inhibitors, and western blots were conducted using these cell lysates, as described above. All 10 viral isolates were capable of expressing the encoded codon-optimized human LamB3 in Vero cells (FIG. 25).

Figure 26:
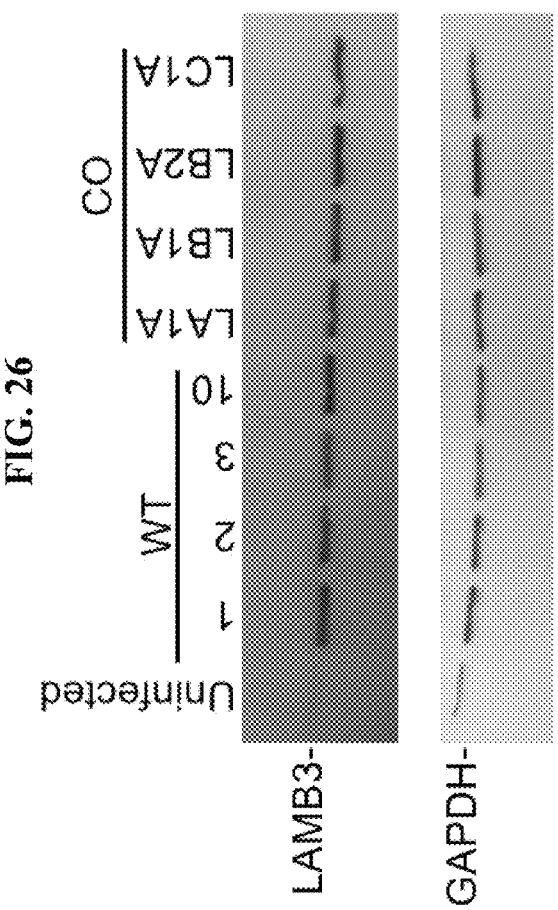
FIG. 26 shows expression of wild-type (WT) or codon-optimized (CO) human LamB3 protein in primary human keratinocytes infected with the indicated viral isolates, as assessed by western blot. Uninfected primary keratinocytes were used as a negative control.

Next, four viral isolates encoding either wild-type or codon-optimized LAMB3 were tested for their capacity to transduce primary human cells and express their cargo. Immortalized primary normal keratinocytes were infected at a multiplicity of infection (MOI) of 1.0 for 48 hours. Uninfected cells were used as a negative control. Expression of LamB3 in the infected human keratinocytes was then examined by western blot. Western blots were carried out as described above using a primary rabbit anti-LamB3 antibody (Abcam, cat. No. ab 128864). In line with the data generated using Vero cells, the viral isolates expressing either wild-type and codon-optimized LamB3 were confirmed to effectively transduce primary human keratinocytes and express their encoded construct at suitable levels (FIG. 26).

Figure 27B:
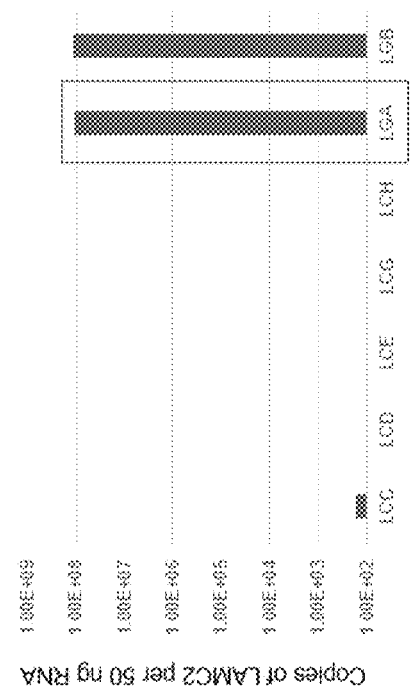
FIGS. 27A-C show expression of wild-type (WT) and codon-optimized (CO) human LamC2 in Vero cells infected with the indicated viral isolates.
Figure 27A:
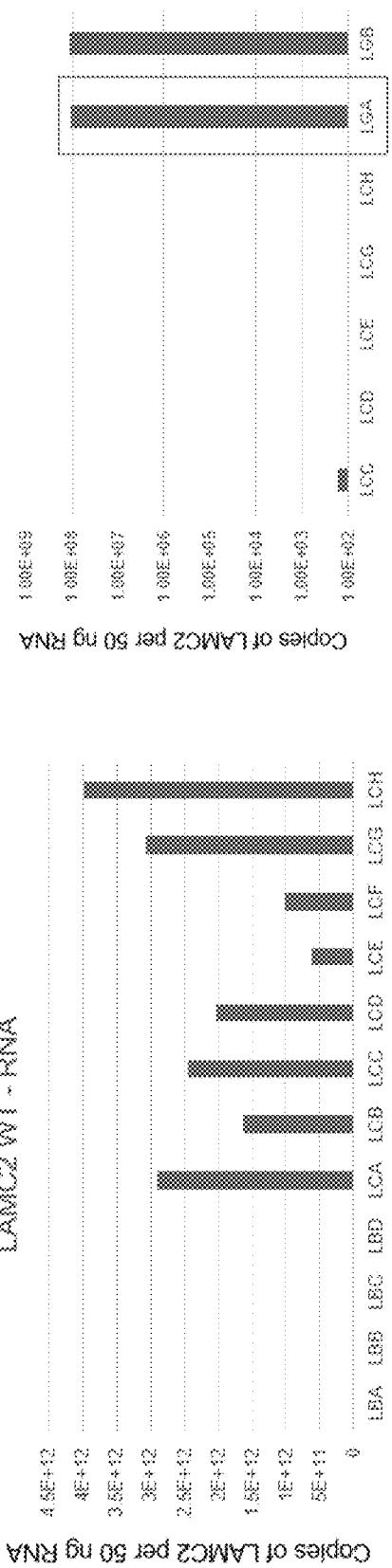
Figure 27C:
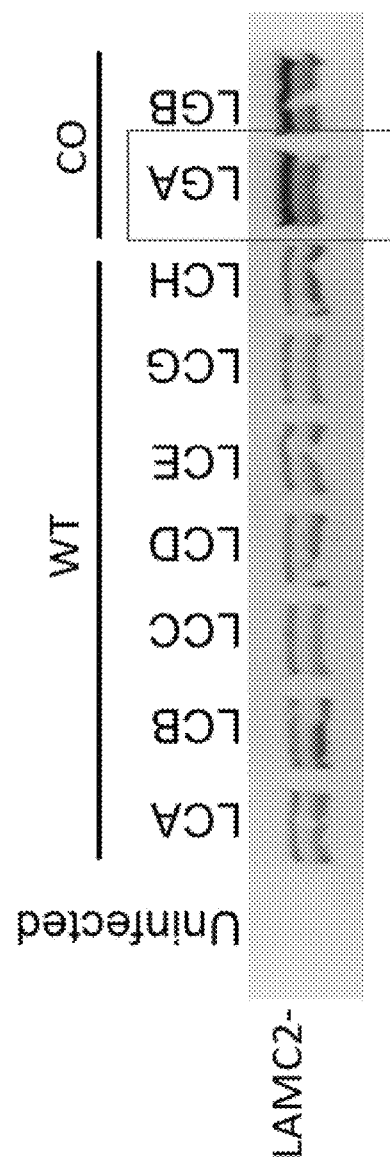

To test whether LamC2-containing isolates were capable of expressing the encoded wild-type or codon-optimized human LAMC2, ICP4-complementing Vero cells were plated in 6-well plates and were infected with a number of untitered wild-type or codon-optimized LamC2-expressing viral isolates until completion of infection. After infection, RNA was harvested, cDNA was generated, and expression of wild-type LamC2 (FIG. 27A) or codon-optimized LamC2 (FIG. 27B) from each isolate was determined by qPCR. 8/12 isolates were capable of expressing wild-type human LamC2 in the transduced Vero cells at varying levels, while 3/7 isolates were capable of expressing codon-optimized human LamC2. The ability of certain wild-type and codon-optimized isolates to express human LamC2 was next tested by western blot. ICP4-complementing Vero cells were plated in 6-well plates and were infected with untitered viral isolates until completion of infection. A well of Vero cells was left uninfected as a negative control. After infection, the cells were collected by gentle scraping, centrifuged to collect cell pellets, culture medium was aspirated, and the cell pellets were washed once with PBS. Following washing, each cell pellet was resuspended in 200 µL RIPA buffer containing protease inhibitors, and the resuspensions were incubated at 4° C. for 20 minutes with gentile agitation every 5 minutes. After incubation, the samples were centrifuged at 17,000×g for 5 minutes, the supernatant was removed, and 4×LDS reducing sample buffer containing 5% 2-mercaptomethanol was added to each clarified supernatant. The samples were then boiled for 10 minutes before loading on a 4-20% Tris-Glycine polyacrylamide gel. After electrophoresis, the protein was transferred to a PVDF membrane, and the membrane was blocked for 30 minutes in 5% milk/TBS. Primary rabbit anti-LamC2 antibody (Abcam, cat. No. ab96327) was then added to the PVDF membrane at 1:1000 dilution in 5% milk/TB S and incubated overnight at RT° C. (~16 hours). The blots were then washed 3× for 5 minutes each with TBS, and then stained with an AP-conjugated goat anti-rabbit IgG antibody (Sigma, cat. No. A3687) in 5% milk/TB S for 1 hour at RT° C. The membranes were then washed 3× for 5 minutes each with TBS, BCIP/NBT was added, and the blots were developed for ~10 minutes at RT° C. In agreement with the qPCR data, all 9 of the tested viral isolates were also able to express the encoded human LamC2 (FIG. 27C).

Figure 28C:
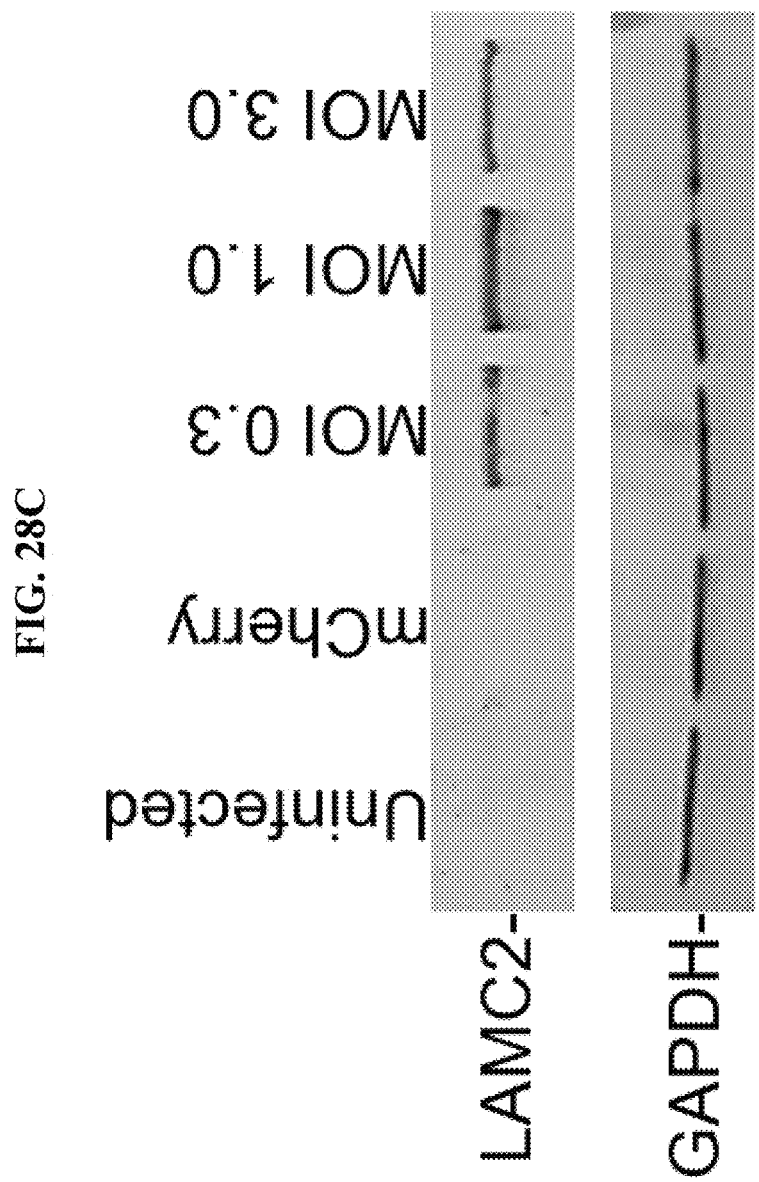

The codon-optimized LamC2-expressing viral isolate "LGA" was selected for further testing in human cells. Immortalized primary normal keratinocytes were infected with the LGA isolate at a multiplicity of infection (MOI) of 0.3, 1.0, or 3.0 for 48 hours. Uninfected (control) and mCherry-expressing virus infected cells were used as a negative control. DNA and RNA were extracted from the immortalized keratinocytes after 48 hours of infection, and qPCR/qRT-PCR was performed (FIGS. 28A-B). A good dose-response was observed for the LGA isolate in the immortalized keratinocytes, as assessed by viral genome copies detected per 50 ng of DNA (FIG. 28A). Interestingly, while a dose response was observed at the transcript level when increasing the MOI from 0.3 to 1.0, no additional increase in transcript levels were observed when increasing from an MOI of 1.0 to 3.0 (FIG. 28B). Expression of LamC2 in the infected human keratinocytes were also examined by western blot. Western blots were carried out as described above (primary rabbit anti-LamC2 antibody (Abcam, cat. No. ab96327) was used). In line with the transcript analysis, a dose response was observed at the protein level when increasing MOI from 0.3 to 1.0, but not from 1.0 to 3.0 (FIG. 28C).

Figure 29D:
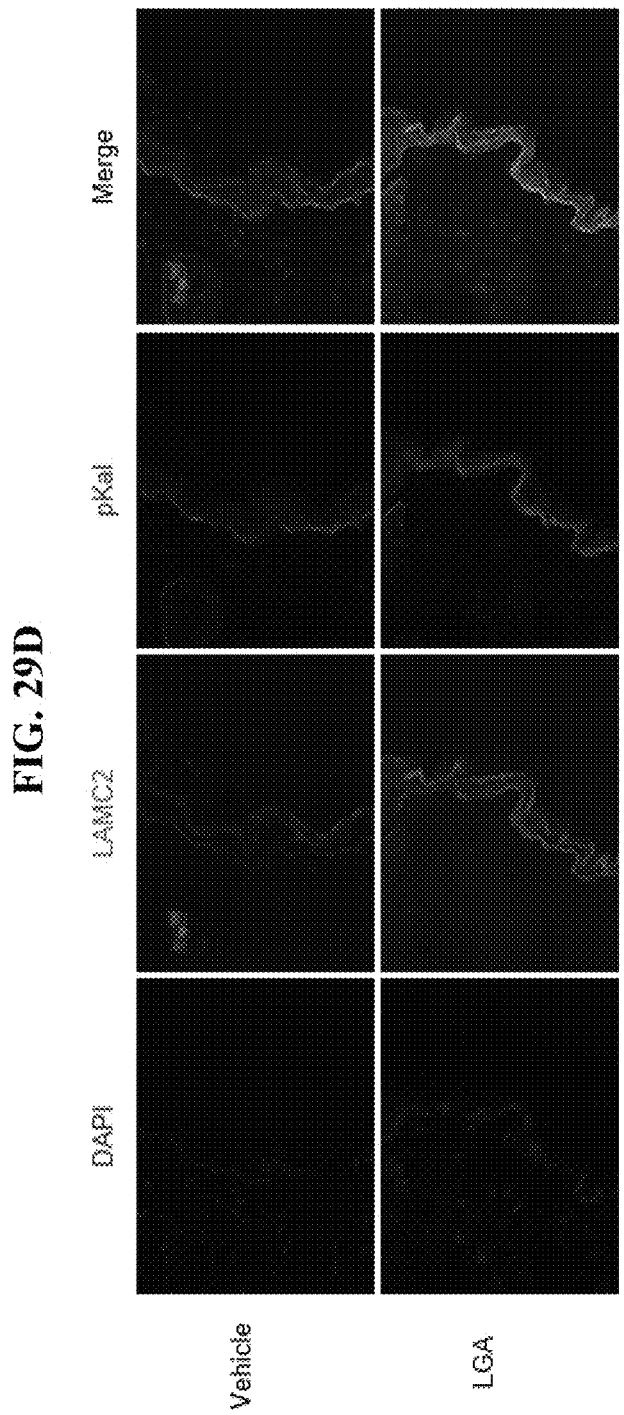

Finally, to test whether isolate "LGA" was capable of expressing its human laminin when delivered in vivo, human LAMC2 expression was assessed by qPCR, qRT-PCR, and immunofluorescence after intradermal injection in animals. $1 \times 10^8$ PFUs of LGA formulated in PBS+10% glycerol (vehicle) was intradermally injected into the dorsal skin and footpads of two mice. An equivalent volume of vehicle alone was intradermally administered to the dorsal skin of one mouse to act as a negative control. A schematic of the injection sites for the two animals treated in this study is provided in FIG. 29A.

72 hours post-administration, a full thickness 8 mm biopsy was taken from each treatment site and split in half. One half of each section was flash frozen in liquid nitrogen and subsequently processed for qPCR and qRT-PCR analysis in order to quantify LAMC2 DNA copy numbers (FIG. 29B) and transcript levels (FIG. 29C) in the dorsal skin. The remaining half of each biopsy was embedded in OCT for immunofluorescence (IF). LAMC2 expression in cryosections was determined by immunofluorescent analysis using an anti-human LAMC2 antibody (Abcam, cat. no. ab96327). To confirm that the human LAMC2 expressed from LGA was correctly localized to the region of the skin where native laminin-332 is found, the dorsal skin samples were also counterstained for mouse laminin-332 (pKal). Intradermal administration of LGA led to successful transduction of mouse skin, with robust expression of the encoded human transgene in the correct layer of the epidermis. Histological evaluation showed no inflammatory infiltration at the treated site, demonstrating the safety of this therapy.

Taken together, the data presented in this example demonstrates that (1) HSV vectors could be successfully engineered to robustly express human laminin proteins (specifically, the β or γ subunit of human laminin-332), (2) an HSV-based vector (LGA) could successfully deliver a human laminin-332 subunit in vivo, and (3) the recombinant human laminin-332 subunit was expressed in, and localized to, the appropriate region of the epidermis of treated animals.

What is claimed is:

1. A pharmaceutical composition for topical, transdermal, superficial, or intradermal administration comprising:
   (a) a herpes simplex virus comprising a recombinant herpes simplex virus genome, wherein the recombinant herpes simplex virus genome comprises a first polynucleotide encoding a first cosmetic protein and a second polynucleotide encoding a second cosmetic protein; and
   (b) a pharmaceutically acceptable excipient;
   wherein the recombinant herpes simplex virus genome comprises an inactivating mutation in both copies of the Infected Cell Protein (ICP4) herpes simplex virus gene;
   wherein the first cosmetic protein is selected from the group consisting of a first collagen protein, a first fibronectin protein, a first elastin protein, a first lumican protein, a first vitronectin protein, a first vitronectin receptor protein, a first laminin protein, a first neuromodulator protein, and a first fibrillin protein; and
   wherein the recombinant herpes simplex virus genome does not comprise a polynucleotide encoding a Collagen alpha-1 (VII) chain polypeptide (COL7).

2. The pharmaceutical composition of claim 1, wherein the herpes simplex virus comprising the recombinant herpes simplex virus genome is replication defective.

3. The pharmaceutical composition of claim 1, wherein the recombinant herpes simplex virus genome is a recombinant herpes simplex virus type 1 (HSV-1) genome.

4. The pharmaceutical composition of claim 3, wherein the recombinant HSV-1 genome comprises an inactivating mutation in a herpes simplex virus gene selected from the group consisting of ICP0, ICP22, ICP27, and ICP47.

5. The pharmaceutical composition of claim 1, wherein the first collagen protein is selected from the group consisting of a human Collagen alpha-1(I) chain polypeptide (COL1-1), a human Collagen alpha-2(I) chain polypeptide (COL1-2), a human Collagen alpha-1(II) chain polypeptide (COL2), a human Collagen alpha-1(III) chain polypeptide (COL3), a human Collagen alpha-1(IV) chain polypeptide (COL4-1), a human Collagen alpha-2(IV) chain polypeptide (COL4-2), a human Collagen alpha-3(IV) chain polypeptide (COL4-3), a human Collagen alpha-4(IV) chain polypeptide (COL4-4), a human Collagen alpha-5(IV) chain polypeptide (COL4-5), a human Collagen alpha-6(IV) chain polypeptide (COL4-6), a human Collagen alpha-1(V) chain polypeptide (COL5-1), a human Collagen alpha-2(V) chain polypeptide (COL5-2), a human Collagen alpha-3(V) chain polypeptide (COL5-3), a human Collagen alpha-1(VI) chain polypeptide (COL6-1), a human Collagen alpha-2(VI) chain polypeptide (COL6-2), a human Collagen alpha-3(VI) chain polypeptide (COL6-3), a human Collagen alpha-4(VI) chain polypeptide (COL6-4), a human Collagen alpha-5(VI) chain polypeptide (COL6-5), a human Collagen alpha-6(VI) chain polypeptide (COL6-6), a human Collagen alpha-1(VIII) chain polypeptide (COLE), a human Collagen alpha-1(IX) chain polypeptide (COL9-1), a human Collagen alpha-2(IX) chain polypeptide (COL9-2), a human Collagen alpha-3(IX) chain polypeptide (COL9-3), a human Collagen alpha-1(X) chain polypeptide (COL10), a human Collagen alpha-1(XI) chain polypeptide (COL11-1), a human Collagen alpha-2(XI) chain polypeptide (COL11-2), a human Collagen alpha-1(XII) chain polypeptide (COL12), a human Collagen alpha-1(XIII) chain polypeptide (COL13), a human Collagen alpha-1(XIV) chain polypeptide (COL14), a human Collagen alpha-1(XV) chain polypeptide (COL15), a human Collagen alpha-1(XVI) chain polypeptide (COL16), a human Collagen alpha-1(XVII) chain polypeptide (COL17), a human Collagen alpha-1(XVIII) chain polypeptide (COL18), a human Collagen alpha-1(XIX) chain polypeptide (COL19), a human Collagen alpha-1(XX) chain polypeptide (COL20), a human Collagen alpha-1(XXI) chain polypeptide (COL21), a human Collagen alpha-1(XXII) chain polypeptide (COL22), a human Collagen alpha-1(XXIII) chain polypeptide (COL23), a human Collagen alpha-1(XXIV) chain polypeptide (COL24), a human Collagen alpha-1(XXV) chain polypeptide (COL25), a human Collagen alpha-1(XXVI) chain polypeptide (COL26), a human Collagen alpha-1(XXVII) chain polypeptide (COL27), and a human Collagen alpha-1(XXVIII) chain polypeptide (COL28).

6. The pharmaceutical composition of claim 1, wherein the first collagen protein is a human COL3 polypeptide.

7. The pharmaceutical composition of claim 1, wherein the first collagen protein is a human COL1-1 polypeptide.

8. The pharmaceutical composition of claim 1, wherein the herpes simplex virus has reduced cytotoxicity as compared to a corresponding wild-type herpes simplex virus.

9. The pharmaceutical composition of claim 1, wherein the pharmaceutical composition is administered via intradermal injection.

10. The pharmaceutical composition of claim 1, wherein the pharmaceutical composition is administered via superficial injection.

11. The pharmaceutical composition of claim 1, wherein the pharmaceutical composition is a cosmetic composition.

12. A method of improving skin condition, quality, and/or appearance in a subject, the method comprising administering to the subject an effective amount of a pharmaceutical composition comprising:
  (a) a herpes simplex virus comprising a recombinant herpes virus simplex genome, wherein the recombinant herpes simplex virus genome comprises a first polynucleotide encoding a first cosmetic protein and a second polynucleotide encoding a second cosmetic protein; and
  (b) a pharmaceutically acceptable excipient;
  wherein the recombinant herpes simplex virus genome comprises an inactivating mutation in both copies of the ICP4 herpes simplex virus gene;
  wherein the first cosmetic protein is selected from the group consisting of a first collagen protein, a first fibronectin protein, a first elastin protein, a first lumican protein, a first vitronectin protein, a first vitronectin receptor protein, a first laminin protein, a first neuromodulator protein, and a first fibrillin protein;
  wherein the recombinant herpes simplex virus genome does not comprise a polynucleotide encoding a Collagen alpha-1 (VII) chain polypeptide (COL7);
  wherein the pharmaceutical composition is administered topically, transdermally, intradermally, or via superficial injection to the subject;
  wherein the recombinant herpes simplex virus genome is delivered to one or more target cell of the skin of a subject; and
  wherein the first cosmetic protein is expressed in one or more target cells of the skin of a subject.

13. The method of claim 12, wherein the subject's skin comprises one or more of sun or UV damage, rough texture, sagging, wrinkles, or any combinations thereof.

14. The method of claim 12, wherein the subject is a human.

15. The method of claim 12, wherein the pharmaceutical composition is administered intradermally to the subject.

16. The method of claim 12, wherein the pharmaceutical composition is administered by superficial injection to the subject.

17. The method of claim 12, wherein the recombinant herpes simplex virus genome is a recombinant herpes simplex virus type 1 (HSV-1) genome.

18. The method of claim 17, wherein the recombinant HSV-1 genome comprises an inactivating mutation in a herpes simplex virus gene selected from the group consisting of ICP0, ICP22, ICP27, and ICP47.

19. The method of claim 12, wherein the first collagen protein is selected from the group consisting of a human Collagen alpha-1(I) chain polypeptide (COL1-1), a human Collagen alpha-2(I) chain polypeptide (COL1-2), a human Collagen alpha-1(II) chain polypeptide (COL2), a human Collagen alpha-1(III) chain polypeptide (COL3), a human Collagen alpha-1(IV) chain polypeptide (COL4-1), a human Collagen alpha-2(IV) chain polypeptide (COL4-2), a human Collagen alpha-3(IV) chain polypeptide (COL4-3), a human Collagen alpha-4(IV) chain polypeptide (COL4-4), a human Collagen alpha-5(IV) chain polypeptide (COL4-5), a human Collagen alpha-6(IV) chain polypeptide (COL4-6), a human Collagen alpha-1(V) chain polypeptide (COL5-1), a human Collagen alpha-2(V) chain polypeptide (COL5-2), a human Collagen alpha-3(V) chain polypeptide (COL5-3), a human Collagen alpha-1(VI) chain polypeptide (COL6-1), a human Collagen alpha-2(VI) chain polypeptide (COL6-2), a human Collagen alpha-3(VI) chain polypeptide (COL6-3), a human Collagen alpha-4(VI) chain polypeptide (COL6-4), a human Collagen alpha-5(VI) chain polypeptide (COL6-5), a human Collagen alpha-6(VI) chain polypeptide (COL6-6), a human Collagen alpha-1(VIII) chain polypeptide (COLE), a human Collagen alpha-1(IX) chain polypeptide (COL5-1), a human Collagen alpha-2(IX) chain polypeptide (COL5-2), a human Collagen alpha-3(IX) chain polypeptide (COL9-3), a human Collagen alpha-1(X) chain polypeptide (COL10), a human Collagen alpha-1(XI) chain polypeptide (COL11-1), a human Collagen alpha-2(XI) chain polypeptide (COL11-2), a human Collagen alpha-1(XII) chain polypeptide (COL12), a human Collagen alpha-1(XIII) chain polypeptide (COL13), a human Collagen alpha-1(XIV) chain polypeptide (COL14), a human Collagen alpha-1(XV) chain polypeptide (COL15), a human Collagen alpha-1(XVI) chain polypeptide (COL16), a human Collagen alpha-1(XVII) chain polypeptide (COL17), a human Collagen alpha-1(XVIII) chain polypeptide (COL18), a human Collagen alpha-1(XIX) chain polypeptide (COL19), a human Collagen alpha-1(XX) chain polypeptide (COL20), a human Collagen alpha-1(XXI) chain polypeptide (COL21), a human Collagen alpha-1(XXII) chain polypeptide (COL22), a human Collagen alpha-1(XXIII) chain polypeptide (COL23), a human Collagen alpha-1(XXIV) chain polypeptide (COL24), a human Collagen alpha-1(XXV) polypeptide (COL25), a human Collagen alpha-1(XXVI) chain polypeptide (COL26), a human Collagen alpha-1(XXVII) chain polypeptide (COL27), and a human Collagen alpha-1(XXVIII) chain polypeptide (COL28).

20. The method of claim 12, wherein the first collagen protein is a human COL3 polypeptide.

21. The method of claim 12, wherein the first collagen protein is a human COL1-1 polypeptide.

22. The method of claim 12, wherein the herpes simplex virus has reduced cytotoxicity as compared to a corresponding wild-type herpes simplex virus.

23. The composition of claim 1, wherein the recombinant herpes simplex virus genome is delivered to one or more target cells of the skin of a subject.

24. The composition of claim 1, wherein the first cosmetic protein is expressed in one or more target cells of the skin of a subject.

25. The composition of claim 1, wherein the first and second cosmetic proteins are the same.

26. The composition of claim 1, wherein the first and second cosmetic proteins are different.

27. The method of claim 12, wherein the first and second cosmetic proteins are the same.

28. The method of claim 12, wherein the first and second cosmetic proteins are different.

* * * * *

SEQUENCE LISTING

```
<160> NUMBER OF SEQ ID NOS: 64

<210> SEQ ID NO 1
<211> LENGTH: 4395
<212> TYPE: DNA
<213> ORGANISM: Homo sapiens

<400> SEQUENCE: 1
atgttcagct ttgtggacct ccggctcctg ctcctcttag cggccaccgc cctcctgacg      60
cacggccaag aggaaggcca agtcgagggc caagacgaag acatcccacc aatcacctgc     120
gtacagaacg gcctcaggta ccatgaccga gacgtgtgga aacccgagcc ctgccggatc     180
tgcgtctgcg acaacggcaa ggtgttgtgc gatgacgtga tctgtgacga gaccaagaac     240
tgccccggcg ccgaagtccc cgagggcgag tgctgtcccg tctgccccga cggctcagag     300
tcacccaccg accaagaaac caccggcgtc gagggaccca agggagacac tggcccccga     360
ggcccaaggg gacccgcagg ccccccctggc cgagatggca tccctggaca gcctggactt     420
cccggacccc ccggaccccc cggacctccc ggacccccctg gcctcggagg aaactttgct     480
ccccagctgt cttatggcta tgatgagaaa tcaaccggag gaatttccgt gcctggcccc     540
atgggtccct ctggtcctcg tggtctccct ggccccccctg gtgcacctgg tccccaaggc     600
ttccaaggtc cccctggtga gcctggcgag cctggagctt caggtcccat gggtccccga     660
ggtcccccag gtccccctgg aaagaatgga gatgatgggg aagctggaaa acctggtcgt     720
cctggtgagc gtgggcctcc tgggcctcag ggtgctcgag gattgcccgg aacagctggc     780
ctccctggaa tgaagggaca cagaggtttc agtggtttgg atggtgccaa gggagatgct     840
```

```
ggtcctgctg gtcctaaggg tgagcctggc agccctggtg aaaatggagc tcctggtcag    900
atgggccccc gtggcctgcc tggtgagaga ggtcgccctg gagcccctgg ccctgctggt    960
gctcgtggaa atgatggtgc tactggtgct gccgggcccc ctggtccac cggccccgct   1020
ggtcctcctg gcttccctgg tgctgttggt gctaagggtg aagctggtcc caagggccc   1080
cgaggctctg aaggtcccca gggtgtgcgt ggtgagcctg gccccctgg ccctgctggt   1140
gctgctggcc ctgctggaaa ccctggtgct gatggacagc ctggtgctaa aggtgccaat   1200
ggtgctcctg gtattgctgg tgctcctggc ttccctggtg cccgaggccc ctctggaccc   1260
cagggccccg gcggccctcc tggtcccaag ggtaacagcg tgaacctgg tgctcctggc   1320
agcaaaggag acactggtgc taagggagag cctggcctg ttggtgttca aggacccct   1380
ggccctgctg gagaggaagg aaagcgagga gctcgaggtg aacccggacc cactggcctg   1440
cccggacccc ctggcgagcg tggtggacct ggtagccgtg gtttcctgg cgcagatggt   1500
gttgctggtc caagggtcc cgctggtgaa cgtggttctc ctggccctgc tggccccaaa   1560
ggatctcctg gtgaagctgg tcgtcccggt gaagctggtc tgcctggtgc aagggtctg   1620
actgaagcc ctggcagccc tggtcctgat ggcaaaactg gccccctgg tcccgccggt   1680
caagatggtc gccccggacc cccaggccca cctggtgccc gtggtcaggc tggtgtgatg   1740
ggattccctg gacctaaagg tgctgctgga gagcccggca aggctggaga gcaggtgtt   1800
cccggaccc ctggcgctgt cggtcctgct ggcaaagatg gagaggctgg agctcaggga   1860
ccccctggcc ctgctggtcc cgctggcgag agaggtgaac aaggccctgc tggctccccc   1920
ggattccagg gtctccctgg tcctgctggt cctccaggtg aagcaggcaa acctggtgaa   1980
cagggtgttc ctggagacct tggcgcccct ggccctctg agcaagagg cgagagaggt   2040
ttccctggcg agcgtggtgt gcaaggtccc cctggtcctg ctggtcccg agggggccaac   2100
ggtgctcccg gcaacgatgg tgctaagggt gatgctggtg ccctggagc tcccggtagc   2160
cagggcgccc ctggccttca gggaatgcct ggtgaacgtg gtgcagctgg tcttccaggg   2220
cctaagggtg acagaggtga tgctggtccc aaaggtgctg atggctctcc tggcaaagat   2280
ggcgtccgtg gtctgactgg ccccattggt cctcctggcc ctgctggtgc cctggtgac   2340
aagggtgaaa gtggtcccag cggccctgct ggtccactg agctcgtgg tgcccccgga   2400
gaccgtggtg agcctggtcc ccccggccct gctggctttg ctggcccccc tggtgctgac   2460
ggccaacctg gtgctaaagg cgaacctggt gatgctggtg ctaaaggcga tgctggtccc   2520
cctggccctg ccggacccgc tggacccct ggccccattg gtaatgttgg tgctcctgga   2580
gccaaaggtg ctcgcggcag cgctggtccc cctggtgcta ctggtttccc tggtgctgct   2640
ggccgagtcg gtcctcctgg cccctctgga aatgctggac ccctggccc tctggtcct   2700
gctggcaaag aaggcggcaa aggtccccgt ggtgagactg gccctgctgg acgtcctggt   2760
gaagttggtc ccctggtcc cctggccct gctggcgaga aggatcccc tggtgctgat   2820
ggtcctgctg gtgctcctgg tactcccggg cctcaaggta ttgctggaca gcgtggtgtg   2880
gtcggcctgc ctggtcagag aggagagaga ggcttcctg tcttcctgg ccctctggt   2940
gaacctggca acaaggtcc ctctggagca agtggtgaac gtggtccccc tggtcccatg   3000
ggccccctg gattggctgg accccctggt gaatctggac gtgaggggc tcctggtgcc   3060
gaaggttccc ctggacgaga cggttctcct ggcgccaagg gtgaccgtgg tgagaccggc   3120
cccgctggac cccctggtgc tcctggtgct cctggtgccc ctggccccgt tggccctgct   3180
```

```
ggcaagagtg gtgatcgtgg tgagactggt cctgctggtc ccgccggtcc tgtcggccct    3240
gttggcgccc gtggcccgc cggacccaa ggccccgtg gtgacaaggg tgagacaggc      3300
gaacagggcg acagaggcat aaagggtcac cgtggcttct ctggcctcca gggtccccct    3360
ggccctcctg gctctcctgg tgaacaaggt ccctctggag cctctggtcc tgctggtccc    3420
cgaggtcccc ctggctctgc tggtgctcct ggcaaagatg gactcaacgg tctccctggc    3480
cccattgggc cccctggtcc tcgcggtcgc actggtgatg ctggtcctgt tggtcccccc    3540
ggccctcctg gacctcctgg tcccctggt cctcccagcg ctggtttcga cttcagcttc     3600
ctgccccagc cacctcaaga gaaggctcac gatggtggcc gctactaccg ggctgatgat    3660
gccaatgtgg ttcgtgaccg tgacctcgag gtggacacca ccctcaagag cctgagccag    3720
cagatcgaga acatccggag cccagagggc agccgcaaga accccgcccg cacctgccgt    3780
gacctcaaga tgtgccactc tgactggaag agtggagagt actggattga ccccaaccaa    3840
ggctgcaacc tggatgccat caaagtcttc tgcaacatgg agactggtga cctgcgtgt    3900 taccccactc agcccagtgt ggcccagaag aactggtaca tcagcaagaa ccccaaggac    3960
aagaggcatg tctggttcgg cgagagcatg accgatggat ccagttcga gtatggcggc    4020 cagggctccg accctgccga tgtggccatc cagctgacct cctgcgcct gatgtccacc    4080 gaggcctccc agaacatcac ctaccactgc aagaacagcg tggcctacat ggaccagcag    4140
actggcaacc tcaagaaggc cctgctcctc agggctccaa cgagatcga gatccgcgcc    4200 gagggcaaca gccgcttcac ctacagcgtc actgtcgatg gctgcacgag tcacaccgga    4260
gcctggggca agacagtgat tgaatacaaa accaccaaga cctcccgcct gcccatcatc    4320
gatgtggccc ccttggacgt tggtgcccca gaccaggaat tcggcttcga cgttggccct    4380
gtctgcttcc tgtaa                                                     4395

<210> SEQ ID NO 2
<211> LENGTH: 4395
<212> TYPE: DNA
<213> ORGANISM: Artificial Sequence
<220> FEATURE:
<223> OTHER INFORMATION: Synthetic Construct

<400> SEQUENCE: 2
atgttcagct tcgtggacct gagactgctg ctgctcctgg ctgctacagc cctgctgaca     60
cacggacaag aggaaggcca ggtcgaagga caggacgagg acatccctcc tatcacctgt    120
gtgcagaacg gcctgagata ccacgaccgg gatgtgtgga gcccgagcc ttgcagaatc     180 tgcgtgtgcg acaatggcaa ggtgctgtgc gacgacgtga tctgcgacga gacaaagaat    240
tgccctggcg ccgaagtgcc tgagggcgaa tgttgtcctg tgtgccctga tggcagcgag    300
agccccacag atcaagagac aacaggcgtg gaaggcccca gggcgatac aggacctaga    360 ggtcctagag gacctgccgg aacctcctgg cagagatgga ttcctggaca gcctggactg    420
cccggaccac ctggacctcc agggcctcca ggtccaccag gactcggagg aaattttgcc    480
ccacagctga gctacggcta cgacgagaaa agcacaggcg gcatctctgt gcctggacct    540
atgggacctt ctggcccaag aggacttcct ggtcctcctg tgctccagg acctcaggga    600 tttcaaggac caccaggcga acctggcgaa ccaggcgcta gtggtccaat gggaccaaga    660
ggccctcctg ggccaccagg caaaaatggc gacgatggcg aagccggaaa gcctggaagg    720 cctgcgaaa gaggcccgcc aggaccgcaa ggcgctagag ggttgcctgg aactgcagga    780
ctgcctggca tgaagggcca cagaggcttt tctggactgg atggcgctaa gggcgacgct    840
```

```
ggaccagcag gacctaaagg cgagcctgga tctcctggcg agaatggtgc acctggacag    900
atgggtccca gaggattgcc aggcgagaga ggtagacctg gcgctccggg accagccggt    960
gctagaggaa atgatggcgc aacaggtgct gctgggcctc ctggaccaac cggaccagct   1020
ggcccacctg gatttccagg cgctgttgga gcaaagggcg aagcaggccc acaaggacct   1080
aggggatctg aaggtcctca gggcgttaga ggcgagccag ggccacctgg gcctgccggt   1140
gcagctggac ctgctggaaa ccctggtgct gatggacagc caggtgccaa aggtgctaat   1200
ggcgcccctg gaattgccgg cgctccaggt tttcccggcg caagagggcc atctggacct   1260
caaggcccag gcggacctcc gggtcctaag ggaaatagcg gagagccagg cgctcctggg   1320
agtaaaggcg atactggcgc aaaaggcgaa cccggacctg tgggagttca aggacctcct   1380
ggaccagctg gcgaggaagg caaaagaggc gctaggggag aaccaggacc aacagggctc   1440
cctggtccac ctggcgagcg cggaggacct ggatctagag gattccctgg cgcagatggc   1500
gtggccggac caaaaggacc tgcaggcgaa aggggatcac caggtcctgc aggccctaag   1560
ggttctccag gcgaggctgg cagacccggc gaagctggac tcccaggtgc taagggactg   1620
acaggctcac caggatctcc cggaccagac ggaaaaacag gacctccagg accggcagga   1680
caggatggta gacccggtcc tcctggaccg cctggtgcaa gaggacaagc tggcgtgatg   1740
ggcttttcctg gaccaaaagg tgcagccggc gaacctggaa agcaggcgga gggggagtt   1800
cccggacctc caggtgctgt tggacctgcc ggaaaagatg gcgaagctgg tgcacaaggt   1860
cctccagggc cagccggacc agccggcgag agaggcgaac aaggaccagc cggatctcca   1920
ggatttcagg gactgccagg gctgctggcc cgcctggcg aggcagggaa gccaggcgaa   1980
cagggtgttc ctggcgatct tggagcccct ggtcctagcg gagctagagg cgaaagagga   2040
tttcctggcg aaagggggcgt tcagggtcca ccgggaccag ctggaccaag gggtgcaaat   2100
ggtgccccag gcaatgacgg tgctaaaggc gacgcaggcg ccccaggtgc tcctggatct   2160
caaggcgcac ctggacttca gggaatgcct ggcgaacggg gagctgctgg acttcccggt   2220
ccaaaaggcg ataggggaga tgctggtcct aagggcgctg atggctctcc tggaaaggat   2280
ggcgtcagag gcctgacagg cccaattggc cctccggac ctgctggcgc tccaggcgat   2340
aagggcgaat ctggacctag tggacccgct ggtcctacag gtgctagggg agccccaggc   2400
gaccggggag agcctggtcc accaggacct gctggatttg ctggacctcc tggcgctgat   2460
ggtcaacctg gtgctaaggg cgagccaggc gacgctggtg caaaaggcga cgctggtcca   2520
cctggaccgc ccgggacctgc tgggccgcca ggacctattg gaaatgttgg tgcccctggc   2580
gccaaaggcg caagaggatc tgctggccca ccaggcgcta caggattccc aggtgccgct   2640
ggaagagttg gaccaccggg gccaagtgga aatgctggac caccgggaccc gcaggacca   2700
gccggcaaag aaggtggaaa aggccctagg ggcgaaactg gccctgcagg caggccaggc   2760
gaagtggggcc ctccaggacc tccggggcct gccggcgaaa aaggatctcc aggcgcagat   2820
ggacccgcag gcgctcccgg aacaccaggt ccacagggaa ttgctggaca agggggaagt   2880
gtcggcctgc caggacagag gggagagaga ggtttttccag gactccctgg gccaagcgga   2940
gaacctggca acagggacc atctggtgcc agcgagaga gagggccacc aggaccaatg   3000
ggtcctccag gattggcagg gcctcctggc gaatctggta gagaaggtgc tccaggcgcc   3060
gagggatctc ctgacgtga tggttctcct ggcgccaagg gcgatagagg cgaaacaggc   3120
ccagctggac ctccaggcgc accggggcgct ccaggcgcac caggacctgt tggccctgct   3180
```

| | | | | |
|---|---|---|---|---|
| ggaaaatctg | gcgacagagg | cgaaactgga | cccgcaggac | cagccggacc | tgttggacct | 3240 |
| gtgggtgcta | gaggacccgc | tggaccacaa | ggtcctagag | gcgacaaggg | cgaaacaggc | 3300 |
| gagcaaggcg | acagaggcat | caagggacac | agaggattca | gcggactgca | gggaccacca | 3360 |
| gggccgcctg | gaagtcccgg | cgagcaggga | ccaagcggag | ctagtggtcc | cgccggacct | 3420 |
| agaggaccac | ctggttctgc | tggtgcaccc | ggaaaggacg | gactgaatgg | gctccccgga | 3480 |
| cctattgggc | cacctggacc | tagaggaaga | acaggcgacg | caggaccagt | ggaccacct | 3540 |
| gggccacctg | gaccgcctgg | tcctcctgga | cctccttctg | ccggattcga | cttcagcttc | 3600 |
| ctgcctcagc | ctcctcaaga | gaaggcccat | gacggcggca | gatattacag | agccgacgac | 3660 |
| gccaacgtcg | tgcgggacag | agatctggaa | gtggacacca | cactgaagtc | cctgtctcag | 3720 |
| cagatcgaga | acatcagaag | ccccgagggc | agcagaaaga | accctgccag | aacctgtcgg | 3780 |
| gacctgaaga | tgtgccacag | cgattggaag | tctggcgagt | actggatcga | ccccaaccag | 3840 |
| ggctgcaacc | tggatgccat | caaggtgttc | tgcaacatgg | aaaccggcga | gacatgcgtg | 3900 |
| taccccacac | agccatctgt | ggctcagaag | aactggtaca | tcagcaagaa | ccccaaggac | 3960 |
| aagcggcacg | tttggttcgg | cgagagcatg | accgatggct | ccagtttga | gtatggcggc | 4020 |
| cagggctctg | accctgccga | tgttgctatc | cagctgacct | tcctgcggct | gatgtctaca | 4080 |
| gaggccagcc | agaacatcac | ctaccactgc | aagaacagcg | tggcctacat | ggatcagcag | 4140 |
| accggcaacc | tgaagaaggc | actgctgctt | cagggcagca | acgagatcga | gatcagagcc | 4200 |
| gagggcaaca | gccggttcac | ctacagcgtg | acagtggatg | gctgcaccag | ccatacaggc | 4260 |
| gcttggggca | agaccgtgat | cgagtacaag | accaccaaga | ccagcagact | gcccatcatc | 4320 |
| gatgtggccc | ctctggatgt | tggggcaccc | gatcaagagt | tcggcttcga | tgtgggccca | 4380 |
| gtgtgcttcc | tgtaa | | | | | 4395 |

<210> SEQ ID NO 3
<211> LENGTH: 4101
<212> TYPE: DNA
<213> ORGANISM: Homo sapiens

<400> SEQUENCE: 3

| | | | | |
|---|---|---|---|---|
| atgctcagct | ttgtggatac | gcggactttg | ttgctgcttg | cagtaacctt | atgcctagca | 60 |
| acatgccaat | ctttacaaga | ggaaactgta | agaaagggcc | cagccggaga | tagaggacca | 120 |
| cgtggagaaa | ggggtccacc | aggccccca | ggcagagatg | gtgaagatgg | tcccacaggc | 180 |
| cctcctggtc | cacctggtcc | tcctggcccc | ctggtctcg | gtgggaactt | tgctgctcag | 240 |
| tatgatggaa | aaggagttgg | acttggccct | ggaccaatgg | gcttaatggg | acctagaggc | 300 |
| ccacctggtg | cagctggagc | cccaggccct | caaggtttcc | aaggacctgc | tggtgagcct | 360 |
| ggtgaacctg | gtcaaactgg | tcctgcaggt | gctcgtggtc | cagctggccc | tcctggcaag | 420 |
| gctggtgaag | atggtcaccc | tggaaaaccc | ggacgacctg | gtgagagagg | agttgttgga | 480 |
| ccacagggtg | ctcgtggttt | ccctggaact | cctggacttc | ctggcttcaa | aggcattagg | 540 |
| ggacacaatg | gtctggatgg | attgaaggga | cagcccggtg | ctcctggtgt | gaagggtgaa | 600 |
| cctggtgccc | ctggtgaaaa | tggaactcca | ggtcaaacag | gagcccgtgg | gcttcctggt | 660 |
| gagagaggac | gtgttggtgc | ccctggccca | gctggtgccc | gtggcagtga | tggaagtgtg | 720 |
| ggtcccgtgg | gtcctgctgg | tcccattggg | tctgctggcc | ctccaggctt | cccaggtgcc | 780 |
| cctggcccca | agggtgaaat | tggagctgtt | ggtaacgctg | gtcctgctgg | tcccgccggt | 840 |
| ccccgtggtg | aagtgggtct | tccaggcctc | tccgcccccg | ttggacctcc | tggtaatcct | 900 |

```
ggagcaaacg gccttactgg tgccaagggt gctgctggcc ttcccggcgt tgctggggct    960
cccggcctcc ctggaccccg cggtattcct ggccctgttg gtgctgccgg tgctactggt   1020
gccagaggac ttgttggtga gcctggtcca gctggctcca aaggagagag cggtaacaag   1080
ggtgagcccg gctctgctgg gccccaaggt cctcctggtc ccagtggtga agaaggaaag   1140
agaggcccta atggggaagc tggatctgcc ggccctccag gacctcctgg gctgagaggt   1200
agtcctggtt ctcgtggtct tcctggagct gatggcagag ctggcgtcat gggccctcct   1260
ggtagtcgtg gtgcaagtgg ccctgctgga gtccgaggac ctaatggaga tgctggtcgc   1320
cctggggagc ctggtctcat gggacccaga ggtcttcctg gttcccctgg aaatatcggc   1380
cccgctggaa aagaaggtcc tgtcggcctc cctggcatcg acggcaggcc tggcccaatt   1440
ggcccagctg agcaagagg agagcctggc aacattggat ccctggacc caaaggcccc   1500
actggtgatc ctggcaaaaa cggtgataaa ggtcatgctg gtcttgctgg tgctcggggt   1560
gctccaggtc ctgatggaaa caatggtgct cagggacctc ctggaccaca gggtgttcaa   1620
ggtggaaaag gtgaacaggg tccccctggt cctccaggct ccagggtct gcctggcccc   1680
tcaggtcccg ctggtgaagt tggcaaacca ggagaaaggg gtctccatgg tgagtttggt   1740
ctccctggtc ctgctggtcc aagaggggaa cgcggtcccc caggtgagag tggtgctgcc   1800
ggtcctactg gtcctattgg aagccgaggt ccttctggac cccagggcc tgatggaaac   1860
aagggtgaac tggtgtggt tggtgctgtg ggcactgctg gtccatctgg tcctagtgga   1920
ctcccaggag agaggggtgc tgctggcata cctggaggca agggagaaaa gggtgaacct   1980
ggtctcagag gtgaaattgg taaccctggc agagatggtg ctcgtggtgc tcctggtgct   2040
gtaggtgccc ctggtcctgc tggagccaca ggtgaccggg gcgaagctgg ggctgctggt   2100
cctgctggtc ctgctggtcc tcggggaagc cctggtgaac gtggtgaggt cggtcctgct   2160
ggcccccaatg gatttgctgg tcctgctggt gctgctggtc aacctggtgc taaaggagaa   2220
agaggagcca aagggcctaa gggtgaaaac ggtgttgttg gtcccacagg ccccgttgga   2280
gctgctggcc cagctggtcc aaatggtccc cccggtcctg ctggaagtcg tggtgatgga   2340
ggccccctg gtatgactgg tttccctggt gctgctggac ggactggtcc cccaggaccc   2400
tctggtattt ctggccctcc tggtcccct ggtcctgctg ggaaagaagg gcttcgtggt   2460
cctcgtggtg accaaggtcc agttggccga actgagaag taggtgcagt tggtccccct   2520
ggcttcgctg gtgagaaggg tccctctgga gaggctggta ctgctggacc tcctggcact   2580
ccaggtcctc agggtcttct tggtgctcct ggtattctgg gtctccctgg ctcgagaggt   2640
gaacgtggtc taccaggtgt tgctggtgct gtgggtgaac ctggtcctct ggcattgcc   2700
ggccctcctg ggcccgtgg tcctcctggt gctgtgggta gtcctggagt caacggtgct   2760
cctggtgaag ctggtcgtga tggcaaccct gggaacgatg gtccccagg tcgcgatggt   2820
caacccggac acaagggaga gcgcggttac cctggcaata ttggtcccgt tggtgctgca   2880
ggtgcacctg gtcctcatgg ccccgtgggt cctgctggca acatggaaa ccgtggtgaa   2940
actggtcctt ctggtcctgt tggtcctgct ggtgctgttg gcccaagagg tcctagtggc   3000
ccacaaggca ttcgtggcga taagggagag cccggtgaaa aggggcccag aggtcttcct   3060
ggcttaaagg gacacaatgg attgcaaggt ctgcctggta tcgctggtca ccatggtgat   3120
caaggtgctc ctggctccgt gggtcctgct ggtcctaggg gccctgctgg tccttctggc   3180
cctgctggaa aagatggtcg cactggacat cctggtacag ttggacctgc tggcattcga   3240
```

```
ggccctcagg gtcaccaagg ccctgctggc cccctggtc ccctggccc tcctggacct    3300 ccaggtgtaa gcggtggtgg ttatgacttt ggttacgatg gagacttcta cagggctgac    3360
cagcctcgct cagcaccttc tctcagaccc aaggactatg aagttgatgc tactctgaag    3420
tctctcaaca accagattga gacccttctt actcctgaag ctctagaaa gaacccagct    3480 cgcacatgcc gtgacttgag actcagccac ccagagtgga gcagtggtta ctactggatt    3540
gaccctaacc aaggatgcac tatggatgct atcaaagtat actgtgattt ctctactggc    3600
gaaacctgta tccgggccca acctgaaaac atcccagcca gaactggta taggagctcc    3660 aaggacaaga aacacgtctg gctaggagaa actatcaatg ctggcagcca gtttgaatat    3720
aatgtagaag gagtgacttc caaggaaatg gctacccaac ttgccttcat gcgcctgctg    3780
gccaactatg cctctcagaa catcacctac cactgcaaga acagcattgc atacatggat    3840
gaggagactg gcaacctgaa aaaggctgtc attctacagg gctctaatga tgttgaactt    3900
gttgctgagg gcaacagcag gttcacttac actgttcttg tagatggctg ctctaaaaag    3960
acaaatgaat ggggaaagac aatcattgaa tacaaaacaa ataagccatc acgcctgccc    4020
ttccttgata ttgcaccttt ggacatcggt ggtgctgacc aggaattctt tgtggacatt    4080
ggcccagtct gtttcaaata a                                              4101

<210> SEQ ID NO 4
<211> LENGTH: 4101
<212> TYPE: DNA
<213> ORGANISM: Artificial Sequence
<220> FEATURE:
<223> OTHER INFORMATION: Synthetic Construct

<400> SEQUENCE: 4
atgctgagct tcgtggacac cagaacactg ctgctgctgg ccgtgacact gtgtctggcc      60
acttgtcaga gcctgcaaga ggaaacagtg cggaaaggac ctgccggcga tagaggacct     120
agaggcgaaa gaggtcctcc tggacctcct ggtagagatg cgaggatgg acctacagga     180 ccacctggtc caccaggacc tcagggcct cctggccttg aggaaatttt gccgctcag     240 tacgatggca aaggcgtcgg acttggcct ggacctatgg acttatggg cccaagagga     300 ccaccaggtg ctgcaggcgc tccaggacca caaggatttc aaggaccagc tggcgagcct     360
ggcgaacctg gacaaacagg tcctgctggt gctagaggac cagccgggcc acctggaaaa     420
gctggcgaag atgggcaccc tggaaagcct ggtagacccg gcgaaagggg tgttgttgga     480
cctcaaggcg ccagaggctt tcctggaaca cctggactgc ctggcttcaa gggcatcaga     540
ggccacaatg gcctggacgg actgaaagga caacctggtg ctcctggcgt gaaaggcgaa     600
ccaggcgcac ctggcgaaaa tggcacacca ggacaaaccg cgcaagagg acttcctggc     660 gagagaggaa gagttggagc cccaggtcca gcaggcgcac gaggatctga tggatctgtg     720
ggacctgttg gccctgccgg acctattgga agtgctggcc ctcctggatt tcctggcgca     780
cccggaccaa agggcgaaat tggagctgtg ggaaacgccg acctgcagg cccagctgga     840 ccaagggag agttggatt gcctggactg agcggaccag ttgggccacc agggaatcct     900
ggtgccaatg gactgacagg cgctaaaggt gcagctggcc ttccaggcgt tgccggtgca     960
ccaggactgc aggaccaag aggtatccct ggtcctgttg gagctgctgg cgctacgggt    1020
gccagaggac ttgttggaga acctgggcca gccggatcta aggcgagtc tggaaacaag    1080 ggcgagccag atctgctgg tccacaaggc ccgcctggac atcaggcga agaaggcaaa    1140 cgaggcccta atggcgaagc cggtagtgcc gggcctcctg gaccaccagg ccttagagga    1200
```

```
tctcctggct ctagaggatt gccaggcgct gatggtagag caggcgttat gggtccacct    1260
ggatcaagag gcgcttctgg ccctgctggc gttagaggtc caaatggcga cgctggcaga    1320
ccaggcgagc ccggtcttat ggggcctaga gggttgcctg aagccctgg caatatcggc     1380 ccagccggaa aagaaggccc tgttggactc cctggcatcg acggtagacc tggaccaatc    1440
ggacccgcag gcgctagggg agagcctgga aatattggct ccctgggcc taaaggcccc     1500 acaggcgatc ctggaaagaa cggcgataag ggccatgctg gactcgctgg tgcaagggga    1560
gcacctggac ctgacggaaa caatggtgct caagggccgc ctgggccaca aggtgttcaa    1620 ggtgaaaag gcgagcaggg cccacctggg cctccaggct tccaaggact cccggacca     1680 tctgggccag caggcgaagt tggaaagcct ggcgaaagag gactgcacgg cgagtttggc    1740
ttgccgggtc ctgccggtcc acggggagag agaggccctc caggcgaatc tggcgccgca    1800
ggacctactg gccctatcgg aagcagagga cctagtggac ctccaggacc tgatggcaac    1860
aaaggcgaac ctggtgttgt gggcgctgtg gaacagctg gaccttctgg tccttctgga    1920
ttgcccggcg agcgcggagc agctggtatt cctggtggca aaggcgaaaa gggcgagcct    1980
ggactcagag gcgagatcgg caatcccgga cgagatggcg ctagaggcgc ccaggtgca    2040 gttggtgccc cgggacctgc tggcgcaaca ggcgacagag gcgaggctgg tgccgctggt    2100
cctgccgggc cagccggtcc tagaggaagt ccaggcgaga ggggcgaagt gggacccgct    2160
ggacccaatg gatttgctgg gccgctggc gctgctggtc aacctggcgc caaaggcgag    2220
cggggagcta aaggtcctaa aggcgagaat ggcgtcgtgg ccctactgg accagtggga    2280 gcagcaggcc ccgcaggtcc taacggacca cctggaccag ctgggtctag aggcgacggc    2340
ggaccgcctg gaatgacagg ttttccaggc gccgctggaa gaacaggtcc tccaggacca    2400
tctggcatct ctggtccacc agggccacct ggtcctgctg aaaagaagg actgagaggc     2460 cctaggggcg atcagggtcc agttggaaga accggcgaag tcggagctgt cggcccacca    2520
ggttttgccg gcgaaaaagg ccctagcgga gaagctggaa ctgcaggacc gccgggaact    2580
cccggtcctc aaggattgct tggcgcccct ggaattctgg gactgccgg tagtcgcgga    2640 gaacgtggac tccaggtgt tgctggcgcc gtcgagaaac cggaccact tggaattgct     2700 ggaccacctg gtgcaagagg tccacctggt gcagttggaa gtcctggcgt taacggtgct    2760
ccaggcgaag ccggcagaga tggaaatccc ggcaatgatg gccgcctgg gagagatgga    2820 cagcctggac ataagggcga gcaggctac ccaggcaata ttggacctgt cggcgcagcc    2880
ggtgctcccg gacctcatgg tccagtcggt ccagccggga agcacggaaa taggggagaa    2940
acaggaccct ccggtcctgt tggcccagct ggcgcagttg gaccaagagg cccatccgga    3000
cctcagggaa tccgcggaga taagggcgaa cctggcgaga agggacctag aggactgcct    3060
gggctgaaag gccataacgg actgcaaggc ctgccaggca ttgctggcca tcatggcgat    3120
caaggtgcac ccggtagtgt gggtcccgcc ggaccgaggg gtcccgctgg tccatctgga    3180
cccgccggaa aagatggcag aacaggacat cctggcacag tggggcctgc cggaattaga    3240
ggcccacagg gacatcaagg ccccgctggg ccgccaggac ctccgggacc gcagggcca    3300 ccaggcgtta gtggcggagg atacgatttc ggctacgacg cgacttcta cagagccgac    3360 cagcctagat ctgcccctag cctgaggcct aaggactacg aagtggacgc cacactgaag    3420
tccctgaaca accagatcga gacactgctg acccctgagg gcagcagaaa gaaccctgcc    3480
agaacctgca gggacctgag actgtctcac cccgaatggt cctccggcta ctactggatc    3540
```

| | |
|---|---:|
| gaccccaatc agggctgcac catggacgcc atcaaggtgt actgcgactt cagcaccggc | 3600 |
| gagacatgca tcagagccca gcctgagaac atccccgcca agaactggta cagaagcagc | 3660 |
| aaggacaaga aacacgtgtg gctgggcgag acaatcaacg ccggcagcca gttcgagtac | 3720 |
| aacgtggaag gcgtgaccag caaagagatg gccacacagc tggctttcat gagactgctg | 3780 |
| gccaattacg ccagccagaa catcacctac cactgcaaga acagcattgc ctacatggac | 3840 |
| gaggaaaccg gcaacctgaa gaaagccgtg atcctgcagg gctctaacga cgtggaactg | 3900 |
| gtggccgagg gcaacagcag attcacctac accgtgctgg tggacggctg cagcaaaaag | 3960 |
| accaacgagt ggggcaagac catcatcgag tataagacca acaagcccag cagactgccc | 4020 |
| ttcctggata tcgcccccact ggatattgga ggcgccgacc aagagttctt tgtggacatc | 4080 |
| ggccccgtgt gcttcaagtg a | 4101 |

```
<210> SEQ ID NO 5
<211> LENGTH: 4401
<212> TYPE: DNA
<213> ORGANISM: Homo sapiens

<400> SEQUENCE: 5
```

| | |
|---|---:|
| atgatgagct ttgtgcaaaa ggggagctgg ctacttctcg ctctgcttca tcccactatt | 60 |
| attttggcac aacaggaagc tgttgaagga ggatgttccc atcttggtca gtcctatgcg | 120 |
| gatagagatg tctggaagcc agaaccatgc caaatatgtg tctgtgactc aggatccgtt | 180 |
| ctctgcgatg acataatatg tgacgatcaa gaattagact gccccaaccc agaaattcca | 240 |
| tttgagaat gttgtgcagt ttgcccacag cctccaactg ctcctactcg ccctcctaat | 300 |
| ggtcaaggac ctcaaggccc caagggagat ccaggccctc ctggtattcc tgggagaaat | 360 |
| ggtgaccctg gtattccagg acaaccaggt cccctggtt ctcctggccc cctggaatc | 420 |
| tgtgaatcat gccctactgg tcctcagaac tattctcccc agtatgattc atatgatgtc | 480 |
| aagtctggag tagcagtagg aggactcgca ggctatcctg accagctgg ccccccaggc | 540 |
| cctcccggtc cccctggtac atctggtcat cctggttccc ctggatctcc aggataccaa | 600 |
| ggaccccctg gtgaacctgg gcaagctggt ccttcaggcc ctccaggacc tcctggtgct | 660 |
| ataggtccat ctggtcctgc tggaaaagat ggagaatcag gtagacccgg acgacctgga | 720 |
| gagcgaggat tgcctggacc tcaggtatc aaaggtccag ctgggatacc tggattccct | 780 |
| ggtatgaaag gacacagagg cttcgatgga cgaaatggag aaaagggtga acaggtgct | 840 |
| cctggattaa agggtgaaaa tggtcttcca ggcgaaaatg gagctcctgg acccatgggt | 900 |
| ccaagagggg ctcctggtga gcgaggacgg ccaggacttc ctgggctgc aggtgctcgg | 960 |
| ggtaatgacg gtgctcgagg cagtgatggt caaccaggcc ctcctggtcc tcctggaact | 1020 |
| gccggattcc ctggatcccc tggtgctaag ggtgaagttg gacctgcagg gtctcctggt | 1080 |
| tcaaatggtg ccccctggaca aagaggagaa cctggacctc agggacacgc tggtgctcaa | 1140 |
| ggtcctcctg gccctcctgg gattaatggt agtcctggtg gtaaaggcga aatgggtccc | 1200 |
| gctggcattc ctggagctcc tggactgatg ggagcccggg gtcctccagg accagccggt | 1260 |
| gctaatggtg ctcctggact gcgaggtggt gcaggtgagc ctggtaagaa tggtgccaaa | 1320 |
| ggagagcccg gaccacgtgg tgaacgcggt gaggctggta ttccaggtgt tccaggagct | 1380 |
| aaaggcgaag atggcaagga tggatcacct ggagaacctg gtgcaaatgg cttccagga | 1440 |
| gctgcaggag aaaggggtgc ccctgggttc gaggacctg ctggaccaaa tggcatccca | 1500 |
| ggagaaaagg gtcctgctgg agagcgtggt gctccaggcc ctgcagggcc cagaggagct | 1560 |

```
gctggagaac ctggcagaga tggcgtccct ggaggtccag gaatgagggg catgcccgga   1620
agtccaggag gaccaggaag tgatgggaaa ccagggcctc ccggaagtca aggagaaagt   1680
ggtcgaccag gtcctcctgg gccatctggt ccccgaggtc agcctggtgt catgggcttc   1740
cccggtccta aggaaatga tggtgctcct ggtaagaatg gagaacgagg tggccctgga    1800
ggacctggcc ctcagggtcc tcctggaaag aatggtgaaa ctggacctca gggaccccca   1860
gggcctactg ggcctggtgg tgacaaagga gacacaggac ccctggtcc acaaggatta    1920 caaggcttgc ctggtacagg tggtcctcca ggagaaaatg gaaaacctgg gaaccaggt    1980 ccaaagggtg atgccggtgc acctggagct ccaggaggca aggtgatgc tggtgcccct    2040 ggtgaacgtg gacctcctgg attggcaggg gccccaggac ttagaggtgg agctggtccc   2100
cctggtcccg aaggaggaaa gggtgctgct ggtcctcctg gccacctgg tgctgctggt    2160 actcctggtc tgcaaggaat gcctggagaa agaggaggtc ttggaagtcc tggtccaaag   2220
ggtgacaagg gtgaaccagg cggtccaggt gctgatggtg tcccagggaa agatggccca   2280
aggggtccta ctggtcctat tggtcctcct ggcccagctg ccagcctgg agataagggt    2340 gaaggtggtc cccccggact tccaggtata gctggacctc gtggtagccc tggtgagaga   2400
ggtgaaactg gccctccagg acctgctggt ttccctggtg ctcctggaca gaatggtgaa   2460
cctggtggta aaggagaaag aggggctccg ggtgagaaag gtgaaggagg ccctcctgga   2520
gttgcaggac cccctggagg ttctggacct gctggtcctc ctggtcccca aggtgtcaaa   2580
ggtgaacgtg gcagtcctgg tggacctggt gctgctggct cccctggtgc cgtggtctt    2640 cctggtcctc ctggtagtaa tggtaaccca ggaccccag gtcccagcgg ttctccaggc    2700
aaggatgggc cccagggtcc tgcgggtaac actggtgctc ctggcagccc tggagtgtct   2760
ggaccaaaag gtgatgctgg ccaaccagga gagaagggat cgcctggtgc ccagggccca   2820
ccaggagctc caggcccact tgggattgct gggatcactg gagcacgggg tcttgcagga   2880
ccaccaggca tgccaggtcc tagggggaagc cctggccctc agggtgtcaa gggtgaaagt   2940
gggaaaccag gagctaacgg tctcagtgga gaacgtggtc ccctggacc ccagggtctt    3000 cctggtctgg ctggtacagc tggtgaacct ggaagagatg gaaaccctgg atcagatggt   3060
cttccaggcc gagatggatc tcctggtggc aagggtgatc gtggtgaaaa tggctctcct   3120
ggtgcccctg gcgctcctgg tcatccaggc ccacctggtc ctgtcggtcc agctggaaag   3180
agtggtgaca gaggagaaag tggccctgct ggccctgctg tgctcccgg tcctgctggt    3240 tcccgaggtg ctcctggtcc tcaaggccca cgtggtgaca aggtgaaaac aggtgaacgt   3300
ggagctgctg gcatcaaagg acatcgagga ttccctggta atccaggtgc cccaggttct   3360
ccaggccctg ctggtcagca gggtgcaatc ggcagtccag gacctgcagg ccccagagga   3420
cctgttggac ccagtggacc tcctggcaaa gatggaacca gtggacatcc aggtcccatt   3480
ggaccaccag gcctcgagg taacagaggt gaaagaggat ctgaggctc cccaggccac   3540 ccagggcaac caggccctcc tggacctcct ggtgcccctg gtccttgctg tggtggtgtt   3600
ggagccgctg ccattgctgg gattggaggt gaaaaagctg gcggttttgc ccgtattat    3660 ggagatgaac caatggattt caaaatcaac accgatgaga ttatgacttc actcaagtct   3720
gttaatggac aaatagaaag cctcattagt cctgatggtt ctcgtaaaaa ccccgctaga   3780
aactgcagag acctgaaatt ctgccatcct gaactcaaga gtgagaaata ctgggttgac   3840
cctaaccaag gatgcaaatt ggatgctatc aaggtattct gtaatatgga aactggggaa   3900
```

```
acatgcataa gtgccaatcc tttgaatgtt ccacggaaac actggtggac agattctagt    3960
gctgagaaga aacacgtttg gtttggagag tccatggatg gtggttttca gtttagctac    4020
ggcaatcctg aacttcctga agatgtcctt gatgtgcagc tggcattcct tcgacttctc    4080
tccagccgag cttcccagaa catcacatat cactgcaaaa atagcattgc atacatggat    4140
caggccagtg aaatgtaaa gaaggccctg aagctgatgg ggtcaaatga aggtgaattc     4200
aaggctgaag gaaatagcaa attcacctac acagttctgg aggatggttg cacgaaacac    4260
actggggaat ggagcaaaac agtctttgaa tatcgaacac gcaaggctgt gagactacct    4320
attgtagata ttgcacccta tgacattggt ggtcctgatc aagaatttgg tgtggacgtt    4380
ggccctgttt gcttttttata a                                             4401
```

<210> SEQ ID NO 6
<211> LENGTH: 4401
<212> TYPE: DNA
<213> ORGANISM: Artificial Sequence
<220> FEATURE:
<223> OTHER INFORMATION: Synthetic Construct

<400> SEQUENCE: 6

```
atgatgagct tcgtgcagaa aggcagctgg ctgctgctgg cactgctgca ccctacaatc      60
attctggccc agcaagaggc cgtggaaggc ggatgttctc acctgggaca gagctacgcc     120
gacagggatg tgtggaagcc tgagccttgc agatctgcg tgtgtgatag cggcagcgtg      180
ctgtgcgacg acatcatctg cgacgaccaa gagctggact gccccaatcc tgagatccct     240
ttcggcgagt gctgtgccgt ttgtccccaa cctcctaccg ctcctaccag acctcctaat     300
ggacagggac ctcagggccc taaaggcgat cctggacctc tggaatcccc ggcagaaat     360 ggcgatccag gcattcctgg acagcctggc tctcctggaa gtccaggtcc acctggcatc     420
tgcgagagct gtcctacagg ccctcagaac tacagcccac agtacgacag ctacgacgtg     480
aagtctggcg tggccgttgg aggactggct ggttatccag acctgctgg accaccaggg      540 cctccaggac cgcctggaac aagtggacat ccaggatctc ccggcagtcc cggttatcag     600
ggaccacctg gcgaacctgg acaggcagga cctagtggtc ctcctggtcc accaggtgcc     660
attggaccat ctggacctgc cggaaaggat ggcgaatctg gcagaccagg cagacctggc     720
gagagaggat tgcctggtcc tccgggtatt aagggcccag ccggcattcc aggattcccc     780
ggaatgaagg gccacagagg cttcgatgga cggaatggcg agaagggcga acaggtgcc      840 cctggactga aaggcgaaaa tggactgcca ggcgagaatg gcgcacccgg acctatggga    900
cctagaggtg ctccaggcga agaggaagg ccaggacttc ctggtgctgc aggcgctaga    960
ggcaatgatg gcgccagagg atctgatggc caacctgggc cgccaggacc tccaggcaca   1020
gctggctttc ccggatctcc tggtgcaaag ggcgaagtgg accagctggg aagccctgga   1080
tctaatggtg ccccaggaca gagggggaga ccaggaccac aaggacatgc tggtgctcaa   1140
ggccctccgg gtcctccagg gatcaatgga tctccaggcg caaggcga atgggccct    1200 gctggaattc ctggcgctcc aggtcttatg ggagccagag gccacctgg accagcaggc   1260 gcaaatggcg ctcctggact tagaggcgga gcaggcgagc ctggaaaaaa tggcgcaaaa   1320
ggcgagcccg accaagggg agaaagaggc gaagctggta ttccaggtgt ccctggtgcc   1380
aaaggcgagg acggcaaaga tggtagtcct ggcgagccag cgccaatgg actccctggc    1440 gcagctggca aaggggagc acctggtttt agaggacccg ccggacctaa tggcattccc   1500
ggcgaaaaag gtccagccgg cgagcgtggt gctcccggac ctgcaggccc aagaggtgct   1560
```

-continued

```
gctggcgaac caggcagaga tggtgtccca ggcggaccag ggatgagagg catgccaggc    1620
tcacccggcg gacctggttc tgatggaaaa cccgggcctc ctggtagcca gggcgaatcc    1680
ggtagacccg gacctccggg accatcagga ccaagaggac aacctggcgt gatgggcttc    1740
cctggaccta agggaaatga cggcgctccc ggaaagaacg gcgaacgcgg tggccctggc    1800
ggtcccggtc ctcaagggcc accaggcaaa aacggcgaaa ccgtccacag aggaccacct    1860
ggacctacag gacctggcgg agataagggc gatacaggtc caccaggacc tcagggactg    1920
caaggactgc ctggaactgg cggacctcct ggcgagaatg gaaaaccagg cgaaccagga    1980
cctaagggcg acgctggtgc acctggcgca ccaggcggaa agggcgacgc aggcgctcca    2040
ggcgagaggg gacctccagg attggctggt gctccaggct gagaggcgg agctggtcct     2100
ccaggacctg aaggtggaaa aggtgctgca ggacctcctg gccacctgg cgctgctgga     2160
actccaggac ttcaagggat gcctggcgaa cgaggtggac ttggaagccc aggaccaaaa    2220
ggcgataagg gcgaacctgg cggaccgggt gcagatggtt tcccggaaa agatggacca     2280
cggggcccaa caggacctat aggccctcca gggccagcag acagccgggg cgacaaaggc    2340
gaaggtggcg cccctggctt gcctggaatt gctggtccta gaggttcacc tggcgagcgg    2400
ggagaaacag gccctcctgg accggccgga tttcccggtg ctcctggcca aaatggcgag    2460
cctggcggaa aaggcgaaag aggtgcaccg ggcgaaaaag gcgaaggcgg acctcctggt    2520
gttgctggac ctcctggcgg atctggacca gctgggcctc ctggtcctca aggtgttaag    2580
ggcgaaagag gctctccagg cggacccggt gctgctggat ttcccggcgc aagaggattg    2640
cccggaccac caggctctaa tggcaatcca ggtcctcctg gacctagcgg ctctcctggc    2700
aaagatggcc caccaggacc agccggaaat actggtgctc ctggatcacc tggcgtgtcc    2760
ggaccgaaag gcgacgccgg acaaccaggc gaaaaaggat ctcctggcgc tcaagggcct    2820
cctggcgcac ctggtccatt gggaattgcc ggaattacag gtgccagagg cctggctggc    2880
ccacctggaa tgcctgggcc aagaggtagc ccggacctc aaggcgtgaa aggcgaatct     2940
ggaaagcctg cgccaacgg actgagcgga gaaagaggac ctccaggtcc acaaggcctg     3000
cctggattgg ctggaacagc tggcgaacct ggaagagatg gcaatcctgg ctctgatggc    3060
ttgccgggga gagatggctc cccaggtggc aagggcgatc gcggagaaaa tggtagccca    3120
ggcgctcccg gcgctccagg acacccagga ccacctggtc cagtcggacc tgctggaaag    3180
tctggcgata gaggcgagtc tggacccgca ggtcccgctg gcgccccagg gcctgccgga    3240
tctaggggag cccctggacc gcaaggacct aggggagaca aggcgagac tggcgaacgc    3300
ggagccgctg gaatcaaagg ccatagagga ttcccaggca accctggtgc acccggatca    3360
ccaggaccgg caggacaaca aggcgctatt ggcagtccgg ggcctgctgg gcgagagga    3420
ccagttggac ctagtggacc accgggcaaa gatggaacaa gcggacaccc tggacctatc    3480
ggaccaccag gacctagagg caatagaggc gagagaggca gcgagggatc tcccggacat    3540
cctggacaac ccggtccacc ggggccacca ggcgcaccag gccatgttg tggcggagtt     3600
ggagctgctg ccattgctgg aatcggcgga gagaaagccg gcggatttgc cccttattac    3660
ggcgacgagc ccatggattt caagatcaac accgacgaga tcatgaccag cctgaagtcc    3720
gtgaacggcc agatcgagag cctgatcagc cctgacggca gcagaaagaa ccccgccaga    3780
aactgccgcg acctgaagtt ctgtcacccc gagctgaaaa gcggcgagta ctgggttgac    3840
cccaaccagg gctgtaaact ggacgccatt aaggtgttct gcaacatgga aaccggcgag    3900
```

```
acatgcatca gcgccaatcc tctgaacgtg cccagaaagc actggtggac agatagcagc    3960
gccgagaaga agcacgtttg gttcggcgag agcatggacg gcggcttcca gttctcttac    4020
ggcaatcccg agctgcccga ggacgtgctg gatgtgcaac tggcctttct gagactgctg    4080
agcagccgcg ccagccagaa tatcacctac cactgcaaga acagcattgc ctacatggat    4140
caggccagcg gcaacgtgaa gaaagccctg aagctgatgg gcagcaacga gggcgagttt    4200
aaggccgagg gcaacagcaa gttcacctac accgtgctgg aagatggctg caccaagcac    4260
acaggcgagt ggtccaagac cgtgttcgag taccggacaa gaaaggccgt gcggctgcct    4320
atcgtggata tcgcccctta cgatatcgga ggccccgatc aagagttcgg cgttgacgtg    4380
ggccctgtgt gtttcctgta a                                              4401

<210> SEQ ID NO 7
<211> LENGTH: 5010
<212> TYPE: DNA
<213> ORGANISM: Homo sapiens

<400> SEQUENCE: 7
atggggcccc ggctcagcgt ctggctgctg ctgctgcccg ccgcccttct gctccacgag      60
gagcacagcc gggccgctgc gaagggtggc tgtgctggct ctggctgtgg caaatgtgac    120
tgccatggag tgaagggaca aaagggtgaa agaggcctcc cggggttaca aggtgtcatt    180
gggtttcctg gaatgcaagg acctgagggg ccacagggac caccaggaca aagggtgat    240 actggagaac caggactacc tggaacaaaa gggacaagag gacctccggg agcatctggc    300
taccctggaa acccaggact tcccggaatt cctggccaag acggcccgcc aggcccccca    360
ggtattccag gatgcaatgg cacaaagggg gagagagggc cgctcgggcc tcctggcttg    420
cctggtttcg ctggaaatcc cggaccacca ggcttaccag gatgaaggg tgatccaggt    480 gagatacttg gccatgtgcc cgggatgctg ttgaaaggtg aaagaggatt tcccggaatc    540
ccagggactc caggcccacc aggactgcca gggcttcaag gtcctgttgg gcctccagga    600
tttaccggac caccaggtcc cccaggccct cccggccctc caggtgaaaa gggacaaatg    660
ggcttaagtt ttcaaggacc aaaaggtgac aagggtgacc aaggggtcag tgggcctcca    720
ggagtaccag acaagctca agttcaagaa aaaggagact cgccaccaa gggagaaaag    780 ggccaaaaag gtgaacctgg atttcagggg atgccagggg tcggagagaa aggtgaaccc    840
ggaaaaccag gacccagagg caaacccgga aaagatggtg acaaagggga aaagggagt    900 cccggttttc ctggtgaacc cgggtaccca ggactcatag ccgccagggg cccgcaggga    960
gaaaagggtg aagcaggtcc tcctggccca cctggaattg ttataggcac aggaccttg   1020 ggagaaaaag gagagagggg ctaccctgga actccgggc caagaggaga gccaggccca   1080 aaaggttcc caggactacc aggccaaccc ggacctccag gcctccctgt acctgggcag   1140
gctggtgccc ctggcttccc tggtgaaaga ggagaaaaag gtgaccgagg atttcctggt   1200
acatctctgc caggaccaag tggaagagat gggctcccgg gtcctcctgg ttcccctggg   1260 cccctgggc agcctggcta cacaaatgga attgtggaat gtcagccgg acctccaggt   1320 gaccagggtc ctcctggaat tccagggcag ccaggattta taggcgaaat tggagagaaa   1380
ggtcaaaaag gagagagttg cctcatctgt gatatagacg gatatcgggg gcctcccggg   1440
ccacagggac cccggggaga ataggtttc ccaggcagc caggggccaa gggcgacaga   1500
ggtttgcctg gcagagatgg tgttgcagga gtgccaggcc ctcaaggtac caggggctg   1560 ataggccagc caggagccaa gggggagcct ggtgagtttt atttcgactt gcggctcaaa   1620
```

```
ggtgacaaag gagacccagg cttccagga cagcccggca tgccaggag agcgggttct    1680
cctggaagag atggccatcc gggtcttcct ggccccaagg gctcgccggg ttctgtagga    1740
ttgaaaggag agcgtggccc ccctggagga gttggattcc caggcagtcg tggtgacacc    1800
ggccccctg gcctccagg atatggtcct gctggtccca ttggtgacaa aggacaagca    1860
ggctttcctg gaggccctgg atccccaggc ctgccaggtc caaagggtga accaggaaaa    1920
attgttcctt taccaggccc ccctggagca gaaggactgc cggggtcccc aggcttccca    1980
ggtcccaag gagaccgagg ctttcccgga accccaggaa ggccaggcct gccaggagag    2040
aagggcgctg tgggccagcc aggcattgga tttccagggc ccccggcccc caaaggtgtt    2100
gacggcttac ctggagacat ggggccaccg gggactccag gtcgcccggg atttaatggc    2160
ttacctggga acccaggtgt gcagggccag aaggagagc ctggagttgg tctaccggga    2220
ctcaaaggtt tgccaggtct tcccggcatt cctggcacac ccggggagaa ggggagcatt    2280
gggtaccag gcgttcctgg agaacatgga gcgatcggac cccctgggct tcaggggatc    2340
agaggtgaac cggaccctcc tggattgcca ggctccgtgg ggtctccagg agttccagga    2400
ataggccccc ctggagctag gggtcccct ggaggacagg gaccaccggg gttgtcaggc    2460
cctcctggaa taaaggaga aagggtttc cccggattcc ctggactgga catgccgggc    2520
cctaaaggag ataaaggggc tcaaggactc cctggcataa cggacagtc ggggctccct    2580
ggccttcctg gacagcaggg ggctcctggg attcctgggt ttccaggttc caaggagaa    2640
atgggcgtca tggggacccc cgggcagccg ggctcaccag gaccagtggg tgctcctgga    2700
ttaccgggtg aaaaagggga ccatggcttt ccgggctcct caggacccag gggagaccct    2760
ggcttgaaag gtgataaggg ggatgtcggt ctccctggca gcctggctc catggataag    2820
gtggacatgg gcagcatgaa gggccagaaa ggagaccaag gagagaaagg acaaattgga    2880
ccaattggtg agaagggatc ccgaggagac cctgggaccc caggagtgcc tggaaaggac    2940
gggcaggcag gacagcctgg gcagccagga cctaaaggtg atccaggtat aagtggaacc    3000
ccaggtgctc caggacttcc gggaccaaaa ggatctgttg gtggaatggg cttgccagga    3060
acacctggag agaaaggtgt gcctggcatc cctggcccac aaggttcacc tggcttacct    3120
ggagacaaag gtgcaaaagg agagaaaggg caggcaggcc cacctggcat aggcatccca    3180
gggctgcgag gtgaaaaggg agatcaaggg atagcgggtt tcccaggaag ccctggagag    3240
aagggagaaa aaggaagcat tgggatccca ggaatgccag ggtccccagg ccttaaaggg    3300
tctccccggga gtgttggcta tccaggaagt cctgggctac ctggagaaaa aggtgacaaa    3360
ggcctccag gattggatgg catccctggt gtcaaaggag aagcaggtct tcctgggact    3420
cctggcccca caggcccagc tggccagaaa ggggagccag gcagtgatgg aatcccgggg    3480
tcagcaggag agaagggtga accaggtcta ccaggaagag gattcccagg gtttccaggg    3540
gccaaaggag acaaaggttc aaaggtgag gtgggtttcc caggattagc cgggagccca    3600
ggaattcctg gatccaaagg agagcaagga ttcatgggtc ctccggggcc ccaggacag    3660
ccggggttac cgggatcccc aggccatgcc acggaggggc ccaaaggaga ccgcggacct    3720
cagggccagc ctgcctgcc aggacttccg ggacccatgg ggcctccagg cttcctggg    3780
attgatggag ttaaaggtga caaaggaaat ccaggctggc caggagcacc cggtgtccca    3840
gggcccaagg gagaccctgg attccagggc atgcctggta ttggtggctc tccaggaatc    3900
acaggctcta agggtgatat ggggcctcca ggagttccag gatttcaagg tccaaaaggt    3960
```

| | |
|---|---|
| cttcctggcc tccagggaat taaaggtgat caaggcgatc aaggcgtccc gggagctaaa | 4020 |
| ggtctcccgg gtcctcctgg cccccaggt ccttacgaca tcatcaaagg ggagcccggg | 4080 |
| ctccctggtc ctgagggccc cccagggctg aaagggcttc agggactgcc aggcccgaaa | 4140 |
| ggccagcaag gtgttacagg attggtgggt atacctggac ctccaggtat tcctgggttt | 4200 |
| gacggtgccc ctggccagaa aggagagatg ggacctgccg gcctactgg tccaagagga | 4260 |
| tttccaggtc caccaggccc cgatgggttg ccaggatcca tggggcccc aggcaccca | 4320 |
| tctgttgatc acggcttcct tgtgaccagg catagtcaaa caatagatga cccacagtgt | 4380 |
| ccttctggga ccaaaattct ttaccacggg tactcttttgc tctacgtgca aggcaatgaa | 4440 |
| cgggcccatg ccaggactt gggcacggcc ggcagctgcc tgcgcaagtt cagcacaatg | 4500 |
| cccttcctgt tctgcaatat taacaacgtg tgcaactttg catcacgaaa tgactactcg | 4560 |
| tactggctgt ccacccctga gcccatgccc atgtcaatgg cacccatcac gggggaaaac | 4620 |
| ataagaccat ttattagtag gtgtgctgtg tgtgaggcgc ctgccatggt gatggccgtg | 4680 |
| cacagccaga ccattcagat cccaccgtgc cccagcgggt ggtcctcgct gtggatcggc | 4740 |
| tactcttttg tgatgcacac cagcgctggt gcagaaggct ctggccaagc cctggcgtcc | 4800 |
| cccggctcct gcctggagga gtttagaagt gcgccattca tcgagtgtca cggccgtggg | 4860 |
| acctgcaatt actacgcaaa cgcttacagc ttttggctcg ccaccataga gaggagcgag | 4920 |
| atgttcaaga agcctacgcc gtccaccttg aaggcagggg agctgcgcac gcacgtcagc | 4980 |
| cgctgccaag tctgtatgag aagaacataa | 5010 |

<210> SEQ ID NO 8
<211> LENGTH: 5010
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| atgggcccta gactgtctgt gtggctgctg ctttcttcctg ccgctctgct gctgcacgag | 60 |
| gaacattcta gagccgccgc taaaggcgga tgtgccggat ctggatgcgg caagtgtgat | 120 |
| tgtcacggcg tgaagggcca aagggcgaa agaggacttc ctggactgca gggcgtgatc | 180 |
| ggatttcctg gaatgcaagg acctgaggga ccacagggac ctccaggaca aaaggcgat | 240 |
| acaggcgaac ctggcctgcc tggcacaaag ggaacaagag gaccacctgg cgcctctggc | 300 |
| tatcctggaa atccaggact gcctggaatc ccaggacagg atggacctcc tggtcctcct | 360 |
| ggcattcctg gctgtaatgg caccaaaggc gagagaggtc cactcggacc accaggactc | 420 |
| ccaggatttg ctggaaaccc tgggccacct ggattgcctg gcatgaaggg cgatcctggc | 480 |
| gaaattctgg acacgttcc cggcatgctg ctgaaaggcg aaagggggctt tcccggaatt | 540 |
| cctggcacac ctggtccacc aggcttgcca ggcttcaag gacttcaag gaccagttgg cccacctggc | 600 |
| tttacaggtc ctccaggtcc accggggcct ccagggccgc caggcaaaaa aggacaaatg | 660 |
| ggactgagct ttcagggccc caagggcgac aaaggcgatc aaggtgttag tggcccctcca | 720 |
| ggtgttcctg gacaggccca ggttcaagag aaaggcgatt tcgccaccaa gggcgagaag | 780 |
| ggacagaaag gcgaaccagg cttcaggga atgcctggcg tgggagaaaa gggcgaaccc | 840 |
| ggaaaaccctg gacctagagg caaacccggc aaggatggcg ataagggcga gaaggatct | 900 |
| cctggattcc ctggcgaacc tggatatcct ggactgatcg gtagacaggg ccctcaaggc | 960 |
| gagaagggcg aagctggacc gcctggacca ccgggaatag tgattggaac aggccctctc | 1020 |

-continued

```
ggagaaaaag gcgagcgagg atacccTGGA ACTCCCGGAC CTAGGGGAGA ACCAGGACCT    1080
aaaggttttc ccggactgcc aggacaacca gggcctcctg ggcttcctgt gcctggacaa    1140
gctggtgctc caggatttcc cggcgaacgt ggcgaaaagg gcgatagagg ttttcctggc    1200
acaagcctgc ctgggccttc tggaagagat ggacttcccg ggccaccagg ttctcccgga    1260
ccacctggac agcctggcta taccaatggc atcgtcgagt gtcaacccgg tccacctggc    1320
gatcaaggac ctcctggaat accaggccag cctggcttta tcggcgagat tggagagaaa    1380
gggcaaaaag gggagagctg cctgatctgc gacatcgatg gatacagagg ccctcctgga    1440
cctcaaggcc caccaggcga gataggtttt ccagggcaac ctggcgcaaa aggcgaccgt    1500
ggactccctg gtagagatgg tgttgctggc gttccaggac acaaggcac ccctggactt     1560
attggacagc caggtgcaaa gggcgagcca ggcgagttct acttcgacct gagacttaaa    1620
ggcgacaagg gcgaccctgg ctttcctgga caacctggaa tgcccggtag agctggatca    1680
ccaggccgtg atggacatcc agggttgccc ggaccaaaag gctctccagg atctgtgggc    1740
ctcaaaggcg aaagaggccc tccaggcgga gttggatttc ctggctctag aggcgatact    1800
ggcccaccag gtccacctgg atatggacct gctggcccta ttggagataa gggccaagca    1860
ggattcccag gcggacccgg ttctccaggc cttccgggtc ctaaaggcga gcctggaaaa    1920
atcgttccac tgcctggacc tccaggcgct gaaggattgc ctggatctcc cggttttcct    1980
ggaccgcaag gcgatagagg attccccgga cacccggta gaccaggcct tcctggcgag     2040
aaaggtgctg tgggtcaacc tggaatcggc tttcctgggc ctcctggtcc aaaaggtgtt    2100
gatggactgc ccggcgatat gggcccaccg ggaacaccag gcagacccgg ctttaatgga    2160
ttgcccggaa atcccggcgt ccaaggccag aaaggcgagc ccgtgttgg ccttcctgga     2220
cttaaaggac ttccaggcct gccaggcata cctgggacac ctggcgaaaa gggatctatc    2280
ggagttcctg gcgtgccagg cgaacatggt gcaattggtc cacctgggct gcaaggcatt    2340
agaggcgaac ccgggcctcc aggactccct ggctctgttg gaagtccagg cgtccccgga    2400
attggaccac caggtgctag gggacctcct ggcggacaag gtccaccagg attgtctgga    2460
ccacctggga tcaaaggcga gaaaggcttc cccggctttc ccggccttga tatgcctgga    2520
cctaaaggcg ataagggtgc ccagggcctg cctggaatta ctggacaaag cggcttgccc    2580
gggcttcccg acaacaggg tgctccgggt attcctgggt ttcccggatc taagggcgaa     2640
atgggcgtga tgggtacacc tggcaaccag gatcaccgg gacctgttgg agcaccgggg     2700
ttgcccggca aaaaggcga ccacggattc ccaggatcaa gcggaccaag aggcgatccg     2760
ggattgaaag gcgataaggg cgacgtggga cttcctggca aaccaggctc tatggacaag    2820
gtggacatgg gctccatgaa gggacaaaag gcgatcagg gcgaaaaggg ccagatcgga    2880
cctatcggcg aaaagggtag tagaggcgat cctggaacac ccggcgttcc cggaaaagat    2940
ggacaagcag gccaaccggg gcagccaggg ccaaaaggcg atcctggtat ttctggaaca    3000
ccaggtgcac caggactgcc cggacctaaa ggatctgttg gaggaatggg attgccaggg    3060
acacccggcg agaaggtgt tcctggaata cctggacctc agggctctcc tggactgcca    3120
ggcgacaaag gtgctaaagg cgaaaaggga caagccggac ctcctggcat ggcatacct    3180
ggacttaggg gagagaaggg cgaccaggga attgctggtt ttcctgggag cccaggcgag    3240
aaaggcgaaa aaggctctat cggcatcccc ggcatgcccg atctccagg tcttaaaggt    3300
tcacctggca gcgtgggcta tccgggatca cctggccttc caggcgaaaa gggcgacaaa    3360
```

| | |
|---|---|
| ggactgcctg gccttgatgg catacctggc gtgaaaggcg aagcaggact tcccggtaca | 3420 |
| cctggaccta caggaccagc tggccaaaaa ggcgaaccgg gatctgatgg aattcccggc | 3480 |
| tctgctggcg aaaaaggcga gccaggcctt cctggaagag gcttcccagg atttcctggc | 3540 |
| gcaaagggcg ataagggctc taagggcgaa gtcggctttc caggacttgc cggttctcct | 3600 |
| ggcatcccag gttccaaggg cgaacaagga ttcatgggtc ctccgggtcc tcagggtcaa | 3660 |
| ccagggttgc ctggaagccc tggacatgcc acagaaggac caaaggcga cagaggacct | 3720 |
| cagggacaac ctgggcttcc cggccttcca ggaccaatgg gtcctcctgg actcccggt | 3780 |
| attgatggcg tcaagggcga caagggaaat ccaggatggc caggtgctcc aggcgttccc | 3840 |
| ggtccaaagg gcgatcccgg gtttcaaggg atgcctggta tcggaggaag ccccggcatt | 3900 |
| actgaagca aaggcgacat gggaccacca ggcgtgcccg gttttcaggg acctaaaggg | 3960 |
| ttgccaggcc tgcagggaat caaaggcgac cagggcgatc aaggcgttcc aggtgccaag | 4020 |
| ggattgcctg gccaccagg accgccagga ccttacgata tcattaaggg cgagcccgga | 4080 |
| ctgcctggtc ctgagggtcc tccaggattg aaaggacttc aggggctccc tggaccaaaa | 4140 |
| ggacagcagg gtgttacagg cctcgtcggt attcctggac ctccggggat acctggattt | 4200 |
| gatggtgctc ctgggcagaa aggcgaaatg ggtccagcag gaccaacagg cccaagaggt | 4260 |
| ttccccggac ctccagggcc tgatggcctg ccaggatcta tgggtccacc agggacacca | 4320 |
| tccgtggatc acggctttct ggtcaccaga cacagccaga ccatcgacga tcctcagtgt | 4380 |
| cctagcggca ccaagatcct gtatcacggc tacagcctgc tgtacgtgca gggcaatgag | 4440 |
| agagcacacg acaggatct gggcacagcc ggcagctgtc tgcggaagtt tagcaccatg | 4500 |
| ccttttctgt tctgcaacat caacaacgtg tgcaacttcg ccagccggaa cgactacagc | 4560 |
| tactggctgt ctaccccctga gcctatgcct atgagcatgg cccctatcac cggggagaac | 4620 |
| atcagaccct tcatcagcag atgtgccgtg tgcgaagccc tgccatggt tatggctgtg | 4680 |
| cactcccaga ccattcagat ccctccatgt ccaagcggct ggtctagcct gtggatcggc | 4740 |
| tactcctttg tgatgcacac atctgccggc gcagaaggat caggacaagc ccttgctagc | 4800 |
| cccggctcct gtctggaaga attcagaagc gccccttttca tcgagtgcca cggcagaggc | 4860 |
| acctgtaact actacgccaa cgcctacagc ttttggctgg ccaccatcga gcggagcgag | 4920 |
| atgttcaaga gcccacacc ttctacactg aaggccggcg agctgagaac acacgtgtcc | 4980 |
| agatgtcaag tgtgcatgcg gcggacctga | 5010 |

<210> SEQ ID NO 9
<211> LENGTH: 3087
<212> TYPE: DNA
<213> ORGANISM: Homo sapiens

<400> SEQUENCE: 9

| | |
|---|---|
| atgagggcgg cccgtgctct gctgcccctg ctgctgcagg cctgctggac agccgcgcag | 60 |
| gatgagccgg agaccccgag ggccgtggcc ttccaggact gccccgtgga cctgttcttt | 120 |
| gtgctggaca cctctgagag cgtggccctg aggctgaagc cctacggggc cctcgtggac | 180 |
| aaagtcaagt ccttcaccaa cgcgcttcatc gacaacctga gggacaggta ctaccgctgt | 240 |
| gaccgaaacc tggtgtggaa cgcaggcgcg ctgcactaca gtgacgaggt ggagatcatc | 300 |
| caaggcctca cgcgcatgcc tggcggccgc gacgcactca aaagcagcgt ggacgcggtc | 360 |
| aagtactttg gaagggcac ctacaccgac tgcgctatca gaaggggct ggagcagctc | 420 |
| ctcgtgggg gctcccacct gaaggagaat aagtacctga ttgtggtgac cgacgggcac | 480 |

| | | | | |
|---|---|---|---|---|
| cccctggagg | gctacaagga | accctgtggg | gggctggagg | atgctgtgaa cgaggccaag | 540 |
| cacctgggcg | tcaaagtctt | ctcggtggcc | atcacacccg | accacctgga gccgcgtctg | 600 |
| agcatcatcg | ccacggacca | cacgtaccgg | cgcaacttca | cggcggctga ctggggccag | 660 |
| agccgcgacg | cagaggaggc | catcagccag | accatcgaca | ccatcgtgga catgatcaaa | 720 |
| aataacgtgg | agcaagtgtg | ctgctccttc | gaatgccagc | ctgcaagagg acctccgggg | 780 |
| ctccggggcg | accccggctt | tgagggagaa | cgaggcaagc | cggggctccc aggagagaag | 840 |
| ggagaagccg | gagatcctgg | aagacccggg | gacctcggac | ctgttgggta ccagggaatg | 900 |
| aagggagaaa | aagggagccg | tggggagaag | ggctccaggg | gacccaaggg ctacaaggga | 960 |
| gagaagggca | agcgtggcat | cgacggggtg | gacggcgtga | aggggagat ggggtaccca | 1020 |
| ggcctgccag | gctgcaaggg | ctcgcccggg | tttgacggca | ttcaaggacc ccctggcccc | 1080 |
| aagggagacc | ccggtgcctt | tggactgaaa | ggagaaaagg | gcgagcctgg agctgacggg | 1140 |
| gaggcgggga | gaccagggag | ctcgggacca | tctggagacg | agggccagcc gggagagcct | 1200 |
| ggcccccccg | gagagaaagg | agaggcgggc | gacgagggga | acccaggacc tgacggtgcc | 1260 |
| cccggggagc | ggggtggccc | tggagagaga | ggaccacggg | ggaccccagg cacgcgggga | 1320 |
| ccaagaggag | accctggtga | agctggcccg | cagggtgatc | agggaagaga aggccccgtt | 1380 |
| ggtgtccctg | gagacccggg | cgaggctggc | cctatcggac | ctaaaggcta ccgaggcgat | 1440 |
| gagggtcccc | cagggtccga | gggtgccaga | ggagcccag | gacctgccgg accccctgga | 1500 |
| gacccggggc | tgatgggtga | aaggggagaa | gacggccccg | ctggaaatgg caccgagggc | 1560 |
| ttccccggct | tccccgggta | tccgggcaac | aggggcgctc | ccgggataaa cggcacgaag | 1620 |
| ggctaccccg | gcctcaaggg | ggacgaggga | gaagccgggg | accccggaga cgataacaac | 1680 |
| gacattgcac | cccgaggagt | caaggagca | aaggggtacc | ggggtcccga gggcccccag | 1740 |
| ggaccccag | gacaccaagg | accgcctggg | ccggacgaat | gcgagatttt ggacatcatc | 1800 |
| atgaaaatgt | gctcttgctg | tgaatgcaag | tgcggcccca | tcgacctcct gttcgtgctg | 1860 |
| gacagctcag | agagcattgg | cctgcagaac | ttcgagattg | ccaaggactt cgtcgtcaag | 1920 |
| gtcatcgacc | ggctgagccg | ggacgagctg | gtcaagttcg | agccagggca gtcgtacgcg | 1980 |
| ggtgtggtgc | agtacagcca | cagccagatg | caggagcacg | tgagcctgcg cagccccagc | 2040 |
| atccggaacg | tgcaggagct | caaggaagcc | atcaagagcc | tgcagtggat ggcgggcggc | 2100 |
| accttcacgg | gggaggccct | gcagtacacg | cggaccagc | tgctgccgcc cagcccgaac | 2160 |
| aaccgcatcg | ccctggtcat | cactgacggg | cgctcagaca | ctcagaggga caccacaccg | 2220 |
| ctcaacgtgc | tctgcagccc | cggcatccag | gtggtctccg | tgggcatcaa agacgtgttt | 2280 |
| gacttcatcc | caggctcaga | ccagctcaat | gtcatttctt | gccaaggcct ggcaccatcc | 2340 |
| cagggccggc | ccggcctctc | gctggtcaag | gagaactatg | cagagctgct ggaggatgcc | 2400 |
| ttcctgaaga | atgtcaccgc | ccagatctgc | atagacaaga | agtgtccaga ttacacctgc | 2460 |
| cccatcacgt | tctcctcccc | ggctgacatc | accatcctgc | tggacggctc cgccagcgtg | 2520 |
| ggcagccaca | actttgacac | caccaagcgc | ttcgccaagc | gcctggccga gcgcttcctc | 2580 |
| acagcgggca | ggacggaccc | cgcccacgac | gtgcgggtgg | cggtggtgca gtacagcggc | 2640 |
| acgggccagc | agcgcccaga | gcgggcgtcg | ctgcagttcc | tgcagaacta cacggccctg | 2700 |
| gccagtgccg | tcgatgccat | ggacttgatc | aacgacgcca | ccgacgtcaa cgatgccctg | 2760 |
| ggctatgtga | cccgcttcta | ccgcgaggcc | tcgtccggcg | ctgccaagaa gaggctgctg | 2820 |

-continued

| | |
|---|---|
| ctcttctcag atggcaactc gcagggcgcc acgcccgctg ccatcgagaa ggccgtgcag | 2880 |
| gaagcccagc gggcaggcat cgagatcttc gtggtggtcg tgggccgcca ggtgaatgag | 2940 |
| ccccacatcc gcgtcctggt caccggcaag acggccgagt acgacgtggc ctacggcgag | 3000 |
| agccacctgt ccgtgtccc cagctaccag gccctgctcc gcggtgtctt ccaccagaca | 3060 |
| gtctccagga aggtggcgct gggctag | 3087 |

<210> SEQ ID NO 10
<211> LENGTH: 3087
<212> TYPE: DNA
<213> ORGANISM: Artificial Sequence
<220> FEATURE:
<223> OTHER INFORMATION: Synthetic Construct

<400> SEQUENCE: 10

| | |
|---|---|
| atgagagccg ctagagccct tctgcctctg ctgctgcaag cctgttggac agccgctcag | 60 |
| gatgagcccg aaacacctag agccgtggca ttccaggact gccccgtgga tctgttcttc | 120 |
| gtgctggata ccagcgagag cgtggccctg agactgaaac cttatggcgc cctggtggac | 180 |
| aaagtgaagt ccttcaccaa gcggttcatc gacaacctgc gcgaccggta ctacagatgc | 240 |
| gacagaaacc tcgtgtggaa cgcaggcgcc ctgcactact ctgacgaggt ggaaatcatc | 300 |
| cagggcctga ccagaatgcc tggcggaaga gatgccctga agtctagcgt ggacgccgtg | 360 |
| aagtactttg caagggcac ctacaccgac tgcgccatca agaaaggcct ggaacagctg | 420 |
| ctcgtcggcg gcagccatct gaaagagaac aagtacctga tcgtggttac cgacggacac | 480 |
| cctctggaag gctacaaaga accttgtggc ggactggaag atgccgtgaa cgaggccaaa | 540 |
| cacctgggcg tgaaggtgtt cagcgtggcc atcacacccg accacctgga acctcggctg | 600 |
| agcatcattg ccaccgacca cacctaccgg cggaatttca cagccgctga ttggggccag | 660 |
| agcagggatg ccgaagaggc catcagccag accatcgaca ccatcgtgga catgatcaag | 720 |
| aacaacgtgg acaagtgtg ctgcagcttc gagtgccagc ctgctagagg acctcctgga | 780 |
| cttagaggcg accctggctt tgagggcgag agaggaaaac ctggactgcc cggcgaaaaa | 840 |
| ggcgaagctg gcgatcctgg tagacctggc gatctgggac ctgtgggcta tcagggaatg | 900 |
| aagggcgaga aggctcccg gggagagaag ggatctagag cccctaaggg ctacaagggc | 960 |
| gaaaaaggca gagggggcat cgatggcgtg gacggcgtca aggcgagat gggatatcct | 1020 |
| ggactccctg gctgtaaagg cagccctggc ttcgatggaa tccagggacc tccaggacct | 1080 |
| aagggcgatc caggcgcctt tggactgaaa ggcgaaaagg cgaaccagg tgccgatggc | 1140 |
| gaagcaggca gacctggatc ttctggccct agcggagatg aaggacagcc tggcgaacct | 1200 |
| ggaccacctg gcgagaaggg cgaagccggc gacgagggaa tccaggacc agatggtgct | 1260 |
| cctggcgaaa gaggtggacc aggcgaaagg ggacctagag aacaccagg cacaagaggc | 1320 |
| ccaagaggcg atcccggcga ggctggacct caaggcgatc agggaagaga aggaccagtg | 1380 |
| ggagttcctg gcgacccagg cgaagcagga cctatcggcc taagggata tagaggcgac | 1440 |
| gaaggccctc ctggatctga aggtgctaga ggcgcaccag gtccagcagg ccctccaggc | 1500 |
| gaccccggac ttatgggaga acgcggagaa gatggccctg ccgcaatgg cacagagggc | 1560 |
| tttccaggct ttcctggcta ccccggaaat agaggcgctc ctggaatcaa cggcaccaag | 1620 |
| ggatatccag gctcaaagg cgacgaaggc gaggcaggcg atccagggga tgacaacaac | 1680 |
| gatatcgccc ctagaggcgt gaaggcgcc aaaggctata gaggaccaga gggaccacaa | 1740 |
| ggcccacctg gtcatcaagg ccaccagga cctgacgagt gcgagatcct ggacatcatt | 1800 |

| | |
|---|---:|
| atgaagatgt gcagctgctg cgagtgcaag tgcggccccta tcgatctgct gtttgtgctg | 1860 |
| gacagctccg agagcatcgg cctgcagaat ttcgagatcg ccaaggactt cgtggtcaaa | 1920 |
| gtgatcgaca gactgagccg ggacgagctg gtcaagtttg agcctggcca gtcttatgcc | 1980 |
| ggcgtggtgc agtacagcca cagccagatg caagagcacg tgtccctgag aagccccagc | 2040 |
| atcagaaacg tgcaagagct gaaagaagcc atcaagtccc tgcagtggat ggctggcgga | 2100 |
| acctttactg gcgaggccct gcagtacacc agagatcaac tgctgcctcc ttctcctaac | 2160 |
| aaccggattg ccctcgtgat caccgacggc agaagcgaca cccagagaga caccacacct | 2220 |
| ctgaacgtgt gtgcagccc cggcattcag gtggtgtctg tgggcatcaa ggacgtgttc | 2280 |
| gacttcatcc ccggcagcga ccagctgaac gtgatctctt gtcaaggact ggcccctagc | 2340 |
| caaggcagac caggactgtc tctggtcaaa gagaactacg ccgagctgct cgaggacgcc | 2400 |
| ttcctgaaga atgtgacagc ccagatctgc atcgacaaga agtgccccga ctacacatgc | 2460 |
| cccatcacct ttagcagccc tgccgacatc accatcctgc tggatggctc tgctagcgtg | 2520 |
| ggcagccaca acttcgacac caccaagaga ttcgccaagc ggctggccga gagatttctg | 2580 |
| acagccggca gaaccgatcc tgctcacgat gtgcgagtgg ccgtggtcca gtattctggc | 2640 |
| acaggccagc aaagacccga gagagcctct ctgcagttcc tgcagaacta cactgccctg | 2700 |
| gcctctgccg tggatgccat ggactttatc aacgacgcca ccgacgtgaa cgacgccctg | 2760 |
| ggctatgtga cccggttta cagagaagcc tctagcggag ccgccaagaa gagactgctg | 2820 |
| ctgttcagcg acggcaactc ccaaggtgct acaccagccg ccattgagaa ggccgtgcaa | 2880 |
| gaagctcaga gagccggcat cgagatcttc gtggtggtcg tgggcagaca agtgaacgag | 2940 |
| cctcacatca gagtgctggt caccggcaag accgccgagt acgatgtggc ttatggcgag | 3000 |
| agccacctgt tcagagtgcc cagctatcag gctctgctga gaggcgtgtt ccaccagacc | 3060 |
| gtgtctagaa aggtggccct gggatga | 3087 |

<210> SEQ ID NO 11
<211> LENGTH: 8835
<212> TYPE: DNA
<213> ORGANISM: Homo sapiens

<400> SEQUENCE: 11

| | |
|---|---:|
| atgacgctgc ggcttctggt ggccgcgctc tgcgccggga tcctggcaga ggcgccccga | 60 |
| gtgcgagccc agcacaggga gagtgacc tgcacgcgcc tttacgccgc tgacattgtg | 120 |
| ttcttactgg atggctcctc atccattggc cgcagcaatt tccgcgaggt ccgcagcttt | 180 |
| ctcgaagggc tggtgctgcc tttctctgga gcagccagtg cacagggtgt gcgctttgcc | 240 |
| acagtgcagt acagcgatga cccacggaca gagttcggcc tggatgcact ggctctgggg | 300 |
| ggtgatgtga tccgcgccat ccgtgagctt agctacaagg ggcaacac tcgcacaggg | 360 |
| gctgcaattc tccatgtggc tgaccatgtc ttcctgcccc agctgccccg acctggtgtc | 420 |
| cccaaggtct gcatcctgat cacagacggg aagtcccagg acctggtgga cacagctgcc | 480 |
| caaaggctga gggggcaggg ggtcaagcta tttgctgtgg ggatcaagaa tgctgaccct | 540 |
| gaggagctga agcgagttgc ctcacagccc accagtgact tcttcttctt cgtcaatgac | 600 |
| ttcagcatct tgaggacact actgccctc gtttccgga gagtgtgcac gactgctggt | 660 |
| ggcgtgcctg tgacccgacc tccggatgac tcgacctctg ctccacgaga cctggtgctg | 720 |
| tctgagccaa gcagccaatc cttgagagta cagtggacag cggccagtgg ccctgtgact | 780 |

```
ggctacaagg tccagtacac tcctctgacg gggctgggac agccactgcc gagtgagcgg    840
caggaggtga acgtcccagc tggtgagacc agtgtgcggc tgcggggtct ccggccactg    900
accgagtacc aagtgactgt gattgccctc tacgccaaca gcatcgggga ggctgtgagc    960
gggacagctc ggaccactgc cctagaaggg ccggaactga ccatccagaa taccacagcc   1020
cacagcctcc tggtggcctg gcggagtgtg ccaggtgcca ctggctaccg tgtgacatgg   1080
cgggtcctca gtggtgggcc cacacagcag caggagctgg gccctgggca gggttcagtg   1140
ttgctgcgtg acttggagcc tggcacggac tatgaggtga ccgtgagcac cctatttggc   1200
cgcagtgtgg ggcccgccac ttccctgatg gctcgcactg acgcttctgt tgagcagacc   1260
ctgcgcccgg tcatcctggg ccccacatcc atcctccttt cctggaactt ggtgcctgag   1320
gcccgtggct accggttgga atggcggcgt gagactggct tggagccacc gcagaaggtg   1380
gtactgccct ctgatgtgac ccgctaccag ttggatgggc tgcagccggg cactgagtac   1440
cgcctcacac tctacactct gctggagggc cacgaggtgg ccaccctgc aaccgtggtt   1500 cccactggac cagagctgcc tgtgagccct gtaacagacc tgcaagccac cgagctgccc   1560
gggcagcggg tgcgagtgtc ctggagccca gtccctggtg ccacccagta ccgcatcatt   1620
gtgcgcagca cccaggggt tgagcggacc ctggtgcttc ctgggagtca gacagcattc   1680
gacttggatg acgttcaggc tgggcttagc tacactgtgc gggtgtctgc tcgagtgggt   1740
ccccgtgagg gcagtgccag tgtcctcact gtccgccggg agccggaaac tccacttgct   1800
gttccagggc tgcgggttgt ggtgtcagat gcaacgcgag tgagggtggc ctggggaccc   1860
gtccctggag ccagtggatt tcggattagc tggagcacag gcagtggtcc ggagtccagc   1920
cagacactgc ccccagactc tactgccaca gacatcacag gctgcagcc tggaaccacc   1980 taccaggtgg ctgtgtcggt actgcgaggc agagaggagg gccctgctgc agtcatcgtg   2040
gctcgaacgg acccactggg cccagtgagg acggtccatg tgactcaggc cagcagctca   2100
tctgtcacca ttacctggac cagggttcct ggcgccacag gatacagggt ttcctggcac   2160
tcagcccacg gcccagagaa atcccagttg gtttctgggg aggccacggt ggctgagctg   2220
gatggactgg agccagatac tgagtatacg gtgcatgtga gggcccatgt ggctggcgtg   2280
gatgggcccc ctgcctctgt ggttgtgagg actgcccctg agcctgtggg tcgtgtgtcg   2340
aggctgcaga tcctcaatgc ttccagcgac gttctacgga tcacctgggt aggggtcact   2400
ggagccacag cttacagact ggcctggggc cggagtgaag gcggccccat gaggcaccag   2460
atactcccag gaaacacaga ctctgcagag atccggggtc tcgaaggtgg agtcagctac   2520
tcagtgcgag tgactgcact tgtcgggac cgcgagggca cctgtctc cattgttgtc   2580 actacgccgc ctgaggctcc gccagccctg ggacgcttc acgtggtgca gcgcggggag   2640
cactcgctga ggctgcgctg ggagccggtg cccagagcgc agggcttcct tctgcactgg   2700
caacctgagg gtggccagga acagtcccgg gtcctggggc ccgagctcag cagctatcac   2760
ctggacgggc tggagccagc gacacagtac cgcgtgagg tgagtgtcct agggccagct   2820
ggagaagggc cctctgcaga ggtgactgcg cgcactgagt cacctcgtgt tccaagcatt   2880
gaactacgtg tggtggacac ctcgatcgac tcggtgactt tggcctggac tccagtgtcc   2940
agggcatcca gctacatcct atcctggcgg ccactcagag gccctggcca ggaagtgcct   3000
gggtccccgc agacacttcc agggatctca agctcccagc gggtgacagg gctagagcct   3060
ggcgtctctt acatcttctc cctgacgcct gtcctggatg gtgtgcgggg tcctgaggca   3120
tctgtcacac agacgccagt gtgcccccgt ggcctggcgg atgtggtgtt cctaccacat   3180
```

```
gccactcaag acaatgctca ccgtgcggag gctacgagga gggtcctgga gcgtctggtg    3240
ttggcacttg ggcctcttgg gccacaggca gttcaggttg gcctgctgtc ttacagtcat    3300
cggcccctcc cactgttccc actgaatggc tcccatgacc ttggcattat cttgcaaagg    3360
atccgtgaca tgcccctacat ggacccaagt gggaacaacc tgggcacagc cgtggtcaca    3420
gctcacagat acatgttggc accagatgct cctgggcgcc gccagcacgt accaggggtg    3480
atggttctgc tagtggatga acccttgaga ggtgacatat tcagccccat ccgtgaggcc    3540
caggcttctg ggcttaatgt ggtgatgttg ggaatggctg gagcggaccc agagcagctg    3600
cgtcgcttgg cgccgggtat ggactctgtc cagaccttct tcgccgtgga tgatgggcca    3660
agcctggacc aggcagtcag tggtctggcc acagccctgt gtcaggcatc cttcactact    3720
cagccccggc cagagccctg cccagtgtat tgtccaaagg ccagaagggg gaacctggaa    3780
gagatgggcc tgagaggaca agttgggcct cctggcgacc ctggcctccc gggcaggacc    3840
ggtgctcccg gccccaggg gccccctgga agtgccactg ccaagggcga gaggggcttc    3900
cctggagcag atgggcgtcc aggcagccct ggccgcgccg gaatcctgg acccctgga    3960
gcccctggcc taaagggctc tccagggttg cctggccctc gtggggaccc gggagagcga    4020
ggacctcgag gcccaaaggg ggagccgggg gctcccggac aagtcatcgg aggtgaagga    4080
cctgggcttc ctgggcggaa aggggaccct ggaccatcgg gccccctgg acctcgtgga    4140
ccactggggg acccaggacc ccgtggcccc ccagggcttc ctggaacagc catgaagggt    4200
gacaaaggcg atcgtgggga gcggtccc cctggaccag gtgaaggtgg cattgctcct    4260
ggggagcctg ggctgccggg tcttcccgga agccctggac ccaaggccc cgttggcccc    4320
cctggaaaga aggagaaaaa aggtgactct gaggatggag ctccaggcct cccaggacaa    4380
cctgggtctc cgggtgagca gggcccacgg ggacctcctg gagctattgg ccccaaaggt    4440
gaccgggggct ttccaggcc cctgggtgag gctggagaga agggcgaacg tggacccccca    4500
ggcccagcgg atcccgggg gctgccaggg gttgctggac gtcctggagc caagggtcct    4560
gaagggccac caggacccac tggccgccaa ggagagaagg gggagcctgg tcgccctggg    4620
gaccctgcag tggtgggacc tgctgttgct ggacccaaag gagaaaaggg agatgtgggg    4680
cccgctgggc ccagaggagc taccggagtc caaggggaac ggggcccacc cggcttggtt    4740
cttcctggag accctggccc caaggagac cctgagacc ggggtccat tggccttact    4800
ggcagagcag gaccccccagg tgactcaggg cctcctggag agaagggaga ccctgggcgg    4860
cctggccccc caggacctgt tggccccccga ggacgagatg tgaagttgg agagaaaggt    4920
gacgagggtc ctccgggtga cccgggtttg cctggaaaag caggcgagcg tggccttcgg    4980
ggggcacctg gagttcgggg gcctgtgggt gaaaagggag accagggaga tcctggagag    5040
gatggacgaa atggcagccc tggatcatct ggacccaagg gtgaccgtgg ggagccgggt    5100
cccccaggac cccggggacg gctggtagac acaggacctg gagccagaga aagggagag    5160
cctggggacc gcggacaaga gggtcctcga gggcccaagg gtgatcctgg cctccctgga    5220
gcccctgggg aaaggggcat tgaagggttt cggggacccc caggcccaca ggggacccca    5280
ggtgtccgag gcccagcagg agaaaagggt gaccggggtc cccctgggct ggatggccgg    5340
agcggactgg atgggaaacc aggagccgct gggccctctg ggccgaatgg tgctgcaggc    5400
aaagctgggg acccagggag agacgggctt ccaggcctcc gtgagaaca gggcctccct    5460
ggccctctg gtccccctgg attaccggga aagccaggcg aggatggcaa acctggcctg    5520
```

```
aatggaaaaa acggagaacc tggggaccct ggagaagacg ggaggaaggg agagaaagga     5580
gattcaggcg cctctgggag agaaggtcgt gatggcccca agggtgagcg tggagctcct     5640
ggtatccttg gaccccaggg gcctccaggc ctcccagggc cagtgggccc tcctggccag     5700
ggttttcctg gtgtcccagg aggcacgggc cccaagggtg accgtgggga gactggatcc     5760
aaagggagc agggcctccc tggagagcgt ggcctgcgag gagagcctgg aagtgtgccg     5820
aatgtggatc ggttgctgga aactgctggc atcaaggcat ctgccctgcg ggagatcgtg     5880
gagacctggg atgagagctc tggtagcttc ctgcctgtgc ccgaacggcg tcgaggcccc     5940
aaggggggact caggcgaaca gggcccccca ggcaaggagg gccccatcgg ctttcctgga     6000
gaacgcgggc tgaagggcga ccgtggagac cctggccctc aggggccacc tggtctggcc     6060
cttggggaga gggccccccc cgggccttcc ggccttgccg gggagcctgg aaagcctggt     6120
attcccgggc tcccaggcag ggctgggggt gtgggagagg caggaaggcc aggagagagg     6180
ggagaacggg gagagaaagg agaacgtgga gaacagggca gagatggccc tcctggactc     6240
cctggaaccc ctgggccccc cggaccccct ggccccaagg tgtctgtgga tgagccaggt     6300
cctggactct ctggagaaca gggacccct ggactcaagg gtgctaaggg ggagccgggc     6360
agcaatggtg accaaggtcc caaggagac aggggtgtgc caggcatcaa aggagaccgg     6420
ggagagcctg gaccgagggg tcaggacggc aacccgggtc taccaggaga gcgtggtatg     6480
gctgggcctg aagggaagcc gggtctgcag ggtccaagag gccccctgg cccagtgggt     6540
ggtcatggag accctggacc acctggtgcc ccgggtcttg ctggccctgc aggacccaa     6600
ggaccttctg gcctgaaggg ggagcctgga gagacaggc ctccaggacg gggcctgact     6660
ggacctactg gagctgtggg acttcctgga ccccccggcc cttcaggcct tgtgggtcca     6720
caggggtctc caggtttgcc tggacaagtg ggggagacag ggaagccggg agccccaggt     6780
cgagatggtg ccagtggaaa agatggagac agagggagcc ctggtgtgcc agggtcacca     6840
ggtctgcctg gccctgtcgg acctaaagga gaacctggcc ccacggggc ccctggacag     6900
gctgtggtcg ggctccctgg agcaaaggga gagaagggag ccctggagg ccttgctgga     6960
gacctggtgg gtgagccggg agccaaaggt gaccgaggac tgccaggcc gcgaggcgag     7020
aagggtgaag ctggccgtgc aggggagccc ggagaccctg gggaagatgg tcagaaaggg     7080
gctccaggac ccaaaggttt caaggggtgac ccaggagtcg gggtcccggg ctcccctggg     7140
cctcctggcc ctccaggtgt gaagggagat ctgggcctcc ctggcctgcc cggtgctcct     7200
ggtgttgttg ggttcccggg tcagacaggc cctcgaggag agatgggtca gccaggccct     7260
agtggagagc ggggtctggc aggccccca gggagagaag gaatcccagg accctgggg     7320
ccacctggac caccgggtc agtgggacca cctgggcct ctggactcaa aggagacaag     7380
ggagaccctg gagtagggct gcctgggccc cgaggcgagc gtggggagcc aggcatccgg     7440
ggtgaagatg gccgcccgg ccaggaggga ccccgaggac tcacggggcc ccctggcagc     7500
agggagagc gtgggagaa gggtgatgtt gggagtgcag gactaaaggg tgacaaggga     7560
gactcagctg tgatcctggg gcctccaggc ccacggggtg ccaaggggga catgggtgaa     7620
cgagggcctc ggggcttgga tgtgacaaaa ggacctcggg gagacaatgg ggaccctggt     7680
gacaagggca gcaagggaga gcctggtgac aagggctcag ccgggttgcc aggactgcgt     7740
ggactcctgg gaccccaggg tcaacctggt gcagcaggga tccctggtga cccgggatcc     7800
ccaggaaagg atgagtgcc tggtatccga ggagaaaaag gagatgttgg cttcatgggt     7860
ccccgggcc tcaagggtga acggggagtg aagggagcct gtggccttga tggagagaag     7920
```

```
ggagacaagg gagaagctgg tcccccaggc cgccccgggc tggcaggaca caaaggagag    7980 atggggagc ctggtgtgcc gggccagtcg ggggcccctg gcaaggaggg cctgatcggt     8040
cccaagggtg accgaggctt tgacgggcag ccaggcccca agggtgacca gggcgagaaa    8100
ggggagcggg gaaccccagg aattgggggc ttcccaggcc ccagtggaaa tgatggctct    8160
gctggtcccc cagggccacc tggcagtgtt ggtcccagag gccccgaagg acttcagggc    8220
cagaagggtg agcgaggtcc ccccggagag agagtggtgg gggctcctgg ggtccctgga    8280
gctcctggcg agagagggga gcaggggcgg ccagggcctg ccggtcctcg aggcgagaag    8340
ggagaagctg cactgacgga ggatgacatc cggggctttg tgcgccaaga gatgagtcag    8400
cactgtgcct gccagggcca gttcatcgca tctggatcac gacccctccc tagttatgct    8460
gcagacactg ccggctccca gctccatgct gtgcctgtgc tccgcgtctc tcatgcagag    8520
gaggaagagc gggtaccccc tgaggatgat gagtactctg aatactccga gtattctgtg    8580
gaggagtacc aggaccctga agctccttgg gatagtgatg accctgttc cctgccactg     8640 gatgagggct cctgcactgc ctacaccctg cgctggtacc atcgggctgt gacaggcagc    8700
acagaggcct gtcaccctt tgtctatggt ggctgtggag ggaatgccaa ccgttttggg     8760
acccgtgagg cctgcgagcg ccgctgccca ccccgggtgg tccagagcca ggggacaggt    8820
actgcccagg actga                                                    8835
```

<210> SEQ ID NO 12
<211> LENGTH: 8835
<212> TYPE: DNA
<213> ORGANISM: Artificial Sequence
<220> FEATURE:
<223> OTHER INFORMATION: Synthetic Construct

<400> SEQUENCE: 12

```
atgaccctga gactgctggt ggctgccctg tgtgctggaa ttctggctga ggctcctaga      60
gtgcgggccc agcatagaga aagagtgacc tgtacacggc tgtacgccgc cgatatcgtg    120
tttctgctgg atgcagcag cagcatcggc cggtccaatt tcagagaagt gcggagcttt     180
ctggaaggcc tggtgctgcc tttttctggc gctgcttctg cccagggcgt cagatttgcc    240
accgtgcagt acagcgacga ccctagaaca gagtttggcc tggatgctct cggcagcggc    300
ggagatgtga tcagagccat cagagagctg agctacaaag gcggcaatac cagaacaggc    360
gccgctattc tgcacgtggc cgaccatgtt tttctgcccc aactggctag acccggcgtg    420
ccaaaagtgt gcatcctgat cacagacggc aagagccagg acctggtgga tacagccgct    480
cagagactga aaggacaggg cgtgaaactg ttcgccgtgg gcatcaagaa cgccgatcct    540
gaggaactga gagagtggc cagccagcct accagcgatt tcttcttctt cgtgaacgac    600
ttcagcatcc tgcggaccct gctgcctctg gtgtctagaa gagtgtgtac aacagccggc    660
ggagtgcctg tgaccagacc tcctgatgat agcacaagcg cccctagaga tctggtgctg    720
tctgagccaa gcagccagag tctgagagtg cagtggacag ctgctagcgg ccctgtgaca    780
ggctacaagg tgcagtatac acctctgaca ggcctgggcc agcctctgcc ttctgagaga    840
caagaagtga acgtcccagc cggcgaaaca tctgtcagac tgagaggact gaggcccctg    900
accgagtacc aagtgacagt gatcgccctg tacgccaatt ctatcggcga ggccgtgtct    960
ggcacagcca aacaacagc tctggaagga ccagagctga ccatccagaa cacaacagcc   1020
cattctctgc tggttgcttg gagatctgtg cctggcgcca ccggctatag agtgacttgg   1080
```

-continued

```
agagttctga gcggaggccc cacacagcag caagaacttg gacctggaca gggctccgtg      1140
ctgctgagag atctcgagcc tggcaccgat tacgaagtga ccgtgtctac cctgttcggc      1200
agatctgtgg gacctgccac aagcctgatg gccagaacag atgccagcgt ggaacagacc      1260
ctgaggcctg tgattctggg ccctacatct atcctgctga gctggaatct ggtgcccgag      1320
gccagaggct atagactgga atggcggaga gaaaccggcc tggaacctcc tcagaaagtg      1380
gtcctgccta gcgacgtgac aagataccag ctggatggac tgcagcccgg caccgagtac      1440
agactgacac tgtatacact gctcgagggc cacgaagtgg ccacaccagc tacagttgtg      1500
ccaacaggac ctgagctgcc tgtgtctcct gtgactgatc tgcaggccac agaactgcct      1560
ggccagagag tcagagttag ctggtcacct gttccaggcg ccacacagta cagaatcatc      1620
gtgcggtcta cacagggcgt cgagagaaca ctggttctgc ctggaagcca gaccgccttc      1680
gatctggatg atgtgcaggc cggactgtcc tacacagtca gagtgtctgc cagagtgggc      1740
cctagagaag gatctgcctc tgtgctgacc gtgcggagag agcctgaaac caccactggca      1800
gtgcctggac tgagagtggt ggtgtcagat gccaccagag ttagagtggc ttggggacca      1860
gttcctggcg cctctggctt tagaatcagc tggtctacag ctctggcccc gaaaagctct      1920
cagacactgc ctccagatag caccgccacc gatattacag cctgcagcc tggaactacc      1980
taccaggtgg ccgttagcgt gctgagagga agagaagaag gccctgccgc cgtcatcgtg      2040
gctagaactg atcctctggg aacctgtgcgg acagtgcacg tgacacaagc ctctagcagc      2100
agcgtgacca tcacctggac aagagtgcca ggcgctacag gatacagagt gtcctggcat      2160
tctgctcacg gccctgagaa gtctcagctg gtgtctggcg aagccacagt ggctgaactc      2220
gacggactgg aacctgacac agagtatact gtgcacgtgc gggctcatgt ggctggtgtt      2280
gatgaccctc ctgcttctgt ggtcgtcaga acagccctg aacctgtggg aagagtgtcc      2340
agactgcaga tcctgaatgc cagcagcgac gtgctgagga tcacatgggt tggagtgacc      2400
ggcgccacag cttatagact cgcctggggt agaagcgaag gcggccctat gagacatcag      2460
atcctgcctg gcaataccga ctccgccgag attagaggcc ttgaaggcgg agtgtcttac      2520
agcgttagag tgacagccct cgtgggcgat agagaaggca cacctgtgtc catcgtggtc      2580
accacacctc cagaagctcc tccagctctg gaacactgc atgtggtgca gagaggcgag      2640
cactctctga gactgagatg ggaacctgtg ccacgcgctc agggatttct gctgcattgg      2700
caaccagaag gcggacaaga gcagagcaga gtgctgggac cagaactgag cagctaccac      2760
ctcgatggac ttgagcctgc cactcagtat agagtcagac tgtcagtgct ggggcctgcc      2820
ggcgaaggac cttctgctga agtgacagct agaaccgagt ctcccagagt gcccagcatc      2880
gagctgagag tcgtggatac ctccatcgat agcgtgacac tggcctggac acccgtgtct      2940
agagccagct cttacatcct gtcttggcgg cctctcagag gaccaggcca agaagttcct      3000
ggatctccac agacactccc aggcatcagt agctcccaga gagtgactgg acttgaacca      3060
ggcgtgtcct acatcttcag cctgacacct gtgctggacg gcgttagagg acctgaagcc      3120
tctgtgaccc agactccagt gtgtcctaga ggactggccg atgtggtgtt cctgcctcac      3180
gctacacagg acaatgccca tagagccgag gccacaagac gcgtgctgga aagactggtt      3240
cttgcccttg gaccactggg acctcaggct gttcaagtgg gcctgctgtc ctactctcac      3300
agaccctctc cactgttccc tctgaacggc tctcacgacc tgggcatcat cctgcagaga      3360
atccgggaca tgccctacat ggaccctctc ggcaacaatc tgggcacagc cgttgtgact      3420
gcccacagat atatgctggc cccagatgct cctggcagac gacaacatgt ccctggcgtt      3480
```

```
atggtgctgc tggtcgatga acccctgcgg ggcgatatct ttagccctat tagagaagcc   3540
caggccagcg gcctgaatgt ggttatgctt ggaatggctg gcgccgatcc agagcagctt   3600
agaaggcttg cccctggcat ggatagcgtg cagaccttct tgccgtggac cgatggacct   3660
tctctggatc aggctgtgtc tggactggct acagcactgt gccaggcaag cttcaccaca   3720
cagcctagac ctgagccttg tccagtgtac tgccctaagg gacagaaggg cgaacctggc   3780
gaaatgggac ttagaggcca agtgggacca cctggcgatc ctggacttcc tggaagaact   3840
ggtgctcctg gacctcaagg tcctcctgga agtgccacag ccaagggcga agaggattc    3900 cctggcgctg atggcagacc aggatctcct ggtagagccg gcaatcctgg aacacctggc   3960
gcaccaggac tcaaaggatc tccaggactg cctggaccta gaggcgatcc aggcgagaga   4020
ggaccaagag gtccaaaagg cgaacccggt gctccaggac aagtgattgg cggagaagga   4080
cccggattgc ccggaagaaa aggcgaccct ggaccaagtg gacctccagg acctagggga   4140
cctttgggag atcccggtcc aagaggccct cctggattgc ctggtacagc catgaagggc   4200
gacaaaggcg ataggggaga agaggaccca ccaggaccag gcgaaggtgg aattgctcct   4260
ggcgaaccag ggttgcctgg actccctggc tcacctggac acaaggacc tgttggccca    4320 cctggaaaga aaggcgaaaa gggcgattct gaggatggcg ccccagggct tcctggacaa   4380
ccaggctctc caggcgaaca aggacccaga gggcctccag gtgctattgg ccctaaaggc   4440
gacagagggt ttcccggacc acttggagaa gctggcgaaa aaggcgaacg aggacctcct   4500
ggacctgccg gatctagagg acttccaggt gttgctggca gacctggcgc taaaggtcct   4560
gaaggcccac cagggcctac aggcagacaa ggcgagaaag gcgagccagg cagacccggc   4620
gatcctgctg ttgttggacc agctgttgca ggcccaaagg gcgagaaggg cgacgttgga   4680
cctgctggac aaggggagc tacaggcgtt caaggcgaaa ggggtccacc tggacttgtt   4740
ttgccgggcg atcccggacc taagggcgac cccggcgaca ggggaccaat tggattgaca   4800
ggcagagctg ggccaccagg cgatagtggg cctccaggcg aaaaaggcga tcctggtaga   4860
cctggacctc ctgggccagt tggaccaaga ggaagagatg gcgaagtcgg agagaaaggc   4920
gacgaaggtc ctccaggcga cccaggactc cctggaaaag caggcgaaag aggtcttaga   4980
ggcgctcctg tgttagagg ccctgttgga gaaaagggcg accaaggcga ccctggcgag   5040 gatgaagaa atggctcccc tggatctagc ggcccaaaag gcgatcgcgg cgagcccggt   5100
ccaccgggtc caccaggcag gcttgttgat actggacccg gcgctcgtga aaaaggcgag   5160
cccggcgatc gtgacaaga aggcccaaga ggacccaagg gcgatccggg actgccaggt   5220
gcaccaggcg agcgaggtat tgaaggattc agaggccctc caggaccaca aggcgatccc   5280
ggtgtcagag gacctgctgg cgagaagggc gatagaggtc ctccaggact ggatggcaga   5340
tccggacttg atggaaaacc cggcgcagct ggcccttctg gacctaatgg tgcagccgga   5400
aaagctggcg acccaggcag agatggattg ccaggattga ggggagaaca gggactcccc   5460
ggaccttctg ggccgcctgg gttgcccgga aagcctggcg aagatggcaa acctggcctg   5520
aacggcaaaa acggcgaacc gggcgatcca ggcgaagatg gcagaaaggg cgaaaaaggc   5580
gacagcggag cctctggccg agagggtaga gatggaccta aaggcgagag gggcgctcct   5640
ggaattttgg accccaaggg accgcctggg ctgccaggtc cagttgggcc tcctggtcaa   5700
ggttttcctg gtgtcccagg cggaactgga ccaaaaggcg atagaggcga acaggctct    5760 aagggcgagc aaggacttcc tggcgaacgt ggactgagag gcgaacctgg aagcgtgccc   5820
```

```
aatgtggaca gactcctgga aaccgccgga atcaaagcca gcgctctgcg ggaaatcgtg    5880
gaaacctggg atgagagcag cggctctttt ctgcctgtgc ctgaaagaag aaggggaccg    5940
aaaggcgatt ctggcgaaca aggtccacct ggcaaagagg gccctatcgg atttcccggc    6000
gagcggggtc ttaaaggcga ccggggagat ccgggacctc aagggccacc aggacttgct    6060
cttggagaaa gaggtcctcc ggggccatct ggacttgctg gcgagcctgg aaaacctgga    6120
ataccaggac ttcccggcag agcaggcgga gttggagagg ccggacgacc tggcgaacgc    6180
ggagaaaggg gagagaaggg cgagcgaggc gaacagggac gagatggacc accgggcctc    6240
cctggaactc ctggaccgcc aggaccacct ggtcctaaag tgtcagtgga tgagcctgga    6300
ccaggtctta gcggagaaca aggacctcca ggcctgaaag cgctaaggg cgaaccaggt     6360
tcaaatggcg atcagggacc caaaggcgat cggggcgttc caggcattaa gggcgaccgt    6420
ggcgaaccag gacctagagg acaagatggc aatcccggac tgcctggcga aagaggaatg    6480
gccgacctg agggaaagcc agggctgcaa gggcctcgcg ggccacctgg gcctgtcgga     6540
ggacatggcg accccggacc accaggtgct cccggacttg ctggaccagc aggacctcaa    6600
ggaccatctg gacttaaagg cgaaccaggc gaaacagggc caccaggcag aggacttaca    6660
ggacctacag gtgctgttgg gttgcctggt ccaccagggc caagtggact tgttggtcct    6720
caaggttcac ctggactgcc cggacaagtg ggagaaactg gcaaaccagg cgcacctggg    6780
cgagatggcg catctggaaa agacggcgat cgaggtagcc ctggtgttcc cggttctcct    6840
gggctcccag gacctgtggg ccccaagggc gaacccggac caactggcgc acctggtcaa    6900
gcagttgttg gattgcctgg cgcaaaggc gagaaaggtg ctccaggcgg attggctggc     6960
gatcttgttg gagaaccagg tgccaaaggc gacagggct tgccaggtcc taggggagag     7020
aaaggcgaag ctggtagagc aggcgagcct ggcgatcccg gcgaggacgg acaaaaaggt    7080
gcccctgggc ctaaaggctt taagggcgat cctggtgtcg gcgtcccagg ttctcctgga    7140
ccacctgggc cgccaggcgt taagggcgat ttgggacttc ctgggctgcc tggcgctcct    7200
ggcgttgtgg gatttccagg acaaactggc cctcggggag aaatgggtca acctgggcct    7260
agcggagaaa gaggccttgc cggacctcct ggaagagagg gaatacctgg accacttgga    7320
ccgcctggac ctccaggttc tgttggacct cctggcgctt caggattgaa gggcgataag    7380
ggcgaccctg tgttggact tcccggtcct cgtggcgaaa gggagaacc aggcattaga     7440
ggcgaagatg gacggcctgg acaagaggga cctagaggtc ttacaggccc accaggctct    7500
agaggcgaaa gggcgagaa aggcgacgtg ggttctgcag gacttaaggg cgacaagggc    7560
gattccgctg tgattttggg accaccggga ccaagaggcg ctaaaggcga tatgggcgag    7620
agaggcccta gaggcctgga tggcgataag gggccaagag gcgacaacgg cgacccaggc    7680
gataagggat ctaaaggcga acccggcgat aagggctctg ctggactgcc aggacttcga    7740
ggacttctgg gtccacaagg ccaacctggc gccgcaggca ttcccggcga tccgggttct    7800
cctggcaaag atggtgttcc tggcatcagg ggcgaaaagg gcgacgtcgg ttttatgggc    7860
cctcgcggat tgaaaggcga gagaggtgtt aagggcgcct gtggacttga cggcgaaaaa    7920
ggcgataagg gcgaagctgg acctcctggc agacctggat tggctggaca aagggcgag     7980
atgggagagc ccggtgttcc tggacaaagt ggcgcccctg gaaaagaagg actgatcggt    8040
ccaaagggcg accgcggatt tgatggccaa ccgggtccta aaggcgatca gggcgagaaa    8100
ggcgaaagag gcactcctgg catcggaggc tttccaggac caagcggcaa tgatggatct    8160
gctggcccgc cagggcctcc tggatctgtt ggtccaagag gaccagaagg cctgcaggga    8220
```

-continued

| | |
|---|---|
| caaaaaggcg agcgcggacc accaggcgaa agagttgttg gagcacccgg cgttcccggt | 8280 |
| gctcccggcg aaagaggcga acaaggcaga cctggaccag ctggccctag aggcgaaaaa | 8340 |
| ggggaagccg ctctgaccga ggacgatatc agaggctttg tgcggcaaga gatgagccag | 8400 |
| cattgtgcct gtcaggggca gtttatcgcc agcggttcta gacctctgcc tagctatgcc | 8460 |
| gctgataccg ccggatctca gctgcatgct gtgcctgtgc ttagagtgtc tcacgccgag | 8520 |
| gaagaggaaa gagtccctcc agaggacgac gagtactccg agtatagcga gtactctgtg | 8580 |
| gaagagtatc aggaccccga ggctccttgg gatagcgacg atccatgttc tctgccactg | 8640 |
| gatgagggca gctgtaccgc ctacacactg aggtggtatc acagagccgt gaccggaagc | 8700 |
| accgaggcct gccatccttt tgtttatggc ggctgcggcg caacgccaa tagatttgga | 8760 |
| acaagagagg cctgcgagcg gagatgccct ccaagagtgg ttcagtctca aggcaccggc | 8820 |
| actgcccagg actaa | 8835 |

<210> SEQ ID NO 13
<211> LENGTH: 4494
<212> TYPE: DNA
<213> ORGANISM: Homo sapiens

<400> SEQUENCE: 13

| | |
|---|---|
| atggatgtaa ccaagaaaaa caaacgagat ggaactgaag tcactgagag aattgtcact | 60 |
| gaaacagtaa ccacaagact tacatcctta ccaccaaaag gcgggaccag caatggctat | 120 |
| gctaaaacag cctctcttgg tggagggagc cggctggaga acaaagcct gactcatggc | 180 |
| agcagcggct acataaactc aactggaagc acacgaggcc atgcctccac ctctagttac | 240 |
| aggagggctc actcacctgc ctccactctg cccaactccc caggctcaac ctttgaaagg | 300 |
| aaaactcacg ttacccgcca tgcgtatgaa gggagctcca gtggcaactc ttctccggag | 360 |
| taccctcgga aggaatttgc atcttcttca accagaggac ggagtcaaac acgagagagt | 420 |
| gaaattcgag ttcgactgca gagtgcgtcc ccatccaccc gatggacaga attggatgat | 480 |
| gttaagcgtt tgctcaaggg gagtcgatcg gcaagtgtga gccccacccg gaattcctcc | 540 |
| aacacactcc ccatcccca gaaaggcact gtggagacca aaattgtgac agcgagctcc | 600 |
| cagtcggtgt caggcaccta cgatgcaacg atcctggatg ccaaccttcc ctcccatgtg | 660 |
| tggtcctcca ccctgccgc ggggtcctcc atggggacct atcacaacaa catgacaacc | 720 |
| cagagctcat ccctcctcaa caccaatgcc tactctgcgg gatcagtctt cggagttcca | 780 |
| aacaacatgg cgtcctgctc acccactttg caccctggac tcagcacatc ctcctcagtg | 840 |
| tttggcatgc agaacaatct ggccccccagc ttgaccaccc tgtcccatgg caccaccacc | 900 |
| acttccacag catatgggt gaagaaaaac atgcccaga gtcctgcggc tgtgaacact | 960 |
| ggcgtttcca cctccgccgc ctgcaccaca agtgtgcaga gcgatgaccct tttgcacaag | 1020 |
| gactgcaagt tcctgatcct agagaaagac aacacacctg caagaagga gatggagctg | 1080 |
| ctcatcatga ccaaggacag cgggaaggtc tttacagcct cccctgccag catcgctgca | 1140 |
| acttcttttt cagaagacac cctaaaaaaa gaaaagcaag ctgcctacaa tgctgactca | 1200 |
| ggcctaaaag ccgaagctaa tggagacctg aagactgtgt ccacaaaggg caagaccacc | 1260 |
| actgcagata tccacagcta cggcagcagt ggtggtggtg gcagtggagg aggtggcggt | 1320 |
| gttggtggcg ctggcggcgg cccttgggga ccagcgccag cctggtgccc ctgcggctcc | 1380 |
| tgctgcagct ggtggaagtg gctgctgggc ctgctgctca cctggctgct actcctgggg | 1440 |

```
ctgctcttcg gcctcattgc tctggcggag gaggtgagga agctgaaggc gcgtgtggat    1500
gagctggaga ggatcaggag gagcatactg ccctatgggg acagcatgga tagaatagaa    1560
aaggaccgcc tccagggcat ggcacccgcg gcgggagcag acctggacaa aattgggctg    1620
cacagtgaca gccaggagga gctctggatg ttcgtgagga agaagctaat gatggaacag    1680
gaaaatggaa atctccgagg aagccctggc cctaaaggtg acatgggaag tccaggccct    1740 aaggagatc gagggttccc tgggactcca ggtatccctg gcccttgggg ccacccaggt     1800
ccacaaggac caaagggtca aaaggcagc gtgggagatc ctggcatgga aggccccatg     1860
ggccagagag ggcgagaagg ccccatggga cctcgtggtg aggcagggcc tcctggatct    1920
ggagagaaag gggaagagg ggctgctggt gaaccaggtc ctcatggccc acctggtgtc     1980
ccaggttctg tgggtcccaa aggttccagc ggctctcctg cccacaggg ccctccaggt     2040 cctgtaggtc tccaagggct ccgaggtgaa gtaggacttc ctggtgtcaa aggtgacaaa    2100
ggaccaatgg gaccaccagg acccaaaggt gaccagggtg agaaaggacc tcgaggcctc    2160
acaggcgagc ctggcatgag aggtttgcct ggtgctgttg gtgagcccgg ggctaaagga    2220
gcaatgggtc ctgctggccc agacggacac caaggcccaa gaggtgaaca aggtcttact    2280
gggatgcctg gaatccgtgg cccaccagga ccttctggag acccaggaaa gccaggtctc    2340 acaggaccccc agggacctca gggacttccc ggtaccctg gccgaccagg aataaaaggt    2400
gaaccaggag ctccaggcaa gatcgtgact tcggaggggt catcgatgct cactgtccca    2460 ggcccccag gacctcctgg agccatggga ccccaggac ctccaggtgc cccaggccct     2520 gccgcccag ctggtctccc aggacatcaa gaagttctta atttacaagg tcccccaggc     2580
ccacccggcc cacgcgggcc accagggcct tccattccag gcccaccagg accccgaggc    2640
ccaccagggg agggtttgcc aggcccacca ggcccaccag gatcgttcct gtccaactca    2700
gaaaccttcc tctccggccc cccagggcca cctggccccc caggtcccaa gggagaccaa    2760
ggtcccccag gccccagagg acaccaaggc gagcaaggcc tcccaggttt ctcaacctca    2820
gggtccagtt ctttcggact caaccttcag ggaccaccag gcccacctgg ccccaggga     2880 cccaaaggtg acaaaggtga tccaggtgtt ccagggctc ttggcattcc tagtggtcct     2940
tctgaagggg gatcatcaag taccatgtac gtgtcaggcc cgccagggcc ccctgggccc    3000
cctgggcctc cgggctctat cagcagctct ggccaggaga ttcagcagta catctctgag    3060
tacatgcaga gtgacagtat tagatcttac ctatccggag ttcagggtcc cccaggccca    3120
cctggtcccc caggacctgt caccaccatc acaggcgaga ctttcgacta ctcagagctg    3180
gcaagccacg ttgtgagcta cttacggact tcggggtacg gtgtcagctt gttctcgtcc    3240
tccatctctt ctgaagacat tctggctgtg ctgcagcggg atgacgtgcg tcagtaccta    3300
cgtcagtact tgatgggccc tcggggtccg ccagggccac caggagccag tggagatggg    3360
tccctcctgt ctttggacta tgcagagctg agtagtcgca ttctcagcta catgtcgagt    3420
tctgggatca gcattgggct tcctggtccc ccggggcccc ctggcttgcc gggaacctcc    3480
tatgaggagc tcctctcctt gctgcgaggg tctgaattca gaggcatcgt tggaccccca    3540
ggtccccggg gtccaccagg gatcccaggc aatgtgtggt ccagcatcag cgtggaggac    3600
ctctcgtctt acttacatac tgccggcttg tcattcatcc caggccctcc aggacctcct    3660 ggtccccag ggcctcgagg gccccggggt gtctcaggag ccctggcaac ctatgcagct    3720
gaaaacagcg acagcttccg gagcgagctg atcagctacc tcacaagtcc tgatgtgcgc    3780
agcttcattg ttgccccccc aggccctcct gggccgcagg gaccccctgg ggacagccgc    3840
```

```
ctcctgtcca cggatgcctc ccacagtcgg ggtagcagct cctcctcaca cagctcatct    3900
gtcaggcggg gcagctccta cagctcttcc atgagcacac gaggaggtgg tgcaggctcc    3960
ctgggtgcag gcggtgcctt tggtgaagct gcaggagaca ggggtcccta tggcactgac    4020
atcggcccag gcggaggcta tggggcagca gcagaaggcg gcatgtatgc tggcaatggc    4080
ggactattgg gagctgactt tgctggagat ctggattaca atgagctggc tgtgagggtg    4140
tcagagagca tgcagcgtca gggcctactg caagggatgg cctacactgt ccagggccca    4200
ccaggccagc ctgggccaca ggggccaccc ggcatcagca aggtcttctc tgcctacagc    4260
aacgtgactg cggacctcat ggacttcttc caaacttatg gagccattca aggaccccct    4320
gggcaaaaag gagagatggg cactccagga cccaaaggtg acaggggccc tgctgggcca    4380
ccaggtcatc ctgggccacc tggccctcga ggacacaagg gagaaaaagg agacaaaggt    4440
gaccaagtct atgctgggcg agaaggaga agaagtattg ctgtcaagcc gtga           4494

<210> SEQ ID NO 14
<211> LENGTH: 4494
<212> TYPE: DNA
<213> ORGANISM: Artificial Sequence
<220> FEATURE:
<223> OTHER INFORMATION: Synthetic Construct

<400> SEQUENCE: 14
atggacgtga ccaagaagaa caagcgcgac ggcaccgaag tgaccgagag aatcgtgacc      60
gaaaccgtga ccaccagact gaccagcctg cctcctaaag gcggcacctc taatggctac     120
gccaagacag cttctctcgg cggaggcagc agactggaaa agcagtctct gacacacggc     180
agcagcggct acatcaatag caccggctct acaagaggcc acgccagcac aagcagctac     240
agaagggctc acagccctgc cagcacactg cctaatagcc aggcagcac cttcgagaga     300 aagacccacg tgaccagaca cgcctacgag ggctctagca gcggcaatag cagccctgag     360
taccccagaa aagagttcgc cagcagcagc accgaggca gaagccagac acgggaaagc     420
gagatcagag tgcggctgca gtctgctagc cctagcacca gatggaccga gctggacgac     480
gtgaagaggc tgctgaaggg aagcagatcc gccagcgtgt cccctaccag aaacagcagc     540
aacaccctgc ctattcctaa gaaaggcacc gtcgagacta agatcgtgac agccagcagc     600
cagagcgtgt ccggcacata cgatgccaca atcctggacg ccaacctgcc tagccatgtg     660
tggtcctcta cactgcctgc cggaagcagc atgggcacct accacaacaa catgaccaca     720
cagagcagca gcctgctgaa caccaatgcc tactctgccg gctccgtgtt cggcgtgcca     780
aacaatatgg ccagctgcag ccctacactg caccctggcc tgagcacaag ctcctccgtg     840
tttggaatgc agaacaatct ggcccctagc ctgacaaccc tgagccacgg aacaaccacc     900
accagcacag cctacggcgt gaagaaaaac atgcctcagt ctccagccgc cgtgaacaca     960
ggcgttagca catctgccgc ctgtaccaca agcgtgcaga gcgacgatct gctgcacaag    1020
gactgcaagt ttctgatcct ggaaaaggac aacacgcccg ccaagaaaga gatggaactg    1080
ctgatcatga ccaaggacag cggcaaggtg ttcaccgcct ctccagcctc tatccgcgcc    1140
acaagcttta gcgaggacac cctgaagaaa gaaaagcagg ccgcctacaa cgccgactct    1200
ggactgaaag ccgaggccaa cggcgacctg aaaaccgtgt ctaccaaggg caagaccacc    1260
accgccgaca tccacagcta tggatctagc ggaggcggaa gatctggtgg tggcggcgga    1320
gttggaggtg ctggcggagg accttgggga cctgctcctg cttggtgtcc ttgtggctcc    1380
```

```
tgttgcagct ggtggaagtg gctgcttggc ctgctgctga cttggctgct tcttctgggc    1440
ctgctgtttg gcctgattgc cctggctgag gaagtgcgga agctgaaggc cagagtggat    1500
gagctggaac ggatcaggcg gagcatcctg ccttacggcg acagcatgga ccggatcgag    1560
aaggacagac tgcaaggcat ggctccagca gctggcgccg atctggataa gatcggactg    1620
cacagcgaca gccaagagga actctggatg ttcgtgcgga agaaactgat gatggaacaa    1680
gagaacggca acctgagagg cagccctgga cctaagggcg atatgggaag cccaggacca    1740
aaaggcgaca gaggctttcc tggcacacct ggcattccag acctctgggg acatcctggt    1800
cctcagggcc ctaaaggcca gaaaggctct gtgggagatc ccggcatgga aggccctatg    1860
ggacagagag gtagagaagg accaatgggc cctagaggcg aagctggacc tcctggatct    1920
ggcgagaaag gcgaaagggg agctgcaggc gaaccaggac acatggacc  tccaggtgtt    1980 cccggatctg tgggccctaa gggatcttct ggttcccctg gaccacaagg cccacctgga    2040
cctgttggac tccaaggact gaggggcgaa gttggactgc caggcgtcaa gggcgacaag    2100
ggtccaatgg gaccacctgg tccaaaggc  gatcagggc  aaaagggacc tagaggactg    2160
acaggcgagc ccggaatgag aggacttcct ggtgctgttg gagagcctgg cgctaaaggt    2220
gctatgggac ctgcaggccc cgacggacat caaggaccta ggggagaaca gggcctgacc    2280
ggcatgcctg gaattagagg tcctcctgga ccttccggcg atcctggcaa accaggattg    2340
actggacctc agggaccaca gggactgcct ggaacaccag gcagacctgg aatcaaaggc    2400
gaacctggcg ctcccggcaa gattgtgaca tctgagggca gctccatgct gaccgtgcct    2460
ggtccacctg gcctccagg  cgccatgggt cctccgggtc caccaggtgc tccaggacca    2520
gccggaccag caggacttcc aggccatcaa gaagtgctga acctgcaggg gcctcctggg    2580
ccgcctggac caagagggcc accagggcca tctattccag accaccagg  tcctagaggc    2640 cctccaggcg aaggattgcc aggtcctcca gggccacctg gcagctttct gagcaacagc    2700
gagacattcc tgagcggccc tccaggacct cctggaccac caggacctaa aggcgatcaa    2760
ggacctccag gaccgagagg acatcagggc gaacaaggac tgcctggctt tagcacaagc    2820
ggcagctcta gcttcggcct caatctgcag ggtccaccag gccaccagg  acctcaaggt    2880 cctaaaggcg ataagggcga tccaggcgtt ccaggcgctc tgggtattcc ttctggacca    2940
tctgaaggcg gctcctccag cactatgtac gtgtcaggtc caccgggtcc acctggaccg    3000
ccaggaccac ctggatctat ctctagctcc ggccaagaga tccagcagta catcagcgag    3060
tacatgcagt ctgacagcat ccggtcctac tgtctggcg  ttcaaggtcc accgggacct    3120 ccgggggcctc ctggacctgt tacaacaatc accggcgaga ctttcgacta cagcgagctg    3180
gcctctcacg tggtgtccta tctgagaacc agcggctatg gcgtgtccct gttcagctcc    3240
agcatcagct ccgaggacat tctggcagtg ctgcagagg  atgacgtgcg gcagtacctg    3300
agacagtatc tgatgggcc  cagagggcca cctggtccac caggcgctag cggagatgga    3360
tctctgctga gcctggatta cgccgagctg agcagcagaa tcctgagcta catgagcagc    3420
tccggcatct ccattgggtt gcctggacct ccaggtccac caggattgcc tggcacaagc    3480
tacgaggaac tgctgtccct gctgagggc  agcgagttta gggaatcgt  tggaccacct    3540 gggccaccag gtccacctgg tatccctgga aatgtgtggt ctagcatcag cgtggaagat    3600
ctgagcagct acctgcacac agccggcctg agctttatcc aggacctccc agggccgcca    3660
gggcctcctg gtcctcgggg accgcctggc gttagcggag cacttgcaac atatgccgcc    3720
gagaacagcg actccttcag aagcgagctg atctcctacc tgactagccc cgatgtgcgg    3780
```

```
agctttatcg ttggcccgcc tggtcctcca ggacctcaag gacctcctgg cgattctaga    3840
ctgctgagca cagatgccag ccacagcaga ggcagctcct ctagctctca ctccagttct    3900
gtgcggagag gctccagcta cagcagctct atgtcaacag gtggcggagg cgctggaagt    3960
cttggagctg gtggcgcttt tggagaagcc gctggcgatc gtggcccata cggaacagat    4020
attggacccg gcggtggata tggcgctgcc gctgaaggcg ggatgtatgc cggaaatggt    4080
ggactgctgg gcgccgattt tgctggcgac ctggactata atgagctggc cgtcagagtg    4140
tccgagagca tgcaaagaca ggggctgctt caaggcatgg cctacacagt tcaaggccca    4200
ccaggacagc ctggtccaca gggaccaccg ggaatcagca agtgttctc tgcctacagc    4260 aacgtgaccg ccgacctgat ggacttcttc cagacctacg cgccattca gggacctcca    4320 ggccaaaagg gcgaaatggg tacacctggg ccgaaaggcg accgaggacc tgctgggcca    4380
cctggacatc ccgggcctcc agggcctaga ggacacaaag gcgaaaaagg cgacaaaggg    4440
gaccaagtct acgccggcag acggcggaga agatccattg ccgtgaagcc ctaa          4494
```

<210> SEQ ID NO 15
<211> LENGTH: 1464
<212> TYPE: PRT
<213> ORGANISM: Homo sapiens

<400> SEQUENCE: 15

```
Met Phe Ser Phe Val Asp Leu Arg Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His
        35                  40                  45

Asp Arg Asp Val Trp Lys Pro Glu Pro Cys Arg Ile Cys Val Cys Asp
    50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
```

-continued

```
            245                 250                 255
Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
            325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
            355                 360                 365

Val Arg Gly Glu Pro Gly Pro Pro Gly Pro Ala Gly Ala Ala Gly Pro
        370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
            660                 665                 670
```

```
Ser Gly Ala Arg Gly Glu Arg Gly Phe Pro Gly Glu Arg Gly Val Gln
    675                 680                 685

Gly Pro Pro Gly Pro Ala Gly Pro Arg Gly Ala Asn Gly Ala Pro Gly
            690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
            755                 760                 765

Ile Gly Pro Pro Gly Ala Gly Ala Pro Gly Asp Lys Gly Glu Ser
            770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
            835                 840                 845

Pro Pro Gly Pro Ile Gly Asn Val Gly Ala Pro Gly Ala Lys Gly Ala
            850                 855                 860

Arg Gly Ser Ala Gly Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
            930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
            995                 1000                1005

Pro Gly Glu Ser Gly Arg Glu Gly Ala Pro Gly Ala Glu Gly Ser Pro
            1010                1015                1020

Gly Arg Asp Gly Ser Pro Gly Ala Lys Gly Asp Arg Gly Glu Thr Gly
1025                1030                1035                1040

Pro Ala Gly Pro Pro Gly Ala Pro Gly Ala Pro Gly Ala Pro Gly Pro
                1045                1050                1055

Val Gly Pro Ala Gly Lys Ser Gly Asp Arg Gly Glu Thr Gly Pro Ala
            1060                1065                1070

Gly Pro Ala Gly Pro Val Gly Pro Val Gly Ala Arg Gly Pro Ala Gly
            1075                1080                1085
```

```
Pro Gln Gly Pro Arg Gly Asp Lys Gly Glu Thr Gly Glu Gln Gly Asp
    1090                1095                1100

Arg Gly Ile Lys Gly His Arg Gly Phe Ser Gly Leu Gln Gly Pro Pro
1105                1110                1115                1120

Gly Pro Pro Gly Ser Pro Gly Glu Gln Gly Pro Ser Gly Ala Ser Gly
            1125                1130                1135

Pro Ala Gly Pro Arg Gly Pro Pro Gly Ser Ala Gly Ala Pro Gly Lys
                1140                1145                1150

Asp Gly Leu Asn Gly Leu Pro Gly Pro Ile Gly Pro Pro Gly Pro Arg
            1155                1160                1165

Gly Arg Thr Gly Asp Ala Gly Pro Val Gly Pro Pro Gly Pro Pro Gly
    1170                1175                1180

Pro Pro Gly Pro Pro Gly Pro Pro Ser Ala Gly Phe Asp Phe Ser Phe
1185                1190                1195                1200

Leu Pro Gln Pro Pro Gln Glu Lys Ala His Asp Gly Gly Arg Tyr Tyr
                1205                1210                1215

Arg Ala Asp Asp Ala Asn Val Val Arg Asp Arg Asp Leu Glu Val Asp
            1220                1225                1230

Thr Thr Leu Lys Ser Leu Ser Gln Gln Ile Glu Asn Ile Arg Ser Pro
            1235                1240                1245

Glu Gly Ser Arg Lys Asn Pro Ala Arg Thr Cys Arg Asp Leu Lys Met
1250                1255                1260

Cys His Ser Asp Trp Lys Ser Gly Glu Tyr Trp Ile Asp Pro Asn Gln
1265                1270                1275                1280

Gly Cys Asn Leu Asp Ala Ile Lys Val Phe Cys Asn Met Glu Thr Gly
            1285                1290                1295

Glu Thr Cys Val Tyr Pro Thr Gln Pro Ser Val Ala Gln Lys Asn Trp
        1300                1305                1310

Tyr Ile Ser Lys Asn Pro Lys Asp Lys Arg His Val Trp Phe Gly Glu
            1315                1320                1325

Ser Met Thr Asp Gly Phe Gln Phe Glu Tyr Gly Gly Gln Gly Ser Asp
        1330                1335                1340

Pro Ala Asp Val Ala Ile Gln Leu Thr Phe Leu Arg Leu Met Ser Thr
1345                1350                1355                1360

Glu Ala Ser Gln Asn Ile Thr Tyr His Cys Lys Asn Ser Val Ala Tyr
                1365                1370                1375

Met Asp Gln Gln Thr Gly Asn Leu Lys Lys Ala Leu Leu Leu Gln Gly
            1380                1385                1390

Ser Asn Glu Ile Glu Ile Arg Ala Glu Gly Asn Ser Arg Phe Thr Tyr
            1395                1400                1405

Ser Val Thr Val Asp Gly Cys Thr Ser His Thr Gly Ala Trp Gly Lys
    1410                1415                1420

Thr Val Ile Glu Tyr Lys Thr Thr Lys Thr Ser Arg Leu Pro Ile Ile
1425                1430                1435                1440

Asp Val Ala Pro Leu Asp Val Gly Ala Pro Asp Gln Glu Phe Gly Phe
                1445                1450                1455

Asp Val Gly Pro Val Cys Phe Leu
        1460

<210> SEQ ID NO 16
<211> LENGTH: 1366
<212> TYPE: PRT
<213> ORGANISM: Homo sapiens

<400> SEQUENCE: 16
```

```
Met Leu Ser Phe Val Asp Thr Arg Thr Leu Leu Leu Ala Val Thr
1               5                   10                  15

Leu Cys Leu Ala Thr Cys Gln Ser Leu Gln Glu Glu Thr Val Arg Lys
                20              25                  30

Gly Pro Ala Gly Asp Arg Gly Pro Arg Gly Glu Arg Gly Pro Pro Gly
            35              40                  45

Pro Pro Gly Arg Asp Gly Glu Asp Gly Pro Thr Gly Pro Pro Gly Pro
    50              55                  60

Pro Gly Pro Pro Gly Pro Gly Leu Gly Gly Asn Phe Ala Ala Gln
65              70              75                  80

Tyr Asp Gly Lys Gly Val Gly Leu Gly Pro Gly Pro Met Gly Leu Met
                85              90                  95

Gly Pro Arg Gly Pro Pro Gly Ala Ala Gly Ala Pro Gly Pro Gln Gly
            100             105                 110

Phe Gln Gly Pro Ala Gly Glu Pro Gly Glu Pro Gly Gln Thr Gly Pro
        115             120             125

Ala Gly Ala Arg Gly Pro Ala Gly Pro Pro Gly Lys Ala Gly Glu Asp
        130             135             140

Gly His Pro Gly Lys Pro Gly Arg Pro Gly Glu Arg Gly Val Val Gly
145             150             155                 160

Pro Gln Gly Ala Arg Gly Phe Pro Gly Thr Pro Gly Leu Pro Gly Phe
                165             170                 175

Lys Gly Ile Arg Gly His Asn Gly Leu Asp Gly Leu Lys Gly Gln Pro
                180             185                 190

Gly Ala Pro Gly Val Lys Gly Glu Pro Gly Ala Pro Gly Glu Asn Gly
            195             200             205

Thr Pro Gly Gln Thr Gly Ala Arg Gly Leu Pro Gly Glu Arg Gly Arg
    210             215             220

Val Gly Ala Pro Gly Pro Ala Gly Ala Arg Gly Ser Asp Gly Ser Val
225             230             235                 240

Gly Pro Val Gly Pro Ala Gly Pro Ile Gly Ser Ala Gly Pro Pro Gly
            245             250             255

Phe Pro Gly Ala Pro Gly Pro Lys Gly Glu Ile Gly Ala Val Gly Asn
            260             265             270

Ala Gly Pro Ala Gly Pro Ala Gly Pro Arg Gly Glu Val Gly Leu Pro
        275             280             285

Gly Leu Ser Gly Pro Val Gly Pro Pro Gly Asn Pro Gly Ala Asn Gly
    290             295             300

Leu Thr Gly Ala Lys Gly Ala Ala Gly Leu Pro Gly Val Ala Gly Ala
305             310             315                 320

Pro Gly Leu Pro Gly Pro Arg Gly Ile Pro Gly Pro Val Gly Ala Ala
            325             330             335

Gly Ala Thr Gly Ala Arg Gly Leu Val Gly Glu Pro Gly Pro Ala Gly
            340             345             350

Ser Lys Gly Glu Ser Gly Asn Lys Gly Glu Pro Gly Ser Ala Gly Pro
        355             360             365

Gln Gly Pro Pro Gly Pro Ser Gly Glu Glu Gly Lys Arg Gly Pro Asn
    370             375             380

Gly Glu Ala Gly Ser Ala Gly Pro Pro Gly Pro Pro Gly Leu Arg Gly
385             390             395             400

Ser Pro Gly Ser Arg Gly Leu Pro Gly Ala Asp Gly Arg Ala Gly Val
            405             410             415
```

-continued

```
Met Gly Pro Pro Gly Ser Arg Gly Ala Ser Gly Pro Ala Gly Val Arg
            420                 425                 430

Gly Pro Asn Gly Asp Ala Gly Arg Pro Gly Glu Pro Gly Leu Met Gly
        435                 440                 445

Pro Arg Gly Leu Pro Gly Ser Pro Gly Asn Ile Gly Pro Ala Gly Lys
    450                 455                 460

Glu Gly Pro Val Gly Leu Pro Gly Ile Asp Gly Arg Pro Gly Pro Ile
465                 470                 475                 480

Gly Pro Ala Gly Ala Arg Gly Glu Pro Gly Asn Ile Gly Phe Pro Gly
            485                 490                 495

Pro Lys Gly Pro Thr Gly Asp Pro Gly Lys Asn Gly Asp Lys Gly His
        500                 505                 510

Ala Gly Leu Ala Gly Ala Arg Gly Ala Pro Gly Pro Asp Gly Asn Asn
    515                 520                 525

Gly Ala Gln Gly Pro Pro Gly Pro Gln Gly Val Gln Gly Gly Lys Gly
530                 535                 540

Glu Gln Gly Pro Pro Gly Pro Pro Gly Phe Gln Gly Leu Pro Gly Pro
545                 550                 555                 560

Ser Gly Pro Ala Gly Glu Val Gly Lys Pro Gly Glu Arg Gly Leu His
            565                 570                 575

Gly Glu Phe Gly Leu Pro Gly Pro Ala Gly Pro Arg Gly Glu Arg Gly
        580                 585                 590

Pro Pro Gly Glu Ser Gly Ala Ala Gly Pro Thr Gly Pro Ile Gly Ser
    595                 600                 605

Arg Gly Pro Ser Gly Pro Pro Gly Pro Asp Gly Asn Lys Gly Glu Pro
610                 615                 620

Gly Val Val Gly Ala Val Gly Thr Ala Gly Pro Ser Gly Pro Ser Gly
625                 630                 635                 640

Leu Pro Gly Glu Arg Gly Ala Ala Gly Ile Pro Gly Gly Lys Gly Glu
            645                 650                 655

Lys Gly Glu Pro Gly Leu Arg Gly Glu Ile Gly Asn Pro Gly Arg Asp
        660                 665                 670

Gly Ala Arg Gly Ala Pro Gly Ala Val Gly Ala Pro Gly Pro Ala Gly
    675                 680                 685

Ala Thr Gly Asp Arg Gly Glu Ala Gly Ala Ala Gly Pro Ala Gly Pro
690                 695                 700

Ala Gly Pro Arg Gly Ser Pro Gly Glu Arg Gly Glu Val Gly Pro Ala
705                 710                 715                 720

Gly Pro Asn Gly Phe Ala Gly Pro Ala Gly Ala Ala Gly Gln Pro Gly
            725                 730                 735

Ala Lys Gly Glu Arg Gly Ala Lys Gly Pro Lys Gly Glu Asn Gly Val
        740                 745                 750

Val Gly Pro Thr Gly Pro Val Gly Ala Ala Gly Pro Ala Gly Pro Asn
    755                 760                 765

Gly Pro Pro Gly Pro Ala Gly Ser Arg Gly Asp Gly Gly Pro Pro Gly
770                 775                 780

Met Thr Gly Phe Pro Gly Ala Ala Gly Arg Thr Gly Pro Pro Gly Pro
785                 790                 795                 800

Ser Gly Ile Ser Gly Pro Pro Gly Pro Pro Gly Pro Ala Gly Lys Glu
            805                 810                 815

Gly Leu Arg Gly Pro Arg Gly Asp Gln Gly Pro Val Gly Arg Thr Gly
        820                 825                 830

Glu Val Gly Ala Val Gly Pro Pro Gly Phe Ala Gly Glu Lys Gly Pro
```

```
                835                 840                 845
Ser Gly Glu Ala Gly Thr Ala Gly Pro Pro Gly Thr Pro Gly Pro Gln
850                 855                 860
Gly Leu Leu Gly Ala Pro Gly Ile Leu Gly Leu Pro Gly Ser Arg Gly
865                 870                 875                 880
Glu Arg Gly Leu Pro Gly Val Ala Gly Ala Val Gly Glu Pro Gly Pro
                885                 890                 895
Leu Gly Ile Ala Gly Pro Pro Gly Ala Arg Gly Pro Pro Gly Ala Val
                900                 905                 910
Gly Ser Pro Gly Val Asn Gly Ala Pro Gly Glu Ala Gly Arg Asp Gly
                915                 920                 925
Asn Pro Gly Asn Asp Gly Pro Pro Gly Arg Asp Gly Gln Pro Gly His
930                 935                 940
Lys Gly Glu Arg Gly Tyr Pro Gly Asn Ile Gly Pro Val Gly Ala Ala
945                 950                 955                 960
Gly Ala Pro Gly Pro His Gly Pro Val Gly Pro Ala Gly Lys His Gly
                965                 970                 975
Asn Arg Gly Glu Thr Gly Pro Ser Gly Pro Val Gly Pro Ala Gly Ala
                980                 985                 990
Val Gly Pro Arg Gly Pro Ser Gly Pro Gln Gly Ile Arg Gly Asp Lys
                995                 1000                1005
Gly Glu Pro Gly Glu Lys Gly Pro Arg Gly Leu Pro Gly Leu Lys Gly
1010                1015                1020
His Asn Gly Leu Gln Gly Leu Pro Gly Ile Ala Gly His His Gly Asp
1025                1030                1035                1040
Gln Gly Ala Pro Gly Ser Val Gly Pro Ala Gly Pro Arg Gly Pro Ala
                1045                1050                1055
Gly Pro Ser Gly Pro Ala Gly Lys Asp Gly Arg Thr Gly His Pro Gly
                1060                1065                1070
Thr Val Gly Pro Ala Gly Ile Arg Gly Pro Gln Gly His Gln Gly Pro
                1075                1080                1085
Ala Gly Pro Pro Gly Pro Pro Gly Pro Pro Gly Pro Pro Gly Val Ser
                1090                1095                1100
Gly Gly Gly Tyr Asp Phe Gly Tyr Asp Gly Asp Phe Tyr Arg Ala Asp
1105                1110                1115                1120
Gln Pro Arg Ser Ala Pro Ser Leu Arg Pro Lys Asp Tyr Glu Val Asp
                1125                1130                1135
Ala Thr Leu Lys Ser Leu Asn Asn Gln Ile Glu Thr Leu Leu Thr Pro
                1140                1145                1150
Glu Gly Ser Arg Lys Asn Pro Ala Arg Thr Cys Arg Asp Leu Arg Leu
                1155                1160                1165
Ser His Pro Glu Trp Ser Ser Gly Tyr Tyr Trp Ile Asp Pro Asn Gln
                1170                1175                1180
Gly Cys Thr Met Asp Ala Ile Lys Val Tyr Cys Asp Phe Ser Thr Gly
1185                1190                1195                1200
Glu Thr Cys Ile Arg Ala Gln Pro Glu Asn Ile Pro Ala Lys Asn Trp
                1205                1210                1215
Tyr Arg Ser Ser Lys Asp Lys Lys His Val Trp Leu Gly Glu Thr Ile
                1220                1225                1230
Asn Ala Gly Ser Gln Phe Glu Tyr Asn Val Glu Gly Val Thr Ser Lys
                1235                1240                1245
Glu Met Ala Thr Gln Leu Ala Phe Met Arg Leu Leu Ala Asn Tyr Ala
                1250                1255                1260
```

Ser Gln Asn Ile Thr Tyr His Cys Lys Asn Ser Ile Ala Tyr Met Asp
1265                1270                1275                1280

Glu Glu Thr Gly Asn Leu Lys Lys Ala Val Ile Leu Gln Gly Ser Asn
        1285                1290                1295

Asp Val Glu Leu Val Ala Glu Gly Asn Ser Arg Phe Thr Tyr Thr Val
        1300                1305                1310

Leu Val Asp Gly Cys Ser Lys Lys Thr Asn Glu Trp Gly Lys Thr Ile
        1315                1320                1325

Ile Glu Tyr Lys Thr Asn Lys Pro Ser Arg Leu Pro Phe Leu Asp Ile
        1330                1335                1340

Ala Pro Leu Asp Ile Gly Gly Ala Asp Gln Phe Phe Val Asp Ile
1345                1350                1355                1360

Gly Pro Val Cys Phe Lys
                1365

<210> SEQ ID NO 17
<211> LENGTH: 1466
<212> TYPE: PRT
<213> ORGANISM: Homo sapiens

<400> SEQUENCE: 17

Met Met Ser Phe Val Gln Lys Gly Ser Trp Leu Leu Ala Leu Leu
1               5                   10                  15

His Pro Thr Ile Ile Leu Ala Gln Gln Glu Ala Val Glu Gly Gly Cys
                20                  25                  30

Ser His Leu Gly Gln Ser Tyr Ala Asp Arg Asp Val Trp Lys Pro Glu
            35                  40                  45

Pro Cys Gln Ile Cys Val Cys Asp Ser Gly Ser Val Leu Cys Asp Asp
        50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Thr Ala Pro Thr
                85                  90                  95

Arg Pro Pro Asn Gly Gln Gly Pro Gln Gly Pro Lys Gly Asp Pro Gly
                100                 105                 110

Pro Pro Gly Ile Pro Gly Arg Asn Gly Asp Pro Gly Ile Pro Gly Gln
            115                 120                 125

Pro Gly Ser Pro Gly Ser Pro Gly Pro Pro Gly Ile Cys Glu Ser Cys
        130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
                180                 185                 190

Ser Pro Gly Ser Pro Gly Tyr Gln Gly Pro Gly Glu Pro Gly Gln
            195                 200                 205

Ala Gly Pro Ser Gly Pro Pro Gly Pro Pro Gly Ala Ile Gly Pro Ser
        210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn

-continued

```
                260                 265                 270
Gly Glu Lys Gly Glu Thr Gly Ala Pro Gly Leu Lys Gly Glu Asn Gly
            275                 280                 285
Leu Pro Gly Glu Asn Gly Ala Pro Gly Pro Met Gly Pro Arg Gly Ala
        290                 295                 300
Pro Gly Glu Arg Gly Arg Pro Gly Leu Pro Gly Ala Ala Gly Ala Arg
305                 310                 315                 320
Gly Asn Asp Gly Ala Arg Gly Ser Asp Gly Gln Pro Gly Pro Pro Gly
                325                 330                 335
Pro Pro Gly Thr Ala Gly Phe Pro Gly Ser Pro Gly Ala Lys Gly Glu
            340                 345                 350
Val Gly Pro Ala Gly Ser Pro Gly Ser Asn Gly Ala Pro Gly Gln Arg
        355                 360                 365
Gly Glu Pro Gly Pro Gln Gly His Ala Gly Ala Gln Gly Pro Pro Gly
    370                 375                 380
Pro Pro Gly Ile Asn Gly Ser Pro Gly Gly Lys Gly Glu Met Gly Pro
385                 390                 395                 400
Ala Gly Ile Pro Gly Ala Pro Gly Leu Met Gly Ala Arg Gly Pro Pro
                405                 410                 415
Gly Pro Ala Gly Ala Asn Gly Ala Pro Gly Leu Arg Gly Gly Ala Gly
            420                 425                 430
Glu Pro Gly Lys Asn Gly Ala Lys Gly Glu Pro Gly Pro Arg Gly Glu
        435                 440                 445
Arg Gly Glu Ala Gly Ile Pro Gly Val Pro Gly Ala Lys Gly Glu Asp
    450                 455                 460
Gly Lys Asp Gly Ser Pro Gly Glu Pro Gly Ala Asn Gly Leu Pro Gly
465                 470                 475                 480
Ala Ala Gly Glu Arg Gly Ala Pro Gly Phe Arg Gly Pro Ala Gly Pro
                485                 490                 495
Asn Gly Ile Pro Gly Glu Lys Gly Pro Ala Gly Glu Arg Gly Ala Pro
            500                 505                 510
Gly Pro Ala Gly Pro Arg Gly Ala Ala Gly Glu Pro Gly Arg Asp Gly
        515                 520                 525
Val Pro Gly Gly Pro Gly Met Arg Gly Met Pro Gly Ser Pro Gly Gly
    530                 535                 540
Pro Gly Ser Asp Gly Lys Pro Gly Pro Pro Gly Ser Gln Gly Glu Ser
545                 550                 555                 560
Gly Arg Pro Gly Pro Pro Gly Pro Ser Gly Pro Arg Gly Gln Pro Gly
                565                 570                 575
Val Met Gly Phe Pro Gly Pro Lys Gly Asn Asp Gly Ala Pro Gly Lys
            580                 585                 590
Asn Gly Glu Arg Gly Gly Pro Gly Gly Pro Gly Pro Gln Gly Pro Pro
        595                 600                 605
Gly Lys Asn Gly Glu Thr Gly Pro Gln Gly Pro Pro Gly Pro Thr Gly
    610                 615                 620
Pro Gly Gly Asp Lys Gly Asp Thr Gly Pro Pro Gly Pro Gln Gly Leu
625                 630                 635                 640
Gln Gly Leu Pro Gly Thr Gly Gly Pro Pro Gly Glu Asn Gly Lys Pro
                645                 650                 655
Gly Glu Pro Gly Pro Lys Gly Asp Ala Gly Ala Pro Gly Ala Pro Gly
            660                 665                 670
Gly Lys Gly Asp Ala Gly Ala Pro Gly Glu Arg Gly Pro Pro Gly Leu
        675                 680                 685
```

```
Ala Gly Ala Pro Gly Leu Arg Gly Gly Ala Gly Pro Pro Gly Pro Glu
        690                 695                 700
Gly Gly Lys Gly Ala Ala Gly Pro Pro Gly Pro Pro Gly Ala Ala Gly
705                 710                 715                 720
Thr Pro Gly Leu Gln Gly Met Pro Gly Glu Arg Gly Gly Leu Gly Ser
                    725                 730                 735
Pro Gly Pro Lys Gly Asp Lys Gly Glu Pro Gly Gly Pro Gly Ala Asp
                740                 745                 750
Gly Val Pro Gly Lys Asp Gly Pro Arg Gly Pro Thr Gly Pro Ile Gly
            755                 760                 765
Pro Pro Gly Pro Ala Gly Gln Pro Gly Asp Lys Gly Glu Gly Gly Ala
770                 775                 780
Pro Gly Leu Pro Gly Ile Ala Gly Pro Arg Gly Ser Pro Gly Glu Arg
785                 790                 795                 800
Gly Glu Thr Gly Pro Pro Gly Pro Ala Gly Phe Pro Gly Ala Pro Gly
                805                 810                 815
Gln Asn Gly Glu Pro Gly Gly Lys Gly Glu Arg Gly Ala Pro Gly Glu
                820                 825                 830
Lys Gly Glu Gly Gly Pro Pro Gly Val Ala Gly Pro Pro Gly Gly Ser
            835                 840                 845
Gly Pro Ala Gly Pro Pro Gly Pro Gln Gly Val Lys Gly Glu Arg Gly
850                 855                 860
Ser Pro Gly Gly Pro Gly Ala Ala Gly Phe Pro Gly Ala Arg Gly Leu
865                 870                 875                 880
Pro Gly Pro Pro Gly Ser Asn Gly Asn Pro Gly Pro Pro Gly Pro Ser
                885                 890                 895
Gly Ser Pro Gly Lys Asp Gly Pro Pro Gly Pro Ala Gly Asn Thr Gly
                900                 905                 910
Ala Pro Gly Ser Pro Gly Val Ser Gly Pro Lys Gly Asp Ala Gly Gln
            915                 920                 925
Pro Gly Glu Lys Gly Ser Pro Gly Ala Gln Gly Pro Pro Gly Ala Pro
930                 935                 940
Gly Pro Leu Gly Ile Ala Gly Ile Thr Gly Ala Arg Gly Leu Ala Gly
945                 950                 955                 960
Pro Pro Gly Met Pro Gly Pro Arg Gly Ser Pro Gly Pro Gln Gly Val
                965                 970                 975
Lys Gly Glu Ser Gly Lys Pro Gly Ala Asn Gly Leu Ser Gly Glu Arg
                980                 985                 990
Gly Pro Pro Gly Pro Gln Gly Leu Pro Gly Leu Ala Gly Thr Ala Gly
            995                 1000                1005
Glu Pro Gly Arg Asp Gly Asn Pro Gly Ser Asp Gly Leu Pro Gly Arg
    1010                1015                1020
Asp Gly Ser Pro Gly Gly Lys Gly Asp Arg Gly Glu Asn Gly Ser Pro
1025                1030                1035                1040
Gly Ala Pro Gly Ala Pro Gly His Pro Gly Pro Pro Gly Pro Val Gly
                1045                1050                1055
Pro Ala Gly Lys Ser Gly Asp Arg Gly Glu Ser Gly Pro Ala Gly Pro
                1060                1065                1070
Ala Gly Ala Pro Gly Pro Ala Gly Ser Arg Gly Ala Pro Gly Pro Gln
            1075                1080                1085
Gly Pro Arg Gly Asp Lys Gly Glu Thr Gly Glu Arg Gly Ala Ala Gly
    1090                1095                1100
```

-continued

Ile Lys Gly His Arg Gly Phe Pro Gly Asn Pro Gly Ala Pro Gly Ser
    1105                1110                1115                1120

Pro Gly Pro Ala Gly Gln Gln Gly Ala Ile Gly Ser Pro Gly Pro Ala
            1125                1130                1135

Gly Pro Arg Gly Pro Val Gly Pro Ser Gly Pro Pro Gly Lys Asp Gly
        1140                1145                1150

Thr Ser Gly His Pro Gly Pro Ile Gly Pro Pro Gly Pro Arg Gly Asn
    1155                1160                1165

Arg Gly Glu Arg Gly Ser Glu Gly Ser Pro Gly His Pro Gly Gln Pro
1170                1175                1180

Gly Pro Pro Gly Pro Pro Gly Ala Pro Gly Pro Cys Cys Gly Gly Val
1185                1190                1195                1200

Gly Ala Ala Ala Ile Ala Gly Ile Gly Gly Glu Lys Ala Gly Gly Phe
            1205                1210                1215

Ala Pro Tyr Tyr Gly Asp Glu Pro Met Asp Phe Lys Ile Asn Thr Asp
            1220                1225                1230

Glu Ile Met Thr Ser Leu Lys Ser Val Asn Gly Gln Ile Glu Ser Leu
        1235                1240                1245

Ile Ser Pro Asp Gly Ser Arg Lys Asn Pro Ala Arg Asn Cys Arg Asp
    1250                1255                1260

Leu Lys Phe Cys His Pro Glu Leu Lys Ser Gly Glu Tyr Trp Val Asp
1265                1270                1275                1280

Pro Asn Gln Gly Cys Lys Leu Asp Ala Ile Lys Val Phe Cys Asn Met
            1285                1290                1295

Glu Thr Gly Glu Thr Cys Ile Ser Ala Asn Pro Leu Asn Val Pro Arg
        1300                1305                1310

Lys His Trp Trp Thr Asp Ser Ser Ala Glu Lys Lys His Val Trp Phe
    1315                1320                1325

Gly Glu Ser Met Asp Gly Gly Phe Gln Phe Ser Tyr Gly Asn Pro Glu
1330                1335                1340

Leu Pro Glu Asp Val Leu Asp Val Gln Leu Ala Phe Leu Arg Leu Leu
1345                1350                1355                1360

Ser Ser Arg Ala Ser Gln Asn Ile Thr Tyr His Cys Lys Asn Ser Ile
            1365                1370                1375

Ala Tyr Met Asp Gln Ala Ser Gly Asn Val Lys Lys Ala Leu Lys Leu
            1380                1385                1390

Met Gly Ser Asn Glu Gly Glu Phe Lys Ala Glu Gly Asn Ser Lys Phe
        1395                1400                1405

Thr Tyr Thr Val Leu Glu Asp Gly Cys Thr Lys His Thr Gly Glu Trp
    1410                1415                1420

Ser Lys Thr Val Phe Glu Tyr Arg Thr Arg Lys Ala Val Arg Leu Pro
1425                1430                1435                1440

Ile Val Asp Ile Ala Pro Tyr Asp Ile Gly Gly Pro Asp Gln Glu Phe
            1445                1450                1455

Gly Val Asp Val Gly Pro Val Cys Phe Leu
            1460                1465

<210> SEQ ID NO 18
<211> LENGTH: 1669
<212> TYPE: PRT
<213> ORGANISM: Homo sapiens

<400> SEQUENCE: 18

Met Gly Pro Arg Leu Ser Val Trp Leu Leu Leu Leu Pro Ala Ala Leu
1               5                   10                  15

```
Leu Leu His Glu Glu His Ser Arg Ala Ala Lys Gly Gly Cys Ala
        20                  25                  30
Gly Ser Gly Cys Gly Lys Cys Asp Cys His Gly Val Lys Gly Gln Lys
        35                  40                  45
Gly Glu Arg Gly Leu Pro Gly Leu Gln Gly Val Ile Gly Phe Pro Gly
        50                  55                  60
Met Gln Gly Pro Glu Gly Pro Gln Gly Pro Gly Gln Lys Gly Asp
65                  70                  75                  80
Thr Gly Glu Pro Gly Leu Pro Gly Thr Lys Gly Thr Arg Gly Pro Pro
                85                  90                  95
Gly Ala Ser Gly Tyr Pro Gly Asn Pro Gly Leu Pro Gly Ile Pro Gly
                100                 105                 110
Gln Asp Gly Pro Pro Gly Pro Pro Gly Ile Pro Gly Cys Asn Gly Thr
                115                 120                 125
Lys Gly Glu Arg Gly Pro Leu Gly Pro Pro Gly Leu Pro Gly Phe Ala
        130                 135                 140
Gly Asn Pro Gly Pro Pro Gly Leu Pro Gly Met Lys Gly Asp Pro Gly
145                 150                 155                 160
Glu Ile Leu Gly His Val Pro Gly Met Leu Leu Lys Gly Glu Arg Gly
                165                 170                 175
Phe Pro Gly Ile Pro Gly Thr Pro Gly Pro Pro Gly Leu Pro Gly Leu
                180                 185                 190
Gln Gly Pro Val Gly Pro Pro Gly Phe Thr Gly Pro Pro Gly Pro Pro
        195                 200                 205
Gly Pro Pro Gly Pro Pro Gly Glu Lys Gly Gln Met Gly Leu Ser Phe
        210                 215                 220
Gln Gly Pro Lys Gly Asp Lys Gly Asp Gln Gly Val Ser Gly Pro Pro
225                 230                 235                 240
Gly Val Pro Gly Gln Ala Gln Val Gln Glu Lys Gly Asp Phe Ala Thr
                245                 250                 255
Lys Gly Glu Lys Gly Gln Lys Gly Glu Pro Gly Phe Gln Gly Met Pro
                260                 265                 270
Gly Val Gly Glu Lys Gly Glu Pro Gly Lys Pro Gly Pro Arg Gly Lys
        275                 280                 285
Pro Gly Lys Asp Gly Asp Lys Gly Glu Lys Gly Ser Pro Gly Phe Pro
        290                 295                 300
Gly Glu Pro Gly Tyr Pro Gly Leu Ile Gly Arg Gln Gly Pro Gln Gly
305                 310                 315                 320
Glu Lys Gly Glu Ala Gly Pro Pro Gly Pro Pro Gly Ile Val Ile Gly
                325                 330                 335
Thr Gly Pro Leu Gly Glu Lys Gly Glu Arg Gly Tyr Pro Gly Thr Pro
                340                 345                 350
Gly Pro Arg Gly Glu Pro Gly Pro Lys Gly Phe Pro Gly Leu Pro Gly
                355                 360                 365
Gln Pro Gly Pro Pro Gly Leu Pro Val Pro Gly Gln Ala Gly Ala Pro
                370                 375                 380
Gly Phe Pro Gly Glu Arg Gly Glu Lys Gly Asp Arg Gly Phe Pro Gly
385                 390                 395                 400
Thr Ser Leu Pro Gly Pro Ser Gly Arg Asp Gly Leu Pro Gly Pro Pro
                405                 410                 415
Gly Ser Pro Gly Pro Gly Gln Pro Gly Tyr Thr Asn Gly Ile Val
                420                 425                 430
```

-continued

```
Glu Cys Gln Pro Gly Pro Pro Gly Asp Gln Gly Pro Pro Gly Ile Pro
            435                 440                 445

Gly Gln Pro Gly Phe Ile Gly Glu Ile Gly Glu Lys Gly Gln Lys Gly
    450                 455                 460

Glu Ser Cys Leu Ile Cys Asp Ile Asp Gly Tyr Arg Gly Pro Pro Gly
465                 470                 475                 480

Pro Gln Gly Pro Pro Gly Glu Ile Gly Phe Pro Gly Gln Pro Gly Ala
                485                 490                 495

Lys Gly Asp Arg Gly Leu Pro Gly Arg Asp Gly Val Ala Gly Val Pro
            500                 505                 510

Gly Pro Gln Gly Thr Pro Gly Leu Ile Gly Gln Pro Gly Ala Lys Gly
        515                 520                 525

Glu Pro Gly Glu Phe Tyr Phe Asp Leu Arg Leu Lys Gly Asp Lys Gly
    530                 535                 540

Asp Pro Gly Phe Pro Gly Gln Pro Gly Met Pro Gly Arg Ala Gly Ser
545                 550                 555                 560

Pro Gly Arg Asp Gly His Pro Gly Leu Pro Gly Pro Lys Gly Ser Pro
            565                 570                 575

Gly Ser Val Gly Leu Lys Gly Glu Arg Gly Pro Pro Gly Gly Val Gly
        580                 585                 590

Phe Pro Gly Ser Arg Gly Asp Thr Gly Pro Pro Gly Pro Pro Gly Tyr
    595                 600                 605

Gly Pro Ala Gly Pro Ile Gly Asp Lys Gly Gln Ala Gly Phe Pro Gly
        610                 615                 620

Gly Pro Gly Ser Pro Gly Leu Pro Gly Pro Lys Gly Glu Pro Gly Lys
625                 630                 635                 640

Ile Val Pro Leu Pro Gly Pro Pro Gly Ala Glu Gly Leu Pro Gly Ser
            645                 650                 655

Pro Gly Phe Pro Gly Pro Gln Gly Asp Arg Gly Phe Pro Gly Thr Pro
        660                 665                 670

Gly Arg Pro Gly Leu Pro Gly Glu Lys Gly Ala Val Gly Gln Pro Gly
    675                 680                 685

Ile Gly Phe Pro Gly Pro Pro Gly Pro Lys Gly Val Asp Gly Leu Pro
        690                 695                 700

Gly Asp Met Gly Pro Pro Gly Thr Pro Gly Arg Pro Gly Phe Asn Gly
705                 710                 715                 720

Leu Pro Gly Asn Pro Gly Val Gln Gly Gln Lys Gly Glu Pro Gly Val
            725                 730                 735

Gly Leu Pro Gly Leu Lys Gly Leu Pro Gly Leu Pro Gly Ile Pro Gly
        740                 745                 750

Thr Pro Gly Glu Lys Gly Ser Ile Gly Val Pro Gly Val Pro Gly Glu
    755                 760                 765

His Gly Ala Ile Gly Pro Pro Gly Leu Gln Gly Ile Arg Gly Glu Pro
    770                 775                 780

Gly Pro Pro Gly Leu Pro Gly Ser Val Gly Ser Pro Gly Val Pro Gly
785                 790                 795                 800

Ile Gly Pro Pro Gly Ala Arg Gly Pro Pro Gly Gly Gln Gly Pro Pro
            805                 810                 815

Gly Leu Ser Gly Pro Gly Ile Lys Gly Glu Lys Gly Phe Pro Gly
        820                 825                 830

Phe Pro Gly Leu Asp Met Pro Gly Pro Lys Gly Asp Lys Gly Ala Gln
    835                 840                 845

Gly Leu Pro Gly Ile Thr Gly Gln Ser Gly Leu Pro Gly Leu Pro Gly
```

```
            850                 855                 860
Gln Gln Gly Ala Pro Gly Ile Pro Gly Phe Pro Gly Ser Lys Gly Glu
865                 870                 875                 880

Met Gly Val Met Gly Thr Pro Gly Gln Pro Gly Ser Pro Gly Pro Val
                885                 890                 895

Gly Ala Pro Gly Leu Pro Gly Glu Lys Gly Asp His Gly Phe Pro Gly
            900                 905                 910

Ser Ser Gly Pro Arg Gly Asp Pro Gly Leu Lys Gly Asp Lys Gly Asp
        915                 920                 925

Val Gly Leu Pro Gly Lys Pro Gly Ser Met Asp Lys Val Asp Met Gly
    930                 935                 940

Ser Met Lys Gly Gln Lys Gly Asp Gln Gly Glu Lys Gly Gln Ile Gly
945                 950                 955                 960

Pro Ile Gly Glu Lys Gly Ser Arg Gly Asp Pro Gly Thr Pro Gly Val
                965                 970                 975

Pro Gly Lys Asp Gly Gln Ala Gly Gln Pro Gly Gln Pro Gly Pro Lys
            980                 985                 990

Gly Asp Pro Gly Ile Ser Gly Thr Pro Gly Ala Pro Gly Leu Pro Gly
        995                 1000                1005

Pro Lys Gly Ser Val Gly Gly Met Gly Leu Pro Gly Thr Pro Gly Glu
    1010                1015                1020

Lys Gly Val Pro Gly Ile Pro Gly Pro Gln Gly Ser Pro Gly Leu Pro
1025                1030                1035                1040

Gly Asp Lys Gly Ala Lys Gly Glu Lys Gly Gln Ala Gly Pro Pro Gly
            1045                1050                1055

Ile Gly Ile Pro Gly Leu Arg Gly Glu Lys Gly Asp Gln Gly Ile Ala
        1060                1065                1070

Gly Phe Pro Gly Ser Pro Gly Glu Lys Gly Glu Lys Gly Ser Ile Gly
    1075                1080                1085

Ile Pro Gly Met Pro Gly Ser Pro Gly Leu Lys Gly Ser Pro Gly Ser
    1090                1095                1100

Val Gly Tyr Pro Gly Ser Pro Gly Leu Pro Gly Glu Lys Gly Asp Lys
1105                1110                1115                1120

Gly Leu Pro Gly Leu Asp Gly Ile Pro Gly Val Lys Gly Glu Ala Gly
            1125                1130                1135

Leu Pro Gly Thr Pro Gly Pro Thr Gly Pro Ala Gly Gln Lys Gly Glu
        1140                1145                1150

Pro Gly Ser Asp Gly Ile Pro Gly Ser Ala Gly Glu Lys Gly Glu Pro
    1155                1160                1165

Gly Leu Pro Gly Arg Gly Phe Pro Gly Phe Pro Gly Ala Lys Gly Asp
    1170                1175                1180

Lys Gly Ser Lys Gly Glu Val Gly Phe Pro Gly Leu Ala Gly Ser Pro
1185                1190                1195                1200

Gly Ile Pro Gly Ser Lys Gly Glu Gln Gly Phe Met Gly Pro Pro Gly
            1205                1210                1215

Pro Gln Gly Gln Pro Gly Leu Pro Gly Ser Pro Gly His Ala Thr Glu
        1220                1225                1230

Gly Pro Lys Gly Asp Arg Gly Pro Gln Gly Gln Pro Gly Leu Pro Gly
    1235                1240                1245

Leu Pro Gly Pro Met Gly Pro Pro Gly Leu Pro Gly Ile Asp Gly Val
    1250                1255                1260

Lys Gly Asp Lys Gly Asn Pro Gly Trp Pro Gly Ala Pro Gly Val Pro
1265                1270                1275                1280
```

-continued

```
Gly Pro Lys Gly Asp Pro Gly Phe Gln Gly Met Pro Gly Ile Gly Gly
            1285                1290                1295
Ser Pro Gly Ile Thr Gly Ser Lys Gly Asp Met Gly Pro Pro Gly Val
        1300                1305                1310
Pro Gly Phe Gln Gly Pro Lys Gly Leu Pro Gly Leu Gln Gly Ile Lys
    1315                1320                1325
Gly Asp Gln Gly Asp Gln Gly Val Pro Gly Ala Lys Gly Leu Pro Gly
1330                1335                1340
Pro Pro Gly Pro Pro Gly Pro Tyr Asp Ile Ile Lys Gly Glu Pro Gly
1345                1350                1355                1360
Leu Pro Gly Pro Glu Gly Pro Pro Gly Leu Lys Gly Leu Gln Gly Leu
            1365                1370                1375
Pro Gly Pro Lys Gly Gln Gln Gly Val Thr Gly Leu Val Gly Ile Pro
        1380                1385                1390
Gly Pro Pro Gly Ile Pro Gly Phe Asp Gly Ala Pro Gly Gln Lys Gly
    1395                1400                1405
Glu Met Gly Pro Ala Gly Pro Thr Gly Pro Arg Gly Phe Pro Gly Pro
1410                1415                1420
Pro Gly Pro Asp Gly Leu Pro Gly Ser Met Gly Pro Pro Gly Thr Pro
1425                1430                1435                1440
Ser Val Asp His Gly Phe Leu Val Thr Arg His Ser Gln Thr Ile Asp
            1445                1450                1455
Asp Pro Gln Cys Pro Ser Gly Thr Lys Ile Leu Tyr His Gly Tyr Ser
        1460                1465                1470
Leu Leu Tyr Val Gln Gly Asn Glu Arg Ala His Gly Gln Asp Leu Gly
    1475                1480                1485
Thr Ala Gly Ser Cys Leu Arg Lys Phe Ser Thr Met Pro Phe Leu Phe
1490                1495                1500
Cys Asn Ile Asn Asn Val Cys Asn Phe Ala Ser Arg Asn Asp Tyr Ser
1505                1510                1515                1520
Tyr Trp Leu Ser Thr Pro Glu Pro Met Pro Met Ser Met Ala Pro Ile
            1525                1530                1535
Thr Gly Glu Asn Ile Arg Pro Phe Ile Ser Arg Cys Ala Val Cys Glu
        1540                1545                1550
Ala Pro Ala Met Val Met Ala Val His Ser Gln Thr Ile Gln Ile Pro
    1555                1560                1565
Pro Cys Pro Ser Gly Trp Ser Ser Leu Trp Ile Gly Tyr Ser Phe Val
1570                1575                1580
Met His Thr Ser Ala Gly Ala Glu Gly Ser Gly Gln Ala Leu Ala Ser
1585                1590                1595                1600
Pro Gly Ser Cys Leu Glu Glu Phe Arg Ser Ala Pro Phe Ile Glu Cys
            1605                1610                1615
His Gly Arg Gly Thr Cys Asn Tyr Tyr Ala Asn Ala Tyr Ser Phe Trp
        1620                1625                1630
Leu Ala Thr Ile Glu Arg Ser Glu Met Phe Lys Lys Pro Thr Pro Ser
    1635                1640                1645
Thr Leu Lys Ala Gly Glu Leu Arg Thr His Val Ser Arg Cys Gln Val
1650                1655                1660
Cys Met Arg Arg Thr
1665

<210> SEQ ID NO 19
<211> LENGTH: 1028
```

```
<212> TYPE: PRT
<213> ORGANISM: Homo sapiens

<400> SEQUENCE: 19

Met Arg Ala Arg Ala Leu Leu Pro Leu Leu Gln Ala Cys Trp
1               5                   10                  15

Thr Ala Ala Gln Asp Glu Pro Glu Thr Pro Arg Ala Val Ala Phe Gln
            20                  25                  30

Asp Cys Pro Val Asp Leu Phe Phe Val Leu Asp Thr Ser Glu Ser Val
        35                  40                  45

Ala Leu Arg Leu Lys Pro Tyr Gly Ala Leu Val Asp Lys Val Lys Ser
    50                  55                  60

Phe Thr Lys Arg Phe Ile Asp Asn Leu Arg Asp Arg Tyr Tyr Arg Cys
65                  70                  75                  80

Asp Arg Asn Leu Val Trp Asn Ala Gly Ala Leu His Tyr Ser Asp Glu
                85                  90                  95

Val Glu Ile Ile Gln Gly Leu Thr Arg Met Pro Gly Gly Arg Asp Ala
            100                 105                 110

Leu Lys Ser Ser Val Asp Ala Val Lys Tyr Phe Gly Lys Gly Thr Tyr
        115                 120                 125

Thr Asp Cys Ala Ile Lys Lys Gly Leu Glu Gln Leu Leu Val Gly Gly
    130                 135                 140

Ser His Leu Lys Glu Asn Lys Tyr Leu Ile Val Val Thr Asp Gly His
145                 150                 155                 160

Pro Leu Glu Gly Tyr Lys Glu Pro Cys Gly Gly Leu Glu Asp Ala Val
                165                 170                 175

Asn Glu Ala Lys His Leu Gly Val Lys Val Phe Ser Val Ala Ile Thr
            180                 185                 190

Pro Asp His Leu Glu Pro Arg Leu Ser Ile Ile Ala Thr Asp His Thr
        195                 200                 205

Tyr Arg Arg Asn Phe Thr Ala Ala Asp Trp Gly Gln Ser Arg Asp Ala
    210                 215                 220

Glu Glu Ala Ile Ser Gln Thr Ile Asp Thr Ile Val Asp Met Ile Lys
225                 230                 235                 240

Asn Asn Val Glu Gln Val Cys Cys Ser Phe Glu Cys Gln Pro Ala Arg
                245                 250                 255

Gly Pro Pro Gly Leu Arg Gly Asp Pro Gly Phe Glu Gly Glu Arg Gly
            260                 265                 270

Lys Pro Gly Leu Pro Gly Glu Lys Gly Glu Ala Gly Asp Pro Gly Arg
        275                 280                 285

Pro Gly Asp Leu Gly Pro Val Gly Tyr Gln Gly Met Lys Gly Glu Lys
    290                 295                 300

Gly Ser Arg Gly Glu Lys Gly Ser Arg Gly Pro Lys Gly Tyr Lys Gly
305                 310                 315                 320

Glu Lys Gly Lys Arg Gly Ile Asp Gly Val Asp Gly Val Lys Gly Glu
                325                 330                 335

Met Gly Tyr Pro Gly Leu Pro Gly Cys Lys Gly Ser Pro Gly Phe Asp
            340                 345                 350

Gly Ile Gln Gly Pro Gly Pro Lys Gly Asp Pro Gly Ala Phe Gly
        355                 360                 365

Leu Lys Gly Glu Lys Gly Glu Pro Gly Ala Asp Gly Glu Ala Gly Arg
    370                 375                 380

Pro Gly Ser Ser Gly Pro Ser Gly Asp Glu Gly Gln Pro Gly Glu Pro
385                 390                 395                 400
```

-continued

```
Gly Pro Pro Gly Glu Lys Gly Glu Ala Gly Asp Gly Asn Pro Gly
                405                 410                 415

Pro Asp Gly Ala Pro Gly Glu Arg Gly Pro Gly Glu Arg Gly Pro
            420                 425                 430

Arg Gly Thr Pro Gly Thr Arg Gly Pro Arg Gly Asp Pro Gly Glu Ala
        435                 440                 445

Gly Pro Gln Gly Asp Gln Gly Arg Glu Gly Pro Val Gly Val Pro Gly
    450                 455                 460

Asp Pro Gly Glu Ala Gly Pro Ile Gly Pro Lys Gly Tyr Arg Gly Asp
465                 470                 475                 480

Glu Gly Pro Pro Gly Ser Glu Gly Ala Arg Gly Ala Pro Gly Pro Ala
            485                 490                 495

Gly Pro Pro Gly Asp Pro Gly Leu Met Gly Glu Arg Gly Glu Asp Gly
        500                 505                 510

Pro Ala Gly Asn Gly Thr Glu Gly Phe Pro Gly Phe Pro Gly Tyr Pro
        515                 520                 525

Gly Asn Arg Gly Ala Pro Gly Ile Asn Gly Thr Lys Gly Tyr Pro Gly
    530                 535                 540

Leu Lys Gly Asp Glu Gly Glu Ala Gly Asp Pro Gly Asp Asp Asn
545                 550                 555                 560

Asp Ile Ala Pro Arg Gly Val Lys Gly Ala Lys Gly Tyr Arg Gly Pro
            565                 570                 575

Glu Gly Pro Gln Gly Pro Pro Gly His Gln Gly Pro Pro Gly Pro Asp
        580                 585                 590

Glu Cys Glu Ile Leu Asp Ile Met Lys Met Cys Ser Cys Cys Glu
        595                 600                 605

Cys Lys Cys Gly Pro Ile Asp Leu Leu Phe Val Leu Asp Ser Ser Glu
    610                 615                 620

Ser Ile Gly Leu Gln Asn Phe Glu Ile Ala Lys Asp Phe Val Val Lys
625                 630                 635                 640

Val Ile Asp Arg Leu Ser Arg Asp Glu Leu Val Lys Phe Glu Pro Gly
            645                 650                 655

Gln Ser Tyr Ala Gly Val Val Gln Tyr Ser His Ser Gln Met Gln Glu
        660                 665                 670

His Val Ser Leu Arg Ser Pro Ser Ile Arg Asn Val Gln Glu Leu Lys
    675                 680                 685

Glu Ala Ile Lys Ser Leu Gln Trp Met Ala Gly Gly Thr Phe Thr Gly
    690                 695                 700

Glu Ala Leu Gln Tyr Thr Arg Asp Gln Leu Leu Pro Pro Ser Pro Asn
705                 710                 715                 720

Asn Arg Ile Ala Leu Val Ile Thr Asp Gly Arg Ser Asp Thr Gln Arg
            725                 730                 735

Asp Thr Thr Pro Leu Asn Val Leu Cys Ser Pro Gly Ile Gln Val Val
        740                 745                 750

Ser Val Gly Ile Lys Asp Val Phe Asp Phe Ile Pro Gly Ser Asp Gln
    755                 760                 765

Leu Asn Val Ile Ser Cys Gln Gly Leu Ala Pro Ser Gln Gly Arg Pro
    770                 775                 780

Gly Leu Ser Leu Val Lys Glu Asn Tyr Ala Glu Leu Leu Glu Asp Ala
785                 790                 795                 800

Phe Leu Lys Asn Val Thr Ala Gln Ile Cys Ile Asp Lys Lys Cys Pro
            805                 810                 815
```

```
Asp Tyr Thr Cys Pro Ile Thr Phe Ser Ser Pro Ala Asp Ile Thr Ile
            820                 825                 830

Leu Leu Asp Gly Ser Ala Ser Val Gly Ser His Asn Phe Asp Thr Thr
        835                 840                 845

Lys Arg Phe Ala Lys Arg Leu Ala Glu Arg Phe Leu Thr Ala Gly Arg
    850                 855                 860

Thr Asp Pro Ala His Asp Val Arg Val Ala Val Val Gln Tyr Ser Gly
865                 870                 875                 880

Thr Gly Gln Gln Arg Pro Glu Arg Ala Ser Leu Gln Phe Leu Gln Asn
                885                 890                 895

Tyr Thr Ala Leu Ala Ser Ala Val Asp Ala Met Asp Phe Ile Asn Asp
            900                 905                 910

Ala Thr Asp Val Asn Asp Ala Leu Gly Tyr Val Thr Arg Phe Tyr Arg
        915                 920                 925

Glu Ala Ser Ser Gly Ala Ala Lys Lys Arg Leu Leu Leu Phe Ser Asp
    930                 935                 940

Gly Asn Ser Gln Gly Ala Thr Pro Ala Ala Ile Glu Lys Ala Val Gln
945                 950                 955                 960

Glu Ala Gln Arg Ala Gly Ile Glu Ile Phe Val Val Val Val Gly Arg
                965                 970                 975

Gln Val Asn Glu Pro His Ile Arg Val Leu Val Thr Gly Lys Thr Ala
            980                 985                 990

Glu Tyr Asp Val Ala Tyr Gly Glu Ser His Leu Phe Arg Val Pro Ser
        995                 1000                1005

Tyr Gln Ala Leu Leu Arg Gly Val Phe His Gln Thr Val Ser Arg Lys
    1010                1015                1020

Val Ala Leu Gly
1025

<210> SEQ ID NO 20
<211> LENGTH: 2944
<212> TYPE: PRT
<213> ORGANISM: Homo sapiens

<400> SEQUENCE: 20

Met Thr Leu Arg Leu Leu Val Ala Ala Leu Cys Ala Gly Ile Leu Ala
1               5                   10                  15

Glu Ala Pro Arg Val Arg Ala Gln His Arg Glu Arg Val Thr Cys Thr
            20                  25                  30

Arg Leu Tyr Ala Ala Asp Ile Val Phe Leu Leu Asp Gly Ser Ser Ser
        35                  40                  45

Ile Gly Arg Ser Asn Phe Arg Glu Val Arg Ser Phe Leu Glu Gly Leu
    50                  55                  60

Val Leu Pro Phe Ser Gly Ala Ala Ser Ala Gln Gly Val Arg Phe Ala
65                  70                  75                  80

Thr Val Gln Tyr Ser Asp Asp Pro Arg Thr Glu Phe Gly Leu Asp Ala
                85                  90                  95

Leu Gly Ser Gly Gly Asp Val Ile Arg Ala Ile Arg Glu Leu Ser Tyr
            100                 105                 110

Lys Gly Gly Asn Thr Arg Thr Gly Ala Ala Ile Leu His Val Ala Asp
        115                 120                 125

His Val Phe Leu Pro Gln Leu Ala Arg Pro Gly Val Pro Lys Val Cys
    130                 135                 140

Ile Leu Ile Thr Asp Gly Lys Ser Gln Asp Leu Val Asp Thr Ala Ala
145                 150                 155                 160
```

```
Gln Arg Leu Lys Gly Gln Gly Val Lys Leu Phe Ala Val Gly Ile Lys
                165                 170                 175

Asn Ala Asp Pro Glu Glu Leu Lys Arg Val Ala Ser Gln Pro Thr Ser
            180                 185                 190

Asp Phe Phe Phe Phe Val Asn Asp Phe Ser Ile Leu Arg Thr Leu Leu
        195                 200                 205

Pro Leu Val Ser Arg Arg Val Cys Thr Thr Ala Gly Gly Val Pro Val
    210                 215                 220

Thr Arg Pro Pro Asp Asp Ser Thr Ser Ala Pro Arg Asp Leu Val Leu
225                 230                 235                 240

Ser Glu Pro Ser Ser Gln Ser Leu Arg Val Gln Trp Thr Ala Ala Ser
                245                 250                 255

Gly Pro Val Thr Gly Tyr Lys Val Gln Tyr Thr Pro Leu Thr Gly Leu
            260                 265                 270

Gly Gln Pro Leu Pro Ser Glu Arg Gln Glu Val Asn Val Pro Ala Gly
        275                 280                 285

Glu Thr Ser Val Arg Leu Arg Gly Leu Arg Pro Leu Thr Glu Tyr Gln
    290                 295                 300

Val Thr Val Ile Ala Leu Tyr Ala Asn Ser Ile Gly Glu Ala Val Ser
305                 310                 315                 320

Gly Thr Ala Arg Thr Thr Ala Leu Glu Gly Pro Glu Leu Thr Ile Gln
                325                 330                 335

Asn Thr Thr Ala His Ser Leu Leu Val Ala Trp Arg Ser Val Pro Gly
            340                 345                 350

Ala Thr Gly Tyr Arg Val Thr Trp Arg Val Leu Ser Gly Gly Pro Thr
        355                 360                 365

Gln Gln Gln Glu Leu Gly Pro Gly Gln Gly Ser Val Leu Leu Arg Asp
    370                 375                 380

Leu Glu Pro Gly Thr Asp Tyr Glu Val Thr Val Ser Thr Leu Phe Gly
385                 390                 395                 400

Arg Ser Val Gly Pro Ala Thr Ser Leu Met Ala Arg Thr Asp Ala Ser
                405                 410                 415

Val Glu Gln Thr Leu Arg Pro Val Ile Leu Gly Pro Thr Ser Ile Leu
            420                 425                 430

Leu Ser Trp Asn Leu Val Pro Glu Ala Arg Gly Tyr Arg Leu Glu Trp
        435                 440                 445

Arg Arg Glu Thr Gly Leu Glu Pro Pro Gln Lys Val Val Leu Pro Ser
    450                 455                 460

Asp Val Thr Arg Tyr Gln Leu Asp Gly Leu Gln Pro Gly Thr Glu Tyr
465                 470                 475                 480

Arg Leu Thr Leu Tyr Thr Leu Leu Glu Gly His Glu Val Ala Thr Pro
                485                 490                 495

Ala Thr Val Val Pro Thr Gly Pro Glu Leu Pro Val Ser Pro Val Thr
            500                 505                 510

Asp Leu Gln Ala Thr Glu Leu Pro Gly Gln Arg Val Arg Val Ser Trp
        515                 520                 525

Ser Pro Val Pro Gly Ala Thr Gln Tyr Arg Ile Ile Val Arg Ser Thr
    530                 535                 540

Gln Gly Val Glu Arg Thr Leu Val Leu Pro Gly Ser Gln Thr Ala Phe
545                 550                 555                 560

Asp Leu Asp Asp Val Gln Ala Gly Leu Ser Tyr Thr Val Arg Val Ser
                565                 570                 575
```

-continued

```
Ala Arg Val Gly Pro Arg Glu Gly Ser Ala Ser Val Leu Thr Val Arg
            580                 585                 590

Arg Glu Pro Glu Thr Pro Leu Ala Val Pro Gly Leu Arg Val Val Val
        595                 600                 605

Ser Asp Ala Thr Arg Val Arg Val Ala Trp Gly Pro Val Pro Gly Ala
    610                 615                 620

Ser Gly Phe Arg Ile Ser Trp Ser Thr Gly Ser Gly Pro Glu Ser Ser
625                 630                 635                 640

Gln Thr Leu Pro Pro Asp Ser Thr Ala Thr Asp Ile Thr Gly Leu Gln
                645                 650                 655

Pro Gly Thr Thr Tyr Gln Val Ala Val Ser Val Leu Arg Gly Arg Glu
            660                 665                 670

Glu Gly Pro Ala Ala Val Ile Val Ala Arg Thr Asp Pro Leu Gly Pro
        675                 680                 685

Val Arg Thr Val His Val Thr Gln Ala Ser Ser Ser Val Thr Ile
    690                 695                 700

Thr Trp Thr Arg Val Pro Gly Ala Thr Gly Tyr Arg Val Ser Trp His
705                 710                 715                 720

Ser Ala His Gly Pro Glu Lys Ser Gln Leu Val Ser Gly Glu Ala Thr
                725                 730                 735

Val Ala Glu Leu Asp Gly Leu Glu Pro Asp Thr Glu Tyr Thr Val His
            740                 745                 750

Val Arg Ala His Val Ala Gly Val Asp Gly Pro Pro Ala Ser Val Val
        755                 760                 765

Val Arg Thr Ala Pro Glu Pro Val Gly Arg Val Ser Arg Leu Gln Ile
    770                 775                 780

Leu Asn Ala Ser Ser Asp Val Leu Arg Ile Thr Trp Val Gly Val Thr
785                 790                 795                 800

Gly Ala Thr Ala Tyr Arg Leu Ala Trp Gly Arg Ser Glu Gly Gly Pro
                805                 810                 815

Met Arg His Gln Ile Leu Pro Gly Asn Thr Asp Ser Ala Glu Ile Arg
            820                 825                 830

Gly Leu Glu Gly Gly Val Ser Tyr Ser Val Arg Val Thr Ala Leu Val
        835                 840                 845

Gly Asp Arg Glu Gly Thr Pro Val Ser Ile Val Val Thr Thr Pro Pro
    850                 855                 860

Glu Ala Pro Pro Ala Leu Gly Thr Leu His Val Val Gln Arg Gly Glu
865                 870                 875                 880

His Ser Leu Arg Leu Arg Trp Glu Pro Val Pro Arg Ala Gln Gly Phe
                885                 890                 895

Leu Leu His Trp Gln Pro Glu Gly Gly Gln Glu Gln Ser Arg Val Leu
            900                 905                 910

Gly Pro Glu Leu Ser Ser Tyr His Leu Asp Gly Leu Glu Pro Ala Thr
        915                 920                 925

Gln Tyr Arg Val Arg Leu Ser Val Leu Gly Pro Ala Gly Glu Gly Pro
    930                 935                 940

Ser Ala Glu Val Thr Ala Arg Thr Glu Ser Pro Arg Val Pro Ser Ile
945                 950                 955                 960

Glu Leu Arg Val Asp Thr Ser Ile Asp Ser Val Thr Leu Ala Trp
                965                 970                 975

Thr Pro Val Ser Arg Ala Ser Ser Tyr Ile Leu Ser Trp Arg Pro Leu
            980                 985                 990

Arg Gly Pro Gly Gln Glu Val Pro Gly Ser Pro Gln Thr Leu Pro Gly
```

```
             995                1000               1005
    Ile Ser Ser Ser Gln Arg Val Thr Gly Leu Glu Pro Gly Val Ser Tyr
        1010                1015               1020

Ile Phe Ser Leu Thr Pro Val Leu Asp Gly Val Arg Gly Pro Glu Ala
    1025                1030               1035               1040

Ser Val Thr Gln Thr Pro Val Cys Pro Arg Gly Leu Ala Asp Val Val
                    1045               1050               1055

Phe Leu Pro His Ala Thr Gln Asp Asn Ala His Arg Ala Glu Ala Thr
                1060               1065               1070

Arg Arg Val Leu Glu Arg Leu Val Leu Ala Leu Gly Pro Leu Gly Pro
            1075               1080               1085

Gln Ala Val Gln Val Gly Leu Leu Ser Tyr Ser His Arg Pro Ser Pro
        1090               1095               1100

Leu Phe Pro Leu Asn Gly Ser His Asp Leu Gly Ile Ile Leu Gln Arg
    1105                1110               1115               1120

Ile Arg Asp Met Pro Tyr Met Asp Pro Ser Gly Asn Asn Leu Gly Thr
                    1125               1130               1135

Ala Val Val Thr Ala His Arg Tyr Met Leu Ala Pro Asp Ala Pro Gly
                1140               1145               1150

Arg Arg Gln His Val Pro Gly Val Met Val Leu Leu Val Asp Glu Pro
            1155               1160               1165

Leu Arg Gly Asp Ile Phe Ser Pro Ile Arg Glu Ala Gln Ala Ser Gly
        1170               1175               1180

Leu Asn Val Val Met Leu Gly Met Ala Gly Ala Asp Pro Glu Gln Leu
    1185                1190               1195               1200

Arg Arg Leu Ala Pro Gly Met Asp Ser Val Gln Thr Phe Phe Ala Val
                    1205               1210               1215

Asp Asp Gly Pro Ser Leu Asp Gln Ala Val Ser Gly Leu Ala Thr Ala
                1220               1225               1230

Leu Cys Gln Ala Ser Phe Thr Thr Gln Pro Arg Pro Glu Pro Cys Pro
            1235               1240               1245

Val Tyr Cys Pro Lys Gly Gln Lys Gly Glu Pro Gly Glu Met Gly Leu
        1250               1255               1260

Arg Gly Gln Val Gly Pro Pro Gly Asp Pro Gly Leu Pro Gly Arg Thr
    1265                1270               1275               1280

Gly Ala Pro Gly Pro Gln Gly Pro Pro Gly Ser Ala Thr Ala Lys Gly
                    1285               1290               1295

Glu Arg Gly Phe Pro Gly Ala Asp Gly Arg Pro Gly Ser Pro Gly Arg
                1300               1305               1310

Ala Gly Asn Pro Gly Thr Pro Gly Ala Pro Gly Leu Lys Gly Ser Pro
            1315               1320               1325

Gly Leu Pro Gly Pro Arg Gly Asp Pro Gly Glu Arg Gly Pro Arg Gly
        1330               1335               1340

Pro Lys Gly Glu Pro Gly Ala Pro Gly Gln Val Ile Gly Gly Glu Gly
    1345                1350               1355               1360

Pro Gly Leu Pro Gly Arg Lys Gly Asp Pro Gly Pro Ser Gly Pro Pro
                    1365               1370               1375

Gly Pro Arg Gly Pro Leu Gly Asp Pro Gly Arg Gly Pro Pro Gly
                1380               1385               1390

Leu Pro Gly Thr Ala Met Lys Gly Asp Lys Gly Asp Arg Gly Glu Arg
            1395               1400               1405

Gly Pro Pro Gly Pro Gly Glu Gly Gly Ile Ala Pro Gly Glu Pro Gly
        1410               1415               1420
```

```
Leu Pro Gly Leu Pro Gly Ser Pro Gly Pro Gln Pro Val Gly Pro
1425                1430                1435                1440

Pro Gly Lys Lys Gly Glu Lys Gly Asp Ser Glu Asp Gly Ala Pro Gly
                1445                1450                1455

Leu Pro Gly Gln Pro Gly Ser Pro Gly Glu Gln Gly Pro Arg Gly Pro
            1460                1465                1470

Pro Gly Ala Ile Gly Pro Lys Gly Asp Arg Gly Phe Pro Gly Pro Leu
            1475                1480                1485

Gly Glu Ala Gly Glu Lys Gly Glu Arg Gly Pro Pro Gly Pro Ala Gly
            1490                1495                1500

Ser Arg Gly Leu Pro Gly Val Ala Gly Arg Pro Gly Ala Lys Gly Pro
1505                1510                1515                1520

Glu Gly Pro Pro Gly Pro Thr Gly Arg Gln Gly Glu Lys Gly Glu Pro
                1525                1530                1535

Gly Arg Pro Gly Asp Pro Ala Val Val Gly Pro Ala Val Ala Gly Pro
                1540                1545                1550

Lys Gly Glu Lys Gly Asp Val Gly Pro Ala Gly Pro Arg Gly Ala Thr
            1555                1560                1565

Gly Val Gln Gly Glu Arg Gly Pro Pro Gly Leu Val Leu Pro Gly Asp
            1570                1575                1580

Pro Gly Pro Lys Gly Asp Pro Gly Asp Arg Gly Pro Ile Gly Leu Thr
1585                1590                1595                1600

Gly Arg Ala Gly Pro Pro Gly Asp Ser Gly Pro Pro Gly Glu Lys Gly
                1605                1610                1615

Asp Pro Gly Arg Pro Gly Pro Pro Gly Pro Val Gly Pro Arg Gly Arg
                1620                1625                1630

Asp Gly Glu Val Gly Glu Lys Gly Asp Glu Gly Pro Pro Gly Asp Pro
                1635                1640                1645

Gly Leu Pro Gly Lys Ala Gly Glu Arg Gly Leu Arg Gly Ala Pro Gly
            1650                1655                1660

Val Arg Gly Pro Val Gly Glu Lys Gly Asp Gln Gly Asp Pro Gly Glu
1665                1670                1675                1680

Asp Gly Arg Asn Gly Ser Pro Gly Ser Ser Gly Pro Lys Gly Asp Arg
                1685                1690                1695

Gly Glu Pro Gly Pro Pro Gly Pro Gly Arg Leu Val Asp Thr Gly
                1700                1705                1710

Pro Gly Ala Arg Glu Lys Gly Glu Pro Gly Arg Gly Gln Glu Gly
            1715                1720                1725

Pro Arg Gly Pro Lys Gly Asp Pro Gly Leu Pro Gly Ala Pro Gly Glu
            1730                1735                1740

Arg Gly Ile Glu Gly Phe Arg Gly Pro Pro Gly Pro Gln Gly Asp Pro
1745                1750                1755                1760

Gly Val Arg Gly Pro Ala Gly Glu Lys Gly Asp Arg Gly Pro Pro Gly
                1765                1770                1775

Leu Asp Gly Arg Ser Gly Leu Asp Gly Lys Pro Gly Ala Ala Gly Pro
            1780                1785                1790

Ser Gly Pro Asn Gly Ala Ala Gly Lys Ala Gly Asp Pro Gly Arg Asp
            1795                1800                1805

Gly Leu Pro Gly Leu Arg Gly Glu Gln Gly Leu Pro Gly Pro Ser Gly
            1810                1815                1820

Pro Pro Gly Leu Pro Gly Lys Pro Gly Glu Asp Gly Lys Pro Gly Leu
1825                1830                1835                1840
```

-continued

Asn Gly Lys Asn Gly Glu Pro Gly Asp Pro Gly Asp Gly Arg Lys
            1845                1850                1855

Gly Glu Lys Gly Asp Ser Gly Ala Ser Gly Arg Glu Gly Arg Asp Gly
            1860                1865                1870

Pro Lys Gly Glu Arg Gly Ala Pro Gly Ile Leu Gly Pro Gln Gly Pro
            1875                1880                1885

Pro Gly Leu Pro Gly Pro Val Gly Pro Gly Gln Gly Phe Pro Gly
            1890                1895                1900

Val Pro Gly Gly Thr Gly Pro Lys Gly Asp Arg Gly Glu Thr Gly Ser
1905                1910                1915                1920

Lys Gly Glu Gln Gly Leu Pro Gly Glu Arg Gly Leu Arg Gly Glu Pro
            1925                1930                1935

Gly Ser Val Pro Asn Val Asp Arg Leu Leu Glu Thr Ala Gly Ile Lys
            1940                1945                1950

Ala Ser Ala Leu Arg Glu Ile Val Glu Thr Trp Asp Glu Ser Ser Gly
            1955                1960                1965

Ser Phe Leu Pro Val Pro Glu Arg Arg Arg Gly Pro Lys Gly Asp Ser
            1970                1975                1980

Gly Glu Gln Gly Pro Pro Gly Lys Glu Gly Pro Ile Gly Phe Pro Gly
1985                1990                1995                2000

Glu Arg Gly Leu Lys Gly Asp Arg Gly Asp Pro Gly Pro Gln Gly Pro
            2005                2010                2015

Pro Gly Leu Ala Leu Gly Glu Arg Gly Pro Pro Gly Pro Ser Gly Leu
            2020                2025                2030

Ala Gly Glu Pro Gly Lys Pro Gly Ile Pro Gly Leu Pro Gly Arg Ala
            2035                2040                2045

Gly Gly Val Gly Glu Ala Gly Arg Pro Gly Glu Arg Gly Glu Arg Gly
            2050                2055                2060

Glu Lys Gly Glu Arg Gly Glu Gln Gly Arg Asp Gly Pro Pro Gly Leu
2065                2070                2075                2080

Pro Gly Thr Pro Gly Pro Pro Gly Pro Pro Gly Pro Lys Val Ser Val
            2085                2090                2095

Asp Glu Pro Gly Pro Gly Leu Ser Gly Glu Gln Gly Pro Pro Gly Leu
            2100                2105                2110

Lys Gly Ala Lys Gly Glu Pro Gly Ser Asn Gly Asp Gln Gly Pro Lys
            2115                2120                2125

Gly Asp Arg Gly Val Pro Gly Ile Lys Gly Asp Arg Gly Glu Pro Gly
            2130                2135                2140

Pro Arg Gly Gln Asp Gly Asn Pro Gly Leu Pro Gly Glu Arg Gly Met
2145                2150                2155                2160

Ala Gly Pro Glu Gly Lys Pro Gly Leu Gln Gly Pro Arg Gly Pro Pro
            2165                2170                2175

Gly Pro Val Gly Gly His Gly Asp Pro Gly Pro Pro Gly Ala Pro Gly
            2180                2185                2190

Leu Ala Gly Pro Ala Gly Pro Gln Gly Pro Ser Gly Leu Lys Gly Glu
            2195                2200                2205

Pro Gly Glu Thr Gly Pro Pro Gly Arg Gly Leu Thr Gly Pro Thr Gly
            2210                2215                2220

Ala Val Gly Leu Pro Gly Pro Pro Gly Pro Ser Gly Leu Val Gly Pro
2225                2230                2235                2240

Gln Gly Ser Pro Gly Leu Pro Gly Gln Val Gly Glu Thr Gly Lys Pro
            2245                2250                2255

Gly Ala Pro Gly Arg Asp Gly Ala Ser Gly Lys Asp Gly Asp Arg Gly

```
              2260              2265              2270

Ser Pro Gly Val Pro Gly Ser Pro Gly Leu Pro Gly Val Gly Pro
        2275              2280              2285

Lys Gly Glu Pro Gly Pro Thr Gly Ala Pro Gly Gln Ala Val Gly
        2290              2295              2300

Leu Pro Gly Ala Lys Gly Glu Lys Gly Ala Pro Gly Gly Leu Ala Gly
2305              2310              2315              2320

Asp Leu Val Gly Glu Pro Gly Ala Lys Gly Asp Arg Gly Leu Pro Gly
            2325              2330              2335

Pro Arg Gly Glu Lys Gly Glu Ala Gly Arg Ala Gly Glu Pro Gly Asp
            2340              2345              2350

Pro Gly Glu Asp Gly Gln Lys Gly Ala Pro Gly Pro Lys Gly Phe Lys
            2355              2360              2365

Gly Asp Pro Gly Val Gly Val Pro Gly Ser Pro Gly Pro Pro Gly Pro
        2370              2375              2380

Pro Gly Val Lys Gly Asp Leu Gly Leu Pro Gly Leu Pro Gly Ala Pro
2385              2390              2395              2400

Gly Val Val Gly Phe Pro Gly Gln Thr Gly Pro Arg Gly Glu Met Gly
        2405              2410              2415

Gln Pro Gly Pro Ser Gly Glu Arg Gly Leu Ala Gly Pro Pro Gly Arg
        2420              2425              2430

Glu Gly Ile Pro Gly Pro Leu Gly Pro Pro Gly Pro Pro Gly Ser Val
        2435              2440              2445

Gly Pro Pro Gly Ala Ser Gly Leu Lys Gly Asp Lys Gly Asp Pro Gly
        2450              2455              2460

Val Gly Leu Pro Gly Pro Arg Gly Glu Arg Gly Glu Pro Gly Ile Arg
2465              2470              2475              2480

Gly Glu Asp Gly Arg Pro Gly Gln Glu Gly Pro Arg Gly Leu Thr Gly
            2485              2490              2495

Pro Pro Gly Ser Arg Gly Glu Arg Gly Glu Lys Gly Asp Val Gly Ser
            2500              2505              2510

Ala Gly Leu Lys Gly Asp Lys Gly Asp Ser Ala Val Ile Leu Gly Pro
        2515              2520              2525

Pro Gly Pro Arg Gly Ala Lys Gly Asp Met Gly Glu Arg Gly Pro Arg
        2530              2535              2540

Gly Leu Asp Gly Asp Lys Gly Pro Arg Gly Asp Asn Gly Asp Pro Gly
2545              2550              2555              2560

Asp Lys Gly Ser Lys Gly Glu Pro Gly Asp Lys Gly Ser Ala Gly Leu
            2565              2570              2575

Pro Gly Leu Arg Gly Leu Leu Gly Pro Gln Gly Gln Pro Gly Ala Ala
            2580              2585              2590

Gly Ile Pro Gly Asp Pro Gly Ser Pro Gly Lys Asp Gly Val Pro Gly
        2595              2600              2605

Ile Arg Gly Glu Lys Gly Asp Val Gly Phe Met Gly Pro Arg Gly Leu
        2610              2615              2620

Lys Gly Glu Arg Gly Val Lys Gly Ala Cys Gly Leu Asp Gly Glu Lys
2625              2630              2635              2640

Gly Asp Lys Gly Glu Ala Gly Pro Pro Gly Arg Pro Gly Leu Ala Gly
            2645              2650              2655

His Lys Gly Glu Met Gly Glu Pro Gly Val Pro Gly Gln Ser Gly Ala
            2660              2665              2670

Pro Gly Lys Glu Gly Leu Ile Gly Pro Lys Gly Asp Arg Gly Phe Asp
        2675              2680              2685
```

```
Gly Gln Pro Gly Pro Lys Gly Asp Gln Gly Glu Lys Gly Glu Arg Gly
            2690                2695                2700

Thr Pro Gly Ile Gly Gly Phe Pro Gly Pro Ser Gly Asn Asp Gly Ser
2705                2710                2715                2720

Ala Gly Pro Pro Gly Pro Pro Gly Ser Val Gly Pro Arg Gly Pro Glu
            2725                2730                2735

Gly Leu Gln Gly Gln Lys Gly Glu Arg Gly Pro Pro Gly Glu Arg Val
            2740                2745                2750

Val Gly Ala Pro Gly Val Pro Gly Ala Pro Gly Glu Arg Gly Glu Gln
            2755                2760                2765

Gly Arg Pro Gly Pro Ala Gly Pro Arg Gly Glu Lys Gly Glu Ala Ala
            2770                2775                2780

Leu Thr Glu Asp Asp Ile Arg Gly Phe Val Arg Gln Glu Met Ser Gln
2785                2790                2795                2800

His Cys Ala Cys Gln Gly Gln Phe Ile Ala Ser Gly Ser Arg Pro Leu
            2805                2810                2815

Pro Ser Tyr Ala Ala Asp Thr Ala Gly Ser Gln Leu His Ala Val Pro
            2820                2825                2830

Val Leu Arg Val Ser His Ala Glu Glu Glu Arg Val Pro Pro Glu
            2835                2840                2845

Asp Asp Glu Tyr Ser Glu Tyr Ser Glu Tyr Ser Val Glu Glu Tyr Gln
            2850                2855                2860

Asp Pro Glu Ala Pro Trp Asp Ser Asp Asp Pro Cys Ser Leu Pro Leu
2865                2870                2875                2880

Asp Glu Gly Ser Cys Thr Ala Tyr Thr Leu Arg Trp Tyr His Arg Ala
            2885                2890                2895

Val Thr Gly Ser Thr Glu Ala Cys His Pro Phe Val Tyr Gly Gly Cys
            2900                2905                2910

Gly Gly Asn Ala Asn Arg Phe Gly Thr Arg Glu Ala Cys Glu Arg Arg
            2915                2920                2925

Cys Pro Pro Arg Val Val Gln Ser Gln Gly Thr Gly Thr Ala Gln Asp
            2930                2935                2940

<210> SEQ ID NO 21
<211> LENGTH: 1497
<212> TYPE: PRT
<213> ORGANISM: Homo sapiens

<400> SEQUENCE: 21

Met Asp Val Thr Lys Lys Asn Lys Arg Asp Gly Thr Glu Val Thr Glu
1               5                   10                  15

Arg Ile Val Thr Glu Thr Val Thr Thr Arg Leu Thr Ser Leu Pro Pro
            20                  25                  30

Lys Gly Gly Thr Ser Asn Gly Tyr Ala Lys Thr Ala Ser Leu Gly Gly
        35                  40                  45

Gly Ser Arg Leu Glu Lys Gln Ser Leu Thr His Gly Ser Ser Gly Tyr
    50                  55                  60

Ile Asn Ser Thr Gly Ser Thr Arg Gly His Ala Ser Thr Ser Ser Tyr
65                  70                  75                  80

Arg Arg Ala His Ser Pro Ala Ser Thr Leu Pro Asn Ser Pro Gly Ser
                85                  90                  95

Thr Phe Glu Arg Lys Thr His Val Thr Arg His Ala Tyr Glu Gly Ser
            100                 105                 110

Ser Ser Gly Asn Ser Ser Pro Glu Tyr Pro Arg Lys Glu Phe Ala Ser
```

```
            115                 120                 125
Ser Ser Thr Arg Gly Arg Ser Gln Thr Arg Glu Ser Glu Ile Arg Val
130                 135                 140

Arg Leu Gln Ser Ala Ser Pro Ser Thr Arg Trp Thr Glu Leu Asp Asp
145                 150                 155                 160

Val Lys Arg Leu Leu Lys Gly Ser Arg Ser Ala Ser Val Ser Pro Thr
                165                 170                 175

Arg Asn Ser Ser Asn Thr Leu Pro Ile Pro Lys Lys Gly Thr Val Glu
            180                 185                 190

Thr Lys Ile Val Thr Ala Ser Ser Gln Ser Val Ser Gly Thr Tyr Asp
        195                 200                 205

Ala Thr Ile Leu Asp Ala Asn Leu Pro Ser His Val Trp Ser Ser Thr
    210                 215                 220

Leu Pro Ala Gly Ser Ser Met Gly Thr Tyr His Asn Asn Met Thr Thr
225                 230                 235                 240

Gln Ser Ser Ser Leu Leu Asn Thr Asn Ala Tyr Ser Ala Gly Ser Val
                245                 250                 255

Phe Gly Val Pro Asn Asn Met Ala Ser Cys Ser Pro Thr Leu His Pro
            260                 265                 270

Gly Leu Ser Thr Ser Ser Ser Val Phe Gly Met Gln Asn Asn Leu Ala
        275                 280                 285

Pro Ser Leu Thr Thr Leu Ser His Gly Thr Thr Thr Thr Ser Thr Ala
    290                 295                 300

Tyr Gly Val Lys Lys Asn Met Pro Gln Ser Pro Ala Ala Val Asn Thr
305                 310                 315                 320

Gly Val Ser Thr Ser Ala Ala Cys Thr Thr Ser Val Gln Ser Asp Asp
                325                 330                 335

Leu Leu His Lys Asp Cys Lys Phe Leu Ile Leu Glu Lys Asp Asn Thr
            340                 345                 350

Pro Ala Lys Lys Glu Met Glu Leu Leu Ile Met Thr Lys Asp Ser Gly
        355                 360                 365

Lys Val Phe Thr Ala Ser Pro Ala Ser Ile Ala Ala Thr Ser Phe Ser
    370                 375                 380

Glu Asp Thr Leu Lys Lys Glu Lys Gln Ala Ala Tyr Asn Ala Asp Ser
385                 390                 395                 400

Gly Leu Lys Ala Glu Ala Asn Gly Asp Leu Lys Thr Val Ser Thr Lys
                405                 410                 415

Gly Lys Thr Thr Thr Ala Asp Ile His Ser Tyr Gly Ser Ser Gly Gly
            420                 425                 430

Gly Gly Ser Gly Gly Gly Gly Val Gly Gly Ala Gly Gly Gly Gly Pro
        435                 440                 445

Trp Gly Pro Ala Pro Ala Trp Cys Pro Cys Gly Ser Cys Cys Ser Trp
    450                 455                 460

Trp Lys Trp Leu Leu Gly Leu Leu Leu Thr Trp Leu Leu Leu Gly
465                 470                 475                 480

Leu Leu Phe Gly Leu Ile Ala Leu Ala Glu Glu Val Arg Lys Leu Lys
                485                 490                 495

Ala Arg Val Asp Glu Leu Glu Arg Ile Arg Arg Ser Ile Leu Pro Tyr
            500                 505                 510

Gly Asp Ser Met Asp Arg Ile Glu Lys Asp Arg Leu Gln Gly Met Ala
        515                 520                 525

Pro Ala Ala Gly Ala Asp Leu Asp Lys Ile Gly Leu His Ser Asp Ser
    530                 535                 540
```

```
Gln Glu Glu Leu Trp Met Phe Val Arg Lys Lys Leu Met Met Glu Gln
545                 550                 555                 560

Glu Asn Gly Asn Leu Arg Gly Ser Pro Gly Pro Lys Gly Asp Met Gly
            565                 570                 575

Ser Pro Gly Pro Lys Gly Asp Arg Gly Phe Pro Gly Thr Pro Gly Ile
        580                 585                 590

Pro Gly Pro Leu Gly His Pro Gly Pro Gln Gly Pro Lys Gly Gln Lys
    595                 600                 605

Gly Ser Val Gly Asp Pro Gly Met Glu Gly Pro Met Gly Gln Arg Gly
610                 615                 620

Arg Glu Gly Pro Met Gly Pro Arg Gly Glu Ala Gly Pro Pro Gly Ser
625                 630                 635                 640

Gly Glu Lys Gly Glu Arg Gly Ala Ala Gly Glu Pro Gly Pro His Gly
            645                 650                 655

Pro Pro Gly Val Pro Gly Ser Val Gly Pro Lys Gly Ser Ser Gly Ser
        660                 665                 670

Pro Gly Pro Gln Gly Pro Pro Gly Pro Val Gly Leu Gln Gly Leu Arg
    675                 680                 685

Gly Glu Val Gly Leu Pro Gly Val Lys Gly Asp Lys Gly Pro Met Gly
690                 695                 700

Pro Pro Gly Pro Lys Gly Asp Gln Gly Glu Lys Gly Pro Arg Gly Leu
705                 710                 715                 720

Thr Gly Glu Pro Gly Met Arg Gly Leu Pro Gly Ala Val Gly Glu Pro
            725                 730                 735

Gly Ala Lys Gly Ala Met Gly Pro Ala Gly Pro Asp Gly His Gln Gly
        740                 745                 750

Pro Arg Gly Glu Gln Gly Leu Thr Gly Met Pro Gly Ile Arg Gly Pro
    755                 760                 765

Pro Gly Pro Ser Gly Asp Pro Gly Lys Pro Gly Leu Thr Gly Pro Gln
770                 775                 780

Gly Pro Gln Gly Leu Pro Gly Thr Pro Gly Arg Pro Gly Ile Lys Gly
785                 790                 795                 800

Glu Pro Gly Ala Pro Gly Lys Ile Val Thr Ser Glu Gly Ser Ser Met
            805                 810                 815

Leu Thr Val Pro Gly Pro Pro Gly Pro Pro Gly Ala Met Gly Pro Pro
        820                 825                 830

Gly Pro Pro Gly Ala Pro Gly Pro Ala Gly Pro Ala Gly Leu Pro Gly
    835                 840                 845

His Gln Glu Val Leu Asn Leu Gln Gly Pro Pro Gly Pro Pro Gly Pro
850                 855                 860

Arg Gly Pro Pro Gly Pro Ser Ile Pro Gly Pro Pro Gly Pro Arg Gly
865                 870                 875                 880

Pro Pro Gly Glu Gly Leu Pro Gly Pro Pro Gly Pro Pro Gly Ser Phe
            885                 890                 895

Leu Ser Asn Ser Glu Thr Phe Leu Ser Gly Pro Pro Gly Pro Pro Gly
        900                 905                 910

Pro Pro Gly Pro Lys Gly Asp Gln Gly Pro Pro Gly Pro Arg Gly His
    915                 920                 925

Gln Gly Glu Gln Gly Leu Pro Gly Phe Ser Thr Ser Gly Ser Ser Ser
930                 935                 940

Phe Gly Leu Asn Leu Gln Gly Pro Pro Gly Pro Pro Gly Pro Gln Gly
945                 950                 955                 960
```

```
Pro Lys Gly Asp Lys Gly Asp Pro Gly Val Pro Gly Ala Leu Gly Ile
            965                 970                 975
Pro Ser Gly Pro Ser Glu Gly Ser Ser Thr Met Tyr Val Ser
        980                 985                 990
Gly Pro Pro Gly Pro Pro Gly Pro Pro Gly Pro Pro Gly Ser Ile Ser
            995                1000                1005
Ser Ser Gly Gln Glu Ile Gln Gln Tyr Ile Ser Glu Tyr Met Gln Ser
        1010                1015                1020
Asp Ser Ile Arg Ser Tyr Leu Ser Gly Val Gln Pro Pro Gly Pro
1025                1030                1035                1040
Pro Gly Pro Pro Gly Pro Val Thr Thr Ile Thr Gly Glu Thr Phe Asp
            1045                1050                1055
Tyr Ser Glu Leu Ala Ser His Val Val Ser Tyr Leu Arg Thr Ser Gly
            1060                1065                1070
Tyr Gly Val Ser Leu Phe Ser Ser Ile Ser Ser Glu Asp Ile Leu
        1075                1080                1085
Ala Val Leu Gln Arg Asp Asp Val Arg Gln Tyr Leu Arg Gln Tyr Leu
        1090                1095                1100
Met Gly Pro Arg Gly Pro Pro Gly Pro Pro Gly Ala Ser Gly Asp Gly
1105                1110                1115                1120
Ser Leu Leu Ser Leu Asp Tyr Ala Glu Leu Ser Ser Arg Ile Leu Ser
            1125                1130                1135
Tyr Met Ser Ser Ser Gly Ile Ser Ile Gly Leu Pro Gly Pro Pro Gly
        1140                1145                1150
Pro Pro Gly Leu Pro Gly Thr Ser Tyr Glu Glu Leu Leu Ser Leu Leu
        1155                1160                1165
Arg Gly Ser Glu Phe Arg Gly Ile Val Gly Pro Pro Gly Pro Pro Gly
        1170                1175                1180
Pro Pro Gly Ile Pro Gly Asn Val Trp Ser Ser Ile Ser Val Glu Asp
1185                1190                1195                1200
Leu Ser Ser Tyr Leu His Thr Ala Gly Leu Ser Phe Ile Pro Gly Pro
            1205                1210                1215
Pro Gly Pro Pro Gly Pro Pro Gly Pro Arg Gly Pro Pro Gly Val Ser
            1220                1225                1230
Gly Ala Leu Ala Thr Tyr Ala Ala Glu Asn Ser Asp Ser Phe Arg Ser
            1235                1240                1245
Glu Leu Ile Ser Tyr Leu Thr Ser Pro Asp Val Arg Ser Phe Ile Val
        1250                1255                1260
Gly Pro Pro Gly Pro Pro Gly Pro Gln Gly Pro Pro Gly Asp Ser Arg
1265                1270                1275                1280
Leu Leu Ser Thr Asp Ala Ser His Ser Arg Gly Ser Ser Ser Ser Ser
            1285                1290                1295
His Ser Ser Ser Val Arg Arg Gly Ser Ser Tyr Ser Ser Ser Met Ser
            1300                1305                1310
Thr Gly Gly Gly Ala Gly Ser Leu Gly Ala Gly Gly Ala Phe Gly
            1315                1320                1325
Glu Ala Ala Gly Asp Arg Gly Pro Tyr Gly Thr Asp Ile Gly Pro Gly
            1330                1335                1340
Gly Gly Tyr Gly Ala Ala Ala Glu Gly Gly Met Tyr Ala Gly Asn Gly
1345                1350                1355                1360
Gly Leu Leu Gly Ala Asp Phe Ala Gly Asp Leu Asp Tyr Asn Glu Leu
            1365                1370                1375
Ala Val Arg Val Ser Glu Ser Met Gln Arg Gln Gly Leu Leu Gln Gly
```

```
            1380           1385           1390
Met Ala Tyr Thr Val Gln Gly Pro Pro Gly Gln Pro Gly Pro Gln Gly
        1395               1400           1405

Pro Pro Gly Ile Ser Lys Val Phe Ser Ala Tyr Ser Asn Val Thr Ala
    1410           1415               1420

Asp Leu Met Asp Phe Phe Gln Thr Tyr Gly Ala Ile Gln Gly Pro Pro
1425           1430               1435           1440

Gly Gln Lys Gly Glu Met Gly Thr Pro Gly Pro Lys Gly Asp Arg Gly
            1445               1450           1455

Pro Ala Gly Pro Pro Gly His Pro Gly Pro Pro Gly Pro Arg Gly His
                1460           1465           1470

Lys Gly Glu Lys Gly Asp Lys Gly Asp Gln Val Tyr Ala Gly Arg Arg
        1475           1480               1485

Arg Arg Arg Ser Ile Ala Val Lys Pro
    1490               1495

<210> SEQ ID NO 22
<211> LENGTH: 148
<212> TYPE: DNA
<213> ORGANISM: Artificial Sequence
<220> FEATURE:
<223> OTHER INFORMATION: Synthetic Construct

<400> SEQUENCE: 22
gaattcgtcg attcggttgc agcatttaaa gcggttgaca actttaaaag aaggaaaaag      60
aaggttgaag aaaagggtgt agtaagtaag tataagtaca gaccggagaa gtacgccggt     120
cctgattcgt ttaatttgaa agaagaaa                                         148

<210> SEQ ID NO 23
<211> LENGTH: 491
<212> TYPE: DNA
<213> ORGANISM: Artificial Sequence
<220> FEATURE:
<223> OTHER INFORMATION: Synthetic Construct

<400> SEQUENCE: 23
gttattttcc accatattgc cgtcttttgg caatgtgagg gcccggaaac ctggccctgt      60
cttcttgacg agcattccta ggggtctttc ccctctcgcc aaaggaatgc aaggtctgtt     120
gaatgtcgtg aaggaagcag ttcctctgga agcttcttga agacaaacaa cgtctgtagc     180 gacccttgc aggcagcgga acccccacc tggcgacagg tgcctctgcg gccaaaagcc      240
acgtgtataa gatacacctg caaaggcggc acaaccccag tgccacgttg tgagttggat     300
agttgtggaa agagtcaaat ggctcacctc aagcgtattc aacaggggc tgaaggatgc      360 ccagaaggta cccattgta tgggatctga tctggggcct cggtgcacat gctttacatg     420
tgtttagtcg aggttaaaaa gcgtctaggc cccccgaacc acgggacgt ggttttcctt     480 tgaaaaacac g                                                           491

<210> SEQ ID NO 24
<211> LENGTH: 75
<212> TYPE: DNA
<213> ORGANISM: Artificial Sequence
<220> FEATURE:
<223> OTHER INFORMATION: Synthetic Construct

<400> SEQUENCE: 24
agggccaaga ggggcagcgg cgagggcagg ggcagcctgc tgacctgcgg cgacgtggag      60
```

```
gagaacccccg gcccc                                                        75

<210> SEQ ID NO 25
<211> LENGTH: 66
<212> TYPE: DNA
<213> ORGANISM: Artificial Sequence
<220> FEATURE:
<223> OTHER INFORMATION: Synthetic Construct

<400> SEQUENCE: 25
ggaagcggag ctactaactt cagcctgctg aagcaggctg agacgtgga ggagaaccct        60 ggacct                                                                  66

<210> SEQ ID NO 26
<211> LENGTH: 69
<212> TYPE: DNA
<213> ORGANISM: Artificial Sequence
<220> FEATURE:
<223> OTHER INFORMATION: Synthetic Construct

<400> SEQUENCE: 26
ggaagcggac agtgtactaa ttatgctctc ttgaaattgg ctggagatgt tgagagcaac       60
cctggacct                                                               69

<210> SEQ ID NO 27
<211> LENGTH: 75
<212> TYPE: DNA
<213> ORGANISM: Artificial Sequence
<220> FEATURE:
<223> OTHER INFORMATION: Synthetic Construct

<400> SEQUENCE: 27
ggaagcggag tgaaacagac tttgaatttt gaccttctca agttggcggg agacgtggag       60
tccaaccctg gacct                                                        75

<210> SEQ ID NO 28
<211> LENGTH: 25
<212> TYPE: PRT
<213> ORGANISM: Artificial Sequence
<220> FEATURE:
<223> OTHER INFORMATION: Synthetic Construct

<400> SEQUENCE: 28

Arg Ala Lys Arg Gly Ser Gly Glu Gly Arg Gly Ser Leu Leu Thr Cys
1               5                   10                  15

Gly Asp Val Glu Glu Asn Pro Gly Pro
            20                  25

<210> SEQ ID NO 29
<211> LENGTH: 22
<212> TYPE: PRT
<213> ORGANISM: Artificial Sequence
<220> FEATURE:
<223> OTHER INFORMATION: Synthetic Construct

<400> SEQUENCE: 29

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 30
<211> LENGTH: 23
```

```
<212> TYPE: PRT
<213> ORGANISM: Artificial Sequence
<220> FEATURE:
<223> OTHER INFORMATION: Synthetic Construct

<400> SEQUENCE: 30

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 31
<211> LENGTH: 25
<212> TYPE: PRT
<213> ORGANISM: Artificial Sequence
<220> FEATURE:
<223> OTHER INFORMATION: Synthetic Construct

<400> SEQUENCE: 31

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 32
<211> LENGTH: 8565
<212> TYPE: DNA
<213> ORGANISM: Artificial Sequence
<220> FEATURE:
<223> OTHER INFORMATION: Synthetic Construct

<400> SEQUENCE: 32
atgttcagct tcgtggacct gagactgctg ctgctcctgg ctgctacagc cctgctgaca        60
cacggacaag aggaaggcca ggtcgaagga caggacgagg acatccctcc tatcacctgt       120
gtgcagaacg gcctgagata ccacgaccgg gatgtgtgga agcccgagcc ttgcagaatc       180
tgcgtgtgcg acaatggcaa ggtgctgtgc gacgacgtga tctgcgacga caaagaat        240
tgccctggcg ccgaagtgcc tgagggcgaa tgttgtcctg tgtgccctga tggcagcgag       300
agccccacag atcaagagac aacaggcgtg gaaggcccca gggcgatac aggacctaga        360
ggtcctagag acctgccgg acctcctggc agagatggaa ttcctggaca gcctggactg       420
cccggaccac ctggacctcc agggcctcca ggtccaccag actcggagg aaattttgcc        480
ccacagctga gctacggcta cgacgagaaa agcacaggcg gcatctctgt gcctggacct       540
atgggacctt ctggcccaag aggacttcct ggtcctcctg tgctccagg acctcaggga       600
tttcaaggac caccaggcga acctggcgaa ccaggcgcta gtggtccaat gggaccaaga       660
ggccctcctg gccaccagg caaaaatggc gacgatggcg aagccggaaa gcctggaagg       720
cctggcgaaa gaggcccgcc aggaccgcaa ggcgctagag ggttgcctgg aactgcagga       780
ctgcctggca tgaagggcca cagaggcttt tctggactgg atggcgctaa gggcgacgct       840
ggaccagcag gacctaaagg cgagcctgga tctcctggcg agaatggtgc acctggacag       900
atgggtccca gaggattgcc aggcgagaga ggtagacctg cgctccgggg accagccggt       960
gctagaggaa atgatggcgc aacaggtgct gctgggcctc ctggaccaac cggaccagct      1020
ggcccacctg gatttccagg cgctgttgga gcaaagggcg aagcaggccc acaaggacct      1080
aggggatctg aaggtcctca gggcgttaga ggcgagccag gccacctgg gcctgccggt      1140
gcagctggac ctgctggaaa ccctggtgct gatggacagc caggtgccaa aggtgctaat      1200
```

-continued

```
ggcgcccctg gaattgccgg cgctccaggt tttcccggcg caagagggcc atctggacct    1260
caaggcccag gcggacctcc gggtcctaag ggaaatagcg gagagccagg cgctcctggg    1320
agtaaaggcg atactggcgc aaaaggcgaa cccggacctg tgggagttca aggacctcct    1380
ggaccagctg gcgaggaagg caaaagaggc gctaggggag aaccaggacc aacagggctc    1440
cctggtccac ctggcgagcg cggaggacct ggatctagag gattccctgg cgcagatggc    1500
gtggccggac caaaaggacc tgcaggcgaa aggggatcac caggtcctgc aggccctaag    1560
ggttctccag gcgaggctgg cagacccggc gaagctggac tcccaggtgc taagggactg    1620
acaggctcac caggatctcc cggaccagac ggaaaaacag gacctccagg accggcagga    1680
caggatggta gacccggtcc tcctggaccg cctggtgcaa gaggacaagc tggcgtgatg    1740
ggctttcctg gaccaaaagg tgcagccggc gaacctggaa aagcaggcga gggggagtt    1800 cccggacctc caggtgctgt tggacctgcc ggaaaagatg gcgaagctgg tgcacaaggt    1860
cctccagggc cagccggacc agccggcgag agaggcgaac aaggaccagc cggatctcca    1920
ggatttcagg gactgccagg gcctgctggc ccgcctgggc aggcagggaa gccaggcgaa    1980
cagggtgttc ctggcgatct tggagcccct ggtcctagcg gagctagagg cgaaagagga    2040
tttcctggcg aaagggggcgt tcaggggtcca ccggaccag ctggaccaag gggtgcaaat    2100
ggtgccccag gcaatgacgg tgctaaaggc gacgcaggcg ccccaggtgc tcctggatct    2160
caaggcgcac ctggacttca gggaatgcct ggcgaacggg gagctgctgg acttcccggt    2220
ccaaaaggcg atagggagat gctggtcct aagggcgctg atggctctcc tggaaaggat    2280
ggcgtcagag gcctgacagg cccaattggc cctccgggac ctgctggcgc tccaggcgat    2340
aagggcgaat ctggacctag tggacccgct ggtcctacag gtgctagggg agccccaggc    2400
gaccggggag agcctggtcc accaggacct gctggatttg ctggacctcc tggcgctgat    2460
ggtcaacctg gtgctaaggg cgagccaggc gacgctggtg caaaaggcga cgctggtcca    2520
cctgaccggg ccggacctgc tgggccgcca ggaccattg gaaatgttgg tgcccctggc    2580
gccaaaggcg caagaggatc tgctggccca ccaggcgcta caggattccc aggtgccgct    2640
ggaagagttg gaccacccgg gccaagtgga aatgctggac caccgggacc gccaggacca    2700
gccggcaaag aaggtggaaa aggccctagg ggcgaaactg gccctgcagg caggccaggc    2760
gaagtgggcc ctccaggacc tccggggcct gccggcgaaa aaggatctcc aggcgcagat    2820
ggacccgcag gcgctcccgg aacaccaggt ccacagggaa ttgctggaca aggggagtt    2880 gtcggcctgc caggacagag ggggagagaga ggttttccag gactccctgg gccaagcgga    2940
gaacctggca acagggacc atctggtgcc agcggagaga gagggccacc aggaccaatg    3000
ggtcctccag gattgcagg gcctcctggc gaatctggta gagaaggtgc tccaggcgcc    3060
gagggatctc ctggacgtga tggttctcct ggcgccaagg gcgatagagg cgaaacaggc    3120
ccagctggac ctccaggcgc acccggcgct ccaggcgcac caggacctgt tggccctgct    3180
ggaaaatctg gcgacagagg cgaaactgga cccgcaggac cagccggacc tgttggacct    3240
gtgggtgcta aggacccgc tggaccacaa ggtcctagag gcgacaaggg cgaaacaggc    3300
gagcaaggcg acagaggcat caagggacac agaggattca gcggactgca gggaccacca    3360
gggccgcctg gaagtcccgg cgagcaggga ccaagcggag ctagtggtcc cgccggacct    3420
agaggaccac ctggttctgc tggtgcaccc ggaaaggacg gactgaatgg gctcccgga    3480 cctattgggc cacctggacc tagaggaaga acaggcgacg caggaccagt tggaccacct    3540
gggccacctg gaccgcctgg tcctcctgga cctccttctg ccggattcga cttcagcttc    3600
```

```
ctgcctcagc ctcctcaaga gaaggcccat gacggcggca gatattacag agccgacgac    3660
gccaacgtcg tgcgggacag agatctggaa gtggacacca cactgaagtc cctgtctcag    3720
cagatcgaga acatcagaag ccccgagggc agcagaaaga accctgccag aacctgtcgg    3780
gacctgaaga tgtgccacag cgattggaag tctggcgagt actggatcga ccccaaccag    3840
ggctgcaacc tggatgccat caaggtgttc tgcaacatgg aaaccggcga gacatgcgtg    3900 tacccacac agccatctgt ggctcagaag aactggtaca tcagcaagaa ccccaaggac     3960
aagcggcacg tttggttcgg cgagagcatg accgatggct ccagtttga gtatggcggc     4020 cagggctctg accctgccga tgttgctatc cagctgacct tcctgcggct gatgtctaca    4080
gaggccagcc agaacatcac ctaccactgc aagaacagcg tggcctacat ggatcagcag    4140
accggcaacc tgaagaaggc actgctgctt cagggcagca acgagatcga gatcagagcc    4200
gagggcaaca gccggttcac ctacagcgtg acagtggatg gctgcaccag ccatacaggc    4260 gcttgggca agaccgtgat cgagtacaag accaccaaga ccagcagact gcccatcatc    4320
gatgtggccc ctctggatgt tggggcaccc gatcaagagt tcggcttcga tgtgggccca    4380
gtgtgcttcc tgagggccaa gaggggcagc ggcgagggca gggcagcct gctgacctgc     4440 ggcgacgtgg aggagaaccc cggcccctg agcttcgtgg acaccagaac actgctgctg     4500
ctggccgtga cactgtgtct ggccacttgt cagagcctgc aagaggaaac agtgcggaaa    4560
ggacctgccg gcgatagagg acctagaggc gaaagaggtc ctcctggacc tcctggtaga    4620
gatggcgagg atggacctac aggaccacct ggtccaccag gacctccagg gcctcctggc    4680
cttggaggaa attttgccgc tcagtacgat ggcaaaggcg tcggacttgg ccctggacct    4740
atgggactta tgggcccaag gaggaccacca ggtgctgcag gcgctccagg accacaagga   4800
tttcaaggac cagctggcga gcctggcgaa cctggacaaa caggtcctgc tggtgctaga    4860
ggaccagccg ggcccacctgg aaaagctggc gaagatgggc accctggaaa gcctggtaga   4920
cccggcgaaa ggggtgttgt tggaccctcaa ggcgccagag gctttcctgg aacacctgga   4980
ctgcctggct tcaagggcat cagaggccac aatggcctgg acggactgaa aggacaacct    5040
ggtgctcctg gcgtgaaagg cgaaccaggc gcacctggcg aaaatggcac accaggacaa    5100
accggcgcaa gaggacttcc tggcgagaga ggaagagttg gagcccccag gtccagcaggc   5160 gcacgaggat ctgatggatc tgtgggacct gttggccctg ccggacctat ggaagtgct    5220 ggccctcctg gatttcctgg cgcacccgga ccaaagggcg aaattggagc tgtgggaaac    5280
gccggacctg caggcccagc tggaccaagg ggagaagttg gattgcctgg actgagcgga    5340
ccagttgggc caccagggaa tcctggtgcc aatggactga caggcgctaa aggtgcagct    5400
ggccttccag gcgttgccgg tgcaccagga ctgccaggac caagaggtat ccctggtcct    5460
gttggagctg ctggcgctac gggtgccaga ggacttgttg gagaacctgg ccagccgga    5520 tctaagggcg agtctggaaa caggggcgag ccaggatctg ctggtccaca aggcccgcct    5580
ggaccatcag gcgaagaagg caaacgaggc cctaatggcg aagccggtag tgccgggcct    5640
cctggaccac caggccttag aggatctcct ggctctagag gattgccagg cgctgatggt    5700
agagcaggcg ttatgggtcc acctggatca agaggcgctt ctggccctgc tggcgttaga    5760
ggtccaaatg gcgacgctgg cagaccaggc gagcccggtc ttatgggcc tagagggttg    5820 cctggaagcc ctggcaatat cggcccagcc ggaaaagaag gcctgttgg actccctggc     5880 atcgacggta gacctggacc aatcggaccc gcaggcgcta ggggagagcc tggaaatatt    5940
```

```
ggcttccctg ggcctaaagg ccccacaggc gatcctggaa agaacggcga taagggccat    6000
gctggactcg ctggtgcaag gggagcacct ggacctgacg gaaacaatgg tgctcaaggg    6060
ccgcctgggc cacaaggtgt tcaaggtgga aaaggcgagc agggcccacc tgggcctcca    6120
ggcttccaag gacttcccgg accatctggg ccagcaggcg aagttggaaa gcctggcgaa    6180
agaggactgc acggcgagtt tggcttgccg ggtcctgccg gtccacgggg agagagaggc    6240
cctccaggcg aatctggcgc cgcaggacct actgggccta tcggaagcag aggacctagt    6300
ggacctccag gacctgatgg caacaaaggc gaacctggtg ttgtgggcgc tgtgggaaca    6360
gctggacctt ctggtccttc tggattgccc ggcgagcgcg gagcagctgg tattcctggt    6420
ggcaaaggcg aaaagggcga gcctggactc agaggcgaga tcggcaatcc cggacgagat    6480
ggcgctagag gcgccccagg tgcagttggt gccccgggac ctgctggcgc aacaggcgac    6540
agaggcgagg ctggtgccgc tggtcctgcc gggccagccg gtcctagagg aagtccaggc    6600
gagaggggcg aagtgggacc cgctggaccc aatggatttg ctgggcccgc tggcgctgct    6660
ggtcaacctg gcgccaaagg cgagcgggga gctaaaggtc ctaaaggcga aatggcgtc    6720 gtgggcccta ctggaccagt gggagcagca ggccccgcag gtcctaacgg accacctgga    6780
ccagctgggt ctagaggcga cggcggaccg cctggaatga caggttttcc aggcgccgct    6840
ggaagaacag gtcctccagg accatctggc atctctggtc caccagggcc acctggtcct    6900
gctgaaaaag aaggactgag aggccctagg ggcgatcagg gtccagttgg aagaaccggc    6960
gaagtcggag ctgtcggccc accaggtttt gccggcgaaa aaggccctag cggagaagct    7020
ggaactgcag gaccgccggg aactcccggt cctcaaggat tgcttggcgc ccctggaatt    7080
ctgggactgc ccggtagtcg cggagaacgt ggactcccag gtgttgctgg cgccgtcgga    7140
gaaccgggac cacttggaat tgctggacca cctggtgcaa gaggtccacc tggtgcagtt    7200
ggaagtcctg gcgttaacgg tgctccaggc gaagccggca gagatggaaa tcccggcaat    7260
gatgccccgc tgggagagaa tggacagcct ggacataagg gcgagcgagg ctacccaggc    7320
aatattggac ctgtcggcgc agccggtgct cccggacctc atggtccagt cggtccagcc    7380
gggaagcacg gaaataaggg agaaacagga ccctccggtc ctgttggccc agctggcgca    7440
gttggaccaa gaggcccatc cggacctcag ggaatccgcg gagataaggg cgaacctggc    7500
gagaagggac ctagaggact gcctgggctg aaaggcccata acggactgca aggcctgcca    7560
ggcattgctg gccatcatgg cgatcaaggt gcacccggta gtgtgggtcc cgccggaccg    7620 agggggccg ctggtccatc tggacccgcc ggaaaagatg gcagaacagg acatcctggc    7680
acagtggggc ctgccggaat tagaggccca cagggacatc aaggccccgc tgggccgcca    7740
ggacctccgg gaccgccagg gccaccaggc gttagtggcg gaggatacga tttcggctac    7800
gacggcgact tctacagagc cgaccagcct agatctgccc ctagcctgag gcctaaggac    7860
tacgaagtgg acgccacact gaagtccctg aacaaccaga tcgagacact gctgaccccct    7920 gagggcagca gaaagaaccc tgccagaacc tgcagggacc tgagactgtc tcaccccgaa    7980
tggtcctccg gctactactg gatcgacccc aatcagggct gcaccatgga cgccatcaag    8040
gtgtactgcg acttcagcac cggcgagaca tgcatcagag cccagcctga aacatccccc    8100
gccaagaact ggtacagaag cagcaaggac aagaaacacg tgtggctggg cgagacaatc    8160
aacgccggca gccagttcga gtacaacgtg aaggcgtga ccagcaaaga gatggccaca    8220
cagctggctt tcatgagact gctggccaat tacgccagcc agaacatcac ctaccactgc    8280
aagaacagca ttgcctacat ggacgaggaa accggcaacc tgaagaaagc cgtgatcctg    8340
```

```
cagggctcta acgacgtgga actggtggcc gagggcaaca gcagattcac ctacaccgtg      8400
ctggtggacg gctgcagcaa aaagaccaac gagtggggca agaccatcat cgagtataag      8460
accaacaagc ccagcagact gcccttcctg gatatcgccc cactggatat tggaggcgcc      8520
gaccaagagt tctttgtgga catcggcccc gtgtgcttca agtga                     8565

<210> SEQ ID NO 33
<211> LENGTH: 8644
<212> TYPE: DNA
<213> ORGANISM: Artificial Sequence
<220> FEATURE:
<223> OTHER INFORMATION: Synthetic Construct

<400> SEQUENCE: 33
atgttcagct tcgtggacct gagactgctg ctgctcctgg ctgctacagc cctgctgaca        60
cacggacaag aggaaggcca ggtcgaagga caggacgagg acatccctcc tatcacctgt      120
gtgcagaacg gcctgagata ccacgaccgg gatgtgtgga agcccgagcc ttgcagaatc      180
tgcgtgtgcg acaatggcaa ggtgctgtgc gacgacgtga tctgcgacga gacaaagaat      240
tgccctggcg ccgaagtgcc tgagggcgaa tgttgtcctg tgtgccctga tggcagcgag      300
agccccacag atcaagagac aacaggcgtg gaaggcccca agggcgatac aggacctaga      360
ggtcctagag gacctgccgg acctcctggc agagatggaa ttcctggaca gcctggactg      420
cccggaccac ctggacctcc agggcctcca ggtccaccag gactcggagg aaattttgcc      480
ccacagctga gctacggcta cgacgagaaa agcacaggcg gcatctctgt gcctggacct      540
atgggaccct ctggcccaag aggacttcct ggtcctcctg gtgctccagg acctcaggga      600
tttcaaggac accaggcga acctggcgaa ccagcgcta gtggtccaat gggaccaaga      660
ggccctcctg ggccaccagg caaaaatggc gacgatggcg aagccggaaa gcctggaagg      720
cctggcgaaa gaggcccgcc aggaccgcaa ggcgctagag ggttgcctgg aactgcagga      780
ctgcctggca tgaagggcca cagaggcttt tctggactgg atggcgctaa gggcgacgct      840
ggaccagcag gacctaaagg cgagcctgga tctcctggcg agaatggtgc acctggacag      900
atgggtccca gaggattgcc aggcgagaga ggtagacctg cgctccggg accagccggt      960 gctagaggaa atgatggcgc aacaggtgct gctgggccctc ctggaccaac cggaccagct     1020
ggcccacctg gatttccagg cgctgttgga gcaaagggcg aagcaggccc acaaggacct     1080
aggggatctg aaggtcctca gggcgttaga ggcgagccag gccacctgg gcctgccggt     1140 gcagctggac tgctggaaa ccctggtgct gatggacagc caggtgccaa aggtgctaat     1200
ggcgcccctg gaattgccgg cgctccaggt tttccggcg caagagggcc atctggacct     1260
caaggcccag gcgacctcc gggtcctaag ggaaatagcg agagccaggc gctcctgggg     1320
agtaaaggcg atactggcgc aaaaggcgaa cccggacctg tgggagttca aggacctcct     1380
ggaccagctg gcgaggaagg caaaagaggc gctaggggag aaccaggacc aacagggctc     1440
cctggtccac ctggcgagcg cggaggacct ggatctagag gattccctgg cgcagatggc     1500
gtggccggac caaaaggacc tgcaggcgaa aggggatcac caggtcctgc aggccctaag     1560
ggttctccag gcgaggctgg cagacccggc gaagctggac tcccaggtgc taagggactg     1620
acaggctcac aggatctccc ggaccagac ggaaaaacag gacctccagg accggcagga     1680
caggatggta ccccggtcc tcctggaccg cctggtgcaa aggacaagc tggcgtgatg     1740 ggctttcctg gaccaaaagg tgcagccggc gaacctggaa aagcaggcga gagggagtt     1800
```

```
cccggaccctc caggtgctgt tggacctgcc ggaaaagatg gcgaagctgg tgcacaaggt    1860
cctccagggc cagccggacc agccggcgag agaggcgaac aaggaccagc cggatctcca    1920
ggatttcagg gactgccagg gcctgctggc ccgcctggcg aggcagggaa gccaggcgaa    1980
cagggtgttc ctggcgatct tggagcccct ggtcctagcg gagctagagg cgaaagagga    2040
tttcctggcg aaagggcgt tcagggtcca ccgggaccag ctggaccaag gggtgcaaat    2100
ggtgccccag gcaatgacgg tgctaaaggc gacgcaggcg ccccaggtgc tcctggatct    2160
caaggcgcac ctggacttca gggaatgcct ggcgaacggg gagctgctgg acttcccggt    2220
ccaaaaggcg ataggggaga tgctggtcct aagggcgctg atggctctcc tggaaaggat    2280
ggcgtcagag gcctgacagg cccaattggc cctccgggac ctgctggcgc tccaggcgat    2340
aagggcgaat ctggacctag tggacccgct ggtcctacag gtgctagggg agccccaggc    2400
gaccggggag agcctggtcc accaggacct gctggatttg ctggacctcc tggcgctgat    2460
ggtcaacctg gtgctaaggg cgagccaggc gacgctggtg caaaaggcga cgctggtcca    2520
cctggaccgg ccggacctgc tgggccgcca ggacctattg gaaatgttgg tgcccctggc    2580
gccaaaggcg caagaggatc tgctggccca ccaggcgcta caggattccc aggtgccgct    2640
ggaagagttg gaccacgggg gccaagtgga aatgctggac caccgggacc gccaggacca    2700
gccggcaaag aaggtggaaa aggccctagg ggcgaaactg gccctgcagg caggccaggc    2760
gaagtgggcc ctccaggacc tccggggcct gccggcgaaa aaggatctcc aggcgcagat    2820
ggacccgcag gcgctcccgg aacaccaggt ccacagggaa ttgctggaca aggggagtt    2880 gtcggcctgc caggacagag gggagagaga ggttttccag gactccctgg gccaagcgga    2940
gaacctggca acagggacc atctggtgcc agcggagaga gagggccacc aggaccaatg    3000
ggtcctccag gattggcagg gcctcctggc gaatctggta gagaaggtgc tccaggcgcc    3060
gagggatctc ctggacgtga tggttctcct ggcgccaagg gcgatagagg cgaaacaggc    3120
ccagctggac ctccaggcgc acccggcgct ccaggcgcac caggacctgt tggccctgct    3180
ggaaaatctg gcgacagagg cgaaactgga cccgcaggac cagccggacc tgttggacct    3240
gtgggtgcta gaggacccgc tggaccacaa ggtcctagag gcgacaaggg cgaaacaggc    3300
gagcaaggcg acagaggcat caagggacac agaggattca gcggactgca gggaccacca    3360
gggccgcctg gaagtcccgg cgagcaggga ccaagcggag ctagtggtcc cgccggacct    3420
agaggaccac ctggttctgc tggtgcaccc ggaaaggacg gactgaatgg gctccccgga    3480
cctattgggc cacctggacc tagaggaaga acaggcgacg caggaccagt ggaccacct    3540 gggccacctg gaccgcctgg tcctcctgga cctccttctg ccggattcga cttcagcttc    3600
ctgcctcagc ctcctcaaga gaaggcccat gacggcggca gatattacag agccgacgac    3660
gccaacgtcg tgcgggacag agatctggaa gtggacacca cactgaagtc cctgtctcag    3720
cagatcgaga acatcagaag ccccgagggc agcagaaaga accctgccag aacctgtcgg    3780
gacctgaaga tgtgccacag cgattggaag tctggcgagt actggatcga ccccaaccag    3840
ggctgcaacc tggatgccat caaggtgttc tgcaacatgg aaaccggcga gacatgcgtg    3900
tacccccaca cagccatctgt ggctcagaag aactggtaca tcagcaagaa ccccaaggac    3960
aagcggcacg tttggttcgg cgagagcatg accgatggct tccagtttga gtatggcggc    4020
cagggctctg accctgccga tgttgctatc cagctgacct tcctgcggct gatgtctaca    4080
gaggccagcc agaacatcac ctaccactgc aagaacagcg tggcctacat ggatcagcag    4140
accggcaacc tgaagaaggc actgctgctt cagggcagca acgagatcga gatcagagcc    4200
```

```
gagggcaaca gccggttcac ctacagcgtg acagtggatg gctgcaccag ccatacaggc    4260
gcttggggca agaccgtgat cgagtacaag accaccaaga ccagcagact gcccatcatc    4320
gatgtggccc ctctggatgt tggggcaccc gatcaagagt tcggcttcga tgtgggccca    4380
gtgtgcttcc tgtaagaatt cgtcgattcg gttgcagcat ttaaagcggt tgacaacttt    4440
aaaagaagga aaagaaggt tgaagaaaag ggtgtagtaa gtaagtataa gtacagaccg    4500
gagaagtacg ccggtcctga ttcgtttaat ttgaaagaag aaaatgctga gcttcgtgga    4560
caccagaaca ctgctgctgc tggccgtgac actgtgtctg gccacttgtc agagcctgca    4620
agaggaaaca gtgcggaaag gacctgccgg cgatagagga cctagaggcg aaagaggtcc    4680
tcctggacct cctggtagag atggcgagga tggacctaca ggaccacctg gtccaccagg    4740
acctccaggg cctcctggcc ttggaggaaa ttttgccgct cagtacgatg gcaaaggcgt    4800
cggacttggc cctggaccta tgggacttat gggcccaaga ggaccaccag gtgctgcagg    4860
cgctccagga ccacaaggat ttcaaggacc agctggcgag cctggcgaac ctggacaaac    4920
aggtcctgct ggtgctagag accagccgg gccacctgga aaagctggcg aagatgggca    4980
ccctggaaag cctggtagac ccggcgaaag gggtgttgtt ggacctcaag cgccagagg    5040 cttttcctgga acacctggac tgcctggctt caagggcatc agaggccaca atggcctgga    5100
cggactgaaa ggacaacctg gtgctcctgg cgtgaaaggc gaaccaggcg cacctggcga    5160
aaatggcaca ccaggacaaa ccggcgcaag aggacttcct ggcgagagag aagagttgg    5220 agccccaggt ccagcaggcg cacgaggatc tgatggatct gtgggacctg ttggccctgc    5280 cggaccctatt ggaagtgctg gccctcctgg attttcctggc gcacccggac caaagggcga    5340
aattggagct gtgggaaacg ccggacctgc aggcccagct ggaccaaggg gagaagttgg    5400
attgcctgga ctgagcggac cagttgggcc accagggaat cctggtgcca atggactgac    5460
aggcgctaaa ggtgcagctg gccttccagg cgttgccggt gcaccaggac tgccaggacc    5520
aagaggtatc cctggtcctg ttggagctgc tggcgctacg ggtgccagag acttgttgg    5580 agaacctggg ccagccggat ctaagggcga gtctggaaac aagggcgagc caggatctgc    5640
tggtccacaa ggcccgcctg gaccatcagg cgaagaaggc aaacgaggcc ctaatggcga    5700
agccggtagt gccgggcctc ctgaccacc aggccttaga ggatctcctg gctctagagg    5760
attgccaggc gctgatggta gagcaggcgt tatgggtcca cctggatcaa gaggcgcttc    5820
tggccctgct ggcgttagag gtccaaatgg cgacgctggc agaccaggcg agcccggtct    5880 tatgggggcct agagggttgc ctggaagccc tggcaatatc ggcccagccg gaaaagaagg    5940
ccctgttgga ctccctggca tcgacggtag acctggacca atcggacccg caggcgctag    6000
gggagagcct ggaaatattg gcttccctgg gcctaaaggc cccacaggcg atcctggaaa    6060
gaacggcgat aagggccatg ctggactcgc tggtgcaagg ggagcacctg accctgacgg    6120
aaacaatggt gctcaaggc cgcctgggcc acaaggtgtt caaggtggaa aaggcgagca    6180
gggcccacct gggcctccag gcttccaagg acttcccgga ccatctgggc cagcaggcga    6240
agttggaaag cctggcgaaa gaggactgca cggcgagttt ggcttgccgg gtcctgccgg    6300
tccacgggga gagagaggcc ctccaggcga atctggcgcc gcaggaccta ctggccctat    6360
cggaagcaga ggacctagtg gacctccagg acctgatggc aacaaaggcg aacctggtgt    6420
tgtgggcgct gtgggaacag ctggaccttc tggtccttct ggattgcccg gcgagcgcgg    6480
agcagctggt attcctggtg gcaaaggcga aaagggcgag cctggactca gaggcgagat    6540
```

| | |
|---|---|
| cggcaatccc ggacgagatg gcgctagagg cgccccaggt gcagttggtg ccccgggacc | 6600 |
| tgctggcgca acaggcgaca gaggcgaggc tggtgccgct ggtcctgccg ggccagccgg | 6660 |
| tcctagagga agtccaggcg agaggggcga agtgggaccc gctggaccca atggatttgc | 6720 |
| tgggcccgct ggcgctgctg gtcaacctgg cgccaaaggc gagcgcggag ctaaaggtcc | 6780 |
| taaaggcgag aatggcgtcg tgggccctac tggaccagtg ggagcagcag gccccgcagg | 6840 |
| tcctaacgga ccacctggac cagctgggtc tagaggcgac ggcggaccgc ctggaatgac | 6900 |
| aggttttcca ggcgccgctg gaagaacagg tcctccagga ccatctggca tctctggtcc | 6960 |
| accagggcca cctggtcctg ctggaaaaga aggactgaga ggccctaggg gcgatcaggg | 7020 |
| tccagttgga agaaccggcg aagtcggagc tgtcggccca ccaggttttg ccggcgaaaa | 7080 |
| aggccctagc ggagaagctg gaactgcagg accgccggga actcccggtc ctcaaggatt | 7140 |
| gcttggcgcc cctggaattc tgggactgcc cggtagtcgc ggagaacgtg gactcccagg | 7200 |
| tgttgctggc gccgtcggag aaccgggacc acttggaatt gctggaccac ctggtgcaag | 7260 |
| aggtccacct ggtgcagttg gaagtcctgg cgttaacggt gctccaggcg aagccggcag | 7320 |
| agatggaaat cccggcaatg atggcccgcc tgggagagat ggacagcctg gacataaggg | 7380 |
| cgagcgaggc tacccaggca atattggacc tgtcggcgca gccggtgctc ccggacctca | 7440 |
| tggtccagtc ggtccagccg ggaagcacgg aaataggggga gaaacaggac cctccggtcc | 7500 |
| tgttggccca gctggcgcag ttggaccaag aggcccatcc ggacctcagg gaatccgcgg | 7560 |
| agataagggc gaacctggcg agaagggacc tagaggactg cctgggctga aaggccataa | 7620 |
| cggactgcaa ggcctgccag gcattgctgg ccatcatggc gatcaaggtg cacccggtag | 7680 |
| tgtgggtccc gccggaccga ggggtcccgc tggtccatct ggaccgccg gaaaagatgg | 7740 |
| cagaacagga catcctggca cagtgggggcc tgccggaatt agaggccac agggacatca | 7800 |
| aggccccgct gggccgccag gacctccggg accgccaggg ccaccaggcg ttagtggcgg | 7860 |
| aggatacgat ttcggctacg acggcgactt ctacagagcc gaccagccta gatctgcccc | 7920 |
| tagcctgagg cctaaggact acgaagtgga cgccacactg aagtccctga caaccagat | 7980 |
| cgagacactg ctgaccccctg agggcagcag aaagaaccct gccagaacct gcagggacct | 8040 |
| gagactgtct caccccgaat ggtcctccgg ctactactgg atcgacccca atcagggctg | 8100 |
| caccatggac gccatcaagg tgtactgcga cttcagcacc ggcgagacat gcatcagagc | 8160 |
| ccagcctgag aacatccccg ccaagaactg gtacagaagc agcaaggaca gaaacacgt | 8220 |
| gtggctgggc gagacaatca cgcggcag ccagttcgag tacaacgtgg aaggcgtgac | 8280 |
| cagcaaagag atggccacac agctggcttt catgagactg ctggccaatt acgccagcca | 8340 |
| gaacatcacc taccactgca agaacagcat tgcctacatg gacgaggaaa ccggcaacct | 8400 |
| gaagaaagcc gtgatcctgc agggctctaa cgacgtggaa ctggtggccg agggcaacag | 8460 |
| cagattcacc tacaccgtgc tggtggacgg ctgcagcaaa aagaccaacg agtggggcaa | 8520 |
| gaccatcatc gagtataaga ccaacaagcc cagcagactg cccttcctgg atatcgcccc | 8580 |
| actggatatt ggaggcgccg accaagagtt ctttgtggac atcggccccg tgtgcttcaa | 8640 |
| gtga | 8644 |

<210> SEQ ID NO 34
<211> LENGTH: 8987
<212> TYPE: DNA
<213> ORGANISM: Artificial Sequence
<220> FEATURE:
<223> OTHER INFORMATION: Synthetic Construct

<400> SEQUENCE: 34

```
atgttcagct tcgtggacct gagactgctg ctgctcctgg ctgctacagc cctgctgaca      60
cacggacaag aggaaggcca ggtcgaagga caggacgagg acatccctcc tatcacctgt     120
gtgcagaacg gcctgagata ccacgaccgg gatgtgtgga agcccgagcc ttgcagaatc     180
tgcgtgtgcg acaatggcaa ggtgctgtgc gacgacgtga tctgcgacga gacaaagaat     240
tgccctggcg ccgaagtgcc tgagggcgaa tgttgtcctg tgtgccctga tggcagcgag     300
agccccacag atcaagagac aacaggcgtg gaaggcccca gggcgatac aggacctaga      360
ggtcctagag gacctgccgg acctcctggc agagatggaa ttcctggaca gcctggactg     420
cccggaccac ctggacctcc agggcctcca ggtccaccag gactcggagg aaattttgcc     480
ccacagctga gctacggcta cgacgagaaa agcacaggcg gcatctctgt gcctggacct     540
atgggacctt ctggcccaag aggacttcct ggtcctcctg gtgctccagg acctcaggga     600
tttcaaggac caccaggcga acctggcgaa ccaggcgcta gtggtccaat gggaccaaga     660
ggccctcctg gccaccagg caaaaatggc gacgatggcg aagccggaaa gcctggaagg     720
cctggcgaaa gaggcccgcc aggaccgcaa ggcgctagag ggttgcctgg aactgcagga     780
ctgcctggca tgaagggcca cagaggcttt tctggactgg atggcgctaa gggcgacgct     840
ggaccagcag gacctaaagg cgagcctgga tctcctggcg agaatggtgc acctggacag     900
atgggtccca gaggattgcc aggcgagaga ggtagacctg gcgctccggg accagccggt     960
gctagaggaa atgatggcgc aacaggtgct gctgggcctc ctggaccaac cggaccagct    1020
ggcccacctg gatttccagg cgctgttgga gcaaagggcg aagcaggccc acaaggacct    1080
agggatctg aaggtcctca gggcgttaga ggcgagccag gccacctgg gcctgccggt      1140
gcagctggac ctgctggaaa ccctggtgct gatggacagc caggtgccaa aggtgctaat    1200
ggcgcccctg gaattgccgg cgctccaggt tttcccggcg caagagggcc atctggacct    1260
caaggcccag gcggacctcc gggtcctaag ggaaatagcg gagagccagg cgctcctggg    1320
agtaaaggcg atactggcgc aaaaggcgaa cccggacctg tgggagttca aggacctcct    1380
ggaccagctg gcgaggaagg caaaagaggc gctaggggag aaccaggacc aacagggctc    1440
cctggtccac ctggcgagcg cggaggacct ggatctagag gattccctgg cgcagatggc    1500
gtggccggac caaaaggacc tgcaggcgaa aggggatcac aggtcctgc aggccctaag     1560
ggttctccag gcgaggctgg cagacccggc gaagctggac tcccaggtgc taagggactg    1620
acaggctcac caggatctcc cggaccagac ggaaaaacag gacctccagg accggcagga    1680
caggatggta gacccggtcc tcctggaccg cctggtgcaa aggacaagc tggcgtgatg     1740
ggctttcctg gaccaaaagg tgcagccggc gaacctggaa agcaggcga gagggggagtt    1800
cccggacctc caggtgctgt tggacctgcc ggaaaagatg gcgaagctgg tgcacaaggt    1860
cctccagggc cagccggacc agccggcgag agaggcgaac aaggaccagc cggatctcca    1920
ggatttcagg gactgccagg gcctgctggc ccgcctggcg aggcagggaa gccaggcgaa    1980
cagggtgttc ctggcgatct tggagcccct ggtcctagcg gagctagagg cgaaagagga    2040
tttcctggcg aaaggggcgt tcagggtcca ccggaccag ctggaccaag gggtgcaaat      2100
ggtgccccag gcaatgacgg tgctaaaggc gacgcaggcg ccccaggtgc tcctggatct    2160
caaggcgcac ctgacttca gggaatgcct ggcgaacggg gagctgctgg acttcccggt     2220
ccaaaaggcg ataggggaga tgctggtcct aagggcgctg atggctctcc tggaaaggat    2280
```

```
ggcgtcagag gcctgacagg cccaattggc cctccgggac ctgctggcgc tccaggcgat    2340
aagggcgaat ctggacctag tggacccgct ggtcctacag gtgctagggg agccccaggc    2400
gaccggggag agcctggtcc accaggacct gctggatttg ctggacctcc tggcgctgat    2460
ggtcaacctg gtgctaaggg cgagccaggc gacgctggtg caaaaggcga cgctggtcca    2520
cctggaccgg ccggacctgc tgggccgcca ggacctattg gaaatgttgg tgcccctggc    2580
gccaaaggcg caagaggatc tgctggccca ccaggcgcta caggattccc aggtgccgct    2640
ggaagagttg gaccaccggg gccaagtgga aatgctggac caccgggacc gccaggacca    2700
gccggcaaag aaggtggaaa aggccctagg ggcgaaactg gccctgcagg caggccaggc    2760
gaagtgggcc ctccaggacc tccggggcct gccggcgaaa aaggatctcc aggcgcagat    2820
ggacccgcag gcgctcccgg aacaccaggt ccacagggaa ttgctggaca aggggagtt    2880 gtcggcctgc caggacagag gggagagaga ggttttccag gactccctgg gccaagcgga    2940
gaacctggca acagggacc atctggtgcc agcggagaga gagggccacc aggaccaatg    3000
ggtcctccag gattggcagg gcctcctggc gaatctggta gagaaggtgc tccaggcgcc    3060
gagggatctc ctggacgtga tggttctcct ggcgccaagg gcgatagagg cgaaacaggc    3120
ccagctggac ctccaggcgc acccggcgct ccaggcgcac caggacctgt ggccctgct    3180 ggaaaatctg gcgacagagg cgaaactgga cccgcaggac cagccggacc tgttggacct    3240
gtgggtgcta gaggacccgc tggaccacaa ggtcctagag gcgacaaggg cgaaacaggc    3300
gagcaaggcg acagaggcat caagggacac agaggattca gcggactgca gggaccacca    3360
gggccgcctg gaagtcccgg cgagcaggga ccaagcggga ctagtggtcc cgccggacct    3420
agaggaccac ctggttctgc tggtgcaccc ggaaaggacg gactgaatgg gctccccgga    3480
cctattgggc cacctggacc tagaggaaga acaggcgacg caggaccagt tggaccacct    3540
gggccacctg gaccgcctgg tcctcctgga cctccttctg ccggattcga cttcagcttc    3600
ctgcctcagc ctcctcaaga gaaggcccat gacggcggca gatattacag agccgacgac    3660
gccaacgtcg tgcgggacag agatctggaa gtggacacca cactgaagtc cctgtctcag    3720
cagatcgaga acatcagaag ccccgagggc agcagaaaga accctgccag aacctgtcgg    3780
gacctgaaga tgtgccacag cgattggaag tctggcgagt actggatcga ccccaaccag    3840
ggctgcaacc tggatgccat caaggtgttc tgcaacatgg aaaccggcga gacatgcgtg    3900
taccccacac agccatctgt ggctcagaag aactggtaca tcagcaagaa ccccaaggac    3960
aagcggcacg tttggttcgg cgagagcatg accgatggct ccagtttga gtatggcggc    4020 cagggctctg accctgccga tgttgctatc cagctgacct tcctgcggct gatgtctaca    4080
gaggccagcc agaacatcac ctaccactgc aagaacagcg tggcctacat ggatcagcag    4140
accggcaacc tgaagaaggc actgctgctt cagggcagca cgagatcga gatcagagcc    4200 gagggcaaca gccggttcac ctacagcgtg acagtggatg gctgcaccag ccatacaggc    4260
gcttggggca agaccgtgat cgagtacaag accaccaaga ccagcagact gcccatcatc    4320
gatgtggccc ctctggatgt tgggcaccc gatcaagagt tcggcttcga tgtgggccca    4380
gtgtgcttcc tgtaagttat tttccaccat attgccgtct tttggcaatg tgagggcccg    4440
gaaacctggc cctgtcttct tgacgagcat tcctaggggt ctttccctc tcgccaaagg    4500 aatgcaaggt ctgttgaatg tcgtgaagga agcagttcct ctggaagctt cttgaagaca    4560
aacaacgtct gtagcgaccc tttgcaggca gcggaacccc ccacctggcg acaggtgcct    4620
ctgcggccaa aagccacgtg tataagatac acctgcaaag gcggcacaac cccagtgcca    4680
```

```
cgttgtgagt tggatagttg tggaaagagt caaatggctc acctcaagcg tattcaacaa   4740
ggggctgaag gatgcccaga aggtacccca ttgtatggga tctgatctgg ggcctcggtg   4800
cacatgcttt acatgtgttt agtcgaggtt aaaaagcgtc taggccccc gaaccacggg   4860 gacgtggttt tcctttgaaa aacacgatgc tgagcttcgt ggacaccaga acactgctgc   4920
tgctggccgt gacactgtgt ctggccactt gtcagagcct gcaagaggaa acagtgcgga   4980
aaggacctgc cggcgataga ggacctagag gcgaaagagg tcctcctgga cctcctggta   5040
gagatggcga ggatggacct acaggaccac ctggtccacc aggacctcca gggcctcctg   5100
gccttggagg aaattttgcc gctcagtacg atggcaaagg cgtcggactt ggccctggac   5160
ctatgggact tatgggccca agaggaccac caggtgctgc aggcgctcca ggaccacaag   5220
gatttcaagg accagctggc gagcctggcg aacctggaca aacaggtcct gctggtgcta   5280
gaggaccagc cgggccacct ggaaaagctg gcgaagatgg gcaccctgga aagcctggta   5340
gacccggcga aaggggtgtt gttggacctc aaggcgccag aggctttcct ggaacacctg   5400
gactgcctgg cttcaagggc atcagaggcc acaatggcct ggacggactg aaaggacaac   5460
ctggtgctcc tggcgtgaaa ggcgaaccag gcgcacctgg cgaaaatggc acaccaggac   5520
aaaccggcgc aagaggactt cctggcgaga gaggaagagt tggagcccca ggtccagcag   5580
gcgcacgagg atctgatgga tctgtgggac ctgttggccc tgccgaccct attggaagtg   5640
ctggccctcc tggatttcct ggcgcacccg gaccaaaggg cgaaattgga gctgtgggaa   5700
acgccggacc tgcaggccca gctggaccaa ggggagaagt tggattgcct ggactgagcg   5760
gaccagttgg gccaccaggg aatcctggtg ccaatggact gacaggcgct aaaggtgcag   5820
ctggccttcc aggcgttgcc ggtgcaccag gactgccagg accaagaggt atccctggtc   5880
ctgttggagc tgctggcgct acgggtgcca gaggacttgt tggagaacct gggccagccg   5940
gatctaaggg cgagtctgga aacaagggcg agccaggatc tgctggtcca caaggcccgc   6000
ctggaccatc aggcgaagaa ggcaaacgag gccctaatgg cgaagccggt agtgccgggc   6060
ctcctggacc accaggcctt agaggatctc ctggctctag aggattgcca ggcgctgatg   6120
gtagagcagg cgttatgggt ccacctggat caagaggcgc ttctggccct gctggcgtta   6180
gaggtccaaa tggcgacgct ggcagaccag gcgagcccgg tcttatgggg cctagagggt   6240
tgcctggaag ccctggcaat atcggcccag ccggaaaaga aggccctgtt ggactccctg   6300
gcatcgacgg tagacctgga ccaatcggac ccgcaggcgc taggggagag cctggaaata   6360
ttggcttccc tgggcctaaa gccccacag gcgatcctgg aaagaacggc gataagggcc   6420
atgctggact cgctggtgca agggagcac ctggacctga cggaaacaat ggtgctcaag   6480
ggccgcctgg gccacaaggt gttcaaggtg aaaaggcga gcaggcccca cctgggcctc   6540
caggcttcca aggacttccc ggaccatctg gccagcagg cgaagttgga aagcctggcg   6600
aaagaggact gcacgcgag tttggcttgc cgggtcctgc cggtccacgg ggagagagag   6660
gccctccagg cgaatctggc gccgcaggac ctactggccc tatcggaagc agaggaccta   6720
gtggacctcc aggacctgat ggcaacaaag gcgaacctgg tgttgtgggc gctgtgggaa   6780
cagctggacc ttctggtcct tctggattgc ccggcgagcg cggagcagct ggtattcctg   6840
gtggcaaagg cgaaaagggc gagcctggac tcagaggcga gatcggcaat cccggacgag   6900
atggcgctag aggcgcccca ggtgcagttg gtgcccggg acctgctggc gcaacaggcg   6960
acagaggcga ggctggtgcc gctggtcctg ccgggccagc cggtcctaga ggaagtccag   7020
```

```
gcgagagggg cgaagtggga cccgctggac ccaatggatt tgctgggccc gctggcgctg    7080
ctggtcaacc tggcgccaaa ggcgagcggg gagctaaagg tcctaaaggc gagaatggcg    7140
tcgtgggccc tactggacca gtgggagcag caggccccgc aggtcctaac ggaccacctg    7200
gaccagctgg gtctagaggc gacggcgac cgcctggaat gacaggtttt ccaggcgccg    7260
ctggaagaac aggtcctcca ggaccatctg gcatctctgg tccaccaggg ccacctggtc    7320
ctgctggaaa agaaggactg agaggcccta ggggcgatca gggtccagtt ggaagaaccg    7380
gcgaagtcgg agctgtcggc ccaccaggtt ttgccggcga aaaggccct agcggagaag    7440
ctggaactgc aggaccgccg ggaactcccg gtcctcaagg attgcttggc gcccctggaa    7500
ttctgggact gcccggtagt cgcggagaac gtggactccc aggtgttgct ggcgccgtcg    7560
gagaaccggg accacttgga attgctggac cacctggtgc aagaggtcca cctggtgcag    7620
ttggaagtcc tggcgttaac ggtgctccag gcgaagccgg cagagatgga aatcccggca    7680
atgatggccc gcctgggaga gatggacagc ctggacataa gggcgagcga ggctacccag    7740
gcaatattgg acctgtcggc gcagccgtg ctcccggacc tcatggtcca gtcggtccag    7800
ccgggaagca cggaaatagg ggagaaacag gaccctccgg tcctgttggc ccagctggcg    7860
cagttggacc aagaggccca tccggacctc agggaatccg cggagataag ggcgaacctg    7920
gcgagaaggg acctagagga ctgcctgggc tgaaaggcca taacggactg caaggcctgc    7980
caggcattgc tggccatcat ggcgatcaag gtgcacccgg tagtgtgggt cccgccggac    8040
cgaggggtcc cgctggtcca tctggacccg ccggaaaaga tggcagaaca ggacatcctg    8100
gcacagtggg gcctgccgga attagaggcc acagggaca tcaaggcccc gctgggccgc    8160
caggacctcc gggaccgcca gggccaccag gcgttagtgg cggaggatac gatttcggct    8220
acgacgcga cttctacaga gccgaccagc ctagatctgc ccctagcctg aggcctaagg    8280
actacgaagt ggacgccaca ctgaagtccc tgaacaacca gatcgagaca ctgctgaccc    8340
ctgagggcag cagaaagaac cctgccagaa cctgcaggga cctgagactg tctcaccccg    8400
aatggtcctc cggctactac tggatcgacc ccaatcaggg ctgcaccatg gacgccatca    8460
aggtgtactg cgacttcagc accggcgaga catgcatcag agcccagcct gagaacatcc    8520
ccgccaagaa ctggtacaga agcagcaagg acaagaaaca cgtgtggctg ggcgagacaa    8580
tcaacgccgg cagccagttc gagtacaacg tggaaggcgt gaccagcaaa gagatggcca    8640
cacagctggc tttcatgaga ctgctggcca attacgccag ccagaacatc acctaccact    8700
gcaagaacag cattgcctac atggacgagg aaaccggcaa cctgaagaaa gccgtgatcc    8760
tgcagggctc taacgacgtg gaactggtgg ccgagggcaa cagcagattc acctacaccg    8820
tgctggtgga cggctgcagc aaaaagacca acgagtgggg caagaccatc atcgagtata    8880
agaccaacaa gcccagcaga ctgcccttcc tggatatcgc cccactggat attggaggcg    8940
ccgaccaaga gttctttgtg gacatcggcc ccgtgtgctt caagtga               8987
```

<210> SEQ ID NO 35
<211> LENGTH: 7434
<212> TYPE: DNA
<213> ORGANISM: Homo sapiens

<400> SEQUENCE: 35

```
atgcttaggg gtccggggcc cgggctgctg ctgctggccg tccagtgcct ggggacagcg     60
gtgccctcca cgggagcctc gaagagcaag aggcaggctc agcaaatggt tcagccccag    120
tccccggtgg ctgtcagtca aagcaagccc ggttgttatg acaatggaaa acactatcag    180
```

```
ataaatcaac agtgggagcg gacctaccta ggcaatgcgt tggtttgtac ttgttatgga    240
ggaagccgag gttttaactg cgagagtaaa cctgaagctg aagagacttg ctttgacaag    300
tacactggga acacttaccg agtgggtgac acttatgagc gtcctaaaga ctccatgatc    360
tgggactgta cctgcatcgg ggctgggcga gggagaataa gctgtaccat cgcaaaccgc    420
tgccatgaag ggggtcagtc ctacaagatt ggtgacacct ggaggagacc acatgagact    480
ggtggttaca tgttagagtg tgtgtgtctt ggtaatggaa aaggagaatg gacctgcaag    540
cccatagctg agaagtgttt tgatcatgct gctgggactt cctatgtggt cggagaaacg    600
tgggagaagc cctaccaagg ctggatgatg gtagattgta cttgcctggg agaaggcagc    660
ggacgcatca cttgcacttc tagaaataga tgcaacgatc aggacacaag gacatcctat    720
agaattggag acacctggag caagaaggat aatcgaggaa acctgctcca gtgcatctgc    780
acaggcaacg gccgaggaga gtggaagtgt gagaggcaca cctctgtgca gaccacatcg    840
agcggatctg gccccttcac cgatgttcgt gcagctgttt accaaccgca gcctcacccc    900
cagcctcctc cctatggcca ctgtgtcaca gacagtggtg tggtctactc tgtggggatg    960
cagtggctga gacacaagg aaataagcaa atgctttgca cgtgcctggg caacggagtc   1020
agctgccaag agacagctgt aacccagact tacggtggca actcaaatgg agagccatgt   1080
gtcttaccat tcacctacaa tggcaggacg ttctactcct gcaccacaga agggcgacag   1140
gacggacatc tttggtgcag cacaacttcg aattatgagc aggaccagaa atactctttc   1200
tgcacagacc acactgtttt ggttcagact cgaggaggaa attccaatgg tgccttgtgc   1260
cacttcccct cctatacaa caaccacaat tacactgatt gcacttctga gggcagaaga   1320
gacaacatga gtggtgtgg gaccacacag aactatgatg ccgaccagaa gtttgggttc   1380
tgccccatgg ctgcccacga ggaaatctgc acaaccaatg aagggggtcat gtaccgcatt   1440
ggagatcagt gggataagca gcatgacatg ggtcacatga tgaggtgcac gtgtgttggg   1500
aatggtcgtg gggaatggac atgcattgcc tactcgcagc ttcgagatca gtgcattgtt   1560
gatgacatca cttacaatgt gaacgacaca ttccacaagc gtcatgaaga ggggcacatg   1620
ctgaactgta catgcttcgg tcagggtcgg ggcaggtgga agtgtgatcc cgtcgaccaa   1680
tgccaggatt cagagactgg gacgttttat caaattggag attcatggga gaagtatgtg   1740
catggtgtca gataccagtg ctactgctat ggccgtggca ttggggagtg gcattgccaa   1800
cctttacaga cctatccaag ctcaagtggt cctgtcgaag tatttatcac tgagactccg   1860
agtcagccca actcccaccc catccagtgg aatgcaccac agccatctca catttccaag   1920
tacattctca ggtggagacc taaaaattct gtaggccgtt ggaaggaagc taccatacca   1980
ggccacttaa actcctacac catcaaaggc ctgaagcctg tgtggtata cgagggccag   2040
ctcatcagca tccagcagta cggccaccaa gaagtgactc gctttgactt caccaccacc   2100
agcaccagca cacctgtgac cagcaacacc gtgacaggag agacgactcc cttttctcct   2160
cttgtggcca cttctgaatc tgtgaccgaa atcacagcca gtagctttgt ggtctcctgg   2220
gtctcagctt ccgacaccgt gtcgggattc cgggtggaat atgagctgag tgaggaggga   2280
gatgagccac agtacctgga tcttccaagc acagccactt ctgtgaacat ccctgacctg   2340
cttcctggcc gaaaatacat tgtaaatgtc tatcagatat ctgaggatgg ggagcagagt   2400
ttgatcctgt ctacttcaca aacaacagcg cctgatgccc ctcctgaccc gactgtggac   2460
caagttgatg acacctcaat tgttgttcgc tggagcagac cccaggctcc catcacaggg   2520
```

```
tacagaatag tctattcgcc atcagtagaa ggtagcagca cagaactcaa ccttcctgaa    2580
actgcaaact ccgtcaccct cagtgacttg caacctggtg ttcagtataa catcactatc    2640
tatgctgtgg aagaaaatca agaaagtaca cctgttgtca ttcaacaaga aaccactggc    2700
accccacgct cagatacagt gccctctccc agggacctgc agtttgtgga agtgacagac    2760
gtgaaggtca ccatcatgtg gacaccgcct gagagtgcag tgaccggcta ccgtgtggat    2820
gtgatccccg tcaacctgcc tggcgagcac gggcagaggc tgcccatcag caggaacacc    2880
tttgcagaag tcaccgggct gtcccctggg gtcacctatt acttcaaagt ctttgcagtg    2940
agccatggga gggagagcaa gcctctgact gctcaacaga caaccaaact ggatgctccc    3000
actaacctcc agtttgtcaa tgaaactgat tctactgtcc tggtgagatg gactccacct    3060
cgggcccaga taacaggata ccgactgacc gtgggcctta cccgaagagg acagcccagg    3120
cagtacaatg tgggtccctc tgtctccaag tacccactga ggaatctgca gcctgcatct    3180
gagtacaccg tatccctcgt ggccataaag ggcaaccaag agagcccaa agccactgga    3240
gtctttacca cactgcagcc tgggagctct attccaccct acaacaccga ggtgactgag    3300
accaccattg tgatcacatg gacgcctgct ccaagaattg gtttttaagct gggtgtacga    3360
ccaagccagg gaggagaggc accacgagaa gtgacttcag actcaggaag catcgttgtg    3420
tccggcttga ctccaggagt agaatacgtc tacaccatcc aagtcctgag agatggacag    3480
gaaagagatg cgccaattgt aaacaaagtg gtgacaccat tgtctccacc aacaaacttg    3540
catctggagg caaaccctga cactggagtg ctcacagtct cctgggagag gagcaccacc    3600
ccagacatta ctggttatag aattaccaca acccctacaa acggccagca gggaaattct    3660
ttggaagaag tggtccatgc tgatcagagc tcctgcactt ttgataaccct gagtcccggc    3720
ctggagtaca atgtcagtgt ttacactgtc aaggatgaca aggaaagtgt ccctatctct    3780
gataccatca tcccagaggt gccccaactc actgacctaa gctttgttga tataaccgat    3840
tcaagcatcg gcctgaggtg gaccccgcta aactcttcca ccattattgg gtaccgcatc    3900
acagtagttg cggcaggaga aggtatccct atttttgaag attttgtgga ctcctcagta    3960
ggatactaca cagtcacagg gctggagccg ggcattgact atgatatcag cgttatcact    4020
ctcattaatg gcggcgagag tgcccctact acactgacac aacaaacggc tgttcctcct    4080
cccactgacc tgcgattcac caacattggt ccagacacca tgcgtgtcac ctgggctcca    4140
cccccatcca ttgatttaac caacttcctg gtgcgttact cacctgtgaa aaatgaggaa    4200
gatgttgcag agttgtcaat ttctccttca gacaatgcag tggtcttaac aaatctcctg    4260
cctggtacag aatatgtagt gagtgtctcc agtgtctacg aacaacatga gagcacacct    4320
cttagaggaa gacagaaaac aggtcttgat tccccaactg gcattgactt ttctgatatt    4380
actgccaact cttttactgt gcactggatt gctcctcgag ccaccatcac tggctacagg    4440
atccgccatc atcccgagca cttcagtggg agacctcgag aagatcgggt gccccactct    4500
cggaattcca tcaccctcac caacctcact ccaggcacag agtatgtggt cagcatcgtt    4560
gctcttaatg gcagagagga aagtcccctta ttgattggcc aacaatcaac agtttctgat    4620
gttccgaggg acctggaagt tgttgctgcg acccccacca gcctactgat cagctgggat    4680
gctcctgctg tcacagtgag atattacagg atcacttacg agagacagg aggaaatagc    4740
cctgtccagg agttcactgt gcctgggagc aagtctacag ctaccatcag cggccttaaa    4800
cctggagttg attataccat cactgtgtat gctgtcactg gccgtggaga cagccccgca    4860
agcagcaagc caatttccat taattaccga acagaaattg acaaaccatc ccagatgcaa    4920
```

```
gtgaccgatg ttcaggacaa cagcattagt gtcaagtggc tgccttcaag ttcccctgtt    4980
actggttaca gagtaaccac cactcccaaa aatggaccag gaccaacaaa aactaaaact    5040
gcaggtccag atcaaacaga aatgactatt gaaggcttgc agcccacagt ggagtatgtg    5100
gttagtgtct atgctcagaa tccaagcgga gagagtcagc ctctggttca gactgcagta    5160
accaacattg atcgccctaa aggactggca ttcactgatg tggatgtcga ttccatcaaa    5220
attgcttggg aaagcccaca ggggcaagtt tccaggtaca gggtgaccta ctcgagccct    5280
gaggatggaa tccatgagct attccctgca cctgatggtg aagaagacac tgcagagctg    5340
caaggcctca gaccgggttc tgagtacaca gtcagtgtgg ttgccttgca cgatgatatg    5400
gagagccagc ccctgattgg aacccagtcc acagctattc ctgcaccaac tgacctgaag    5460
ttcactcagg tcacacccac aagcctgagc gcccagtgga caccacccaa tgttcagctc    5520
actggatatc gagtgcgggt gaccccccaag gagaagaccg gaccaatgaa agaaatcaac    5580
cttgctcctg acagctcatc cgtggttgta tcaggactta tggtggccac caaatatgaa    5640
gtgagtgtct atgctcttaa ggacactttg acaagcagac cagctcaggg agttgtcacc    5700
actctggaga atgtcagccc accaagaagg gctcgtgtga cagatgctac tgagaccacc    5760
atcaccatta gctggagaac caagactgag acgatcactg gcttccaagt tgatgccgtt    5820
ccagccaatg ccagactccc aatccagaga accatcaagc cagatgtcag aagctacacc    5880
atcacaggtt acaaccagg cactgactac aagatctacc tgtacacctt gaatgacaat    5940
gctcggagct cccctgtggt catcgacgcc tccactgcca ttgatgcacc atccaacctg    6000
cgtttcctgg ccaccacacc caattccttg ctggtatcat ggcagccgcc acgtgccagg    6060
attaccggct acatcatcaa gtatgagaag cctgggtctc ctcccagaga agtggtccct    6120
cggccccgcc ctggtgtcac agaggctact attactggcc tggaaccggg aaccgaatat    6180
acaatttatg tcattgccct gaagaataat cagaagagcg agcccctgat tggaaggaaa    6240
aagacagacg agcttcccca actggtaacc cttccacacc ccaatcttca tggaccagag    6300
atcttggatg ttccttccac agttcaaaag acccctttcg tcacccaccc tgggtatgac    6360
actggaaatg gtattcagct tcctggcact tctggtcagc aacccagtgt tgggcaacaa    6420
atgatctttg aggaacatgg ttttaggcgg accacaccgc ccacaacggc cacccccata    6480
aggcataggc caagaccata cccgccgaat gtaggtgagg aaatccaaat tggtcacatc    6540
cccagggaag atgtagacta tcacctgtac ccacacggtc cgggactcaa tccaaatgcc    6600
tctacaggac aagaagctct ctctcagaca accatctcat gggccccatt ccaggacact    6660
tctgagtaca tcatttcatg tcatcctgtt ggcactgatg aagaaccctt acagttcagg    6720
gttcctggaa cttctaccag tgccactctg acaggcctca ccagaggtgc cacctacaac    6780
atcatagtgg aggcactgaa agaccagcag aggcataagg ttcgggaaga ggttgttacc    6840
gtgggcaact ctgtcaacga aggcttgaac caacctacgg atgactcgtg ctttgacccc    6900
tacacagttt cccattatgc cgttggagat gagtgggaac gaatgtctga atcaggcttt    6960
aaactgttgt gccagtgctt aggctttgga agtggtcatt tcagatgtga ttcatctaga    7020
tggtgccatg acaatggtgt gaactacaag attgagagaa gtgggaccg tcaggagaaa    7080 aatggccaga tgatgagctg cacatgtctt gggaacggaa aaggagaatt caagtgtgac    7140
cctcatgagg caacgtgtta tgatgatggg aagacatacc acgtaggaga acagtggcag    7200
aaggaatatc tcggtgccat ttgctcctgc acatgctttg gaggccagcg gggctggcgc    7260
```

-continued

| | |
|---|---|
| tgtgacaact gccgcagacc tgggggtgaa cccagtcccg aaggcactac tggccagtcc | 7320 |
| tacaaccagt attctcagag ataccatcag agaacaaaca ctaatgttaa ttgcccaatt | 7380 |
| gagtgcttca tgcctttaga tgtacaggct gacagagaag attcccgaga gtaa | 7434 |

<210> SEQ ID NO 36
<211> LENGTH: 7434
<212> TYPE: DNA
<213> ORGANISM: Artificial Sequence
<220> FEATURE:
<223> OTHER INFORMATION: Synthetic Construct

<400> SEQUENCE: 36

| | |
|---|---|
| atgctgagag gacctggacc aggactgctg ctgctggctg ttcagtgtct gggaacagcc | 60 |
| gtgcctagca caggcgccag caagtctaaa agacaggccc agcagatggt gcagcctcag | 120 |
| tctcctgtgg ccgtgtctca gtctaagccc ggctgctacg acaacggcaa gcactaccag | 180 |
| atcaaccagc agtgggagag aacctacctg ggcaacgccc tcgtgtgtac atgttacggc | 240 |
| ggcagcagag gcttcaactg cgagtctaaa cccgaggccg aggaaacctg cttcgacaag | 300 |
| tacaccggca cacctacag agtgggcgac acctacgaga ggcccaagga cagcatgatc | 360 |
| tgggactgca catgtatcgg agccggcaga ggcagaatca gctgcacaat cgccaaccgg | 420 |
| tgtcacgaag gcggccagag ctataagatc ggcgacactt ggagaaggcc ccacgagaca | 480 |
| ggcggctaca tgctggaatg cgtgtgtctc ggcaacggca aggcgagtg gacctgcaag | 540 |
| cctatcgccg agaagtgctt cgatcatgcc gccggaacaa gctacgtcgt gggcgagaca | 600 |
| tgggagaagc cttaccaagg ctggatgatg gtggactgta cctgcctcgg cgaaggcagc | 660 |
| ggaagaatca cctgtaccag ccggaaccgg tgcaacgacc aggataccag aaccagctac | 720 |
| cggatcggcg atacctggtc caagaaggac aaccggggca acctgctgca gtgcatctgt | 780 |
| accggaaatg gaagaggcga atggaagtgc gagcggcaca aagcgtgca gacaacatct | 840 |
| tctggcagcg gccccttttac cgatgtgcgg gctgctgttt atcagcccca gcctcatcct | 900 |
| cagcctccac cttatggcca ctgcgtgaca gatagcggcg tggtgtatag cgtgggcatg | 960 |
| cagtggctga aaacccaggg caacaagcag atgctgtgca catgcctcgg caatggcgtg | 1020 |
| tcctgccaag agacagccgt gacacagacc tatggcggca atagcaatgg cgagccttgc | 1080 |
| gtgctgccct tcacctacaa tggccggacc ttctacagct gcaccaccga gggtagacag | 1140 |
| gacggacacc tgtggtgtag caccaccagc aactacgagc aggaccagaa gtacagcttc | 1200 |
| tgcaccgacc acaccgtgct ggtgcaaacc agaggcggca ttctaacgg cgccctgtgt | 1260 |
| cacttcccct ttctgtacaa caaccacaac tacaccgact gcacctccga aggcagacgg | 1320 |
| gacaacatga gtggtgcgg cacaacccag aactacgacg ccgatcagaa gttcggcttc | 1380 |
| tgtcccatgg ccgctcacga ggaaatctgt accaccaacg aaggcgtgat gtacagaatc | 1440 |
| ggcgaccagt gggacaagca gcacgacatg ggccacatga tgcggtgtac ctgcgttggc | 1500 |
| aatggtcgcg gagagtggac atgcattgcc tacagccagc tgcggaccca gtgcatcgtg | 1560 |
| gacgacatca catacaacgt gaacgacacc ttccacaagc ggcacgaaga gggacacatg | 1620 |
| ctgaactgca cctgtttcgg ccaaggcaga ggccggtgga gtgtgatcc tgtggatcag | 1680 |
| tgccaggaca gcgaaaccgg caccttttac cagatcggag actcctggga gaaatacgtg | 1740 |
| cacggcgtgc gctaccagtg ctactgttac ggcagaggaa ttggcgagtg gcactgtcag | 1800 |
| cccctgcaga cataccctag ctctagcgga cctgtcgagg tgttcatcac cgagacaccc | 1860 |
| agccagccta actctcaccc catccagtgg aatgcccctc agcctagcca catcagcaag | 1920 |

```
tacatcctga gatggcggcc caagaactcc gtcggcagat ggaaagaggc caccattcct    1980
ggccacctga acagctacac catcaaggga ctgaagcccg gcgtggtcta tgagggccag    2040
ctgatctcta tccagcagta cggccaccaa gaagtgacca gattcgactt caccaccacc    2100
tccaccagca cacccgtgac cagcaatacc gtgaccggcg agacaacccc tttctctcca    2160
ctggtggcca aagcgagag cgtgaccgag attaccgcca gcagctttgt ggtgtcttgg    2220
gtgtccgcca gcgatacagt gtccggcttc agagtggaat acgagctgag cgaggaaggc    2280
gacgagcccc agtatctgga tctgccaagc accgccacca gcgtgaacat ccctgatctg    2340
ctgcccggca gaaagtacat cgtgaacgtg taccagatct ccgaggacgg cgagcagagc    2400
ctgatcctga gcacaagcca gacaacagcc cctgacgctc ctcctgatcc taccgttgat    2460
caggtggacg ataccagcat cgtcgtgcgg tggtcaagac cccaggctcc tatcaccggc    2520
tacaggatcg tgtacagccc tagcgtggaa ggcagcagca ccgagctgaa tctgcccgag    2580
acagccaata gcgtgaccct gtctgatctg cagcctggcg tgcagtacaa tatcaccatc    2640
tacgccgtgg aagagaatca agagtctacc cctgtggtca tccagcaaga caaccggc    2700 actcccagat ccgacaccgt tccatctcca cgggatctgc agttcgtgga agtgaccgac    2760
gtgaaagtga caatcatgtg gacccccacct gagagcgccg tgacaggcta tagagtggac    2820
gtgatccccg tgaacctgcc aggcgaacat ggacagagac tgcccatcag cagaaacacc    2880
tttgccgaag tgacaggact gtcccctggc gtgacctact acttcaaggt gttcgctgtg    2940
tcccacggca gagagagcaa acctctgaca gctcagcaga ccaccaagct ggacgcccct    3000
accaacctgc agtttgtgaa cgagacagac agcacagtgc ttgtgcggtg gacccctcca    3060
agagcacaga tcacaggata ccggctgacc gtgggcctga ccagaagagg acagcccaga    3120
cagtacaacg tgggccccag cgtgtccaag tatcccctga gaaatctcca gcctgccagc    3180
gagtacaccg tgtctctggt ggctatcaag gcaatcaag agagcctaa ggccaccggc    3240 gtgttcacta cactgcagcc cggaagcagc atccctccat acaacacaga agtgactgaa    3300
accaccatcg tgatcacctg gacacccgct cctcggatcg gcttaaagct gggcgtcaga    3360
ccttctcaag gcggcgaagc tcccagagaa gtgacaagcg atagcggcag catcgtggtg    3420
tctggactga caccaggcgt ggaatatgtg taccatcc aggtgctgcg cgacggccaa    3480
gaaagggatg cccctatcgt gaacaaggtg gtcacccctc tgagcccacc aacaaacctg    3540
cacctggaag ccaatcctga taccggcgtg ctgactgtgt cctgggaaag aagccaccca    3600
cctgacatta ccggctatcg gatcaccaca acacccacca atggcagca gggcaactcc    3660 ctggaagagg tggtgcatgc cgatcagtcc agctgtacct tcgacaatct gagccctggc    3720
ctcgagtaca atgtgtccgt gtacacagtg aaggacgaca agaaagcgt gcccatctcc    3780 gacacaatca tccctgaggt gccccagctg accgacctga gcttcgtgga tatcaccgac    3840
agcagcatcg gcctgaggtg gacacctctg aactcctcta ccatcatcgg atacagaatc    3900
accgtggtgg ccgctggcga gggcatccca atcttcgagg actttgtgga cagcagcgtg    3960
ggctactaca ccgtgactgg actggaaccc ggcatcgact acgacatcag cgtcatcacc    4020
ctgatcaatg gcgcgagag cgcccctaca acactgacac aacagactgc cgtgcctcct    4080
cctaccgatc tgcggttcac aaatatcggc cccgacacca tgagagtgac ttggctcct    4140 ccaccaagta tcgacctgac caacttcctc gtgcggtaca gccccgtgaa gaacgaggaa    4200
gatgtggccg agctgtccat ctctcccagc gataatgccg tggtgctgac caatctgctc    4260
```

```
cccggaacag agtacgtggt gtccgttagc agcgtgtacg aacagcacga gagcacaccc    4320
ctgcggggca gacaaaaaac aggcctggat agccccaccg gaatcgactt cagcgatatc    4380
acagccaaca gcttcaccgt gcattggatc gcccctagag ccaccatcac cgggtataga    4440
atccggcatc accccgagca cttcagcggc agacctagag aagatagagt gccccactcc    4500
agaaacagca tcaccctcac caatctgaca cccggcaccg aatatgtggt gtccatcgtg    4560
gccctgaacg gcagggaaga gtctcctctg ctgatcggcc agcagagcac agtgtctgac    4620
gtgcccagag atctggaagt ggtggctgcc acacctacca gcctgctgat tagctgggat    4680
gctcctgctg tgacagtgcg gtattaccgg atcacctacg cgagactgg cggcaactct     4740
cccgtgcaag agtttacagt gcctggcagc aagagcaccg ctaccatctc tggactcaag    4800
ccaggcgtcg actacaccat taccgtgtac gctgtgaccg gcaggggcga ttctcctgcc    4860
tcttctaagc ctatcagcat caactaccgg accgagatcg acaagccaag ccagatgcaa    4920
gtgacagatg tgcaggacaa cagcatctcc gtgaagtggc tgcctagcag ctctccagtg    4980
accgggtaca gagtgaccac cacaccaaag aacggccctg acctaccaa gaccaagacc     5040
gctggacctg atcagaccga gatgaccatt gagggcctgc agcctaccgt cgagtatgtc    5100
gtgtctgtgt acgccagaa tcctagcggc gagtctcagc tcttgtgca gaccgccgtg     5160
accaacatcg acagacctaa aggcctggcc ttcaccgacg tggacgtgga ctctatcaag    5220
atcgcctggg agtcccctca gggccaagtg tccagatata gagtgaccta cagctcccct    5280
gaggacggca tccacgagct gtttccagca ccagacggcg aagaggatac cgccgaactg    5340
caaggactga ggcctggctc cgagtataca gtctcagtgg tggccctgca cgacgacatg    5400
gaaagccagc ctctgatcgg aacccagtcc accgctattc ccgctcctac agacctgaag    5460
ttcacccaag tgaccccaac cagcctgagc gcacaatgga ctcctccaaa cgtccagctg    5520
actggttata gagtgcgcgt gacacccaaa gaaaagactg gccccatgaa ggaaatcaat    5580
ctggcccctg actccagctc cgtggttgtg tctggtctta tggtggctac caatacgag     5640
gtttccgtgt atgccctgaa ggacacctg acctccagac ctgcacaggg cgttgtgacc     5700
acactggaaa acgtgtcccc acctcggaga gccagagtga cagacgccac cgaaaccaca    5760
atcaccattt cttggcggac caagacagag acaatcaccg gattccaggt cgacgccgtg    5820
cctgccaatg gacagacacc tatccagcgg accatcaagc tgacgtgcg gagctacaca    5880
atcacaggcc tgcaacctgg caccgactac aagatctacc tgtacaccct gaacgacaac    5940
gcccgctcta gccccgtggt tatcgatgcc tctaccgcca tcgacgcccc aagcaatctg    6000
agatttctgg ccacaactcc caacagtctg ctcgtgtctt ggcagcctcc tcgggccaga    6060
atcactggct acatcattaa gtacgagaag ccaggcagcc ctcctagaga ggtggtccct    6120
agacctagac ctggcgtcac agaggccaca attaccggac tcgagcccgg cactgagtac    6180
acaatctacg tgatcgccct gaagaacaac cagaagtccg agccactgat tggccggaag    6240
aaaaccgacg agctgcctca gctggtcacc ctgcctcatc caaatctgca cggccccgag    6300
atcctggatg tgccatctac cgtgcagaaa accccattg tgacacaccc cggctacgac    6360
accggaaacg gaattcagct gcctggaacc tctgggcagc agccttctgt gggacagcag    6420
atgatctttg aggaacacgg cttccggcgg accacacctc ctacaacagc cacaccaatc    6480
aggcacagac cccggcctta tcctcctaac gtgggcgaag agattcagat cggacacatc    6540
cccagagagg atgtcgacta ccacctgtat cctcacggcc caggactgaa ccctaatgcc    6600
agcacaggac aagaggccct gagccagacc actatcagct gggctccatt ccaggacacc    6660
```

| | | | | |
|---|---|---|---|---|
| tccgagtaca | tcatctcttg | tcaccccgtg | ggcaccgacg | aggaaccact gcaattcaga | 6720 |
| gtgcccggca | cctctaccag | cgccacactt | acaggactga | ctagaggcgc cacctataac | 6780 |
| atcatcgtgg | aagccctgaa | agaccagcag | cggcacaaag | tgcgcgaaga ggttgtgact | 6840 |
| gtgggcaatt | ccgtgaacga | gggcctgaat | cagcccaccg | acgacagctg ctttgacccc | 6900 |
| tacacagtgt | cccactatgc | cgtgggagat | gagtgggaac | gcatgtccga gagcggcttc | 6960 |
| aagctgctct | gtcagtgcct | cggctttggc | tccggccact | tcagatgcga tagctccagg | 7020 |
| tggtgccacg | ataacggcgt | gaactacaaa | atcggagaga | agtgggacag acagggcgag | 7080 |
| aacgccaga | tgatgagctg | cacttgtctc | ggaaatggaa | agggcgagtt caagtgcgac | 7140 |
| cctcacgagg | ccacctgtta | cgacgatggc | aagacctacc | acgtgggaga gcagtggcag | 7200 |
| aaagagtacc | tgggcgccat | ctgtagctgc | acatgctttg | gcgggcagcg cggctggcgc | 7260 |
| tgtgataatt | gccgtagacc | aggcggcgag | ccatctcctg | agggaacaac aggccagtcc | 7320 |
| tacaaccagt | acagccagag | ataccaccag | cgcaccaaca | ccaatgtgaa ctgccccatc | 7380 |
| gagtgcttca | tgcccctgga | cgtgcaggcc | gacagggaag | attctagaga gtga | 7434 |

<210> SEQ ID NO 37
<211> LENGTH: 2361
<212> TYPE: DNA
<213> ORGANISM: Homo sapiens

<400> SEQUENCE: 37

| | | | | |
|---|---|---|---|---|
| atggcgggtc | tgacggcggc | ggccccgcgg | cccggagtcc | tcctgctcct gctgtccatc | 60 |
| ctccacccct | ctcggcctgg | aggggtccct | ggggccattc | ctggtggagt tcctggagga | 120 |
| gtcttttatc | caggggctgg | tctcggagcc | cttggaggag | gagcgctggg gcctggaggc | 180 |
| aaacctctta | agccagttcc | cggagggctt | gcgggtgctg | gccttggggc agggctcggc | 240 |
| gccttccccg | cagttaccctt | tccgggggct | ctggtgcctg | gtggagtggc tgacgctgct | 300 |
| gcagcctata | aagctgctaa | ggctggcgct | gggcttggtg | gtgtcccagg agttggtggc | 360 |
| ttaggagtgt | ctgcaggtgc | ggtggttcct | cagcctggag | ccggagtgaa gcctgggaaa | 420 |
| gtgccgggtg | tggggctgcc | aggtgtatac | ccaggtggcg | tgctcccagg agctcggttc | 480 |
| cccggtgtgg | gggtgctccc | tggagttccc | actggagcag | gagttaagcc caaggctcca | 540 |
| ggtgtaggtg | gagcttttgc | tggaatccca | ggagttggac | cctttggggg accgcaacct | 600 |
| ggagtcccac | tggggtatcc | catcaaggcc | cccaagctgc | ctggtggcta tggactgccc | 660 |
| tacaccacag | ggaaactgcc | ctatggctat | gggcccggag | gagtggctgg tgcagcgggc | 720 |
| aaggctggtt | acccaacagg | gacaggggtt | ggcccccagg | cagcagcagc agcggcagct | 780 |
| aaagcagcag | caaagttcgg | tgctggagca | gccgagtccc | tccctggtgt ggagggggct | 840 |
| ggtgttcctg | gcgtgcctgg | ggcaattcct | ggaattggag | gcatcgcagg cgttgggact | 900 |
| ccagctgcag | ctgcagctgc | agcagcagcc | gctaaggcag | ccaagtatgg agctgctgca | 960 |
| ggcttagtgc | ctggtgggcc | aggctttggc | ccgggagtag | ttggtgtccc aggagctggc | 1020 |
| gttccaggtg | ttggtgtccc | aggagctggg | attccagttg | tcccaggtgc tgggatccca | 1080 |
| ggtgctgcgt | tcagggggt | tgtgtcacca | gaagcagctg | ctaaggcagc tgcaaaggca | 1140 |
| gccaaatacg | ggccaggcc | cggagtcgga | gttggaggca | ttcctactta cggggttgga | 1200 |
| gctgggggct | ttcccggctt | tggtgtcgga | gtcggaggta | tccctggagt cgcaggtgtc | 1260 |
| cctggtgtcg | gaggtgttcc | cggagtcgga | ggtgtcccgg | gagttggcat tccccccgaa | 1320 |

| | |
|---|---:|
| gctcaggcag cagctgccgc caaggctgcc aagtacggtg ctgcaggagc aggagtgctg | 1380 |
| ggtgggctag tgccaggtgc cccaggcgca gtcccaggtg tgccgggcac gggaggagtg | 1440 |
| ccaggagtgg ggaccccagc agctgcagct gctaaagcag ccgccaaagc cgcccagttt | 1500 |
| gggttagttc ctggtgtcgg cgtggctcct ggagttggcg tggctcctgg tgtcggtgtg | 1560 |
| gctcctggag ttggcttggc tcctggagtt ggcgtggctc ctggagttgg tgtggctcct | 1620 |
| ggcgttggcg tggctcccgg cattggccct ggtggagttg cagctgcagc aaaatccgct | 1680 |
| gccaaggtgg ctgccaaagc ccagctccga gctgcagctg gcttggtgc tggcatccct | 1740 |
| ggacttggag ttggtgtcgg cgtccctgga cttggagttg gtgctggtgt tcctggactt | 1800 |
| ggagttggtg ctggtgttcc tggcttcggg gcaggtgcag atgagggagt taggcggagc | 1860 |
| ctgtcccctg agctcaggga aggagatccc tcctcctctc agcacctccc cagcacccc | 1920 |
| tcatcaccca gggtacctgg agccctggct gccgctaaag cagccaaata tggagcagca | 1980 |
| gtgcctgggg tccttggagg gctcggggct ctcgtggag taggcatccc aggcggtgtg | 2040 |
| gtgggagccg gacccgccgc cgccgctgcc gcagccaaag ctgctgccaa gccgcccag | 2100 |
| tttggcctag tgggagccgc tgggctcgga ggactcggag tcggagggct ggagttcca | 2160 |
| ggtgttgggg gccttggagg tatacctcca gctgcagccg ctaaagcagc taaatacggt | 2220 |
| gctgctggcc ttgaggtgt cctaggggt gccgggcagt tcccacttgg aggagtggca | 2280 |
| gcaagacctg gcttcggatt gtctcccatt ttcccaggtg gggcctgcct ggggaaagct | 2340 |
| tgtggccgga agagaaaatg a | 2361 |

<210> SEQ ID NO 38
<211> LENGTH: 2361
<212> TYPE: DNA
<213> ORGANISM: Artificial Sequence
<220> FEATURE:
<223> OTHER INFORMATION: Synthetic Construct

<400> SEQUENCE: 38

| | |
|---|---:|
| atggctggac tgacagccgc tgctcctaga cctggtgttc tgctgctgct cctgagcatt | 60 |
| ctgcacccctt ctagaccagg cggagtgcct ggtgctattc ctggcggagt tcccggcgga | 120 |
| gtgtttatc ctggtgctgg actgggagcc cttggcggag gtgctcttgg acctggtgga | 180 |
| aagcctctga acctgtgcc tggcggactt gctggtgcag tcttggagc cggacttgga | 240 |
| gcttttcccg ccgtgacatt tcctggcgct cttgtgccag gtggcgtggc agatgctgcc | 300 |
| gctgcttata aggctgccaa agccggcgct ggactcggag tgttcctgg tgttggaggc | 360 |
| ctgggagttt ctgctggtgc tgtggttcct caacctggcg ctggtgttaa gcctggcaaa | 420 |
| gttccaggcg ttgactgcc tggtgtttac cctggtggtg ttctccctgg cgctagattc | 480 |
| cctggcgttg gagttcttcc tggcgtgcca acaggtgccg gcgtgaaacc taaagctcct | 540 |
| ggtgtcggcg gagccttcgc tggaatacct ggcgtgggac ttttggcgg acctcaacca | 600 |
| ggtgtccctc tgggctatcc tatcaaggcc cctaaactgc caggcggcta cggcctgcct | 660 |
| tacacaactg gcaagctgcc ctatggctat ggacctggcg tgttgctgg cgccgctgga | 720 |
| aaagctggat accctactgg aacaggcgtg ggccctcaag cagcagctgc cgcagcagct | 780 |
| aaagccgccg ctaaatttgg agctggcgct gcaggcgttt gccccggcgt tggcggagca | 840 |
| ggcgtcccag tgttccagg gcaatacct ggaatcggag gaattgccgg cgtcggaact | 900 |
| ccagctgcag cagccgcagc cgccgctgcc gcaaaagctc taaatatgg cgcagctgca | 960 |
| ggcttggtcc caggcggacc tggatttgga ccaggtgttg ttggagtgcc aggcgctggc | 1020 |

```
gtccccggcg tgggagttcc tggtgccgga attcctgttg ttcctggcgc tggtattcct    1080
ggcgctgctg ttccaggtgt tgtgtctcct gaagccgctg ccaaggccgc tgctaaggca    1140
gctaaatacg gtgcccgacc aggcgtcgga gttggcggaa ttccaacata tggtgtcgga    1200
gccggcggat tcccaggatt tggagttgga gtcggaggca tcccgggtgt tgcaggcgtt    1260
ccaggcgtcg gcggagttcc tggcgttggt ggtgttccag gcgtgggaat ttctcctgaa    1320
gctcaggccg ctgccgctgc caaagcagcc aaatatggcg ctgccggtgc tggcgttctc    1380
ggaggattgg ttccgggtgc tccaggtgct gttccgggcg ttcccggaac tggcggtgtc    1440
cctggtgtcg gaacaccagc cgctgcagca gcaaaggctg ctgctaaagc cgctcagttt    1500
ggactggttc ctggcgtcgg agtggcacca ggtgttggag ttgcacctgg cgttggcgtg    1560
gcccctggcg tgggtcttgc tcctggtgtt ggtgttgccc caggtgtcgg agtcgctccc    1620
ggtgtcggtg tcgcacctgg tattggtcct ggtggcgttg ccgcagctgc caaatctgct    1680
gcaaaggtgg ccgccaaagc acagctgaga gctgctgccg tcttggcgc tggaatccca    1740 ggactcggtg ttggagtggg agtgccaggt cttggtgttg gagcaggcgt gcccggactc    1800
ggagtcggag ctggtgtccc aggttttgga gctggtgcag atgaaggcgt gcggagatct    1860
ctgagccctg agctgagaga gggcgatcct agctctagcc agcatctccc tagcacacct    1920
agcagcccta gagtccctgg ggctcttgct gcagccaaag ccgctaagta tggggctgct    1980
gtccctggtg ttcttggagg acttggagca ctcggcggag tgggaattcc aggcggtgtc    2040
gttggtgcag gacctgctgc tgccgccgca gctgcaaaag cagcagctaa ggcagcccag    2100
tttggccttg ttggagccgc tggacttggt ggcctcggag ttggtggtct tggtgtcccc    2160
ggtgttggcg gacttggagg aattccacca gccgcagcag ccaaggctgc taaatacggc    2220
gctgcaggac ttggcggtgt tcttggcgga gctggacagt ttccacttgg aggcgttgca    2280
gccagacctg gctttggcct gtctcctatt tttcctggcg gcgcttgtct gggcaaagcc    2340
tgcggcagaa agcggaagta a                                              2361

<210> SEQ ID NO 39
<211> LENGTH: 1017
<212> TYPE: DNA
<213> ORGANISM: Homo sapiens

<400> SEQUENCE: 39
atgagtctaa gtgcatttac tctcttcctg gcattgattg gtggtaccag tggccagtac     60
tatgattatg attttcccct atcaatttat gggcaatcat caccaaactg tgcaccagaa    120
tgtaactgcc ctgaaagcta cccaagtgcc atgtactgtg atgagctgaa attgaaaagt    180
gtaccaatgg tgcctcctgg aatcaagtat ctttaccttg gaataaccag gattgaccat    240
attgatgaaa aggcctttga gaatgtaact gatctgcagt ggctcattct agatcacaac    300
cttctagaaa actccaagat aaagggaga gttttctcta aattgaaaca actgaagaag    360
ctgcatataa accacaacaa cctgacagag tctgtgggcc cacttcccaa atctctggag    420
gatctgcagc ttactcataa caagatcaca aagctgggct cttttgaagg attggtaaac    480
ctgaccttca tccatctcca gcacaatcgg ctgaagagg atgctgtttc agctgctttt    540
aaaggtctta aatcactcga ataccttgac ttgagcttca atcagatagc cagactgcct    600
tctggtctcc ctgtctctct tctaactctc tacttagaca caataagat cagcaacatc    660 cctgatgagt atttcaagcg tttaatgca ttgcagtatc tgcgtttatc tcacaacgaa    720
```

| | |
|---|---|
| ctggctgata gtggaatacc tggaaattct ttcaatgtgt catccctggt tgagctggat | 780 |
| ctgtcctata acaagcttaa aaacatacca actgtcaatg aaaaccttga aaactattac | 840 |
| ctggaggtca atcaacttga gaagtttgac ataaagagct tctgcaagat cctggggcca | 900 |
| ttatcctact ccaagatcaa gcatttgcgt ttggatggca atcgcatctc agaaaccagt | 960 |
| cttccaccgg atatgtatga atgtctacgt gttgctaacg aagtcactct taattaa | 1017 |

<210> SEQ ID NO 40
<211> LENGTH: 1017
<212> TYPE: DNA
<213> ORGANISM: Artificial Sequence
<220> FEATURE:
<223> OTHER INFORMATION: Synthetic Construct

<400> SEQUENCE: 40

| | |
|---|---|
| atgagcctga gcgccttcac actgtttctg gccctgatcg gcggcacaag cggccagtac | 60 |
| tacgactacg atttcccact gagcatctac ggccagagca gccctaattg cgcccctgag | 120 |
| tgcaattgcc ccgagagcta tcctagcgcc atgtactgcg acgagctgaa gctgaagtcc | 180 |
| gtgcctatgg tgcctcctgg catcaagtac ctgtacctgc ggaacaacca gatcgaccac | 240 |
| atcgacgaga aggcctttga gaacgtgacc gacctgcagt ggctgatcct ggaccacaac | 300 |
| ctgctggaaa acagcaagat caagggccgc gtgttcagca gctgaagca gctgaagaaa | 360 |
| ctgcacatca accacaacaa cctgaccgag agcgtgggcc tctgcctaa gtctctggaa | 420 |
| gatctgcagc tgacccacaa caagatcacc aagctgggca gcttcgaggg cctcgtgaac | 480 |
| ctgacccttca tccatctgca gcacaaccgg ctgaaagagg atgccgttag cgccgccttc | 540 |
| aagggcctga gagtctggga atacctggac ctgagcttca atcagatcgc cagactgcct | 600 |
| agcggcctgc ctgtttctct gctgacactg tacctggaca caacaaaat cagcaacatc | 660 |
| cccgacgagt acttcaagcg gttcaacgcc ctgcagtacc tgagactgag ccacaacgag | 720 |
| ctggccgatt ctggcatccc cggcaacagc ttcaatgtgt ccagcctggt ggaactggac | 780 |
| ctgtcctaca acaagctgaa aaacatcccc accgtgaacg agaacctcga gaactactac | 840 |
| ctggaagtga accagctcga gaagttcgat atcaagagct tctgcaagat cctggggcct | 900 |
| ctgagctact ccaagattaa gcacctgagg ctggacggca accggatcag cgaaacaagc | 960 |
| ctgcctcctg atatgtacga gtgcctgaga gtggccaacg aagtgaccct gaactga | 1017 |

<210> SEQ ID NO 41
<211> LENGTH: 1437
<212> TYPE: DNA
<213> ORGANISM: Homo sapiens

<400> SEQUENCE: 41

| | |
|---|---|
| atggcacccc tgagacccct ctcatactg gccctgctgg catgggttgc tctggctgac | 60 |
| caagagtcat gcaagggccg ctgcactgag ggcttcaacg tggacaagaa gtgccagtgt | 120 |
| gacgagctct gctcttacta ccagagctgc tgcacagact atacggctga gtgcaagccc | 180 |
| caagtgactc gcggggatgt gttcactatg ccggaggatg agtacacggt ctatgacgat | 240 |
| ggcgaggaga aaaacaatgc cactgtccat gaacaggtgg ggggccctc cctgacctct | 300 |
| gacctccagg cccagtccaa agggaatcct gagcagacac tgttctgaa acctgaggaa | 360 |
| gaggcccctg cgcctgaggt gggcgcctct aagcctgagg ggatagactc aaggcctgag | 420 |
| acccttcatc cagggagacc tcagccccca gcagaggagg agctgtgcag tgggaagccc | 480 |
| ttcgacgcct tcaccgacct caagaacggt tccctctttg ccttccgagg gcagtactgc | 540 |

```
tatgaactgg acgaaaaggc agtgaggcct gggtacccca agctcatccg agatgtctgg      600
ggcatcgagg gccccatcga tgccgccttc acccgcatca actgtcaggg gaagacctac      660
ctcttcaagg gtagtcagta ctggcgcttt gaggatggtg tcctggaccc tgattacccc      720
cgaaatatct ctgacggctt cgatggcatc ccggacaacg tggatgcagc cttggccctc      780
cctgcccata gctacagtgg ccgggagcgg gtctacttct tcaaggggaa acagtactgg      840
gagtaccagt tccagcacca gcccagtcag gaggagtgtg aaggcagctc cctgtcggct      900
gtgtttgaac actttgccat gatgcagcgg gacagctggg aggacatctt cgagcttctc      960
ttctggggca gaacctctgc tggtaccaga cagccccagt tcattagccg ggactggcac     1020
ggtgtgccag ggcaagtgga cgcagccatg ctggccgcca tctacatctc aggcatggca     1080
ccccgcccct ccttggccaa gaaacaaagg tttaggcatc gcaaccgcaa aggctaccgt     1140
tcacaacgag gccacagccg tggccgcaac cagaactccc gccggccatc ccgcgccacg     1200
tggctgtcct tgttctccag tgaggagagc aacttgggag ccaacaacta tgatgactac     1260
aggatggact ggcttgtgcc tgccacctgt gaacccatcc agagtgtctt cttcttctct     1320
ggagacaagt actaccgagt caatcttcgc acacggcgag tggacactgt ggaccctccc     1380
tacccacgct ccatcgctca gtactggctg ggctgcccag ctcctggcca tctgtag       1437
```

<210> SEQ ID NO 42
<211> LENGTH: 1437
<212> TYPE: DNA
<213> ORGANISM: Artificial Sequence
<220> FEATURE:
<223> OTHER INFORMATION: Synthetic Construct

<400> SEQUENCE: 42

```
atggcccctc ttagacccct gctgattctg gctctgctgg cttgggttgc cctggccgat       60
caagagtctt gcaagggcag atgcaccgag ggcttcaacg tggacaagaa atgccagtgc      120
gacgagctgt gcagctacta ccagagctgc tgcaccgatt acaccgccga gtgcaagccc      180
caagtgacaa gaggcgacgt gttcaccatg cctgaggacg agtacaccgt gtacgacgac      240
ggcgaggaaa agaacaacgc caccgtgcac gagcaagttg gcggaccttc tctgaccagc      300
gatctgcagg ctcagagcaa gggcaatcct gagcagaccc ctgtgctgaa gcctgaggaa      360
gaagcccctg ctcctgaagt gggagcctct aagcctgaag gcatcgacag cagacccgag      420
acactgcatc aggcagacc tcagcctcct gccgaagagg aactgtgtag cggcaagcct      480
ttcgacgcct tcaccgacct gaagaacggc agcctgttcg cctttagagg ccagtactgc      540
tacgagctgg acgagaaggc cgtgcggcct ggatatccta agctgatcag agatgtgtgg      600
ggcatcgagg gccccatcga cgccgctttc accagaatca actgtcaggg caagacctac      660
ctgttcaagg gcagccagta ttggagattc gaggacggcg tgctggaccc tgactacccc      720
agaaatatca gcgacggctt cgacggcatc ccgacaatg ttgatgctgc ctgccctg       780 cctgctcaca gctactctgg cagagaacgg gtgtacttct taagggcaa acagtactgg      840 gagtaccagt tccagcacca gcctagccaa gaggaatgcg agggcagctc tctgagcgcc      900
gtgtttgagc acttcgccat gatgcagaga cagctgggg aagatattttt cgagctgctg      960 ttctggggca gaaccagcgc cggaacaaga cagcctcagt tcatcagcag agactggcat     1020
ggcgtgccag acaagtgga tgctgccatg ccggcagaa tctacatcag cggaatggcc      1080
cctagaccta gcctggccaa gaagcagcgg ttccggcaca gaaaccggaa gggctacaga     1140
```

| | |
|---|---|
| agccagagag gccactccag aggccggaac cagaatagca gaaggccctc tagagccacc | 1200 |
| tggctgagcc tgtttagcag cgaggaaagc aacctgggcg ccaacaacta cgacgactac | 1260 |
| cggatggatt ggctggtgcc tgccacatgc gagcctatcc agagcgtgtt cttcttcagc | 1320 |
| ggcgacaaat attaccgcgt gaacctgcgg actcggagag tggatacagt ggaccctcct | 1380 |
| tatcctcggt ctatcgctca gtattggctg ggctgtccag ctcctggaca cctgtaa | 1437 |

<210> SEQ ID NO 43
<211> LENGTH: 5175
<212> TYPE: DNA
<213> ORGANISM: Homo sapiens

<400> SEQUENCE: 43

| | |
|---|---|
| atgcctccag cagtgaggcg gtcagcctgc agcatgggat ggctgtggat ctttggggca | 60 |
| gccctggggc agtgtctggg ctacagttca cagcagcaaa gggtgccatt tcttcagcct | 120 |
| cccggtcaaa gtcaactgca agcgagttat gtggagttta acccagcca gggttgtagc | 180 |
| cctggatact atcgggatca taaaggcttg tataccggac ggtgtgttcc ctgcaattgc | 240 |
| aacggacatt caaatcaatg ccaggatggc tcaggcatat gtgttaactg tcagcacaac | 300 |
| accgcgggag agcactgtga cgctgccag gagggctact atggcaacgc cgtccacgga | 360 |
| tcctgcaggg cctgcccatg tcctcacact aacagctttg ccactggctg tgtggtgaat | 420 |
| ggggagacg tgcggtgctc ctgcaaagct gggtacacag aacacagtg tgaaaggtgt | 480 |
| gcaccgggat atttcgggaa tccccagaaa ttcgaggta gctgccaacc atgcagttgt | 540 |
| aacagcaatg ccagctggg cagctgtcat ccctgactg gagactgcat aaaccaagaa | 600 |
| cccaaagata gcagccctgc agaagaatgt gatgattgcg acagctgtgt gatgaccctc | 660 |
| ctgaacgacc tggccaccat gggcgagcag ctccgcctgg tcaagtctca gctgcagggc | 720 |
| ctgagtgcca gcgcagggct tctggagcag atgaggcaca tggagaccca ggccaaggac | 780 |
| ctgaggaatc agttgctcaa ctaccgttct gccatttcaa atcatggatc aaaaatagaa | 840 |
| ggcctggaaa gagaactgac tgatttgaat caagaatttg agactttgca agaaaaggct | 900 |
| caagtaaatt ccagaaaagc acaaacatta acaacaatg ttaatcgggc aacacaaagc | 960 |
| gcaaaagaac tggatgtgaa gattaaaaat gtcatccgga atgtgcacat tcttttaaag | 1020 |
| cagatctctg gacagatgg agagggaaac aacgtgcctt caggtgactt ttccagagag | 1080 |
| tgggctgaag cccagcgcat gatgagggaa ctgcggaaca ggaactttgg aaagcacctc | 1140 |
| agaagcag aagctgataa aagggagtcg cagctcttgc tgaaccggat aaggacctgg | 1200 |
| cagaaaaccc accaggggga gaacaatggg cttgctaaca gtatccggga ttctttaaat | 1260 |
| gaatacgaag ccaaactcag tgaccttcgt gctcggctgc aggaggcagc tgcccaagcc | 1320 |
| aagcaggcaa atgcttgaa ccaagaaaac gagagagctt tgggagccat tcagagacaa | 1380 |
| gtgaaagaaa taattccct gcagagtgat ttcaccaagt atctaaccac tgcagactca | 1440 |
| tctttgttgc aaccaacat tgcgctgcag ctgatggaga aaagccagaa ggaatatgaa | 1500 |
| aaattagctg ccagttttaa tgaagcaaga caagaactaa gtgacaaagt aagagaactt | 1560 |
| tccagatctg ctggcaaaac atcccttgtg gaggaggcag aaaagcacgc gcggtcctta | 1620 |
| caagagctgg caaagcagct ggaagagatc aagagaaacg ccagcgggga tgagctggtg | 1680 |
| cgctgtgctg tggatgccgc caccgcctac gagaacatcc tcaatgccat caaagcggcc | 1740 |
| gaggacgcag ccaacaggg tgccagtgca tctgaatctg ccctccagac agtgataaag | 1800 |
| gaagatctgc caagaaaagc taaaaccctg agttccaaca gtgataaact gttaaatgaa | 1860 |

```
gccaagatga cacaaaagaa gctaaagcaa gaagtcagtc cagctctcaa caacctacag    1920
caaaccctga atattgtgac agttcagaaa gaagtgatag acaccaatct cacaactctc    1980
cgagatggtc ttcatgggat acagagaggt gatattgatg ctatgatcag tagtgcaaag    2040
agcatggtca gaaaggccaa cgacatcaca gatgaggttc tggatgggct caaccccatc    2100
cagacagatg tggaaagaat taaggacacc tatgggagga cacagaacga agacttcaaa    2160
aaggctctga ctgatgcaga taactcggtg aataagttaa ccaacaaact acctgatctt    2220
tggcgcaaga ttgaaagtat caaccaacag ctgttgccct tgggaaacat ctctgacaac    2280
atggacagaa tacgagaact aattcagcag gccagatgc tgccagtaa ggttgctgtc    2340 cccatgaggt tcaatggtaa atctggagtc gaagtccgac tgccaaatga cctggaagat    2400
ttgaaaggat atacatctct gtccttgttt ctccaaaggc ccaactcaag agaaaatggg    2460
ggtactgaga atatgtttgt gatgtacctt ggaaataaag atgcctcccg ggactacatc    2520
ggcatggcag ttgtggatgg ccagctcacc tgtgtctaca acctggggga ccgtgaggct    2580
gaactccaag tggaccagat cttgaccaag agtgagacta aggaggcagt tatggatcgg    2640
gtgaaatttc agagaattta tcagtttgca aggcttaatt acaccaaagg agccacatcc    2700
agtaaaccag aaacacccgg agtctatgac atggatggta gaaatagcaa tacactcctt    2760
aatttggatc ctgaaaatgt tgtattttat gttggaggtt acccacctga ttttaaactt    2820
cccagtcgac taagtttccc tccatacaaa ggttgtattg aattagatga cctcaatgaa    2880
aatgttctga gcttgtacaa cttcaaaaaa acattcaatc tcaacacaac tgaagtggag    2940
ccttgtagaa ggaggaagga agagtcagac aaaaattatt ttgaaggtac gggctatgct    3000
cgagttccaa ctcaaccaca tgctcccatc ccaacctttg acagacaat tcagaccacc    3060 gtggatagag gcttgctgtt ctttgcagaa aacggggatc gcttcatatc tctaaatata    3120
gaagatggca agctcatggt gagatacaaa ctgaattcag agctaccaaa agagagagga    3180
gttggagacg ccataaacaa cggcagagac cattcgattc agatcaaaat tggaaaactc    3240
caaaagcgta tgtggataaa tgtggacgtt caaaacacta taattgatgg tgaagtattt    3300
gatttcagca catattatct gggaggaatt ccaattgcaa tcagggaaag atttaacatt    3360
tctacgcctg ctttccgagg ctgcatgaaa aatttgaaga aaaccagtgg tgtcgttaga    3420
ttgaatgata ctgtgggagt aaccaaaaag tgctcggaag actggaagct tgtgcgatct    3480
gcctcattct ccagaggagg acaattgagt ttcactgatt tgggcttacc acctactgac    3540
cacctccagg cctcatttgg atttcagacc tttcaaccca gtggcatatt attagatcat    3600
cagacatgga caaggaacct gcaggtcact ctggaagatg gttacattga attgagcacc    3660
agcgatagcg gcggcccaat ttttaaatct ccacagacgt atatgatgg tttactgcat    3720 tatgtatctg taataagcga caactctgga ctacggcttc tcatcgatga ccagcttctg    3780
agaaatagca aaaggctaaa acacatttca agttcccggc agtctctgcg tctgggcggg    3840
agcaattttg agggttgtat tagcaatgtt tttgtccaga ggttatcact gagtcctgaa    3900
gtcctagatt tgaccagtaa ctctctcaag agagatgtgt ccctgggagg ctgcagttta    3960
aacaaaccac ctttctaat gttgcttaaa ggttctacca ggtttaacaa gaccaagact    4020
tttcgtatca accagctgtt gcaggacaca ccagtggcct ccccaaggag cgtgaaggtg    4080
tggcaagatg cttgctcacc acttcccaag acccaggcca atcatggagc cctccagttt    4140
ggggacattc ccaccagcca cttgctattc aagcttcctc aggagctgct gaaacccagg    4200
```

```
tcacagtttg ctgtggacat gcagacaaca tcctccagag gactggtgtt tcacacgggc   4260
actaagaact cctttatggc tctttatctt tcaaaaggac gtctggtctt tgcactgggg   4320
acagatggga aaaaattgag gatcaaaagc aaggagaaat gcaatgatgg gaaatggcac   4380
acggtggtgt ttggccatga tggggaaaag ggcgcttgg ttgtggatgg actgagggcc    4440

cgggagggaa gtttgcctgg aaactccacc atcagcatca gagcgccagt ttacctggga   4500
tcacctccat cagggaaacc aaagagcctc cccacaaaca gctttgtggg atgcctgaag   4560
aactttcagc tggattcaaa acccttgtat accccttctt caagcttcgg ggtgtcttcc   4620
tgcttgggtg gtcctttgga gaaaggcatt tatttctctg aagaaggagg tcatgtcgtc   4680
ttggctcact ctgtattgtt ggggccagaa tttaagcttg ttttcagcat ccgcccaaga   4740
agtctcactg ggatcctaat acacatcgga agtcagcccg ggaagcactt atgtgtttac   4800
ctggaggcag gaaaggtcac ggcctctatg gacagtgggg caggtgggac ctcaacgtcg   4860
gtcacaccaa agcagtctct gtgtgatgga cagtggcact cggtggcagt caccataaaa   4920
caacacatcc tgcacctgga actggacaca gacagtagct acacagctgg acagatcccc   4980
ttcccacctg ccagcactca agagccacta caccttggag gtgctccagc caatttgacg   5040
acactgagga tccctgtgtg gaaatcattc tttggctgtc tgaggaatat tcatgtcaat   5100
cacatccctg tccctgtcac tgaagccttg gaagtccagg ggcctgtcag tctgaatggt   5160
tgtcctgacc agtaa                                                    5175
```

```

<210> SEQ ID NO 44
<211> LENGTH: 5175
<212> TYPE: DNA
<213> ORGANISM: Artificial Sequence
<220> FEATURE:
<223> OTHER INFORMATION: Synthetic Construct

<400> SEQUENCE: 44

```

```
atgcctcctg ctgtgcggag aagcgcctgt tctatgggat ggctgtggat ctttggcgcc     60
gctctgggac agtgtctggg ctactcttct cagcagcagc gggtgccatt tctgcagcca    120
cctggacagt ctcagctgca ggccagctac gtggaattca gacctagcca gggctgtagc    180
cccggctact acagagatca caagggcctg tacaccggca gatgcgtgcc ctgcaactgt    240
aacggccaca gcaaccagtg tcaggacggc tctggcatct gcgtgaactg ccagcataat    300
actgccggcg agcactgcga gagatgccaa gagggctact acggcaatgc cgtgcatggc    360
agctgtcggg cttgtccttg tcctcacacc aacagctttg ccaccggctg cgttgtgaac    420
ggcggagatg ttcggtgttc ttgcaaggcc ggctacacag gcacacagtg cgaaagatgt    480
gcccctggct actttggcaa ccctcagaag tttggcggct cctgccagcc ttgctcctgc    540
aattctaatg gccagctggg ctcttgtcac cctctgaccg gcgactgcat caatcaagag    600
cctaaggaca gcagccctgc cgaggaatgc gacgattgcg atagctgcgt gatgaccctg    660
ctgaacgacc tggccacaat gggagaacag ctgcggctgg ttaagagcca gctccaggga    720
ctgtctgcct ctgctggact gctggaacag atgcggcaca tggaaaccca ggccaaggac    780
ctgagaaacc agctgctgaa ctacagaagc gccatctcca accacggcag caagatcgaa    840
ggcctggaaa gagagctgac cgacctgaat caagagttcg agacactgca agagaaggcc    900
caagtgaaca gccggaaggc ccagactctg aacaacaacg tgaaccgggc cacacagtcc    960
gccaaagaac tggacgtgaa gatcaagaac gtgatccgga acgtgcacat cctgctgaag   1020
cagatcagcg gcacagatgg cgagggcaac aatgtgccta gcggcgactt tagcagagag   1080
```

```
tgggccgaag ctcagcggat gatgagagag ctgcggaacc ggaacttcgg caagcacctg    1140
agagaagccg aggccgacaa gagagagagc caactgctgc tcaaccggat cagaacctgg    1200
cagaaaaccc accagggcga gaacaacggc ctggccaaca gcatcagaga cagcctgaat    1260
gagtacgagg ccaagctgag cgatctgcgg gccagacttc aagaagctgc cgctcaggcc    1320
aagcaggcca acggccttaa tcaagagaac gagagagccc tgggcgccat ccagagacaa    1380
gtgaaagaga tcaacagcct gcagagcgac ttcaccaagt acctgaccac cgccgatagc    1440
agcctgctgc agacaaatat cgccctgcag ctcatggaaa agagccagaa agagtacgaa    1500
aagctggccg ccagcctgaa cgaggccagg caagaactgt ctgacaaagt gcgcgagctg    1560
agcagatccg ccggcaagac atctctggtg aagaggccg agaagcacgc cagatctctg     1620
caagagctgg ccaaacagct ggaagagatt aagcggaacg ccagcggcga cgaactcgtc    1680
agatgtgcag tggatgccgc caccgcctac gagaacatcc tgaatgccat caaggccgcc    1740
gaggacgccg ctaatagagc cgcttctgct tctgagtctg ccctgcagac cgtgatcaaa    1800
gaggacctgc ctagaaaggc caagacactg agcagcaaca gcgacaaact gctgaatgag    1860
gccaagatga cccagaagaa actgaagcaa gaggtgtccc ctgcactgaa caacctgcag    1920
cagaccctga acatcgtgac cgtgcagaaa gaagtgatcg acaccaacct gacaaccctg    1980
agagatggcc tgcacggaat ccagagaggc gacatcgacg ccatgatcag cagcgccaag    2040
agcatggttc gaaaagccaa cgacatcacc gacgaggtgc tggacggcct gaatcctatc    2100
cagaccgacg tggaacggat caaggacacc tacggcagaa cccagaacga ggatttcaag    2160
aaggccctga ccgacgccga caactccgtg aacaagctga ccaacaagct gcccgatctg    2220
tggcggaaga tcgagagcat caaccagcaa ctgctcccte tgggcaacat cagcgacaac    2280
atggacagaa tccgggaact gatccagcag gccagagatg ccgcctccaa agtggctgtg    2340
cccatgagat tcaacggcaa gagcggagtg gaagtgcggc tgcccaacga tctggaagat    2400
ctgaagggct ataccagcct gagcctgttc ctgcagaggc caacagcag agagaatggc     2460 ggcaccgaga atatgttcgt gatgtacctg ggaaacaagg acgccagccg ggactatatc    2520
ggaatggccg ttgtggacgg ccagctgacc tgcgtgtaca acctgggaga cagagaagct    2580
gaactgcagg tcgaccagat cctgaccaag agcgagacaa agaggccgt gatggacaga    2640 gtgaagttcc agcggatcta ccagttcgcc cggctgaatt acaccaaggg cgccacaagc    2700
agcaagcccg aaacacctgg cgtgtacgac atggacggcc ggaactctaa cactctgctg    2760
aatctggacc ccgagaacgt ggtgttttac gtcggcggct acccctcctga cttcaagctg    2820 cctagcagac tgagcttccc accttacaag ggctgcatcg agctggatga cctgaacgaa    2880
aacgtgctgt ccctgtacaa cttcaaaaag accttcaacc tgaacaccac cgaggtggaa    2940
ccctgcaggc gcagaaaaga ggaatccgac aagaactact tcgaaggcac cggctacgcc    3000
agagtgccta caacacctca cgctcccatt cctaccttcg ccagaccat ccagacaacc     3060 gtggatagag gcctgctgtt cttcgccgag aacggcgaca gattcatctc cctgaatatc    3120
gaggatggca agctgatggt ccgatacaag ctgaatagcg agctgcccaa agaaagaggc    3180
gtgggcgacg ccatcaacaa cggcagggat cacagcatcc agatcaagat cggcaaactg    3240
cagaaacgga tgtggatcaa cgtggacgtg cagaacacca tcatcgacgg cgaggtgttc    3300
gacttcagca cctactatct cggcggaatc cctatcgcca tcagagagcg gttcaatatc    3360
agcacccctg ccttccgggg ctgcatgaag aacctgaaaa agaccagcgg cgtcgtgcgg    3420
```

```
ctgaatgata cagtgggcgt gaccaagaag tgcagcgagg actggaagct tgtgcggagc    3480
gccagttttt ctagaggcgg acagctgagc tttaccgacc tgggactgcc tcctaccgat    3540
catctgcagg caagcttcgg attccagacc ttccagccaa gcggaatcct gctggaccac    3600
cagacctgga ccagaaacct gcaagtgacc ctggaagatg ctacatcga actgagcacc     3660 agcgactctg gcggccctat ctttaagagc cctcagacct acatggatgg gctgctgcac    3720
tacgtgtccg tgatcagcga taacagcggc ctgagactgc tgatcgacga ccagctcctg    3780
cggaacagca agcggctgaa gcacatctcc agcagcagac agagtctgag actcggcggc    3840
agcaatttcg agggctgtat cagcaacgtg ttcgtgcagc gcctgagtct gtctccagaa    3900
gtgctggacc tgaccagcaa tagcctgaag agggatgtgt ctctcggcgg ctgctccctg    3960
aacaaacctc ctttcctgat gctgctgaag ggcagcaccc ggttcaacaa gaccaagacc    4020
tttcggatca atcagctgct ccaggacacc cctgtggcta gccctagaag cgtgaaagtg    4080
tggcaggacg cctgcagtcc cctgcctaaa acacaggcca atcacggggc tctgcagttc    4140
ggcgatatcc ccacaagcca tctgctgttt aagctgcccc aagagctgct caagcctcgg    4200
agccagttcg ctgtggatat gcagaccacc tcctccagag gactggtgtt tcacaccggc    4260
accaagaaca gcttcatggc cctgtacctg agcaaaggca ggctggtgtt tgccctgggc    4320
accgacggaa agaaactgcg gatcaagagc aaagagaagt gcaacgacgg caagtggcac    4380
accgtggtgt tcgacacgga tggcgagaaa ggcagactcg tggtggatgg cctgagagcc    4440
agagagggat ctctgcctgg caactccacc atctccatca gagcccctgt gtatctgggc    4500
agccctccta gcggaaagcc taagagcctg cctaccaact ccttcgtggg ctgtctgaag    4560
aactttcagc tggacagcaa gcctctgtac accctagca gcagctttgg cgtgtcctcc    4620
tgtctcggag gccctctgga aaagggcatc tacttctctg aggaaggcgg ccacgttgtc    4680
ctggctcatt ctgttctgct gggccccgag ttcaagctgg tgttctctat ccggcctaga    4740
agcctgaccg gcatcctgat tcacatcggc agccagcctg gaagcacct gtgtgtgtat    4800 ctcgaggccg gcaaagtgac cgccagcatg gattctggtg ctggcggcac aagcacctcc    4860
gtgacaccta gcagagcct gtgtgatggc cagtggcaca gtgtggccgt gacaatcaag    4920
cagcacattc tgcacctgga actggacacc gacagcagct ataccgccgg acagatccca    4980
tttcctccag ccagcacaca agagcctctg caccttggag gcgcccctgc caatctgacc    5040
acactgagaa tccccgtgtg gaagtccttc ttcggctgcc tgcggaatat ccatgtgaac    5100
cacattccag tgcctgtgac agaggccctg gaagtgcagg acccgtgtc tctgaatgga    5160 tgccccgatc agtga                                                     5175
```

```
<210> SEQ ID NO 45
<211> LENGTH: 3519
<212> TYPE: DNA
<213> ORGANISM: Homo sapiens

<400> SEQUENCE: 45
atgagaccat tcttcctctt gtgttttgcc ctgcctggcc tcctgcatgc ccaacaagcc      60
tgctcccgtg gggcctgcta tccacctgtt ggggacctgc ttgttgggag gacccggttt    120
ctccgagctt catctaccctg tggactgacc aagcctgaga cctactgcac ccagtatggc    180
gagtggcaga tgaaatgctg caagtgtgac tccaggcagc ctcacaacta ctacagtcac    240
cgagtagaga atgtggcttc atcctccggc cccatgcgct ggtggcagtc acagaatgat    300
gtgaaccctg tctctctgca gctggacctg gacaggagat tccagcttca agaagtcatg    360
```

```
atggagttcc aggggcccat gcccgccggc atgctgattg agcgctcctc agacttcggt      420
aagacctggc gagtgtacca gtacctggct gccgactgca cctccacctt ccctcgggtc      480
cgccagggtc ggcctcagag ctggcaggat gttcggtgcc agtccctgcc tcagaggcct      540
aatgcacgcc taaatggggg gaaggtccaa cttaacctta tggatttagt gtctgggatt      600
ccagcaactc aaagtcaaaa aattcaagag gtgggggaga tcacaaactt gagagtcaat      660
ttcaccaggc tggcccctgt gccccaaagg ggctaccacc ctcccagcgc ctactatgct      720
gtgtcccagc tccgtctgca ggggagctgc ttctgtcacg gccatgctga tcgctgcgca      780
cccaagcctg gggcctctgc aggcccctcc accgctgtgc aggtccacga tgtctgtgtc      840
tgccagcaca acactgccgg cccaaattgt gagcgctgtg cacccttcta caacaaccgg      900
ccctggagac cggcggaggg ccaggacgcc atgaatgcc aaaggtgcga ctgcaatggg      960
cactcagaga catgtcactt tgaccccgct gtgtttgccg ccagccaggg ggcatatgga     1020
ggtgtgtgtg acaattgccg ggaccacacc gaaggcaaga actgtgagcg tgtcagctg     1080 cactatttcc ggaaccggcg cccgggagct tccattcagg agacctgcat ctcctgcgag     1140
tgtgatccgg atggggcagt gccagggct ccctgtgacc cagtgaccgg gcagtgtgtg     1200
tgcaaggagc atgtgcaggg agagcgctgt gacctatgca agccgggctt cactggactc     1260
acctacgcca acccgcaggg ctgccaccgc tgtgactgca acatcctggg gtcccggagg     1320
gacatgccgt gtgacgagga gagtgggcgc tgcctttgtc tgcccaacgt ggtgggtccc     1380
aaatgtgacc agtgtgctcc ctaccactgg aagctggcca gtggccaggg ctgtgaaccg     1440
tgtgcctgcg acccgcacaa ctccctcagc ccacagtgca accagttcac agggcagtgc     1500
ccctgtcggg aaggctttgg tggcctgatg tgcagcgctg cagccatccg ccagtgtcca     1560
gaccggacct atggagacgt ggccacagga tgccgagcct gtgactgtga tttccgggga     1620
acagagggcc cggctgcga caaggcatca ggccgctgcc tctgccgccc tggcttgacc     1680 gggcccccgct gtgaccagtg ccagcgaggc tactgtaatc gctacccggt gtgcgtggcc     1740
tgccaccctt gcttccagac ctatgatgcg gacctccggg agcaggccct gcgctttggt     1800
agactccgca atgccaccgc cagcctgtgg tcagggcctg ggctggagga ccgtggcctg     1860
gcctcccgga tcctagatgc aaagagtaag attgagcaga tccgagcagt tctcagcagc     1920
cccgcagtca cagagcagga ggtggctcag gtggccagtg ccatcctctc cctcaggcga     1980
actctccagg gcctgcagct ggatctgccc ctggaggagg agacgttgtc ccttccgaga     2040
gacctggaga gtcttgacag aagcttcaat ggtctcctta ctatgtatca gaggaagagg     2100
gagcagtttg aaaaaataag cagtgctgat ccttcaggag ccttccggat gctgagcaca     2160
gcctacgagc agtcagccca ggctgctcag caggtctccg acagctcgcg ccttttggac     2220
cagctcaggg acagccggag agaggcagag aggctggtgc ggcaggcggg aggaggagga     2280
ggcaccggca gccccaagct gtggccctg aggctggaga tgtcttcgtt gcctgacctg     2340
acacccacct tcaacaagct ctgtggcaac tccaggcaga tggcttgcac cccaatatca     2400
tgccctggtg agctatgtcc ccaagacaat ggcacagcct gtggctcccg ctgcaggggt     2460
gtccttccca gggccggtgg ggccttcttg atggcggggc aggtggctga gcagctgcgg     2520
ggcttcaatg cccagctcca gcggaccagg cagatgatta gggcagccga ggaatctgcc     2580
tcacagattc aatccagtgc ccagcgcttg gagacccagg tgagcgccag ccgctcccag     2640
atggaggaag atgtcagacg cacacggctc ctaatccagc aggtccggga cttcctaaca     2700
```

| | |
|---|---|
| gaccccgaca ctgatgcagc cactatccag gaggtcagcg aggccgtgct ggccctgtgg | 2760 |
| ctgcccacag actcagctac tgttctgcag aagatgaatg agatccaggc cattgcagcc | 2820 |
| aggctcccca acgtggactt ggtgctgtcc cagaccaagc aggacattgc gcgtgcccgc | 2880 |
| cggttgcagg ctgaggctga ggaagccagg agccgagccc atgcagtgga gggccaggtg | 2940 |
| gaagatgtgg ttgggaacct gcggcagggg acagtggcac tgcaggaagc tcaggacacc | 3000 |
| atgcaaggca ccagccgctc ccttcggctt atccaggaca gggttgctga ggttcagcag | 3060 |
| gtactgcggc agcagaaaaa gctggtgaca agcatgacca agcagctggg tgacttctgg | 3120 |
| acacggatgg aggagctccg ccaccaagcc cggcagcagg gggcagaggc agtccaggcc | 3180 |
| cagcagcttg cggaaggtgc cagcgagcag gcattgagtg cccaagaggg atttgagaga | 3240 |
| ataaaacaaa agtatgctga gttgaaggac cggttgggtc agagttccat gctgggtgag | 3300 |
| cagggtgccc ggatccagag tgtgaagaca gaggcagagg agctgtttgg ggagaccatg | 3360 |
| gagatgatgg acaggatgaa agacatggag ttggagctgc tgcggggcag ccaggccatc | 3420 |
| atgctgcgct cagcggacct gacaggactg gagaagcgtg tggagcagat ccgtgaccac | 3480 |
| atcaatgggc gcgtgctcta ctatgccacc tgcaagtga | 3519 |

<210> SEQ ID NO 46
<211> LENGTH: 3519
<212> TYPE: DNA
<213> ORGANISM: Artificial Sequence
<220> FEATURE:
<223> OTHER INFORMATION: Synthetic Construct

<400> SEQUENCE: 46

| | |
|---|---|
| atgaggccct tcttcctgct gtgctttgcc ctgcctggac tgctgcatgc tcagcaggct | 60 |
| tgtagcagag gcgcctgcta tcctcctgtg ggcgatctgc ttgtgggcag aaccagattc | 120 |
| ctgcgggcca gctctacatg cggcctgaca aagcctgaga catactgcac ccagtacggc | 180 |
| gagtggcaga tgaagtgctg caagtgcgac agcagacagc cccacaacta ctacagccac | 240 |
| agagtggaaa acgtggccag cagcagcggc cctatgagat ggtggcagag ccagaacgac | 300 |
| gtgaaccccg ttagcctgca gctggacctg acagacggt tcagctgca agaagtgatg | 360 |
| atggaatttc agggccccat gcctgccggc atgctgatcg agagaagcag cgatttcggc | 420 |
| aagacctggc gggtgtacca gtatctggcc gccgattgca ccagcacatt ccccagagtt | 480 |
| agacagggca gaccccagag ctggcaggat gttcgttgtc agtctctgcc ccagcggcct | 540 |
| aacgctagac tgaatggcgg aaaggtgcag ctcaacctga tggacctggt gtctggcatc | 600 |
| cctgccacac agtcccagaa aatccaagaa gtgggcgaga tcaccaacct gagagtgaac | 660 |
| ttcacccggc tggctcccgt tcctcagaga ggatatcatc ctcctagcgc ctactacgcc | 720 |
| gtgtctcagc ttagactgca gggcagctgc ttctgtcacg ccacgctga tagatgcgcc | 780 |
| cctaaacctg gtgcctctgc cggaccttct acagccgtgc aagtgcacga tgtgtgcgtg | 840 |
| tgccagcaca ataccgccgg acctaactgc gagagatgtg ccccttttct aacaaccgg | 900 |
| ccttggaggc ctgccgaagg acaggatgct cacgagtgcc agagatgcga ctgcaacggc | 960 |
| cacagcgaga catgccactt tgaccctgcc gtgtttgccg cttctcaggg cgcttatggc | 1020 |
| ggcgtgtgtg acaactgcag agatcacacc gagggcaaga actgcgagcg ctgtcagctg | 1080 |
| cactacttcc ggaatagaag gccaggcgcc agcatccaag agacatgcat cagctgcgag | 1140 |
| tgcgatcccg atggtgctgt tcctggcgct ccttgtgatc ctgtgacagg ccagtgcgtg | 1200 |
| tgtaaagaac acgtgcaggg cgaaagatgc gacctgtgca agcctggctt taccggcctg | 1260 |

```
acctacgcca atcctcaggg ctgccacaga tgtgattgca acatcctggg cagcagacgg    1320
gacatgccct gtgatgaaga gtctggcaga tgcctgtgcc tgcctaatgt cgtgggcccc    1380
aagtgcgatc agtgtgcccc atatcactgg aagctggcct ctggccaggg atgcgaacct    1440
tgtgcctgcg atccccacaa cagcctgtct ccacagtgca accagttcac cggccagtgt    1500
ccttgcagag aaggctttgg cggcctgatg tgttctgccg ccgctatcag acagtgcccc    1560
gatagaacat atgcgacgt ggccacaggc tgcagagcct gcgattgtga cttccgggga    1620
acagaaggac ccggctgcga taaggccagc ggaagatgtc tgtgtcggcc tggactcaca    1680
ggccccagat gtgaccagtg tcagcggggc tactgcaaca gataccctgt gtgtgtggcc    1740
tgccatcctt gcttccagac ctacgacgcc gacctgagag aacaggccct gagattcggc    1800
agactgagaa atgccaccgc cagcctttgg agcggacctg gccttgaaga tagaggcctg    1860
gcctccagaa tcctggacgc caagtctaag atcgagcaga tcagagccgt gctgtctagc    1920
ccagccgtga ccgaacaaga ggtggcccaa gtggctagcg ccatcctgag cctgagaaga    1980
actctgcagg gactgcagct cgatctgccc ctggaagagg aaacactgag cctgcctaga    2040
gatctggaaa gcctggatcg gagcttcaac ggcctgctga caatgtacca gagaaagaga    2100
gagcagttcg agaagatcag cagcgccgat cctagcggcg ccttcagaat gctgagcaca    2160
gcctatgagc agagcgccca ggctgctcag caagtgtccg atagcagcag actgctggac    2220
cagctgcggg actctagaag agaagccgaa agacttgtgc ggcaggcagg cggcggaggt    2280
ggaacaggat ctcctaaact ggtggccctg cggctggaaa tgtcctctct gcctgatctg    2340
acccctacct tcaacaagct gtgcggcaac agccggcaga tggcctgcac acctattagc    2400
tgtcctggcg agctgtgccc tcaggataat ggaaccgcct gcggctccag atgtagaggc    2460
gttttgccaa gagccggcgg agccttctg atggctggac aagttgccga gcagctgaga    2520
ggcttcaacg ctcagctgca gcggaccaga cagatgatta gagccgccga ggaaagcgcc    2580
agccagattc aatctagcgc ccagagactg gaaacccagg tgtccgccag cagatcccag    2640
atggaagaag atgtgcggcg gacaagactg ctgatccagc aagtgcggga cttcctgacc    2700
gatcctgata ccgatgccgc cacaatccaa gaggtgtccg aagctgttct ggcactgtgg    2760
ctgcctaccg atagcgctac agtgctgcag aagatgaacg agatccaggc aatcgccgcc    2820
agactgccca atgtggatct ggtgctgagc cagaccaagc aggatatcgc cagagctaga    2880
aggctgcagg ccgaggccga agaggcaaga tctagagccc atgccgtgga aggccaagtc    2940
gaggacgttg tgggcaatct gagacaggga accgtggctc tgcaagaggc ccaggataca    3000
atgcagggca ccagcagaag cctgcgcctg atccaggata gagtggccga agtgcagcag    3060 gtcctgagc cagccgaaaa gctggtcacc agcatgacca acagctgggc gatttctgg    3120 acgcgcatgg aagaactgag gcatcaggca agacagcagg gcgctgaagc agtgcaggct    3180
caacaacttg ccgagggcgc ttctgaacag gctctgtctg cccaagaggg cttcgagcgg    3240
atcaagcaga agtacgccga gctgaaggac agactgggcc agagttctat gctgggcgaa    3300
cagggcgcca gaattcagag cgtgaaaaca gaggccgagg aactgttcgg cgagacaatg    3360
gaaatgatgg accggatgaa ggacatggaa ctggaactgc tgaggggcag ccaggccatc    3420
atgctgagaa gtgccgatct gacaggcctg gaaaagagag tggaacagat ccgggaccac    3480
atcaacggcc gggtgctgta ctacgccaca tgcaagtaa                          3519
```

<210> SEQ ID NO 47

<211> LENGTH: 3582
<212> TYPE: DNA
<213> ORGANISM: Homo sapiens

<400> SEQUENCE: 47

```
atgcctgcgc tctggctggg ctgctgcctc tgcttctcgc tcctcctgcc cgcagcccgg      60
gccacctcca ggagggaagt ctgtgattgc aatgggaagt ccaggcagtg tatctttgat     120
cgggaacttc acagacaaac tggtaatgga ttccgctgcc tcaactgcaa tgacaacact     180
gatggcattc actgcgagaa gtgcaagaat ggcttttacc ggcacagaga agggaccgc      240
tgtttgccct gcaattgtaa ctccaaaggt tctcttagtg ctcgatgtga caactccgga     300
cggtgcagct gtaaaccagg tgtgacagga gccagatgcg accgatgtct gccaggcttc     360
cacatgctca cggatgcggg gtgcacccaa gaccagagac tgctagactc caagtgtgac     420
tgtgacccag ctggcatcgc agggccctgt gacgcgggcc gctgtgtctg caagccagct     480
gtcactggag aacgctgtga taggtgtcga tcaggttact ataatctgga tggggggaac     540
cctgagggct gtacccagtg tttctgctat gggcattcag ccagctgccg cagctctgca     600
gaatacagtg tccataagat cacctctacc tttcatcaag atgttgatgg ctggaaggct     660
gtccaacgaa atgggtctcc tgcaaagctc aatggtcac agcgccatca agatgtgttt      720
agctcagccc aacgactaga ccctgtctat tttgtggctc ctgccaaatt tcttgggaat     780
caacaggtga gctatggtca agcctgtccc tttgactacc gtgtggacag aggaggcaga     840
cacccatctg cccatgatgt gattctggaa ggtgctggtc tacggatcac agctcccttg     900
atgccacttg gcaagacact gccttgtggg ctcaccaaga cttacacatt caggttaaat     960
gagcatccaa gcaataattg agccccccag ctgagttact ttgagtatcg aaggttactg    1020
cggaatctca cagccctccg catccgagct acatatggag aatacagtac tgggtacatt    1080
gacaatgtga ccctgatttc agcccgccct gtctctggag ccccagcacc tgggttgaa     1140
cagtgtatat gtcctgttgg gtacaagggg caattctgcc aggattgtgc ttctggctac    1200
aagagagatt cagcgagact ggggccttt ggcacctgta ttccttgtaa ctgtcaaggg     1260
ggagggcct gtgatccaga cacaggagat tgttattcag gggatgagaa tcctgacatt     1320
gagtgtgctg actgcccaat tggtttctac aacgatccgc acgaccccg cagctgcaag    1380
ccatgtccct gtcataacgg gttcagctgc tcagtgatgc cggagacgga ggaggtggtg    1440
tgcaataact gccctcccgg ggtcaccggt gcccgctgtg agctctgtgc tgatggctac    1500
tttgggacc cctttggtga acatggccca gtgaggcctt gtcagccctg tcaatgcaac    1560
aacaatgtgg accccagtgc ctctgggaat tgtgaccggc tgacaggcag gtgtttgaag    1620
tgtatccaca cacagccggg catctactgc gaccagtgca aagcaggcta cttcgggggac    1680
ccattggctc ccaacccagc agacaagtgt cgagcttgca ctgtaaccc catgggctca    1740
gagcctgtag gatgtcgaag tgatggcacc tgtgtttgca agccaggatt tggtggcccc    1800
aactgtgagc atggagcatt cagctgtcca gcttgctata atcaagtgaa gattcagatg    1860
gatcagttta tgcagcagct tcagagaatg gaggccctga tttcaaaggc tcagggtggt    1920
gatggagtag tacctgatac agagctggaa ggcaggatgc agcaggctga gcaggccctt    1980
caggacattc tgagagatgc ccagatttca gaaggtgcta gcagatccct tggtctccag    2040
ttggccaagg tgaggagcca agagaacagc taccagagcc gctggatga cctcaagatg    2100
actgtggaaa gagttcgggc tctgggaagt cagtaccaga accgagttcg ggatactcac    2160
aggctcatca ctcagatgca gctgagcctg gcagaaagtg aagcttcctt gggaaacact    2220
```

| | |
|---|---|
| aacattcctg cctcagacca ctacgtgggg ccaaatggct ttaaaagtct ggctcaggag | 2280 |
| gccacaagat tagcagaaag ccacgttgag tcagccagta acatggagca actgacaagg | 2340 |
| gaaactgagg actattccaa acaagccctc tcactggtgc gcaaggccct gcatgaagga | 2400 |
| gtcggaagcg gaagcggtag cccggacggt gctgtggtgc aagggcttgt ggaaaaattg | 2460 |
| gagaaaacca agtccctggc ccagcagttg acaagggagg ccactcaagc ggaaattgaa | 2520 |
| gcagataggt cttatcagca cagtctccgc ctcctggatt cagtgtctcg gcttcaggga | 2580 |
| gtcagtgatc agtcctttca ggtggaagaa gcaaagagga tcaaacaaaa agcggattca | 2640 |
| ctctcaagcc tggtaaccag gcatatggat gagttcaagc gtacacagaa gaatctggga | 2700 |
| aactggaaag aagaagcaca gcagctctta cagaatggaa aaagtgggag agagaaatca | 2760 |
| gatcagctgc tttcccgtgc caatcttgct aaaagcagag cacaagaagc actgagtatg | 2820 |
| ggcaatgcca cttttttatga agttgagagc atccttaaaa acctcagaga gtttgacctg | 2880 |
| caggtggaca acagaaaagc agaagctgaa gaagccatga agagactctc ctacatcagc | 2940 |
| cagaaggttt cagatgccag tgacaagacc cagcaagcag aaagagccct ggggagcgct | 3000 |
| gctgctgatg cacagagggc aaagaatggg gccggggagg ccctggaaat ctccagtgag | 3060 |
| attgaacagg agattgggag tctgaacttg gaagccaatg tgacagcaga tggagccttg | 3120 |
| gccatggaaa agggactggc ctctctgaag agtgagatga gggaagtgga aggagagctg | 3180 |
| gaaaggaagg agctggagtt tgacacgaat atggatgcag tacagatggt gattacagaa | 3240 |
| gcccagaagg ttgataccag agccaagaac gctgggggtta caatccaaga cacactcaac | 3300 |
| acattagacg gcctcctgca tctgatggac cagcctctca gtgtagatga agaggggctg | 3360 |
| gtcttactgg agcagaagct ttcccgagcc aagacccaga tcaacagcca actgcggccc | 3420 |
| atgatgtcag agctggaaga gagggcacgt cagcagaggg gccacctcca tttgctggag | 3480 |
| acaagcatag atgggattct ggctgatgtg aagaacttgg agaacattag ggacaacctg | 3540 |
| cccccaggct gctacaatac ccaggctctt gagcaacagt ga | 3582 |

<210> SEQ ID NO 48
<211> LENGTH: 3582
<212> TYPE: DNA
<213> ORGANISM: Artificial Sequence
<220> FEATURE:
<223> OTHER INFORMATION: Synthetic Construct

<400> SEQUENCE: 48

| | |
|---|---|
| atgcctgctc tgtggctggg ctgctgcctg tgttttagtc tgctgctgcc agccgccaga | 60 |
| gccacatcta gaagagaagt gtgcgactgc aacggcaaga gccggcagtg catcttcgac | 120 |
| agagagctgc acagacagac cggcaacggc ttcagatgcc tgaactgcaa cgacaacacc | 180 |
| gacggcatcc actgcgagaa gtgcaagaac ggcttctacc ggcaccgcga gagggataga | 240 |
| tgcctgcctt gcaactgcaa ctccaagggc agcctgagcg ccagatgcga caatagcggc | 300 |
| agatgtagct gcaagcctgg cgtgacaggc gctagatgcg atagatgtct ccccggcttc | 360 |
| cacatgctga ccgatgccgg atgtacccag gaccagagac tgctggacag caagtgcgat | 420 |
| tgcgaccctg ccggaattgc cggaccttgt gatgccggaa gatgcgtgtg taaacctgcc | 480 |
| gtgaccggcg agagatgtga cagatgtaga agcggctact acaacctgga cggcggcaat | 540 |
| cctgaaggct gcacccagtg cttttgctac ggccacagcg ccagctgtag aagcagcgcc | 600 |
| gaatactccg tgcacaagat caccagcacc ttccaccagg atgtggacgg atggaaggcc | 660 |

```
gtgcagagaa atggctctcc tgccaagctg cagtggtccc agagacacca ggacgtgttc    720
agcagcgctc agagactgga ccccgtgtac tttgtggccc ctgccaagtt cctgggcaac    780
cagcaagtgt cttacggcca gagcctgagc ttcgactaca gagtggatag aggcggcaga    840
caccccagcg ctcacgatgt gattcttgaa ggcgccggac tgcggatcac agcccctctt    900
atgcctctgg caagaccct gccttgtggc ctgaccaaga cctacacctt ccggctgaat     960
gagcacccca gcaacaactg gtccccacag ctgagctact cgagtacag acggctgctg    1020 cggaacctga cagccctgag aatcagagcc acctacggcg agtacagcac cggctacatc    1080
gacaacgtga ccctgatcag cgccagacct gtttctggtg ctcctgctcc ttgggtcgag    1140
cagtgtatct gtcccgtggg ctacaagggc cagttctgcc aggattgtgc cagcggctac    1200
aagagagact ctgccagact gggccccttc ggcacatgca tcccttgtaa ttgtcaaggc    1260
ggcggagcct gcgatcccga tacaggcgat tgctacagcg gcgacgagaa ccccgatatc    1320
gagtgcgccg attgtcccat cggcttttac aacgaccctc acgacccag atcctgcaag    1380 ccatgtcctt gccacaatgg cttcagctgc agcgtgatgc cgaaaccga agaggtcgtg    1440 tgcaacaatt gcccaccagg cgttacaggg gccagatgtg aactgtgtgc cgacggctac    1500
ttcggcgatc cttttggaga acacggaccc gtgcgacctt gccagccttg tcagtgcaac    1560
aacaacgtgg acccaagcgc cagcggcaac tgcgatagac tgacaggcag atgtctgaag    1620
tgcatccaca ataccgccgg gatctactgt gaccagtgca aggccggcta ttttggcgac    1680
cctctggctc ccaatcctgc cgataagtgc agagcctgca actgtaaccc tatgggctct    1740
gagcctgtgg gctgcagatc tgatggaacc tgcgtgtgca gccaggctt tggcggacct    1800 aattgtgaac acggcgcctt tagctgcccc gcctgctaca atcaagtgaa gatccagatg    1860
gaccagttca tgcagcagct gcagaggatg gaagccctga tctctaaagc ccaaggcgga    1920
gatggcgtgg tgcctgatac agagctggaa ggcagaatgc agcaggccga acaggccctg    1980
caggacattc tgagagatgc ccagattagc gagggcgcct ctagaagtct gggactgcag    2040
ctggctaaag tgcggagcca agagaacagc taccagagca gactggacga cctgaagatg    2100
accgtggaaa gagtcagagc cctgggcagc cagtaccaga acagagtgcg ggataccac    2160 cggctgatca cccagatgca actgtctctg ccgagagcg aagccagcct gggcaatacc    2220
aatattcccg ccagcgacca ctacgtgggc cccaacggtt taagagcct ggctcaagag    2280 gccaccagac tggccgaaag ccatgtggaa agcgcctcca acatggaaca gctgacccgg    2340
gaaaccgagg actactctaa gcaggccctg agcctcgtca gaaagcctc gcatgaaggc    2400 gtcggcagcg gctctggatc tcctgatggt gctgtggtgc agggactcgt ggaaaagctg    2460
gaaaagacca aatctctggc ccagcagctg accagagaag ccacacaggc cgagatcgag    2520
gccgacagaa gctaccagca ctcactgagg ctgctggact ccgtgtctag actgcagggc    2580
gtgtccgacc agagcttcca ggtggaagag gccaagcgga tcaagcagaa ggccgatagc    2640
ctgagcagcc tggtcaccag acacatggac gagttcaagc ggacccagaa gaacctcggc    2700
aactggaaag aggaagccca gcaactgctg cagaacggca gtctggaag agagaagtct    2760 gaccagctgc tgagcagagc caacctggcc aagtctagag cccaagaggc cctgtctatg    2820
ggcaacgcca ccttctacga ggtggaatcc atcctgaaga acctgcgcga gttcgacctg    2880
caagtggaca acagaaaggc cgaggccgag aagccatga agagactgag ctacatcagc    2940
cagaaagtgt ccgacgcctc cgacaagaca cagcaggcag aaagagcact gggatctgcc    3000
gcagccgatg ctcagagagc taaaaacggc gctggcgagg ccctggaaat cagctctgag    3060
```

```
atcgagcaag agatcggctc cctgaatctg aagccaatg tgacagccga tggcgccctg    3120
gccatggaaa aaggactggc ctctctgaag tccgagatga gagaggtgga aggcgagctg    3180
gaacggaaag aactggaatt cgacaccaat atggacgctg tgcagatggt catcacagag    3240
gcccagaagg tggacaccag agccaaaaat gccggcgtga ccatccagga cacccctgaat   3300 actctggacg gactgctgca cctgatggat cagcctctga gcgtggacga ggaaggactg    3360
gttctgctgg aacagaagct gagccgggcc aagactcaga tcaacagcca gctgaggccc    3420
atgatgagcg aactggaaga acgggccaga cagcagaggg gccatctgca tctgctcgaa    3480
accagcatcg atggcatcct ggccgacgtg aagaatctcg agaacatccg ggacaacctg    3540
ccacctggct gctacaacac acaggcactg gaacagcagt ga                      3582
```

```
<210> SEQ ID NO 49
<211> LENGTH: 3891
<212> TYPE: DNA
<213> ORGANISM: Clostridium botulinum

<400> SEQUENCE: 49
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat atttgagag aatttattca      300 actgatcttg gaagaatgtt gttaacatca atagtaaggg gaataccatt tgggggtgga     360
agtacaatag atcagaatt aaaagttatt gatactaatt gtattaatgt gatacaacca     420
gatggtagtt atagatcaga agaacttaat ctagtaataa taggaccctc agctgatatt     480
atacagtttg aatgtaaaag ctttggacat gaagttttga atcttacgcg aaatggttat     540
ggctctactc aatacattag atttagccca gattttacat ttggttttga ggagtcactt     600
gaagttgata caaatcctct tttaggtgca ggcaaatttg ctacagatcc agcagtaaca     660
ttagcacatg aacttataca tgctggacat agattatatg gaatagcaat taatccaaat     720
agggttttta agtaaatac taatgcctat tatgaaatga gtgggttaga agtaagcttt      780
gaggaactta aacatttgg gggacatgat gcaaagttta gatagttt acaggaaaac       840 gaatttcgtc tatattatta taataagttt aaagatatag caagtacact taataaagct     900
aaatcaatag taggtactac tgcttcatta cagtatatga aaaatgtttt taaagagaaa     960
tatctcctat ctgaagatac atctggaaaa ttttcggtag ataaattaaa atttgataag    1020
ttatacaaaa tgttaacaga gatttacaca gaggataatt tgttaagtt tttttaaagta    1080 cttaacagaa aaacatatt gaatttgat aaagccgtat ttaagataaa tatagtacct    1140
aaggtaaatt acacaatata tgatggattt aatttaagaa atacaaattt agcagcaaac    1200
tttaatggtc aaaatacaga aattaataat atgaatttta ctaaactaaa aaatttact     1260 ggattgtttg aattttataa gttgctatgt gtaagaggga taataacttc taaaactaaa    1320
tcattagata aaggatacaa taaggcatta atgatttat gtatcaaagt aataattgg      1380 gacttgtttt ttagtccttc agaagataat tttactaatg atctaaataa aggagaagaa    1440
attacatctg atactaatat agaagcagca gaagaaaata ttagttaga tttaatacaa     1500 caatattatt taacctttaa ttttgataat gaaccctgaaa atatttcaat agaaaatctt    1560
```

```
tcaagtgaca ttataggcca attagaactt atgcctaata tagaaagatt tcctaatgga    1620
aaaaagtatg agttagataa atatactatg ttccattatc ttcgtgctca agaatttgaa    1680
catggtaaat ctaggattgc tttaacaaat tctgttaacg aagcattatt aaatcctagt    1740
cgtgtttata catttttttc ttcagactat gtaaagaaag ttaataaagc tacggaggca    1800
gctatgtttt taggctgggt agaacaatta gtatatgatt ttaccgatga aactagcgaa    1860
gtaagtacta cggataaaat tgcggatata actataatta ttccatatat aggacctgct    1920
ttaaatatag gtaatatgtt atataaagat gattttgtag gtgctttaat attttcagga    1980
gctgttattc tgttagaatt tataccagag attgcaatac ctgtattagg tacttttgca    2040
cttgtatcat atattgcgaa taaggttcta accgttcaaa caatagataa tgctttaagt    2100
aaaagaaatg aaaatgggga tgaggtctat aaatatatag taacaaattg gttagcaaag    2160
gttaatacac agattgatct aataagaaaa aaaatgaaag aagctttaga aaatcaagca    2220
gaagcaacaa aggctataat aaactatcag tataatcaat atactgagga agagaaaaat    2280
aatattaatt ttaatattga tgatttaagt tcgaaactta atgagtctat aaataaagct    2340
atgattaata taaataaatt tttgaatcaa tgctctgttt catatttaat gaattctatg    2400
atcccttatg gtgttaaacg gttagaagat tttgatgcta gtcttaaaga tgcattatta    2460
aagtatatat atgataatag aggaacttta attggtcaag tagatagatt aaaagataaa    2520
gttaataata cacttagtac agatatacct tttcagcttt ccaaatacgt agataatcaa    2580
agattattat ctacatttac tgaatatatt aagaatatta ttaatacttc tatattgaat    2640
ttaagatatg aaagtaatca tttaatagac ttatctaggt atgcatcaaa aataaatatt    2700
ggtagtaaag taaattttga tccaatagat aaaaatcaaa ttcaattatt taatttagaa    2760
agtagtaaaa ttgaggtaat tttaaaaaat gctattgtat ataatagtat gtatgaaaat    2820
tttagtacta gcttttggat aagaattcct aagtatttta acagtataag tctaaataat    2880
gaatatacaa taataaattg tatggaaaat aattcaggat ggaaagtatc acttaattat    2940
ggtgaaataa tctggacttt acaggatact caggaaataa aacaaagagt agtttttaaa    3000
tacagtcaaa tgattaatat atcagattat ataaacagat ggattttgt aactatcact    3060
aataatagat taaataactc taaaatttat ataaatggaa gattaataga tcaaaaacca    3120
atttcaaatt taggtaatat tcatgctagt aataatataa tgtttaaatt agatggttgt    3180
agagatacac atagatatat ttggataaaa tattttaatc tttttgataa ggaattaaat    3240
gaaaagaaa tcaagatttt atatgataat caatcaaatt caggtatttt aaaagacttt    3300
tggggtgatt atttacaata tgataaacca tactatatgt taaatttata tgatccaaat    3360
aaatatgtcg atgtaaataa tgtaggtatt agaggttata tgtatcttaa agggcctaga    3420
ggtagcgtaa tgactacaaa catttattta aattcaagtt tgtataggg gacaaaattt    3480
attataaaaa aatatgcttc tggaaataaa gataatattg ttagaaataa tgatcgtgta    3540
tatattaatg tagtagttaa aaataaagaa tataggttag ctactaatgc atcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa tatagctaaa    3780
ctagtagcaa gtaattggta taatagacaa atagaaagat ctagtaggac tttgggttgc    3840
tcatgggaat ttattcctgt agatgatgga tggggagaaa ggccactgta a             3891
```

<210> SEQ ID NO 50
<211> LENGTH: 3891
<212> TYPE: DNA
<213> ORGANISM: Artificial Sequence
<220> FEATURE:
<223> OTHER INFORMATION: Synthetic Construct

<400> SEQUENCE: 50

| | | | | | |
|---|---|---|---|---|---|
| atgcccttcg | tgaacaagca | gttcaactac | aaggaccccg | tgaacggcgt | ggacattgcc | 60 |
| tacatcaaga | tccccaacgc | cggccagatg | cagcccgtga | aggcctttaa | gatccacaac | 120 |
| aagatctggg | tcatccccga | gcgggacacc | ttcacaaatc | ccgaggaagg | cgacctgaat | 180 |
| cctccacctg | aagccaaaca | ggtgcccgtg | tcctactacg | acagcaccta | cctgagcacc | 240 |
| gacaacgaga | aggacaacta | cctgaagggc | gtgaccaagc | tgttcgagcg | gatctacagc | 300 |
| accgatctgg | gcagaatgct | gctgacctct | atcgtgcggg | catcccatt | ttggggcggc | 360 |
| agcacaatcg | acaccgagct | gaaagtgatc | gacaccaact | gcatcaacgt | gatccagcct | 420 |
| gacggcagct | acagaagcga | ggaactgaac | ctggtcatca | tcggcccag | cgccgacatc | 480 |
| atccagttcg | agtgcaagag | cttcggccac | gaggtgctga | acctgaccag | aaatggctac | 540 |
| ggcagcaccc | agtacatccg | gttcagcccc | gatttcacct | tcggcttcga | ggaatccctg | 600 |
| gaagtggaca | ccaatcctct | gctcggagcc | ggcaagtttg | ccaccgatcc | tgctgtgaca | 660 |
| ctggcccacg | aactgattca | cgccggacac | agactgtacg | aatcgccat | caatcccaac | 720 |
| cgggtgttca | agtgaacac | caacgcctac | tatgagatga | gcggactgga | agtgtccttt | 780 |
| gaggaactgc | ggaccttcgg | cggacacgac | gccaagttta | tcgacagcct | gcaagagaac | 840 |
| gagttccggc | tgtactacta | caacaagttc | aaggatatcg | ccagcacgct | gaacaaggcc | 900 |
| aagagcatcg | tgggcacaac | agccagcctg | cagtacatga | agaacgtttt | caaagagaag | 960 |
| tacctgctga | gcgaggacac | cagcggcaag | ttctccgtgg | acaagctgaa | gttcgacaag | 1020 |
| ctgtacaaga | tgctgaccga | gatctacacc | gaggacaact | cgtgaagtt | cttcaaggtg | 1080 |
| ctcaaccgca | agacctacct | caacttcgac | aaggccgtgt | tcaagatcaa | catcgtgccc | 1140 |
| aaagtcaact | acaccatcta | cgacggcttc | aacctgcgca | acaccaacct | ggccgccaac | 1200 |
| ttcaacggcc | agaacaccga | gatcaacaac | atgaacttca | ccaagctgaa | aaacttcacc | 1260 |
| ggcctgttcg | agttctataa | gctgctgtgc | gtgcgcggca | tcatcaccag | caagaccaag | 1320 |
| agcctggaca | agggctataa | caaggccctg | aacgacctgt | gcatcaaagt | aacaactgg | 1380 |
| gacctgttct | tcagccccag | cgaggataat | ttcaccaacg | acctgaacaa | aggcgaggaa | 1440 |
| atcaccagcg | acaccaatat | cgaggccgcc | gaggaaaaca | tcagcctgga | cctgatccag | 1500 |
| cagtactacc | tgaccttcaa | tttcgataac | gagcccgaga | acatcagcat | cgagaacctg | 1560 |
| agcagcgata | tcatcggaca | gctggaactg | atgcccaaca | tcgagagatt | ccccaacggc | 1620 |
| aagaagtacg | agctggacaa | gtacaccatg | ttccactacc | tgcgggccca | agagttcgag | 1680 |
| cacggcaagt | ctagaatcgc | cctgaccaac | agcgtgaacg | aggccctgct | gaaccccagc | 1740 |
| agagtgtaca | ccttcttcag | cagcgactac | gtgaagaaag | tcaacaaggc | tacagaggcc | 1800 |
| gccatgttcc | tcggctgggt | tgagcagctg | gtgtacgact | tcaccgacga | gacaagcgag | 1860 |
| gtgtccacca | ccgacaagat | cgccgatatc | accatcatca | tcccttacat | cggccctgct | 1920 |
| ctgaacatcg | gcaacatgct | gtataaggac | gatttcgtgg | gcgccctgat | cttctctggc | 1980 |
| gccgtgattc | tgctcgagtt | catccctgag | atcgctatcc | ccgtgctggg | gcacatttgct | 2040 |
| ctggtgtctt | atatcgccaa | caaggtgctg | acagtgcaga | ccatcgacaa | cgccctgagc | 2100 |

```
aagcggaacg agaagtggga cgaagtgtac aagtacatcg tgaccaactg gctggccaaa    2160
gtgaataccc agatcgacct gattcggaag aagatgaagg aagccctcga gaaccaggcc    2220
gaggccacaa aggccatcat caactaccag tacaatcagt acacagagga agagaagaac    2280
aacatcaatt tcaacatcga cgacctgtcc tccaagctca acgagagcat caacaaagcc    2340
atgatcaata tcaacaagtt tctgaaccag tgcagcgtca gctacctgat gaacagcatg    2400
atcccctacg gcgtgaagcg gctggaagat ttcgatgcca gcctgaagga cgctctgctg    2460
aagtacatct acgataaccg gggcaccctg atcggccagt ggacagact gaaggacaaa    2520 gtgaacaata ccctgtccac cgacattccg tttcagctga gcaaatacgt ggacaaccag    2580
agactgctga gcacattcac cgagtatatc aagaatatca tcaacacctc catcctgaac    2640
ctccgctacg agagcaacca cctgatcgat ctgagcagat acgccagcaa gatcaatatt    2700
ggctctaaag tgaacttcga cccgatcgac aagaaccaga tccagctgtt caatctcgag    2760
tctagcaaga tcgaagtgat cctgaagaac gccatcgtgt acaactctat gtacgagaac    2820
ttctccacca gcttttggat cagaatcccc aagtacttca cagcatctc cctgaacaac    2880 gagtacacga tcatcaattg catggaaaac aactccggct ggaaagtgtc cctgaactac    2940
ggcgagatca tctggacact gcaggacacc caagagatca agcagagagt ggtgttcaag    3000
tactctcaga tgatcaacat tagcgactac atcaaccggt ggatcttcgt gaccatcacc    3060
aacaaccggc tgaacaactc caagatctac atcaatggcc ggctcatcga ccagaagcct    3120
atcagcaacc tgggaaacat ccacgcctcc aacaatatca tgttcaagct ggacggctgc    3180
cgggacaccc accggtatat ctggatcaag tactttaacc tgttcgacaa agagctgaac    3240
gagaaagaga ttaaggacct gtacgacaac cagtccaaca gcggcatcct gaaggatttc    3300
tggggcgact acctgcagta tgacaagccc tactacatgc tgaatctgta cgaccccaac    3360
aaatatgtgg acgtgaacaa cgtggggatc agaggctaca tgtacctgaa aggccccaga    3420
ggcagcgtga tgaccaccaa catctacctg aactccagcc tgtacagagg caccaagttc    3480
atcatcaaga gtatgcctc cggcaacaag acaacattg tgcggaacaa cgaccgggtg    3540
tacattaacg tggtggtcaa gaacaaagag taccggctgg ccaccaatgc ctctcaggca    3600
ggcgtggaaa agatcctgag cgccctggaa atccccgacg tgggcaatct gtctcaggtg    3660
gtcgtgatga gtccaagaa cgaccagggc atcacaaaca gtgcaagat gaacctccag    3720 gacaacaacg gcaacgacat cggctttatc ggcttccacc agtttaacaa cattgccaag    3780
ctggtcgcca gcaactggta caaccggcag atcgagagaa gcagcagaac cctgggctgc    3840
agctgggagt ttatccctgt ggatgatggc tggggcgaaa gacccctgta a           3891
```

<210> SEQ ID NO 51
<211> LENGTH: 3876
<212> TYPE: DNA
<213> ORGANISM: Clostridium botulinum

<400> SEQUENCE: 51

```
atgccagtta caataaataa ttttaattat aatgatccta ttgataataa taatattatt      60
atgatggagc tccatttgc gagaggtacg gggagatatt ataaagcttt taaaatcaca     120
gatcgtattt ggataatacc ggaaagatat acttttggat ataaacctga ggattttaat     180
aaaagttccg gtatttttaa tagagatgtt tgtgaatatt atgatccaga ttacttaaat     240
actaatgata aaaagaatat attttttacaa acaatgatca agttatttaa tagaatcaaa     300
tcaaaaccat tgggtgaaaa gttattagag atgattataa atggtatacc ttatcttgga     360
```

-continued

```
gatagacgtg ttccactcga agagtttaac acaaacattg ctagtgtaac tgttaataaa       420
ttaatcagta atccaggaga agtggagcga aaaaaaggta ttttcgcaaa tttaataata       480
tttggacctg ggccagtttt aaatgaaaat gagactatag ataggtat acaaaatcat         540 tttgcatcaa gggaaggctt cggggtata atgcaaatga agttttgccc agaatatgta        600
agcgtattta ataatgttca agaaaacaaa ggcgcaagta tatttaatag acgtggatat       660
ttttcagatc cagccttgat attaatgcat gaacttatac atgttttaca tggattatat      720
ggcattaaag tagatgattt accaattgta ccaaatgaaa aaaattttt tatgcaatct        780 acagatgcta tacaggcaga agaactatat acatttggag acaagatcc cagcatcata       840 actccttcta cggataaaag tatctatgat aaagttttgc aaaattttag agggatagtt      900
gatagactta acaaggtttt agtttgcata tcagatccta acattaatat taatatatat      960
aaaaataaat ttaagataa atataaattc gttgaagatt ctgagggaaa atatagtata      1020
gatgtagaaa gttttgataa attatataaa agcttaatgt ttggttttac agaaactaat     1080
atagcagaaa attataaaat aaaaactaga gcttcttatt ttagtgattc cttaccacca     1140
gtaaaaataa aaaatttatt agataatgaa atctatacta tagaggaagg gtttaatata    1200
tctgataaag atatggaaaa agaatataga ggtcagaata aagctataaa taaacaagct     1260
tatgaagaaa ttagcaagga gcatttggct gtatataaga tacaaatgtg taaaagtgtt     1320
aaagctccag gaatatgtat tgatgttgat aatgaagatt tgttctttat agctgataaa     1380
aatagttttt cagatgattt atctaaaaac gaaagaatag aatataatac acagagtaat    1440
tatatagaaa atgacttccc tataaatgaa ttaattttag atactgattt aataagtaaa     1500
atagaattac caagtgaaaa tacagaatca cttactgatt ttaatgtaga tgttccagta     1560
tatgaaaaac aacccgctat aaaaaaaatt tttacagatg aaaataccat cttttcaatat    1620 ttatactctc agacatttcc tctagatata agagatataa gtttaacatc ttcatttgat    1680
gatgcattat tattttctaa caaagtttat tcatttttt ctatggatta tattaaaact     1740
gctaataaag tggtagaagc aggattattt gcaggttggg tgaaacagat agtaaatgat    1800
tttgtaatcg aagctaataa aagcaatact atggataaaa ttgcagatat atctctaatt    1860
gttccttata taggattagc tttaaatgta ggaaatgaaa cagctaaagg aaattttgaa    1920
aatgcttttg agattgcagg agccagtatt ctactagaat ttataccaga acttttaata    1980
cctgtagttg gagcctttt attagaatca tatattgaca ataaaaataa aattattaaa    2040
acaatagata atgctttaac taaaagaaat gaaaaatgga gtgatatgta cggattaata   2100
gtagcgcaat ggctctcaac agttaatact caattttata caataaaaga gggaatgtat    2160
aaggctttaa attatcaagc acaagcattg gaagaaataa taaatacag atataatata    2220 tattctgaaa aagaaaagtc aaatattaac atcgatttta atgatataaa ttctaaactt    2280
aatgagggta ttaaccaagc tatagataat ataaataatt ttataaatgg atgttctgta    2340
tcatatttaa tgaaaaaat gattccatta gctgtagaaa aattactaga ctttgataat    2400
actctcaaaa aaaatttgtt aaattatata gatgaaaata aattatattt gattggaagt    2460
gcagaatatg aaaaatcaaa agtaaataaa tacttgaaaa ccattatgcc gtttgatctt    2520
tcaatatata ccaatgatac aatactaata gaaatgttta ataaatataa tagcgaaatt    2580
ttaataataa ttatcttaaa tttaagatat aaggataata atttaataga tttatcagga    2640 tatgggggcaa aggtagaggt atatgatgga gtcgagctta atgataaaaa tcaatttaaa    2700
```

```
ttaactagtt cagcaaatag taagattaga gtgactcaaa atcagaatat catatttaat   2760
agtgtgttcc ttgattttag cgttagcttt tggataagaa tacctaaata taagaatgat   2820
ggtatacaaa attatattca taatgaatat acaataatta attgtatgaa aaataattcg   2880
ggctggaaaa tatctattag gggtaatagg ataaatgga ctttaattga tataaatgga    2940
aaaaccaaat cggtatttttt tgaatataac ataagagaag atatatcaga gtatataaat  3000
agatggtttt ttgtaactat tactaataat ttgaataacg ctaaaattta tattaatggt   3060
aagctagaat caaatacaga tattaaagat ataagagaag ttattgctaa tggtgaaata   3120
atatttaaat tagatggtga tatagataga acacaattta tttggatgaa atatttcagt   3180
atttttaata cggaattaag tcaatcaaat attgaagaaa gatataaaat tcaatcatat   3240
agcgaatatt taaagatttt tggggaaaat cctttaatgt acaataaaga atattatatg   3300
tttaatgcgg ggaataaaaa ttcatatatt aaactaaaga aagattcacc tgtaggtgaa   3360
attttaacac gtagcaaata taatcaaaat tctaaatata taattatag agatttatat    3420 attggagaaa aatttattat aagaagaaag tcaaattctc aatctataaa tgatgatata   3480
gttagaaaag aagattatat atatctagat tttttttaatt taaatcaaga gtggagagta  3540
tatacctata aatattttaa gaaagaggaa gaaaaattgt ttttagctcc tataagtgat   3600
tctgatgagt tttacaatac tatacaaata aaagaatatg atgaacagcc aacatatagt   3660
tgtcagttgc ttttttaaaaa agatgaagaa agtactgatg ataggatt gattggtatt    3720 catcgtttct acgaatctgg aattgtattt gaagagtata agattatttt ttgtataagt   3780
aaatggtact taaagagagt aaaaaggaaa ccatataatt taaaattggg atgtaattgg   3840
cagtttattc ctaaagatga agggtggact gaataa                             3876
```

<210> SEQ ID NO 52
<211> LENGTH: 3876
<212> TYPE: DNA
<213> ORGANISM: Artificial Sequence
<220> FEATURE:
<223> OTHER INFORMATION: Synthetic Construct

<400> SEQUENCE: 52

```
atgcccgtga ccatcaacaa cttcaactac aacgacccca tcgacaacaa caacatcatt    60
atgatggaac cgccttcgc cagaggcaca ggccggtact acaaggcctt caagatcacc    120
gaccggatct ggatcatccc cgagagatac accttcggct acaagcccga ggacttcaac   180
aagagcagcg gcatcttcaa ccgggacgtg tgcgagtact acgaccccga ctacctgaac   240
accaacgaca agaagaacat cttcctgcag accatgatca agctgttcaa ccggatcaag   300
agcaagcccc tggcgagaa gctgctggaa atgatcatca cggcatccc ttacctgggc     360 gacagaagag tgcccctgga agagttcaac accaatatcg ccagcgtgac cgtgaacaag   420
ctgatctcta cccccggcga ggtggaacgg aagaagggca tcttcgccaa cctgatcatc   480
ttcggccctg gacctgtgct gaacgagaac gagacaatcg catcggcat ccagaaccac    540 ttcgccagca gagaaggctt cggcggcatc atgcagatga gttctgcccc gagtacgtg    600 tccgtgttca acaacgtgca agagaacaag ggcgccagca tctttaacag acggggctac   660
ttcagcgacc ccgctctgat tctgatgcac gagctgatcc acgtgctgca cggcctgtat   720
ggcatcaagg tggacgacct gcctatcgtg cccaacgaga gaaattctt catgcagtcc   780 accgacgcca tccaggccga ggaactgtac acatttggcg acaggaccc cagcatcatc   840 accctagca ccgacaagag catctacgac aaggtgctgc agaatttccg gggcatcgtg    900
```

```
gaccggctga acaaagtgct cgtgtgcatc agcgatccca acatcaatat caacatctac    960
aagaacaagt tcaaggataa gtacaagttc gtcgaggaca gcgagggcaa gtacagcatc   1020
gacgtggaaa gcttcgacaa gctgtacaag agcctgatgt tcggcttcac cgagacaaat   1080
atcgccgaga actacaagat caagacccgg gccagctact tctccgactc tctgcctcct   1140
gtgaagatta agaacctgct ggacaacgag atctacacca tcgaggaagg cttcaacatc   1200
agcgacaagg acatggaaaa agagtaccgg ggccagaaca aggccattaa caagcaggcc   1260
tacgaggaaa tcagcaaaga acacctggcc gtgtacaaga ttcagatgtg caagagcgtg   1320
aaggcccctg catctgcat tgacgtggac aatgaggacc tgttctttat cgccgacaag   1380
aacagcttta gcgacgacct gagcaagaac gagcggatcg agtacaacac ccagagcaac   1440
tacatcgaga acgacttccc catcaacgaa ctgatcctgg acaccgacct gatcagcaag   1500
atcgagctgc cagcgagaa caccgagagc ctgaccgact caatgtgga cgtgcccgtg   1560
tacgagaagc agcccgccat caagaagatc tttaccgacg agaataccat cttccagtac   1620
ctgtacagcc agacctttcc tctggacatc cgggacatca gcctgacctc cagcttcgat   1680
gatgccctgc tgttcagcaa caaggtctac agcttcttca gcatggacta catcaagacc   1740
gccaacaagg tggtggaagc cggcctgttt gccggctggg ttaagcagat cgtgaacgat   1800
ttcgtgatcg aggccaacaa gtccaacacc atggacaaga tcgccgatat ctccctgatc   1860
gtgcccctaca tcggactggc cctgaacgtg ggaaacgaga cagccaaggg caacttcgag   1920
aatgccttcg agattgccgg cgctagcatc ctgctcgagt tcatccctga gctgctgatc   1980
cctgtcgtgg gcgcttttct gctggaatcc tacatcgata caaaaacaa gatcatcaag   2040
acgatcgaca cgccctgac caagcggaac gagaagtgga gcgatatgta cggactgatc   2100
gtggcccagt ggctgagcac cgtgaatacc cagtttttaca ccatcaaaga agggatgtac   2160
aaggccctga attaccaggc tcaggctctg gaagagatca ttaagtaccg ctacaatatc   2220
tacagcgaga aagagaagtc taacatcaac atcgacttca cgacatcaa cagcaagctc   2280
aacgagggca tcaaccaggc cattgacaac attaacaact ttatcaacgg ctgcagcgtg   2340
tcctacctga tgaagaagat gattcctctg gccgtggaaa agctgctcga cttcgacaat   2400
accctgaaga gaacctcct gaactacatt gacgagaaca agctctacct gatcggcagc   2460
gccgagtacg agaaaagcaa agtgaacaag tacctcaaga ccatcatgcc cttcgacctg   2520
tccatctaca caaacgacac catcctgatc gagatgttta acaagtacaa cagcgagatc   2580
ctgaacaata tcatcctgaa cctgcggtac aaggacaaca atctgatcga tctgagcggc   2640
tacggcgcca aggtggaagt gtatgatggc gtggaactga acgataagaa tcagttcaag   2700
ctgaccagca gcgccaactc caagatcaga gtgacccaga accagaacat tatcttcaac   2760
agcgtgttcc tggacttctc cgtgtccttc tggatcagaa tccccaagta caagaacgac   2820
ggcattcaga actacatcca caacgagtac acaatcatca ctgtatgaa gaacaacagc   2880
ggctggaaga tcagcatccg gggcaacaga atcatctgga ccctgatcga catcaatggc   2940
aagacaaaga gcgtgttctt cgagtataac atccgcgagg acatctccga gtacatcaac   3000
cggtggttct tcgtgacaat caccaacaac ctgaacaacg ccaagatcta catcaacggg   3060
aagctcgaga gcaacaccga catcaaggat atccgggaag tgatcgccaa cggcgagatc   3120
atctttaagc tggacggcga catcgaccgg acacagttca tctggatgaa gtactttccc   3180
atcttcaata ccgagctgag ccagagcaat atcgaagaga ggtacaagat ccagtcttac   3240
```

```
agcgagtacc tgaaggactt ctggggcaac cctctgatgt caacaaaga atattacatg    3300 ttcaacgccg gcaacaagaa ctcttacatc aagctgaaga agacagccc cgtgggagaa    3360 atcctgacca ggtctaagta caaccagaac tccaagtata tcaactaccg ggacctgtac   3420
atcggcgaga agttcatcat ccggcgcaag agcaacagcc agtccatcaa tgacgacatc   3480
gtgcggaaag aggactatat ctacctcgac ttcttcaacc tcaatcaaga gtggcgcgtg   3540
tacacctaca gtactttaa gaaagaggaa gagaagctgt tcctggctcc tatcagcgac    3600
tccgacgagt tctacaatac catccagatc aaagagtacg acgagcagcc cacctacagc   3660
tgccagctgc tgtttaagaa ggacgaggaa tccaccgatg gatcggcct gattggcatc    3720 caccggttct acgagagcgg catcgtgttc gaagagtaca aggattactt ctgcatcagc   3780
aagtggtatc tgaaagaagt gaagcggaag ccctacaatc tgaagctggg ctgcaactgg   3840
cagtttatcc ccaaggacga aggctggacc gagtga                            3876
```

<210> SEQ ID NO 53
<211> LENGTH: 2477
<212> TYPE: PRT
<213> ORGANISM: Homo sapiens

<400> SEQUENCE: 53

```
Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
```

```
                260                 265                 270
His Thr Ser Val Gln Thr Thr Ser Ser Gly Ser Gly Pro Phe Thr Asp
            275                 280                 285
Val Arg Ala Ala Val Tyr Gln Pro Gln Pro His Pro Gln Pro Pro Pro
        290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
            340                 345                 350
Gly Asn Ser Asn Gly Glu Pro Cys Val Leu Pro Phe Thr Tyr Asn Gly
        355                 360                 365
Arg Thr Phe Tyr Ser Cys Thr Thr Glu Gly Arg Gln Asp Gly His Leu
        370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
            420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
        450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
            500                 505                 510
Gln Leu Arg Asp Gln Cys Ile Val Asp Asp Ile Thr Tyr Asn Val Asn
        515                 520                 525
Asp Thr Phe His Lys Arg His Glu Glu Gly His Met Leu Asn Cys Thr
        530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
        595                 600                 605
Ser Gly Pro Val Glu Val Phe Ile Thr Glu Thr Pro Ser Gln Pro Asn
        610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
        675                 680                 685
```

-continued

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln Ile
1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
        1075                1080                1085

Ser Ser Ile Pro Pro Tyr Asn Thr Glu Val Thr Glu Thr Thr Ile Val
            1090                1095                1100

```
Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
        1125                1130                1135

Ser Ile Val Val Ser Gly Leu Thr Pro Gly Val Glu Tyr Val Tyr Thr
        1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
        1205                1210                1215

Gln Gly Asn Ser Leu Glu Glu Val Val His Ala Asp Gln Ser Ser Cys
        1220                1225                1230

Thr Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile Ile
        1250                1255                1260

Pro Glu Val Pro Gln Leu Thr Asp Leu Ser Phe Val Asp Ile Thr Asp
1265                1270                1275                1280

Ser Ser Ile Gly Leu Arg Trp Thr Pro Leu Asn Ser Ser Thr Ile Ile
        1285                1290                1295

Gly Tyr Arg Ile Thr Val Val Ala Ala Gly Glu Gly Ile Pro Ile Phe
        1300                1305                1310

Glu Asp Phe Val Asp Ser Ser Val Gly Tyr Tyr Thr Val Thr Gly Leu
        1315                1320                1325

Glu Pro Gly Ile Asp Tyr Asp Ile Ser Val Ile Thr Leu Ile Asn Gly
        1330                1335                1340

Gly Glu Ser Ala Pro Thr Thr Leu Thr Gln Gln Thr Ala Val Pro Pro
1345                1350                1355                1360

Pro Thr Asp Leu Arg Phe Thr Asn Ile Gly Pro Asp Thr Met Arg Val
        1365                1370                1375

Thr Trp Ala Pro Pro Pro Ser Ile Asp Leu Thr Asn Phe Leu Val Arg
        1380                1385                1390

Tyr Ser Pro Val Lys Asn Glu Glu Asp Val Ala Glu Leu Ser Ile Ser
        1395                1400                1405

Pro Ser Asp Asn Ala Val Val Leu Thr Asn Leu Leu Pro Gly Thr Glu
        1410                1415                1420

Tyr Val Val Ser Val Ser Ser Val Tyr Glu Gln His Glu Ser Thr Pro
1425                1430                1435                1440

Leu Arg Gly Arg Gln Lys Thr Gly Leu Asp Ser Pro Thr Gly Ile Asp
        1445                1450                1455

Phe Ser Asp Ile Thr Ala Asn Ser Phe Thr Val His Trp Ile Ala Pro
        1460                1465                1470

Arg Ala Thr Ile Thr Gly Tyr Arg Ile Arg His His Pro Glu His Phe
        1475                1480                1485

Ser Gly Arg Pro Arg Glu Asp Arg Val Pro His Ser Arg Asn Ser Ile
        1490                1495                1500

Thr Leu Thr Asn Leu Thr Pro Gly Thr Glu Tyr Val Val Ser Ile Val
1505                1510                1515                1520

Ala Leu Asn Gly Arg Glu Glu Ser Pro Leu Leu Ile Gly Gln Gln Ser
```

```
                    1525              1530              1535

Thr Val Ser Asp Val Pro Arg Asp Leu Glu Val Val Ala Ala Thr Pro
            1540              1545              1550

Thr Ser Leu Leu Ile Ser Trp Asp Ala Pro Ala Val Thr Val Arg Tyr
        1555              1560              1565

Tyr Arg Ile Thr Tyr Gly Glu Thr Gly Gly Asn Ser Pro Val Gln Glu
    1570              1575              1580

Phe Thr Val Pro Gly Ser Lys Ser Thr Ala Thr Ile Ser Gly Leu Lys
1585              1590              1595              1600

Pro Gly Val Asp Tyr Thr Ile Thr Val Tyr Ala Val Thr Gly Arg Gly
                1605              1610              1615

Asp Ser Pro Ala Ser Ser Lys Pro Ile Ser Ile Asn Tyr Arg Thr Glu
            1620              1625              1630

Ile Asp Lys Pro Ser Gln Met Gln Val Thr Asp Val Gln Asp Asn Ser
        1635              1640              1645

Ile Ser Val Lys Trp Leu Pro Ser Ser Pro Val Thr Gly Tyr Arg
    1650              1655              1660

Val Thr Thr Thr Pro Lys Asn Gly Pro Gly Pro Thr Lys Thr Lys Thr
1665              1670              1675              1680

Ala Gly Pro Asp Gln Thr Glu Met Thr Ile Glu Gly Leu Gln Pro Thr
                1685              1690              1695

Val Glu Tyr Val Val Ser Val Tyr Ala Gln Asn Pro Ser Gly Glu Ser
            1700              1705              1710

Gln Pro Leu Val Gln Thr Ala Val Thr Asn Ile Asp Arg Pro Lys Gly
        1715              1720              1725

Leu Ala Phe Thr Asp Val Asp Val Asp Ser Ile Lys Ile Ala Trp Glu
    1730              1735              1740

Ser Pro Gln Gly Gln Val Ser Arg Tyr Arg Val Thr Tyr Ser Ser Pro
1745              1750              1755              1760

Glu Asp Gly Ile His Glu Leu Phe Pro Ala Pro Asp Gly Glu Glu Asp
                1765              1770              1775

Thr Ala Glu Leu Gln Gly Leu Arg Pro Gly Ser Glu Tyr Thr Val Ser
            1780              1785              1790

Val Val Ala Leu His Asp Asp Met Glu Ser Gln Pro Leu Ile Gly Thr
        1795              1800              1805

Gln Ser Thr Ala Ile Pro Ala Pro Thr Asp Leu Lys Phe Thr Gln Val
    1810              1815              1820

Thr Pro Thr Ser Leu Ser Ala Gln Trp Thr Pro Pro Asn Val Gln Leu
1825              1830              1835              1840

Thr Gly Tyr Arg Val Arg Val Thr Pro Lys Glu Lys Thr Gly Pro Met
                1845              1850              1855

Lys Glu Ile Asn Leu Ala Pro Asp Ser Ser Ser Val Val Val Ser Gly
            1860              1865              1870

Leu Met Val Ala Thr Lys Tyr Glu Val Ser Val Tyr Ala Leu Lys Asp
        1875              1880              1885

Thr Leu Thr Ser Arg Pro Ala Gln Gly Val Val Thr Thr Leu Glu Asn
    1890              1895              1900

Val Ser Pro Pro Arg Arg Ala Arg Val Thr Asp Ala Thr Glu Thr Thr
1905              1910              1915              1920

Ile Thr Ile Ser Trp Arg Thr Lys Thr Glu Thr Ile Thr Gly Phe Gln
                1925              1930              1935

Val Asp Ala Val Pro Ala Asn Gly Gln Thr Pro Ile Gln Arg Thr Ile
            1940              1945              1950
```

```
Lys Pro Asp Val Arg Ser Tyr Thr Ile Thr Gly Leu Gln Pro Gly Thr
            1955                1960                1965

Asp Tyr Lys Ile Tyr Leu Tyr Thr Leu Asn Asp Asn Ala Arg Ser Ser
        1970                1975                1980

Pro Val Val Ile Asp Ala Ser Thr Ala Ile Asp Ala Pro Ser Asn Leu
1985                1990                1995                2000

Arg Phe Leu Ala Thr Thr Pro Asn Ser Leu Leu Val Ser Trp Gln Pro
            2005                2010                2015

Pro Arg Ala Arg Ile Thr Gly Tyr Ile Ile Lys Tyr Glu Lys Pro Gly
            2020                2025                2030

Ser Pro Pro Arg Glu Val Val Pro Arg Pro Arg Pro Gly Val Thr Glu
            2035                2040                2045

Ala Thr Ile Thr Gly Leu Glu Pro Gly Thr Glu Tyr Thr Ile Tyr Val
            2050                2055                2060

Ile Ala Leu Lys Asn Asn Gln Lys Ser Glu Pro Leu Ile Gly Arg Lys
2065                2070                2075                2080

Lys Thr Asp Glu Leu Pro Gln Leu Val Thr Leu Pro His Pro Asn Leu
            2085                2090                2095

His Gly Pro Glu Ile Leu Asp Val Pro Ser Thr Val Gln Lys Thr Pro
            2100                2105                2110

Phe Val Thr His Pro Gly Tyr Asp Thr Gly Asn Gly Ile Gln Leu Pro
            2115                2120                2125

Gly Thr Ser Gly Gln Gln Pro Ser Val Gly Gln Gln Met Ile Phe Glu
            2130                2135                2140

Glu His Gly Phe Arg Arg Thr Thr Pro Pro Thr Thr Ala Thr Pro Ile
2145                2150                2155                2160

Arg His Arg Pro Arg Pro Tyr Pro Pro Asn Val Gly Glu Glu Ile Gln
            2165                2170                2175

Ile Gly His Ile Pro Arg Glu Asp Val Asp Tyr His Leu Tyr Pro His
            2180                2185                2190

Gly Pro Gly Leu Asn Pro Asn Ala Ser Thr Gly Gln Glu Ala Leu Ser
            2195                2200                2205

Gln Thr Thr Ile Ser Trp Ala Pro Phe Gln Asp Thr Ser Glu Tyr Ile
            2210                2215                2220

Ile Ser Cys His Pro Val Gly Thr Asp Glu Glu Pro Leu Gln Phe Arg
2225                2230                2235                2240

Val Pro Gly Thr Ser Thr Ser Ala Thr Leu Thr Gly Leu Thr Arg Gly
            2245                2250                2255

Ala Thr Tyr Asn Ile Ile Val Glu Ala Leu Lys Asp Gln Gln Arg His
            2260                2265                2270

Lys Val Arg Glu Glu Val Val Thr Val Gly Asn Ser Val Asn Glu Gly
            2275                2280                2285

Leu Asn Gln Pro Thr Asp Asp Ser Cys Phe Asp Pro Tyr Thr Val Ser
            2290                2295                2300

His Tyr Ala Val Gly Asp Glu Trp Glu Arg Met Ser Glu Ser Gly Phe
2305                2310                2315                2320

Lys Leu Leu Cys Gln Cys Leu Gly Phe Gly Ser Gly His Phe Arg Cys
            2325                2330                2335

Asp Ser Ser Arg Trp Cys His Asp Asn Gly Val Asn Tyr Lys Ile Gly
            2340                2345                2350

Glu Lys Trp Asp Arg Gln Gly Glu Asn Gly Gln Met Met Ser Cys Thr
            2355                2360                2365
```

Cys Leu Gly Asn Gly Lys Gly Glu Phe Lys Cys Asp Pro His Glu Ala
         2370            2375                2380

Thr Cys Tyr Asp Asp Gly Lys Thr Tyr His Val Gly Glu Gln Trp Gln
2385            2390            2395                2400

Lys Glu Tyr Leu Gly Ala Ile Cys Ser Cys Thr Cys Phe Gly Gly Gln
             2405            2410            2415

Arg Gly Trp Arg Cys Asp Asn Cys Arg Arg Pro Gly Gly Glu Pro Ser
         2420            2425            2430

Pro Glu Gly Thr Thr Gly Gln Ser Tyr Asn Gln Tyr Ser Gln Arg Tyr
         2435            2440            2445

His Gln Arg Thr Asn Thr Asn Val Asn Cys Pro Ile Glu Cys Phe Met
     2450            2455            2460

Pro Leu Asp Val Gln Ala Asp Arg Glu Asp Ser Arg Glu
2465            2470            2475

<210> SEQ ID NO 54
<211> LENGTH: 786
<212> TYPE: PRT
<213> ORGANISM: Homo sapiens

<400> SEQUENCE: 54

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
             20                  25                  30

Ile Pro Gly Gly Val Pro Gly Gly Val Phe Tyr Pro Gly Ala Gly Leu
         35                  40                  45

Gly Ala Leu Gly Gly Gly Ala Leu Gly Pro Gly Gly Lys Pro Leu Lys
     50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
             85                  90                  95

Ala Asp Ala Ala Ala Ala Tyr Lys Ala Ala Lys Ala Gly Ala Gly Leu
         100                 105                 110

Gly Gly Val Pro Gly Val Gly Gly Leu Gly Val Ser Ala Gly Ala Val
     115                 120                 125

Val Pro Gln Pro Gly Ala Gly Val Lys Pro Gly Lys Val Pro Gly Val
130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
             165                 170                 175

Pro Lys Ala Pro Gly Val Gly Gly Ala Phe Ala Gly Ile Pro Gly Val
         180                 185                 190

Gly Pro Phe Gly Gly Pro Gln Pro Gly Val Pro Leu Gly Tyr Pro Ile
     195                 200                 205

Lys Ala Pro Lys Leu Pro Gly Gly Tyr Gly Leu Pro Tyr Thr Thr Gly
210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
             245                 250                 255

Ala Ala Ala Ala Lys Ala Ala Ala Lys Phe Gly Ala Gly Ala Ala Gly
         260                 265                 270

-continued

```
Val Leu Pro Gly Val Gly Gly Ala Gly Val Pro Gly Val Pro Gly Ala
            275                 280                 285
Ile Pro Gly Ile Gly Gly Ile Ala Gly Val Gly Thr Pro Ala Ala Ala
290                 295                 300
Ala Ala Ala Ala Ala Ala Lys Ala Ala Lys Tyr Gly Ala Ala Ala
305                 310                 315                 320
Gly Leu Val Pro Gly Gly Pro Gly Phe Gly Pro Gly Val Val Gly Val
                325                 330                 335
Pro Gly Ala Gly Val Pro Gly Val Gly Val Pro Gly Ala Gly Ile Pro
            340                 345                 350
Val Val Pro Gly Ala Gly Ile Pro Gly Ala Ala Val Pro Gly Val Val
            355                 360                 365
Ser Pro Glu Ala Ala Ala Lys Ala Ala Ala Lys Ala Ala Lys Tyr Gly
370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Ile Pro Gly
                405                 410                 415
Val Ala Gly Val Pro Gly Val Gly Val Pro Gly Val Gly Gly Val
            420                 425                 430
Pro Gly Val Gly Ile Ser Pro Glu Ala Gln Ala Ala Ala Ala Lys
            435                 440                 445
Ala Ala Lys Tyr Gly Ala Ala Gly Ala Gly Val Leu Gly Gly Leu Val
            450                 455                 460
Pro Gly Ala Pro Gly Ala Val Pro Gly Val Pro Gly Thr Gly Gly Val
465                 470                 475                 480
Pro Gly Val Gly Thr Pro Ala Ala Ala Ala Lys Ala Ala Ala Lys
                485                 490                 495
Ala Ala Gln Phe Gly Leu Val Pro Gly Val Gly Val Ala Pro Gly Val
                500                 505                 510
Gly Val Ala Pro Gly Val Gly Val Ala Pro Gly Val Gly Leu Ala Pro
            515                 520                 525
Gly Val Gly Val Ala Pro Gly Val Gly Val Ala Pro Gly Val Gly Val
            530                 535                 540
Ala Pro Gly Ile Gly Pro Gly Gly Val Ala Ala Ala Lys Ser Ala
545                 550                 555                 560
Ala Lys Val Ala Ala Lys Ala Gln Leu Arg Ala Ala Gly Leu Gly
                565                 570                 575
Ala Gly Ile Pro Gly Leu Gly Val Gly Val Gly Val Pro Gly Leu Gly
            580                 585                 590
Val Gly Ala Gly Val Pro Gly Leu Gly Val Gly Ala Gly Val Pro Gly
            595                 600                 605
Phe Gly Ala Gly Ala Asp Glu Gly Val Arg Arg Ser Leu Ser Pro Glu
            610                 615                 620
Leu Arg Glu Gly Asp Pro Ser Ser Ser Gln His Leu Pro Ser Thr Pro
625                 630                 635                 640
Ser Ser Pro Arg Val Pro Gly Ala Leu Ala Ala Lys Ala Ala Lys
                645                 650                 655
Tyr Gly Ala Ala Val Pro Gly Val Leu Gly Gly Leu Gly Ala Leu Gly
                660                 665                 670
Gly Val Gly Ile Pro Gly Gly Val Val Gly Ala Gly Pro Ala Ala Ala
            675                 680                 685
```

```
Ala Ala Ala Lys Ala Ala Ala Lys Ala Ala Gln Phe Gly Leu Val
    690             695             700

Gly Ala Ala Gly Leu Gly Gly Leu Gly Val Gly Gly Leu Gly Val Pro
705             710             715             720

Gly Val Gly Gly Leu Gly Gly Ile Pro Pro Ala Ala Ala Lys Ala
                725             730             735

Ala Lys Tyr Gly Ala Ala Gly Leu Gly Gly Val Leu Gly Gly Ala Gly
            740             745             750

Gln Phe Pro Leu Gly Gly Val Ala Arg Pro Gly Phe Gly Leu Ser
        755             760             765

Pro Ile Phe Pro Gly Gly Ala Cys Leu Gly Lys Ala Cys Gly Arg Lys
770             775             780

Arg Lys
785

<210> SEQ ID NO 55
<211> LENGTH: 338
<212> TYPE: PRT
<213> ORGANISM: Homo sapiens

<400> SEQUENCE: 55

Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
            20                  25                  30

Ser Ser Pro Asn Cys Ala Pro Glu Cys Asn Cys Pro Glu Ser Tyr Pro
        35                  40                  45

Ser Ala Met Tyr Cys Asp Glu Leu Lys Leu Lys Ser Val Pro Met Val
50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
            100                 105                 110

Ser Lys Leu Lys Gln Leu Lys Lys Leu His Ile Asn His Asn Asn Leu
        115                 120                 125

Thr Glu Ser Val Gly Pro Leu Pro Lys Ser Leu Glu Asp Leu Gln Leu
130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270
```

```
Asn Glu Asn Leu Glu Asn Tyr Tyr Leu Glu Val Asn Gln Leu Glu Lys
            275                 280                 285

Phe Asp Ile Lys Ser Phe Cys Lys Ile Leu Gly Pro Leu Ser Tyr Ser
    290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn

<210> SEQ ID NO 56
<211> LENGTH: 478
<212> TYPE: PRT
<213> ORGANISM: Homo sapiens

<400> SEQUENCE: 56

Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
    50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Ala Pro Ala Pro Glu Val Gly
        115                 120                 125

Ala Ser Lys Pro Glu Gly Ile Asp Ser Arg Pro Glu Thr Leu His Pro
    130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
    210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300
```

```
Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
                340                 345                 350

Arg Ile Tyr Ile Ser Gly Met Ala Pro Arg Pro Ser Leu Ala Lys Lys
                355                 360                 365

Gln Arg Phe Arg His Arg Asn Arg Lys Gly Tyr Arg Ser Gln Arg Gly
                370                 375                 380

His Ser Arg Gly Arg Asn Gln Asn Ser Arg Pro Ser Arg Ala Thr
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
                420                 425                 430

Ile Gln Ser Val Phe Phe Ser Gly Asp Lys Tyr Tyr Arg Val Asn
                435                 440                 445

Leu Arg Thr Arg Arg Val Asp Thr Val Asp Pro Pro Tyr Pro Arg Ser
450                 455                 460

Ile Ala Gln Tyr Trp Leu Gly Cys Pro Ala Pro Gly His Leu
465                 470                 475

<210> SEQ ID NO 57
<211> LENGTH: 1724
<212> TYPE: PRT
<213> ORGANISM: Homo sapiens

<400> SEQUENCE: 57

Met Pro Pro Ala Val Arg Arg Ser Ala Cys Ser Met Gly Trp Leu Trp
1               5                   10                  15

Ile Phe Gly Ala Ala Leu Gly Gln Cys Leu Gly Tyr Ser Ser Gln Gln
                20                  25                  30

Gln Arg Val Pro Phe Leu Gln Pro Pro Gly Gln Ser Gln Leu Gln Ala
                35                  40                  45

Ser Tyr Val Glu Phe Arg Pro Ser Gln Gly Cys Ser Pro Gly Tyr Tyr
            50                  55                  60

Arg Asp His Lys Gly Leu Tyr Thr Gly Arg Cys Val Pro Cys Asn Cys
65                  70                  75                  80

Asn Gly His Ser Asn Gln Cys Gln Asp Gly Ser Gly Ile Cys Val Asn
                85                  90                  95

Cys Gln His Asn Thr Ala Gly Glu His Cys Glu Arg Cys Gln Glu Gly
                100                 105                 110

Tyr Tyr Gly Asn Ala Val His Gly Ser Cys Arg Ala Cys Pro Cys Pro
                115                 120                 125

His Thr Asn Ser Phe Ala Thr Gly Cys Val Val Asn Gly Gly Asp Val
            130                 135                 140

Arg Cys Ser Cys Lys Ala Gly Tyr Thr Gly Thr Gln Cys Glu Arg Cys
145                 150                 155                 160

Ala Pro Gly Tyr Phe Gly Asn Pro Gln Lys Phe Gly Gly Ser Cys Gln
                165                 170                 175

Pro Cys Ser Cys Asn Ser Asn Gly Gln Leu Gly Ser Cys His Pro Leu
                180                 185                 190

Thr Gly Asp Cys Ile Asn Gln Glu Pro Lys Asp Ser Ser Pro Ala Glu
```

```
            195                 200                 205
Glu Cys Asp Asp Cys Asp Ser Cys Val Met Thr Leu Leu Asn Asp Leu
210                 215                 220

Ala Thr Met Gly Glu Gln Leu Arg Leu Val Lys Ser Gln Leu Gln Gly
225                 230                 235                 240

Leu Ser Ala Ser Ala Gly Leu Leu Glu Gln Met Arg His Met Glu Thr
                245                 250                 255

Gln Ala Lys Asp Leu Arg Asn Gln Leu Leu Asn Tyr Arg Ser Ala Ile
            260                 265                 270

Ser Asn His Gly Ser Lys Ile Glu Gly Leu Glu Arg Glu Leu Thr Asp
        275                 280                 285

Leu Asn Gln Glu Phe Glu Thr Leu Gln Glu Lys Ala Gln Val Asn Ser
290                 295                 300

Arg Lys Ala Gln Thr Leu Asn Asn Asn Val Asn Arg Ala Thr Gln Ser
305                 310                 315                 320

Ala Lys Glu Leu Asp Val Lys Ile Lys Asn Val Ile Arg Asn Val His
                325                 330                 335

Ile Leu Leu Lys Gln Ile Ser Gly Thr Asp Gly Glu Gly Asn Asn Val
            340                 345                 350

Pro Ser Gly Asp Phe Ser Arg Glu Trp Ala Glu Ala Gln Arg Met Met
        355                 360                 365

Arg Glu Leu Arg Asn Arg Asn Phe Gly Lys His Leu Arg Glu Ala Glu
370                 375                 380

Ala Asp Lys Arg Glu Ser Gln Leu Leu Leu Asn Arg Ile Arg Thr Trp
385                 390                 395                 400

Gln Lys Thr His Gln Gly Glu Asn Asn Gly Leu Ala Asn Ser Ile Arg
                405                 410                 415

Asp Ser Leu Asn Glu Tyr Glu Ala Lys Leu Ser Asp Leu Arg Ala Arg
            420                 425                 430

Leu Gln Glu Ala Ala Gln Ala Lys Gln Ala Asn Gly Leu Asn Gln
        435                 440                 445

Glu Asn Glu Arg Ala Leu Gly Ala Ile Gln Arg Gln Val Lys Glu Ile
450                 455                 460

Asn Ser Leu Gln Ser Asp Phe Thr Lys Tyr Leu Thr Thr Ala Asp Ser
465                 470                 475                 480

Ser Leu Leu Gln Thr Asn Ile Ala Leu Gln Leu Met Glu Lys Ser Gln
                485                 490                 495

Lys Glu Tyr Glu Lys Leu Ala Ala Ser Leu Asn Glu Ala Arg Gln Glu
            500                 505                 510

Leu Ser Asp Lys Val Arg Glu Leu Ser Arg Ser Ala Gly Lys Thr Ser
        515                 520                 525

Leu Val Glu Glu Ala Glu Lys His Ala Arg Ser Leu Gln Glu Leu Ala
530                 535                 540

Lys Gln Leu Glu Glu Ile Lys Arg Asn Ala Ser Gly Asp Glu Leu Val
545                 550                 555                 560

Arg Cys Ala Val Asp Ala Ala Thr Ala Tyr Glu Asn Ile Leu Asn Ala
                565                 570                 575

Ile Lys Ala Ala Glu Asp Ala Ala Asn Arg Ala Ala Ser Ala Ser Glu
            580                 585                 590

Ser Ala Leu Gln Thr Val Ile Lys Glu Asp Leu Pro Arg Lys Ala Lys
        595                 600                 605

Thr Leu Ser Ser Asn Ser Asp Lys Leu Leu Asn Glu Ala Lys Met Thr
610                 615                 620
```

```
Gln Lys Lys Leu Lys Gln Glu Val Ser Pro Ala Leu Asn Asn Leu Gln
625                 630                 635                 640

Gln Thr Leu Asn Ile Val Thr Val Gln Lys Glu Val Ile Asp Thr Asn
            645                 650                 655

Leu Thr Thr Leu Arg Asp Gly Leu His Gly Ile Gln Arg Gly Asp Ile
        660                 665                 670

Asp Ala Met Ile Ser Ser Ala Lys Ser Met Val Arg Lys Ala Asn Asp
        675                 680                 685

Ile Thr Asp Glu Val Leu Asp Gly Leu Asn Pro Ile Gln Thr Asp Val
    690                 695                 700

Glu Arg Ile Lys Asp Thr Tyr Gly Arg Thr Gln Asn Glu Asp Phe Lys
705                 710                 715                 720

Lys Ala Leu Thr Asp Ala Asp Asn Ser Val Asn Lys Leu Thr Asn Lys
            725                 730                 735

Leu Pro Asp Leu Trp Arg Lys Ile Glu Ser Ile Asn Gln Gln Leu Leu
        740                 745                 750

Pro Leu Gly Asn Ile Ser Asp Asn Met Asp Arg Ile Arg Glu Leu Ile
        755                 760                 765

Gln Gln Ala Arg Asp Ala Ala Ser Lys Val Ala Val Pro Met Arg Phe
770                 775                 780

Asn Gly Lys Ser Gly Val Glu Val Arg Leu Pro Asn Asp Leu Glu Asp
785                 790                 795                 800

Leu Lys Gly Tyr Thr Ser Leu Ser Leu Phe Leu Gln Arg Pro Asn Ser
            805                 810                 815

Arg Glu Asn Gly Gly Thr Glu Asn Met Phe Val Met Tyr Leu Gly Asn
        820                 825                 830

Lys Asp Ala Ser Arg Asp Tyr Ile Gly Met Ala Val Val Asp Gly Gln
        835                 840                 845

Leu Thr Cys Val Tyr Asn Leu Gly Asp Arg Glu Ala Glu Leu Gln Val
    850                 855                 860

Asp Gln Ile Leu Thr Lys Ser Glu Thr Lys Glu Ala Val Met Asp Arg
865                 870                 875                 880

Val Lys Phe Gln Arg Ile Tyr Gln Phe Ala Arg Leu Asn Tyr Thr Lys
            885                 890                 895

Gly Ala Thr Ser Ser Lys Pro Glu Thr Pro Gly Val Tyr Asp Met Asp
        900                 905                 910

Gly Arg Asn Ser Asn Thr Leu Leu Asn Leu Asp Pro Glu Asn Val Val
        915                 920                 925

Phe Tyr Val Gly Gly Tyr Pro Pro Asp Phe Lys Leu Pro Ser Arg Leu
    930                 935                 940

Ser Phe Pro Pro Tyr Lys Gly Cys Ile Glu Leu Asp Asp Leu Asn Glu
945                 950                 955                 960

Asn Val Leu Ser Leu Tyr Asn Phe Lys Lys Thr Phe Asn Leu Asn Thr
            965                 970                 975

Thr Glu Val Glu Pro Cys Arg Arg Lys Glu Ser Asp Lys Asn
        980                 985                 990

Tyr Phe Glu Gly Thr Gly Tyr Ala Arg Val Pro Thr Gln Pro His Ala
    995                 1000                1005

Pro Ile Pro Thr Phe Gly Gln Thr Ile Gln Thr Thr Val Asp Arg Gly
        1010                1015                1020

Leu Leu Phe Phe Ala Glu Asn Gly Asp Arg Phe Ile Ser Leu Asn Ile
1025                1030                1035                1040
```

-continued

```
Glu Asp Gly Lys Leu Met Val Arg Tyr Lys Leu Asn Ser Glu Leu Pro
                1045                1050                1055

Lys Glu Arg Gly Val Gly Asp Ala Ile Asn Asn Gly Arg Asp His Ser
            1060                1065                1070

Ile Gln Ile Lys Ile Gly Lys Leu Gln Lys Arg Met Trp Ile Asn Val
        1075                1080                1085

Asp Val Gln Asn Thr Ile Ile Asp Gly Glu Val Phe Asp Phe Ser Thr
    1090                1095                1100

Tyr Tyr Leu Gly Gly Ile Pro Ile Ala Ile Arg Glu Arg Phe Asn Ile
1105                1110                1115                1120

Ser Thr Pro Ala Phe Arg Gly Cys Met Lys Asn Leu Lys Lys Thr Ser
                1125                1130                1135

Gly Val Val Arg Leu Asn Asp Thr Val Gly Val Thr Lys Lys Cys Ser
            1140                1145                1150

Glu Asp Trp Lys Leu Val Arg Ser Ala Ser Phe Ser Arg Gly Gly Gln
        1155                1160                1165

Leu Ser Phe Thr Asp Leu Gly Leu Pro Pro Thr Asp His Leu Gln Ala
    1170                1175                1180

Ser Phe Gly Phe Gln Thr Phe Gln Pro Ser Gly Ile Leu Leu Asp His
1185                1190                1195                1200

Gln Thr Trp Thr Arg Asn Leu Gln Val Thr Leu Glu Asp Gly Tyr Ile
                1205                1210                1215

Glu Leu Ser Thr Ser Asp Ser Gly Gly Pro Ile Phe Lys Ser Pro Gln
            1220                1225                1230

Thr Tyr Met Asp Gly Leu Leu His Tyr Val Ser Val Ile Ser Asp Asn
        1235                1240                1245

Ser Gly Leu Arg Leu Leu Ile Asp Asp Gln Leu Leu Arg Asn Ser Lys
    1250                1255                1260

Arg Leu Lys His Ile Ser Ser Arg Gln Ser Leu Arg Leu Gly Gly
1265                1270                1275                1280

Ser Asn Phe Glu Gly Cys Ile Ser Asn Val Phe Val Gln Arg Leu Ser
                1285                1290                1295

Leu Ser Pro Glu Val Leu Asp Leu Thr Ser Asn Ser Leu Lys Arg Asp
            1300                1305                1310

Val Ser Leu Gly Gly Cys Ser Leu Asn Lys Pro Pro Phe Leu Met Leu
        1315                1320                1325

Leu Lys Gly Ser Thr Arg Phe Asn Lys Thr Lys Thr Phe Arg Ile Asn
    1330                1335                1340

Gln Leu Leu Gln Asp Thr Pro Val Ala Ser Pro Arg Ser Val Lys Val
1345                1350                1355                1360

Trp Gln Asp Ala Cys Ser Pro Leu Pro Lys Thr Gln Ala Asn His Gly
                1365                1370                1375

Ala Leu Gln Phe Gly Asp Ile Pro Thr Ser His Leu Leu Phe Lys Leu
            1380                1385                1390

Pro Gln Glu Leu Leu Lys Pro Arg Ser Gln Phe Ala Val Asp Met Gln
        1395                1400                1405

Thr Thr Ser Ser Arg Gly Leu Val Phe His Thr Gly Thr Lys Asn Ser
    1410                1415                1420

Phe Met Ala Leu Tyr Leu Ser Lys Gly Arg Leu Val Phe Ala Leu Gly
1425                1430                1435                1440

Thr Asp Gly Lys Lys Leu Arg Ile Lys Ser Lys Glu Lys Cys Asn Asp
                1445                1450                1455

Gly Lys Trp His Thr Val Val Phe Gly His Asp Gly Glu Lys Gly Arg
```

```
                    1460                1465                 1470
Leu Val Val Asp Gly Leu Arg Ala Arg Glu Gly Ser Leu Pro Gly Asn
            1475                1480                1485
Ser Thr Ile Ser Ile Arg Ala Pro Val Tyr Leu Gly Ser Pro Pro Ser
        1490                1495                1500
Gly Lys Pro Lys Ser Leu Pro Thr Asn Ser Phe Val Gly Cys Leu Lys
1505                1510                1515                1520
Asn Phe Gln Leu Asp Ser Lys Pro Leu Tyr Thr Pro Ser Ser Ser Phe
                1525                1530                1535
Gly Val Ser Ser Cys Leu Gly Gly Pro Leu Glu Lys Gly Ile Tyr Phe
            1540                1545                1550
Ser Glu Glu Gly Gly His Val Val Leu Ala His Ser Val Leu Leu Gly
        1555                1560                1565
Pro Glu Phe Lys Leu Val Phe Ser Ile Arg Pro Arg Ser Leu Thr Gly
    1570                1575                1580
Ile Leu Ile His Ile Gly Ser Gln Pro Gly Lys His Leu Cys Val Tyr
1585                1590                1595                1600
Leu Glu Ala Gly Lys Val Thr Ala Ser Met Asp Ser Gly Ala Gly Gly
                1605                1610                1615
Thr Ser Thr Ser Val Thr Pro Lys Gln Ser Leu Cys Asp Gly Gln Trp
            1620                1625                1630
His Ser Val Ala Val Thr Ile Lys Gln His Ile Leu His Leu Glu Leu
        1635                1640                1645
Asp Thr Asp Ser Ser Tyr Thr Ala Gly Gln Ile Pro Phe Pro Pro Ala
    1650                1655                1660
Ser Thr Gln Glu Pro Leu His Leu Gly Gly Ala Pro Ala Asn Leu Thr
1665                1670                1675                1680
Thr Leu Arg Ile Pro Val Trp Lys Ser Phe Phe Gly Cys Leu Arg Asn
                1685                1690                1695
Ile His Val Asn His Ile Pro Val Pro Val Thr Glu Ala Leu Glu Val
            1700                1705                1710
Gln Gly Pro Val Ser Leu Asn Gly Cys Pro Asp Gln
        1715                1720

<210> SEQ ID NO 58
<211> LENGTH: 1172
<212> TYPE: PRT
<213> ORGANISM: Homo sapiens

<400> SEQUENCE: 58

Met Arg Pro Phe Phe Leu Leu Cys Phe Ala Leu Pro Gly Leu Leu His
1               5                   10                  15
Ala Gln Gln Ala Cys Ser Arg Gly Ala Cys Tyr Pro Pro Val Gly Asp
                20                  25                  30
Leu Leu Val Gly Arg Thr Arg Phe Leu Arg Ala Ser Ser Thr Cys Gly
            35                  40                  45
Leu Thr Lys Pro Glu Thr Tyr Cys Thr Gln Tyr Gly Glu Trp Gln Met
        50                  55                  60
Lys Cys Cys Lys Cys Asp Ser Arg Gln Pro His Asn Tyr Tyr Ser His
65                  70                  75                  80
Arg Val Glu Asn Val Ala Ser Ser Gly Pro Met Arg Trp Trp Gln
                85                  90                  95
Ser Gln Asn Asp Val Asn Pro Val Ser Leu Gln Leu Asp Leu Asp Arg
            100                 105                 110
```

```
Arg Phe Gln Leu Gln Glu Val Met Met Glu Phe Gln Gly Pro Met Pro
            115                 120                 125

Ala Gly Met Leu Ile Glu Arg Ser Ser Asp Phe Gly Lys Thr Trp Arg
        130                 135                 140

Val Tyr Gln Tyr Leu Ala Ala Asp Cys Thr Ser Thr Phe Pro Arg Val
145                 150                 155                 160

Arg Gln Gly Arg Pro Gln Ser Trp Gln Asp Val Arg Cys Gln Ser Leu
                165                 170                 175

Pro Gln Arg Pro Asn Ala Arg Leu Asn Gly Gly Lys Val Gln Leu Asn
            180                 185                 190

Leu Met Asp Leu Val Ser Gly Ile Pro Ala Thr Gln Ser Gln Lys Ile
        195                 200                 205

Gln Glu Val Gly Glu Ile Thr Asn Leu Arg Val Asn Phe Thr Arg Leu
210                 215                 220

Ala Pro Val Pro Gln Arg Gly Tyr His Pro Ser Ala Tyr Tyr Ala
225                 230                 235                 240

Val Ser Gln Leu Arg Leu Gln Gly Ser Cys Phe Cys His Gly His Ala
                245                 250                 255

Asp Arg Cys Ala Pro Lys Pro Gly Ala Ser Ala Gly Pro Ser Thr Ala
            260                 265                 270

Val Gln Val His Asp Val Cys Val Cys Gln His Asn Thr Ala Gly Pro
        275                 280                 285

Asn Cys Glu Arg Cys Ala Pro Phe Tyr Asn Asn Arg Pro Trp Arg Pro
290                 295                 300

Ala Glu Gly Gln Asp Ala His Glu Cys Gln Arg Cys Asp Cys Asn Gly
305                 310                 315                 320

His Ser Glu Thr Cys His Phe Asp Pro Ala Val Phe Ala Ala Ser Gln
                325                 330                 335

Gly Ala Tyr Gly Gly Val Cys Asp Asn Cys Arg Asp His Thr Glu Gly
            340                 345                 350

Lys Asn Cys Glu Arg Cys Gln Leu His Tyr Phe Arg Asn Arg Arg Pro
        355                 360                 365

Gly Ala Ser Ile Gln Glu Thr Cys Ile Ser Cys Glu Cys Asp Pro Asp
370                 375                 380

Gly Ala Val Pro Gly Ala Pro Cys Asp Pro Val Thr Gly Gln Cys Val
385                 390                 395                 400

Cys Lys Glu His Val Gln Gly Glu Arg Cys Asp Leu Cys Lys Pro Gly
                405                 410                 415

Phe Thr Gly Leu Thr Tyr Ala Asn Pro Gln Gly Cys His Arg Cys Asp
            420                 425                 430

Cys Asn Ile Leu Gly Ser Arg Arg Asp Met Pro Cys Asp Glu Glu Ser
        435                 440                 445

Gly Arg Cys Leu Cys Leu Pro Asn Val Val Gly Pro Lys Cys Asp Gln
450                 455                 460

Cys Ala Pro Tyr His Trp Lys Leu Ala Ser Gly Gln Gly Cys Glu Pro
465                 470                 475                 480

Cys Ala Cys Asp Pro His Asn Ser Leu Ser Pro Gln Cys Asn Gln Phe
                485                 490                 495

Thr Gly Gln Cys Pro Cys Arg Glu Gly Phe Gly Gly Leu Met Cys Ser
            500                 505                 510

Ala Ala Ala Ile Arg Gln Cys Pro Asp Arg Thr Tyr Gly Asp Val Ala
        515                 520                 525

Thr Gly Cys Arg Ala Cys Asp Cys Asp Phe Arg Gly Thr Glu Gly Pro
```

-continued

```
            530                 535                 540
Gly Cys Asp Lys Ala Ser Gly Arg Cys Leu Cys Arg Pro Gly Leu Thr
545                 550                 555                 560

Gly Pro Arg Cys Asp Gln Cys Gln Arg Gly Tyr Cys Asn Arg Tyr Pro
                565                 570                 575

Val Cys Val Ala Cys His Pro Cys Phe Gln Thr Tyr Asp Ala Asp Leu
                580                 585                 590

Arg Glu Gln Ala Leu Arg Phe Gly Arg Leu Arg Asn Ala Thr Ala Ser
                595                 600                 605

Leu Trp Ser Gly Pro Gly Leu Glu Asp Arg Gly Leu Ala Ser Arg Ile
                610                 615                 620

Leu Asp Ala Lys Ser Lys Ile Glu Gln Ile Arg Ala Val Leu Ser Ser
625                 630                 635                 640

Pro Ala Val Thr Glu Gln Glu Val Ala Gln Val Ala Ser Ala Ile Leu
                645                 650                 655

Ser Leu Arg Arg Thr Leu Gln Gly Leu Gln Leu Asp Leu Pro Leu Glu
                660                 665                 670

Glu Glu Thr Leu Ser Leu Pro Arg Asp Leu Glu Ser Leu Asp Arg Ser
                675                 680                 685

Phe Asn Gly Leu Leu Thr Met Tyr Gln Arg Lys Arg Glu Gln Phe Glu
                690                 695                 700

Lys Ile Ser Ser Ala Asp Pro Ser Gly Ala Phe Arg Met Leu Ser Thr
705                 710                 715                 720

Ala Tyr Glu Gln Ser Ala Gln Ala Ala Gln Val Ser Asp Ser Ser
                725                 730                 735

Arg Leu Leu Asp Gln Leu Arg Asp Ser Arg Arg Glu Ala Glu Arg Leu
                740                 745                 750

Val Arg Gln Ala Gly Gly Gly Gly Thr Gly Ser Pro Lys Leu Val
                755                 760                 765

Ala Leu Arg Leu Glu Met Ser Ser Leu Pro Asp Leu Thr Pro Thr Phe
                770                 775                 780

Asn Lys Leu Cys Gly Asn Ser Arg Gln Met Ala Cys Thr Pro Ile Ser
785                 790                 795                 800

Cys Pro Gly Glu Leu Cys Pro Gln Asp Asn Gly Thr Ala Cys Gly Ser
                805                 810                 815

Arg Cys Arg Gly Val Leu Pro Arg Ala Gly Ala Phe Leu Met Ala
                820                 825                 830

Gly Gln Val Ala Glu Gln Leu Arg Gly Phe Asn Ala Gln Leu Gln Arg
                835                 840                 845

Thr Arg Gln Met Ile Arg Ala Ala Glu Glu Ser Ala Ser Gln Ile Gln
                850                 855                 860

Ser Ser Ala Gln Arg Leu Glu Thr Gln Val Ser Ala Arg Ser Gln
865                 870                 875                 880

Met Glu Glu Asp Val Arg Arg Thr Arg Leu Leu Ile Gln Gln Val Arg
                885                 890                 895

Asp Phe Leu Thr Asp Pro Asp Thr Asp Ala Ala Thr Ile Gln Glu Val
                900                 905                 910

Ser Glu Ala Val Leu Ala Leu Trp Leu Pro Thr Asp Ser Ala Thr Val
                915                 920                 925

Leu Gln Lys Met Asn Glu Ile Gln Ala Ile Ala Ala Arg Leu Pro Asn
                930                 935                 940

Val Asp Leu Val Leu Ser Gln Thr Lys Gln Asp Ile Ala Arg Ala Arg
945                 950                 955                 960
```

```
Arg Leu Gln Ala Glu Ala Glu Ala Arg Ser Arg Ala His Ala Val
            965                 970                 975

Glu Gly Gln Val Glu Asp Val Val Gly Asn Leu Arg Gln Gly Thr Val
                980                 985                 990

Ala Leu Gln Glu Ala Gln Asp Thr Met Gln Gly Thr Ser Arg Ser Leu
            995                1000                1005

Arg Leu Ile Gln Asp Arg Val Ala Glu Val Gln Gln Val Leu Arg Pro
           1010                1015                1020

Ala Glu Lys Leu Val Thr Ser Met Thr Lys Gln Leu Gly Asp Phe Trp
1025                1030                1035                1040

Thr Arg Met Glu Glu Leu Arg His Gln Ala Arg Gln Gln Gly Ala Glu
           1045                1050                1055

Ala Val Gln Ala Gln Gln Leu Ala Glu Gly Ala Ser Glu Gln Ala Leu
           1060                1065                1070

Ser Ala Gln Glu Gly Phe Glu Arg Ile Lys Gln Lys Tyr Ala Glu Leu
           1075                1080                1085

Lys Asp Arg Leu Gly Gln Ser Ser Met Leu Gly Glu Gln Gly Ala Arg
           1090                1095                1100

Ile Gln Ser Val Lys Thr Glu Ala Glu Glu Leu Phe Gly Glu Thr Met
1105                1110                1115                1120

Glu Met Met Asp Arg Met Lys Asp Met Glu Leu Glu Leu Leu Arg Gly
           1125                1130                1135

Ser Gln Ala Ile Met Leu Arg Ser Ala Asp Leu Thr Gly Leu Glu Lys
           1140                1145                1150

Arg Val Glu Gln Ile Arg Asp His Ile Asn Gly Arg Val Leu Tyr Tyr
           1155                1160                1165

Ala Thr Cys Lys
           1170

<210> SEQ ID NO 59
<211> LENGTH: 1193
<212> TYPE: PRT
<213> ORGANISM: Homo sapiens

<400> SEQUENCE: 59

Met Pro Ala Leu Trp Leu Gly Cys Cys Leu Cys Phe Ser Leu Leu Leu
1               5                  10                  15

Pro Ala Ala Arg Ala Thr Ser Arg Arg Glu Val Cys Asp Cys Asn Gly
                20                  25                  30

Lys Ser Arg Gln Cys Ile Phe Asp Arg Glu Leu His Arg Gln Thr Gly
            35                  40                  45

Asn Gly Phe Arg Cys Leu Asn Cys Asn Asp Asn Thr Asp Gly Ile His
        50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
                100                 105                 110

Cys Asp Arg Cys Leu Pro Gly Phe His Met Leu Thr Asp Ala Gly Cys
            115                 120                 125

Thr Gln Asp Gln Arg Leu Leu Asp Ser Lys Cys Asp Cys Asp Pro Ala
        130                 135                 140

Gly Ile Ala Gly Pro Cys Asp Ala Gly Arg Cys Val Cys Lys Pro Ala
```

```
         145                 150                 155                 160
Val Thr Gly Glu Arg Cys Asp Arg Cys Arg Ser Gly Tyr Tyr Asn Leu
                    165                 170                 175
Asp Gly Gly Asn Pro Glu Gly Cys Thr Gln Cys Phe Cys Tyr Gly His
                    180                 185                 190
Ser Ala Ser Cys Arg Ser Ser Ala Glu Tyr Ser Val His Lys Ile Thr
                    195                 200                 205
Ser Thr Phe His Gln Asp Val Asp Gly Trp Lys Ala Val Gln Arg Asn
                    210                 215                 220
Gly Ser Pro Ala Lys Leu Gln Trp Ser Gln Arg His Gln Asp Val Phe
225                 230                 235                 240
Ser Ser Ala Gln Arg Leu Asp Pro Val Tyr Phe Val Ala Pro Ala Lys
                    245                 250                 255
Phe Leu Gly Asn Gln Gln Val Ser Tyr Gly Gln Ser Leu Ser Phe Asp
                    260                 265                 270
Tyr Arg Val Asp Arg Gly Gly Arg His Pro Ser Ala His Asp Val Ile
                    275                 280                 285
Leu Glu Gly Ala Gly Leu Arg Ile Thr Ala Pro Leu Met Pro Leu Gly
                    290                 295                 300
Lys Thr Leu Pro Cys Gly Leu Thr Lys Thr Tyr Thr Phe Arg Leu Asn
305                 310                 315                 320
Glu His Pro Ser Asn Asn Trp Ser Pro Gln Leu Ser Tyr Phe Glu Tyr
                    325                 330                 335
Arg Arg Leu Leu Arg Asn Leu Thr Ala Leu Arg Ile Arg Ala Thr Tyr
                    340                 345                 350
Gly Glu Tyr Ser Thr Gly Tyr Ile Asp Asn Val Thr Leu Ile Ser Ala
                    355                 360                 365
Arg Pro Val Ser Gly Ala Pro Ala Pro Trp Val Glu Gln Cys Ile Cys
                    370                 375                 380
Pro Val Gly Tyr Lys Gly Gln Phe Cys Gln Asp Cys Ala Ser Gly Tyr
385                 390                 395                 400
Lys Arg Asp Ser Ala Arg Leu Gly Pro Phe Gly Thr Cys Ile Pro Cys
                    405                 410                 415
Asn Cys Gln Gly Gly Ala Cys Asp Pro Asp Thr Gly Asp Cys Tyr
                    420                 425                 430
Ser Gly Asp Glu Asn Pro Asp Ile Glu Cys Ala Asp Cys Pro Ile Gly
                    435                 440                 445
Phe Tyr Asn Asp Pro His Asp Pro Arg Ser Cys Lys Pro Cys Pro Cys
                    450                 455                 460
His Asn Gly Phe Ser Cys Ser Val Met Pro Glu Thr Glu Glu Val Val
465                 470                 475                 480
Cys Asn Asn Cys Pro Pro Gly Val Thr Gly Ala Arg Cys Glu Leu Cys
                    485                 490                 495
Ala Asp Gly Tyr Phe Gly Asp Pro Phe Gly Glu His Gly Pro Val Arg
                    500                 505                 510
Pro Cys Gln Pro Cys Gln Cys Asn Asn Asn Val Asp Pro Ser Ala Ser
                    515                 520                 525
Gly Asn Cys Asp Arg Leu Thr Gly Arg Cys Leu Lys Cys Ile His Asn
                    530                 535                 540
Thr Ala Gly Ile Tyr Cys Asp Gln Cys Lys Ala Gly Tyr Phe Gly Asp
545                 550                 555                 560
Pro Leu Ala Pro Asn Pro Ala Asp Lys Cys Arg Ala Cys Asn Cys Asn
                    565                 570                 575
```

-continued

```
Pro Met Gly Ser Glu Pro Val Gly Cys Arg Ser Asp Gly Thr Cys Val
            580                 585                 590
Cys Lys Pro Gly Phe Gly Gly Pro Asn Cys Glu His Gly Ala Phe Ser
        595                 600                 605
Cys Pro Ala Cys Tyr Asn Gln Val Lys Ile Gln Met Asp Gln Phe Met
    610                 615                 620
Gln Gln Leu Gln Arg Met Glu Ala Leu Ile Ser Lys Ala Gln Gly Gly
625                 630                 635                 640
Asp Gly Val Val Pro Asp Thr Glu Leu Glu Gly Arg Met Gln Gln Ala
            645                 650                 655
Glu Gln Ala Leu Gln Asp Ile Leu Arg Asp Ala Gln Ile Ser Glu Gly
        660                 665                 670
Ala Ser Arg Ser Leu Gly Leu Gln Leu Ala Lys Val Arg Ser Gln Glu
    675                 680                 685
Asn Ser Tyr Gln Ser Arg Leu Asp Asp Leu Lys Met Thr Val Glu Arg
        690                 695                 700
Val Arg Ala Leu Gly Ser Gln Tyr Gln Asn Arg Val Arg Asp Thr His
705                 710                 715                 720
Arg Leu Ile Thr Gln Met Gln Leu Ser Leu Ala Glu Ser Glu Ala Ser
            725                 730                 735
Leu Gly Asn Thr Asn Ile Pro Ala Ser Asp His Tyr Val Gly Pro Asn
        740                 745                 750
Gly Phe Lys Ser Leu Ala Gln Glu Ala Thr Arg Leu Ala Glu Ser His
    755                 760                 765
Val Glu Ser Ala Ser Asn Met Glu Gln Leu Thr Arg Glu Thr Glu Asp
770                 775                 780
Tyr Ser Lys Gln Ala Leu Ser Leu Val Arg Lys Ala Leu His Glu Gly
785                 790                 795                 800
Val Gly Ser Gly Ser Gly Ser Pro Asp Gly Ala Val Val Gln Gly Leu
            805                 810                 815
Val Glu Lys Leu Glu Lys Thr Lys Ser Leu Ala Gln Gln Leu Thr Arg
        820                 825                 830
Glu Ala Thr Gln Ala Glu Ile Glu Ala Asp Arg Ser Tyr Gln His Ser
    835                 840                 845
Leu Arg Leu Leu Asp Ser Val Ser Arg Leu Gln Gly Val Ser Asp Gln
850                 855                 860
Ser Phe Gln Val Glu Glu Ala Lys Arg Ile Lys Gln Lys Ala Asp Ser
865                 870                 875                 880
Leu Ser Ser Leu Val Thr Arg His Met Asp Glu Phe Lys Arg Thr Gln
            885                 890                 895
Lys Asn Leu Gly Asn Trp Lys Glu Glu Ala Gln Gln Leu Leu Gln Asn
        900                 905                 910
Gly Lys Ser Gly Arg Glu Lys Ser Asp Gln Leu Leu Ser Arg Ala Asn
    915                 920                 925
Leu Ala Lys Ser Arg Ala Gln Glu Ala Leu Ser Met Gly Asn Ala Thr
930                 935                 940
Phe Tyr Glu Val Glu Ser Ile Leu Lys Asn Leu Arg Glu Phe Asp Leu
945                 950                 955                 960
Gln Val Asp Asn Arg Lys Ala Glu Ala Glu Glu Ala Met Lys Arg Leu
            965                 970                 975
Ser Tyr Ile Ser Gln Lys Val Ser Asp Ala Ser Asp Lys Thr Gln Gln
        980                 985                 990
```

```
Ala Glu Arg Ala Leu Gly Ser Ala Ala Ala Asp Ala Gln Arg Ala Lys
            995                 1000                1005

Asn Gly Ala Gly Glu Ala Leu Glu Ile Ser Ser Glu Ile Glu Gln Glu
        1010                1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
            1045                1050                1055

Glu Gly Glu Leu Glu Arg Lys Glu Leu Glu Phe Asp Thr Asn Met Asp
        1060                1065                1070

Ala Val Gln Met Val Ile Thr Glu Ala Gln Lys Val Asp Thr Arg Ala
        1075                1080                1085

Lys Asn Ala Gly Val Thr Ile Gln Asp Thr Leu Asn Thr Leu Asp Gly
        1090                1095                1100

Leu Leu His Leu Met Asp Gln Pro Leu Ser Val Asp Glu Glu Gly Leu
1105                1110                1115                1120

Val Leu Leu Glu Gln Lys Leu Ser Arg Ala Lys Thr Gln Ile Asn Ser
            1125                1130                1135

Gln Leu Arg Pro Met Met Ser Glu Leu Glu Glu Arg Ala Arg Gln Gln
            1140                1145                1150

Arg Gly His Leu His Leu Leu Glu Thr Ser Ile Asp Gly Ile Leu Ala
            1155                1160                1165

Asp Val Lys Asn Leu Glu Asn Ile Arg Asp Asn Leu Pro Pro Gly Cys
        1170                1175                1180

Tyr Asn Thr Gln Ala Leu Glu Gln Gln
1185                1190

<210> SEQ ID NO 60
<211> LENGTH: 1296
<212> TYPE: PRT
<213> ORGANISM: Clostridium botulinum

<400> SEQUENCE: 60

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175
```

-continued

```
Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
            485                 490                 495

Asp Leu Ile Gln Gln Tyr Tyr Leu Thr Phe Asn Phe Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
            580                 585                 590
```

-continued

```
Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
```

```
                       1010                1015                1020
Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
        1060                1065                1070

Asn Leu Phe Asp Lys Glu Leu Asn Glu Lys Glu Ile Lys Asp Leu Tyr
            1075                1080                1085

Asp Asn Gln Ser Asn Ser Gly Ile Leu Lys Asp Phe Trp Gly Asp Tyr
        1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
        1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 61
<211> LENGTH: 1291
<212> TYPE: PRT
<213> ORGANISM: Clostridium botulinum

<400> SEQUENCE: 61

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95
```

-continued

```
Asn Arg Ile Lys Ser Lys Pro Leu Gly Glu Lys Leu Leu Glu Met Ile
                100                 105                 110
Ile Asn Gly Ile Pro Tyr Leu Gly Asp Arg Arg Val Pro Leu Glu Glu
            115                 120                 125
Phe Asn Thr Asn Ile Ala Ser Val Thr Val Asn Lys Leu Ile Ser Asn
        130                 135                 140
Pro Gly Glu Val Glu Arg Lys Lys Gly Ile Phe Ala Asn Leu Ile Ile
145                 150                 155                 160
Phe Gly Pro Gly Pro Val Leu Asn Glu Asn Glu Thr Ile Asp Ile Gly
                165                 170                 175
Ile Gln Asn His Phe Ala Ser Arg Glu Gly Phe Gly Ile Met Gln
            180                 185                 190
Met Lys Phe Cys Pro Glu Tyr Val Ser Val Phe Asn Asn Val Gln Glu
        195                 200                 205
Asn Lys Gly Ala Ser Ile Phe Asn Arg Arg Gly Tyr Phe Ser Asp Pro
210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
                245                 250                 255
Phe Met Gln Ser Thr Asp Ala Ile Gln Ala Glu Glu Leu Tyr Thr Phe
            260                 265                 270
Gly Gly Gln Asp Pro Ser Ile Ile Thr Pro Ser Thr Asp Lys Ser Ile
        275                 280                 285
Tyr Asp Lys Val Leu Gln Asn Phe Arg Gly Ile Val Asp Arg Leu Asn
290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
        355                 360                 365
Thr Arg Ala Ser Tyr Phe Ser Asp Ser Leu Pro Pro Val Lys Ile Lys
370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys Ala Pro Gly Ile Cys Ile Asp
        435                 440                 445
Val Asp Asn Glu Asp Leu Phe Phe Ile Ala Asp Lys Asn Ser Phe Ser
450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
                485                 490                 495
Leu Ile Ser Lys Ile Glu Leu Pro Ser Glu Asn Thr Glu Ser Leu Thr
            500                 505                 510
Asp Phe Asn Val Asp Val Pro Val Tyr Glu Lys Gln Pro Ala Ile Lys
```

```
            515                 520                 525
Lys Ile Phe Thr Asp Glu Asn Thr Ile Phe Gln Tyr Leu Tyr Ser Gln
530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                    565                 570                 575

Tyr Ile Lys Thr Ala Asn Lys Val Val Glu Ala Gly Leu Phe Ala Gly
                580                 585                 590

Trp Val Lys Gln Ile Val Asn Asp Phe Val Ile Glu Ala Asn Lys Ser
                595                 600                 605

Asn Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                    645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
                675                 680                 685

Arg Asn Glu Lys Trp Ser Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                    725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
                755                 760                 765

Asp Asn Ile Asn Asn Phe Ile Asn Gly Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                    805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
            850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                    885                 890                 895

Asn Gln Phe Lys Leu Thr Ser Ser Ala Asn Ser Lys Ile Arg Val Thr
                    900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
930                 935                 940
```

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
            965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu Ser
1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
            1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
            1075                1080                1085

Gly Asn Pro Leu Met Tyr Asn Lys Glu Tyr Tyr Met Phe Asn Ala Gly
            1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
            1125                1130                1135

Arg Asp Leu Tyr Ile Gly Glu Lys Phe Ile Ile Arg Arg Lys Ser Asn
            1140                1145                1150

Ser Gln Ser Ile Asn Asp Asp Ile Val Arg Lys Glu Asp Tyr Ile Tyr
            1155                1160                1165

Leu Asp Phe Phe Asn Leu Asn Gln Glu Trp Arg Val Tyr Thr Tyr Lys
            1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
            1205                1210                1215

Pro Thr Tyr Ser Cys Gln Leu Leu Phe Lys Lys Asp Glu Glu Ser Thr
            1220                1225                1230

Asp Glu Ile Gly Leu Ile Gly Ile His Arg Phe Tyr Glu Ser Gly Ile
            1235                1240                1245

Val Phe Glu Glu Tyr Lys Asp Tyr Phe Cys Ile Ser Lys Trp Tyr Leu
            1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
            1285                1290

<210> SEQ ID NO 62
<211> LENGTH: 2871
<212> TYPE: PRT
<213> ORGANISM: Homo sapiens

<400> SEQUENCE: 62

Met Arg Arg Gly Arg Leu Leu Glu Ile Ala Leu Gly Phe Thr Val Leu
1               5                   10                  15

Leu Ala Ser Tyr Thr Ser His Gly Ala Asp Ala Asn Leu Glu Ala Gly

-continued

```
                    20                  25                  30
Asn Val Lys Glu Thr Arg Ala Ser Arg Ala Lys Arg Arg Gly Gly Gly
                35                  40                  45
Gly His Asp Ala Leu Lys Gly Pro Asn Val Cys Gly Ser Arg Tyr Asn
        50                  55                  60
Ala Tyr Cys Cys Pro Gly Trp Lys Thr Leu Pro Gly Gly Asn Gln Cys
 65                 70                  75                  80
Ile Val Pro Ile Cys Arg His Ser Cys Gly Asp Gly Phe Cys Ser Arg
                85                  90                  95
Pro Asn Met Cys Thr Cys Pro Ser Gly Gln Ile Ala Pro Ser Cys Gly
            100                 105                 110
Ser Arg Ser Ile Gln His Cys Asn Ile Arg Cys Met Asn Gly Gly Ser
            115                 120                 125
Cys Ser Asp Asp His Cys Leu Cys Gln Lys Gly Tyr Ile Gly Thr His
        130                 135                 140
Cys Gly Gln Pro Val Cys Glu Ser Gly Cys Leu Asn Gly Gly Arg Cys
145                 150                 155                 160
Val Ala Pro Asn Arg Cys Ala Cys Thr Tyr Gly Phe Thr Gly Pro Gln
                165                 170                 175
Cys Glu Arg Asp Tyr Arg Thr Gly Pro Cys Phe Thr Val Ile Ser Asn
            180                 185                 190
Gln Met Cys Gln Gly Gln Leu Ser Gly Ile Val Cys Thr Lys Thr Leu
            195                 200                 205
Cys Cys Ala Thr Val Gly Arg Ala Trp Gly His Pro Cys Glu Met Cys
        210                 215                 220
Pro Ala Gln Pro His Pro Cys Arg Arg Gly Phe Ile Pro Asn Ile Arg
225                 230                 235                 240
Thr Gly Ala Cys Gln Asp Val Asp Glu Cys Gln Ala Ile Pro Gly Leu
                245                 250                 255
Cys Gln Gly Gly Asn Cys Ile Asn Thr Val Gly Ser Phe Glu Cys Lys
            260                 265                 270
Cys Pro Ala Gly His Lys Leu Asn Glu Val Ser Gln Lys Cys Glu Asp
            275                 280                 285
Ile Asp Glu Cys Ser Thr Ile Pro Gly Ile Cys Glu Gly Gly Glu Cys
        290                 295                 300
Thr Asn Thr Val Ser Ser Tyr Phe Cys Lys Cys Pro Pro Gly Phe Tyr
305                 310                 315                 320
Thr Ser Pro Asp Gly Thr Arg Cys Ile Asp Val Arg Pro Gly Tyr Cys
                325                 330                 335
Tyr Thr Ala Leu Thr Asn Gly Arg Cys Ser Asn Gln Leu Pro Gln Ser
            340                 345                 350
Ile Thr Lys Met Gln Cys Cys Cys Asp Ala Gly Arg Cys Trp Ser Pro
            355                 360                 365
Gly Val Thr Val Ala Pro Glu Met Cys Pro Ile Arg Ala Thr Glu Asp
        370                 375                 380
Phe Asn Lys Leu Cys Ser Val Pro Met Val Ile Pro Gly Arg Pro Glu
385                 390                 395                 400
Tyr Pro Pro Pro Pro Leu Gly Pro Ile Pro Val Leu Pro Val Pro
                405                 410                 415
Pro Gly Phe Pro Pro Gly Pro Gln Ile Pro Val Pro Arg Pro Pro Val
            420                 425                 430
Glu Tyr Leu Tyr Pro Ser Arg Glu Pro Pro Arg Val Leu Pro Val Asn
            435                 440                 445
```

```
Val Thr Asp Tyr Cys Gln Leu Val Arg Tyr Leu Cys Gln Asn Gly Arg
    450                 455                 460

Cys Ile Pro Thr Pro Gly Ser Tyr Arg Cys Glu Cys Asn Lys Gly Phe
465                 470                 475                 480

Gln Leu Asp Leu Arg Gly Glu Cys Ile Asp Val Asp Glu Cys Glu Lys
                485                 490                 495

Asn Pro Cys Ala Gly Glu Cys Ile Asn Asn Gln Gly Ser Tyr Thr
                500                 505                 510

Cys Gln Cys Arg Ala Gly Tyr Gln Ser Thr Leu Thr Arg Thr Glu Cys
        515                 520                 525

Arg Asp Ile Asp Glu Cys Leu Gln Asn Gly Arg Ile Cys Asn Asn Gly
    530                 535                 540

Arg Cys Ile Asn Thr Asp Gly Ser Phe His Cys Val Cys Asn Ala Gly
545                 550                 555                 560

Phe His Val Thr Arg Asp Gly Lys Asn Cys Glu Asp Met Asp Glu Cys
                565                 570                 575

Ser Ile Arg Asn Met Cys Leu Asn Gly Met Cys Ile Asn Glu Asp Gly
            580                 585                 590

Ser Phe Lys Cys Ile Cys Lys Pro Gly Phe Gln Leu Ala Ser Asp Gly
        595                 600                 605

Arg Tyr Cys Lys Asp Ile Asn Glu Cys Glu Thr Pro Gly Ile Cys Met
    610                 615                 620

Asn Gly Arg Cys Val Asn Thr Asp Gly Ser Tyr Arg Cys Glu Cys Phe
625                 630                 635                 640

Pro Gly Leu Ala Val Gly Leu Asp Gly Arg Val Cys Val Asp Thr His
                645                 650                 655

Met Arg Ser Thr Cys Tyr Gly Gly Tyr Lys Arg Gly Gln Cys Ile Lys
            660                 665                 670

Pro Leu Phe Gly Ala Val Thr Lys Ser Glu Cys Cys Cys Ala Ser Thr
        675                 680                 685

Glu Tyr Ala Phe Gly Glu Pro Cys Gln Pro Cys Pro Ala Gln Asn Ser
    690                 695                 700

Ala Glu Tyr Gln Ala Leu Cys Ser Ser Gly Pro Gly Met Thr Ser Ala
705                 710                 715                 720

Gly Ser Asp Ile Asn Glu Cys Ala Leu Asp Pro Asp Ile Cys Pro Asn
                725                 730                 735

Gly Ile Cys Glu Asn Leu Arg Gly Thr Tyr Lys Cys Ile Cys Asn Ser
            740                 745                 750

Gly Tyr Glu Val Asp Ser Thr Gly Lys Asn Cys Val Asp Ile Asn Glu
        755                 760                 765

Cys Val Leu Asn Ser Leu Leu Cys Asp Asn Gly Gln Cys Arg Asn Thr
    770                 775                 780

Pro Gly Ser Phe Val Cys Thr Cys Pro Lys Gly Phe Ile Tyr Lys Pro
785                 790                 795                 800

Asp Leu Lys Thr Cys Glu Asp Ile Asp Glu Cys Glu Ser Ser Pro Cys
                805                 810                 815

Ile Asn Gly Val Cys Lys Asn Ser Pro Gly Ser Phe Ile Cys Glu Cys
            820                 825                 830

Ser Ser Glu Ser Thr Leu Asp Pro Thr Lys Thr Ile Cys Ile Glu Thr
        835                 840                 845

Ile Lys Gly Thr Cys Trp Gln Thr Val Ile Asp Gly Arg Cys Glu Ile
    850                 855                 860
```

-continued

```
Asn Ile Asn Gly Ala Thr Leu Lys Ser Gln Cys Cys Ser Leu Gly
865                 870                 875                 880

Ala Ala Trp Gly Ser Pro Cys Thr Leu Cys Gln Val Asp Pro Ile Cys
            885                 890                 895

Gly Lys Gly Tyr Ser Arg Ile Lys Gly Thr Gln Cys Glu Asp Ile Asp
            900                 905                 910

Glu Cys Glu Val Phe Pro Gly Val Cys Lys Asn Gly Leu Cys Val Asn
            915                 920                 925

Thr Arg Gly Ser Phe Lys Cys Gln Cys Pro Ser Gly Met Thr Leu Asp
            930                 935                 940

Ala Thr Gly Arg Ile Cys Leu Asp Ile Arg Leu Glu Thr Cys Phe Leu
945                 950                 955                 960

Arg Tyr Glu Asp Glu Glu Cys Thr Leu Pro Ile Ala Gly Arg His Arg
            965                 970                 975

Met Asp Ala Cys Cys Cys Ser Val Gly Ala Ala Trp Gly Thr Glu Glu
            980                 985                 990

Cys Glu Glu Cys Pro Met Arg Asn Thr Pro Gly Tyr Glu Glu Leu Cys
            995                 1000                1005

Pro Arg Gly Pro Gly Phe Ala Thr Lys Glu Ile Thr Asn Gly Lys Pro
            1010                1015                1020

Phe Phe Lys Asp Ile Asn Glu Cys Lys Met Ile Pro Ser Leu Cys Thr
1025                1030                1035                1040

His Gly Lys Cys Arg Asn Thr Ile Gly Ser Phe Lys Cys Arg Cys Asp
            1045                1050                1055

Ser Gly Phe Ala Leu Asp Ser Glu Glu Arg Asn Cys Thr Asp Ile Asp
            1060                1065                1070

Glu Cys Arg Ile Ser Pro Asp Leu Cys Gly Arg Gly Gln Cys Val Asn
            1075                1080                1085

Thr Pro Gly Asp Phe Glu Cys Lys Cys Asp Glu Gly Tyr Glu Ser Gly
            1090                1095                1100

Phe Met Met Met Lys Asn Cys Met Asp Ile Asp Glu Cys Gln Arg Asp
1105                1110                1115                1120

Pro Leu Leu Cys Arg Gly Gly Val Cys His Asn Thr Glu Gly Ser Tyr
            1125                1130                1135

Arg Cys Glu Cys Pro Pro Gly His Gln Leu Ser Pro Asn Ile Ser Ala
            1140                1145                1150

Cys Ile Asp Ile Asn Glu Cys Glu Leu Ser Ala His Leu Cys Pro Asn
            1155                1160                1165

Gly Arg Cys Val Asn Leu Ile Gly Lys Tyr Gln Cys Ala Cys Asn Pro
            1170                1175                1180

Gly Tyr His Ser Thr Pro Asp Arg Leu Phe Cys Val Asp Ile Asp Glu
1185                1190                1195                1200

Cys Ser Ile Met Asn Gly Gly Cys Glu Thr Phe Cys Thr Asn Ser Glu
            1205                1210                1215

Gly Ser Tyr Glu Cys Ser Cys Gln Pro Gly Phe Ala Leu Met Pro Asp
            1220                1225                1230

Gln Arg Ser Cys Thr Asp Ile Asp Glu Cys Glu Asp Asn Pro Asn Ile
            1235                1240                1245

Cys Asp Gly Gly Gln Cys Thr Asn Ile Pro Gly Glu Tyr Arg Cys Leu
            1250                1255                1260

Cys Tyr Asp Gly Phe Met Ala Ser Glu Asp Met Lys Thr Cys Val Asp
1265                1270                1275                1280

Val Asn Glu Cys Asp Leu Asn Pro Asn Ile Cys Leu Ser Gly Thr Cys
```

```
                1285                1290                1295
Glu Asn Thr Lys Gly Ser Phe Ile Cys His Cys Asp Met Gly Tyr Ser
                1300                1305                1310

Gly Lys Lys Gly Lys Thr Gly Cys Thr Asp Ile Asn Glu Cys Glu Ile
        1315                1320                1325

Gly Ala His Asn Cys Gly Lys His Ala Val Cys Thr Asn Thr Ala Gly
        1330                1335                1340

Ser Phe Lys Cys Ser Cys Ser Pro Gly Trp Ile Gly Asp Gly Ile Lys
1345                1350                1355                1360

Cys Thr Asp Leu Asp Glu Cys Ser Asn Gly Thr His Met Cys Ser Gln
            1365                1370                1375

His Ala Asp Cys Lys Asn Thr Met Gly Ser Tyr Arg Cys Leu Cys Lys
        1380                1385                1390

Glu Gly Tyr Thr Gly Asp Gly Phe Thr Cys Thr Asp Leu Asp Glu Cys
        1395                1400                1405

Ser Glu Asn Leu Asn Leu Cys Gly Asn Gly Gln Cys Leu Asn Ala Pro
        1410                1415                1420

Gly Gly Tyr Arg Cys Glu Cys Asp Met Gly Phe Val Pro Ser Ala Asp
1425                1430                1435                1440

Gly Lys Ala Cys Glu Asp Ile Asp Glu Cys Ser Leu Pro Asn Ile Cys
            1445                1450                1455

Val Phe Gly Thr Cys His Asn Leu Pro Gly Leu Phe Arg Cys Glu Cys
        1460                1465                1470

Glu Ile Gly Tyr Glu Leu Asp Arg Ser Gly Gly Asn Cys Thr Asp Val
        1475                1480                1485

Asn Glu Cys Leu Asp Pro Thr Thr Cys Ile Ser Gly Asn Cys Val Asn
        1490                1495                1500

Thr Pro Gly Ser Tyr Ile Cys Asp Cys Pro Pro Asp Phe Glu Leu Asn
1505                1510                1515                1520

Pro Thr Arg Val Gly Cys Val Asp Thr Arg Ser Gly Asn Cys Tyr Leu
            1525                1530                1535

Asp Ile Arg Pro Arg Gly Asp Asn Gly Asp Thr Ala Cys Ser Asn Glu
        1540                1545                1550

Ile Gly Val Gly Val Ser Lys Ala Ser Cys Cys Cys Ser Leu Gly Lys
        1555                1560                1565

Ala Trp Gly Thr Pro Cys Glu Met Cys Pro Ala Val Asn Thr Ser Glu
        1570                1575                1580

Tyr Lys Ile Leu Cys Pro Gly Gly Glu Gly Phe Arg Pro Asn Pro Ile
1585                1590                1595                1600

Thr Val Ile Leu Glu Asp Ile Asp Glu Cys Gln Glu Leu Pro Gly Leu
            1605                1610                1615

Cys Gln Gly Gly Lys Cys Ile Asn Thr Phe Gly Ser Phe Gln Cys Arg
        1620                1625                1630

Cys Pro Thr Gly Tyr Tyr Leu Asn Glu Asp Thr Arg Val Cys Asp Asp
        1635                1640                1645

Val Asn Glu Cys Glu Thr Pro Gly Ile Cys Gly Pro Gly Thr Cys Tyr
        1650                1655                1660

Asn Thr Val Gly Asn Tyr Thr Cys Ile Cys Pro Pro Asp Tyr Met Gln
1665                1670                1675                1680

Val Asn Gly Gly Asn Asn Cys Met Asp Met Arg Arg Ser Leu Cys Tyr
            1685                1690                1695

Arg Asn Tyr Tyr Ala Asp Asn Gln Thr Cys Asp Gly Glu Leu Leu Phe
        1700                1705                1710
```

Asn Met Thr Lys Lys Met Cys Cys Cys Ser Tyr Asn Ile Gly Arg Ala
        1715                1720                1725

Trp Asn Lys Pro Cys Glu Gln Cys Pro Ile Pro Ser Thr Asp Glu Phe
        1730                1735                1740

Ala Thr Leu Cys Gly Ser Gln Arg Pro Gly Phe Val Ile Asp Ile Tyr
1745                1750                1755                1760

Thr Gly Leu Pro Val Asp Ile Asp Glu Cys Arg Glu Ile Pro Gly Val
                1765                1770                1775

Cys Glu Asn Gly Val Cys Ile Asn Met Val Gly Ser Phe Arg Cys Glu
                1780                1785                1790

Cys Pro Val Gly Phe Phe Tyr Asn Asp Lys Leu Leu Val Cys Glu Asp
                1795                1800                1805

Ile Asp Glu Cys Gln Asn Gly Pro Val Cys Gln Arg Asn Ala Glu Cys
                1810                1815                1820

Ile Asn Thr Ala Gly Ser Tyr Arg Cys Asp Cys Lys Pro Gly Tyr Arg
1825                1830                1835                1840

Phe Thr Ser Thr Gly Gln Cys Asn Asp Arg Asn Glu Cys Gln Glu Ile
                    1845                1850                1855

Pro Asn Ile Cys Ser His Gly Gln Cys Ile Asp Thr Val Gly Ser Phe
                1860                1865                1870

Tyr Cys Leu Cys His Thr Gly Phe Lys Thr Asn Asp Asp Gln Thr Met
            1875                1880                1885

Cys Leu Asp Ile Asn Glu Cys Glu Arg Asp Ala Cys Gly Asn Gly Thr
            1890                1895                1900

Cys Arg Asn Thr Ile Gly Ser Phe Asn Cys Arg Cys Asn His Gly Phe
1905                1910                1915                1920

Ile Leu Ser His Asn Asn Asp Cys Ile Asp Val Asp Glu Cys Ala Ser
                1925                1930                1935

Gly Asn Gly Asn Leu Cys Arg Asn Gly Gln Cys Ile Asn Thr Val Gly
                1940                1945                1950

Ser Phe Gln Cys Gln Cys Asn Glu Gly Tyr Glu Val Ala Pro Asp Gly
        1955                1960                1965

Arg Thr Cys Val Asp Ile Asn Glu Cys Leu Leu Glu Pro Arg Lys Cys
        1970                1975                1980

Ala Pro Gly Thr Cys Gln Asn Leu Asp Gly Ser Tyr Arg Cys Ile Cys
1985                1990                1995                2000

Pro Pro Gly Tyr Ser Leu Gln Asn Glu Lys Cys Glu Asp Ile Asp Glu
                2005                2010                2015

Cys Val Glu Glu Pro Glu Ile Cys Ala Leu Gly Thr Cys Ser Asn Thr
            2020                2025                2030

Glu Gly Ser Phe Lys Cys Leu Cys Pro Glu Gly Phe Ser Leu Ser Ser
            2035                2040                2045

Ser Gly Arg Arg Cys Gln Asp Leu Arg Met Ser Tyr Cys Tyr Ala Lys
        2050                2055                2060

Phe Glu Gly Gly Lys Cys Ser Ser Pro Lys Ser Arg Asn His Ser Lys
2065                2070                2075                2080

Gln Glu Cys Cys Cys Ala Leu Lys Gly Glu Gly Trp Gly Asp Pro Cys
            2085                2090                2095

Glu Leu Cys Pro Thr Glu Pro Asp Glu Ala Phe Arg Gln Ile Cys Pro
            2100                2105                2110

Tyr Gly Ser Gly Ile Ile Val Gly Pro Asp Asp Ser Ala Val Asp Met
        2115                2120                2125

```
Asp Glu Cys Lys Glu Pro Asp Val Cys Lys His Gly Gln Cys Ile Asn
            2130                2135                2140
Thr Asp Gly Ser Tyr Arg Cys Glu Cys Pro Phe Gly Tyr Ile Leu Ala
2145                2150                2155                2160
Gly Asn Glu Cys Val Asp Thr Asp Glu Cys Ser Val Gly Asn Pro Cys
            2165                2170                2175
Gly Asn Gly Thr Cys Lys Asn Val Ile Gly Gly Phe Glu Cys Thr Cys
            2180                2185                2190
Glu Glu Gly Phe Glu Pro Gly Pro Met Met Thr Cys Glu Asp Ile Asn
            2195                2200                2205
Glu Cys Ala Gln Asn Pro Leu Leu Cys Ala Phe Arg Cys Val Asn Thr
    2210                2215                2220
Tyr Gly Ser Tyr Glu Cys Lys Cys Pro Val Gly Tyr Val Leu Arg Glu
2225                2230                2235                2240
Asp Arg Arg Met Cys Lys Asp Glu Asp Glu Cys Glu Glu Gly Lys His
            2245                2250                2255
Asp Cys Thr Glu Lys Gln Met Glu Cys Lys Asn Leu Ile Gly Thr Tyr
            2260                2265                2270
Met Cys Ile Cys Gly Pro Gly Tyr Gln Arg Arg Pro Asp Gly Glu Gly
            2275                2280                2285
Cys Val Asp Glu Asn Glu Cys Gln Thr Lys Pro Gly Ile Cys Glu Asn
            2290                2295                2300
Gly Arg Cys Leu Asn Thr Arg Gly Ser Tyr Thr Cys Glu Cys Asn Asp
2305                2310                2315                2320
Gly Phe Thr Ala Ser Pro Asn Gln Asp Glu Cys Leu Asp Asn Arg Glu
            2325                2330                2335
Gly Tyr Cys Phe Thr Glu Val Leu Gln Asn Met Cys Gln Ile Gly Ser
            2340                2345                2350
Ser Asn Arg Asn Pro Val Thr Lys Ser Glu Cys Cys Cys Asp Gly Gly
            2355                2360                2365
Arg Gly Trp Gly Pro His Cys Glu Ile Cys Pro Phe Gln Gly Thr Val
            2370                2375                2380
Ala Phe Lys Lys Leu Cys Pro His Gly Arg Gly Phe Met Thr Asn Gly
2385                2390                2395                2400
Ala Asp Ile Asp Glu Cys Lys Val Ile His Asp Val Cys Arg Asn Gly
            2405                2410                2415
Glu Cys Val Asn Asp Arg Gly Ser Tyr His Cys Ile Cys Lys Thr Gly
            2420                2425                2430
Tyr Thr Pro Asp Ile Thr Gly Thr Ser Cys Val Asp Leu Asn Glu Cys
            2435                2440                2445
Asn Gln Ala Pro Lys Pro Cys Asn Phe Ile Cys Lys Asn Thr Glu Gly
            2450                2455                2460
Ser Tyr Gln Cys Ser Cys Pro Lys Gly Tyr Ile Leu Gln Glu Asp Gly
2465                2470                2475                2480
Arg Ser Cys Lys Asp Leu Asp Glu Cys Ala Thr Lys Gln His Asn Cys
            2485                2490                2495
Gln Phe Leu Cys Val Asn Thr Ile Gly Gly Phe Thr Cys Lys Cys Pro
            2500                2505                2510
Pro Gly Phe Thr Gln His His Thr Ser Cys Ile Asp Asn Asn Glu Cys
            2515                2520                2525
Thr Ser Asp Ile Asn Leu Cys Gly Ser Lys Gly Ile Cys Gln Asn Thr
            2530                2535                2540
Pro Gly Ser Phe Thr Cys Glu Cys Gln Arg Gly Phe Ser Leu Asp Gln
```

-continued

```
            2545                2550                2555                2560

Thr Gly Ser Ser Cys Glu Asp Val Asp Glu Cys Glu Gly Asn His Arg
                    2565                2570                2575

Cys Gln His Gly Cys Gln Asn Ile Ile Gly Gly Tyr Arg Cys Ser Cys
                    2580                2585                2590

Pro Gln Gly Tyr Leu Gln His Tyr Gln Trp Asn Gln Cys Val Asp Glu
                    2595                2600                2605

Asn Glu Cys Leu Ser Ala His Ile Cys Gly Gly Ala Ser Cys His Asn
                    2610                2615                2620

Thr Leu Gly Ser Tyr Lys Cys Met Cys Pro Ala Gly Phe Gln Tyr Glu
        2625                2630                2635                2640

Gln Phe Ser Gly Gly Cys Gln Asp Ile Asn Glu Cys Gly Ser Ala Gln
                    2645                2650                2655

Ala Pro Cys Ser Tyr Gly Cys Ser Asn Thr Glu Gly Gly Tyr Leu Cys
                    2660                2665                2670

Gly Cys Pro Pro Gly Tyr Phe Arg Ile Gly Gln Gly His Cys Val Ser
                    2675                2680                2685

Gly Met Gly Met Gly Arg Gly Asn Pro Glu Pro Val Ser Gly Glu
                    2690                2695                2700

Met Asp Asp Asn Ser Leu Ser Pro Glu Ala Cys Tyr Glu Cys Lys Ile
        2705                2710                2715                2720

Asn Gly Tyr Pro Lys Arg Gly Arg Lys Arg Arg Ser Thr Asn Glu Thr
                    2725                2730                2735

Asp Ala Ser Asn Ile Glu Asp Gln Ser Glu Thr Glu Ala Asn Val Ser
                    2740                2745                2750

Leu Ala Ser Trp Asp Val Glu Lys Thr Ala Ile Phe Ala Phe Asn Ile
                    2755                2760                2765

Ser His Val Ser Asn Lys Val Arg Ile Leu Glu Leu Leu Pro Ala Leu
                    2770                2775                2780

Thr Thr Leu Thr Asn His Asn Arg Tyr Leu Ile Glu Ser Gly Asn Glu
        2785                2790                2795                2800

Asp Gly Phe Phe Lys Ile Asn Gln Lys Glu Gly Ile Ser Tyr Leu His
                    2805                2810                2815

Phe Thr Lys Lys Lys Pro Val Ala Gly Thr Tyr Ser Leu Gln Ile Ser
                    2820                2825                2830

Ser Thr Pro Leu Tyr Lys Lys Lys Glu Leu Asn Gln Leu Glu Asp Lys
                    2835                2840                2845

Tyr Asp Lys Asp Tyr Leu Ser Gly Glu Leu Gly Asp Asn Leu Lys Met
                    2850                2855                2860

Lys Ile Gln Val Leu Leu His
        2865                2870

<210> SEQ ID NO 63
<211> LENGTH: 2912
<212> TYPE: PRT
<213> ORGANISM: Homo sapiens

<400> SEQUENCE: 63

Met Gly Arg Arg Arg Arg Leu Cys Leu Gln Leu Tyr Phe Leu Trp Leu
        1               5                   10                  15

Gly Cys Val Val Leu Trp Ala Gln Gly Thr Ala Gly Gln Pro Gln Pro
                    20                  25                  30

Pro Pro Pro Lys Pro Pro Arg Pro Gln Pro Pro Gln Gln Val Arg
                    35                  40                  45
```

-continued

```
Ser Ala Thr Ala Gly Ser Glu Gly Gly Phe Leu Ala Pro Glu Tyr Arg
 50                  55                  60

Glu Glu Gly Ala Ala Val Ala Ser Arg Val Arg Arg Gly Gln Gln
 65                  70                  75                  80

Asp Val Leu Arg Gly Pro Asn Val Cys Gly Ser Arg Phe His Ser Tyr
                 85                  90                  95

Cys Cys Pro Gly Trp Lys Thr Leu Pro Gly Gly Asn Gln Cys Ile Val
                100                 105                 110

Pro Ile Cys Arg Asn Ser Cys Gly Asp Gly Phe Cys Ser Arg Pro Asn
            115                 120                 125

Met Cys Thr Cys Ser Ser Gly Gln Ile Ser Ser Thr Cys Gly Ser Lys
130                 135                 140

Ser Ile Gln Gln Cys Ser Val Arg Cys Met Asn Gly Gly Thr Cys Ala
145                 150                 155                 160

Asp Asp His Cys Gln Cys Gln Lys Gly Tyr Ile Gly Thr Tyr Cys Gly
                165                 170                 175

Gln Pro Val Cys Glu Asn Gly Cys Gln Asn Gly Gly Arg Cys Ile Gly
            180                 185                 190

Pro Asn Arg Cys Ala Cys Val Tyr Gly Phe Thr Gly Pro Gln Cys Glu
            195                 200                 205

Arg Asp Tyr Arg Thr Gly Pro Cys Phe Thr Gln Val Asn Asn Gln Met
210                 215                 220

Cys Gln Gly Gln Leu Thr Gly Ile Val Cys Thr Lys Thr Leu Cys Cys
225                 230                 235                 240

Ala Thr Ile Gly Arg Ala Trp Gly His Pro Cys Glu Met Cys Pro Ala
                245                 250                 255

Gln Pro Gln Pro Cys Arg Arg Gly Phe Ile Pro Asn Ile Arg Thr Gly
            260                 265                 270

Ala Cys Gln Asp Val Asp Glu Cys Gln Ala Ile Pro Gly Ile Cys Gln
            275                 280                 285

Gly Gly Asn Cys Ile Asn Thr Val Gly Ser Phe Glu Cys Arg Cys Pro
290                 295                 300

Ala Gly His Lys Gln Ser Glu Thr Thr Gln Lys Cys Glu Asp Ile Asp
305                 310                 315                 320

Glu Cys Ser Ile Ile Pro Gly Ile Cys Glu Thr Gly Glu Cys Ser Asn
                325                 330                 335

Thr Val Gly Ser Tyr Phe Cys Val Cys Pro Arg Gly Tyr Val Thr Ser
                340                 345                 350

Thr Asp Gly Ser Arg Cys Ile Asp Gln Arg Thr Gly Met Cys Phe Ser
            355                 360                 365

Gly Leu Val Asn Gly Arg Cys Ala Gln Glu Leu Pro Gly Arg Met Thr
370                 375                 380

Lys Met Gln Cys Cys Cys Glu Pro Gly Arg Cys Trp Gly Ile Gly Thr
385                 390                 395                 400

Ile Pro Glu Ala Cys Pro Val Arg Gly Ser Glu Glu Tyr Arg Arg Leu
                405                 410                 415

Cys Met Asp Gly Leu Pro Met Gly Ile Pro Gly Ser Ala Gly Ser
            420                 425                 430

Arg Pro Gly Gly Thr Gly Asn Gly Phe Ala Pro Ser Gly Asn Gly
            435                 440                 445

Asn Gly Tyr Gly Pro Gly Gly Thr Gly Phe Ile Pro Ile Pro Gly Gly
450                 455                 460

Asn Gly Phe Ser Pro Gly Val Gly Gly Ala Gly Val Gly Ala Gly Gly
```

```
            465                 470                 475                 480
Gln Gly Pro Ile Ile Thr Gly Leu Thr Ile Leu Asn Gln Thr Ile Asp
                485                 490                 495
Ile Cys Lys His His Ala Asn Leu Cys Leu Asn Gly Arg Cys Ile Pro
            500                 505                 510
Thr Val Ser Ser Tyr Arg Cys Glu Cys Asn Met Gly Tyr Lys Gln Asp
        515                 520                 525
Ala Asn Gly Asp Cys Ile Asp Val Asp Glu Cys Thr Ser Asn Pro Cys
    530                 535                 540
Thr Asn Gly Asp Cys Val Asn Thr Pro Gly Ser Tyr Tyr Cys Lys Cys
545                 550                 555                 560
His Ala Gly Phe Gln Arg Thr Pro Thr Lys Gln Ala Cys Ile Asp Ile
                565                 570                 575
Asp Glu Cys Ile Gln Asn Gly Val Leu Cys Lys Asn Gly Arg Cys Val
            580                 585                 590
Asn Thr Asp Gly Ser Phe Gln Cys Ile Cys Asn Ala Gly Phe Glu Leu
        595                 600                 605
Thr Thr Asp Gly Lys Asn Cys Val Asp His Asp Glu Cys Thr Thr Thr
    610                 615                 620
Asn Met Cys Leu Asn Gly Met Cys Ile Asn Glu Asp Gly Ser Phe Lys
625                 630                 635                 640
Cys Ile Cys Lys Pro Gly Phe Val Leu Ala Pro Asn Gly Arg Tyr Cys
                645                 650                 655
Thr Asp Val Asp Glu Cys Gln Thr Pro Gly Ile Cys Met Asn Gly His
            660                 665                 670
Cys Ile Asn Ser Glu Gly Ser Phe Arg Cys Asp Cys Pro Pro Gly Leu
        675                 680                 685
Ala Val Gly Met Asp Gly Arg Val Cys Val Asp Thr His Met Arg Ser
    690                 695                 700
Thr Cys Tyr Gly Gly Ile Lys Lys Gly Val Cys Val Arg Pro Phe Pro
705                 710                 715                 720
Gly Ala Val Thr Lys Ser Glu Cys Cys Cys Ala Asn Pro Asp Tyr Gly
                725                 730                 735
Phe Gly Glu Pro Cys Gln Pro Cys Pro Ala Lys Asn Ser Ala Glu Phe
            740                 745                 750
His Gly Leu Cys Ser Ser Gly Val Gly Ile Thr Val Asp Gly Arg Asp
        755                 760                 765
Ile Asn Glu Cys Ala Leu Asp Pro Asp Ile Cys Ala Asn Gly Ile Cys
    770                 775                 780
Glu Asn Leu Arg Gly Ser Tyr Arg Cys Asn Cys Asn Ser Gly Tyr Glu
785                 790                 795                 800
Pro Asp Ala Ser Gly Arg Asn Cys Ile Asp Ile Asp Glu Cys Leu Val
                805                 810                 815
Asn Arg Leu Leu Cys Asp Asn Gly Leu Cys Arg Asn Thr Pro Gly Ser
            820                 825                 830
Tyr Ser Cys Thr Cys Pro Pro Gly Tyr Val Phe Arg Thr Glu Thr Glu
        835                 840                 845
Thr Cys Glu Asp Ile Asn Glu Cys Glu Ser Asn Pro Cys Val Asn Gly
    850                 855                 860
Ala Cys Arg Asn Asn Leu Gly Ser Phe Asn Cys Glu Cys Ser Pro Gly
865                 870                 875                 880
Ser Lys Leu Ser Ser Thr Gly Leu Ile Cys Ile Asp Ser Leu Lys Gly
                885                 890                 895
```

```
Thr Cys Trp Leu Asn Ile Gln Asp Ser Arg Cys Glu Val Asn Ile Asn
            900                 905                 910
Gly Ala Thr Leu Lys Ser Glu Cys Cys Ala Thr Leu Gly Ala Ala Trp
            915                 920                 925
Gly Ser Pro Cys Glu Arg Cys Glu Leu Asp Thr Ala Cys Pro Arg Gly
            930                 935                 940
Leu Ala Arg Ile Lys Gly Val Thr Cys Glu Asp Val Asn Glu Cys Glu
945                 950                 955                 960
Val Phe Pro Gly Val Cys Pro Asn Gly Arg Cys Val Asn Ser Lys Gly
            965                 970                 975
Ser Phe His Cys Glu Cys Pro Glu Gly Leu Thr Leu Asp Gly Thr Gly
            980                 985                 990
Arg Val Cys Leu Asp Ile Arg Met Glu Gln Cys Tyr Leu Lys Trp Asp
            995                 1000                1005
Glu Asp Glu Cys Ile His Pro Val Pro Gly Lys Phe Arg Met Asp Ala
            1010                1015                1020
Cys Cys Cys Ala Val Gly Ala Ala Trp Gly Thr Glu Cys Glu Glu Cys
1025                1030                1035                1040
Pro Lys Pro Gly Thr Lys Glu Tyr Glu Thr Leu Cys Pro Arg Gly Ala
            1045                1050                1055
Gly Phe Ala Asn Arg Gly Asp Val Leu Thr Gly Arg Pro Phe Tyr Lys
            1060                1065                1070
Asp Ile Asn Glu Cys Lys Ala Phe Pro Gly Met Cys Thr Tyr Gly Lys
            1075                1080                1085
Cys Arg Asn Thr Ile Gly Ser Phe Lys Cys Arg Cys Asn Ser Gly Phe
            1090                1095                1100
Ala Leu Asp Met Glu Glu Arg Asn Cys Thr Asp Ile Asp Glu Cys Arg
1105                1110                1115                1120
Ile Ser Pro Asp Leu Cys Gly Ser Gly Ile Cys Val Asn Thr Pro Gly
            1125                1130                1135
Ser Phe Glu Cys Glu Cys Phe Glu Gly Tyr Glu Ser Gly Phe Met Met
            1140                1145                1150
Met Lys Asn Cys Met Asp Ile Asp Glu Cys Glu Arg Asn Pro Leu Leu
            1155                1160                1165
Cys Arg Gly Gly Thr Cys Val Asn Thr Glu Gly Ser Phe Gln Cys Asp
            1170                1175                1180
Cys Pro Leu Gly His Glu Leu Ser Pro Ser Arg Glu Asp Cys Val Asp
1185                1190                1195                1200
Ile Asn Glu Cys Ser Leu Ser Asp Asn Leu Cys Arg Asn Gly Lys Cys
            1205                1210                1215
Val Asn Met Ile Gly Thr Tyr Gln Cys Ser Cys Asn Pro Gly Tyr Gln
            1220                1225                1230
Ala Thr Pro Asp Arg Gln Gly Cys Thr Asp Ile Asp Glu Cys Met Ile
            1235                1240                1245
Met Asn Gly Gly Cys Asp Thr Gln Cys Thr Asn Ser Glu Gly Ser Tyr
            1250                1255                1260
Glu Cys Ser Cys Ser Glu Gly Tyr Ala Leu Met Pro Asp Gly Arg Ser
1265                1270                1275                1280
Cys Ala Asp Ile Asp Glu Cys Glu Asn Asn Pro Asp Ile Cys Asp Gly
            1285                1290                1295
Gly Gln Cys Thr Asn Ile Pro Gly Glu Tyr Arg Cys Leu Cys Tyr Asp
            1300                1305                1310
```

```
Gly Phe Met Ala Ser Met Asp Met Lys Thr Cys Ile Asp Val Asn Glu
             1315                1320                1325

Cys Asp Leu Asn Ser Asn Ile Cys Met Phe Gly Glu Cys Glu Asn Thr
             1330                1335                1340

Lys Gly Ser Phe Ile Cys His Cys Gln Leu Gly Tyr Ser Val Lys Lys
1345                1350                1355                1360

Gly Thr Thr Gly Cys Thr Asp Val Asp Glu Cys Glu Ile Gly Ala His
             1365                1370                1375

Asn Cys Asp Met His Ala Ser Cys Leu Asn Ile Pro Gly Ser Phe Lys
             1380                1385                1390

Cys Ser Cys Arg Glu Gly Trp Ile Gly Asn Gly Ile Lys Cys Ile Asp
             1395                1400                1405

Leu Asp Glu Cys Ser Asn Gly Thr His Gln Cys Ser Ile Asn Ala Gln
             1410                1415                1420

Cys Val Asn Thr Pro Gly Ser Tyr Arg Cys Ala Cys Ser Glu Gly Phe
1425                1430                1435                1440

Thr Gly Asp Gly Phe Thr Cys Ser Asp Val Asp Glu Cys Ala Glu Asn
             1445                1450                1455

Ile Asn Leu Cys Glu Asn Gly Gln Cys Leu Asn Val Pro Gly Ala Tyr
             1460                1465                1470

Arg Cys Glu Cys Glu Met Gly Phe Thr Pro Ala Ser Asp Ser Arg Ser
             1475                1480                1485

Cys Gln Asp Ile Asp Glu Cys Ser Phe Gln Asn Ile Cys Val Phe Gly
             1490                1495                1500

Thr Cys Asn Asn Leu Pro Gly Met Phe His Cys Ile Cys Asp Asp Gly
1505                1510                1515                1520

Tyr Glu Leu Asp Arg Thr Gly Gly Asn Cys Thr Asp Ile Asp Glu Cys
             1525                1530                1535

Ala Asp Pro Ile Asn Cys Val Asn Gly Leu Cys Val Asn Thr Pro Gly
             1540                1545                1550

Arg Tyr Glu Cys Asn Cys Pro Pro Asp Phe Gln Leu Asn Pro Thr Gly
             1555                1560                1565

Val Gly Cys Val Asp Asn Arg Val Gly Asn Cys Tyr Leu Lys Phe Gly
             1570                1575                1580

Pro Arg Gly Asp Gly Ser Leu Ser Cys Asn Thr Glu Ile Gly Val Gly
1585                1590                1595                1600

Val Ser Arg Ser Ser Cys Cys Ser Leu Gly Lys Ala Trp Gly Asn
             1605                1610                1615

Pro Cys Glu Thr Cys Pro Pro Val Asn Ser Thr Glu Tyr Tyr Thr Leu
             1620                1625                1630

Cys Pro Gly Gly Glu Gly Phe Arg Pro Asn Pro Ile Thr Ile Ile Leu
             1635                1640                1645

Glu Asp Ile Asp Glu Cys Gln Glu Leu Pro Gly Leu Cys Gln Gly Gly
             1650                1655                1660

Asn Cys Ile Asn Thr Phe Gly Ser Phe Gln Cys Glu Cys Pro Gln Gly
1665                1670                1675                1680

Tyr Tyr Leu Ser Glu Asp Thr Arg Ile Cys Glu Asp Ile Asp Glu Cys
             1685                1690                1695

Phe Ala His Pro Gly Val Cys Gly Pro Gly Thr Cys Tyr Asn Thr Leu
             1700                1705                1710

Gly Asn Tyr Thr Cys Ile Cys Pro Pro Glu Tyr Met Gln Val Asn Gly
             1715                1720                1725

Gly His Asn Cys Met Asp Met Arg Lys Ser Phe Cys Tyr Arg Ser Tyr
```

-continued

```
            1730                1735                1740
Asn Gly Thr Thr Cys Glu Asn Glu Leu Pro Phe Asn Val Thr Lys Arg
1745                1750                1755                1760
Met Cys Cys Cys Thr Tyr Asn Val Gly Lys Ala Trp Asn Lys Pro Cys
                1765                1770                1775
Glu Pro Cys Pro Thr Pro Gly Thr Ala Asp Phe Lys Thr Ile Cys Gly
            1780                1785                1790
Asn Ile Pro Gly Phe Thr Phe Asp Ile His Thr Gly Lys Ala Val Asp
            1795                1800                1805
Ile Asp Glu Cys Lys Glu Ile Pro Gly Ile Cys Ala Asn Gly Val Cys
        1810                1815                1820
Ile Asn Gln Ile Gly Ser Phe Arg Cys Glu Cys Pro Thr Gly Phe Ser
1825                1830                1835                1840
Tyr Asn Asp Leu Leu Leu Val Cys Glu Asp Ile Asp Glu Cys Ser Asn
                1845                1850                1855
Gly Asp Asn Leu Cys Gln Arg Asn Ala Asp Cys Ile Asn Ser Pro Gly
            1860                1865                1870
Ser Tyr Arg Cys Glu Cys Ala Ala Gly Phe Lys Leu Ser Pro Asn Gly
        1875                1880                1885
Ala Cys Val Asp Arg Asn Glu Cys Leu Glu Ile Pro Asn Val Cys Ser
        1890                1895                1900
His Gly Leu Cys Val Asp Leu Gln Gly Ser Tyr Gln Cys Ile Cys His
1905                1910                1915                1920
Asn Gly Phe Lys Ala Ser Gln Asp Gln Thr Met Cys Met Asp Val Asp
                1925                1930                1935
Glu Cys Glu Arg His Pro Cys Gly Asn Gly Thr Cys Lys Asn Thr Val
            1940                1945                1950
Gly Ser Tyr Asn Cys Leu Cys Tyr Pro Gly Phe Glu Leu Thr His Asn
        1955                1960                1965
Asn Asp Cys Leu Asp Ile Asp Glu Cys Ser Ser Phe Phe Gly Gln Val
    1970                1975                1980
Cys Arg Asn Gly Arg Cys Phe Asn Glu Ile Gly Ser Phe Lys Cys Leu
1985                1990                1995                2000
Cys Asn Glu Gly Tyr Glu Leu Thr Pro Asp Gly Lys Asn Cys Ile Asp
                2005                2010                2015
Thr Asn Glu Cys Val Ala Leu Pro Gly Ser Cys Ser Pro Gly Thr Cys
            2020                2025                2030
Gln Asn Leu Glu Gly Ser Phe Arg Cys Ile Cys Pro Pro Gly Tyr Glu
        2035                2040                2045
Val Lys Ser Glu Asn Cys Ile Asp Ile Asn Glu Cys Asp Glu Asp Pro
    2050                2055                2060
Asn Ile Cys Leu Phe Gly Ser Cys Thr Asn Thr Pro Gly Gly Phe Gln
2065                2070                2075                2080
Cys Leu Cys Pro Pro Gly Phe Val Leu Ser Asp Asn Gly Arg Arg Cys
                2085                2090                2095
Phe Asp Thr Arg Gln Ser Phe Cys Phe Thr Asn Phe Glu Asn Gly Lys
            2100                2105                2110
Cys Ser Val Pro Lys Ala Phe Asn Thr Thr Lys Ala Lys Cys Cys Cys
        2115                2120                2125
Ser Lys Met Pro Gly Glu Gly Trp Gly Asp Pro Cys Glu Leu Cys Pro
    2130                2135                2140
Lys Asp Asp Glu Val Ala Phe Gln Asp Leu Cys Pro Tyr Gly His Gly
2145                2150                2155                2160
```

```
Thr Val Pro Ser Leu His Asp Thr Arg Glu Asp Val Asn Glu Cys Leu
            2165                2170                2175

Glu Ser Pro Gly Ile Cys Ser Asn Gly Gln Cys Ile Asn Thr Asp Gly
            2180                2185                2190

Ser Phe Arg Cys Glu Cys Pro Met Gly Tyr Asn Leu Asp Tyr Thr Gly
            2195                2200                2205

Val Arg Cys Val Asp Thr Asp Glu Cys Ser Ile Gly Asn Pro Cys Gly
            2210                2215                2220

Asn Gly Thr Cys Thr Asn Val Ile Gly Ser Phe Glu Cys Asn Cys Asn
2225                2230                2235                2240

Glu Gly Phe Glu Pro Gly Pro Met Met Asn Cys Glu Asp Ile Asn Glu
            2245                2250                2255

Cys Ala Gln Asn Pro Leu Leu Cys Ala Phe Arg Cys Met Asn Thr Phe
            2260                2265                2270

Gly Ser Tyr Glu Cys Thr Cys Pro Ile Gly Tyr Ala Leu Arg Glu Asp
            2275                2280                2285

Gln Lys Met Cys Lys Asp Leu Asp Glu Cys Ala Glu Gly Leu His Asp
            2290                2295                2300

Cys Glu Ser Arg Gly Met Met Cys Lys Asn Leu Ile Gly Thr Phe Met
2305                2310                2315                2320

Cys Ile Cys Pro Pro Gly Met Ala Arg Arg Pro Asp Gly Glu Gly Cys
            2325                2330                2335

Val Asp Glu Asn Glu Cys Arg Thr Lys Pro Gly Ile Cys Glu Asn Gly
            2340                2345                2350

Arg Cys Val Asn Ile Ile Gly Ser Tyr Arg Cys Glu Cys Asn Glu Gly
            2355                2360                2365

Phe Gln Ser Ser Ser Ser Gly Thr Glu Cys Leu Asp Asn Arg Gln Gly
            2370                2375                2380

Leu Cys Phe Ala Glu Val Leu Gln Thr Ile Cys Gln Met Ala Ser Ser
2385                2390                2395                2400

Ser Arg Asn Leu Val Thr Lys Ser Glu Cys Cys Cys Asp Gly Gly Arg
            2405                2410                2415

Gly Trp Gly His Gln Cys Glu Leu Cys Pro Leu Pro Gly Thr Ala Gln
            2420                2425                2430

Tyr Lys Lys Ile Cys Pro His Gly Pro Gly Tyr Thr Thr Asp Gly Arg
            2435                2440                2445

Asp Ile Asp Glu Cys Lys Val Met Pro Asn Leu Cys Thr Asn Gly Gln
            2450                2455                2460

Cys Ile Asn Thr Met Gly Ser Phe Arg Cys Phe Cys Lys Val Gly Tyr
2465                2470                2475                2480

Thr Thr Asp Ile Ser Gly Thr Ser Cys Ile Asp Leu Asp Glu Cys Ser
            2485                2490                2495

Gln Ser Pro Lys Pro Cys Asn Tyr Ile Cys Lys Asn Thr Glu Gly Ser
            2500                2505                2510

Tyr Gln Cys Ser Cys Pro Arg Gly Tyr Val Leu Gln Glu Asp Gly Lys
            2515                2520                2525

Thr Cys Lys Asp Leu Asp Glu Cys Gln Thr Lys Gln His Asn Cys Gln
            2530                2535                2540

Phe Leu Cys Val Asn Thr Leu Gly Gly Phe Thr Cys Lys Cys Pro Pro
2545                2550                2555                2560

Gly Phe Thr Gln His His Thr Ala Cys Ile Asp Asn Asn Glu Cys Gly
            2565                2570                2575
```

```
Ser Gln Pro Ser Leu Cys Gly Ala Lys Gly Ile Cys Gln Asn Thr Pro
            2580                2585                2590

Gly Ser Phe Ser Cys Glu Cys Gln Arg Gly Phe Ser Leu Asp Ala Thr
        2595                2600                2605

Gly Leu Asn Cys Glu Asp Val Asp Glu Cys Asp Gly Asn His Arg Cys
        2610                2615                2620

Gln His Gly Cys Gln Asn Ile Leu Gly Gly Tyr Arg Cys Gly Cys Pro
2625                2630                2635                2640

Gln Gly Tyr Ile Gln His Tyr Gln Trp Asn Gln Cys Val Asp Glu Asn
            2645                2650                2655

Glu Cys Ser Asn Pro Asn Ala Cys Gly Ser Ala Ser Cys Tyr Asn Thr
        2660                2665                2670

Leu Gly Ser Tyr Lys Cys Ala Cys Pro Ser Gly Phe Ser Phe Asp Gln
        2675                2680                2685

Phe Ser Ser Ala Cys His Asp Val Asn Glu Cys Ser Ser Ser Lys Asn
        2690                2695                2700

Pro Cys Asn Tyr Gly Cys Ser Asn Thr Glu Gly Gly Tyr Leu Cys Gly
2705                2710                2715                2720

Cys Pro Pro Gly Tyr Tyr Arg Val Gly Gln Gly His Cys Val Ser Gly
            2725                2730                2735

Met Gly Phe Asn Lys Gly Gln Tyr Leu Ser Leu Asp Thr Glu Val Asp
        2740                2745                2750

Glu Glu Asn Ala Leu Ser Pro Glu Ala Cys Tyr Glu Cys Lys Ile Asn
        2755                2760                2765

Gly Tyr Ser Lys Lys Asp Ser Arg Gln Lys Arg Ser Ile His Glu Pro
        2770                2775                2780

Asp Pro Thr Ala Val Glu Gln Ile Ser Leu Glu Ser Val Asp Met Asp
2785                2790                2795                2800

Ser Pro Val Asn Met Lys Phe Asn Leu Ser His Leu Gly Ser Lys Glu
            2805                2810                2815

His Ile Leu Glu Leu Arg Pro Ala Ile Gln Pro Leu Asn Asn His Ile
        2820                2825                2830

Arg Tyr Val Ile Ser Gln Gly Asn Asp Asp Ser Val Phe Arg Ile His
        2835                2840                2845

Gln Arg Asn Gly Leu Ser Tyr Leu His Thr Ala Lys Lys Lys Leu Met
        2850                2855                2860

Pro Gly Thr Tyr Thr Leu Glu Ile Thr Ser Ile Pro Leu Tyr Lys Lys
2865                2870                2875                2880

Lys Glu Leu Lys Lys Leu Glu Glu Ser Asn Glu Asp Asp Tyr Leu Leu
            2885                2890                2895

Gly Glu Leu Gly Glu Ala Leu Arg Met Arg Leu Gln Ile Gln Leu Tyr
        2900                2905                2910

<210> SEQ ID NO 64
<211> LENGTH: 2809
<212> TYPE: PRT
<213> ORGANISM: Homo sapiens

<400> SEQUENCE: 64

Met Thr Leu Glu Gly Leu Tyr Leu Ala Arg Gly Pro Leu Ala Arg Leu
1               5                   10                  15

Leu Leu Ala Trp Ser Ala Leu Leu Cys Met Ala Gly Gly Gln Gly Arg
            20                  25                  30

Trp Asp Gly Ala Leu Glu Ala Ala Gly Pro Gly Arg Val Arg Arg Arg
        35                  40                  45
```

```
Gly Ser Pro Gly Ile Leu Gln Gly Pro Asn Val Cys Gly Ser Arg Phe
         50                  55                  60
His Ala Tyr Cys Cys Pro Gly Trp Arg Thr Phe Pro Gly Arg Ser Gln
 65                  70                  75                  80
Cys Val Val Pro Ile Cys Arg Arg Ala Cys Gly Glu Gly Phe Cys Ser
                 85                  90                  95
Gln Pro Asn Leu Cys Thr Cys Ala Asp Gly Thr Leu Ala Pro Ser Cys
            100                 105                 110
Gly Val Ser Arg Gly Ser Gly Cys Ser Val Ser Cys Met Asn Gly Gly
            115                 120                 125
Thr Cys Arg Gly Ala Ser Cys Leu Cys Gln Lys Gly Tyr Thr Gly Thr
130                 135                 140
Val Cys Gly Gln Pro Ile Cys Asp Arg Gly Cys His Asn Gly Gly Arg
145                 150                 155                 160
Cys Ile Gly Pro Asn Arg Cys Ala Cys Val Tyr Gly Phe Met Gly Pro
                165                 170                 175
Gln Cys Glu Arg Asp Tyr Arg Thr Gly Pro Cys Phe Gly Gln Val Gly
            180                 185                 190
Pro Glu Gly Cys Gln His Gln Leu Thr Gly Leu Val Cys Thr Lys Ala
            195                 200                 205
Leu Cys Cys Ala Thr Val Gly Arg Ala Trp Gly Leu Pro Cys Glu Leu
210                 215                 220
Cys Pro Ala Gln Pro His Pro Cys Arg Arg Gly Phe Ile Pro Asn Ile
225                 230                 235                 240
His Thr Gly Ala Cys Gln Asp Val Asp Glu Cys Gln Ala Val Pro Gly
                245                 250                 255
Leu Cys Gln Gly Gly Ser Cys Val Asn Met Val Gly Ser Phe His Cys
            260                 265                 270
Arg Cys Pro Val Gly His Arg Leu Ser Asp Ser Ser Ala Ala Cys Glu
            275                 280                 285
Asp Tyr Arg Ala Gly Ala Cys Phe Ser Val Leu Phe Gly Gly Arg Cys
            290                 295                 300
Ala Gly Asp Leu Ala Gly His Tyr Thr Arg Arg Gln Cys Cys Cys Asp
305                 310                 315                 320
Arg Gly Arg Cys Trp Ala Ala Gly Pro Val Pro Glu Leu Cys Pro Pro
                325                 330                 335
Arg Gly Ser Asn Glu Phe Gln Gln Leu Cys Ala Gln Arg Leu Pro Leu
            340                 345                 350
Leu Pro Gly His Pro Gly Leu Phe Pro Gly Leu Leu Gly Phe Gly Ser
            355                 360                 365
Asn Gly Met Gly Pro Pro Leu Gly Pro Ala Arg Leu Asn Pro His Gly
            370                 375                 380
Ser Asp Ala Arg Gly Ile Pro Ser Leu Gly Pro Gly Asn Ser Asn Ile
385                 390                 395                 400
Gly Thr Ala Thr Leu Asn Gln Thr Ile Asp Ile Cys Arg His Phe Thr
                405                 410                 415
Asn Leu Cys Leu Asn Gly Arg Cys Leu Pro Thr Pro Ser Ser Tyr Arg
            420                 425                 430
Cys Glu Cys Asn Val Gly Tyr Thr Gln Asp Val Arg Gly Glu Cys Ile
            435                 440                 445
Asp Val Asp Glu Cys Thr Ser Ser Pro Cys His His Gly Asp Cys Val
450                 455                 460
```

```
Asn Ile Pro Gly Thr Tyr His Cys Arg Cys Tyr Pro Gly Phe Gln Ala
465                 470                 475                 480

Thr Pro Thr Arg Gln Ala Cys Val Asp Val Asp Glu Cys Ile Val Ser
            485                 490                 495

Gly Gly Leu Cys His Leu Gly Arg Cys Val Asn Thr Glu Gly Ser Phe
            500                 505                 510

Gln Cys Val Cys Asn Ala Gly Phe Glu Leu Ser Pro Asp Gly Lys Asn
            515                 520                 525

Cys Val Asp His Asn Glu Cys Ala Thr Ser Thr Met Cys Val Asn Gly
530                 535                 540

Val Cys Leu Asn Glu Asp Gly Ser Phe Ser Cys Leu Cys Lys Pro Gly
545                 550                 555                 560

Phe Leu Leu Ala Pro Gly Gly His Tyr Cys Met Asp Ile Asp Glu Cys
            565                 570                 575

Gln Thr Pro Gly Ile Cys Val Asn Gly His Cys Thr Asn Thr Glu Gly
            580                 585                 590

Ser Phe Arg Cys Gln Cys Leu Gly Gly Leu Ala Val Gly Thr Asp Gly
            595                 600                 605

Arg Val Cys Val Asp Thr His Val Arg Ser Thr Cys Tyr Gly Ala Ile
610                 615                 620

Glu Lys Gly Ser Cys Ala Arg Pro Phe Pro Gly Thr Val Thr Lys Ser
625                 630                 635                 640

Glu Cys Cys Cys Ala Asn Pro Asp His Gly Phe Gly Glu Pro Cys Gln
                645                 650                 655

Leu Cys Pro Ala Lys Asp Ser Ala Glu Phe Gln Ala Leu Cys Ser Ser
            660                 665                 670

Gly Leu Gly Ile Thr Thr Asp Gly Arg Asp Ile Asn Glu Cys Ala Leu
            675                 680                 685

Asp Pro Glu Val Cys Ala Asn Gly Val Cys Glu Asn Leu Arg Gly Ser
690                 695                 700

Tyr Arg Cys Val Cys Asn Leu Gly Tyr Glu Ala Gly Ala Ser Gly Lys
705                 710                 715                 720

Asp Cys Thr Asp Val Asp Glu Cys Ala Leu Asn Ser Leu Leu Cys Asp
            725                 730                 735

Asn Gly Trp Cys Gln Asn Ser Pro Gly Ser Tyr Ser Cys Ser Cys Pro
            740                 745                 750

Pro Gly Phe His Phe Trp Gln Asp Thr Glu Ile Cys Lys Asp Val Asp
            755                 760                 765

Glu Cys Leu Ser Ser Pro Cys Val Ser Gly Val Cys Arg Asn Leu Ala
770                 775                 780

Gly Ser Tyr Thr Cys Lys Cys Gly Pro Gly Ser Arg Leu Asp Pro Ser
785                 790                 795                 800

Gly Thr Phe Cys Leu Asp Ser Thr Lys Gly Thr Cys Trp Leu Lys Ile
            805                 810                 815

Gln Glu Ser Arg Cys Glu Val Asn Leu Gln Gly Ala Ser Leu Arg Ser
            820                 825                 830

Glu Cys Cys Ala Thr Leu Gly Ala Ala Trp Gly Ser Pro Cys Glu Arg
            835                 840                 845

Cys Glu Ile Asp Pro Ala Cys Ala Arg Gly Phe Ala Arg Met Thr Gly
            850                 855                 860

Val Thr Cys Asp Asp Val Asn Glu Cys Glu Ser Phe Pro Gly Val Cys
865                 870                 875                 880

Pro Asn Gly Arg Cys Val Asn Thr Ala Gly Ser Phe Arg Cys Glu Cys
```

-continued

```
                885                 890                 895
Pro Glu Gly Leu Met Leu Asp Ala Ser Gly Arg Leu Cys Val Asp Val
                900                 905                 910
Arg Leu Glu Pro Cys Phe Leu Arg Trp Asp Glu Asp Glu Cys Gly Val
                915                 920                 925
Thr Leu Pro Gly Lys Tyr Arg Met Asp Val Cys Cys Cys Ser Ile Gly
                930                 935                 940
Ala Val Trp Gly Val Glu Cys Glu Ala Cys Pro Asp Pro Ser Leu
945                 950                 955                 960
Glu Phe Ala Ser Leu Cys Pro Arg Gly Leu Gly Phe Ala Ser Arg Asp
                965                 970                 975
Phe Leu Ser Gly Arg Pro Phe Tyr Lys Asp Val Asn Glu Cys Lys Val
                980                 985                 990
Phe Pro Gly Leu Cys Thr His Gly Thr Cys Arg Asn Thr Val Gly Ser
                995                 1000                1005
Phe His Cys Ala Cys Ala Gly Gly Phe Ala Leu Asp Ala Gln Glu Arg
                1010                1015                1020
Asn Cys Thr Asp Ile Asp Glu Cys Arg Ile Ser Pro Asp Leu Cys Gly
1025                1030                1035                1040
Gln Gly Thr Cys Val Asn Thr Pro Gly Ser Phe Glu Cys Glu Cys Phe
                1045                1050                1055
Pro Gly Tyr Glu Ser Gly Phe Met Leu Met Lys Asn Cys Met Asp Val
                1060                1065                1070
Asp Glu Cys Ala Arg Asp Pro Leu Leu Cys Arg Gly Gly Thr Cys Thr
                1075                1080                1085
Asn Thr Asp Gly Ser Tyr Lys Cys Gln Cys Pro Pro Gly His Glu Leu
                1090                1095                1100
Thr Ala Lys Gly Thr Ala Cys Glu Asp Ile Asp Glu Cys Ser Leu Ser
1105                1110                1115                1120
Asp Gly Leu Cys Pro His Gly Gln Cys Val Asn Val Ile Gly Ala Phe
                1125                1130                1135
Gln Cys Ser Cys His Ala Gly Phe Gln Ser Thr Pro Asp Arg Gln Gly
                1140                1145                1150
Cys Val Asp Ile Asn Glu Cys Arg Val Gln Asn Gly Gly Cys Asp Val
                1155                1160                1165
His Cys Ile Asn Thr Glu Gly Ser Tyr Arg Cys Ser Cys Gly Gln Gly
                1170                1175                1180
Tyr Ser Leu Met Pro Asp Gly Arg Ala Cys Ala Asp Val Asp Glu Cys
1185                1190                1195                1200
Glu Glu Asn Pro Arg Val Cys Asp Gln Gly His Cys Thr Asn Met Pro
                1205                1210                1215
Gly Gly His Arg Cys Leu Cys Tyr Asp Gly Phe Met Ala Thr Pro Asp
                1220                1225                1230
Met Arg Thr Cys Val Asp Val Asp Glu Cys Asp Leu Asn Pro His Ile
                1235                1240                1245
Cys Leu His Gly Asp Cys Glu Asn Thr Lys Gly Ser Phe Val Cys His
                1250                1255                1260
Cys Gln Leu Gly Tyr Met Val Arg Lys Gly Ala Thr Gly Cys Ser Asp
1265                1270                1275                1280
Val Asp Glu Cys Glu Val Gly Gly His Asn Cys Asp Ser His Ala Ser
                1285                1290                1295
Cys Leu Asn Ile Pro Gly Ser Phe Ser Cys Arg Cys Leu Pro Gly Trp
                1300                1305                1310
```

```
Val Gly Asp Gly Phe Glu Cys His Asp Leu Asp Glu Cys Val Ser Gln
        1315                1320                1325

Glu His Arg Cys Ser Pro Arg Gly Asp Cys Leu Asn Val Pro Gly Ser
    1330                1335                1340

Tyr Arg Cys Thr Cys Arg Gln Gly Phe Ala Gly Asp Gly Phe Phe Cys
1345                1350                1355                1360

Glu Asp Arg Asp Glu Cys Ala Glu Asn Val Asp Leu Cys Asp Asn Gly
        1365                1370                1375

Gln Cys Leu Asn Ala Pro Gly Gly Tyr Arg Cys Glu Cys Glu Met Gly
            1380                1385                1390

Phe Asp Pro Thr Glu Asp His Arg Ala Cys Gln Asp Val Asp Glu Cys
        1395                1400                1405

Ala Gln Gly Asn Leu Cys Ala Phe Gly Ser Cys Glu Asn Leu Pro Gly
        1410                1415                1420

Met Phe Arg Cys Ile Cys Asn Gly Gly Tyr Glu Leu Asp Arg Gly Gly
1425                1430                1435                1440

Gly Asn Cys Thr Asp Ile Asn Glu Cys Ala Asp Pro Val Asn Cys Ile
            1445                1450                1455

Asn Gly Val Cys Ile Asn Thr Pro Gly Ser Tyr Leu Cys Ser Cys Pro
        1460                1465                1470

Gln Asp Phe Glu Leu Asn Pro Ser Gly Val Gly Cys Val Asp Thr Arg
        1475                1480                1485

Ala Gly Asn Cys Phe Leu Glu Thr His Asp Arg Gly Asp Ser Gly Ile
        1490                1495                1500

Ser Cys Ser Ala Glu Ile Gly Val Gly Val Thr Arg Ala Ser Cys Cys
1505                1510                1515                1520

Cys Ser Leu Gly Arg Ala Trp Gly Asn Pro Cys Glu Leu Cys Pro Met
            1525                1530                1535

Ala Asn Thr Thr Glu Tyr Arg Thr Leu Cys Pro Gly Gly Glu Gly Phe
            1540                1545                1550

Gln Pro Asn Arg Ile Thr Val Ile Leu Glu Asp Ile Asp Glu Cys Gln
        1555                1560                1565

Glu Leu Pro Gly Leu Cys Gln Gly Gly Asp Cys Val Asn Thr Phe Gly
        1570                1575                1580

Ser Phe Gln Cys Glu Cys Pro Pro Gly Tyr His Leu Ser Glu His Thr
1585                1590                1595                1600

Arg Ile Cys Glu Asp Ile Asp Glu Cys Ser Thr His Ser Gly Ile Cys
        1605                1610                1615

Gly Pro Gly Thr Cys Tyr Asn Thr Leu Gly Asn Tyr Thr Cys Val Cys
        1620                1625                1630

Pro Ala Glu Tyr Leu Gln Val Asn Gly Gly Asn Asn Cys Met Asp Met
        1635                1640                1645

Arg Lys Ser Val Cys Phe Arg His Tyr Asn Gly Thr Cys Gln Asn Glu
        1650                1655                1660

Leu Ala Phe Asn Val Thr Arg Lys Met Cys Cys Cys Ser Tyr Asn Ile
1665                1670                1675                1680

Gly Gln Ala Trp Asn Arg Pro Cys Glu Ala Cys Pro Thr Pro Ile Ser
        1685                1690                1695

Pro Asp Tyr Gln Ile Leu Cys Gly Asn Gln Ala Pro Gly Phe Leu Thr
            1700                1705                1710

Asp Ile His Thr Gly Lys Pro Leu Asp Ile Asp Glu Cys Gly Glu Ile
        1715                1720                1725
```

```
Pro Ala Ile Cys Ala Asn Gly Ile Cys Ile Asn Gln Ile Gly Ser Phe
    1730                1735                1740

Arg Cys Glu Cys Pro Ala Gly Phe Asn Tyr Asn Ser Ile Leu Leu Ala
1745                1750                1755                1760

Cys Glu Asp Val Asp Glu Cys Gly Ser Arg Glu Ser Pro Cys Gln Gln
                1765                1770                1775

Asn Ala Asp Cys Ile Asn Ile Pro Gly Ser Tyr Arg Cys Lys Cys Thr
            1780                1785                1790

Arg Gly Tyr Lys Leu Ser Pro Gly Gly Ala Cys Val Gly Arg Asn Glu
        1795                1800                1805

Cys Arg Glu Ile Pro Asn Val Cys Ser His Gly Asp Cys Met Asp Thr
    1810                1815                1820

Glu Gly Ser Tyr Met Cys Leu Cys His Arg Gly Phe Gln Ala Ser Ala
1825                1830                1835                1840

Asp Gln Thr Leu Cys Met Asp Ile Asp Glu Cys Asp Arg Gln Pro Cys
                1845                1850                1855

Gly Asn Gly Thr Cys Lys Asn Ile Ile Gly Ser Tyr Asn Cys Leu Cys
            1860                1865                1870

Phe Pro Gly Phe Val Val Thr His Asn Gly Asp Cys Val Asp Phe Asp
        1875                1880                1885

Glu Cys Thr Thr Leu Val Gly Gln Val Cys Arg Phe Gly His Cys Leu
    1890                1895                1900

Asn Thr Ala Gly Ser Phe His Cys Leu Cys Gln Asp Gly Phe Glu Leu
1905                1910                1915                1920

Thr Ala Asp Gly Lys Asn Cys Val Asp Thr Asn Glu Cys Leu Ser Leu
                1925                1930                1935

Ala Gly Thr Cys Leu Pro Gly Thr Cys Gln Asn Leu Glu Gly Ser Phe
            1940                1945                1950

Arg Cys Ile Cys Pro Pro Gly Phe Gln Val Gln Ser Asp His Cys Ile
        1955                1960                1965

Asp Ile Asp Glu Cys Ser Glu Pro Asn Leu Cys Leu Phe Gly Thr
    1970                1975                1980

Cys Thr Asn Ser Pro Gly Ser Phe Gln Cys Leu Cys Pro Pro Gly Phe
1985                1990                1995                2000

Val Leu Ser Asp Asn Gly His Arg Cys Phe Asp Thr Arg Gln Ser Phe
                2005                2010                2015

Cys Phe Thr Arg Phe Glu Ala Gly Lys Cys Ser Val Pro Lys Ala Phe
            2020                2025                2030

Asn Thr Thr Lys Thr Arg Cys Cys Cys Ser Lys Arg Pro Gly Glu Gly
        2035                2040                2045

Trp Gly Asp Pro Cys Glu Leu Cys Pro Gln Glu Gly Ser Ala Ala Phe
    2050                2055                2060

Gln Glu Leu Cys Pro Phe Gly His Gly Ala Val Pro Gly Pro Asp Asp
2065                2070                2075                2080

Ser Arg Glu Asp Val Asn Glu Cys Ala Glu Asn Pro Gly Val Cys Thr
                2085                2090                2095

Asn Gly Val Cys Val Asn Thr Asp Gly Ser Phe Arg Cys Glu Cys Pro
            2100                2105                2110

Phe Gly Tyr Ser Leu Asp Phe Thr Gly Ile Asn Cys Val Asp Thr Asp
        2115                2120                2125

Glu Cys Ser Val Gly His Pro Cys Gly Gln Gly Thr Cys Thr Asn Val
    2130                2135                2140

Ile Gly Gly Phe Glu Cys Ala Cys Ala Asp Gly Phe Glu Pro Gly Leu
```

```
                2145                2150                2155                2160
        Met Met Thr Cys Glu Asp Ile Asp Glu Cys Ser Leu Asn Pro Leu Leu
                        2165                2170                2175
        Cys Ala Phe Arg Cys His Asn Thr Glu Gly Ser Tyr Leu Cys Thr Cys
                        2180                2185                2190
        Pro Ala Gly Tyr Thr Leu Arg Glu Asp Gly Ala Met Cys Arg Asp Val
                        2195                2200                2205
        Asp Glu Cys Ala Asp Gly Gln Gln Asp Cys His Ala Arg Gly Met Glu
                        2210                2215                2220
        Cys Lys Asn Leu Ile Gly Thr Phe Ala Cys Val Cys Pro Pro Gly Met
        2225                2230                2235                2240
        Arg Pro Leu Pro Gly Ser Gly Glu Cys Thr Asp Asp Asn Glu Cys
                        2245                2250                2255
        His Ala Gln Pro Asp Leu Cys Val Asn Gly Arg Cys Val Asn Thr Ala
                        2260                2265                2270
        Gly Ser Phe Arg Cys Asp Cys Asp Glu Gly Phe Gln Pro Ser Pro Thr
                        2275                2280                2285
        Leu Thr Glu Cys His Asp Ile Arg Gln Gly Pro Cys Phe Ala Glu Val
                        2290                2295                2300
        Leu Gln Thr Met Cys Arg Ser Leu Ser Ser Ser Glu Ala Val Thr
        2305                2310                2315                2320
        Arg Ala Glu Cys Cys Cys Gly Gly Gly Arg Gly Trp Gly Pro Arg Cys
                        2325                2330                2335
        Glu Leu Cys Pro Leu Pro Gly Thr Ser Ala Tyr Arg Lys Leu Cys Pro
                        2340                2345                2350
        His Gly Ser Gly Tyr Thr Ala Glu Gly Arg Asp Val Asp Glu Cys Arg
                        2355                2360                2365
        Met Leu Ala His Leu Cys Ala His Gly Glu Cys Ile Asn Ser Leu Gly
                        2370                2375                2380
        Ser Phe Arg Cys His Cys Gln Ala Gly Tyr Thr Pro Asp Ala Thr Ala
        2385                2390                2395                2400
        Thr Thr Cys Leu Asp Met Asp Glu Cys Ser Gln Val Pro Lys Pro Cys
                        2405                2410                2415
        Thr Phe Leu Cys Lys Asn Thr Lys Gly Ser Phe Leu Cys Ser Cys Pro
                        2420                2425                2430
        Arg Gly Tyr Leu Leu Glu Glu Asp Gly Arg Thr Cys Lys Asp Leu Asp
                        2435                2440                2445
        Glu Cys Thr Ser Arg Gln His Asn Cys Gln Phe Leu Cys Val Asn Thr
                        2450                2455                2460
        Val Gly Ala Phe Thr Cys Arg Cys Pro Pro Gly Phe Thr Gln His His
        2465                2470                2475                2480
        Gln Ala Cys Phe Asp Asn Asp Glu Cys Ser Ala Gln Pro Gly Pro Cys
                        2485                2490                2495
        Gly Ala His Gly His Cys His Asn Thr Pro Gly Ser Phe Arg Cys Glu
                        2500                2505                2510
        Cys His Gln Gly Phe Thr Leu Val Ser Ser Gly His Gly Cys Glu Asp
                        2515                2520                2525
        Val Asn Glu Cys Asp Gly Pro His Arg Cys Gln His Gly Cys Gln Asn
                        2530                2535                2540
        Gln Leu Gly Gly Tyr Arg Cys Ser Cys Pro Gln Gly Phe Thr Gln His
        2545                2550                2555                2560
        Ser Gln Trp Ala Gln Cys Val Asp Glu Asn Glu Cys Ala Leu Ser Pro
                        2565                2570                2575
```

```
Pro Thr Cys Gly Ser Ala Ser Cys Arg Asn Thr Leu Gly Gly Phe Arg
            2580                2585                2590

Cys Val Cys Pro Ser Gly Phe Asp Phe Asp Gln Ala Leu Gly Gly Cys
        2595                2600                2605

Gln Glu Val Asp Glu Cys Ala Gly Arg Arg Gly Pro Cys Ser Tyr Ser
    2610                2615                2620

Cys Ala Asn Thr Pro Gly Gly Phe Leu Cys Gly Cys Pro Gln Gly Tyr
2625                2630                2635                2640

Phe Arg Ala Gly Gln Gly His Cys Val Ser Gly Leu Gly Phe Ser Pro
                2645            2650                2655

Gly Pro Gln Asp Thr Pro Asp Lys Glu Glu Leu Leu Ser Glu Ala
            2660                2665                2670

Cys Tyr Glu Cys Lys Ile Asn Gly Leu Ser Pro Arg Asp Arg Pro Arg
        2675                2680                2685

Arg Ser Ala His Arg Asp His Gln Val Asn Leu Ala Thr Leu Asp Ser
    2690                2695                2700

Glu Ala Leu Leu Thr Leu Gly Leu Asn Leu Ser His Leu Gly Arg Ala
2705            2710                2715                2720

Glu Arg Ile Leu Glu Leu Arg Pro Ala Leu Glu Gly Leu Glu Gly Arg
            2725                2730                2735

Ile Arg Tyr Val Ile Val Arg Gly Asn Glu Gln Gly Phe Phe Arg Met
            2740                2745                2750

His His Leu Arg Gly Val Ser Ser Leu Gln Leu Gly Arg Arg Arg Pro
            2755                2760                2765

Gly Pro Gly Thr Tyr Arg Leu Glu Val Val Ser His Met Ala Gly Pro
        2770                2775                2780

Trp Gly Val Gln Pro Glu Gly Gln Pro Gly Pro Trp Gly Gln Ala Leu
2785            2790                2795                2800

Arg Leu Lys Val Gln Leu Gln Leu Leu
                2805
```

UNITED STATES PATENT AND TRADEMARK OFFICE
CERTIFICATE OF CORRECTION

PATENT NO. : 10,786,438 B2  
APPLICATION NO. : 16/395896  
DATED : September 29, 2020  
INVENTOR(S) : Suma Krishnan, Trevor Parry and Pooja Agarwal Page 1 of 1

It is certified that error appears in the above-identified patent and that said Letters Patent is hereby corrected as shown below:

In the Claims

In Column 423, Line 4, for Claim 5: please replace "COLE" with --COL8--;

In Column 424, Line 47, for Claim 19: please replace "COLE" with --COL8--;

In Column 424, Line 48, for Claim 19: please replace "COL5-1" with --COL9-1--;

In Column 424, Line 49, for Claim 19: please replace "COL5-2" with --COL9-2--.

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*